(12) United States Patent
Regev et al.

(10) Patent No.: US 11,566,279 B2
(45) Date of Patent: Jan. 31, 2023

(54) DROPLET-BASED METHOD AND APPARATUS FOR COMPOSITE SINGLE-CELL NUCLEIC ACID ANALYSIS

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Aviv Regev, Cambridge, MA (US); Evan Zane Macosko, Cambridge, MA (US); Steven Andrew McCarroll, Cambridge, MA (US); Alexander K. Shalek, Cambridge, MA (US); Anindita Basu, Cambridge, MA (US); Christopher B. Ford, Cambridge, MA (US); Hongkun Park, Cambridge, MA (US); David A. Weitz, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 20 days.

(21) Appl. No.: 16/244,058

(22) Filed: Jan. 9, 2019

(65) Prior Publication Data

US 2019/0127782 A1    May 2, 2019

Related U.S. Application Data

(60) Division of application No. 15/453,405, filed on Mar. 8, 2017, which is a continuation-in-part of application No. PCT/US2015/049178, filed on Sep. 9, 2015.

(60) Provisional application No. 62/146,642, filed on Apr. 13, 2015, provisional application No. 62/048,227, filed on Sep. 9, 2014.

(51) Int. Cl.
| | |
|---|---|
| C12Q 1/6809 | (2018.01) |
| C12Q 1/6834 | (2018.01) |
| C12Q 1/6869 | (2018.01) |
| C12N 15/10 | (2006.01) |
| G06K 19/06 | (2006.01) |

(52) U.S. Cl.
CPC ....... *C12Q 1/6809* (2013.01); *C12N 15/1096* (2013.01); *C12Q 1/6834* (2013.01); *C12Q 1/6869* (2013.01); *G06K 19/06* (2013.01)

(58) Field of Classification Search
CPC .. C12Q 1/6809; C12Q 1/6834; C12Q 1/6869; C12Q 2521/107; C12Q 2525/15; C12Q 2525/161; C12Q 2563/149; C12Q 2563/159; C12Q 2565/629; C12Q 2525/173; C12Q 2563/179; C12N 15/1096; G06K 19/06
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,668,268 A * | 9/1997 | Tang ...................... | C07H 21/00 435/6.19 |
| 5,919,523 A * | 7/1999 | Sundberg ............. | B01J 19/0046 427/333 |
| 6,033,880 A | 3/2000 | Haff et al. | |
| 6,524,456 B1 | 2/2003 | Ramsey et al. | |
| 6,617,145 B2 | 9/2003 | Boone et al. | |
| 6,716,642 B1 * | 4/2004 | Wu ....................... | B01J 19/0046 250/338.2 |
| 7,041,481 B2 | 5/2006 | Anderson et al. | |
| 7,129,091 B2 | 10/2006 | Ismagilov et al. | |
| 7,708,949 B2 | 5/2010 | Stone et al. | |
| RE41,780 E | 9/2010 | Anderson et al. | |
| 8,273,573 B2 | 9/2012 | Ismagilov et al. | |
| 8,304,193 B2 | 11/2012 | Ismagilov et al. | |
| 8,329,407 B2 | 12/2012 | Ismagilov et al. | |
| 8,658,430 B2 | 2/2014 | Miller et al. | |
| 8,822,148 B2 | 9/2014 | Ismagliov | |
| 8,835,358 B2 | 9/2014 | Fodor et al. | |
| 8,889,083 B2 | 11/2014 | Ismagilov et al. | |
| 9,089,844 B2 | 7/2015 | Hiddessen et al. | |
| 9,126,160 B2 | 9/2015 | Ness et al. | |
| 9,216,392 B2 | 12/2015 | Hindson et al. | |
| 9,290,808 B2 | 3/2016 | Fodor et al. | |
| 9,290,809 B2 | 3/2016 | Fodor et al. | |
| 9,315,857 B2 | 4/2016 | Fu et al. | |
| 9,347,059 B2 | 5/2016 | Saxonov | |

(Continued)

FOREIGN PATENT DOCUMENTS

| | | |
|---|---|---|
| EP | 2047910 A2 | 4/2009 |
| WO | 02099078 A2 | 12/2002 |

(Continued)

OTHER PUBLICATIONS

U.S. Appl. No. 61/982,001, filed Apr. 21, 2014 (Year: 2014).*
U.S. Appl. No. 61/952,036, 2014 (Year: 2014).*
Islam et al "Quantitative single-cell RNA-seq with unique molecular identifiers", Nature methods, Feb. 2014 11 (2): 163-168 (Year: 2014).*
Islam et al (supplemental table 2) (Year: 2014).*

(Continued)

*Primary Examiner* — Narayan K Bhat
(74) *Attorney, Agent, or Firm* — F. Brent Nix, Esq.; Johnson, Marcou, Isaacs & Nix, LLC; Michael B. Scher, Esq.

(57) ABSTRACT

The present invention generally relates to a combination of molecular barcoding and emulsion-based microfluidics to isolate, lyse, barcode, and prepare nucleic acids from individual cells in a high-throughput manner.

19 Claims, 42 Drawing Sheets
Specification includes a Sequence Listing.

(56) References Cited

U.S. PATENT DOCUMENTS

| | | | |
|---|---|---|---|
| 9,388,465 | B2 | 7/2016 | Hindson et al. |
| 9,500,664 | B2 | 11/2016 | Ness et al. |
| 9,567,631 | B2 | 2/2017 | Hindson et al. |
| 9,567,645 | B2 | 2/2017 | Fan et al. |
| 9,567,646 | B2 | 2/2017 | Fan et al. |
| 9,598,736 | B2 | 3/2017 | Fan et al. |
| 9,636,682 | B2 | 5/2017 | Hiddessen et al. |
| 9,637,799 | B2 | 5/2017 | Fan et al. |
| 9,644,204 | B2 | 5/2017 | Hindson et al. |
| 9,649,635 | B2 | 5/2017 | Hiddessen et al. |
| 9,689,024 | B2 | 6/2017 | Hindson et al. |
| 9,695,468 | B2 | 7/2017 | Hindson et al. |
| 9,708,654 | B2 | 7/2017 | Hunicke-Smith et al. |
| 9,708,659 | B2 | 7/2017 | Fodor et al. |
| 9,816,121 | B2 | 11/2017 | Agresti et al. |
| 9,816,137 | B2 | 11/2017 | Fodor et al. |
| 9,826,137 | B2 | 11/2017 | Yokomizo |
| 9,845,502 | B2 | 12/2017 | Fodor et al. |
| 9,856,530 | B2 | 1/2018 | Hindson et al. |
| 9,885,034 | B2 | 2/2018 | Saxonov |
| 2002/0172965 | A1 | 11/2002 | Kamb et al. |
| 2005/0142577 | A1* | 6/2005 | Jones ............... C12Q 1/6809 435/6.12 |
| 2005/0172476 | A1 | 8/2005 | Stone et al. |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2009/0042737 | A1 | 2/2009 | Katz et al. |
| 2010/0002241 | A1 | 1/2010 | Hirose |
| 2010/0022414 | A1 | 1/2010 | Link et al. |
| 2010/0137163 | A1 | 6/2010 | Link et al. |
| 2010/0172803 | A1 | 7/2010 | Stone et al. |
| 2011/0319298 | A1 | 12/2011 | Benner et al. |
| 2012/0122714 | A1 | 5/2012 | Samuels et al. |
| 2012/0219947 | A1 | 8/2012 | Yurkovetsky et al. |
| 2012/0220494 | A1 | 8/2012 | Samuels et al. |
| 2013/0274117 | A1* | 10/2013 | Church ............ C12Q 1/6806 506/4 |
| 2014/0155295 | A1 | 6/2014 | Hindson et al. |
| 2014/0235506 | A1 | 8/2014 | Hindson et al. |
| 2014/0357500 | A1 | 12/2014 | Vigneault et al. |
| 2015/0005199 | A1 | 1/2015 | Hindson et al. |
| 2015/0011430 | A1 | 1/2015 | Saxonov |
| 2018/0030515 | A1 | 2/2018 | Regev et al. |

FOREIGN PATENT DOCUMENTS

| | | | |
|---|---|---|---|
| WO | 2004002627 | A2 | 1/2004 |
| WO | 2004016767 | A2 | 2/2004 |
| WO | 2005003291 | A2 | 1/2005 |
| WO | 2007089541 | A2 | 8/2007 |
| WO | 2009036379 | A2 | 3/2009 |
| WO | 2013188872 | A1 | 12/2013 |
| WO | 2014026032 | A2 | 2/2014 |
| WO | 2014047561 | A1 | 3/2014 |
| WO | 2015/031691 | A1 | 3/2015 |
| WO | 2015/164212 | A1 | 10/2015 |
| WO | 2016040476 | A1 | 3/2016 |

OTHER PUBLICATIONS

Chung, et al., "Statistical Significance of Variables Driving Systematic Variation in High-Dimensional Data", Bioinformatics, vol. 31, No. 4, pp. 545-554, Advance Access publication: Oct. 21, 2014.
Collins, "Biomedical Research Highlighted in Science's 2018 Breakthroughs", NIH Director's Blog, pp. 1-9, Jan. 8, 2019.
Corbo, et al., "A Typology of Photoreceptor Gene Expression Patterns in the Mouse", PNAS, vol. 104, Issue 29, pp. 12069-12074, Jul. 17, 2007.
Cuatrecasas, Pedro, "Protein Purification by Affinity Chromatography", J Biol Chem, vol. 245, Issue 12, pp. 3059-3065, Jun. 25, 1970.
Damha, et al., "An improved procedure for derivatization of controlled-pore glass beads for solid-phase oligonucleotide synthesis", Nucleic Acids Res., vol. 18, No. 13, pp. 3813-3821, Accepted: May 17, 1990.
Descamps, et al., "Gelatinase B/matrix Metalloproteinase-9 Pprovokes Cataract by Cleaving Lens BetaB 1 Crystallin", The FASEB Journal, vol. 19, Issue 1, pp. 29-35, Jan. 2005.
Ding, et al., "Progress Towards a Systematic Comparison of Single Cell RNA-Seq Methods", Broad Institute, Feb. 12, 2019.
Dixit, et al., "Perturb-Seq: Dissecting Molecular Circuits with Scalable Single-Cell RNA Profiling of Pooled Genetic Screens", Cell, vol. 167, Issue 7, pp. 1853-1866, Dec. 15, 2016.
Dobin, et al., "STAR: Ultrafast Universal RNA-seq Aligner", Bioinformatics, vol. 29, Issue 1, pp. 15-21, Advance Access publication: Oct. 25, 2012.
Dressman, et al., "Transforming single DNA molecules into fluorescent magnetic particles for detection and enumeration of genetic variations", PNAS, vol. 100, No. 15, pp. 8817-8822, Jul. 22, 2003.
Droege, et al., "The Genome Sequencer FLX System—longer reads, more applications, straight forward bioinformatics and more complete data sets.", J Biotechnol., vol. 136, Issues 1-2, pp. 3-10, Accepted: Mar. 31, 2008.
Edd, et al., "Controlled Encapsulation of Single Cells into Monodisperse Picoliter Drops", Lab Chip, vol. 8, Issue 8, pp. 1262-1264, Aug. 2008.
Ester, et al., "A Density-Based Algorithm for Discovering Clusters in Large Spatial Databases with Noise", pp. 226-231, KDD-96, 1996.
Farmer, et al., "Defining epithelial cell dynamics and lineage relationships in the developing lacrimal gland", Development, The Company of Biologists, vol. 144, Issue 13, pp. 2517-2528, Accepted: May 31, 2017.
Feigenspan, et al., "Expression of Neuronal Connexin36 in All Amacrine Cells of the Mammalian Retina", The Journal of Neuroscience, vol. 21, Issue 1, pp. 230-239, Jan. 1, 2001.
Gao, et al., "Secondary structure effects on DNA hybridization kinetics: a solution versus surface comparison", Nucleic Acids Research, 2006, vol. 34, No. 11, pp. 3370-3377, Accepted: May 27, 2006.
Glatthar, et al., "A New Photocleavable Linker in Solid-Phase Chemistry for Ether Cleavage", Org. Lett. 2000, vol. 2, No. 15, pp. 2315-2317.
Greenfieldboyce, "Biological cartographers seek to map the trillions of cells in the human body", NPR, pp. 1-5, Jan. 5, 2019.
Greer, et al., "Linked read sequencing resolves complex genomic rearrangements in gastric cancer metastases", Genome Medicine, vol. 9, No. 57, pp. 1-17, 2017.
Gueroult, et al., "How Cations Can Assist DNase I in DNA Binding and Hydrolysis", PLoS Comput Biol., vol. 6, Issue 11:e1001000, pp. 1-11, Nov. 18, 2010.
Haber, et al., "A single-cell survey of the small intestinal epithelium", Nature, vol. 551, No. 7680, pp. 333-339, Nov. 16, 2017.
Hamady, et al., "Error-correcting barcoded primers for pyrosequencing hundreds of samples in multiplex", Nature Methods, vol. 5, No. 3, pp. 235-237, Mar. 2008.
Hamady, et al., "Microbial community profiling for human microbiome projects: Tools, techniques, and challenges", Genome Res., vol. 19, No. 7, pp. 1141-1152, ISSN 1088-9051/09, Jul. 2009.
He, et al., "High-resolution crystal structures reveal plasticity in the metal binding site of apurinic/apyrimidinic endonuclease I.", Biochemistry, vol. 53, No. 41, pp. 6520-6529, Published: Sep. 24, 2014.
Hoffmann, et al., "DNA bar coding and pyrosequencing to identify rare HIV drug resistance mutations", Nucleic Acids Res., vol. 35, No. 13, e91, pp. 1-8, Published online: Jun. 18, 2007.
Holmberg, et al., "The biotin-streptavidin interaction can be reversibly broken using water at elevated temperatures.", Electrophoresis, vol. 26, No. 3, pp. 501-510, Feb. 2005.
Islam, et al., "Quantitative single-cell RNA-seq with unique molecular identifiers", Nature Methods, , vol. 11, No. 2, pp. 163-166, Feb. 2014.
Kaiser, et al., "Huge trove of British biodata is unlocking secrets of depression, sexual orientation, and more", Science | AAAS, pp. 1-12, Jan. 3, 2019.

(56) References Cited

OTHER PUBLICATIONS

Kovall, et al., "Structural, functional, and evolutionary relationships between exonuclease and the type II restriction endonucleases", Proc Natl Acad Sci U S A., vol. 95, No. 14, pp. 7893-7897, Jul. 1998.

Kumaresan, et al., "High-Throughput Single Copy DNA Amplification and Cell Analysis in Engineered Nanoliter Droplets", Anal. Chem., vol. 80, No. 10, pp. 3522-3529, May 15, 2008.

Kutnjak, et al., "Calorimetric study of octylcyanobiphenyl liquid crystal confined to a controlled-pore glass.", Physical Review E, The American Physical Society, pp. 021705-1-021705-12, Published: Aug. 22, 2003.

Litosh, et al., "Improved nucleotide selectivity and termination of 3'-OH unblocked reversible terminators by molecular tuning of 2-nitrobenzyl alkylated HOMedU triphosphates.", Nucleic Acids Res., vol. 39, No. 6, pp. 1-13, Published online: Jan. 11, 2011.

Macosko, et al., "Highly Parallel Genome-Wide Expression Profiling of Individual Cells Using Nanoliter Droplets", Cell, vol. 161, No. 5, pp. 1202-1214, May 21, 2015.

Malone, et al., "Bringing Renal Biopsy Interpretation Into the Molecular Age With Single-Cell RNA Sequencing", Seminars in Nephrology, vol. 38, Issue 1, pp. 1-17, Author Manuscript; available in PMC: Jan. 1, 2019.

Margulies, et al., "Genome Sequencing in Open Microfabricated High Density Picoliter Reactors", Nature, vol. 437, No. 7057, pp. 376-380, Sep. 15, 2005.

McKenna, et al., "The Macaque Gut Microbiome in Health, Lentiviral Infection, and Chronic Enterocolitis", PLoS Pathog., vol. 4, Issue 2, e20, pp. 0001-0012, Feb. 8, 2008.

Metzker, "Emerging technologies in DNA sequencing.", Genome Res., vol. 15, No. 12, pp. 1767-1776, Dec. 2005.

Miller, et al., "Basic Concepts of Microarrays and Potential Applications in Clinical Microbiology", Clinical Microbiology Reviews, vol. 22, No. 4, pp. 611-633, Oct. 2009.

Mol, et al., "DNA-bound structures and mutants reveal abasic DNA binding by APE1 and DNA repair coordination.", Nature, vol. 403, No. 6768, pp. 451-456, Jan. 27, 2000.

Narasimhan, et al., "Health and population effects of rare gene knockouts in adult humans with related parents", Science, vol. 352, No. 6284, pp. 474-477, Apr. 22, 2016.

Nguyen, "Optical detection for droplet size control in microfluidic droplet-based analysis systems", Nguyen et al., Optical detection for droplet size control in microfluidic droplet-based analysis systems, 117 Sensors and Actuators B 117, pp. 431-436, Available online: Jan. 18, 2006.

Novak, et al., "Single cell multiplex gene detection and sequencing with microfluidically generated agarose emulsions", Angew. Chem. Int. Ed., pp. 1-11, 2010.

Novak, et al., "Single Cell Multiplex Gene Detection and Sequencing with Microfluidically Generated Agarose Emulsions", Agnew. Chem. Int. Ed., pp. 390-395, Jan. 10, 2011.

Pal, et al., "Construction of developmental lineage relationships in the mouse mammary gland by single-cell RNA profiling", Nature Communications, vol. 8, Article No. 1627, pp. 1-14, Nov. 20, 2017.

Parameswaran, et al., "A pyrosequencing-tailored nucleotide barcode design unveils opportunities for large-scale sample multiplexing", Nucleic Acids Res., vol. 35, No. 19, e130, pp. 1-9, Published online: Oct. 11, 2007.

Pennisi, "Development Cell by Cell", Science, vol. 362, Issue 6421, pp. 1344-1345, Dec. 21, 2018.

Perona, "Type II restriction endonucleases.", Methods, vol. 28, No. 3, pp. 353-364, Accepted: Jul. 30, 2002.

Peterson, et al., "The effect of surface probe density on DNA hybridization", Nucleic Acids Res., vol. 29, No. 24, pp. 5163-5168, Dec. 15, 2001.

Qi, et al., "Digital analysis of the expression levels of multiple colorectal cancer-related genes by multiplexed digital-PCR coupled with hydrogel bead-array.", Analyst, vol. 136, No. 11, pp. 2252-2259, Accepted: Mar. 11, 2011.

Final Office Action for U.S. Appl. No. 15/453,405, issued by the U.S. Patent Office dated Mar. 27, 2019, 17 pages.

"Online Methods", Nature Methods, vol. 11, No. 2, https://media.nature.com/original/natureassets/nmeth/journal/v11/n2/extref/nmeth.2772-S1 pdf, Dec. 2013, 21 pages.

The Broad Institute, Inc., Notice of Rejection for JP 2017-513231, dated Sep. 17, 2019, 12 pages.

Rothberg, et al., "An integrated semiconductor device enabling non-optical genome sequencing", Nature, vol. 475, pp. 348-352, Jul. 21, 2011.

Shimkus, et al., "A chemically cleavable biotinylated nucleotide: usefulness in the recovery of protein-DNA complexes from avidin affinity columns.", Proc Natl Acad Sci U S A., vol. 82, No. 9, pp. 2593-2597, May 1985.

Song, et al., "A Microfluidic System for Controlling Reaction Networks in Time", Angew. Chem. Int. Ed. 2003, vol. 42, No. 7, pp. 767-772.

Soumillon, et al., "Characterization of Directed Differentiation by High-Throughput Single-Cell RNA-Seq", BioRxiv, pp. 1-13, Preprint: Mar. 5, 2014.

Spies, et al., "Genome-wide reconstruction of complex structural variants using read clouds", Nat Methods, vol. 14, No. 9, pp. 915-920, Sep. 2017.

Stoeckius, et al., "Large-scale simultaneous measurement of epitopes and transcriptomes in single cells", Nature Methods, vol. 14, No. 9, pp. 865-868, Sep. 2017.

Taylor, et al., "A scalable high-throughput method for RNA-Seq analysis of thousands of single cells", illumina I Bio-Rad, 2016.

Tewhey, et al., "Microdroplet-based PCR enrichment for large-scale targeted sequencing", Nature Biotechnology, vol. 27, No. 11, pp. 1025-1031, Nov. 1, 2009.

The Broad Institute, Inc., "Communication Pursuant to Rule 164(2)(b) and Article 94(3) EPC", Jul. 11, 2018, 12 pages.

Tice, et al., "Formation of Droplets and Mixing in Multiphase Microfluidics at Low Values of the Reynolds and the Capillary Numbers", Langmuir, vol. 19, No. 22, pp. 9127-9132, Published on Web: Aug. 12, 2003.

Wilson, "Ape1 abasic endonuclease activity is regulated by magnesium and potassium concentrations and is robust on alternative DNA structures.", J Mol Biol., vol. 345, No. 5, pp. 1003-1014, Feb. 4, 2005.

Wu, et al., "Termination of DNA synthesis by N6-alkylated, not 3'-O-alkylated, photocleavable 2'-deoxyadenosine triphosphates", Nucleic Acids Res., vol. 35, No. 19, pp. 6339-6349, Sep. 18, 2007.

Yan, et al., "Intestinal enteroendocrine lineage cells possess homeostatic and injury-inducible stem cell activity", Cell Stem Cell, vol. 21, No. 1, pp. 78-90, Jul. 6, 2017.

Yan, et al., "Non-equivalence of Wnt and R-spondin ligands during Lgr5+ intestinal stem cell self-renewal", Nature, vol. 545, No. 7653, pp. 238-242, May 11, 2017.

Zhang, et al., "Massively Parallel Single-Molecule and Single-Cell Emulsion Reverse Transcription Polymerase Chain Reaction Using Agarose Droplet Microfluidics", Anal. Chem., vol. 84, No. 8, pp. 3599-3606, Published: Mar. 27, 2012.

Zheng, et al., "Massively parallel digital transcriptional profiling of single cells", Nature Communications, vol. 8, Article No. 14049, pp. 1-12, Published: Jan. 16, 2017.

Metzker, "Sequencing technologies—the next generation", Nature Reviews, Genetics, vol. 11, pp. 31-46, Published online: Dec. 8, 2009.

"Markman Order in re Certain Microfluidic Systems and Components Thereof and Products Containing Same", Docket Alarm, pp. 1-6, Oct. 31, 2018.

"Molecular and Genomics Core Facility Equipment", Molecular and Genomics Core Facility, pp. 1-7, 2018.

"N,N'-Methylenebis(acrylamide)", 146072 Sigma-Aldrich, CAS No. 110-26-9, 2018.

"Neuroscience 2017 Program", Society for Neuroscience, pp. 1-2, 2017.

"Notice of Intent to Certify Sole Source", Sole Source Certification No. SS5098 for Bio-Rad ddSeq Single Cell Isolation System and associated accessories, pp. 1-5, Jun. 5, 2017.

(56) References Cited

OTHER PUBLICATIONS

"Nucleic Acid Sample Preparation for Downstream Analyses", GE Healthcare Life Sciences Manual, pp. 1-168, 2009.
"Omniscript Reverse Transcription Handbook", Qiagen, pp. 1-32, Oct. 2010.
"Phosphate-buffered saline (PBS)", pdb.rec8247-, Cold Spring Harbor Protocols (2006).
"Powerful New Tool for Genome Analysis", Georgia Tech Bioinformatics, pp. 1-3, Nov. 14, 2017.
"Q Sepharose High Performance SP Sepharose High Performance", GE Healthcare, Data File 18-1172-88 AB, pp. 1-8, Apr. 2006.
"Research Highlights: Human Cell Atlas", Human Cell Atlas | Broad Institute, pp. 1-4, Jan. 8, 2019.
"Restriction Endonucleases Technical Guide", BioLabs Inc., pp. 1-24, Aug. 2015.
"Reverse Transcription Reaction Setup—Seven Important Considerations", ThermoFisher Scientific, pp. 1-15, 2018.
"Sequencing Power for Every Scale Systems for every application. For every lab.", Illumina, pp. 1-70, 2016.
"Single-Cell RNA Data Analysis Workflow RNA analysis from single cells using the Illumina Bio-Rad Single-Cell Sequencing Solution with the BaseSpace® SureCellTM RNA Single-Cell App.", illumina | Bio-Rad, pp. 1-4, 2017.
"Single-cell RNAseq (Biorad/Illumina ddSEQ)", UNC School of Medicine, pp. 1-3, 2018.
"SITC 2017 Scientific Highlights—Nov. 11", The Sentinel—The Official Blog of the Society for Immunotherapy of Cancer (SITC)., pp. 1-4, Nov. 12, 2017.
"SureCell WTA 3' Library Prep Kit Support, Questions & Answers", Illumina, pp. 1-4, 2019.
"SureCell WTA 3' Library Prep Kit for the ddSEQ System", Ilumina, pp. 1-6, 2019.
"The Illumina Bio-Rad Single Cell Sequencing Solution", illumina | Bio-Rad, pp. 1-3, 2018.
"The Illumina Bio-Rad Single-Cell Sequencing Solution Robust and scalable single-cell sequencing", illumina | BioRad, pp. 1-4, 2016.
"Top 10 Innovations 2015", The Scientist, pp. 1-12, Dec. 1, 2015.
"Transcriptor Reverse Transcriptase", Roche, Ver. 13, pp. 1-13, Jun. 2017.
"Types of Restriction Endonucleases", pp. 1-2, 2018.
U.S. Office Action issued in copending U.S. Appl. No. 15/453,405, filed Aug. 28, 2018, dated Aug. 28, 2018, 16 pages.
"University of Mississippi Medical Center, Molecular and Genomics Core Facility, Service Home", pp. 1-2, 2018.
"Genomics Resources Core Facility", Weill Cornell Medicine, pp. 1-5, 2018.
Abate, et al., "Beating Poisson encapsulation statistics using close-packed ordering", Lab Chip, vol. 9, pp. 2628-2631, Accepted: Jul. 24, 2009.
Adamson, et al., "A multiplexed single-cell CRISPR screening platform enables systematic dissection of the unfolded protein response", Cell., vol. 167, Issue 7, pp. 1867-18822, Dec. 15, 2016.
International Search Report and Written Opinion issued in International Application No. PCT/US2015/049178 dated Feb. 22, 2016, 18 pages.
Andersen, et al., "A Quantitative Study of the Human Cerebellum with Unbiased Stereological Techniques", The Journal of comparative neurology, vol. 326, Issue 4, pp. 549-560, Dec. 22, 1992.
Ascoli, et al., "Petilla Terminology: Nomenclature of Features of GABAergic Interneurons of the Cerebral Cortex", Nature reviews Neuroscience, vol. 9, pp. 557-568, Jul. 2008.
International Preliminary Report on Patentability issues in International Application No. PCT/US2015/049178 dated Mar. 23, 2017, 12 pages.
Barany, Francis, "Genetic Disease Detection and DNA Amplification Using Cloned Thermostable Ligase", PNAS, vol. 88, Issue 1, pp. 189-193, Jan. 1991.
Barany, Francis, "The Ligase Chain Reaction in a PCR World", PCR Methods and Applications, vol. 1, pp. 5-16, 1991.

Bar-Joseph, et al., "Genome-Wide Transcriptional Analysis of the Human Cell Cycle Identifies Genes Differentially Regulated in Normal and Cancer Cells", PNAS, vol. 105, Issue 3, pp. 955-960, Jan. 22, 2008.
Barres, et al., "Immunological, Morphological, and Electrophysiological Variation Among Retinal Ganglion Cells Purified by Panning", Neuron, vol. 1, Issue 9, pp. 791-803, Nov. 1988.
Beer, et al., "On-Chip Single-Copy Real-Time Reverse-Transcription PCR in Isolated Picoliter Droplets", Analytical Chemistry, vol. 80, Issue 6, pp. 1854-1858, Mar. 15, 2008.
Bentley, et al., "Accurate whole human genome sequencing using reversible terminator chemistry.", Nature, 456 (7218), pp. 53-59, Nov. 6, 2008.
Berman, et al., "Mapping the Stereotyped Behaviour of Free Moving Fruit Flies", Journal of the Royal Society Interface, vol. 11, Issue 99, 20140672, pp. 1-12, Aug. 20, 2014.
Binladen, et al., "The Use of Coded PCR Primers Enables High-Throughput Sequencing of Multiple Homolog Amplification Products by 454 Parallel Sequencing", PLoS One; vol. 2, Issue 2: e197, pp. 1-9, Feb. 14, 2007.
Bitinaite, et al., "USER™ friendly DNA engineering and cloning method by uracil excision", Nucleic Acids Res., vol. 35, No. 6, pp. 1992-2002, Publised online Mar. 6, 2007.
Black, Chris, "The ChromiumTM System: Linked Read and Single Cell RNA-Seq Applications Powered by GemCode Technology", 10X Genomics, pp. 1-57, Jul. 17, 2017.
Bochet, Christian G., "Photolabile protecting groups and linkers", J. Chem. Soc., Perkin Trans. 1, 2002,0, pp. 125-142, First published as an Advance Article on the Web: Dec. 13, 2001.
Brennecke, et al., "Accounting for Technical Noise in Single-Cell RNA-seq Experiments", Nature methods, vol. 10, Issue 11, 1093-1095, Sep. 22, 2013.
Bringer, et al., "Microfluidic Systems for Chemical Kinetics that Rely on Chaotic Mixing in Droplets", Philosophical Transactions of the Royal Society a Mathematical Physical and Engineering Sciences, vol. 362, Issue 1818, pp. 1087-1104, Jun. 2004.
Britten, et al., "Repeated Sequences in DNA. Hundreds of Thousands of DNA Sequences have been Incorporated into the Genomes of Higher Organisms", Science, vol. 161, Issue 3841, pp. 529-540, Aug. 9, 1968.
Brouzes, et al., "Droplet Microfluidic Technology for Single-Cell High-Throughput Screening", Proceedings of the National Academy of Sciences, vol. 106, No. 34, pp. 14195-14200, Aug. 25, 2009.
Brown, et al., "Chemical Synthesis and Cloning of a Tyrosine tRNA Gene", Methods in Enzymology, vol. 68, pp. 109-151, 1979.
Buettner, et al., "Computational Analysis of Cell-to-Cell Heterogeneity in Single-Cell RNA-Sequencing Data Reveals Hidden Subpopulations of Cells", Nature Biotechnology, vol. 33, Issue 2, pp. 155-160, Feb. 2015.
Macosko, et al., "Highly Parallel Genome-Wide Expression Profiling of Individual Cells Using Nanoliter Droplets", Cell, vol. 161, No. 5, May 21, 2015, 1202-1214.
Novak, et al., "Single Cell Multiplex Gene Detection and Sequencing with Microfluidically Generated Agarose Emulsions", Agnew. Chem. Int. Ed., 2011, pp. 390-395.
Shapiro, et al., "Single-Cell Sequencing-Based Technologies will Revolutionize Whole-Organism Science", Nature Reviews Genetics, vol. 14, No. 9, Jul. 30, 2013, 618-630.
Soumillon, et al., "Characterization of Directed Differentiation by High-Throughput Single-Cell RNA-Seq", BioRxiv Preprint, Mar. 5, 2014, 1-13.
Beer, et al., "On-Chip Single-Copy Real-Time Reverse-Transcription PCR in Isolated Picoliter Droplets", Analytical chemistry, vol. 80, Issue 6, Mar. 15, 2008, 1854-1858.
Berman, et al., "Mapping the Stereotyped Behaviour of Free Moving Fruit Flies", Journal of the Royal Society Interface, vol. 11, Issue 99, 20140672, Aug. 2014, 12 pages.
Brennecke, et al., "Accounting for Technical Noise in Single-Cell RNA-seq Experiments", Nature methods, vol. 10, Issue 11, Sep. 22, 2013, 1093-1095.
Bringer, et al., "Microfluidic Systems for Chemical Kinetics that Rely on Chaotic Mixing in Droplets", Philosophical Transactions of

(56) References Cited

OTHER PUBLICATIONS the Royal Society a Mathematical Physical and Engineering Sciences, vol. 362, Issue 1818, Jun. 2004, 1087-1104.
Brouzes, et al., "Droplet Microfluidic Technology for Single-Cell High-Throughput Screening", Proceedings of the National Academy of Sciences, vol. 106, No. 34, Aug. 25, 2009, 14195-14200.
Buettner, et al., "Computational Analysis of Cell-to-Cell Heterogeneity in Single-Cell RNA-Sequencing Data Reveals Hidden Subpopulations of Cells", Nature Biotechnology, vol. 33, Issue 2, Jan. 2015, 155-160.
Cheong, et al., "Rapid Preparation of RNA Samples Using DNA-Affinity Chromatography and DNAzyme Methods", Methods in molecular biology, vol. 941, 2012, 113-121.
Chung, et al., "Statistical Significance of Variables Driving Systematic Variation in High-Dimensional Data", Bioinformatics, vol. 31, No. 4, 2014, 545-554.
Edd, et al., "Controlled Encapsulation of Single Cells into Monodisperse Picoliter Drops", Lab Chip, vol. 8, Issue 8, Aug. 2008, 1262-1264.
Grun, et al., "Validation of Noise Models for Single-Cell Transcriptomics", Nature Methods, vol. 11, Issue 6, Jun. 2014, 637-640.
Guo, et al., "Droplet Microfluidics for High-throughput Biological Assays", Lab Chip, Issue 12, Feb. 9, 2012, 2146-2155.
Hashimshony, et al., "CEL-Seq: Single-Cell RNA-Seq by Multiplexed Linear Amplification", Cell Reports, vol. 2, Sep. 27, 2012, 666-673.
Hindson, et al., "High-Throughput Droplet Digital PCR System for Absolute Quantitation of DNA Copy Number", Analytical Chemistry, vol. 83, 2011, 8604-8610.
Islam, et al., "Highly Multiplexed and Strand-Specific Single-Cell RNA 5' end Sequencing", Nature protocols, vol. 7, Issue 5, Apr. 5, 2012, 813-828.
Islam, et al., "Quantitative Single-Cell RNA-seq with Unique Molecular Identifiers", Nature methods, vol. 11, Issue 2, 2014, 163-166.
Jaitin, et al., "Massively Parallel Single-Cell RNA-Seq for Marker-Free Decomposition of Tissues into Cell Types", Science, vol. 343, Issue 6172, Feb. 2014, 776-779.
Jarosz, et al., "Cross-Kingdom Chemical Communication Drives a Heritable, Mutually Beneficial Prion-based Transformations of Metabolism", Cell, vol. 158, Issue 5, Aug. 28, 2014, 1083-1093.
Kadonaga, et al., "Purification of Sequence-Specific DNA-Binding Proteins by Affinity Chromatography", Methods in enzymology, vol. 208, 1991, 10-23.
Kharchenko, et al., "Bayesian Approach to Single-Cell Differential Expression Analysis", Nature Methods, vol. 11, Issue 7, Jul. 2014, 740-742.
Kivioja, et al., "Counting Absolute Number of Molecules Using Unique Molecular Identifiers", Nature Methods, vol. 9, No. 1, Nov. 20, 2011, 72-74.
Kurimoto, et al., "An Improved Single-Cell cDNA Amplification Method for Efficient High-Density Oligonucleotide Microarray Analysis", Nucleic acids research, vol. 34, Issue 5, e42, 2006, 17 pages.
Mazutis, et al., "Single-Cell Analysis and Sorting using Droplet-Based Microfluidics", Nature Protocols, vol. 8, Issue 5, May 2013, 870-891.
McDonald, et al., "Fabrication of Microfluidic Systems in Poly(dimethylsiloxane)", Electrophoresis, vol. 21, Issue 1, Jan. 2000, 27-40.
Peres-Neto, et al., "How Many Principal Components? Stopping Rules for Determining the Number of Non-Trivial Axes Revisited", Computational Statistics and Data Analysis, vol. 49, Issue 4, Jun. 15, 2005, 974-997.
Picelli, et al., "Smart-Seq2 for Sensitive Full-Length Transcriptome Profiling in Single Cells", Nature methods, vol. 10, Issue 11, Nov. 2013, 1096-1098.

Pollen, et al., "Low-Coverage Single-Cell mRNA Sequencing Reveals Cellular Heterogeneity and Activated Signaling Pathways in Developing Cerebral Cortex", Nature Biotechnology, vol. 32, Issue 10, Aug. 2014, 47 pages.
Ryan, et al., "Single-Cell Assays", Biomicrofluidics, vol. 5, 021501, 2011, 9 pages.
Shalek, et al., "Single-Cell RNA-Seq Reveals Dynamic Paracrine Control of Cellular Variation", Nature, vol. 510, Jun. 19, 2014, 363-369.
Shalek, et al., "Single-cell transcriptomics reveals bimodality in expression and splicing in immune cells", Nature, 498 (7453), 2013, pp. 236-240.
Shekhar, et al., "Automatic Classification of Cellular Expression by Nonlinear Stochastic Embedding (ACCENSE)", Proceedings of the National Academy of Sciences of the United States of America, vol. 111, Issue 1, Jan. 7, 2014, 202-207.
Srivastava, et al., "RNA Synthesis: Phosphoramidites for RNA Synthesis in the Reverse Direction. Highly Efficient Synthesis and Application to Convenient Introduction of Ligands, Chromophores and Modifications of Synthetic RNA al the 3'-end", Nucleic acids symposium series, vol. 52, 2008, 103-104.
Tang, et al., "Mma-Seq WholeTranscriptome Analysis of a Single Cell", Nature Methods, vol. 6, No. 5, May 2009, 377-382.
The Broad Institute, Inc., "Communication Pursuant to Rule 164(2)(b) and Article 94(3) EPC for EP 15767655.2", dated Jul. 11, 2018, 12 pages.
Thorsen, et al., "Dynamic Pattern Formation in a Vesicle-Generating Microfluidic Device", Physical review letters, vol. 86, No. 18, Apr. 30, 2001, 4163-4166.
Umbanhowar, et al., "Monodisperse Emulsion Generation via Drop Break Off in a Coflowing Stream", Langmuir, vol. 16, No. 2, 2000, 347-351.
Utada, et al., "Dripping to Jetting Transitions in Coflowing Liquid Streams", Physical review letters, vol. 99, Issue 9, Aug. 31, 2007, 094502, 4 pages.
Van der Maaten, et al., "Visualizing Data using t-SNE", Journal of Machine Learning Research, vol. 9, 2008, 2579-2605.
Vogelstein, et al., "Digital PCR", PNAS, vol. 96, Aug. 1999, 9236-9241.
White, et al., "High-Throughput Microfluidic Single-Cell RTqPCR", PNAS, vol. 108, No. 34, Aug. 23, 2011, 13999-14004.
Zhu, et al., "Reverse Transcriptase Template Switching: a SMART Approach for Full-Length eDNA Library Construction", BioTechniques, vol. 30, No. 4, Apr. 2001, 892-897.
Shapiro, et al., "Single-Cell Sequencing-Based Technologies will Revolutionize Whole-Organism Science," Nature Reviews Genetics, vol. 14, No. 9, pp. 618-630, Jul. 30, 2013.
The Broad Institute, Inc., International Preliminary Reporton Patentability issues in International Application No. PCT/US2015/049178, dated Mar. 23, 2017, 12 pages.
The Broad Institute, Inc., "Communication pursuant to Article 94(3) EPC for EP 15767655.2", dated Jan. 21, 2020, 4 pages.
The Broad Institute, Inc., "Notice of Rejection for JP 2017-513231", dated Jun. 2, 2020, 10 pages.
"2017 Top 10 Innovations", 2017 Top 10 Innovations, The Scientist, pp. 1-11, Dec. 1, 2017.
"Acrylamide Product Information Sheet", Sigma Aldrich 1996 Product Information Sheet, A8887, pp. 1-2, 1996.
"American Cell Biology Meeting Program 2017", The 2017 ASCB EMBO Meeting, pp. 1-198, Dec. 2017.
"An Introduction to Linked-Read Technology for a More Comprehensive Genome and Exome Analysis", 10X Genomics Technical Note, pp. 1-5, 2016.
Bio-Rad and Illumina to Co-Develop Comprehensive Solution for Single-Cell Genomics, "Scalable, High-Throughput Platform to Offer Unprecedented Insight into Gene Expression of Individual Cells," Bio-Rad Newsroom, pp. 1-2, Jan. 11, 2016.
"Bio-Rad ddSEQ Single-Cell Isolator Instruction Manual", Bio-Rad, Catalog #12004336, pp. 1-24, 2017.
"Bio-Rad Laboratories, Inc. Form 10-K for the year ended Dec. 31, 2016", pp. 1-92.
"Bio-Rad Life Science Research Product Catalog", Bio-Rad Life Science Research 2017 Product Catalog, pp. 1-500, 2017.

(56) References Cited

OTHER PUBLICATIONS

"Boston Medical Center/ Boston University School of Medicine Department of Medicine Newsletter", pp. 1-20, 2017.
"Cancer Moonshot", National Cancer Institute, pp. 1-4, Jan. 8, 2019.
"ChromiumTM Genome Reagent Kits v2 User Guide," Multiplex Kit, 96 rxns, PN-120262, 10X Genomics, pp. 1-71, 2016.
"ChromiumTM Single Cell 3' Reagent Kits Quick Reference Cards", ChromiumTM Single Cell 3' Chip Kit PN-120232, 10X Genomics, pp. 1-10, 2016.
"ChromiumTM Chromium Single Cell 3' Reagent Kits Safety Data Sheets", ChromiumTM Single Cell 3' Gel Bead Kit PN-120231, 10X Genomics, pp. 1-10, Jul. 11, 2016.
"ChromiumTM Chromium Single Cell 3' Reagent Kits v2 Safety Data Sheets," Chromium Single Cell 3' Gel Bead Kit v2, 16 runs, PN-120235, 10X Genomics, pp. 1-10, Oct. 7, 2016.
"Chromium Single Cell 3' Reagent Kits v3 with Feature Barcoding technology for CRISPR Screening", Chromium Single Cell 3' GEM, Library & Gel Bead Kit v3, 4 rxns PN-1000092, 10X Genomics, pp. 1-70, CG000184 | Rev A, 2018.
"ChromiumTM Single Cell 3' Reagent Kits v2 Quick Reference Cards," ChromiumTM Single Cell 3' Library & Gel Bead Kit, 4 rxns PN-120267, 10X Genomics, CG000075 | RevC, pp. 1-10, 2017.
"ChromiumTM Single Cell 3' Reagent Kits Safety Data Sheets," ChromiumTM Single Cell 3' Library Kit, 10X Genomics, PN-120230, pp. 1-139, May 25, 2016.
"ChromiumTM Single Cell 3' Reagent Kits v2 Safety Data Sheets," ChromiumTM Single Cell 3' Library Kit v2 16 rxns, PN-120234, 10X Genomics, pp. 1-121, Oct. 7, 2016.
"Chromium Single Cell 3' Reagent Kits v2 User Guide," Chromium Single Cell 3' Library & Gel Bead Kit v2, 16 rxns PN-120237, 10X Genomics, pp. 1-74, 2018.
"ChromiumTM Single Cell V(D)J Reagent Kits User Guide," ChromiumTM Single Cell 5' Library & Gel Bead Kit, 16 rxns PN-1000006, 10X Genomics, pp. 1-73, 2017.
"Chromium Single Cell 3' Reagent Kits v2 User Guide", Chromium Single Cell a Chip Kit, 16 rxns PN-1000009, 10X Genomics, pp. 1-74, CG00052 | RevE, 2018.
"Chromium Single Cell 3' Reagent Kits v2 Safety Data Sheets, Chromium Single Cell a Chip Kit, 48 runs", 10X Genomics, PN-120236, Oct. 6, 2016.
"Chromium Single Cell ATAC Reagent Kits," Chromium Single Cell ATAC Library & Gel Bead Kit, 16 rxns PN-1000110, 10X Genomics, CG000168 | Rev A, pp. 1-47, 2018.
"Chromium Single Cell DNA Reagent Kits", Chromium Single Cell DNA Library & Gel Bead Kit, 16 rxns PN-1000040, 10X Genomics, CG000153 | Rev B, pp. 1-65, 2018.
"ChromiumTM Controller Training Kit User Guide", 10X Genomics, CG00021 | Rev B, pp. 1-27, (Product ID 120244), 2016.
"ChromiumTM Training Kits Safety Data Sheets", ChromiumTM Training Reagents and Gel Bead Kit, 10X Genomics, PN-120238, Rev A, pp. 1-33, May 24, 2016.
"DdSEQ™ Cartridge Holder", Bio-Rad ddSEQ™ Cartridge Holder #12004739, 2016.
"DdSEQ™ Single-Cell Isolator—Accessories", ddSEQ™ Single-Cell Isolator—Accessories—Bio-Rad, pp. 1-2, 2016.
"DdSEQ™ Single-Cell Isolator—Ordering", ddSEQ™ Single-Cell Isolator Bio-Rad, 2016.
"DdSEQ™ Single-Cell Isolator by Bio-Rad", Bio-Rad, pp. 1-8, Select Science, 2019.
"DdSEQ™ Single-Cell Isolator by Bio-Rad", ddSEQ™ Single-Cell Isolator, Bio-Rad, pp. 1-2, 2016.
"DdSEQ™ Test Cartridges", Bio-Rad ddSEQ™ Test Cartridges #12003862, 2016.
"Deoxyribonuclease I from bovine pancreas", Sigma-Aldrich Deoxyribonuclease I from bovine pancreas, CAS No. 9003-98-9, 2018.
"DNase I (RNase-free)", New England Biolabs, Inc. (NEB), pp. 1-6, 2018.
"DTT 1,4-Dithiothreitol", Sigma-Aldrich, CAS No. 3483-12-3, pp. 1-4, 2015.
Office Action issued by the European Patent Office in Application No. 15767655.2 dated Apr. 17, 2018, 4 pages.
Office Action issued by the European Patent Office in Application No. 15767655.2 dated Jul. 11, 2018, 12 pages.
Banga, J.P., "SDS-Polyacrylamide Gel Electrophoresis (SDS-PAGE)", Encyclopedia of Immunology ISBN:0-12-226765-6, pp. 2143-2144, 1998.
"Generation of Human Tumor Atlases—Cancer Moonshot Recommendation", National Cancer Institute, pp. 1-4, Jan. 8, 2019.
"Genome Analysis Core", pp. 1-2, Georgia Institute of Technology, 2019.
"Georgia Tech—Shared User Management System", pp. 1-12, Georgia Institute of Technology, 2015.
"Hydrophobic Interaction Chromatography", Amersham Pharmacia Biotech 2000, Edition AB, pp. 1-104, ISBN 91-970490-4-2, 2000.
"Illumina and Bio-Rad Launch Solution for Single-Cell Genomic Sequencing to Enable Robust Study of Complex Diseases", Bio-Rad, pp. 1-2, Jan. 9, 2017.
"Illumina and Bio-Rad Launch Solution for Single-Cell Genomic Sequencing to Enable Robust Study of Complex Diseases", 69th AACC Annual Scientific Meeting Press Program, Article ID: 678428, pp. 1-6, Jul. 25, 2017.
"Illumina Bio-Rad SureCell WTA 3' Library Prep Reference Guide", Illumina, Document # 1000000021452 v01, pp. 1-53, Jun. 2017.
"Illumina SureCell WTA 3' Checklist", Illumina, Document# 1000000021454 v00, pp. 1-6, Feb. 2017.
"Illumina® | Bio-Rad® Single Cell Sequencing", illumina I Bio-Rad, pp. 1-37, 2015.
"Illumina® Bio-Rad® SureCellTM WTA 3' Library Prep Kit for the ddSEQTM System", illumina I Bio-Rad, pp. 1-4, 2015.
"Infoporte—Cores", Infoporte | Version: 7.1.1 | © 2019 The University of North Carolina at Chapel Hill.
"The Instrument—Chromium Controller Compatible Solutions", 10X Genomics, pp. 1-7, 2019.
The Broad Institute, Inc., "Notification of the First Office Action for CN 2015800607182", dated Sep. 23, 2020, 14 pages.
The Broad Institute, Inc., "Decision of Rejection for JP 2017-513231", dated Jan. 12, 2021, 8 pages.
The Broad Institute, Inc., "Office Action for Canadian Patent Application No. 2,997,906", dated Oct. 4, 2021, 4 pages.
The Broad Institute, Inc., "Summons to attend oral proceedings pursuant to Rule 115(1) EPC for European Patent Application No. 15767655.2", May 21, 2021, 8 pages.
The Broad Institute, Inc., "Notification of Second Office Action for Chinese Patent Application No. 2015800607182", Oct. 8, 2021, 13 pages.
The Broad Institute, Inc., "Notice of Reasons for Rejection for JP 2021-080271", dated Jun. 21, 2022, 13 pages.
Evan et al., "Highly Parallel Genome-wide Expression Profiling of Individual Cells Using Nanoliter Droplets,Cell," May 21, 2015, Supplemental Information, 33 pages.

* cited by examiner

Drop-Seq

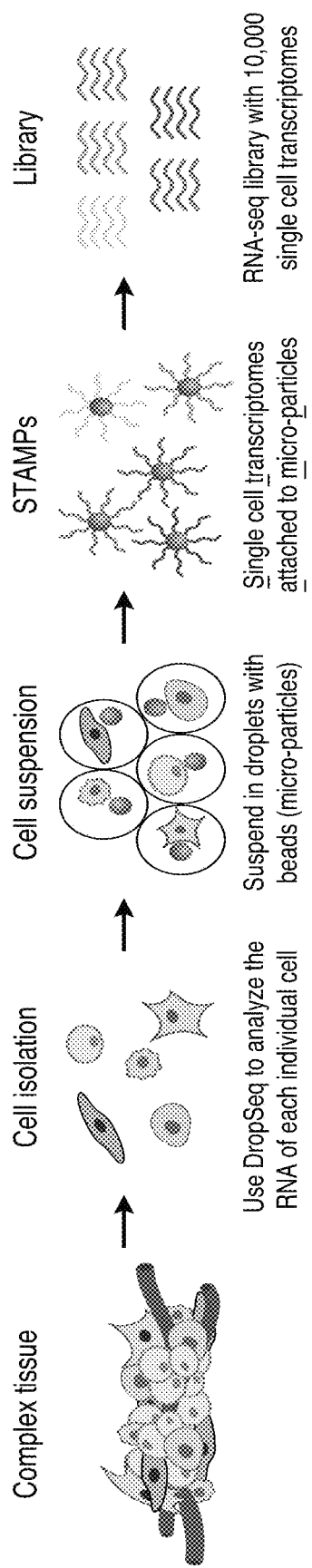
FIG. 7A
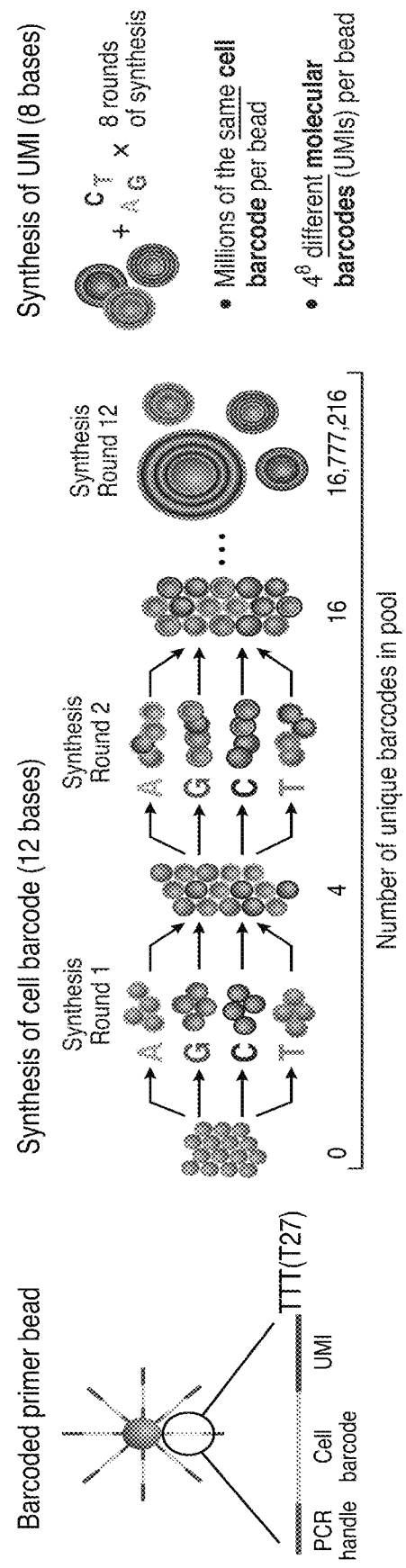
FIG. 7B
FIG. 7C
FIG. 7D

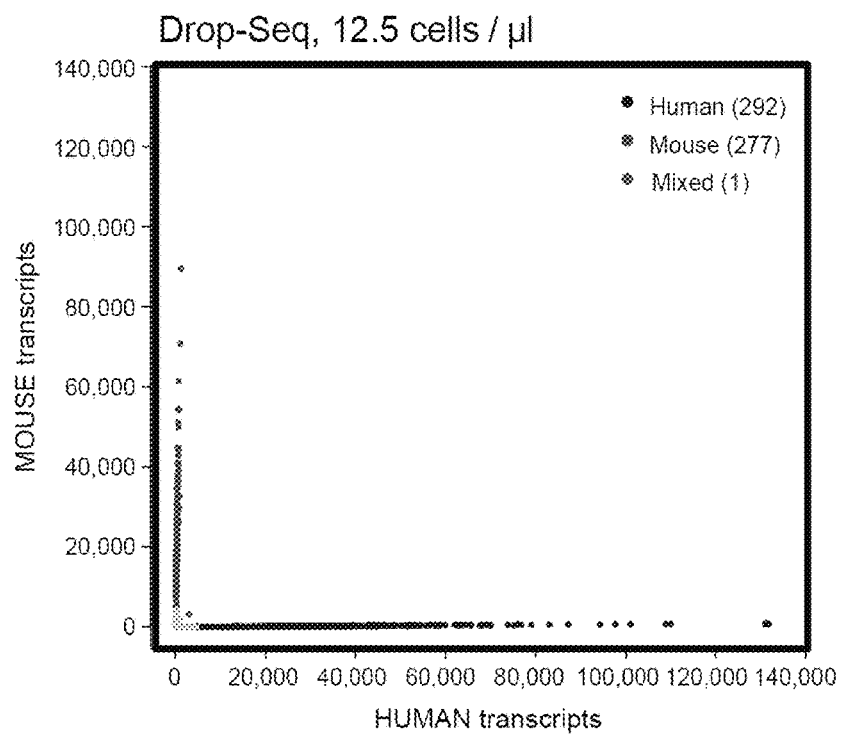
FIG. 9D
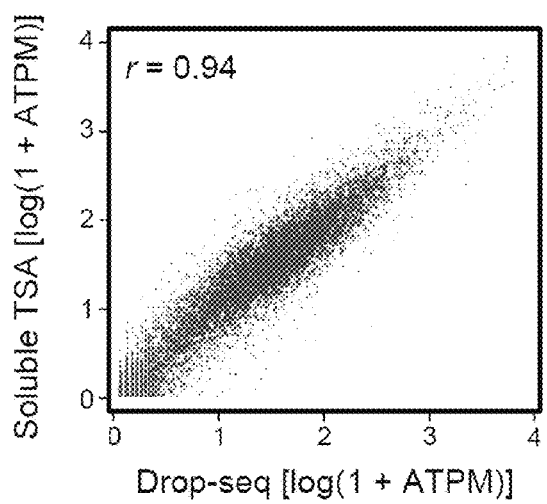 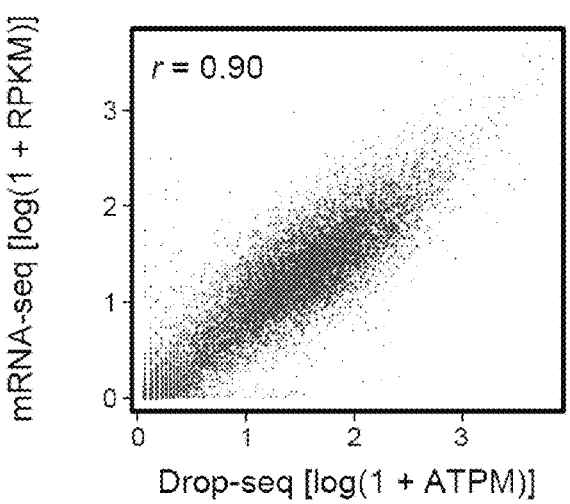
FIG. 9E          FIG. 9F

| Classic cell cycle genes | | Novel, conserved cell cycle genes | |
|---|---|---|---|
| CCNB1 | MCM6 | ATF4 | OTUB1 |
| CCNB2 | MCM7 | ARHGAP11A | PARPBP |
| MCM2 | MCM10 | ARPC2 | RPL26 |
| MCM3 | AURKA | CDCA4 | SNHG3 |
| MCM4 | AURKB | E2F7 | SRP9 |
| MCM5 | | HISTH1E | TCF19 |
| | | MCMBP | WDHD1 |
| | | NCAPG | ZFHX4 |
| | | NXT1 | |
FIG. 10C
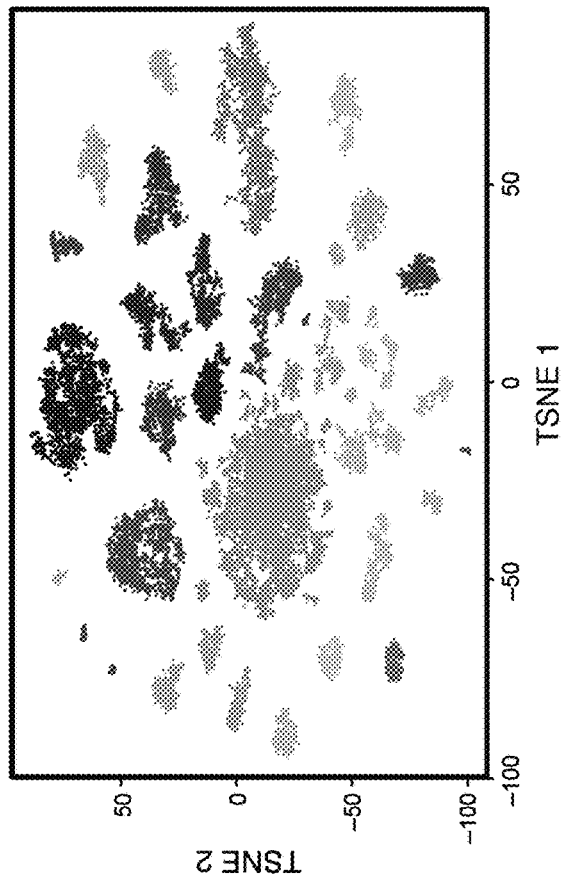
FIG. 11B
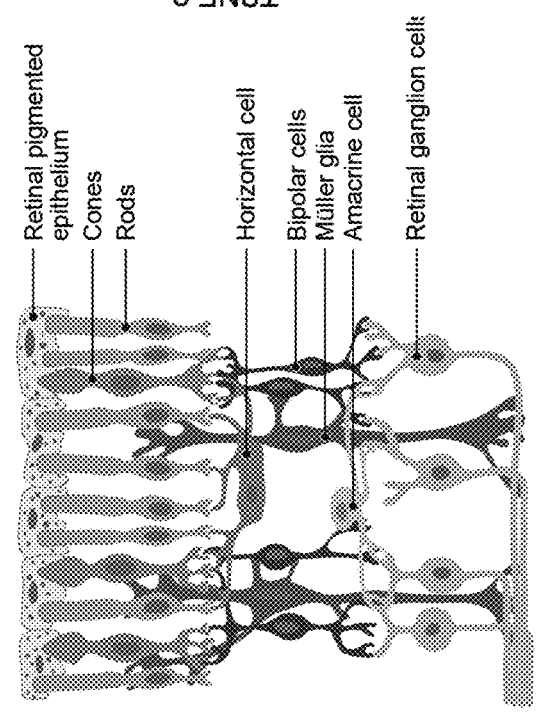
FIG. 11A

DROPLET-BASED METHOD AND APPARATUS FOR COMPOSITE SINGLE-CELL NUCLEIC ACID ANALYSIS

RELATED APPLICATIONS AND INCORPORATION BY REFERENCE

This application is a divisional of prior U.S. patent application Ser. No. 15/453,405 filed Mar. 8, 2017, which is a continuation-in-part of International Application No. PCT/US15/49178, filed Sep. 9, 2015 and which claims the benefit of U.S. Provisional Application Nos. 62/048,227 filed Sep. 9, 2014, and 62/146,642 filed Apr. 13, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created Mar. 6, 2017 is named 480092041_SL.txt and is 17.492 bytes in size.

FEDERAL FUNDING LEGEND

This invention was made with government support under Grant No. HG006193 awarded by the National Institutes of Health. The government has certain rights to the invention.

FIELD OF THE INVENTION

The present invention generally relates to a combination of molecular barcoding and emulsion-based microfluidics to isolate, lyse, barcode, and prepare nucleic acids from individual cells in a high-throughput manner.

BACKGROUND OF THE INVENTION

Cells come in different types, sub-types and activity states, which Applicants classify based on their shape, location, function, or molecular profiles, such as the set of RNAs that they express. RNA profiling is in principle particularly informative, as cells express thousands of different RNAs. Approaches that measure for example the level of every type of RNA have until recently been applied to "homogenized" samples—in which the contents of all the cells are mixed together. This has greatly limited our ability to use such techniques to understand human tissue function and pathology, for example in the brain. In the past two years, new technologies have begun emerging to conduct such measurements in single cells, but they are not yet scalable to large numbers of cells, and are very costly. Here, Applicants develop a method to profile the RNA content of tens and hundreds of thousands of individual human cells, including from brain tissues, quickly and inexpensively. To do so, Applicants use special microfluidic devices to encapsulate each cell in an individual drop, associate the RNA of each cell with a 'cell barcode' unique to that cell/drop, measure the expression level of each RNA with sequencing, and then use the cell barcodes to determine which cell each RNA molecule came from. Applicants can use this approach to better understand almost any biological sample; it is particularly important for understanding samples from any complex tissue, for example the retina.

Performing studies that require data resolution at the single cell (or single molecule) level can be challenging or cost prohibitive under the best circumstances. Although techniques or instruments for single molecule or single cell analysis exist (e.g., digital polymerase chain reactions (PCR) or Fluidigm C1, respectively), none currently allows a scalable method for dynamically delivering reagents and/or appending molecular "information" to individual reactions such that a large population of reactions/assays can be processed and analyzed en masse while still maintaining the ability to partition results by individual reactions/assays.

Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Citation or identification of any document in this application is not an admission that such document is available as prior art to the present invention.

SUMMARY OF THE INVENTION

The invention particularly relates to a combination of molecular barcoding and emulsion-based microfluidics to isolate, lyse, barcode, and prepare nucleic acids from individual cells in a high-throughput manner.

The invention provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

The invention provides a method for creating a single-cell sequencing library comprising: merging one uniquely barcoded mRNA capture microbead with a single-cell in an emulsion droplet having a diameter of 75-125 µm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library.

The invention provides a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique barcodes on the surface of each bead in the pool. (See www.ncbi.nlm.nih.gov/pmc/articles/PMC206447).

Generally, the invention provides a method for preparing a large number of beads, particles, microbeads, nanoparticles, or the like with unique nucleic acid barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorially large number of distinct nucleic acid barcodes. Invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Previous and well-known methods synthesize the oligonucleotides separately then "glue" the entire desired sequence onto the bead enzymatically. Applicants present a complexed bead and a novel process for producing these beads where nucleotides are chemically built onto the bead material in a high-throughput manner. Moreover, Applicants generally describe delivering a "packet" of beads which allows one to deliver millions of sequences into separate compartments and then screen all at once.

The invention further provides an apparatus for creating a single-cell sequencing library via a microfluidic system, comprising: a oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 7 A-D illustrate molecular barcoding of cellular transcriptomes in droplets.

DETAILED DESCRIPTION OF THE INVENTION

Figure 1:
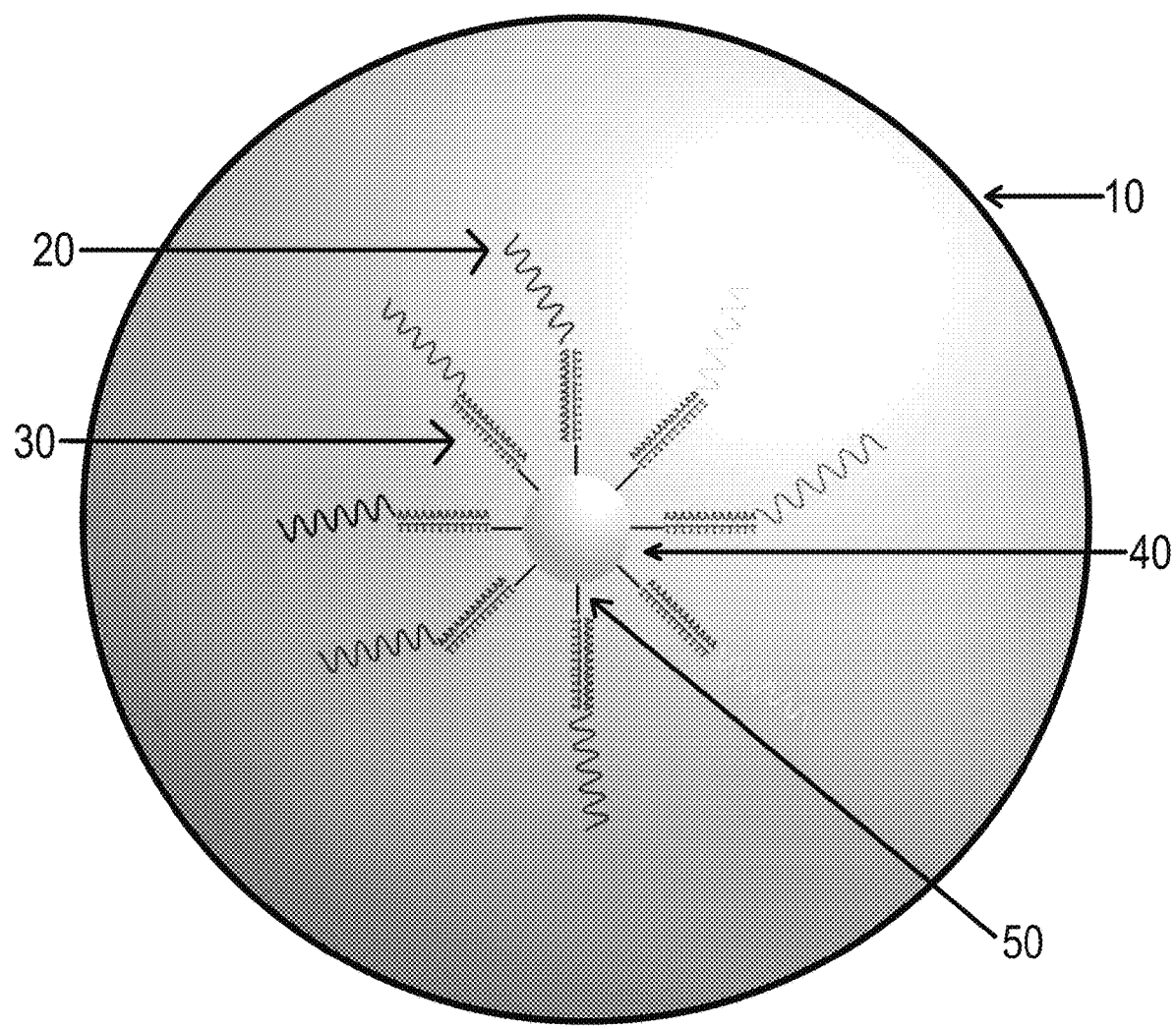
FIG. 1 illustrates a microfluidic droplet according to an exemplary disclosed embodiment.

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

The invention provides a nucleotide- or oligonucleotide-adorned bead wherein said bead comprises: a linker; an identical sequence for use as a sequencing priming site; a uniform or near-uniform nucleotide or oligonucleotide sequence; a Unique Molecular Identifier which differs for each priming site; optionally an oligonucleotide redundant sequence for capturing polyadenylated mRNAs and priming reverse transcription; and optionally at least one other oligonucleotide barcode which provides an additional substrate for identification.

In an embodiment of the invention, the nucleotide or oligonucleotide sequences on the surface of the bead is a molecular barcode. In an further embodiment the barcode ranges from 4 to 1000 nucleotides in length. In another embodiment, the oligonucleotide sequence for capturing polyadenylated mRNAs and priming reverse transcription is an oligo dT sequence.

In an embodiment of the invention, the linker is a non-cleavable, straight-chain polymer. In another embodiment, the linker is a chemically-cleavable, straight-chain polymer. In a further embodiment, the linker is a non-cleavable, optionally substituted hydrocarbon polymer. In another embodiment, the linker is a photolabile optionally substituted hydrocarbon polymer. In another embodiment, the linker is a polyethylene glycol. In another embodiment, the linker is a PEG-$C_3$ to PEG-$_{24}$.

The invention provides a mixture comprising a plurality of nucleotide- or oligonucleotide-adorned beads, wherein said beads comprises: a linker; an identical sequence for use as a sequencing priming site; a uniform or near-uniform nucleotide or oligonucleotide sequence; a Unique Molecular Identifier which differs for each priming site; an oligonucleotide redundant sequence for capturing polyadenylated mRNAs and priming reverse transcription; and optionally at least one additional oligonucleotide sequences, which provide substrates for downstream molecular-biological reactions; wherein the uniform or near-uniform nucleotide or oligonucleotide sequence is the same across all the priming sites on any one bead, but varies among the oligonucleotides on an individual bead.

In an embodiment of the invention, the nucleotide or oligonucleotide sequence on the surface of the bead is a molecular barcode. In an further embodiment the barcode ranges from 4 to 1000 nucleotides in length. In another embodiment, the oligonucleotide sequence for capturing polyadenylated mRNAs and priming reverse transcription is an oligo dT sequence.

In an embodiment of the invention, the mixture comprises at least one oligonucleotide sequences, which provide for substrates for downstream molecular-biological reactions. In another embodiment, the downstream molecular biological reactions are for reverse transcription of mature mRNAs; capturing specific portions of the transcriptome, priming for DNA polymerases and/or similar enzymes; or priming throughout the transcriptome or genome. In an embodiment of the invention, the additional oligonucleotide sequence comprises a oligo-dT sequence. In another embodiment of the invention, the additional oligonucleotide sequence comprises a primer sequence. In an embodiment of the invention, the additional oligonucleotide sequence comprises a oligo-dT sequence and a primer sequence.

The invention provides an error-correcting barcode bead wherein said bead comprises: a linker; an identical sequence for use as a sequencing priming site; a uniform or near-uniform nucleotide or oligonucleotide sequence which comprises at least a nucleotide base duplicate; a Unique Molecular Identifier which differs for each priming site; and an an oligonucleotide redundant for capturing polyadenylated mRNAs and priming reverse transcription.

In an embodiment of the invention, the error-correcting barcode beads fail to hybridize to the mRNA thereby failing to undergo reverse transcription.

The invention also provides a kit which comprises a mixture of oligonucleotide bound beads and self-correcting barcode beads.

The invention provides a method for creating a single-cell sequencing library comprising: merging one uniquely barcoded RNA capture microbead with a single-cell in an emulsion droplet having a diameter from 50 µm to 210 µm; lysing the cell thereby capturing the RNA on the RNA capture microbead; breaking droplets and pooling beads in solution; performing a reverse transcription reaction to convert the cells' RNA to first strand cDNA that is covalently linked to the RNA capture microbead; or conversely reverse transcribing within droplets and thereafter breaking droplets and collecting cDNA-attached beads; preparing and sequencing a single composite RNA-Seq library, containing cell barcodes that record the cell-of-origin of each RNA, and molecular barcodes that distinguish among RNAs from the same cell.

In an embodiment the diameter of the emulsion droplet is between 50-210 µm. In a further embodiment, the method wherein the diameter of the mRNA capture microbeads is from 10 µm to 95 µm. In a further embodiment the diameter of the emulsion droplet is 125 µm.

The invention provides a method for preparing a plurality of beads with unique nucleic acid sequence comprising: performing polynucleotide synthesis on the surface of the plurality of beads in a pool-and-split process, such that in each cycle of synthesis the beads are split into a plurality of subsets wherein each subset is subjected to different chemical reactions; repeating the pool-and-split process from anywhere from 2 cycles to 200 cycles.

In an embodiment of the invention the polynucleotide synthesis is phosphoramidite synthesis. In another embodiment of the invention the polynucleotide synthesis is reverse direction phosphoramidite chemistry. In an embodiment of the invention, each subset is subjected to a different nucleotide. In another embodiment, each subset is subjected to a different canonical nucleotide. In an embodiment of the invention the method is repeated three, four, or twelve times.

In an embodiment the covalent bond is polyethylene glycol. In another embodiment the diameter of the mRNA capture microbeads is from 10 µm to 95 µm. In an embodiment, wherein the multiple steps is twelve steps.

In a further embodiment the method further comprises a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A); 2) repeating this process a large number of times, at least six, and optimally more than twelve, such that, in the latter, there are more than 16 million unique barcodes on the surface of each bead in the pool.

In an embodiment, the diameter of the mRNA capture microbeads is from 10 µm to 95 µm.

The invention provides a method for simultaneously preparing a plurality of nucleotide- or oligonucleotide-adorned beads wherein a uniform, near-uniform, or patterned nucleotide or oligonucleotide sequence is synthesized upon any individual bead while vast numbers of different nucleotide or oligonucleotide sequences are simultaneously synthesized on different beads, comprising: forming a mixture comprising a plurality of beads; separating the beads into subsets; extending the nucleotide or oligonucleotide sequence on the surface of the beads by adding an individual nucleotide via chemical synthesis; pooling the subsets of beads in (c) into a single common pool; repeating steps (b), (c) and (d) multiple times to produce a combinatorially a thousand or more nucleotide or oligonucleotide sequences; and collecting the nucleotide- or oligonucleotide-adorned beads.

In an embodiment of the invention, the nucleotide or oligonucleotide sequence on the surface of the bead is a molecular barcode. In a further embodiment, the pool-and-split synthesis steps occur every 2-10 cycles, rather than every cycle.

In an embodiment of the invention, the barcode contains built-in error correction. In another embodiment, the barcode ranges from 4 to 1000 nucleotides in length. In embodiment of the invention the polynucleotide synthesis is phosphoramidite synthesis. In a further embodiment, the polynucleotide synthesis is reverse direction phosphoramidite chemistry. In an embodiment of the invention each subset is subjected to a different nucleotide. In a further embodiment, one or more subsets receive a cocktail of two nucleotides. In an embodiment, each subset is subjected to a different canonical nucleotide.

The method provided by the invention contemplates a variety of embodiments wherein the bead is a microbead, a nanoparticle, or a macrobead. Similarly, the invention contemplates that the oligonucleotide sequence is a dinucleotide or trinucleotide.

The invention provides a method for simultaneously preparing a thousand or more nucleotide- or oligonucleotide-adorned beads wherein a uniform or near-uniform nucleotide or oligonucleotide sequence is synthesized upon any individual bead while a plurality of different nucleotide or oligonucleotide sequences are simultaneously synthesized on different beads, comprising: forming a mixture comprising a plurality of beads; separating the beads into subsets; extending the nucleotide or oligonucleotide sequence on the surface of the beads by adding an individual nucleotide via chemical synthesis; pooling the subsets of beads in (c) into a single common pool; repeating steps (b), (c) and (d) multiple times to produce a combinatorially large number of nucleotide or oligonucleotide sequences; and collecting the nucleotide- or oligonucleotide-adorned beads; performing polynucleotide synthesis on the surface of the plurality of beads in a pool-and-split synthesis, such that in each cycle of synthesis the beads are split into a plurality of subsets wherein each subset is subjected to different chemical reactions; repeating the pool-and-split synthesis multiple times.

In an embodiment of the invention, the nucleotide or oligonucleotide sequence on the surface of the bead is a molecular barcode. In an embodiment, the pool-and-split synthesis steps occur every 2 to 10 cycles, rather than every cycle. In an embodiment, the generated barcode contains built-in error correction. In another embodiment, the barcode ranges from 4 to 1000 nucleotides in length. In embodiment of the invention the polynucleotide synthesis is phosphoramidite synthesis. In a further embodiment, the polynucleotide synthesis is reverse direction phosphoramidite chemistry. In an embodiment of the invention each subset is subjected to a different nucleotide. In a further embodiment, one or more subsets receive a cocktail of two nucleotides. In an embodiment, each subset is subjected to a different canonical nucleotide.

The method provided by the invention contemplates a variety of embodiments wherein the bead is a microbead, a nanoparticle, or a macrobead. Similarly, the invention contemplates that the oligonucleotide sequence is a dinucleotide or trinucleotide.

The invention further provides an apparatus for creating a composite single-cell sequencing library via a microfluidic system, comprising: an oil-surfactant inlet comprising a filter and two carrier fluid channels, wherein said carrier fluid channel further comprises a resistor; an inlet for an analyte comprising a filter and two carrier fluid channels, wherein said carrier fluid channel further comprises a resistor; an inlet for mRNA capture microbeads and lysis reagent comprising a carrier fluid channel; said carrier fluid channels have a carrier fluid flowing therein at an adjustable and predetermined flow rate; wherein each said carrier fluid channels merge at a junction; and said junction being connected to a constriction for droplet pinch-off followed by a mixer, which connects to an outlet for drops.

In an embodiment of the apparatus, the analyte comprises a chemical reagent, a genetically perturbed cell, a protein, a drug, an antibody, an enzyme, a nucleic acid, an organelle like the mitochondrion or nucleus, a cell or any combination thereof. In an embodiment of the apparatus the analyte is a cell. In a further embodiment, the analyte is a mammalian cell. In another embodiment, the analyte of the apparatus is complex tissue. In a further embodiment, the cell is a brain cell. In an embodiment of the invention, the cell is a retina cell. In another embodiment the cell is a human bone marrow cell. In an embodiment, the cell is a host-pathogen cell.

In an embodiment of the apparatus the lysis reagent comprises an anionic surfactant such as sodium lauroyl sarcosinate, or a chaotropic salt such as guanidinium thiocyanate. In an embodiment of the apparatus the filter is consists of square PDMS posts; the filter on the cell channel consists of such posts with sides ranging between 125-135 µm with a separation of 70-100 mm between the posts. The filter on the oil-surfactant inlet comprises square posts of two sizes; one with sides ranging between 75-100 µm and a separation of 25-30 µm between them and the other with sides ranging between 40-50 µm and a separation of 10-15 µm. In an embodiment of the apparatus the resistor is serpentine having a length of 7000-9000 µm, width of 50-75 µm and depth of 100-150 mm. In an embodiment of the apparatus the channels have a length of 8000-12,000 µm for oil-surfactant inlet, 5000-7000 for analyte (cell) inlet, and 900-1200 µm for the inlet for microbead and lysis agent. All channels have a width of 125-250 mm, and depth of 100-150 mm. In another embodiment, the width of the cell channel is 125-250 µm and the depth is 100-150 µm. In an embodiment of the apparatus the mixer has a length of 7000-9000 µm, and a width of 110-140 µm with 35-45° zig-zigs every 150 µm. In an embodiment, the width of the mixer is 125 µm. In an embodiment of the apparatus the oil-surfactant is PEG Block Polymer, such as BIORAD™ QX200 Droplet Generation Oil. In an embodiment of the apparatus the carrier fluid is water-glycerol mixture.

A mixture comprising a plurality of microbeads adorned with combinations of the following elements: bead-specific oligonucleotide barcodes created by the methods provided; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

In another embodiment, a mixture comprising a plurality of microbeads, wherein said microbeads comprise the following elements: at least one bead-specific oligonucleotide barcode obtainable by the process outlined; at least one additional identifier oligonucleotide barcode sequence, which varies among the oligonucleotides on an individual bead, and thereby assisting in the identification and of the bead specific oligonucleotide molecules; optionally at least one additional oligonucleotide sequences, which provide substrates for downstream molecular-biological reactions. In another embodiment the mixture comprises at least one oligonucleotide sequences, which provide for substrates for downstream molecular-biological reactions. In a further embodiment the downstream molecular biological reactions are for reverse transcription of mature mRNAs; capturing specific portions of the transcriptome, priming for DNA polymerases and/or similar enzymes; or priming throughout the transcriptome or genome. In a further embodiment the mixture the additional oligonucleotide sequence comprising a oligo-dT sequence. In another embodiment the mixture further comprises the additional oligonucleotide sequence comprises a primer sequence. In another embodiment the mixture further comprises the additional oligonucleotide sequence comprising a oligo-dT sequence and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}$P, $^{14}$C, $^{125}$I, $^{3}$H, and $^{131}$I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4',6-diamidino-2-phenylindole (DAPI); 5'5"-dibromopyrogallol-sulfonphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, one or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

The invention described herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. Disclosed embodiments provide thousands of single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue (e.g., retinal or human bone marrow), peripheral blood mononuclear cell, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A variety of analytes may be contemplated for use with the foregoing Drop-Sequencing methods. Examples of cells which are contemplated are mammalian cells, however the invention contemplates a method for profiling host-pathogen cells. To characterize the expression of host-pathogen interactions it is important to grow the host and pathogen in the same cell without multiple opportunities of pathogen infection.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensers. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that $10^{11}$ or $10^{15}$ different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

The present invention also provides an emulsion library which may comprise at least a first aqueous droplet and at least a second aqueous droplet within a fluorocarbon oil which may comprise at least one fluorosurfactant, wherein the at least first and the at least second droplets are uniform in size and comprise a different aqueous fluid and a different library element. The present invention also provides a method for forming the emulsion library which may comprise providing at least a first aqueous fluid which may comprise at least a first library of elements, providing at least a second aqueous fluid which may comprise at least a second library of elements, encapsulating each element of said at least first library into at least a first aqueous droplet within an immiscible fluorocarbon oil which may comprise at least one fluorosurfactant, encapsulating each element of said at least second library into at least a second aqueous droplet within an immiscible fluorocarbon oil which may comprise at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil which may comprise at least one fluorosurfactant thereby forming an emulsion library.

One of skill in the art will recognize that methods and systems of the invention are not limited to any particular type of sample, and methods and systems of the invention may be used with any type of organic, inorganic, or biological molecule (see, e.g, US Patent Publication No. 20120122714). In particular embodiments the sample may include nucleic acid target molecules. Nucleic acid molecules may be synthetic or derived from naturally occurring sources. In one embodiment, nucleic acid molecules may be isolated from a biological sample containing a variety of other components, such as proteins, lipids and non-template nucleic acids. Nucleic acid target molecules may be obtained from any cellular material, obtained from an animal, plant, bacterium, fungus, or any other cellular organism. In certain embodiments, the nucleic acid target molecules may be obtained from a single cell. Biological samples for use in the present invention may include viral particles or preparations. Nucleic acid target molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules may also be isolated from cultured cells, such as a primary cell culture or a cell line. The cells or tissues from which target nucleic acids are obtained may be infected with a virus or other intracellular pathogen. A sample may also be total RNA extracted from a biological specimen, a cDNA library, viral, or genomic DNA.

Generally, nucleic acid may be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Nucleic acid obtained from biological samples typically may be fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules may be from about 40 bases to about 40 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent may be up to an amount where the detergent remains soluble in the solution. In one embodiment, the concentration of the detergent is between 0.1% to about 2%. The detergent, particularly a mild one that is nondenaturing, may act to solubilize the sample. Detergents may be ionic or nonionic. Examples of nonionic detergents include triton, such as the Triton™ X series (Triton™ X-100 t-Oct-C6H4-(OCH2-CH2)xOH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™. 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments may be partitioned into fractions which may comprise a desired number of fragments using any suitable method known in the art. Suitable methods to limit the fragment size in each fragment are known in the art. In various embodiments of the invention, the fragment size is limited to between about 10 and about 100 Kb or longer.

In another embodiment, the sample includes individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. In one embodiment of the invention protein targets are isolated from biological samples containing a variety of other components including lipids, non-template nucleic acids, and nucleic acids. In certain embodiments, protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue. Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, S-carboxymethylation, acetylation, and methylation. Protein/nucleic acid complexes include cross-linked or stable protein-nucleic acid complexes.

Extraction or isolation of individual proteins, protein complexes, proteins with translational modifications, and protein/nucleic acid complexes is performed using methods known in the art.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41, 780) and European publication number EP2047910 to Raindance Technologies Inc. The content of each of which is incorporated by reference herein in its entirety.

The present invention relates to systems and methods for manipulating droplets within a high throughput microfluidic system. Turning to FIG. 1, a microfluid droplet (10) encapsulates a differentiated cell (not shown in the figure). The cell is lysed and its mRNA (20) is hybridized onto a capture bead containing barcoded oligo dT primers on the surface (30) (40), all inside the droplet. The barcode is covalently attached to the capture bead via a flexible multi-atom linker like PEG. (50). In a preferred embodiment, the droplets are broken by addition of a fluorosurfactant (like perfluorooctanol), washed, and collected. A reverse transcription (RT) reaction is then performed to convert each cell's mRNA into a first strand cDNA that is both uniquely barcoded and covalently linked to the mRNA capture bead. Subsequently, a universal primer via a template switching reaction is amended using conventional library preparation protocols to prepare an RNA-Seq library. Since all of the mRNA from any given cell is uniquely barcoded, a single library is sequenced and then computationally resolved to determine which mRNAs came from which cells. In this way, through a single sequencing run, tens of thousands (or more) of distinguishable transcriptomes can be simultaneously obtained.

Figure 2A:
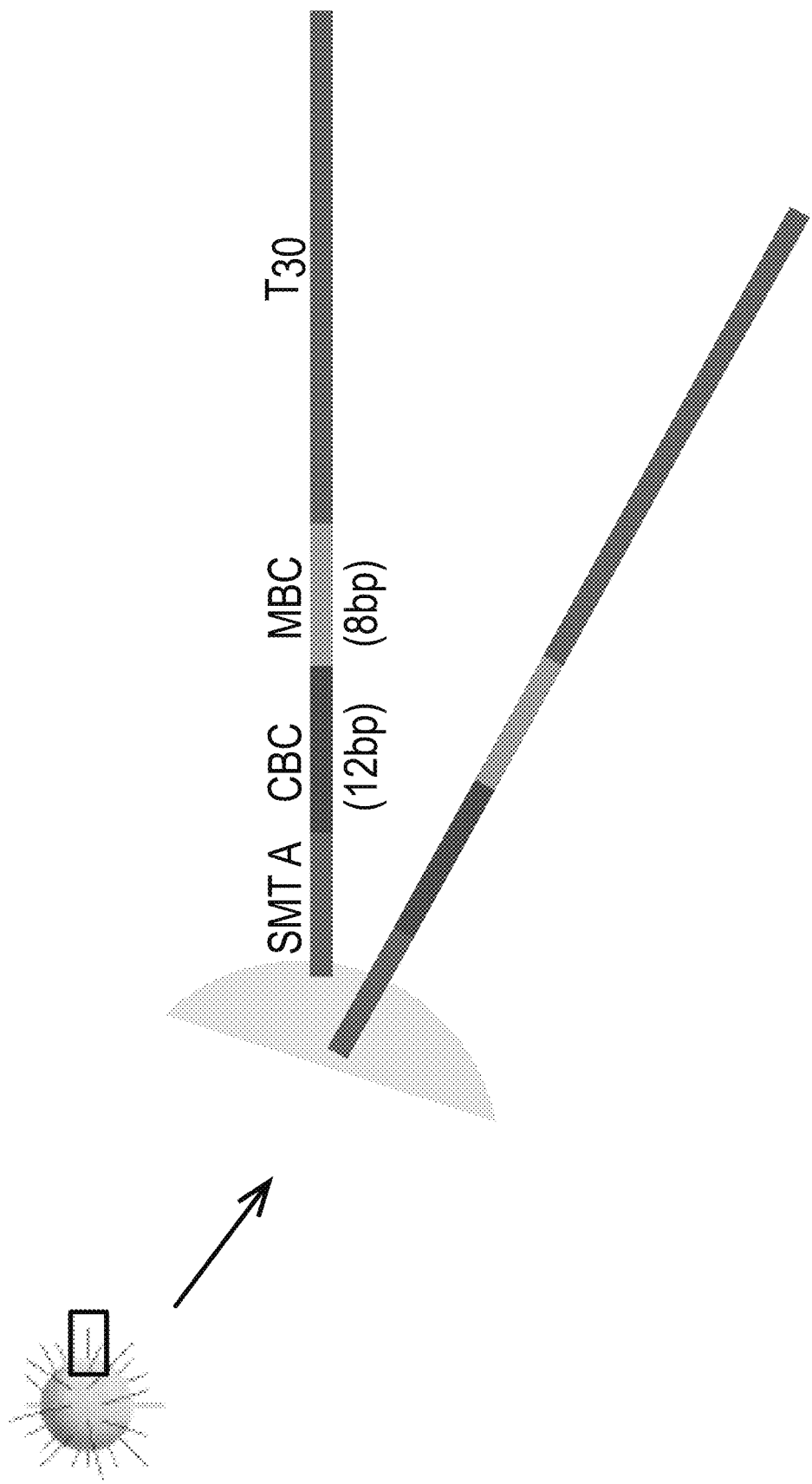
FIGS. 2A and 2B illustrates an embodiment of the present invention which builds barcodes by split-and-pool synthesis on beads using single bases and a final oligo-dT tail for mRNA capture.
Figure 2B:
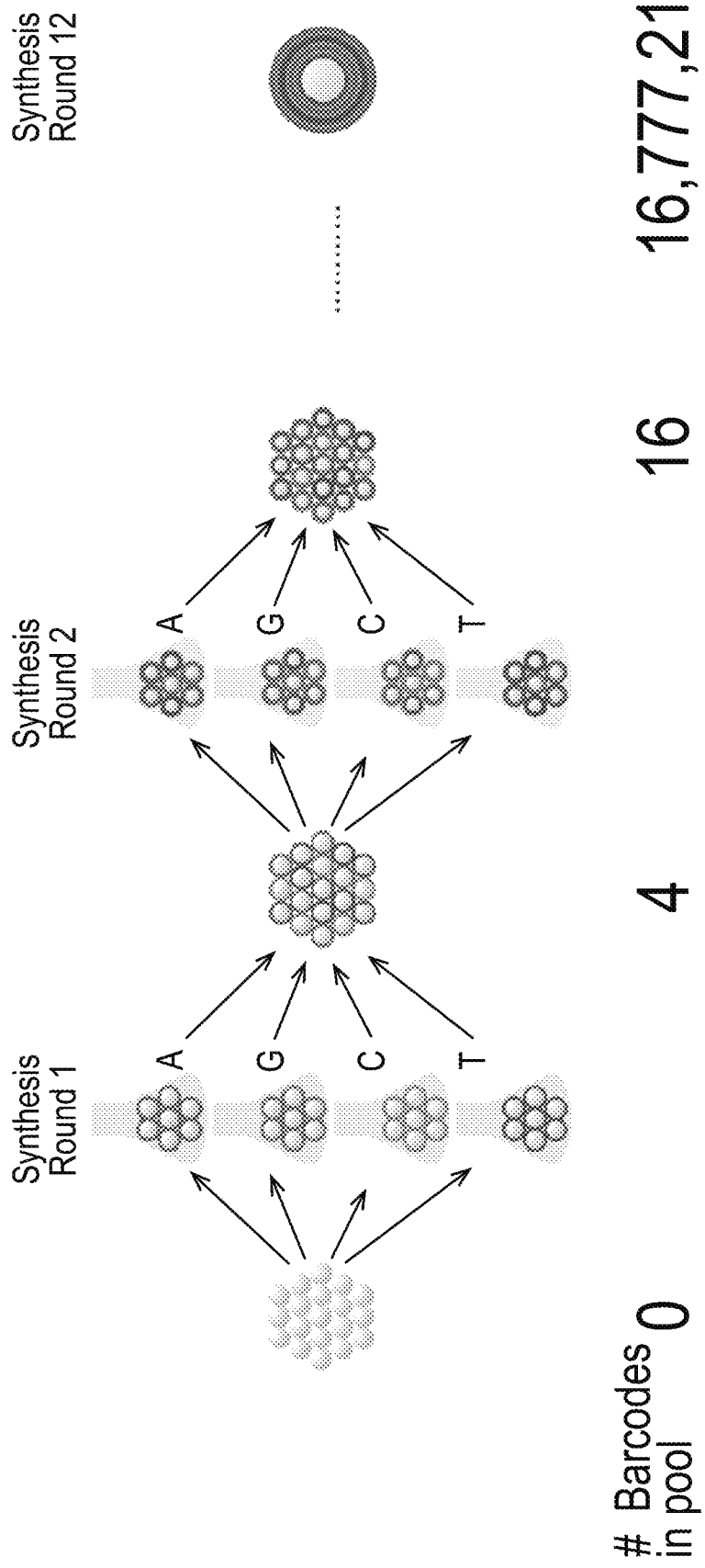

Turning to FIGS. 2A and 2B, the oligonucleotide sequence generated on the bead surface is shown in FIG. 2A. During these cycles, beads were removed from the synthesis column, pooled, and aliquoted into four equal portions by mass; these bead aliquots were then placed in a separate synthesis column and reacted with either dG, dC, dT, or dA phosphoramidite. In other instances, dinucleotide, trinucleotides, or oligonucleotides that are greater in length are used, in other instances, the oligo-dT tail is replaced by gene specific oligonucleotides to prime specific targets (singular or plural), random sequences of any length for the capture of all or specific RNAs. This process was repeated 12 times for a total of $4^{12}=16,777,216$ unique barcode sequences (FIG. 2B). Upon completion of these cycles, 8 cycles of degenerate oligonucleotide synthesis were performed on all the beads, (the molecular barcode "MBC" in FIG. 2A) followed by 30 cycles of dT addition. In other embodiments, the degenerate synthesis is omitted, shortened (less than 8 cycles), or extended (more than 8 cycles); in others, the 30 cycles of dT addition are replaced with gene specific primers (single target or many targets) or a degenerate sequence.

Figure 3A:
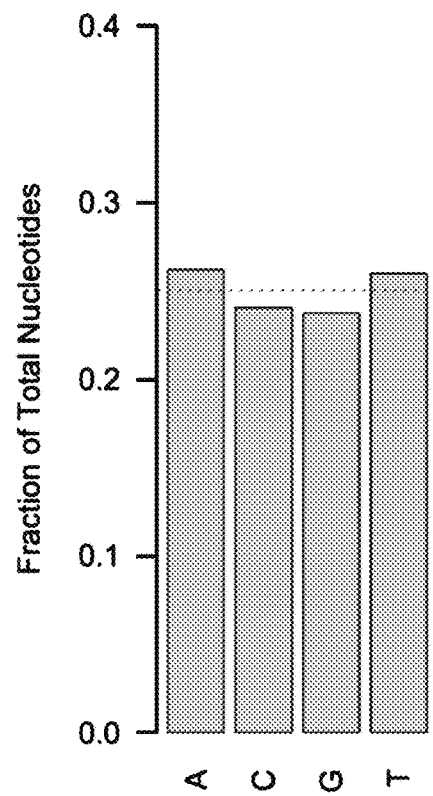
FIGS. 3A-3D illustrate cell barcode sequences approaching the theoretical level of complexity.
Figure 3B:
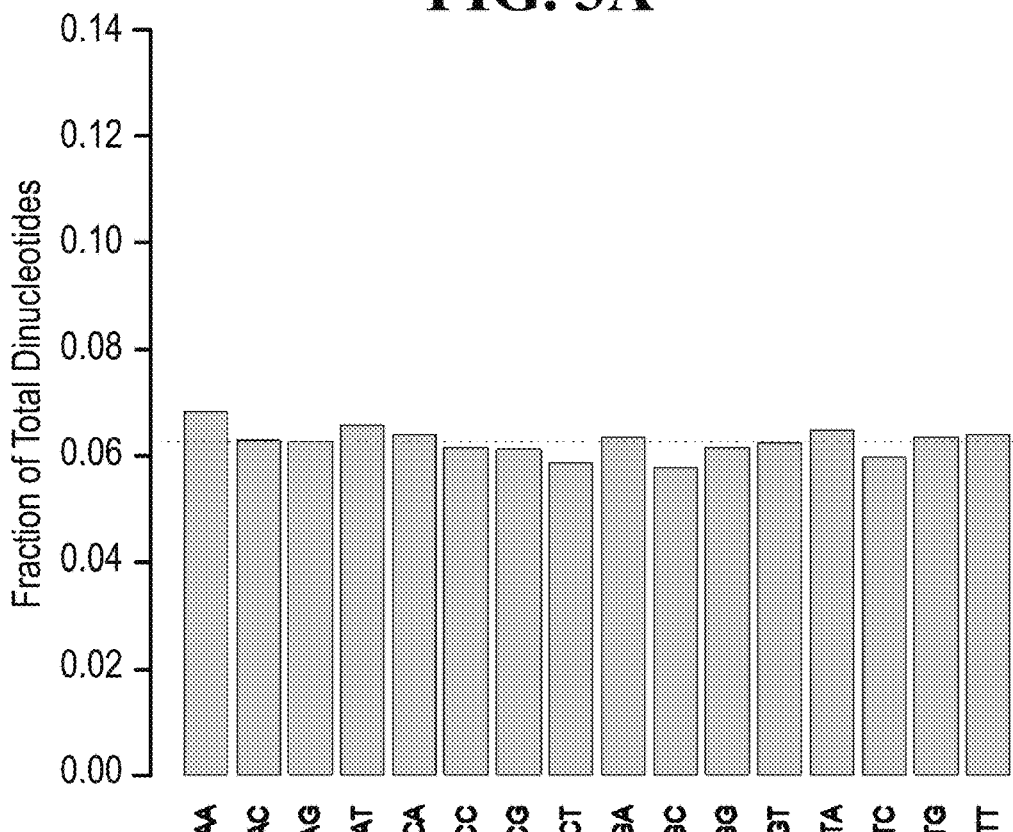

In FIGS. 3A through 3D, one-thousand cell barcode sequences were analysed to determine cell barcode complexity (FIG. 3A).

Figure 4:
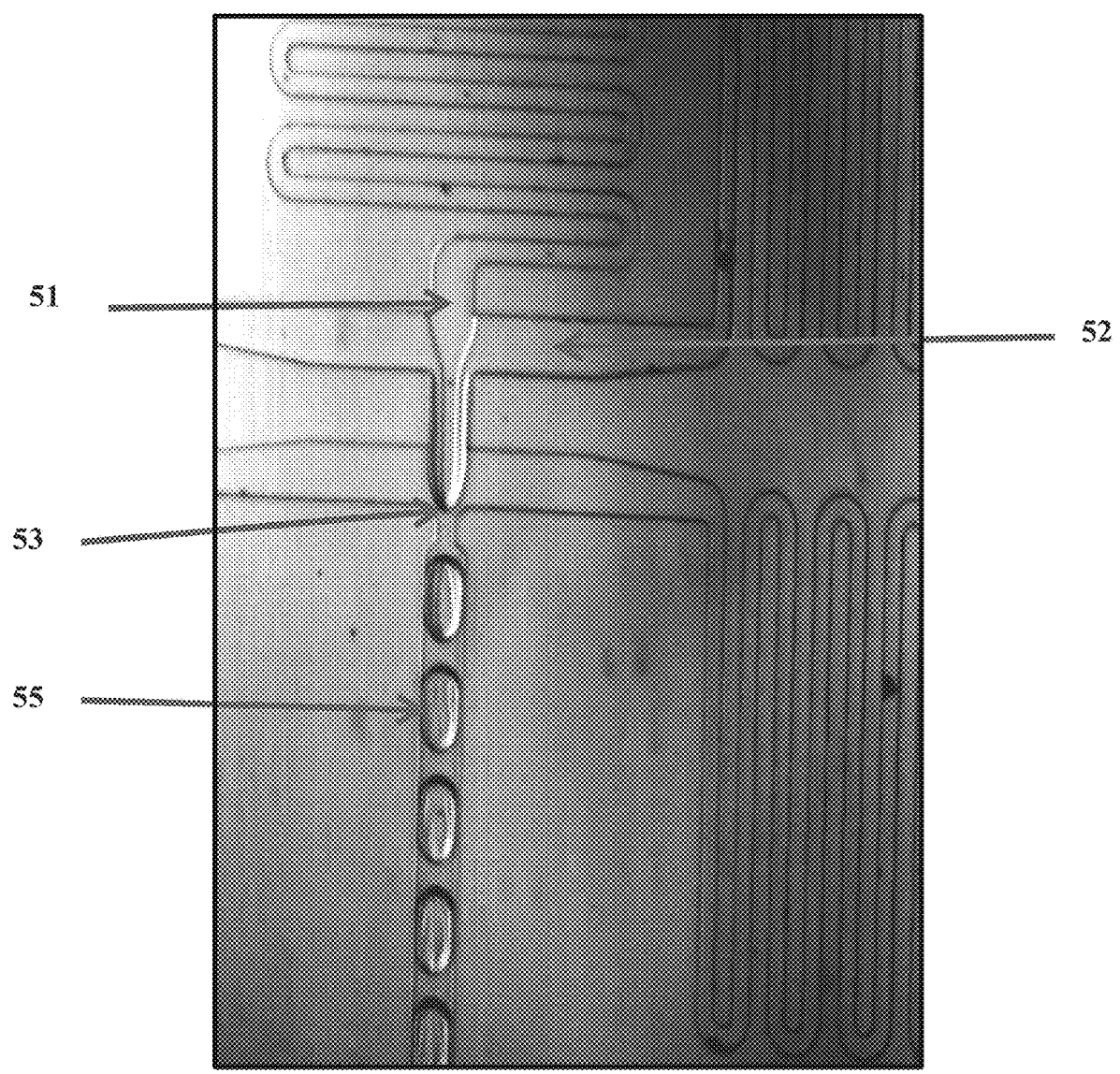
FIG. 4. Microfluidic device illustrating co-encapsulation of cells in PBS injected (once).

The aforementioned microfluidic system is regarded as the reagent delivery system microfluidic library printer or droplet library printing system of the present invention (FIG. 4). Droplets (55) are formed as sample fluid flows from droplet generator (51) which contains lysis reagent and barcodes through microfluidic outlet channel (52) which contains oil (53), towards junction (54). Defined volumes of loaded reagent emulsion, corresponding to defined numbers of droplets, are dispensed on-demand into the flow stream of carrier fluid.

The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil).

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

Figure 5:
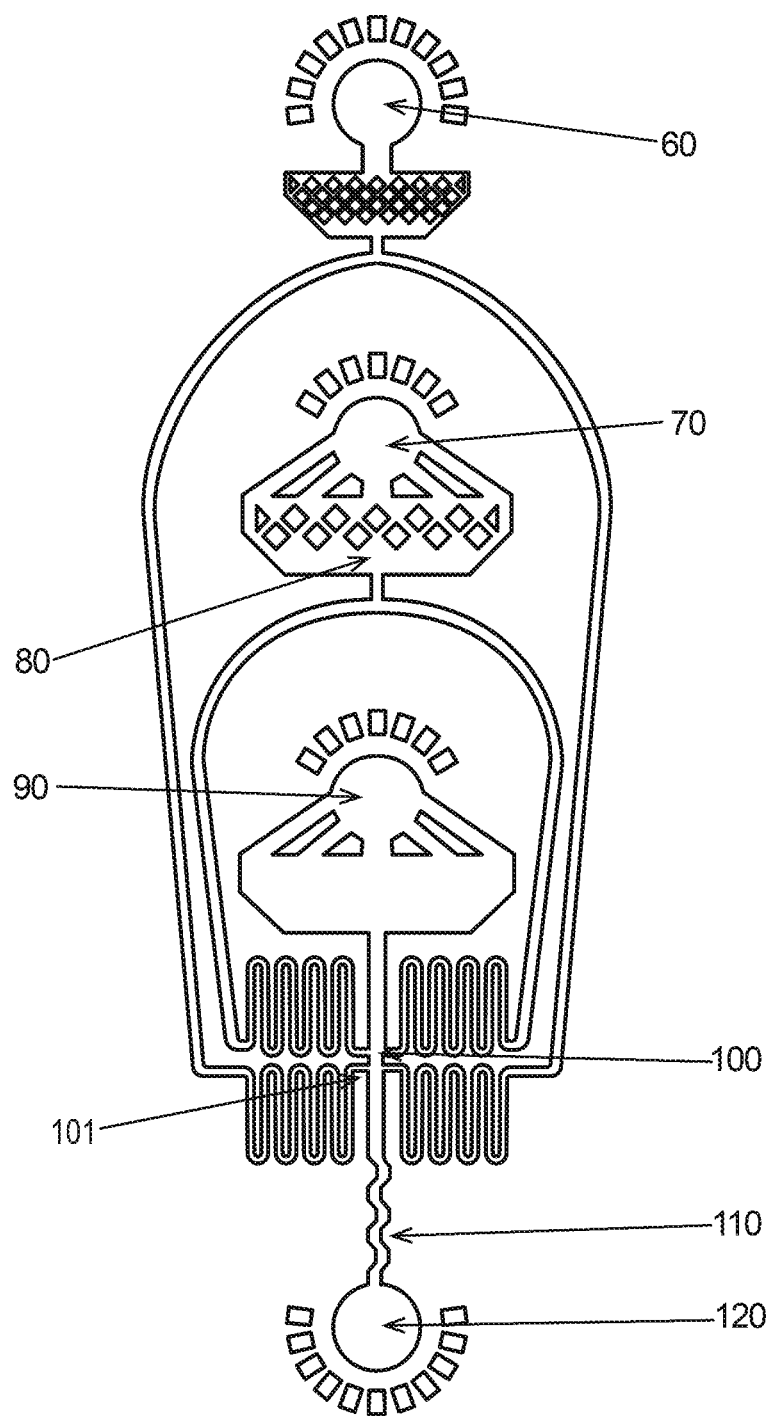
FIG. 5. Schematic illustration of microfluidic device.

FIG. 5 illustrates a schematic of an apparatus for creating a single-cell sequencing library via a microfluidic system. In some cases, the device provides for volume-driven flow, wherein constant volumes are injected over time. The pressure in fluidic channels is a function of injection rate and channel dimensions. In an embodiment of the scheme according to FIG. 5, the device provides a oil/surfactant inlet (60); an inlet for an analyte (70); a filter (80), an inlet for mRNA capture microbeads and lysis reagent (90); a carrier fluid channel which connects the inlets as illustrated in FIG. 5; a resistor (100); a constriction for droplet pinch-off (101); a mixer (110); and an outlet for drops (120). In an embodiment the invention provides apparatus for creating a single-cell sequencing library via a microfluidic system, comprising: a oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

Figure 6:
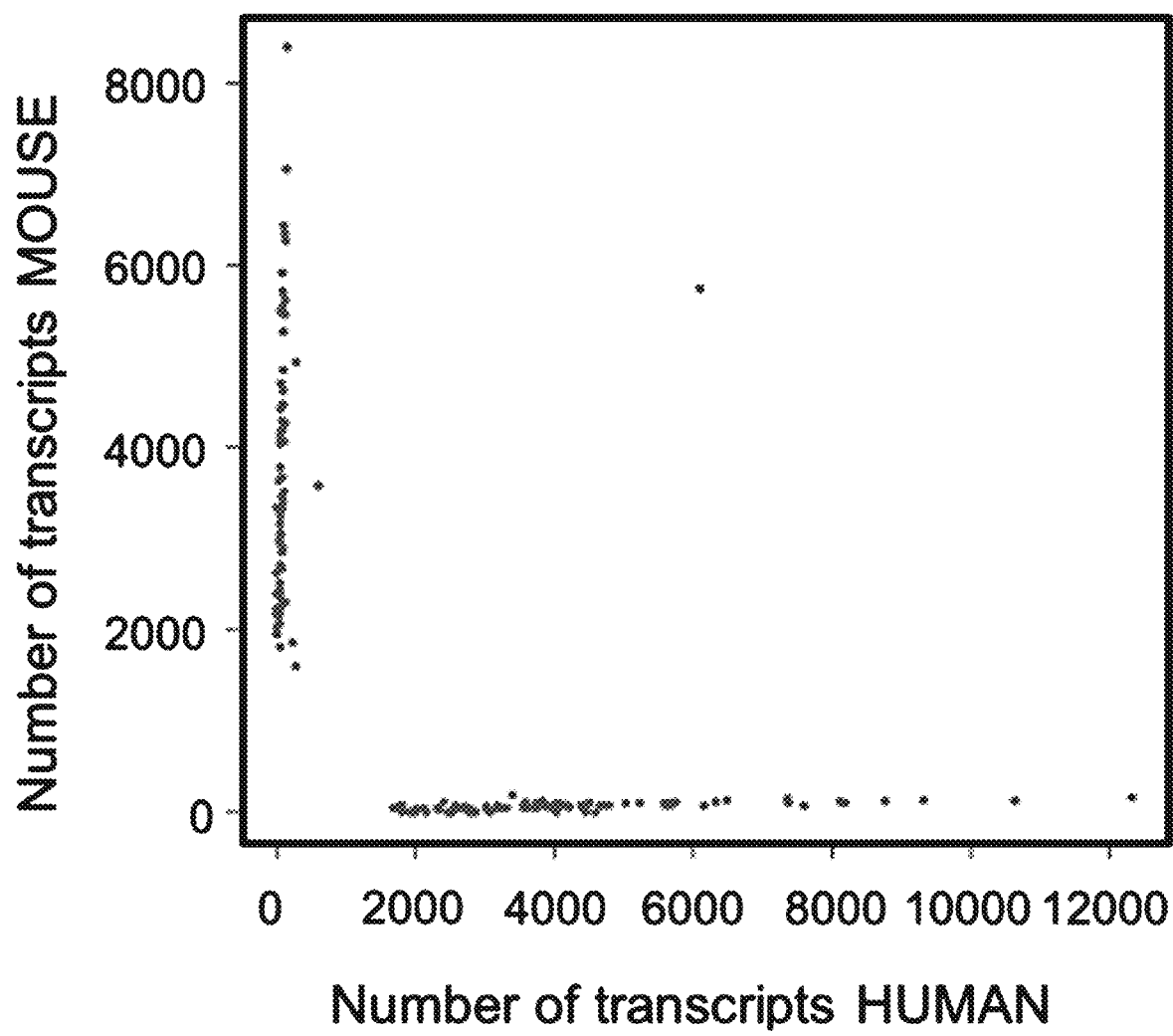
FIG. 6. illustrates sorted drops of interest using the drop-seq method generated from the microfluidic device.

FIG. 6 illustrates a (a) Microfluidic flow scheme for single-cell RNA-seq. Two channels, one carrying cell suspensions, and the other carrying uniquely barcoded mRNA capture bead, lysis buffer and library preparation reagents meet at a junction and is immediately co-encapsulated in an inert carrier oil, at the rate of one cell and one bead per drop. In each drop, using the bead's barcode tagged oligonucleotides as cDNA template, each mRNA is tagged with a unique, cell-specific identifier. (b) Drop-Seq library of a mixture of mouse and human cells. Each dot represents a unique barcode, and indicates the number of genes that could aligned to human (x axis) and mouse (y axis) genomes.

FIG. 7 illustrates molecular barcoding of cellular transcriptomes in droplets. (A) Drop-Seq barcoding schematic. A complex tissue is dissociated into individual cells, which are then encapsulated in droplets together with microparticles (gray circles) that deliver barcoded primers. Each cell is lysed within a droplet; its mRNAs bind to the primers on its companion microparticle. The mRNAs are reverse-transcribed into cDNAs, generating a set of beads called "single-cell transcriptomes attached to microparticles" (STAMPs). The barcoded STAMPs can then be amplified in pools for high-throughput mRNA-seq to analyze any desired number of individual cells. (B) Sequence of primers on the microparticle. The primers on all beads contain a common sequence ("PCR handle") to enable PCR amplification after STAMP formation. Each microparticle contains more than $10^8$ individual primers that share the same "cell barcode" (panel C) but have different unique molecular identifiers (UMIs), enabling mRNA transcripts to be digitally counted (panel D). A 30 bp oligo dT sequence is present at the end of all primer sequences for capture of mRNAs via their polyadenylated 3' ends. (C) Split-and-pool synthesis of the cell barcode. To generate the cell barcode, the pool of microparticles is repeatedly split into four equally sized oligonucleotide synthesis reactions, to which one of the four DNA bases is added, and then pooled together after each cycle, in a total of 12 split-pool cycles. The barcode synthesized on any individual bead reflects that bead's unique path through the series of synthesis reactions. The result is a pool of microparticles, each possessing one of $4^{12}$ (16,777,216) possible sequences on its entire complement of primers. (D) Synthesis of a unique molecular identifier (UMI). Following the completion of the "split-and-pool" synthesis cycles, all microparticles are together subjected to eight rounds of degenerate synthesis with all four DNA bases available during each cycle, such that each individual primer receives one of $4^8$ (65,536) possible sequences (UMIs).

FIG. 8 illustrates extraction and processing of single-cell transcriptomes by Drop-Seq. (A) Schematic of single-cell mRNA-Seq library preparation with Drop-Seq. A custom-designed microfluidic device joins two aqueous flows before their compartmentalization into discrete droplets. One flow contains cells, and the other flow contains barcoded primer beads suspended in a lysis buffer. Immediately following droplet formation, the cell is exposed to the lysis agent and releases its mRNAs, which then hybridize to the primers on the microparticle surface. The droplets are broken by adding a reagent to destabilize the oil-water interface (Extended Experimental Procedures), and the microparticles collected and washed. The mRNAs are then reverse-transcribed in bulk, forming STAMPs, and template switching is used to introduce a PCR handle downstream of the synthesized cDNA (Zhu et al., 2001). (B) Microfluidic device used in Drop-Seq. Beads (brown in image), suspended in a lysis agent, enter the device from the central channel; cells enter from the top and bottom. Laminar flow prevents mixing of the two aqueous inputs prior to droplet formation; this is evident in the image from the refraction of light along the interface of the two flows (see also Movie S1). (C) Molecular elements of a Drop-Seq sequencing library. The first read yields the cell barcode and UMI. The second, paired read interrogates sequence from the cDNA (50 bp is typically sequenced, though longer or shorter reads are also possible); this sequence is then aligned to the genome to determine a transcript's gene of origin. The cell barcode is used to determine the transcript's cell of origin. (D) In silico reconstruction of thousands of single-cell transcriptomes. Millions of paired-end reads are generated from a Drop-Seq library by a high-throughput sequencer (e.g. MiSeq, NextSeq, or HiSeq). The reads are first aligned to a reference genome to identify the gene-of-origin of the cDNA. Next, reads are organized by their cell barcodes, and individual UMIs are counted for each gene in each cell (Extended Experimental Procedures). The result, shown at far right, is a "digital expression matrix" in which each column corresponds to a cell, each row corresponds to a gene, and each entry is the integer number of transcripts detected from that gene, in that cell.

Figure 15A:
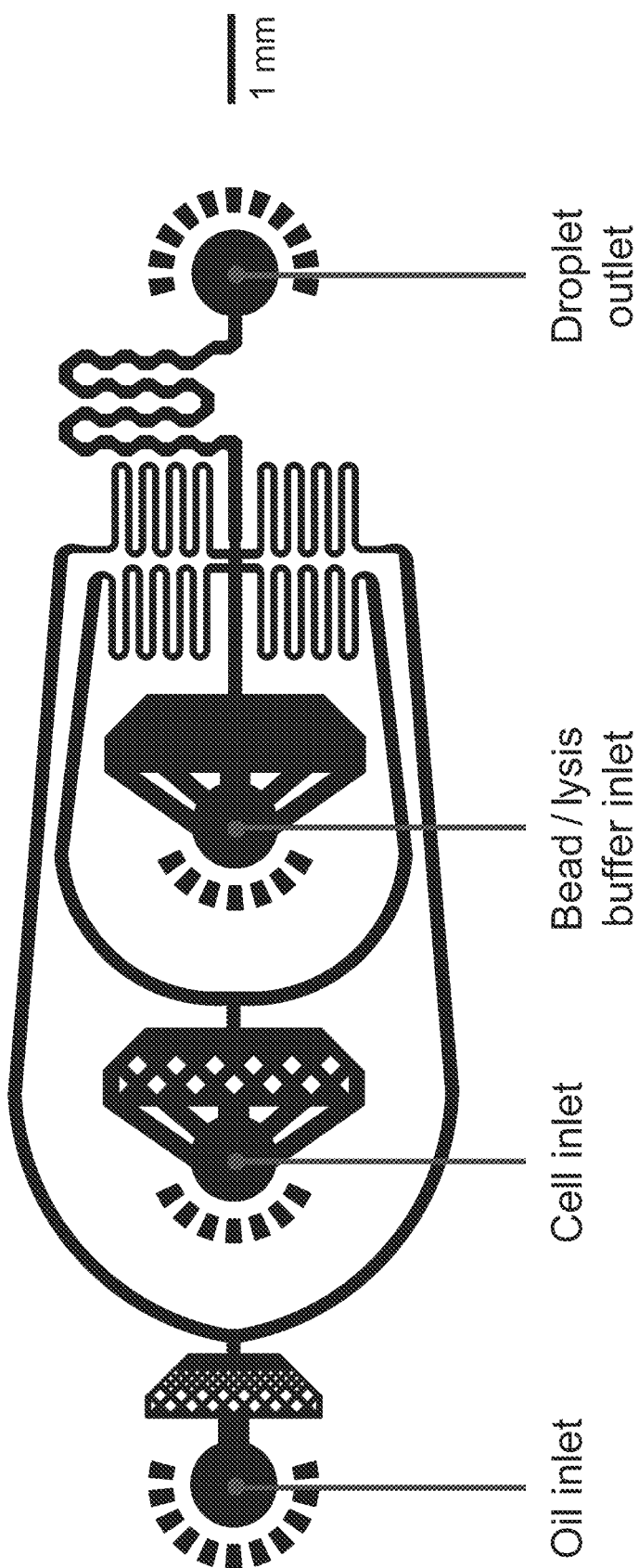
FIG. 15 A-E illustrate device design and dissection of technical contributions to single-cell impurities in Drop-Seq library preparations.
Figure 15B:
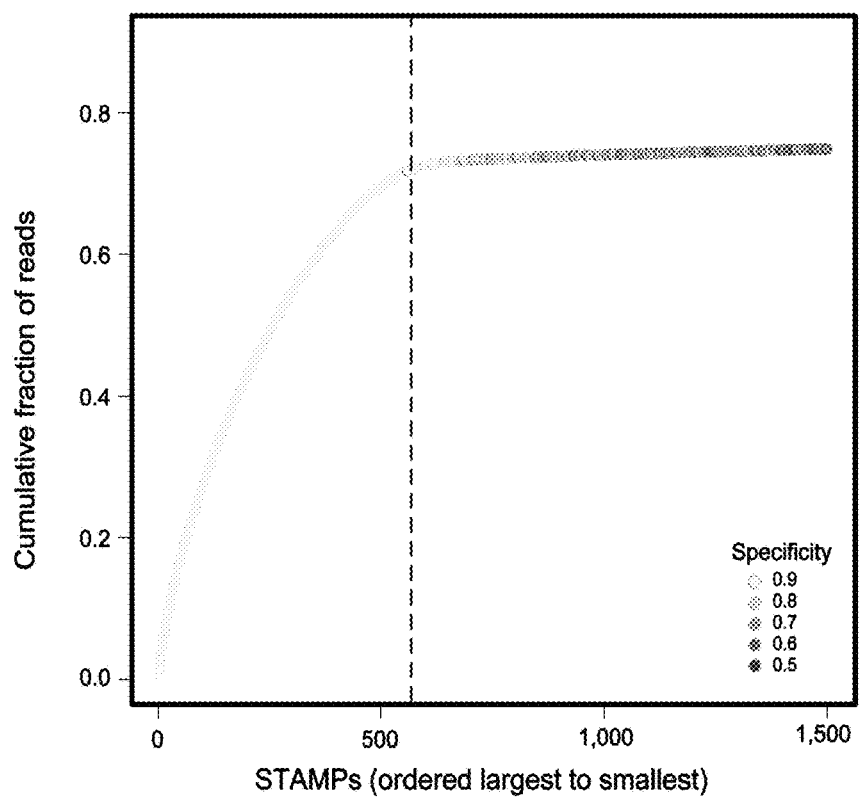
Figure 15C:
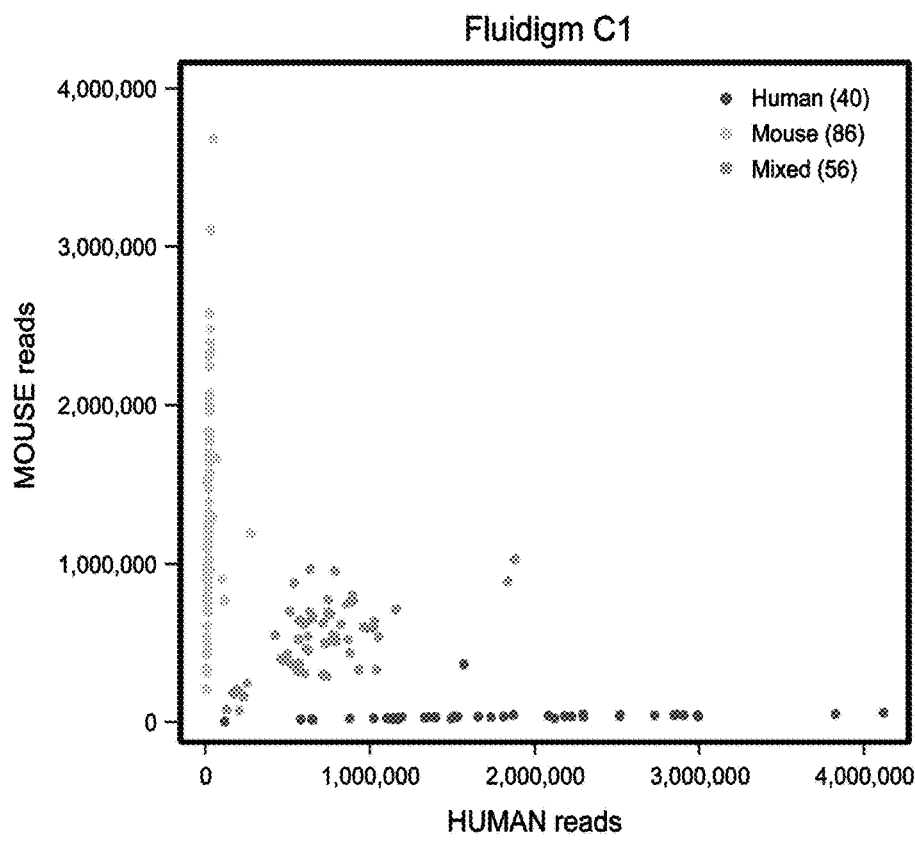

FIG. 9 illustrates critical evaluation of Drop-Seq using species-mixing experiments. (A,B) Drop-Seq analysis of mixtures of mouse and human cells. Mixtures of human (HEK) and mouse (3T3) cells were analyzed by Drop-Seq at the concentrations shown. The scatter plot shows the number of human and mouse transcripts associating to each STAMP. Blue dots indicate STAMPs that were designated from these data as containing human-specific sets of transcripts (average of 99% human transcripts); red dots indicate STAMPs inferred to be mouse-specific (average 99%). At the lower cell concentration, one STAMP barcode (of 570) associated with a mixture of human and mouse transcripts (panel A, purple). At the higher cell concentration, about 1.9% of STAMP barcodes associated with mouse-human mixtures (panel B). Data for other cell concentrations and a different single-cell analysis platform are in FIGS. 15C and 15D. (C,D) Sensitivity analysis of Drop-Seq at high read-depth. Violin plots show the distribution of the number of transcripts (B, scored by UMIs) and genes (C) detected per cell for 54 HEK (human) STAMPs (blue) and 28 3T3 (mouse)

STAMPs (green) that were sequenced to a mean read depth of 737,240 high-quality aligned reads per cell. (E,F) Correlation between gene expression measurements in Drop-Seq and non-single-cell RNA-seq methods. Comparison of Drop-Seq gene expression measurements (averaged across 550 STAMPs) to measurements from bulk RNA analyzed in (E) an mRNA-seq library prepared by an in-solution template switch amplification (TSA) procedure similar to Smart-Seq2 (Picelli et al., 2013) (Extended Experimental Procedures); and (F) Illumina Tru-Seq mRNA-Seq. All comparisons involve RNA derived from the same cell culture flask (3T3 cells). All expression counts were converted to average transcripts per million (ATPM) and plotted as log (1+ATPM). (G) Quantitation of Drop-Seq capture efficiency by ERCC spike-ins. Drop-Seq was performed with ERCC control synthetic RNAs, spiked in at an estimated concentration of 100,000 ERCC RNA molecules per droplet. 84 STAMPs were sequenced at a mean depth of 2.4 million reads, aligned to the ERCC reference sequences, and UMIs counted for each ERCC species, after applying a stringent down-correction for potential sequencing errors (Extended Experimental Procedures). For each ERCC RNA species present at at least one molecule per droplet, the predicted number of molecules per droplet was plotted in log space (x-axis), versus the actual number of molecules detected per droplet by Drop-Seq, also in log space (y-axis). The intercept of a regression line, constrained to have a slope of 1 and fitted to the seven highest points, was used to estimate a conversion factor (0.128). A second estimation, using the average number of detected transcripts divided by the number of ERCC molecules used (100,000), yielded a conversion factor of 0.125.

FIG. 10 illustrates cell-cycle analysis of HEK and 3T3 cells analyzed by Drop-Seq. (A) Cell-cycle state of 589 HEK cells (left) and 412 3T3 cells (right) measured by Drop-Seq. Cells were assessed for their progression through the cell cycle by comparison of each cell's global pattern of gene expression with gene sets known to be enriched in one of five phases of the cycle (horizontal rows). A phase-specific score was calculated for each cell across each of these five phases (Extended Experimental Procedures), and the cells ordered by their phase scores. (B) Discovery of cell cycle regulated genes. Heat map showing the average normalized expression of 544 human and 668 mouse genes found to be regulated by the cell cycle in the Drop-Seq-sequenced cells. To find genes that were cell cycle regulated, maximal and minimal expression was calculated for each gene across a sliding window of the ordered cells, and compared with shuffled cells to obtain a false discovery rate (FDR) (Experimental Procedures). The plotted genes (FDR threshold of 5%) were then clustered by k-means analysis to identify sets of genes with similar expression patterns. Cluster boundaries are represented by dashed gray lines. (C) Representative cell cycle regulated genes discovered by Drop-Seq. Selected genes that were found to be cell cycle regulated in both the HEK and 3T3 cell sets. Left, selected genes that are well-known to be cell cycle regulated. On the right are some genes identified in this analysis that were not previously known to be associated with the cell cycle (Experimental Procedures). A complete list of cell cycle regulated genes can be found in Table 4.

FIG. 11 illustrates Ab initio reconstruction of retinal cell types from 44,808 single-cell transcription profiles prepared by Drop-Seq. (A) Schematic representation of major cell classes in the retina. Photoreceptors (rods or cones) detect light and pass information to bipolar cells, which in turn contact retinal ganglion cells that extend axons into other CNS tissues. Amacrine and horizontal cells are retinal interneurons; Müller glia act as support cells for surrounding neurons. (B) Clustering of 44,808 Drop-Seq single-cell expression profiles into 39 retinal cell populations. The plot shows a two-dimensional representation of global gene expression relationships among 44,808 cells; clusters are colored by cell class (colored according to FIG. 11A). (C) Differentially expressed genes across 39 retinal cell populations. In this heat map, rows correspond to individual genes found to be selectively upregulated in individual clusters (p<0.01, Bonferroni corrected); columns are individual cells, ordered by cluster (1-39). Clusters >1,000 cells were downsampled to 1,000 cells to prevent them from dominating the plot. (D) Gene expression similarity relationships among 39 inferred cell populations. Average gene expression across all detected genes was calculated for the cells in each of 39 cell clusters, and the relative (Euclidean) distances between gene-expression patterns for the 39 clusters were represented by a dendrogram. (The dendrogram represents global gene expression similarity relationships; it does not represent a developmental lineage.) The branches of the dendrogram were annotated by examining the differential expression of known markers for retina cell classes and types. Twelve examples are shown at right, using violin plots to represent the distribution of expression within the clusters. Violin plots for additional genes are in FIG. S6. (E) Representation of experimental replicates in each cell population. tSNE plot from FIG. 8B, with each cell now colored by experimental replicate. Each of the 7 replicates contributes to all 39 cell populations. Cluster 36 (arrow), in which these replicates are unevenly represented, expressed markers of fibroblasts which are not native to the retina and are presumably a dissection artifact. (F) Trajectory of amacrine clustering as a function of number of cells analyzed. Three different downsampled datasets were generated: (1) 500, (2) 2,000, or (3) 9,451 cells (Extended Experimental Procedures). Cells identified as amacrines (clusters 3-23) in the full analysis are here colored by their cluster identities in that analysis. Analyses of smaller numbers of cells incompletely distinguished these subpopulations from one another.

FIG. 12. Finer-scale expression distinctions among amacrine cells, cones and retinal ganglion cells. (A) Pan-amacrine markers. The expression levels of the six genes identified (Nrxn2, Atp1b1, Pax6, Slc32a1, Slc6a1, Elavl3) are represented as dot plots across all 39 clusters; larger dots indicate broader expression within the cluster; deeper red denotes a higher expression level. (B) Identification of known amacrine types among clusters. The twenty-one amacrine clusters consisted of twelve GABAergic, five glycinergic, one glutamatergic and three non-GABAergic non-glycinergic clusters. Starburst amacrines were identified in cluster 3 by their expression of Chat; excitatory amacrines were identified by expression of Slc17a8; A-II amacrines were identified in cluster 16 by their expression of Gjd2; and SEG amacrine neurons were identified in clusters 17 and 20 by their expression of Ebf3. (C) Nomination of novel candidate markers of amacrine subpopulations. Each cluster was screened for genes differentially expressed in that cluster relative to all other amacrine clusters (p<0.01, Bonferroni corrected) (McDavid et al., 2013), and filtered for those with highest relative enrichment. Expression of a single candidate marker for each cluster is shown across all retinal cell clusters (all genes differentially expressed in a cluster can be found in Table 6; genes differentially expressed between all cluster pairs can be found in Table 7). (D) Validation of MAF as a marker for a GABAergic amacrine population. Staining of a fixed adult retina from wild-type mice for MAF (panels i, ii, v, and green staining in iv and vii), GAD1 (panels iii and iv, red staining), and SLC6A9 (panels vi and vii, red staining; MAF staining is shown in green), demonstrating co-localization of MAF with GAD1, but not SLC6A9. (E) Differential expression of cluster 7 (MAF+) with nearest neighboring amacrine cluster (#6). Average gene expression was compared between cells in clusters 6 and 7; sixteen genes (red dots) were identified with >2.8-fold enrichment in cluster 7 ($p<10^{-9}$). (F) Validation of PPP1R17 as a marker for an amacrine subpopulation. Staining of a fixed adult retina from Mito-P mice, which express CFP in both nGnG amacrines and type 1 bipolars (Kay et al., 2011). Asterisks (*) denote bipolar cells labeled in the Mito-P line, while arrows indicate the nGnG amacrine neurons, which are labeled by both the Mito-P transgenic line (red) and the PPP1R17 antibody (green). 85% of CFP+ cells were PPP1R17+; 50% of the PPP1R17+ were CFP−, suggesting a second amacrine type expressing this marker. (G) Differential expression of cluster 20 (PPP1R17+) with nearest neighboring amacrine cluster (#21). Average gene expression was compared between cells in clusters 20 and 21; twelve genes (red dots) were identified with >2.8-fold enrichment in cluster 7 ($p<10^{-9}$). (H) Differential expression of M-opsin and S-opsin cones. Cells in cluster 25 were identified as cone photoreceptors, which express M-opsin (for detecting green light) and/or S-opsin (for detecting blue light). Average gene expression was compared between cells expressing M-opsin only (x-axis) and cells-expressing S-opsin only (y-axis). Eight genes showing greater than 2-fold differences in expression ($p<10^{-9}$) are labeled on the plot along with the two opsin genes Opn1sw and Opn1mw. Green points are genes enriched in M-cones, while red points are genes enriched in S-cones. (I) Differential expression of melanopsin-positive and negative RGCs. Twenty-four retinal ganglion cells expressing Opn4, the gene encoding melanopsin, were identified in cluster 2 and average expression was compared between these cells and the remainder of cluster 2. Seven genes were identified as differentially expressed (red dots, >2-fold, $p<10^{-9}$).

Figure 13A:
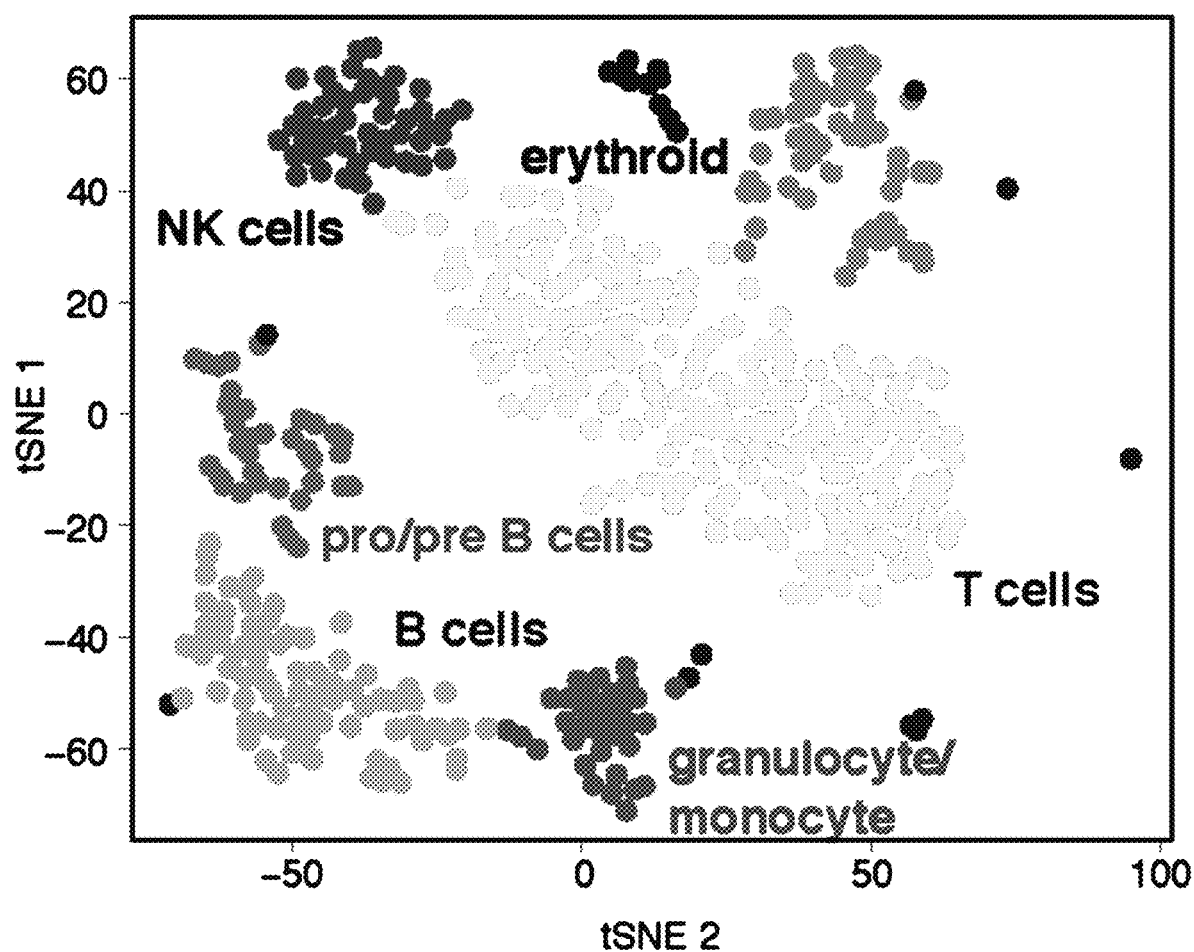
FIG. 13 A-C illustrate Ab initio reconstruction of human bone marrow cell types from 471 single-cell transcription profiles prepared by Drop-Seq.
Figure 13B:
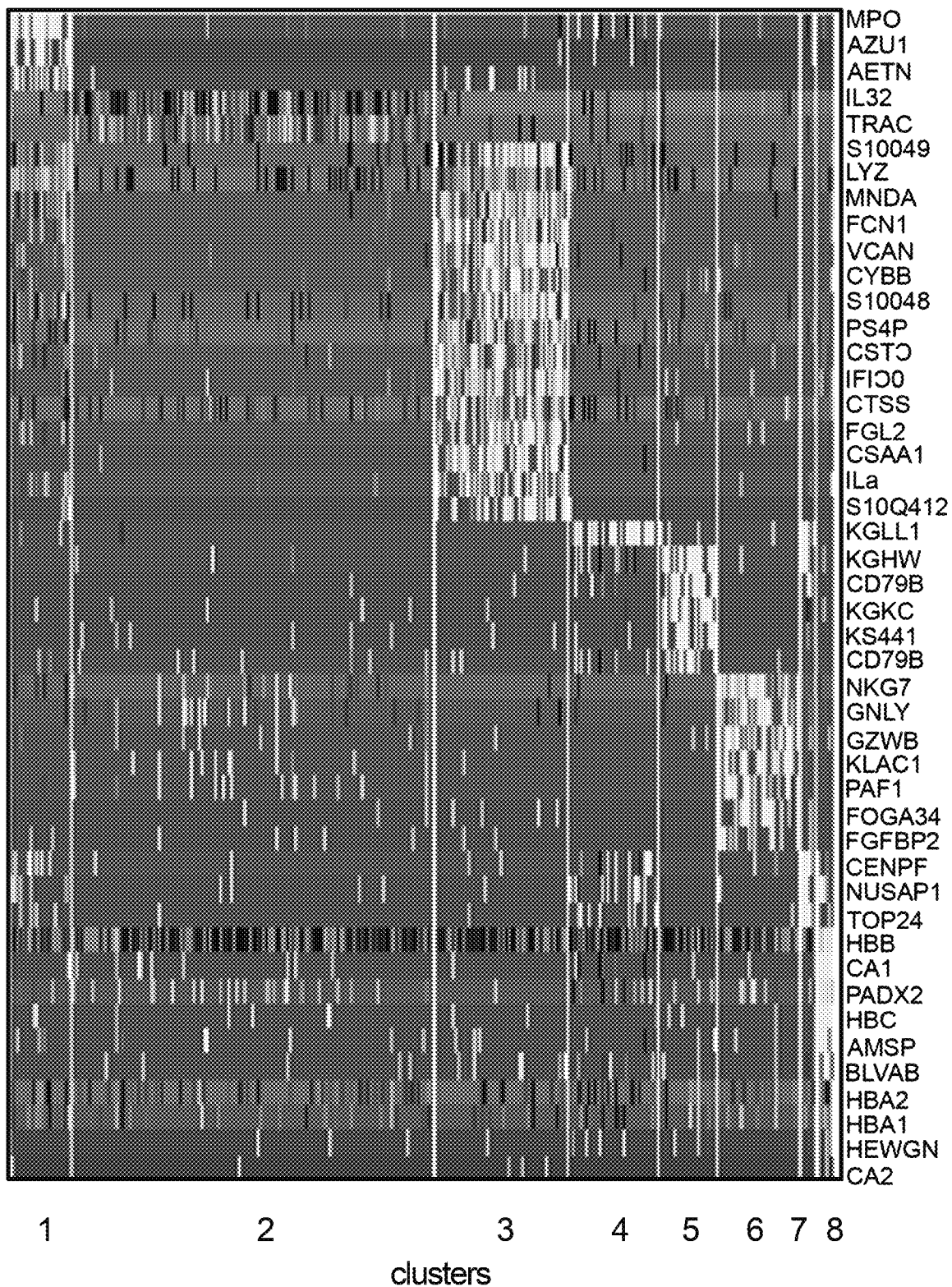
Figure 13C:
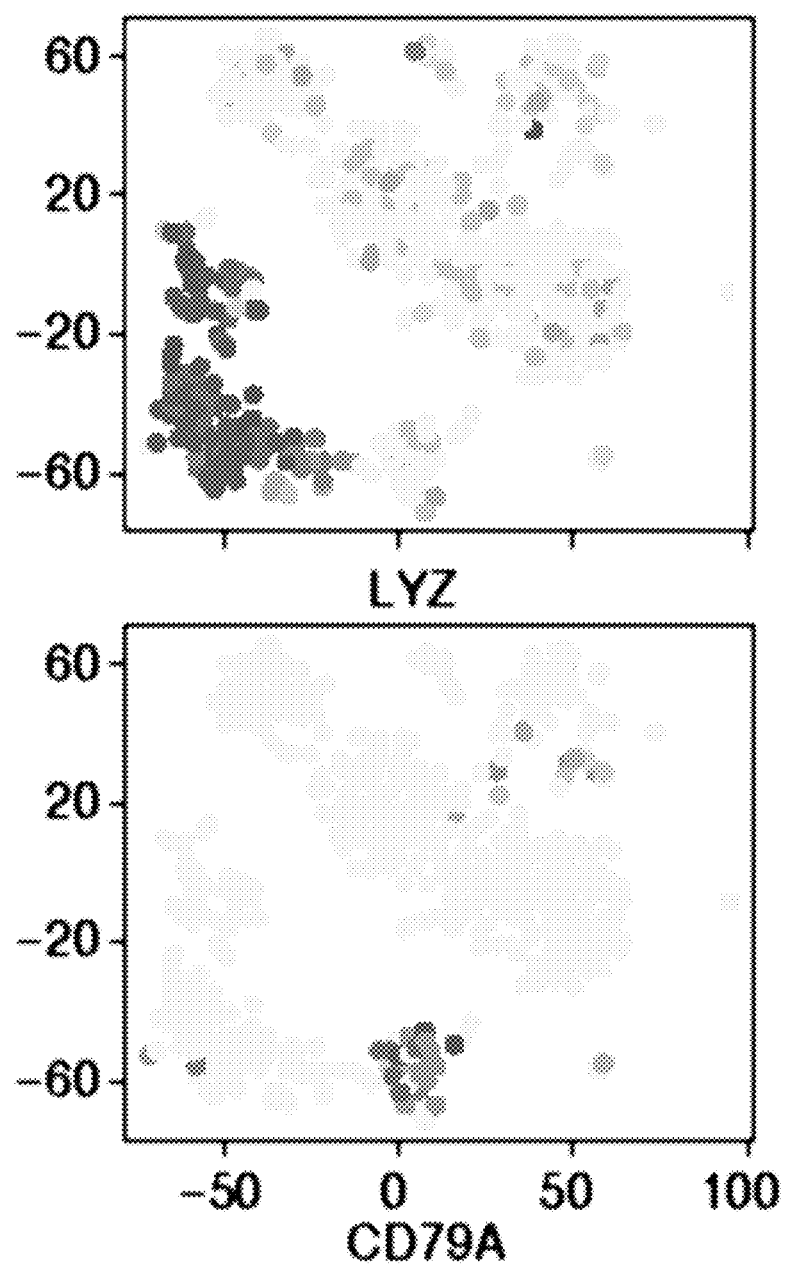

FIGS. 13A-C illustrate Ab initio reconstruction of human bone marrow cell types from 471 single-cell transcription profiles prepared by Drop-Seq. (A) Clustering of single-cell expression profiles into 8 cell classes. The plot shows a two-dimensional representation (tSNE) of global gene expression relationships among cells; clusters are colored and labeled by cell class. (B) A heatmap of differentially expressed genes across 8 cell classes. Rows correspond to individual marker genes; columns are individual cells, ordered by cluster (1-8). (C) Examples of marker genes expression (red is high) showed on tSNE map.

Figure 14A:
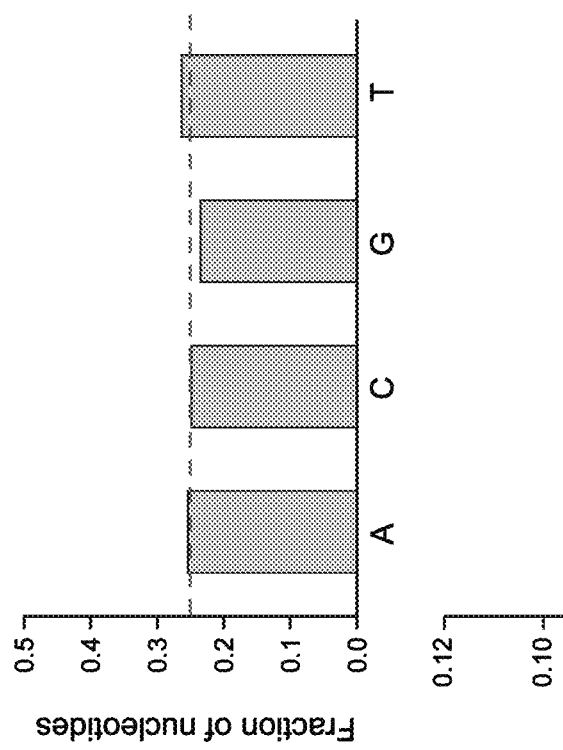
FIG. 14 A-C illustrate an assessment of the properties of barcoded primers on the surface of microparticles (beads).
Figure 14C:
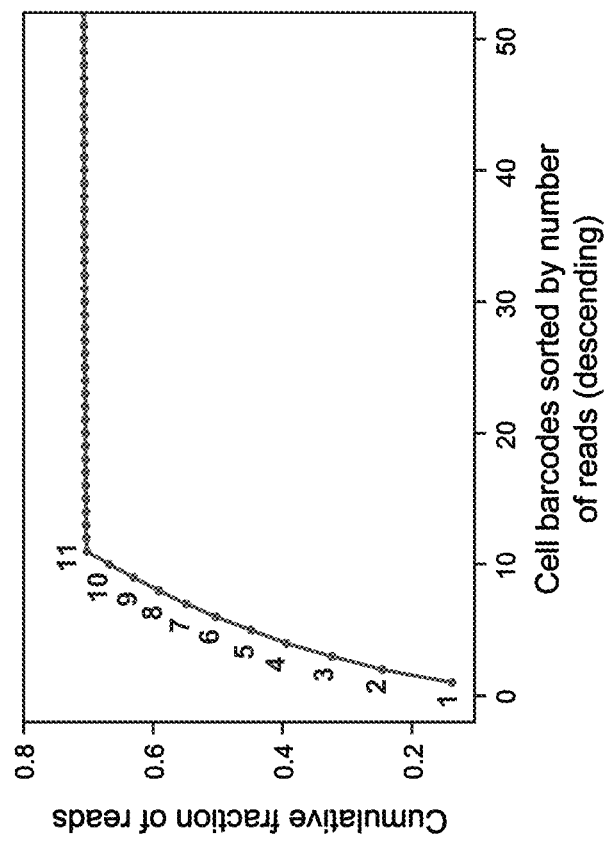
Figure 14B:
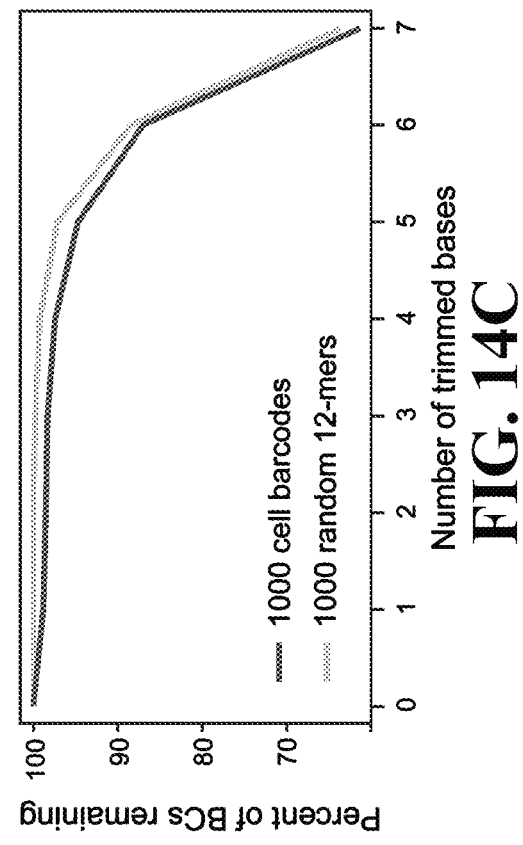

FIGS. 14A-C illustrate an assessment of the properties of barcoded primers on the surface of microparticles (beads). (A) Identification of individual bead barcodes in a multiplexed experiment. A synthetic polyadenylated RNA was reverse transcribed onto the surface of barcoded primer beads. Eleven of these beads were then manually selected and used as a template for construction of a sequencing library (Extended Experimental Procedures). The library was sequenced on a MiSeq, and the cell barcode sequences gathered and counted. A sharp distinction was observed between the numbers of reads carrying the eleventh and twelfth most abundant 12mers at the barcode position in the sequencing read, demonstrating that cell barcodes from each bead can be recognized from their high representation in the results of a sequencing experiment. (B) Base composition analysis of 12 bp cell barcodes. The sequences of 1,000 cell barcodes, ascertained in another sequencing experiment, were assessed for overall nucleotide and dinucleotide composition. Red dotted lines represent the values for completely random barcode sets that would lack any sequence bias. (C) Computational truncation of 12 bp cell barcodes. The 1,000 cell barcode sequences in (B) were trimmed from the 3' end, and the number of unique barcodes remaining was calculated at each number of trimmed bases (blue line). The number of unique barcodes at each number of trimmings was compared to a randomly generated set of 1,000 12-mers (green line).

FIGS. 15A-E illustrate device design and dissection of technical contributions to single-cell impurities in Drop-Seq library preparations. (A) Microfluidic co-flow device design. Three inlets—for oil, cell suspension, and microparticles—converge and generate aqueous droplets composed of equal volume contributions from the cell suspension and microparticle channels. A winding, bumpy outlet improves mixing of the droplets to promote hybridization of released RNAs onto the beads. A CAD file of the device can be found in DataFile 1. (B) Identification of STAMPs in a pool of amplified beads. Drop-Seq involves generation of single-cell profiles by diluting cells to poisson-limiting concentrations in droplets; therefore, the great majority of amplified beads (90-99%) were not exposed to a cell's RNA, only ambient RNA. To identify the cell barcodes corresponding to STAMPs, cell barcodes from the experiment shown in FIG. 3A are arranged in decreasing order of size (number of reads), and the cumulative fraction of reads is plotted. An inflection point (vertical dotted line at 570) is observed very close to the number of cells predicted by Poisson statistics for the counted and aliquoted number of beads (~500). Confirmation of this inflection point was observed by plotting the species specificity of individual STAMPs, and observing a dramatic drop in specificity at the inflection point, indicating the transition from beads that sampled cellular RNA, to the beads that sampled ambient RNA. (C) Human-mouse experiments on Fluidigm C1. Human (HEK) and mouse (3T3) cells were mixed at equal concentrations and run on two Fluidigm C1 chips according to the manufacturer's instructions. Reads were aligned to a joint human-mouse reference in exactly the same analysis pipeline as Drop-Seq. Fifty-six mixed-organism libraries were identified out of 182, placing a lower bound of 31% on cell-cell doublets. Twelve C1 ports were identified as possessing >1 cell by microscopy, of which five were mixed species by sequencing. (D) Concentration dependence of Drop-Seq library purity. STAMPs were prepared using a mixture of human (HEK) and mouse (3T3) cells at four different concentrations (N=1150, 690, 595, and 560 STAMPs for 100 cells/µl, 50 cells/µl, 25 cells/µl, and 12.5 cells/µl respectively). The rate of cell doublets was calculated by multiplying by two the number of mixed species STAMPs; single-cell purity was calculated by summing the mean human-cell and mean mouse-cell purities. (E) Single-cell impurity analysis. Drop-Seq libraries were prepared from combinations of human and mouse cells pooled at three different stages of DropSeq library preparation. In the first condition, human and mouse cells were mixed together prior to droplet formation (red violin plot, "Cell Mix"). In the second condition, human and mouse cells were separately encapsulated in droplets, which were then mixed before breaking them and performing subsequent analyses on the mixture (blue, "Droplet Mix"). In the third condition, human and mouse cells were separately encapsulated in droplets, which were broken in separate reactions and then reverse-transcribed to form separate pools of covalent STAMPs, which were mixed prior to PCR amplification (green, "PCR Mix"). The twenty largest STAMPs from each organism were selected for each of the three conditions, downsampled to the same read depth, and the organism purity represented as violin plots. The black dot is the average organism purity of the forty STAMPs in each distribution. The cell mixes used were diluted to a final concentration of 50 cells/µl in droplets. From these data Applicants estimate that (at this cell concentration) cell suspension contributes 48% of impurities, RNA transfer after droplet breakage contributes 40%, and PCR artifacts contribute 12%.

FIGS. 16A-F illustrate specificity and sensitivity as a function of sequencing coverage, evaluated by down-sampling low-depth and high-depth species-mixed (HEK/293T) Drop-Seq libraries prepared at a concentration of 50 cells/µl. (A,B) Analysis of specificity. Downsampling analysis of species specificity for human-specific STAMPs and mouse-specific STAMPs that were sequenced at lower read-depth (panel A, 589 human-specific and 412 mouse-specific STAMPs) or higher read-depth (panel B, 54 human and 28 mouse). (C-F) Analysis of sensitivity. Downsampling analysis of single-cell library sensitivity by average number of genes detected (C and D) and average number of transcripts detected (E and F) for the lower read-depth Drop-Seq run (C and E) and higher read-depth sequencing (D and F).

FIGS. 17A-F illustrate estimation of Drop-Seq expression bias and capture efficiency. (A) GC content bias between average gene expression in Drop-Seq and in-solution template-switch amplification (TSA). Comparison of average gene expression in low GC content genes (<0.4 average content, red dots) from a library of 550 3T3 STAMPs, and an mRNA-seq library prepared by an in-solution template switch amplification (TSA) procedure similar to Smart-Seq2 (Picelli et al., 2013) (Extended Experimental Procedures), using RNA derived from the same cell culture flask that was used in Drop-Seq. (B) GC content bias between average gene expression in Drop-Seq and standard mRNA-seq. Comparison of average gene expression in low GC content genes (<0.4 average content, red dots) from a library of 550 3T3 STAMPs, and an mRNA-seq library prepared by standard methods (Extended Experimental Procedures), using RNA derived from the same cell culture flask that was used in Drop-Seq. (C) Length bias between average gene expression in Drop-Seq and standard mRNA-seq. Comparison of average gene expression in long transcripts (>5000 average transcript length, red dots) from a library of 550 3T3 STAMPs, and an mRNA-seq library prepared by standard methods (Extended Experimental Procedures), using RNA derived from the same cell culture flask that was used in Drop-Seq. The bias observed here was not found in a comparison of Drop-Seq and in-solution TSA (data not shown), indicating that this bias is likely the result of template suppression PCR, which preferentially amplifies longer fragments (Zhu et al., 2001). (D) Sensitivity estimation by ddPCR. RNA was isolated from a culture of 50,000 HEK cells, and levels of ten genes (ACTB, B2M, CCNB1, GAPDH, EEF2, ENO1, PSMB4, TOP2A, YBX3, and YWHAH) were digitally quantitated in this bulk solution using RT-ddPCR. These transcript counts were then compared to the average number of unique transcripts counted per cell by Drop-Seq. Error bars show the standard error for individual ddPCR measurements (horizontal bars, N=3 replicates) or across STAMPs (vertical bars, N=54). Based upon the mean of these ten gene expression measurements, Applicants estimate that DropSeq captures approximately 10.7% of cellular mRNAs. (E) Capture efficiency of barcoded primer beads. The same barcoded primer beads used in Drop-Seq were hybridized in solution to purified human brain RNA at a concentration of 20 ng/µl (Extended Experimental Procedures). The beads were then spun down and washed three times, and the bound RNA eluted by heating the beads in the presence of water. The concentrations of two mRNA transcripts, GAPDH and ACTB, were measured in each of the five steps. Error bars, standard error of the mean. (F) Assessment of barcoded bead primer binding saturation. The same procedure described in (E) was performed using three different input RNA concentrations: 20 ng/µl, 50 ng/µl and 100 ng/µl. The fraction of input RNA that was eluted off the beads scaled linearly with input RNA concentration, indicating that hybridization to the beads was not limited by a saturation of mRNA binding sites.

Figure 18:
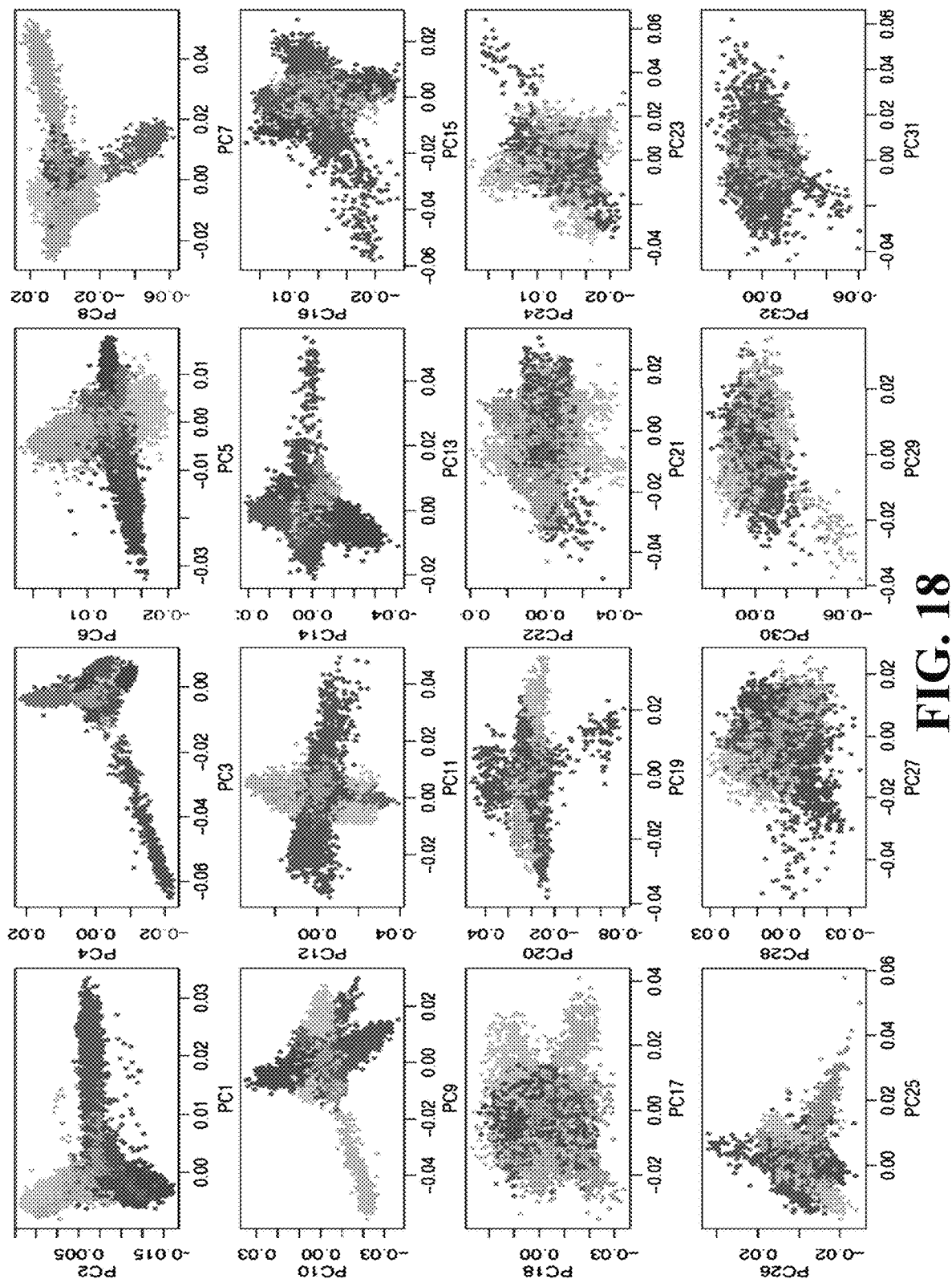
FIG. 18 illustrates plots of principal components 1-32 of the 44,808 retinal cell STAMPs used in analysis.

FIG. 18 illustrates plots of principal components 1-32 of the 44,808 retinal cell STAMPs used in analysis. (A) Uncolored PCA plots of 44,808 STAMPs; (B) the same PCA plots in (A), but each cell is colored by their final cluster identity, using the colors in FIG. 11B.

Figure 19:
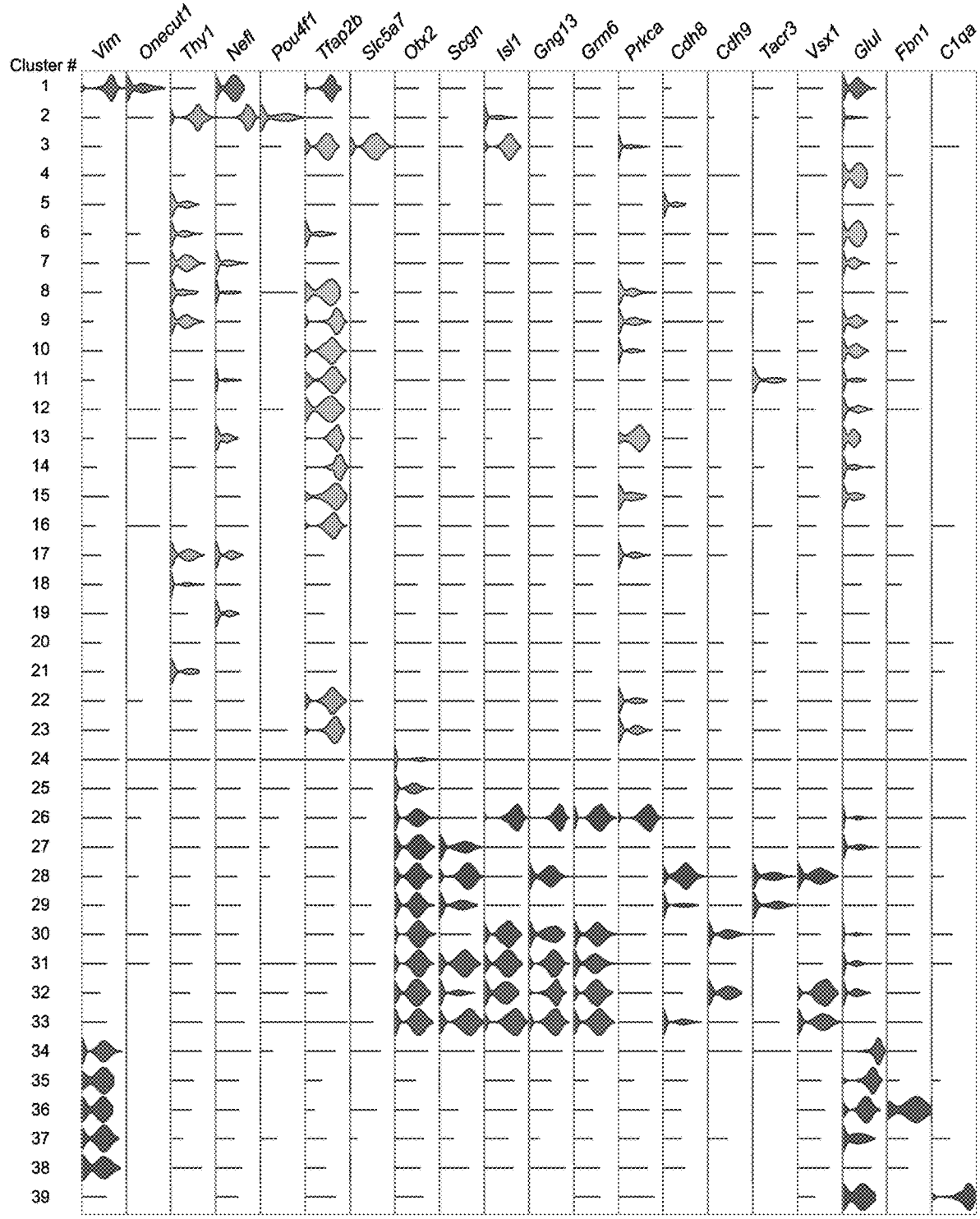
FIG. 19 illustrates violin plots showing expression of selected marker genes in the 39 retinal cell clusters generated by unsupervised analysis of single-cell gene expression.

FIG. 19 illustrates violin plots showing expression of selected marker genes in the 39 retinal cell clusters generated by unsupervised analysis of single-cell gene expression.

Figure 20:
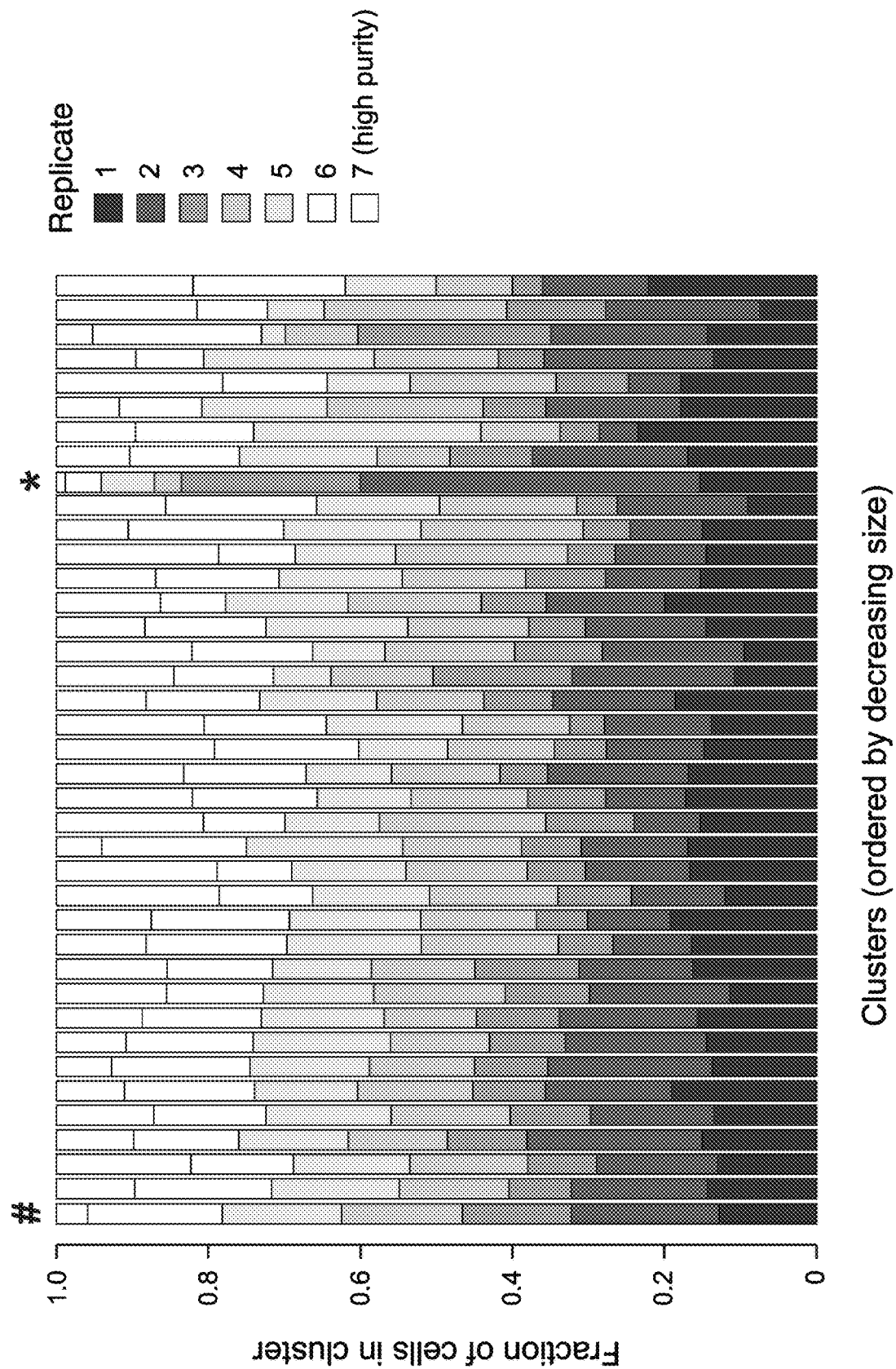
FIG. 20 shows the fraction of each cluster composed of cells deriving from one of the seven replicates that composed the full 44,808-cell data set.

FIG. 20 shows the fraction of each cluster composed of cells deriving from one of the seven replicates (prepared over four different days, (Extended Experimental Procedures), that composed the full 44,808-cell data set. The fractions of each replicate are represented as a stacked barplot. Replicates 1-6 were prepared in an "aggressive mode" of Drop-Seq (~90% single-cell, ~90% purity); replicate 7 was prepared in a "pure mode" (>99% single-cell, 98.6% purity). The stars designate two imbalanced cluster, #36, corresponding to contaminating fibroblasts that result from imperfect retinal dissection.

Figure 21:
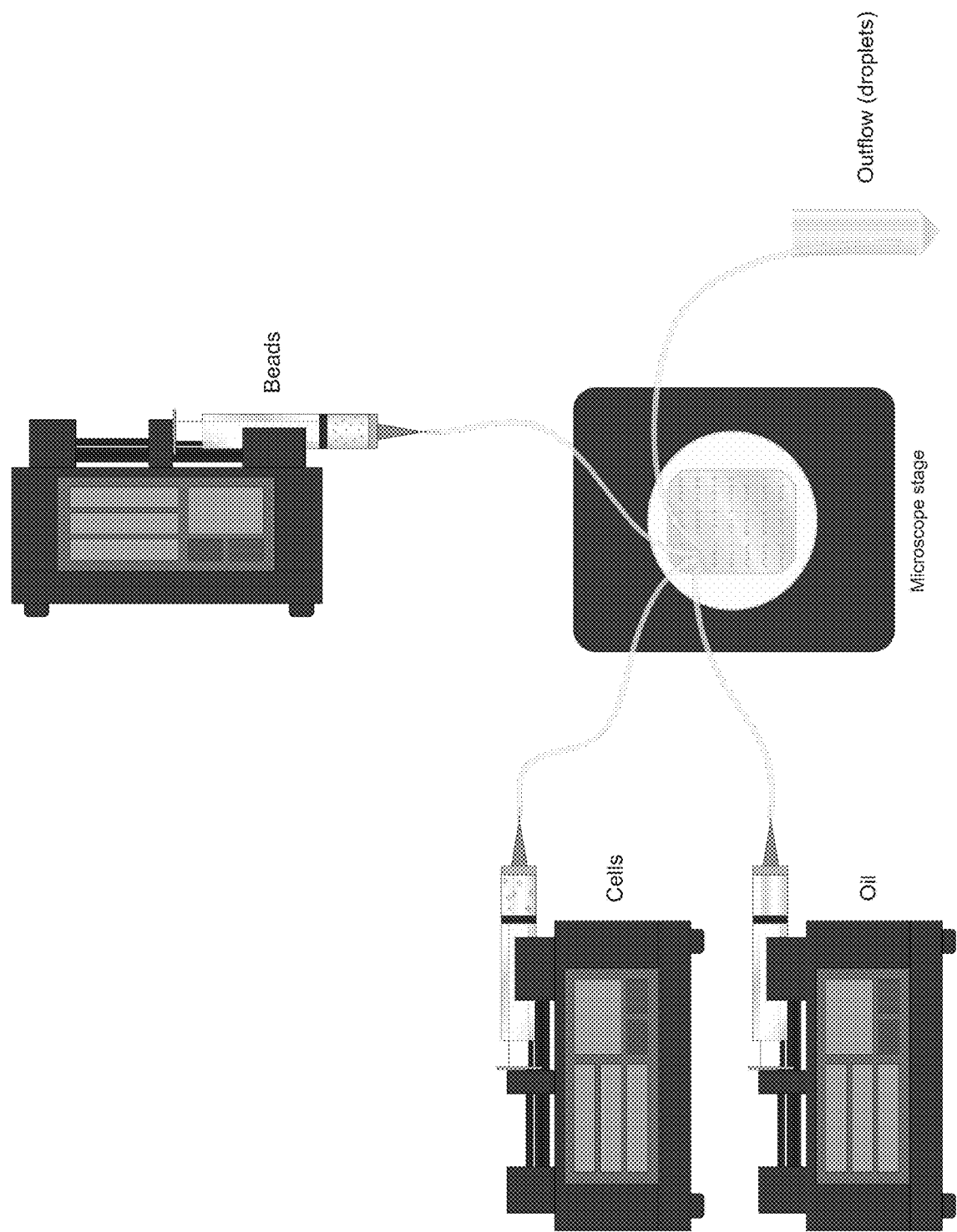
FIG. 21 illustrates a schematic representation of Drop-Seq setup.

FIG. 21 illustrates a schematic representation of Drop-Seq setup. Three syringe pumps, loaded with oil, cells, and beads, respectively, are connected to the PDMS device in FIG. S2A via flexible tubing. The device rests on the stage of an inverted microscope so that droplet generation can be monitored in real-time. Tubing connects the outlet channel to a 50 mL conical tube for collection of droplets.

In certain embodiments, the carrier fluid may be caused to flow through the outlet channel so that the surfactant in the carrier fluid coats the channel walls. In one embodiment, the fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Fluorinert (3M)), which then serves as the carrier fluid.

Activation of sample fluid reservoirs 1012 to produce regent droplets 1006 is now described. The disclosed invention is based on the concept of dynamic reagent delivery (e.g., combinatorial barcoding) via an on demand capability. The on demand feature may be provided by one of a variety of technical capabilities for releasing delivery droplets to a primary droplet, as described herein.

An aspect in developing this device will be to determine the flow rates, channel lengths, and channel geometries. Once these design specifications are established, droplets containing random or specified reagent combinations can be generated on demand and merged with the "reaction chamber" droplets containing the samples/cells/substrates of interest.

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device described herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

A plurality of biological assays as well as biological synthesis are contemplated for the present invention.

In an advantageous embodiment, polymerase chain reactions (PCR) are contemplated (see, e.g., US Patent Publication No. 20120219947). Methods of the invention may be used for merging sample fluids for conducting any type of chemical reaction or any type of biological assay. In certain embodiments, methods of the invention are used for merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The first sample fluid contains nucleic acid templates. Droplets of the first sample fluid are formed as described above. Those droplets will include the nucleic acid templates. In certain embodiments, the droplets will include only a single nucleic acid template, and thus digital PCR may be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. This type of partitioning of the reagents between the two sample fluids is not the only possibility. In certain embodiments, the first sample fluid will include some or all of the reagents necessary for the PCR whereas the second sample fluid will contain the balance of the reagents necessary for the PCR together with the detection probes.

Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

A droplet containing the nucleic acid is then caused to merge with the PCR reagents in the second fluid according to methods of the invention described above, producing a droplet that includes Taq polymerase, deoxynucleotides of type A, C, G and T, magnesium chloride, forward and reverse primers, detectably labeled probes, and the target nucleic acid.

Once mixed droplets have been produced, the droplets are thermal cycled, resulting in amplification of the target nucleic acid in each droplet. In certain embodiments, the droplets are flowed through a channel in a serpentine path between heating and cooling lines to amplify the nucleic acid in the droplet. The width and depth of the channel may be adjusted to set the residence time at each temperature, which may be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001).

In certain embodiments, the three temperature zones are controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme.

The nucleic acids undergo the same thermal cycling and chemical reaction as the droplets pass through each thermal cycle as they flow through the channel. The total number of cycles in the device is easily altered by an extension of thermal zones. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double stranded nucleic acid in the droplets is fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

After amplification, droplets may be flowed to a detection module for detection of amplification products. The droplets may be individually analyzed and detected using any methods known in the art, such as detecting for the presence or amount of a reporter. Generally, the detection module is in communication with one or more detection apparatuses. The detection apparatuses may be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In another embodiment, examples of assays are ELISA assays (see, e.g., US Patent Publication No. 20100022414). The present invention provides another emulsion library which may comprise a plurality of aqueous droplets within an immiscible fluorocarbon oil which may comprise at least one fluorosurfactant, wherein each droplet is uniform in size and may comprise at least a first antibody, and a single element linked to at least a second antibody, wherein said first and second antibodies are different. In one example, each library element may comprise a different bead, wherein each bead is attached to a number of antibodies and the bead is encapsulated within a droplet that contains a different antibody in solution. These antibodies may then be allowed to form "ELISA sandwiches," which may be washed and prepared for a ELISA assay. Further, these contents of the droplets may be altered to be specific for the antibody contained therein to maximize the results of the assay.

In another embodiment, single-cell assays are also contemplated as part of the present invention (see, e.g., Ryan et al., Biomicrofluidics 5, 021501 (2011) for an overview of applications of microfluidics to assay individual cells). A single-cell assay may be contemplated as an experiment that quantifies a function or property of an individual cell when the interactions of that cell with its environment may be controlled precisely or may be isolated from the function or property under examination. The research and development of single-cell assays is largely predicated on the notion that genetic variation causes disease and that small subpopulations of cells represent the origin of the disease. Methods of assaying compounds secreted from cells, subcellular components, cell-cell or cell-drug interactions as well as methods of patterning individual cells are also contemplated within the present invention.

In other embodiments, chemical prototyping and synthetic chemical reactions are also contemplated within the methods of the invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

In this protocol, uniquely barcoded beads are synthesized for use as primers for reverse transcription. Beads begin first with having a fixed sequence (SMT A in FIG. 2A) synthesized on the surface, which is used as a priming site for downstream PCR. Next, beads are split and pooled into four equal reaction vessels a total of 12 times, to generate $4^{\wedge}12$ unique barcode sequences that are unique to each bead (FIG. 2B). This 12 bp region will serve as the cell barcode, since it is specific to each bead. Next, the beads are all pooled together for 8 rounds of degenerate synthesis with all four bases; this 8 bp region is a "molecular barcode" and will tag each mRNA uniquely, so that each mRNA molecule in a cell can be digitally counted. Finally, 30 dT bases are synthesized, which serves as the capture region for the polyadenylated tails of mRNAs (referred to frequently in the literature as "oligo dT").

Synthesis of Uniquely Barcoded Beads

Toyopearl HW-65S resin was purchased from Tosoh Biosciences, inc. Surface hydroxyls were reacted with a PEG derivative to generate an 18-carbon long, flexible-chain linker. The derivatized bead was then used as a solid support for reverse 5'→3' phosphoramidite synthesis on an Expedite 8909 DNA/RNA synthesizer using DNA Synthesis 10 µmol cycle scale and a coupling time of 3 minutes. Amidites used were: $N^6$—Benzoyl-3'-O-DMT-2'-deoxyadenosine-5'-cyanoethyl-N,N-diisopropyl-phosphoramidite (dA-N-Bz); $N^4$-Acetyl-3'-O-DMT-2'-deoxy-cytidine-5'-cyanoethyl-N, N-diisopropyl-phosphoramidite (dC-N-Ac); $N^2$-DMF-3'-O-DMT-2'-deoxyguanosine-5'-cyanoethyl-N,N-diisopropylphosphoramidite (dG-N-DMF); 3'-O-DMT-2'-deoxythymidine-5'-cyanoethyl-N,N-diisopropylphosphoramidite; and 3'-O-DMT-2'-deoxyuridine-5'-cyanoethyl-N,N-diisopropylphosphoramidite. Acetic anhydride and N-methylimidazole were used in the capping step; ethylthiotetrazole was used in the activation step; iodine was used in the oxidation step, and dichloroacetic acid was used in the deblocking step. The oligonucleotide sequence generated on the bead surface is shown in FIG. 2A. A constant sequence ("SMT A in figure") for use as a PCR handle, is synthesized. Then, 12 cycles of pool-and-split phosphoramidite synthesis are performed (the cell barcode or "CBC" in FIG. 2A). During these cycles, beads were removed from the synthesis column, pooled, and aliquoted into four equal portions by mass; these bead aliquots were then placed in a separate synthesis column and reacted with either dG, dC, dT, or dA phosphoramidite. This process was repeated 12 times for a total of $4^{\wedge}12 = 16,777,216$ unique barcode sequences (FIG. 2B). Upon completion of these cycles, 8 cycles of degenerate oligonucleotide synthesis were performed on all the beads, (the molecular barcode "MBC" in FIG. 2A) followed by 30 cycles of dT addition.

Characterization of Beads

1) Determination of bead binding capacity for polyadenylated RNA. Saturating quantities (100 pmol per 20,000 beads) of polyadenylated synthetic RNA was annealed to barcodes beads in 2×SSC for 5 min. The beads were then washed 3× with 200 ul of 1×TE+0.01% Tween, and resuspended in 10 ul of TE. The beads were then heated at 65 C for 5 min, and a ul of the supernatant was quantified on the Nanodrop Spectrophotometer at 260 nm.

2) Determination of quality and homogeneity of cell barcode sequences. Synthetic RNA was flowed into a 125 µl microfluidic co-flow droplet generation device at a concentration of 0.2 uM. The other flow contained a 2× reverse transcription mix. The droplets were incubated at 42° C. for 30 minutes, then broken. 11 beads were picked to a PCR tube and amplified with 17 cycles of PCR. The amplicon product was purified and quantified on the Bioanalyzer 2100, then sequenced on MiSeq. The cell barcode sequences were extracted and collapsed at edit distance 1 to obtain FIG. 3B.

Figure 3C:
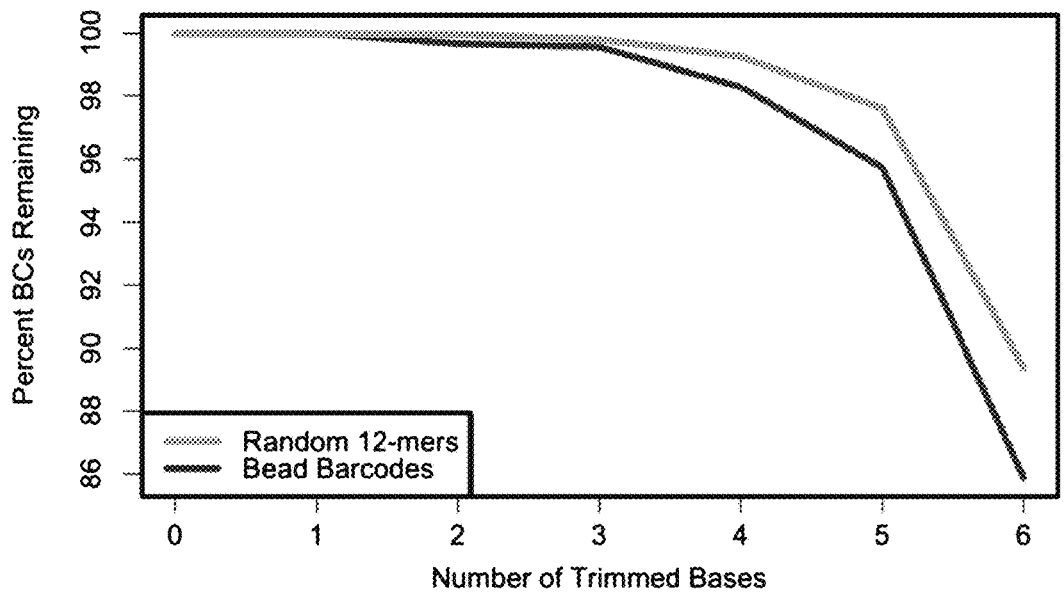
Figure 3D:
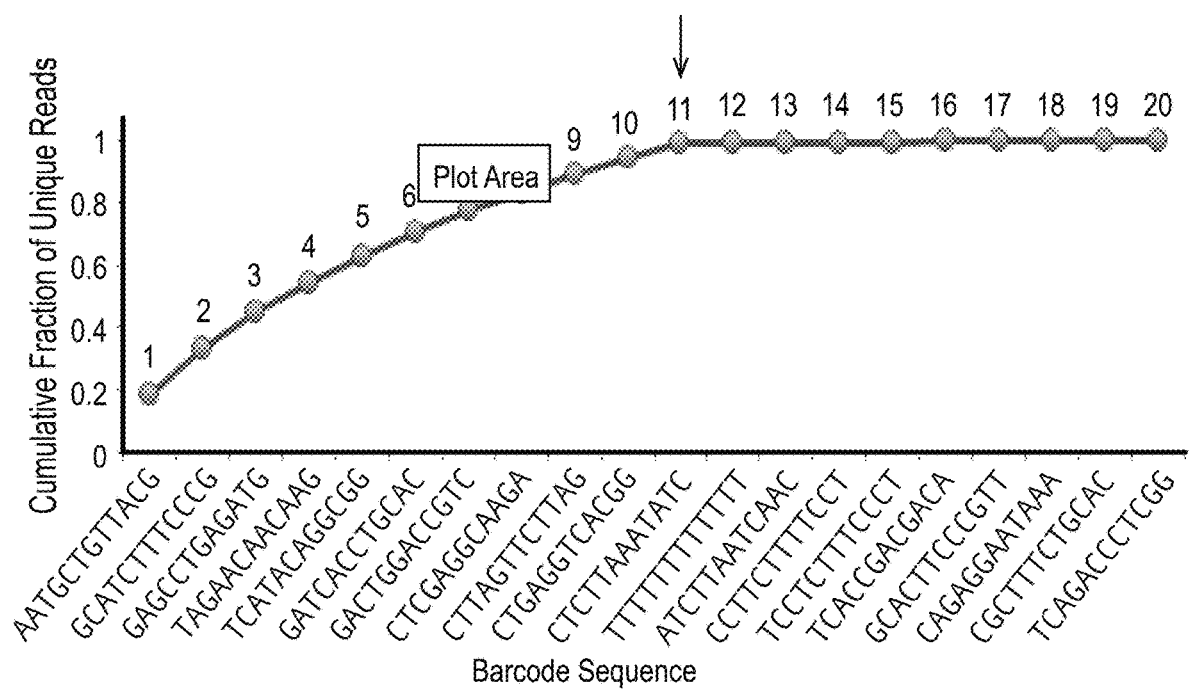

3) Determination of cell barcode complexity. 1000 cell barcode sequences were analyzed for base composition (FIG. 3A), dinucleotide composition (FIG. 3B), and were serially trimmed from the 3' end and checked for duplicate sequences (FIG. 3C). In all three analyses, the empirical cell barcodes displayed complexity that was only slightly below the theoretical limit of their complexity given their length ($4^{\wedge}12$ unique sequences).

DropSeq Protocol

| 1. Reagents for preparing cells and beads for processing: Lysis Buffer (per mL): |
|---|
| 680 µl H$_2$O |
| 120 µl 50% Ficoll |
| 10 µl 20% Sarkosyl |
| 40 µl EDTA |
| 100 µl 2M Tris pH 7.5 |
| 50 µl 1M DTT (add at the end) |

| PBS-BSA: |
|---|
| 995 µl cold 1x PBS |
| 5 µl NEB BSA (20 mg/ml) |

Prepare the oil and device: Load oil into a 10 mL syringe. Affix needle (27G1/2) and tubing (PE-2), push oil through the tubing to the end, and load into pump. Place the tubing end in the left-most channel of a clean device (See FIG. 6, all features on device are 125 µm deep).

Cell Culture

Human 293 T cells were purchased as well as murine NIH/3T3 cells. 293T and 3T3 cells were grown in DMEM supplemented with 10% FBS and 1% penicillin-streptomycin.

Cells were grown to a confluence of 30-60% and treated with TrypLE for five min, quenched with equal volume of growth medium, and spun down at 300× g for 5 min. The supernatant was removed, and cells were resuspended in 1 mL of 1×PBS+0.2% BSA and re-spun at 300×g for 3 min. The supernatant was again removed, and the cells re-suspended in 1 mL of 1×PBS, passed through a 40-micron cell strainer, and counted. For Drop-Seq, cells were diluted to the final concentration in 1×PBS+200 µg/mL BSA.

Generation of Whole Retina Suspensions

Single cell suspensions were prepared from P14 mouse retinas by adapting previously described methods for purifying retinal ganglion cells from rat retina (Barres et al., 1988). Briefly, mouse retinas were digested in a papain solution (40U papain/10 mL DPBS) for 45 minutes. Papain was then neutralized in a trypsin inhibitor solution (0.15% ovomucoid in DPBS) and the tissue was triturated to generate a single cell suspension. Following trituration, the cells were pelleted and resuspended and the cell suspension was filtered through a 20 µm Nitex mesh filter to eliminate any clumped cells and this suspension was then used for Drop-Seq. The cells were then diluted in DPBS+0.2% BSA to either 200 cells/µl (replicates 1-6) or 30 cells/µl (replicate 7).

Retina suspensions were processed through Drop-Seq on four separate days. One library was prepared on day 1 (replicate 1); two libraries on day 2 (replicates 2 and 3); three libraries on day 3 (replicates 4-6); and one library on day 4 (replicate 7, high purity). To replicates 4-6, human HEK cells were spiked in at a concentration of 1 cell/µl (0.5%) but the wide range of cell sizes in the retina data made it impossible to calibrate single-cell purity or doublets using the cross-species comparison method. Each of the seven replicates was sequenced separately.

Preparation of Beads

Beads (either Barcoded Bead SeqA or Barcoded Bead SeqB) were washed twice with 30 mL of 100% EtOH and twice with 30 mL of TE/TW (10 mM Tris pH 8.0, 1 mM EDTA, 0.01% Tween). The bead pellet was resuspended in 10 mL TE/TW and passed through a 100 µm filter into a 50 mL Falcon tube for long-term storage at 4° C. The stock concentration of beads (in beads/µL) was assessed using a Fuchs-Rosenthal cell counter. For Drop-Seq, an aliquot of beads was removed from the stock tube, washed in 500 µL of Drop-Seq Lysis Buffer (DLB, 200 mM Tris pH 7.5, 6% Ficoll PM-400, 0.2% Sarkosyl, 20 mM EDTA), then resuspended in the appropriate volume of DLB+50 mM DTT for a bead concentration of 100 beads/µL.

Cell lysis and mRNA hybridization to beads on the microfluidic device. 1) Surfactant-containing oil; 2) cells suspended in aqueous solution (like PBS); and 3) barcoded beads suspended in a lysis agent (i.e., detergent). Cells and beads are flowed simultaneously into the device, where they unite and form droplets. Once inside the droplets, the cells lyse, RNA is released, and captured onto the surface of the barcoded bead by hybridization.

Syringe Pump: 14,000 µl/hr for oil; 4,100 µl/hr each for beads and cells; collect droplets in 50 mL falcon tubes; use 1 falcon tube per 1500 µl of aqueous solution (750 µl of each flow).

3. Post-Device Processing of RNA-Hybridized Beads into cDNA

| BREAK DROPLETS: |
|---|
| Immediately after completing droplet generation, remove oil from the bottom. |
| Add 30 mL of room temperature 6x SSC. Shake. |
| 6x SSC |
| Add 600 µl of Perfluorooctanol (PFO). Mix well. |
| Spin at 1000xg for 1 minute. |
| Remove all but ~2-3 mL of liquid. Add 30 mL 6x SSC and spin again. |
| Remove all but <1 mL of liquid. Transfer to eppendorf tubes and spin down to remove the supernatant. |
| Wash 2x with 1 mL of 6x SSC then once with 300 µl of 5x RT buffer. |

| Reverse transcription: RT Mix (per 90,000 beads): |
|---|
| 75 µl H$_2$O |
| 40 µl Maxima 5x RT Buffer |
| 40 µl 20% Ficoll PM-400 |
| 20 µl 10 mM dNTPs (Clontech) |
| 5 µl RNase Inhibitor (Lucigen) |
| 10 µl 50 µM Template Switch Oligo |
| 10 µl Maxima H-RT (add just before starting RT) |

| Incubate and rotate at: |
|---|
| RT for 30 minutes |
| 42° C. for 90 minutes |

| Wash |
|---|
| Wash beads once with TE + 0.5% SDS, |
| then 2x with TE + TW (0.02%), |
| then add 1 mL 10 mm Tris pH 7.5. |

Microfluidic device is fabricated using polydimethylsiloxane (PDMS) from a master made of SU8 photo-resist1. The PDMS device is then plasma-treated to bond with a glass microscope slide (75 mm×50 mm×1 mm). Since we work with a continuous oil phase, the channels are rendered hydrophobic by flowing in Aquapel (Rider, Mass., USA)

through the oil inlet and flushing out the excess fluid through the remaining inlets/outlets using pressurized air. See McDonald, J. C. et al. Fabrication of microfluidic systems in poly(dimethylsiloxane). *Electrophoresis* 21, 27 (2000).

Example 2: Genome-Wide Expression Profiling of Thousands of Individual Cells Using Nanoliter Droplets Disease takes place within complex tissues, made of different types of cells, and (almost) never involves a single cell acting on its own: cells interact with each other constantly, making collective decisions, coordinating dynamic changes and working together. In normal tissue this results in homeostasis; in disease a malfunction in one or more interactions can lead to or exacerbate pathology.

Cells, the basic units of biological structure and function, vary broadly in type and state. Single cell genomics can characterize cell identity and function, but limitations of ease and scale have prevented its broad application. Here Applicants describe Drop-Seq, a strategy for quickly profiling thousands of individual cells by separating them into nanoliter-sized aqueous droplets, applying a different barcode to each cell's RNAs, and sequencing them all together. Drop-Seq analyzes mRNA transcripts from thousands of individual cells while remembering transcripts' cell of origin. Applicants analyzed transcriptomes from 44,808 mouse retinal cells and defined thirty-nine distinct cell populations, recapitulating the major retinal cell classes, identifying candidate markers of subtypes, and profiling gene expression in each. Applicants also analyzed 471 human bone marrow cells and defined eight distinct cell populations. Drop-Seq will accelerate biological discovery by enabling routine transcriptional profiling at single-cell resolution.

Individual cells are the building blocks of tissues, organs, and organisms. Each tissue contains cells of many types, and cells of each type can switch among biological states. The number of cell types in a tissue can be over 100, and the number of states per cell is unknown. Because each type and state has unique functional capacities, responses and molecular compositions, it will be necessary to ascertain cell types and states to understand tissue physiology, developmental processes, and disease.

In most biological systems, Applicants' knowledge of cellular diversity is incomplete. For example, the cell-type complexity of the brain is unknown and widely debated (Luo et al., 2008; Petilla Interneuron Nomenclature et al., 2008). Many important but rare cell populations likely are undiscovered. Such rare types can play critical roles. Purkinje neurons, for example, are essential to brain function though they comprise less than 0.05% of neurons in the cerebellum (Andersen et al., 1992). Discovering a rare cell population may require analyzing large numbers of cells, ideally in an unbiased manner.

A major determinant of each cell's function is its transcriptional program. Recent advances now enable mRNA-seq analysis of individual cells (Kurimoto et al., 2006; Tang et al., 2009). HoFIGS.ver, current methods of preparing cells for profiling are applied to hundreds (Hashimshony et al., 2012; Islam et al., 2012; Picelli et al., 2013; Pollen et al., 2014; Shalek et al., 2014) or (with automation) a few thousand cells (Jaitin et al., 2014), typically after first separating the cells by sorting (Shalek et al., 2013), picking (Hashimshony et al., 2012), or microfluidics (Shalek et al., 2014), and then amplifying each cell's transcriptome in its own well or microfluidics chamber. Scalable approaches will be needed to characterize complex tissues with many cell types and states, under diverse conditions and perturbations. Profiling large numbers of cells may also be important for distinguishing noise from biologically meaningful patterns (sometimes involving small numbers of genes) that recur in many cells (Grun et al., 2014; Kharchenko et al., 2014).

The major obstacles to large-scale single-cell studies have been the cost and time involved in preparing large numbers of individual cells for sequencing. Here, Applicants describe a way to circumvent this obstacle by encapsulating thousands of individual cells in tiny "droplets"—nanoliter-scale aqueous compartments formed when water and oil mix—then barcoding the RNAs in each droplet in order to pool thousands of barcoded single-cell transcriptomes into one sample for sequencing. While single mRNA-sequence analysis is presently described, other types of nucleotides can be captured such as DNA and viruses from a cell or any molecular compound which can leverage phosphoramidite chemistry. Microfluidic devices can create tens of thousands of precisely sized ("monodisperse") picoliter- or nanoliter-scale droplets per minute (Thorsen et al., 2001; Umbanhowar, 2000). These droplets, which serve as tiny reaction chambers, have been used for PCR (Hindson et al., 2011; Vogelstein and Kinzler, 1999), reverse transcription (Beer et al., 2008), cell viability screens (Brouzes et al., 2009), and fluorescence microscopy (Jarosz et al., 2014). However, a basic challenge of using droplets for transcriptomics is to retain a molecular memory of the identity of the cell from which each mRNA transcript was isolated. The lack of effective molecular barcoding has prevented the application of droplets in many areas of genetics and genomics (Guo et al., 2012).

Here, Applicants address this challenge by introducing a barcoding system that endows each transcript with a droplet-specific molecular tag. Applicants' method, called Drop-Seq, combines droplet microfluidics with massive molecular barcoding to simultaneously label and process the mRNA transcripts from thousands of cells in one reaction for sequencing, without requiring mechanical sorting or picking of individual cells.

To demonstrate Drop-Seq's power to categorize cells in complex tissues, Applicants applied it to mouse retina. The retina is a powerful model for analysis of neural structure, function and development because, although it is about as complicated as any other part of the brain, it provides a complete and accessible circuit in a compact volume (Hoon et al., 2014; Masland, 2012; Masland and Sanes, 2015; Sanes and Zipursky, 2010). The retina contains five neuronal classes that are divided into ~100 types, only a minority of which have been molecularly characterized. Applicants used Drop-Seq to analyze 44,808 single cells from the mouse retina, from which Applicants computationally assembled an ab initio cell classification of 39 cell types based solely on patterns among the transcriptional profiles of many individual cells. This classification reproduces—in a single experiment—discoveries from decades of molecular, physiological, and anatomical investigations of the retina, while nominating many novel putative subtypes and specific markers. The results suggest how large-scale single-cell analysis will deepen Applicants' understanding of the biology of complex tissues and cell populations.

To further demonstrate Drop-Seq's capability and capacity to categorize cells in complex tissues, Applicants applied Drop-Seq in human bone marrow cells. Applicants explored human bone marrow cellular complexity on a limited number of cells and confirmed known key classifications based solely on their profiles.

Results

To efficiently profile vast numbers of individual cells, Applicants developed Drop-Seq, in which Applicants encapsulate cells in tiny droplets and barcode the transcripts from each individual droplet (encapsulated cell) to remember their cell of origin. Drop-Seq consists of the following steps (FIG. 7A): (1) prepare a single-cell suspension from a tissue; (2) co-encapsulate each individual cell with one distinctly barcoded microparticle, bead or particle (e.g., microbead, macrobead, nanoparticle, etc.) in a nanoliter-scale droplet; (3) lyse cells only after they have been isolated in droplets; (4) capture a cell's mRNAs on its companion microparticle, forming STAMPs (Single-cell Transcriptomes Attached to Microparticles); (5) reverse-transcribe, amplify, and sequence thousands of STAMPs in a single reaction; and (6) use the STAMP barcodes to infer each transcript's cell of origin. Applicants describe the key components of this approach and their validation.

A split-pool synthesis approach to generating large numbers of distinctly barcoded beads. The split-and-pool can occur after each cycle, or after any specified number of cycles. Thus, each barcode of information can range from a single nucleotide, to a dinucleotide or trinucleotide, etc.

To deliver large numbers of barcoded primer molecules into individual droplets, Applicants synthesized oligonucleotides directly on beads. As a bead material, Applicants used a methacrylate resin, originally developed for chromatography (Extended Experimental Procedures), composed of porous microparticles with substantial surface area. A variety of bead materials are envisioned as useful bead substrates. Examples of bead materials which may be employed include any bead which can leverage phosphoramidate chemistry such as those used in oligonucleotide synthesis known to those skilled in the art. Specific examples include, but are not limited to, functionalized polymers (e.g., methylacrylates, polysterenes, polyacrylamides, polyethyleneglycols), paramagnetic beads, and magnetic beads.

Applicants then used reverse-direction phosphoramidite synthesis to build oligonucleotides outwards from the microparticles from 5' to 3', yielding free 3' ends available for enzymatic priming (Cheong et al., 2012; Kadonaga, 1991; Srivastava et al., 2008). Phosphoramidite synthesis which is used to generate the barcodes, enables the chemical modification of any base along the oligonucleotide which can leverage this type of chemistry. Specific examples include, but are not limited to, barcoding with DNA bases, RNA bases, LNA bases, biotin-modified bases, fluorophore-conjugated bases, and non-canonical bases (i.e., iso-G, iso-C, iso-A, etc.). Additionally, these barcoded beads can be combined with other forms of barcoding, such as optional barcoding by patterning the bead or fluorescent labelling with various fluorophores or combinations of fluorophores.

Each microparticle-bound oligonucleotide is composed of five parts (FIG. 7B): (1) a constant sequence (identical on all primers) for use as a priming site for PCR and sequencing; (2) a "cell barcode" that is the same across all the primers on the surface of any one bead, but different from the cell barcodes on all other beads; (3) a Unique Molecular Identifier (UMI), different on each primer, that enables sequence reads derived from the same original mRNA molecule (amplification and PCR duplicates) to be identified computationally so that they are not double-counted (Kivioja et al., 2012); (4) an oligo dT sequence (30 bases) for capturing polyadenylated mRNAs and priming reverse transcription; and (5) a non-cleavable linker attached to the surface of the bead material (not labelled) and the priming sequence.

To efficiently generate massive numbers of beads, each with millions of copies of a cell barcode distinct from the barcodes on the other beads, Applicants developed a "split-and-pool" synthesis strategy (FIG. 7C). A pool of millions of microparticles is divided into four equally sized groups; a different DNA base (A, G, C, or T) is added to each of the four groups. The four groups of microparticles are then re-pooled, mixed, and re-split at random into another four groups, and another DNA base (A, G, C, or T) is added to each of the four new groups. After repeating this split-pool process 12 times, each bead's barcode reflects that bead's unique path through twelve synthesis reactions (FIG. 7C), such that all primers on a single microparticle possess the same one of $4^{12}=16,777,216$ possible 12-bp barcodes. The entire microparticle pool then undergoes eight rounds of degenerate oligonucleotide synthesis to generate the UMI on each oligo (FIG. 7D); finally, an oligo dT sequence (T30) is synthesized on 3' the end of all oligos on all beads.

In various embodiments of oligonucleotide bound bead synthesis, optional "floppy bases" may be used, such as oligo dT which is presently described. However, these "floppy bases" are not limited to T-bases and any suitable base can be used anywhere from 0 to 20 bases.

While microbeads are presently described, this method is not limited to "micro" sized beads and any appropriately sized bead is useful in an application where primers, PCR templates, transposons, siRNAs, or capture probes are delivered to a target compartment. The bead can simultaneously deliver both oligonucleotides and other chemical compounds, biological particles, or even reagents. Examples include but are not limited to a small molecule library, siRNA, an antibody, a virus, a bacterium, and so on. Thus, the bead size is related to the application of the bead. For example, a bead which is 1 cm in diameter can accommodate millions of primers then deliver the primers to a 96-well titer plate, where then the linker is cleaved to release and deliver the primers to these wells. Cleavable linkers can include a variety of polymers (or other types of "flexible" strain-chain compound) which hydrolyze under aqueous acidic or basic conditions, undergo photolysis, cleave under hydrogenation, or any method known to one of skill in the art to release the bead from the mRNA or nucleotide sequence.

Applicants assessed the quality and complexity of Applicants' barcoded beads in several ways. First, to estimate the number of primers per microparticle, Applicants hybridized synthetic polyadenylated RNA to microparticles, eluted the synthetic RNA, and measured its concentration; from these experiments, Applicants estimate that each bead contains more than 108 primer sites (Extended Experimental Procedures). Second, to determine the ability to distinguish RNA based on attached barcodes, Applicants reverse-transcribed synthetic RNA hybridized to 11 microparticles, amplified these barcoded cDNAs in a single solution, and created a sequencing library (Extended Experimental Procedures). In the resulting sequence data, 11 cell barcodes each constituted 3.5%-14% of the sequencing reads, whereas the next most abundant 12-mer at the barcode position constituted only 0.06% of reads (FIG. 14A). These results suggested that the microparticle-of-origin for most cDNAs can be recognized by sequencing. Finally, to assess the barcode complexity, Applicants sequenced cell barcodes from 1,000 microparticles and measured base and dinucleotide composition (FIG. 14B), along with the number of unique cell barcodes that remained as the sequence was computationally truncated (FIG. 14C). All three analyses suggested that the sequence diversity of the cell barcodes approached theoretical limits, and therefore that the cell barcodes could easily discriminate among thousands of STAMPs.

Figure 8A:
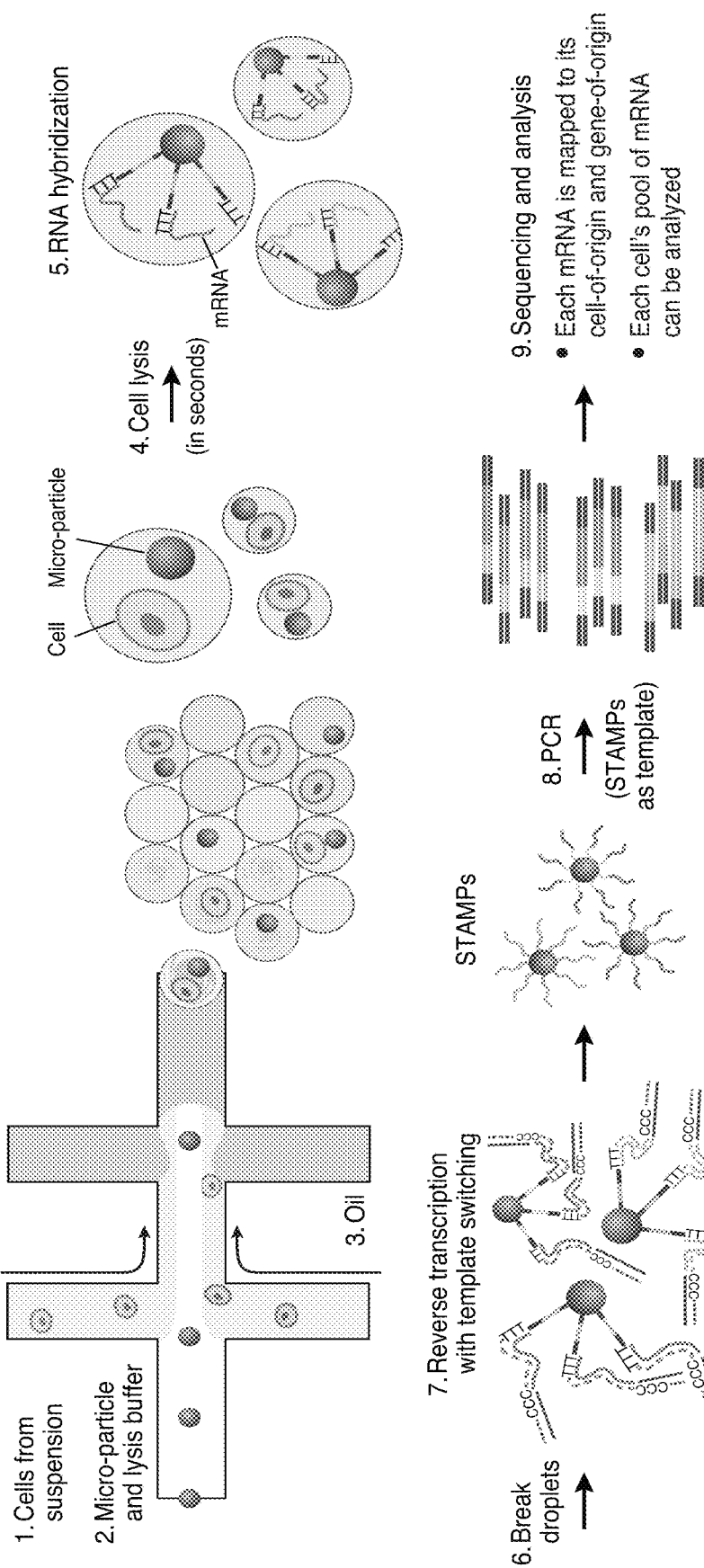
FIGS. 8 A-D illustrate extraction and processing of single-cell transcriptomes by Drop-Seq.
Figures 8B, 8C:
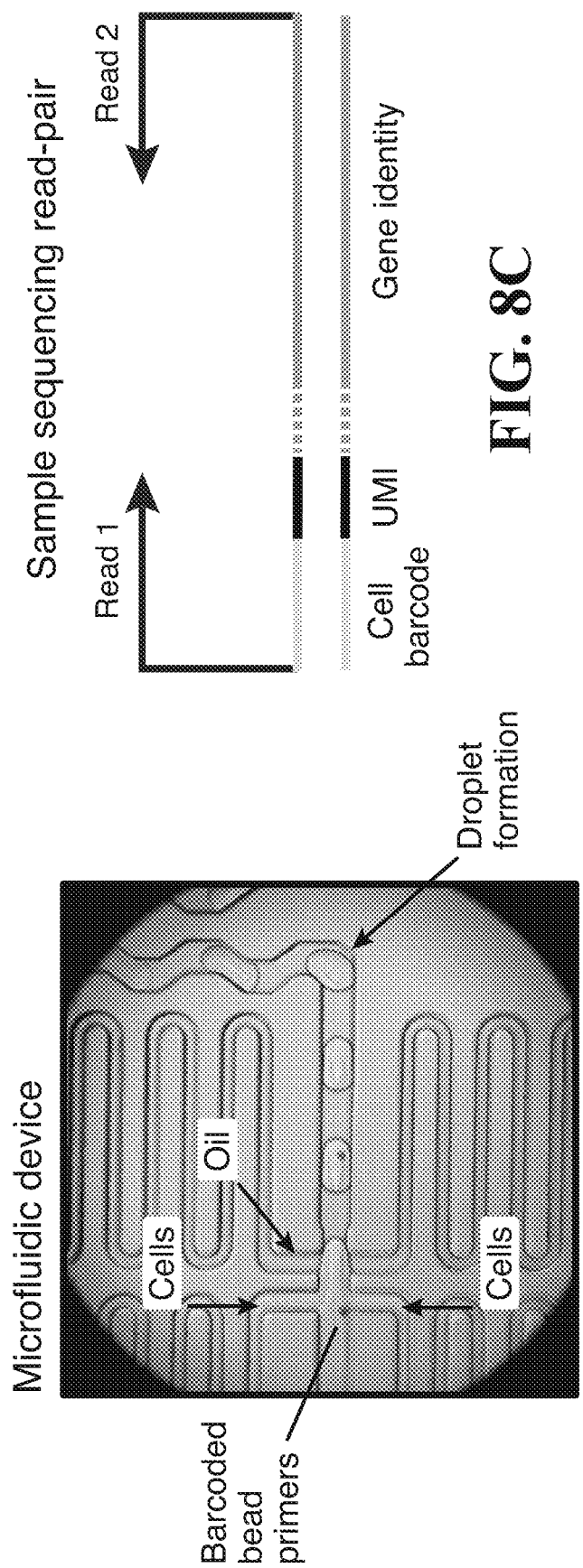

Microfluidics device for co-encapsulating cells with beads. Applicants designed a microfluidic "co-flow" device (Utada et al., 2007) to co-encapsulate cells with barcoded microparticles (FIGS. 8A, 14A). This device can quickly co-flow two aqueous solutions across an oil channel to form more than 50,000 nanoliter-sized droplets per minute. One flow contains the barcoded microparticles, suspended in a lysis buffer; the other flow contains a cell suspension (FIG. 8A, left). Flow is laminar prior to encapsulation, so that the two solutions mix only after droplet formation. To maximize cell lysis and the diffusion of mRNAs onto the bead's surface, Applicants' device contains "mixers" in which rapid mixing by chaotic advection occurs in a bumpy, winding microfluidic channel (Bringer et al., 2004).

The relative numbers of droplets, cells, and microparticles are key to the efficacy of Drop-Seq. The number of droplets created greatly exceeds the number of beads or cells injected, so that a droplet will generally contain zero or one cells, and zero or one beads. Carefully selecting the concentration of cells is also important for regulating cell-cell doublets and potential single-cell impurities, as Applicants discuss below. Millions of nanoliter-sized droplets are generated per hour, of which thousands contain both a bead and a cell. STAMPs are produced only in the subset of droplets that contain both a bead and a cell.

Figure 8D:
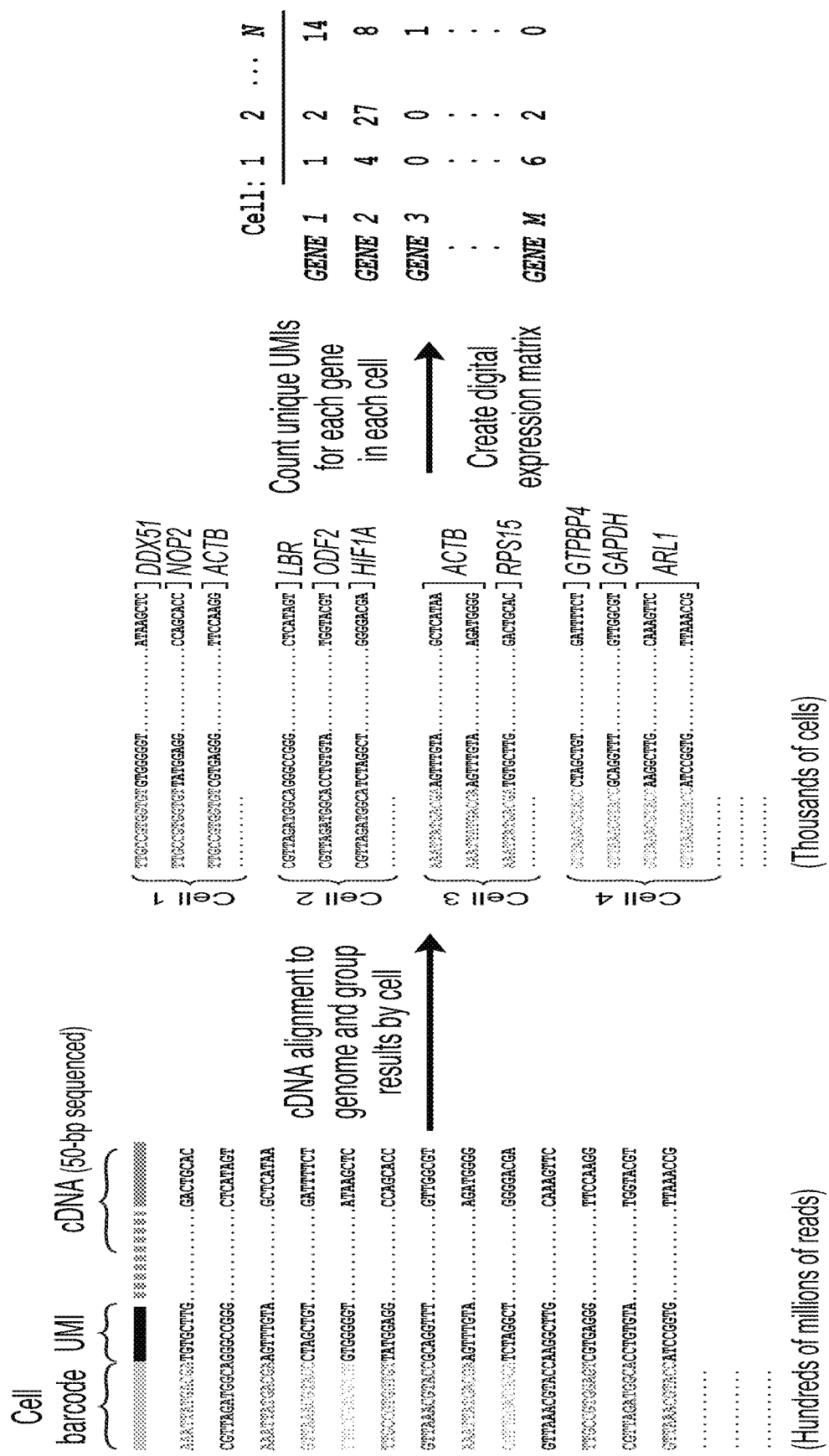

Sequencing and analysis of many STAMPs in a single reaction. To efficiently analyze thousands of STAMPs at once, Applicants developed a way to process the nucleic acids bound to any desired number of microparticles in one reaction. Applicants first break the droplets in a large volume of high-salt solution, to minimize the transfer of RNAs from bead to bead (Experimental Procedures). The mRNAs associated with the microparticles are then reverse-transcribed together in one reaction, forming covalent STAMPs (FIG. 8A, step 7). (Reverse transcription can in principle be performed within the droplets, though Applicants found it to be more efficient outside the droplets, potentially due to cell lysate-derived factors that inhibit the reaction (White et al., 2011).) Critically, at this stage, a scientist can select any desired number of STAMPs for analysis, much as one would select a desired number of cells from a cell suspension. STAMPs can be "banked" across multiple experiments; Applicants have stored STAMPs for more than two months without observing significant cDNA degradation (data not shown). Applicants PCR-amplify the barcoded cDNAs attached to STAMPs, then prepare 3'-end libraries by using a transposase to insert a sequencing adapter into the cDNA (Experimental Procedures). Applicants sequence the resulting molecules from each end (FIG. 8C) using high-capacity parallel sequencing (e.g., Illumina MiSeq, NextSeq, or HiSeq), and use these reads to assemble a matrix of digital gene-expression measurements (counts of each gene in each cell) for further analysis (FIG. 8D, Experimental Procedures).

Drop-Seq has high single-cell specificity, as assessed in species-mixing experiments. To determine whether Drop-Seq correctly remembers the cell from which individual transcripts were isolated, Applicants designed species-mixing experiments in which Applicants made suspensions containing cultured human (HEK) and mouse (3T3) cells. Nearly all human or mouse mRNA sequence fragments can be unambiguously assigned to the correct genome of origin; a cell library's "organism purity" can therefore be used to estimate its single-cell purity.

Figure 9A:
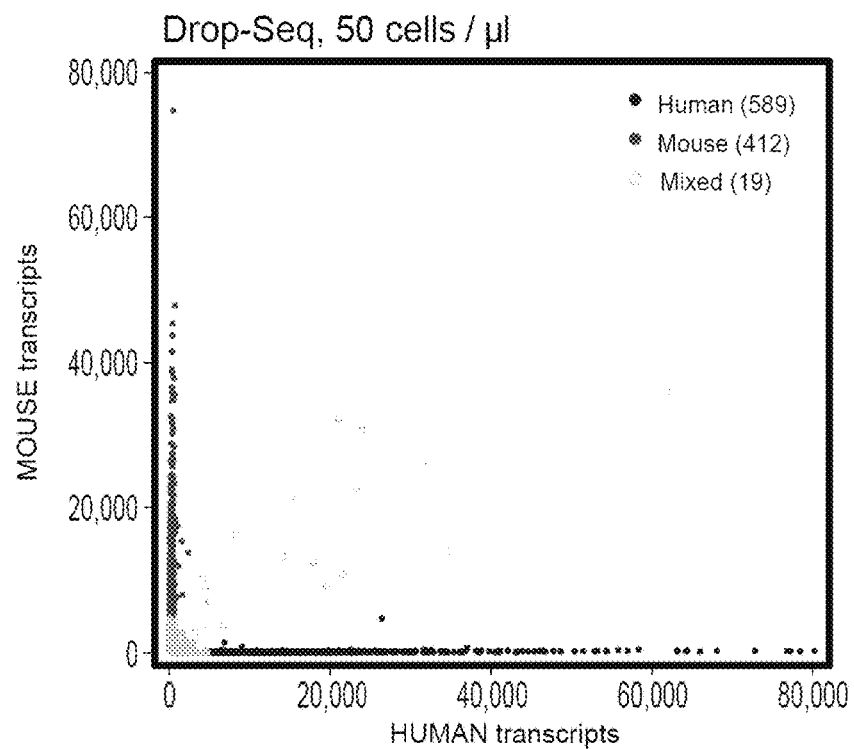
FIG. 9 A-G illustrate critical evaluation of Drop-Seq using species-mixing experiments.
Figure 9B:
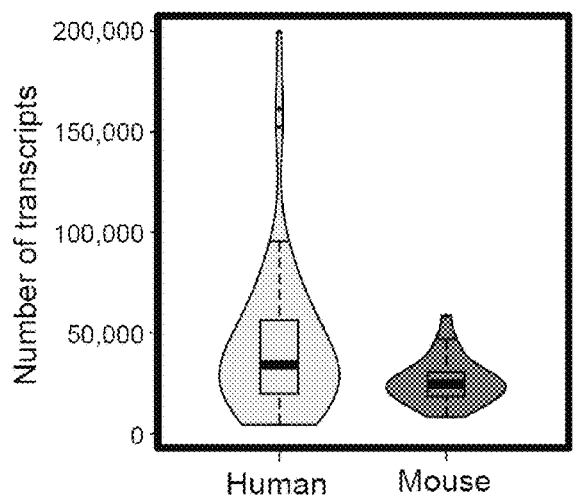
Figure 9C:
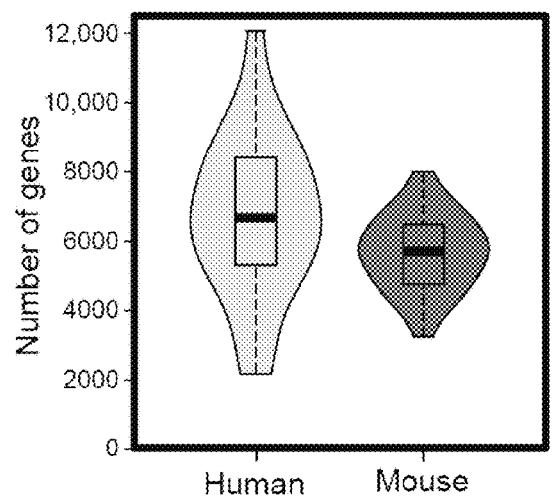
Figure 9G:
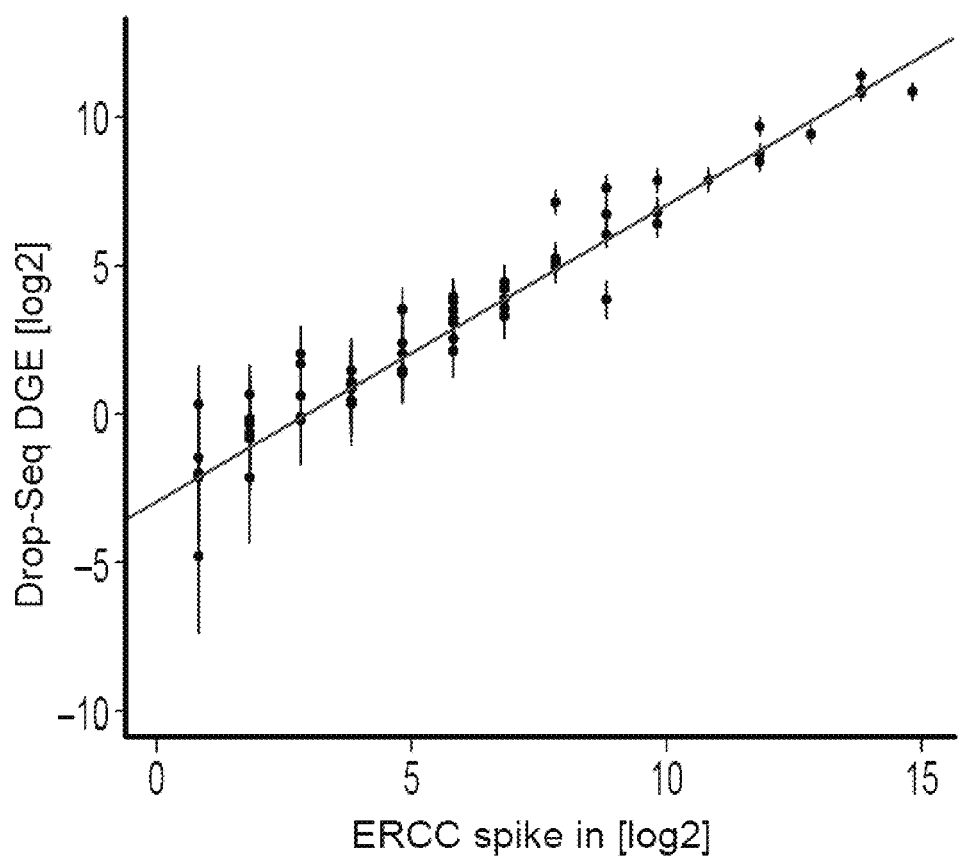

Applicants prepared Drop-Seq libraries from mixtures of human and mouse cells, scoring the numbers of human and mouse transcripts that associated with each cell barcode in the sequencing data (FIGS. 9A, 9B, 14B). This analysis revealed that STAMPs associated to highly organism-specific sets of transcripts (FIGS. 9A and 9B), a result that would not be possible without high single-cell specificity. At deep levels of sequencing that largely saturated sequencing of 82 STAMPs (737,240 reads per cell, FIG. 15) Applicants detected an average of 44,295 transcripts from 6,722 genes in BEK cells, and 26,044 transcripts from 5,663 genes in 3T3 cells (FIGS. 9C and 9D).

Single-cell purity of Drop-Seq libraries. It is important to understand the limitations as well as the strengths of new technologies. Applicants therefore characterized two sources of impurity in single-cell libraries.

Cell doublets. One mode of failure in any single-cell method involves cells that stick together or happen to otherwise be co-isolated for library preparation. In some earlier methods, microscopy imaging of wells has been used to identify "visible doublets" and establish a lower bound on doublet rates. A previous study that used FACS to sort single cells reported that 2.3% of wells contained visible cell doublets (Jaitin et al., 2014). The main commercial single-cell analysis platform (Fluidigm C1) images sets of 96 microfluidically isolated cells, in part so that users can identify doublets from these images; one recent study identified visible doublets in 11%±9% of the capture chambers that contained cells (Shalek et al., 2014).

Molecular analysis by species mixing offers a powerful and sensitive new way to identify libraries prepared from doublets, and may identify many doublets that are not detected by microscopy. For example, when Applicants prepared species-mixed cell populations exactly as in the analysis of Drop-Seq (FIGS. 9A, 9B) and analyzed them on the Fluidigm C1, Applicants found 30% of the prepared libraries to be species-mixed (FIG. 14C) of which about one-third were visible doublets in the microscopy images. When Applicants prepared Drop-Seq libraries from cell suspensions at a cell concentration of 12.5 cells/µl (that allows processing of about 1,200 cells per hour), almost all libraries were species-specific (FIG. 9A). When Applicants prepared Drop-Seq libraries from cell suspensions at a higher cell concentration (50 cells/µl), accommodating faster processing of cells (4,800 cells/hour), 1.9% of the sequenced STAMPs were species-mixed (FIG. 9B). Across four conditions spanning 12.5 cells/µl to 100 cells/µl, there was a strong linear relationship between the cell concentration used and the fraction of species-mixed STAMPs (FIG. 15D; Experimental Procedures), reflecting the greater chance that droplets encapsulate both a mouse and a human cell at higher cell concentrations. Since human-mouse doublets account for half of all cell-cell doublets, Applicants calculated overall doublet rates of 0.36% to 11.3% for the Drop-Seq conditions ranging from highest-purity to highest-throughput.

Figure 15D:
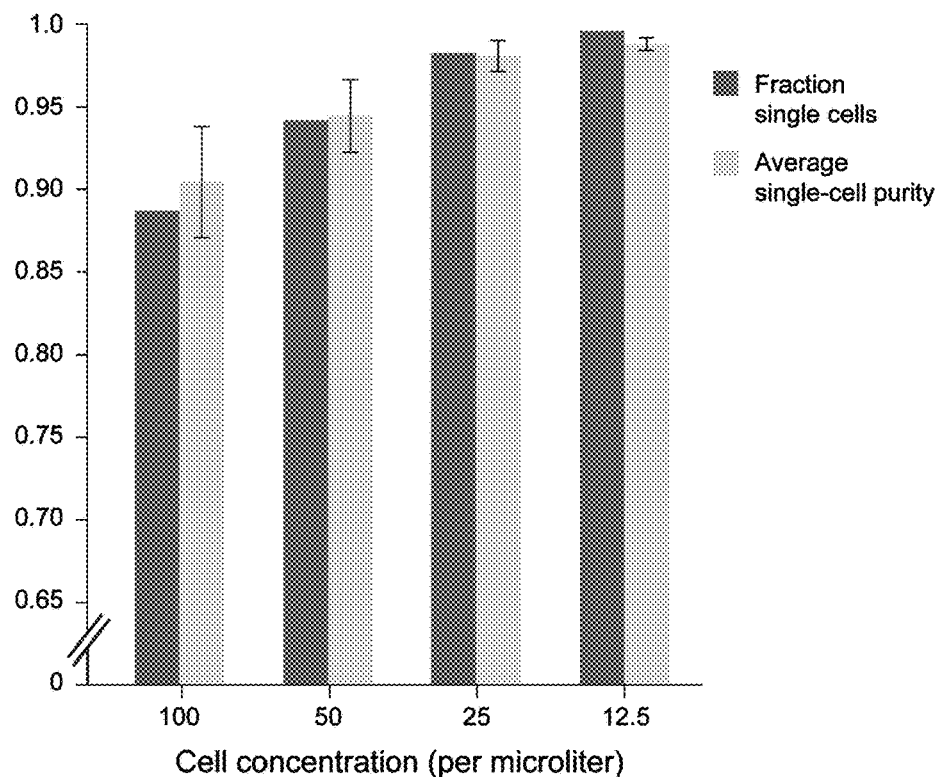
Figure 15E:
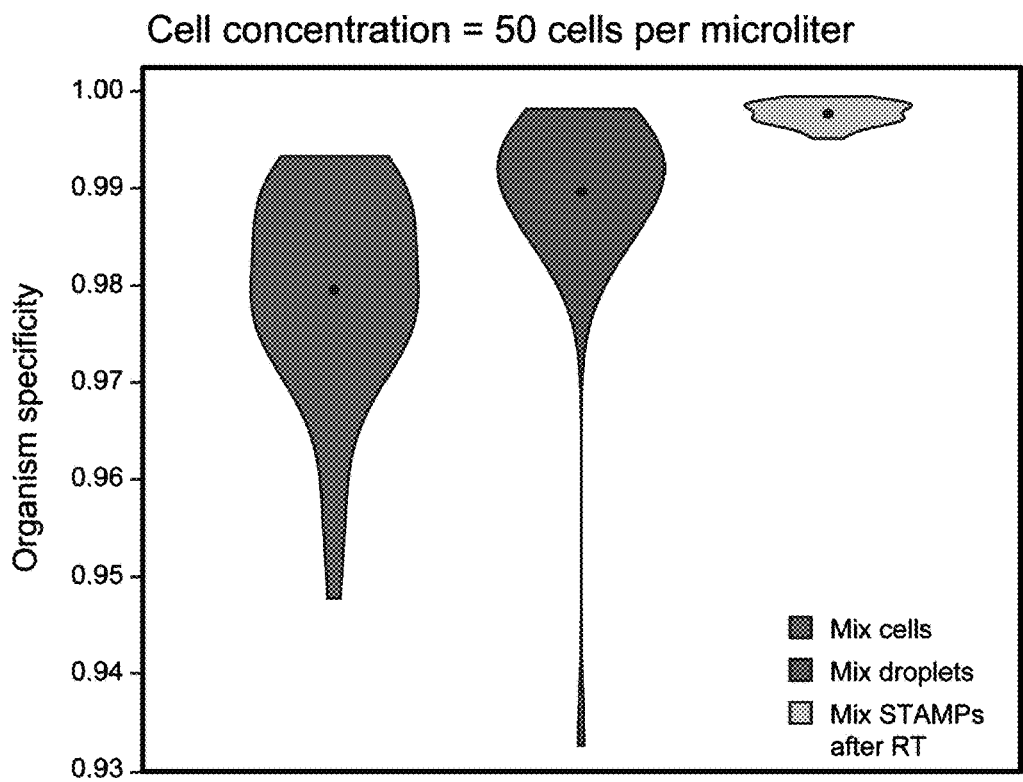
Figure 16A:
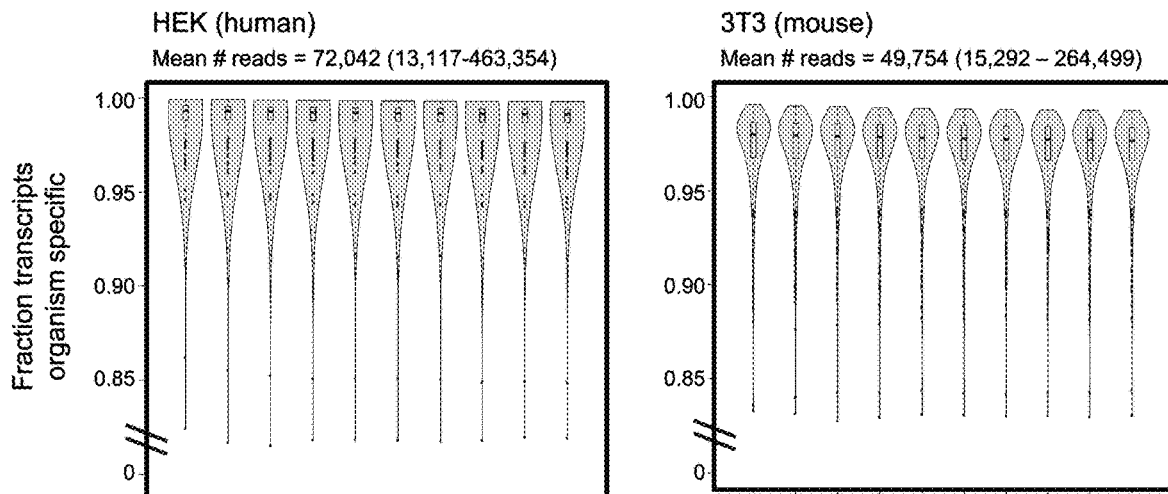
FIG. 16 A-F illustrates specificity and sensitivity as a function of sequencing coverage, evaluated by down-sampling low-depth and high-depth species-mixed (HEK/293T) Drop-Seq libraries prepared at a concentration of 50 cells/µl. (A,B) Analysis of specificity.
Figure 16B:
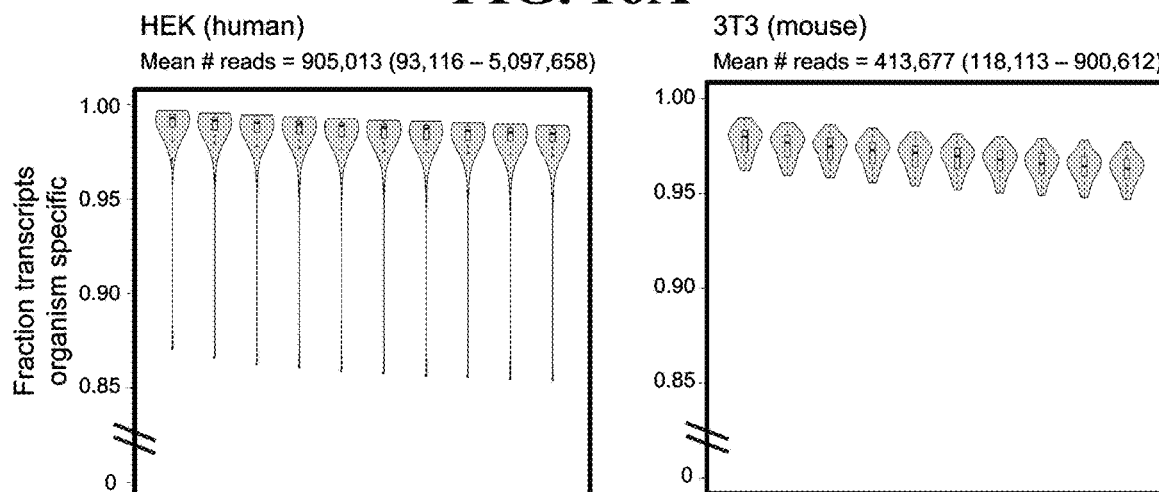
Figure 16C:
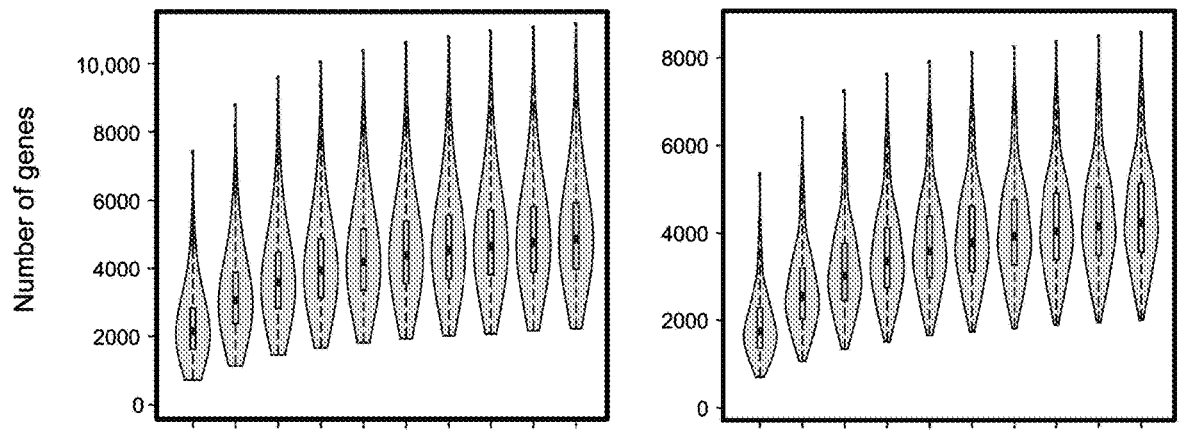
Figure 16D:
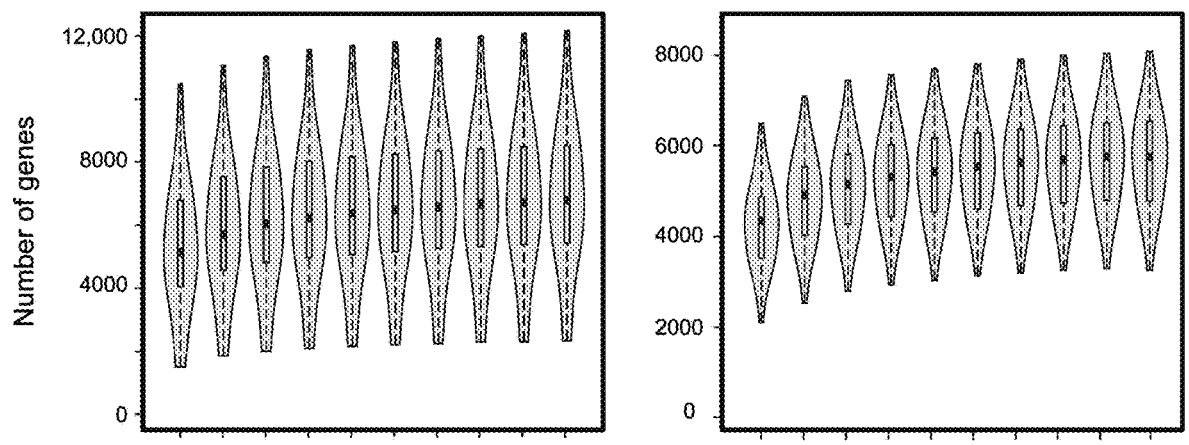
Figure 16E:
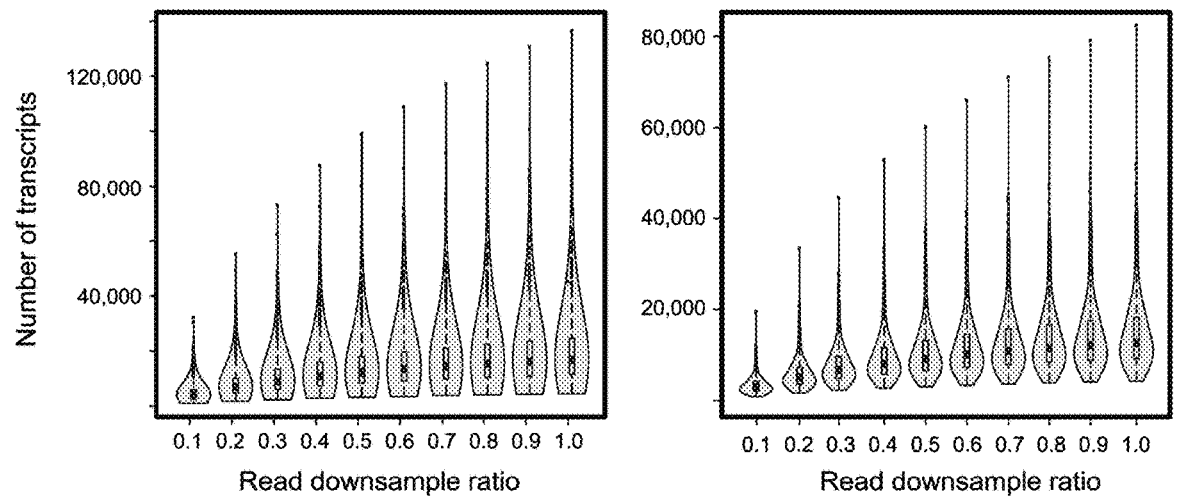
Figure 16F:
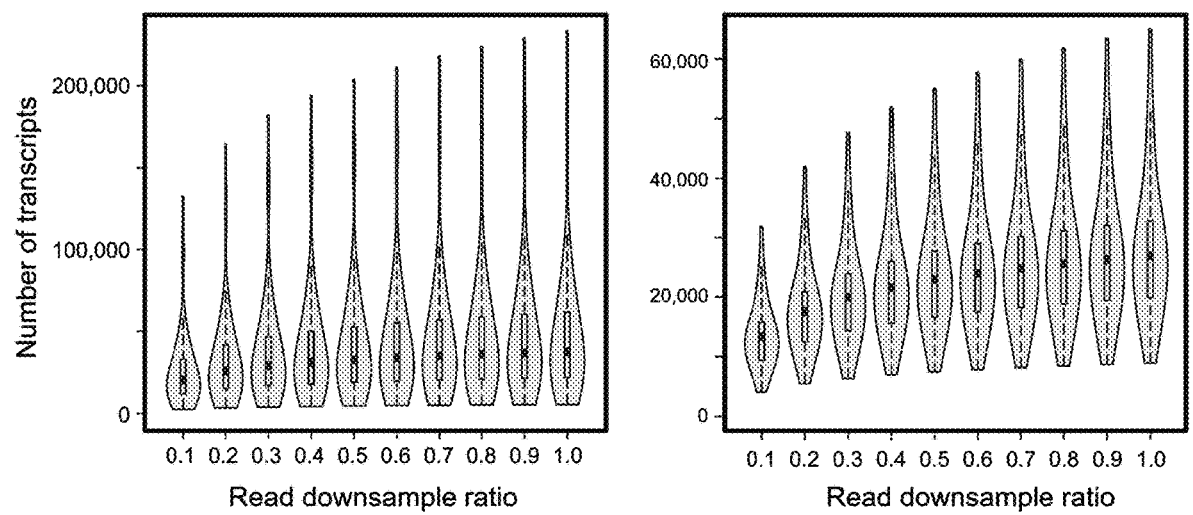

Single-cell impurity. A largely unexplored issue in single-cell analysis involves the extent to which single-cell libraries become contaminated with transcripts from other cells. The high throughput of Drop-Seq and Applicants' use of species-mixing experiments allowed us to carefully measure single-cell purity across thousands of single-cell libraries prepared at different cell concentrations. Applicants found that impurity was strongly related to the concentration at which cell suspensions were loaded: organism purity ranged from 98.8% at 12.5 cells/µl to 90.4% at 100 cells/µl (FIG. 15D). By mixing human and mouse cell-to-library pipelines at different stages (cell suspension; droplets containing beads and lysed cells; post-droplet STAMPs), Applicants found that the cell suspension contributed 48% of impurities, RNA transfer after droplet breakage contributed 40%, and PCR artifacts contributed 12% (FIG. 15E). Thus, the largest source of contamination appears to be ambient RNA that is present in the cell suspension at the beginning of the experiment and presumably results from cells that are damaged during preparation. This result is important for single-cell transcriptomics studies, as the creation of cell suspensions is an indispensable first step of almost all such methods. Indeed, when Applicants analyzed the same species-mixed cell populations on a commercial single-cell sequencing platform (Fluidigm C1), Applicants measured a mean single-cell purity of 95.8% (FIG. 15C), similar to Drop-Seq at 50 cells/µl. It will be important to carefully evaluate all single-cell methods using the kinds of species-mixing experiments performed here.

While the high-purity modes of Drop-Seq (FIG. 9A) would seem preferable to the highest-throughput modes (FIG. 9B) on these grounds, Applicants note that in may experimental contexts it may be desirable to process living cells as quickly as possible, because ultra-fast processing of living cells may strengthen reproducibility and thereby help to realize a potential strength of Drop-Seq relative to slower-throughput, existing methods. Applicants further explore these questions in the retina experiments below.

Drop-Seq samples about 12% of the transcripts in a cell. Applicants next sought to understand how the digital single-cell transcriptomes ascertained by Drop-Seq relate to the underlying mRNA content of cells.

Figures 17A, 17B, 17C:
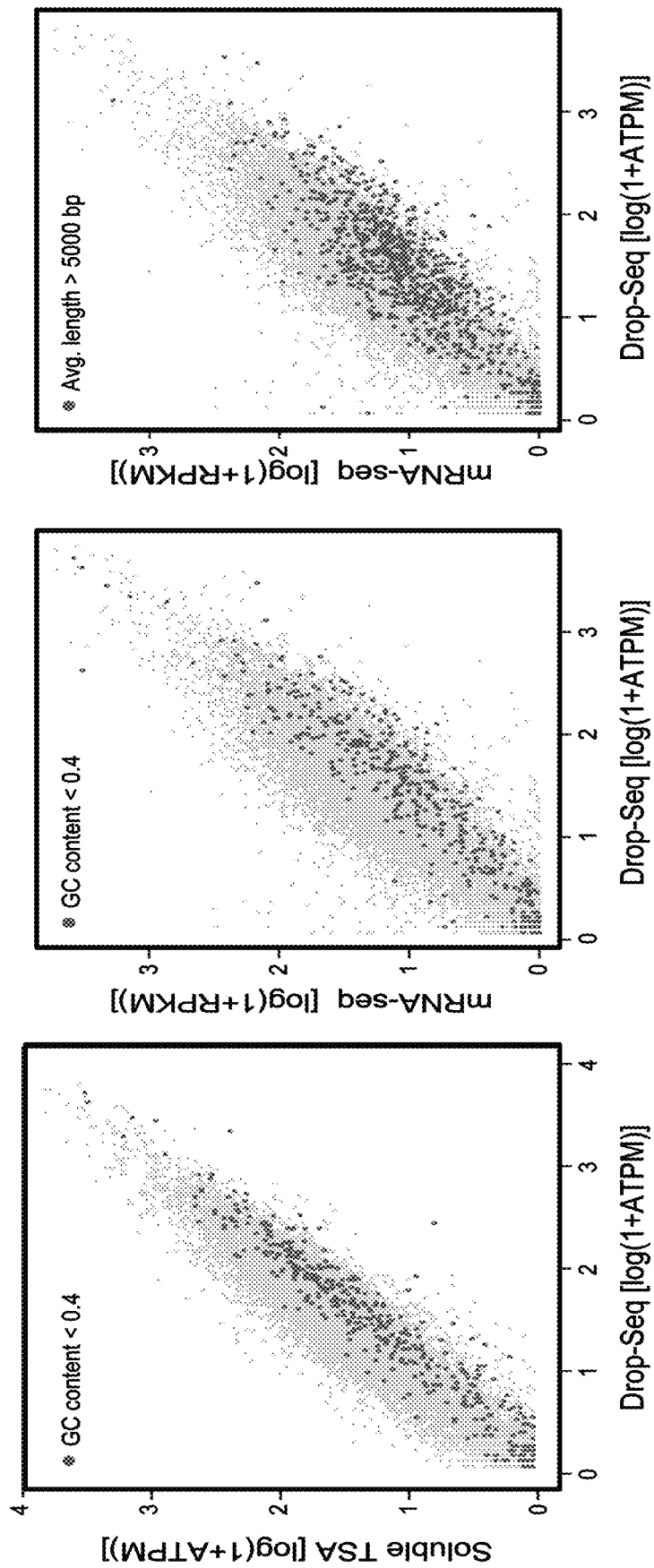
FIG. 17 A-F illustrates estimation of Drop-Seq expression bias and capture efficiency.

Drop-Seq involves hybridization of RNAs to beads, which might affect measurements of genes' absolute expression levels, so Applicants compared Drop-Seq expression measurements to those from a commonly used in-solution cDNA amplification process, template switch amplification (Extended Experimental Procedures). While template switch amplification is presently described, T7 linear amplification or exponential isothermal amplification can also be used to amplify the product. Gene-level log-expression measurements in the two libraries were highly correlated (r=0.94, FIG. 9E), though Drop-Seq showed quantitatively lower ascertainment of GC-rich transcripts (FIG. 17A). Applicants also compared Drop-Seq single-cell log-expression measurements with measurements from bulk mRNA-seq, and observed a correlation of r=0.90 (FIG. 9F).

Figures 17D, 17E, 17F:
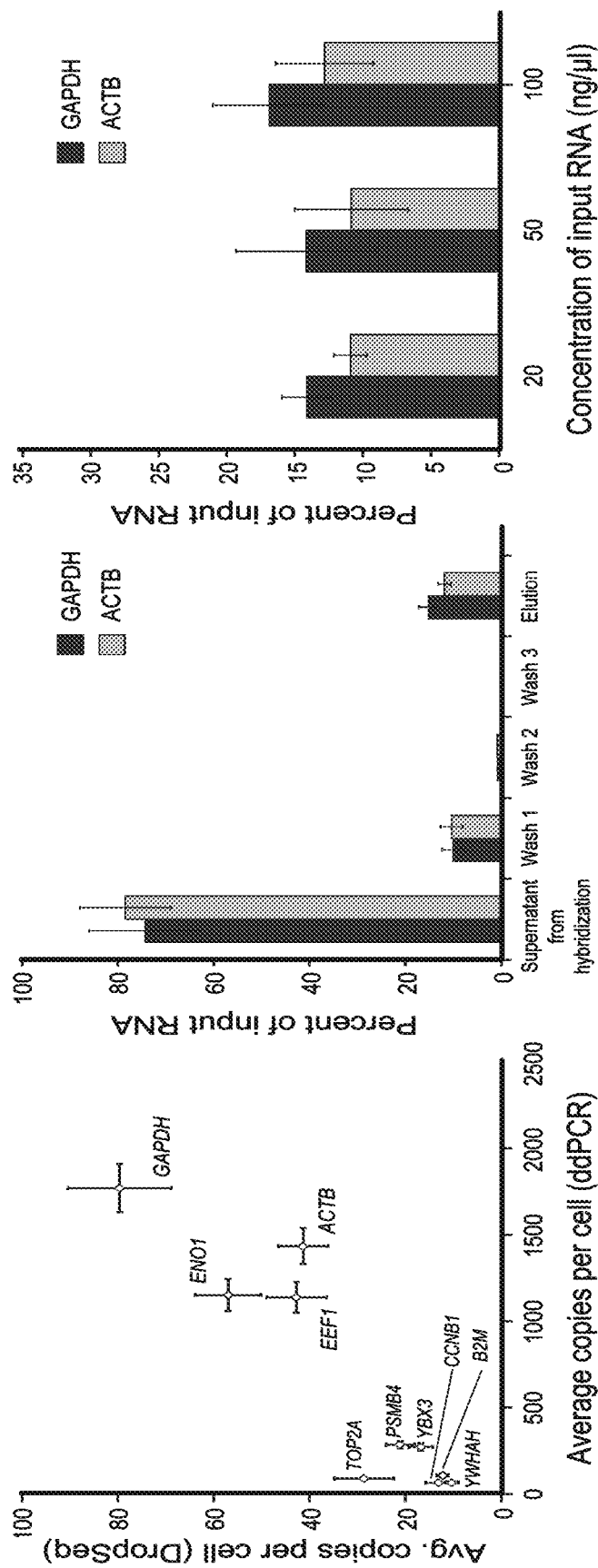

An important and longstanding challenge in single-cell transcriptomics is to understand how the RNAs ascertained in an experiment relate to the original RNA contents of the cells. The increasing use of External RNA Controls Consortium (ERCC) "spike-in" controls at known concentrations, together with UMIs to avoid double-counting, now allows estimation of capture rates for digital single-cell expression technologies (Brennecke et al., 2013). Three recent studies estimated capture rates of current single-cell digital-expression technologies at 3% (MARS-Seq) (Jaitin et al., 2014), 3.4% (CEL-Seq) (Grun et al., 2014), and 48% (5'-end SMART-seq) (Islam et al., 2014). Estimation of Drop-Seq capture rates using the correction method of Islam et al. (to try to avoid double-counting UMIs due to PCR or sequencing errors), generated a capture-rate estimate of 47% for Drop-Seq; however, Applicants identified evidence that sequencing errors can still inflate UMI counts, even when that correction method is used (Extended Experimental Procedures), so Applicants utilized the 8 bp UMI in Drop-Seq to derive a more conservative estimate (12.8%, FIG. 9G) based on a novel approach of collapsing similar UMI sequences into a single count. To further evaluate capture rates, Applicants made independent digital expression measurements (on bulk RNA from 50,000 HEK cells) on 10 genes using droplet digital PCR (ddPCR) (Hindson et al., 2011). Drop-Seq captured on average 10.7% of the number of RNAs predicted by digital PCR (FIGS. 17D, 17E, and 17F). These data indicate that the sensitivity of Drop-Seq is within the range established by recently developed digital expression methods, even when Applicants' novel and extremely conservative UMI counting method is used to evaluate Drop-Seq.

Figure 10A:
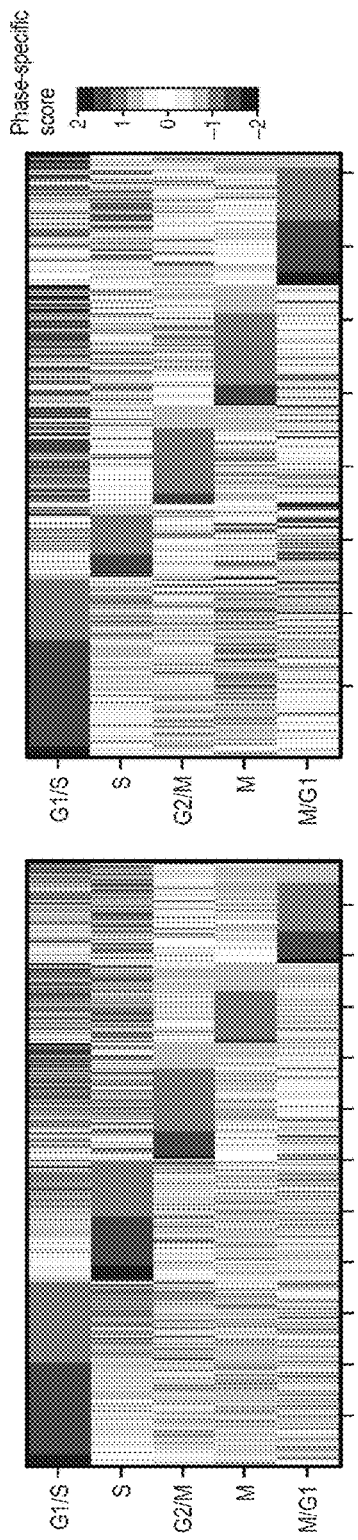
FIG. 10 A-C illustrate cell-cycle analysis of HEK and 3T3 cells analyzed by Drop-Seq.
Figure 10B:
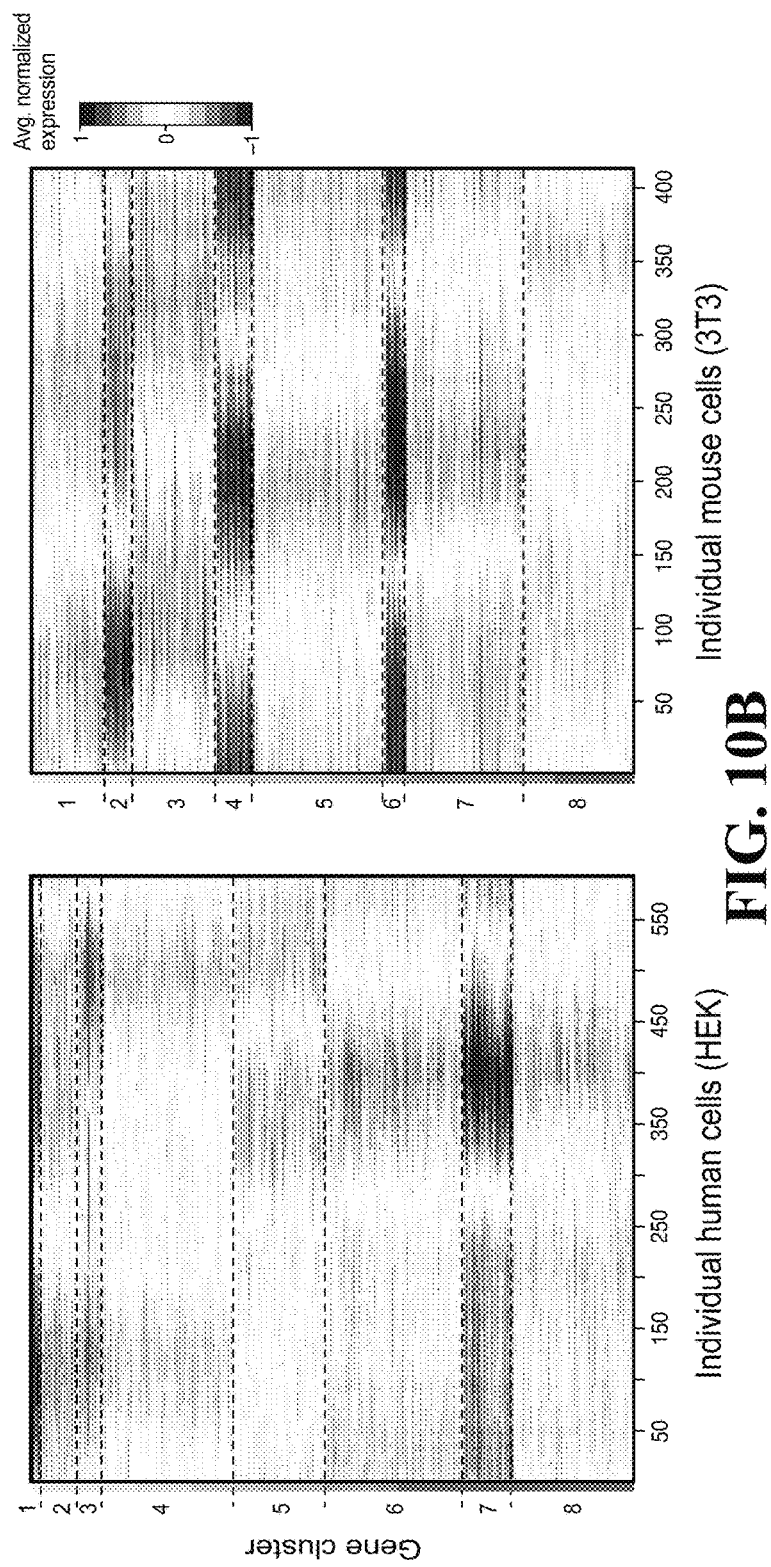

Single-cell analysis of the cell cycle reveals continuously varying cell states. To evaluate the visibility of cell states by Drop-Seq, Applicants first examined cell-to-cell variation among the 589 HEK and 412 3T3 cells for which Applicants had prepared STAMPs in the above experiment (61,697 reads per cell). Both cultures consist of asynchronously dividing cells; principal components analysis (PCA) of the single-cell expression profiles showed the top components to be dominated by genes with roles in protein synthesis, growth, DNA replication, and other aspects of the cell cycle (Table 5). Applicants inferred the cell-cycle phase of each of the 1,001 cells by scoring for gene sets (signatures) reflecting five phases of the cell cycle previously characterized in chemically synchronized cells (G1/S, S, G2/M, M, and M/G1) (Table 6) (Whitfield et al., 2002). Genes in each signature co-varied across individual cells, allowing us to temporally order the cells along the cell cycle (FIG. 10A). Using this ordering, Applicants identified genes with expression patterns that vary along the cell cycle (at a false discovery rate of 5%; Experimental Procedures), yielding 544 and 668 genes in human (HEK) and mouse (3T3) cells, respectively (FIG. 10B). Most of the genes had peak expression in either the G1+S or in the G2+M phases (FIG. 10B), with a minority displaying other patterns, such as peak expression at the M/G1 transition (e.g. cluster 8 in mouse cells, FIG. 10B). Among these genes, there was a significant overlap in orthologous genes between the two species (200 shared orthologs, $P<10^{-65}$ by hypergeometric test), consistent with a conserved cell cycle program. Most (82.5%) of these "conserved" cycling genes (the genes identified as cell cycle regulated in both species) have been previously annotated as related to the cell cycle in at least one species. Among the 17.5% of conserved cycling genes that were not previously annotated as cell-cycle-regulated, Applicants found some that would be expected to show cell cycle variation (e.g. E2F7, NCAPG, CDCA4, DNMT1 and PARPBP), as well as some that to Applicants' knowledge were not previously connected to the cell cycle, including transcription factors (TCF19, ATF4, ZFHX4) and other genes (FIG. 10C).

Finally, Applicants found that in each species, four of the five top PCs were highly correlated with at least one of the cell cycle phase-specific scores ($P<10^{-10}$), indicating a dominant role of the cell cycle in cell-to-cell variation in these cells, consistent with other reports in dividing cells (Buettner et al., 2015). Thus, Drop-Seq single-cell profiles can uncover sets of genes that vary according to subpopulation phenotypes. In particular, this enables study of the cell cycle without chemical synchronization and at high temporal resolution across a large number of cells, which may have assisted in identifying conserved human-mouse gene pairs not previously known to oscillate with the cell cycle.

Figure 11C:
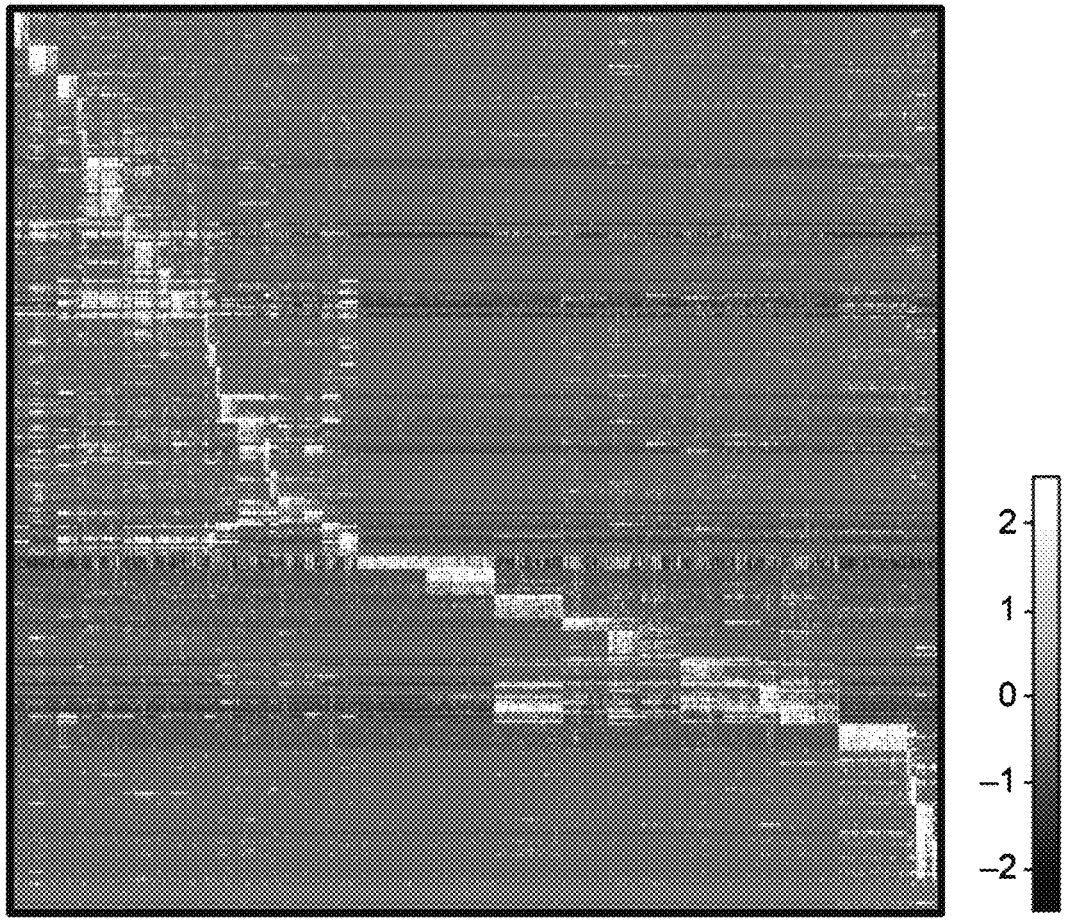
FIG. 11 A-F illustrate Ab initio reconstruction of retinal cell types from 44,808 single-cell transcription profiles prepared by Drop-Seq.

Drop-Seq analysis of the retina reveals cell classes. Applicants selected the retina to study with Drop-Seq because work over many decades has generated information about many retinal cell types (Masland, 2012; Sanes and Zipursky, 2010), providing an opportunity to relate Applicants' single-cell RNA-seq data to existing cell classification schemes. The retina contains five classes of neuronal cells, each defined by a combination of morphologic, physiologic, and molecular criteria (FIG. 11A). The outermost of three cellular layers contains photoreceptors, which transduce light into electrical signals. The middle layer contains three classes of interneurons—horizontal, bipolar and amacrine cells—as well as Müller glial cells. The innermost layer contains retinal ganglion cells and some amacrine cells. Photoreceptors synapse onto interneurons, which process visual signals and pass them to retinal ganglion cells, which in turn send them to the rest of the brain. Most of the classes are divisible into discrete types—a total currently estimated at about 100—but well under half possess molecular markers that distinguish them specifically from other, related types. Drop-Seq provides an opportunity to identify molecular signatures of cell types previously defined exclusively by morphological or physiological criteria.

The retina presents formidable technical challenges for large-scale single cell profiling. First, about 70% of the cells in the retina are rod photoreceptors; the other retinal cell classes each comprise 0.5-8% of retinal cells and are further divided into types. The problem in the retina is therefore to identify a large number of individually rare cell types. Second, the size variation among retinal cells—ranging from 1.2 microns (rods) to 20 microns (retinal ganglion cells) in diameter and thus spanning three orders of magnitude in volume—can pose not only technical challenges for unbiased isolation of cells, but also complicate analysis because of huge cell-to-cell differences in mRNA content.

Applicants performed Drop-Seq on cell suspensions made from whole retinas of 14-day-old mice, sequencing 49,300 STAMPs to an average depth of 14,084 reads (STAMPs were collected in seven experimental batches over four days). To discover cell types from single-cell expression profiles ab initio, Applicants first performed principal components analysis, using the genes that showed a greater degree of expression variance (across cells) than could be explained by random statistical sampling of the transcripts (within cells), and initially focusing on the 13,155 cells with the largest numbers of transcripts, to reduce the otherwise-disproportionate contribution of tiny photoreceptor cells to the analysis (Experimental Procedures). Applicants utilized a classic permutation test (Peres-Neto et al., 2005) and a recently developed resampling procedure (Chung and Storey, 2014) to identify statistically significant principal components (PCs), finding 32 significant PCs in these data (FIG. 18). Almost all of the significant PCs were strongly shaped by genes that are well-known markers of retinal cell types. Applicants used the cell loadings associated with these principal components as input for t-Distributed Stochastic Neighbor Embedding (tSNE) (van der Maaten and Hinton, 2008), to reduce these 32 PCs to two dimensions. Applicants projected the remaining 36,145 cells in the data onto the tSNE, and combined a density clustering approach with differential expression analysis to identify distinct clusters of cells from this tSNE analysis (Extended Experimental Procedures). These steps left us with 39 transcriptionally distinct cell populations—the largest containing 29,400 cells, the smallest containing 50 cells, altogether composed of 44,808 cells (FIG. 11B). Finally, Applicants organized the 39 cell populations into larger categories (classes) of transcriptionally similar clusters, by building a dendrogram of similarity relationships among the 39 cell populations based upon their Euclidean distances in gene-expression space (FIG. 11D, left).

Figure 11D:
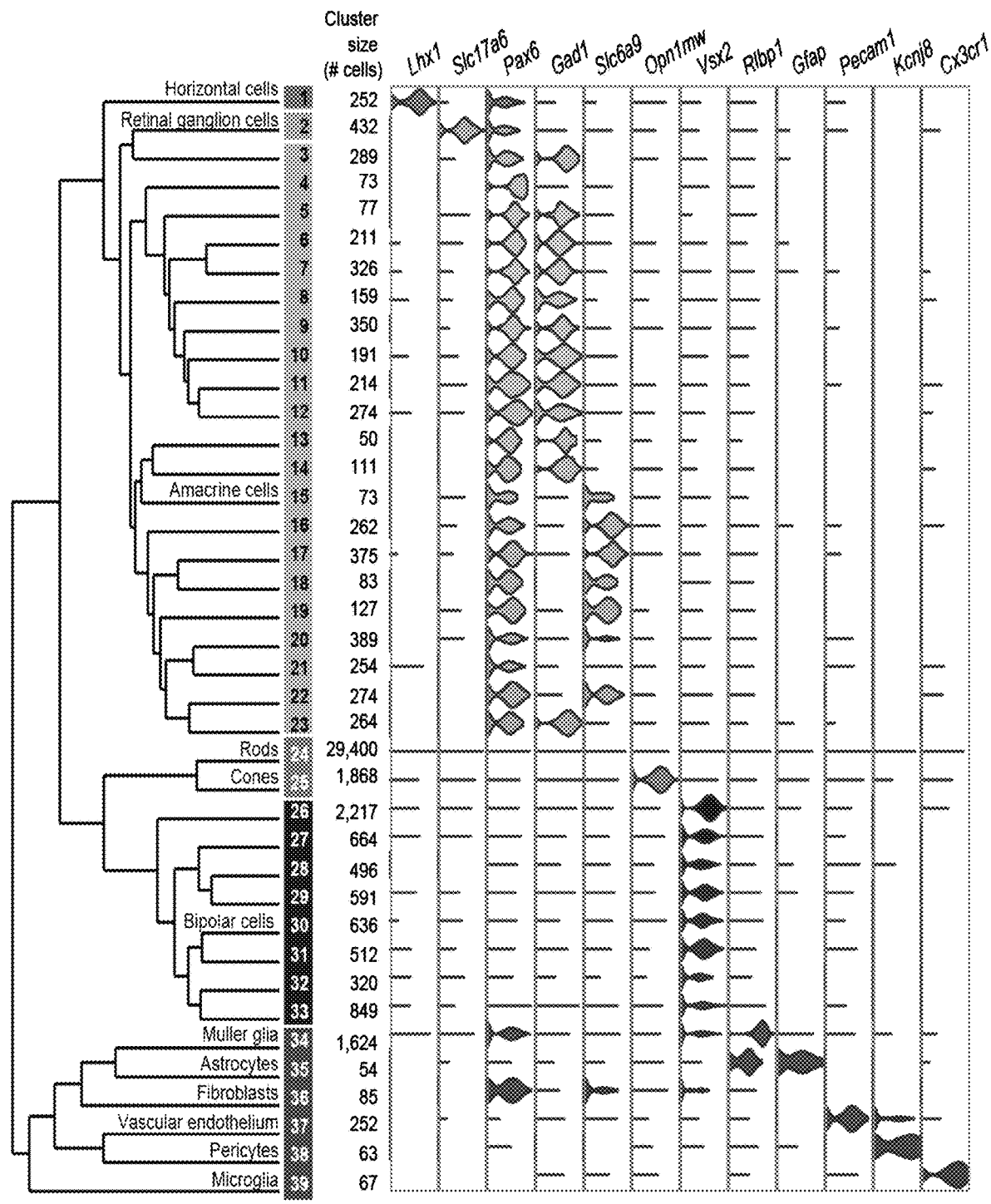

Applicants found that their unsupervised clustering results—which were derived entirely from clustering the single-cell transcriptome data itself, rather than being "instructed" by known markers-correlated strikingly with expression of the known molecular markers that exist for many retinal cell types (FIG. 11D, right). Well-known markers of retinal cell types include Slc17a6 (Vglut2) and Thy1 for retinal ganglion cells, Vsx2 for bipolar cells, Lhx1 for horizontal cells, opsins for photoreceptors, Tfap2b and Pax6 for amacrine cells, and Rlbp1 for Müller glia. Each of these markers showed single-cell patterns of gene expression that corresponded to a branch or leaf of the dendrogram derived from Applicants' unsupervised analysis (FIG. 11D). Photoreceptors clustered into two groups that were readily identifiable as rods and cones based on their expression of rod and cone opsins. Additional clusters corresponded to non-neural cells associated with retina, including astrocytes (associated with retinal ganglion cell axons exiting the retina), resident microglia (Provis et al., 1996), endothelial cells (from intra-retinal vasculature), pericytes (cells that surround the endothelium), and fibroblasts (FIG. 11D). Furthermore, Applicants found that the relative proportions of the major cell classes in Applicants' data largely agreed with earlier estimates from microscopy (Jeon et al., 1998). The ability of an unsupervised analysis to identify all of these biologically known cell classes at the expected ratios suggests that such analyses may be applicable to many other tissues whose resident cell populations are far less characterized.

Figure 11E:
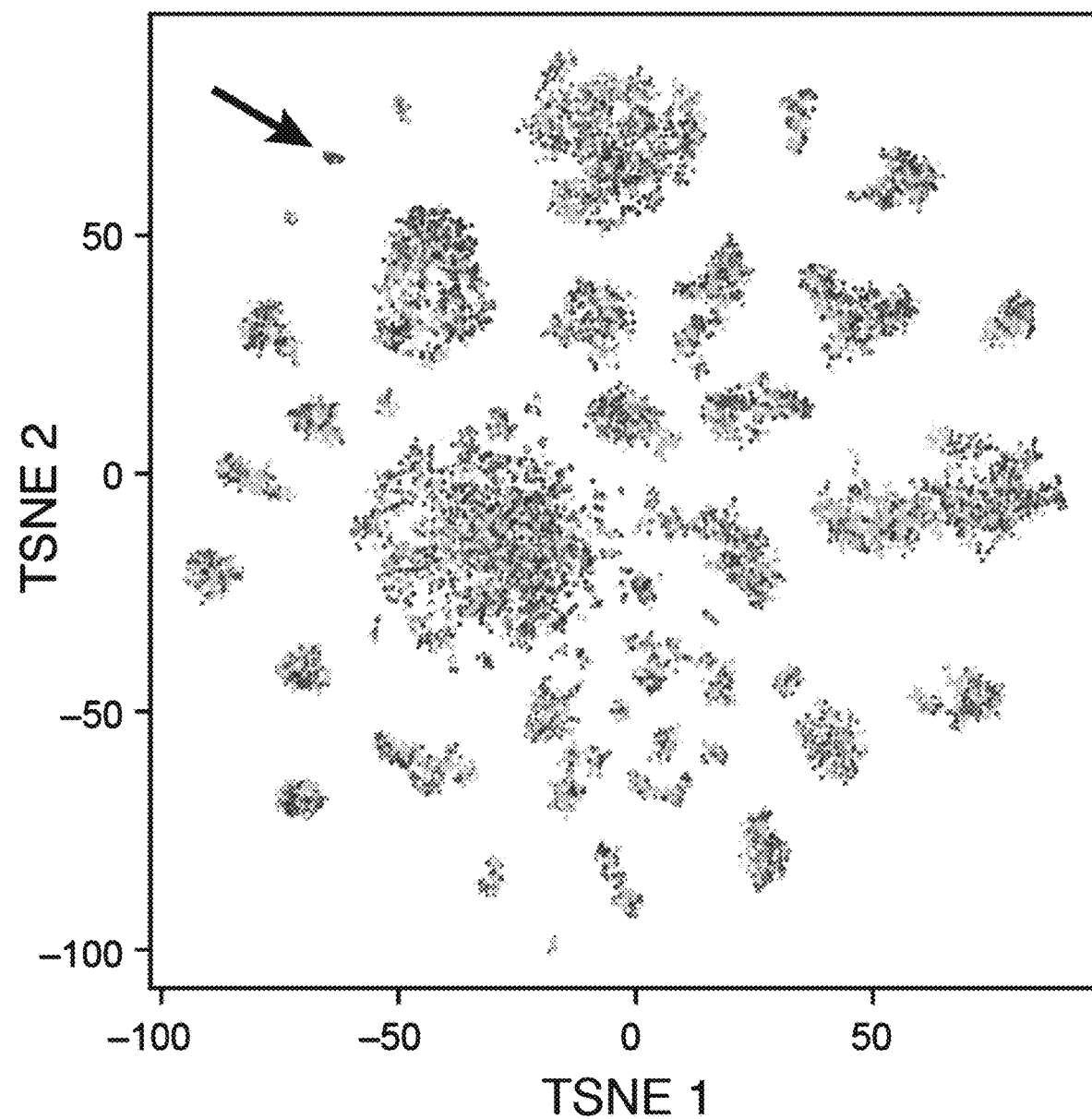

Replication and cumulative power of Drop-Seq data. Replication across experimental sessions enables the construction of cumulatively more powerful datasets for detection of subtle biological signals. The retinal STAMPs were generated on four different days (weeks apart), utilizing four different mouse litters, with several sessions generating multiple replicate Drop-Seq runs, for a total of seven replicates. Applicants prepared one of these replicates at a particularly low cell concentration (15 cells/µl) and high purity, to evaluate whether any analytical results were artifacts of cell-cell doublets or single-cell impurity (i.e. whether they excluded these "high-purity" cells), as Drop-Seq's fastest-throughput modes allow extremely fast processing of living cells (valuable for maintaining correspondence to the in vivo system) but at some cost in single-cell purity relative to its highest-purity modes (FIG. 9A, 9B), and the correspondence between transcriptional patterns identified in these modes was important to understand. A key question, then, was whether every experimental session contributed cells to each of the 39 populations that Applicants had observed in the above analysis (FIG. 11B). Applicants found that all 39 clusters contained cells from every experimental session and condition. However, Cluster 36 (arrow in FIG. 11E; star in FIG. 20), drew disproportionately from replicates two and three. This cluster expresses markers of fibroblasts, a cell type that is not native to the retina but is instead present in tissue surrounding the retina; the inclusion of larger numbers of fibroblasts in two replicates most likely represents the challenge of dissecting around the retinal perimeter. Most importantly, the 3,226 cells prepared under high-purity conditions (replicate 7) contributed to every cluster, indicating that none of the clusters is an artifact of doublets or other impurities (FIG. 11E). While Applicants cannot exclude the possibility that experimental variation influences gene expression measurements in Drop-Seq, in these experiments such effects appeared to be small relative to the differences even between highly similar cell subtypes (e.g. the 21 populations of amacrines cells described below).

Figure 11F:
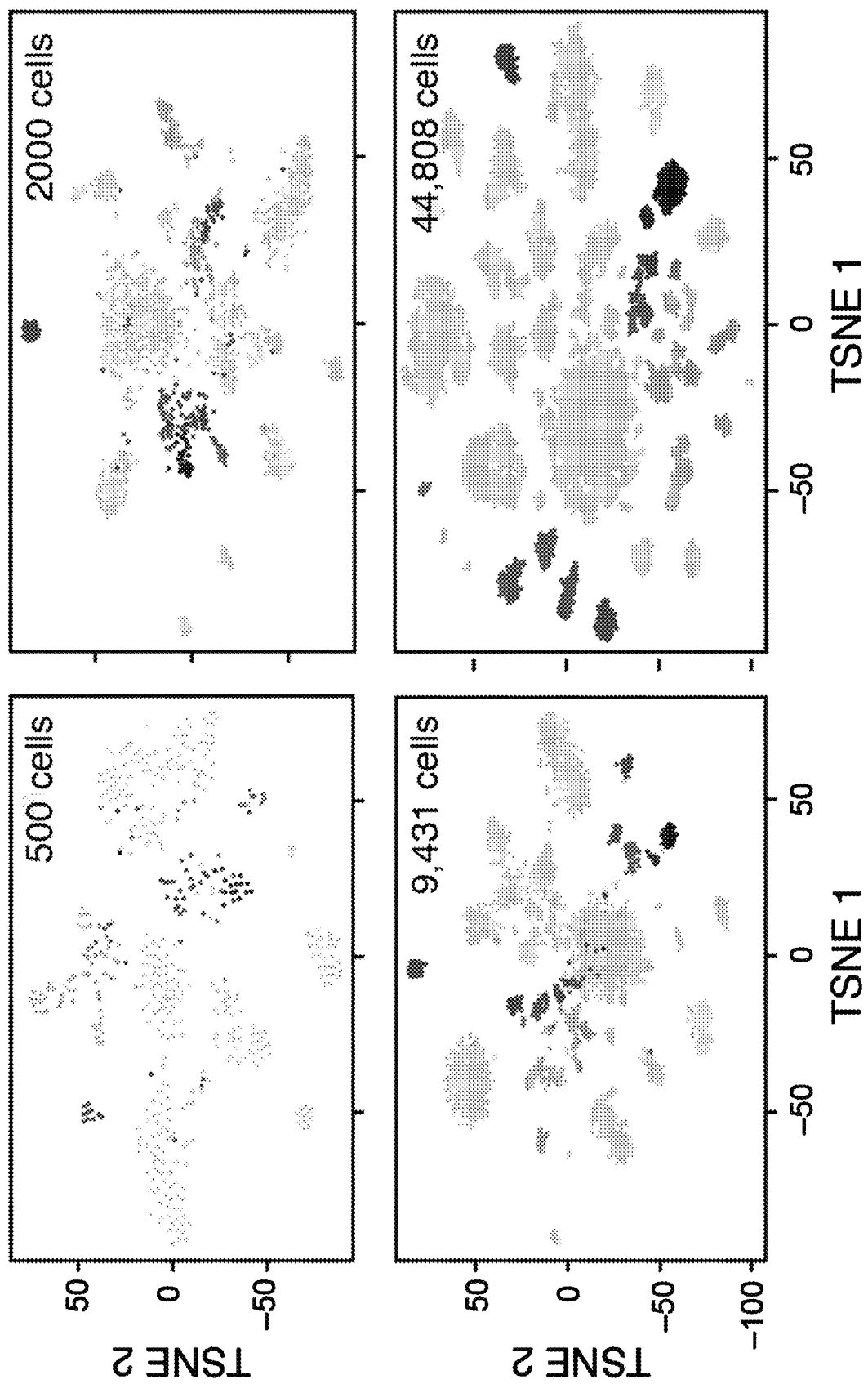

Applicants next examined how the classification of cells (based on their patterns of gene expression) evolved as a function of the numbers of cells in analysis, in order to evaluate both the robustness of the clustering analysis and the scientific return to analyzing large numbers of cells. Applicants used 500, 2,000, or 9,431 cells from Applicants' dataset, and asked how (for example) amacrine cells identified in the full (44,808-cell analysis) had clustered in analyses of smaller numbers of cells (FIG. 11F). Applicants found that as the number of cells in the data increased, distinctions between related clusters become clearer, stronger, and finer in resolution, with the result that a greater number of rare amacrine cell populations (each representing 0.1-0.9% of the cells in the experiment) could ultimately be distinguished from one another (FIG. 11F). In analyses of smaller numbers of cells, these cells were often co-clustered into "supertypes", reflecting the challenge of distinguishing recurring patterns (often involving small numbers of genes) from single-cell biological, technical, and statistical noise in genome-wide experiments.

Profiles of 21 candidate amacrine cell types. To better understand the ability of single-cell analysis to distinguish between closely related cell types, Applicants focused on the 21 clusters identified as amacrine neurons, the neuronal class considered to be the most morphologically diverse (Masland, 2012). Most amacrine cells are inhibitory, with around half using glycine and the other half using GABA as a neurotransmitter. Excitatory amacrine cells, expressing Slc17a8 (VGlut3) and releasing glutamate, have also been identified (Haverkamp and Wassle, 2004). Another recently discovered amacrine cell population release no known classical neurotransmitter (nGnG amacrines) (Kay et al., 2011).

Figure 12A:
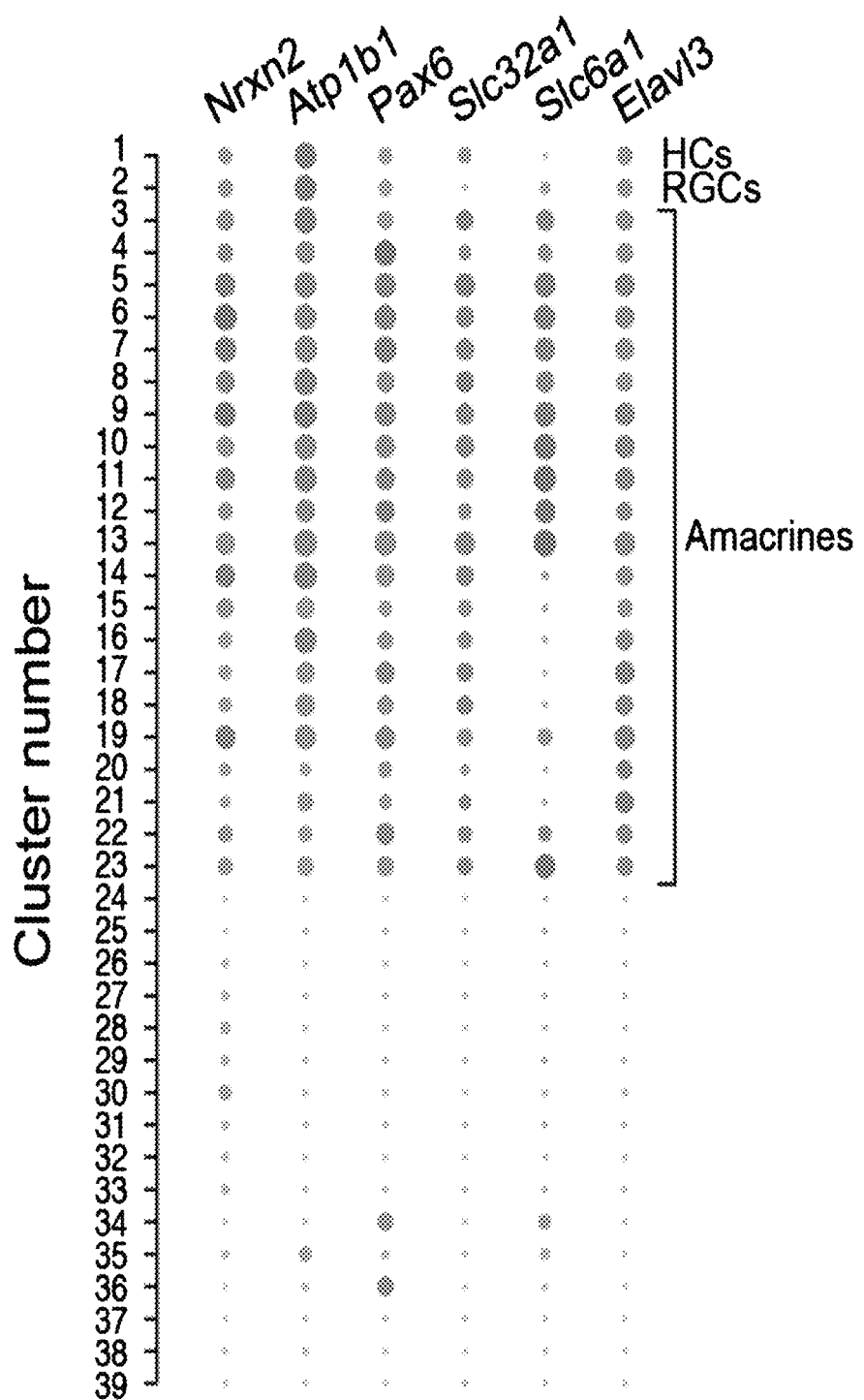
FIG. 12 A-I Finer-scale expression distinctions among amacrine cells, cones and retinal ganglion cells.
Figure 12B:
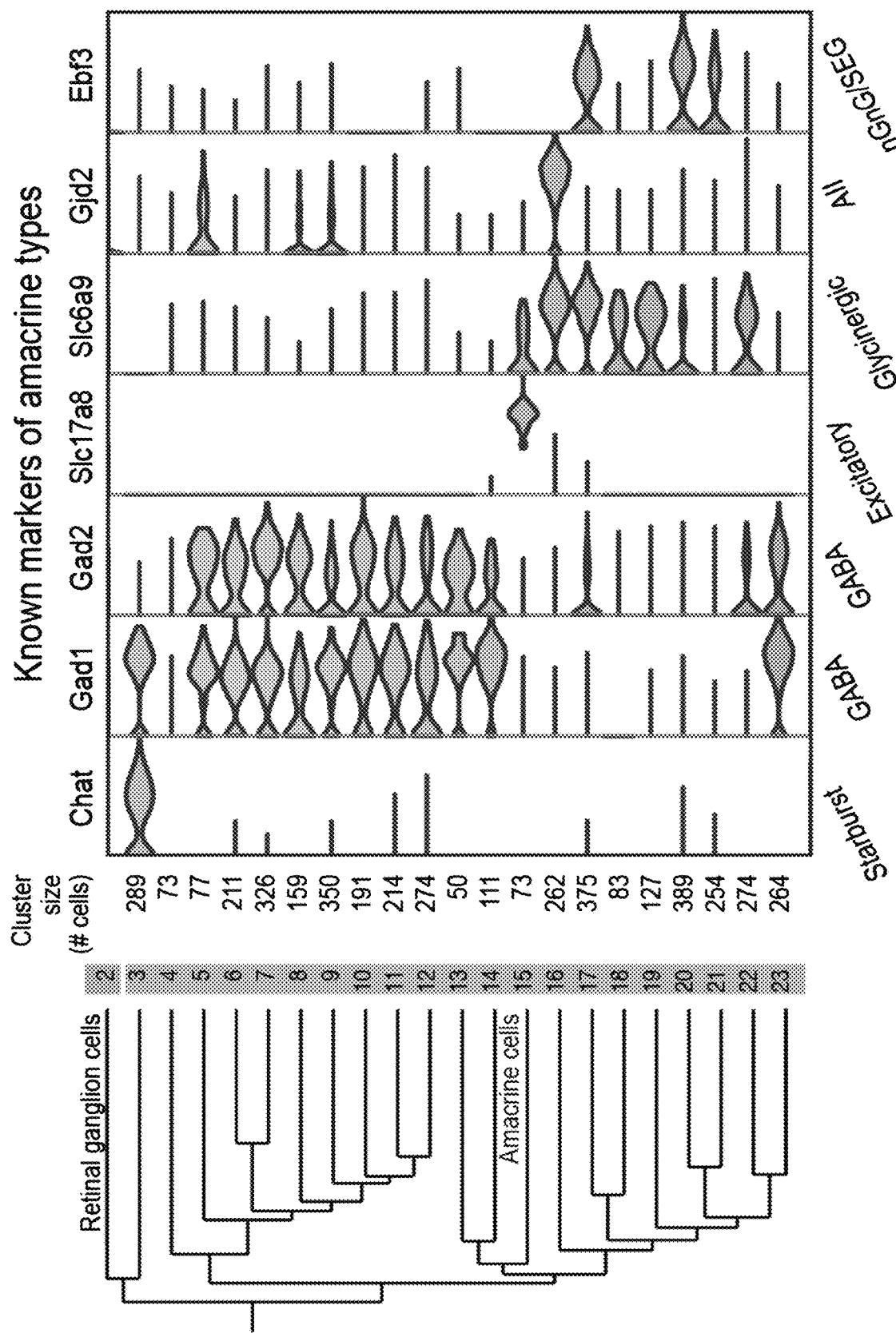

Applicants first identified potential amacrine markers that were the most universally expressed by amacrine clusters relative to other cell classes (FIG. 12A). Applicants then assessed the expression of known glycinergic and GABAergic markers; their mutually exclusive expression is seen as a fundamental distinction with a morphological correlate: most GABAergic amacrines have broad dendritic arbors restricted to a single sublamina (wide-field) whereas glycinergic amacrines have narrow dendritic arbors that span multiple sublaminae (narrow-field). Of the 21 clusters of amacrine cells, 12 groups (together comprising 2,516 cells) were identifiable as GABAergic and a distinct 5 clusters (together comprising 1,121 cells) as glycinergic, based on expression of the GABA synthetic enzyme, glutamate decarboxylase (two isoforms, encoded by Gad1 and Gad2) and the glycine transporter (Slc6a9), respectively (FIG. 12B). An additional cell population (comprising 73 cells) was identified as excitatory by its expression of Slc17a8, which was not expressed in other amacrine populations (FIG. 12B). The remaining three amacrine cell populations (clusters 4, 20, and 21) had absent or low levels of Gad1, Gad2, Slc6a9, and Slc17a8; these likely include nGnG amacrines, as described below.

The amacrine types with known molecular markers were readily assigned to specific cell populations (clusters) from the analysis. Glycinergic A-II amacrine neurons appeared to correspond to the most divergent glycinergic cluster (FIG. 12B, cluster 16), as this was the only cluster to strongly express the Gjd2 gene encoding the gap junction protein connexin 36 (Feigenspan et al., 2001; Mills et al., 2001). Ebf3, a transcription factor found in SEG glycinergic as well as nGnG amacrines, was specific to clusters 17 and 20. Starburst amacrine neurons (SACs), the only retinal cells that use acetylcholine as a co-transmitter, were identifiable as cluster 3 by those cells' expression of the choline acetyltransferase gene Chat (FIG. 12B); the Drop-Seq data also suggested that SACs, unlike the other GABAergic cells, expressed Gad1 but not Gad2, as previously observed in rabbit (Famiglietti and Sundquist, 2010).

Figure 12C:
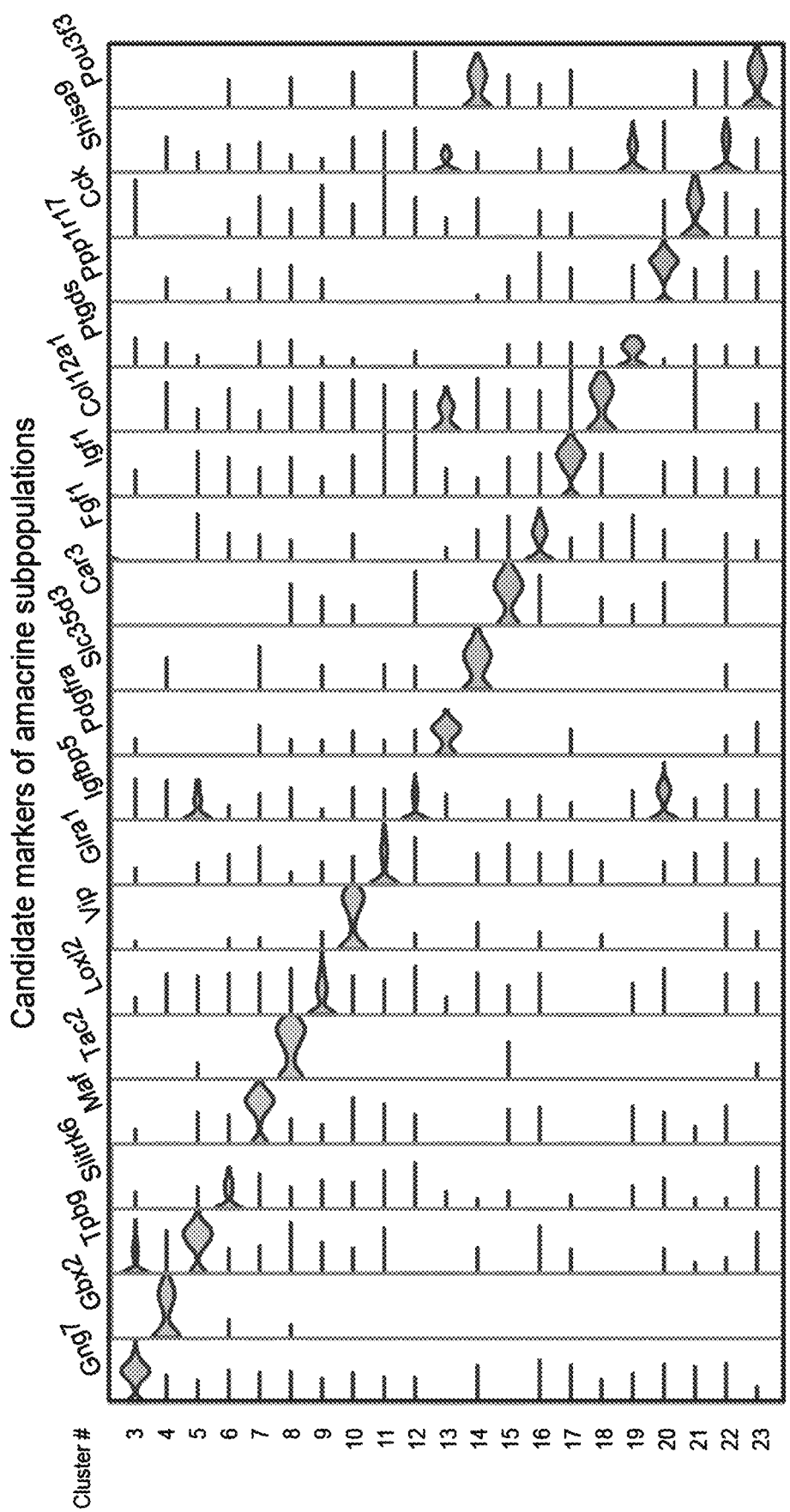
Figure 12E:
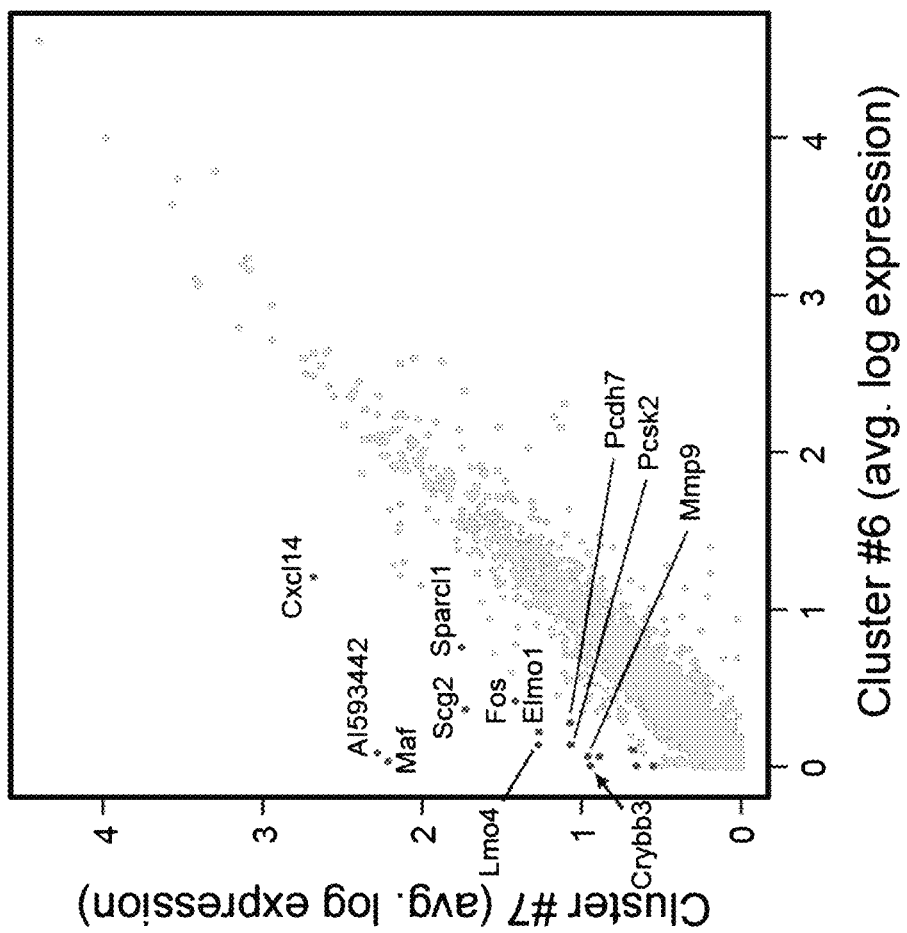

Beyond the above distinctions, little is known about molecular distinctions among the physiologically and morphologically diverse amacrine types. Molecular markers of these types would be powerful tools for more comprehensively studying amacrines' circuitry, development, and function. For each of the 21 amacrine cell populations (clusters), Applicants identified multiple genes that were highly enriched in each cluster relative to the other amacrines (FIG. 12C). Many markers of each cluster (FIG. 12C) are genes involved in neurotransmission or neuromodulation; such genes have historically been good markers of individual neuronal cell types in other brain regions.

Figure 12D:
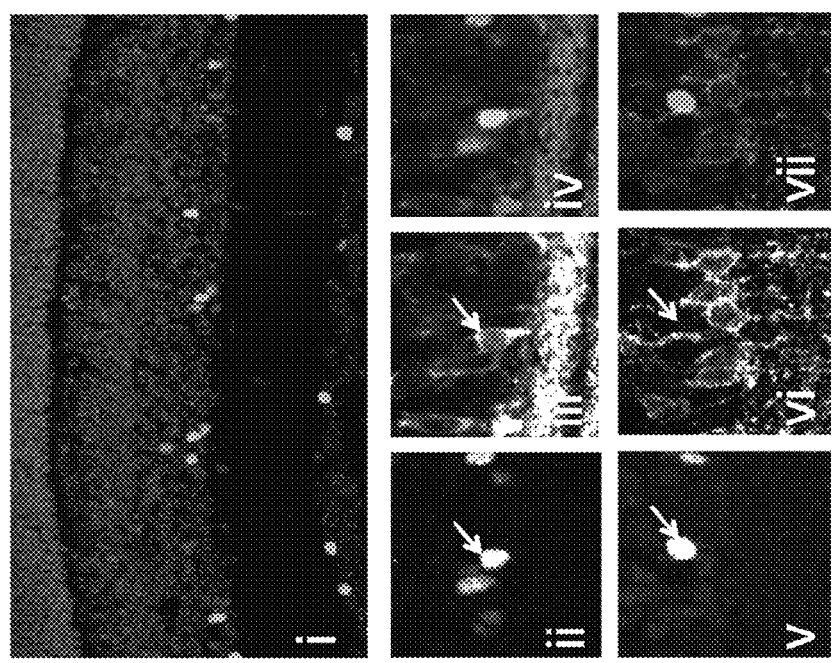
Figure 12G:
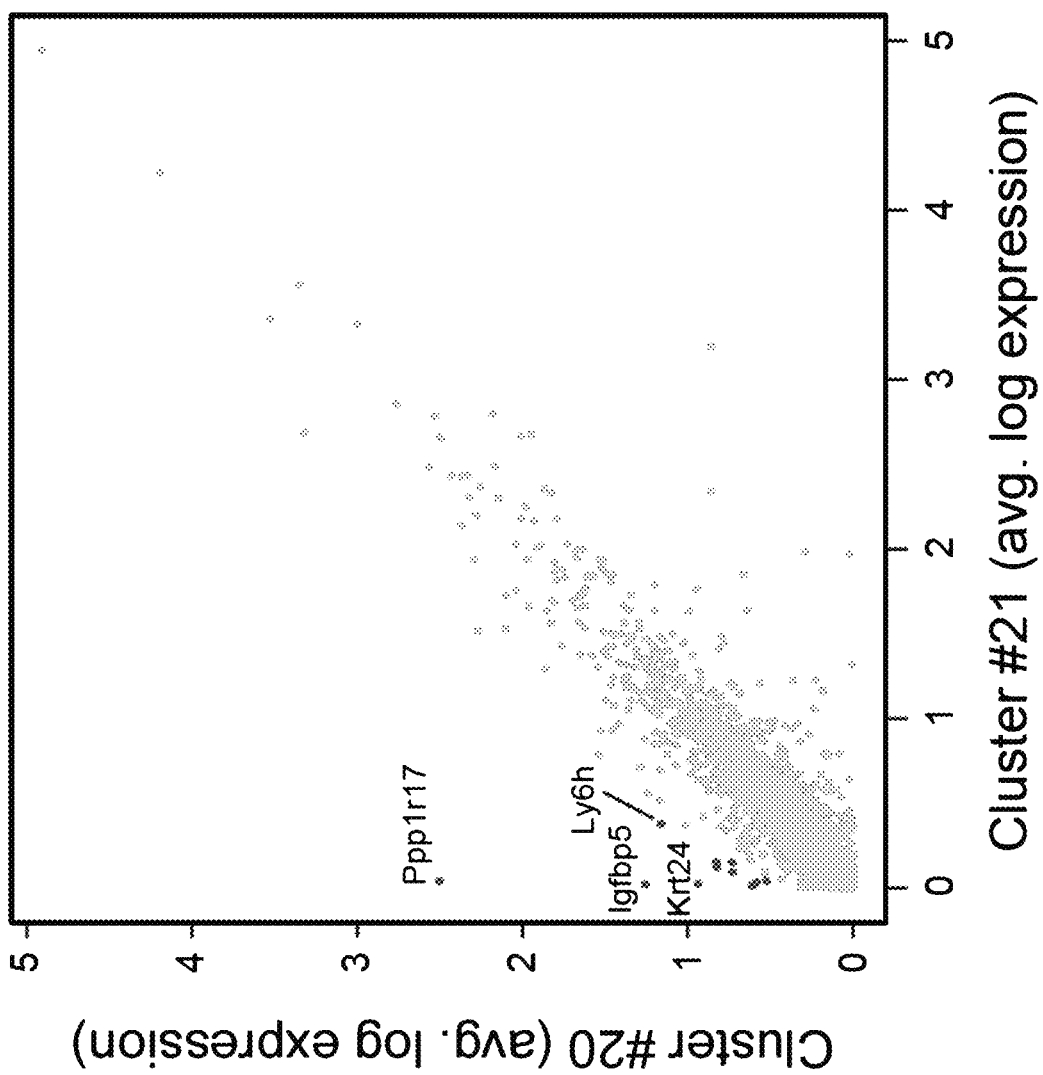
Figure 12F:
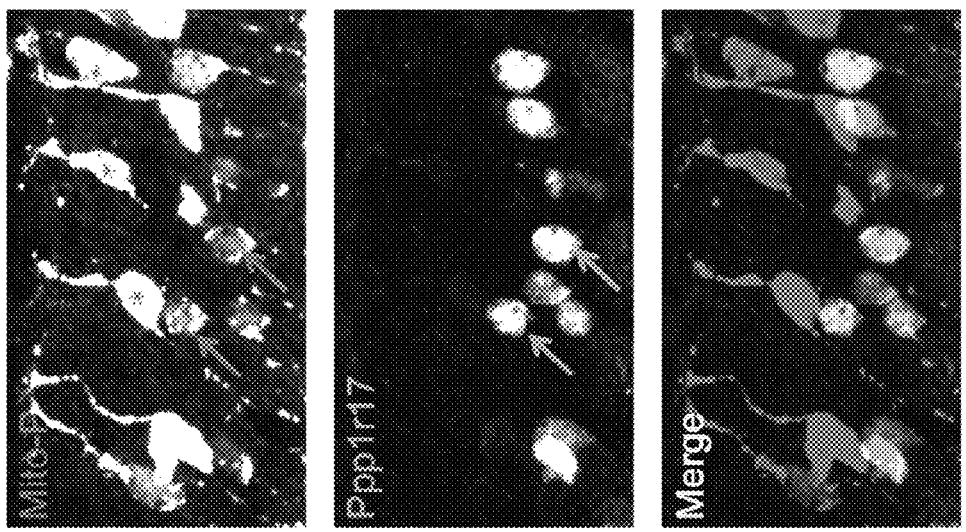
Figure 12H:
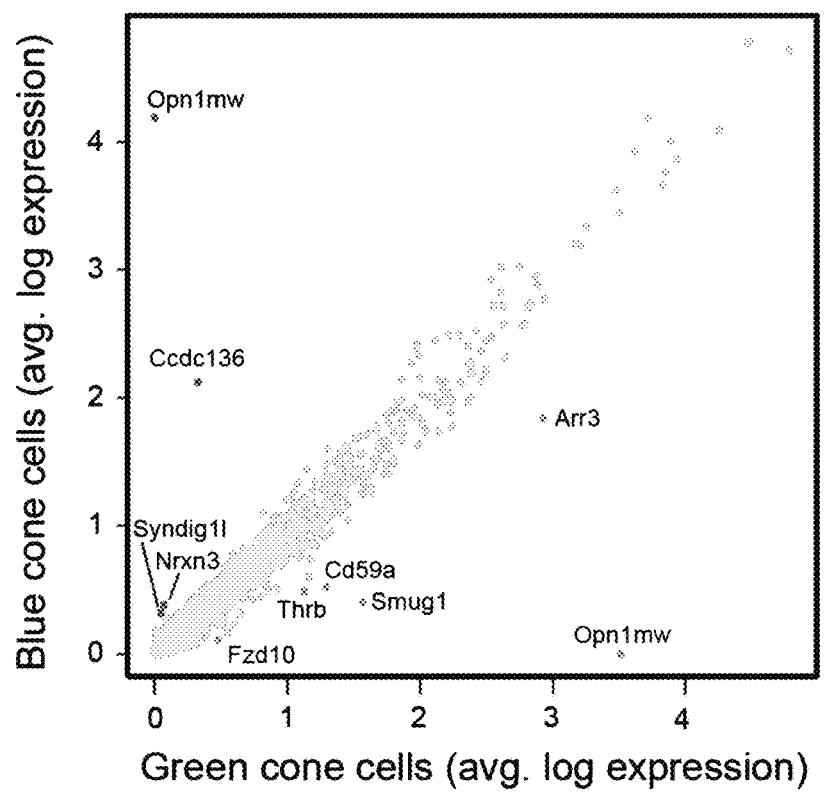

Can Drop-Seq identify novel markers of cell types? Applicants analyzed genes expressed in two of the amacrine clusters: cluster 7, a GABAergic cluster, and cluster 20, which had a mixture of glycinergic and nGnG cells. First, Applicants co-stained retinal sections with antibodies to the transcription factor MAF, the top marker of cluster 7, plus antibodies to either GAD1 or SLC6A9, markers of GABAergic and glycinergic transmission, respectively. As predicted by Drop-Seq data, MAF was found specifically in a small subset of amacrine cells that were GABAergic and not glycinergic (FIG. 12D). Cluster 7 had numerous genes that were enriched relative to its nearest neighbor, cluster 6 (FIG. 12E, 16 genes >2.8-fold enrichment, $p<10^{-9}$), including Crybb3, which belongs to the crystallin family of proteins that are known to be directly upregulated by Maf during ocular lens development (Yang and Cvekl, 2005), and another, the matrix metalloproteinase Mmp9, that has been shown to accept crystallins as a substrate (Descamps et al., 2005; Starckx et al., 2003). Second, Applicants stained sections with antibodies to PPP1R17, which was selectively expressed in cluster 20. Cluster 20 shows weak, infrequent glycine transporter expression and is one of only two clusters (with cluster 21) that express Neurod6, a marker of nGnG neurons (Kay et al., 2011), which are neither glycinergic nor GABAergic. Applicants used a transgenic strain (MitoP) that has been shown to express cyan fluorescent protein (CFP) specifically in nGnG amacrines (Kay et al., 2011). PPP1R17 stained in 85% of all CFP-positive amacrines in the MitoP line, validating this as a marker of nGnG cells. The absence of PPP1R17 from putative nGnG amacrines in Cluster 21 suggests a hitherto unsuspected level of heterogeneity among nGnG amacrines. Like cluster 7, cluster 20 expressed numerous markers distinguishing it from its closest neighbor (FIG. 12G; 12 genes >2.8-fold enrichment, $p<10^{-9}$).

Identification of additional cellular diversity within individual clusters. Applicants' unsupervised clustering analysis grouped cells into 39 distinct populations; as many as 100 retinal cell types are proposed to exist based on morphology or physiology. Applicants therefore asked whether additional heterogeneity and population structure might exist within clusters and be visible in supervised analyses; this would suggest that still-deeper classification will become possible with larger numbers of cells, or with combinations of unsupervised and known-marker-driven analyses. Here Applicants focus on cone photoreceptors and retinal ganglion cells.

Cones. Mice are dichromats, having only short-wavelength (blue or S-) and middle-wavelength (green or M-) opsins, encoded by the genes Opn1sw and Opn1mw, respectively. The S- and M-opsins are expressed in opposing gradients along the dorsal-ventral axis, with many cones, especially in central retina, expressing both of these opsins (Szel et al., 2000). No other genes have been identified that selectively mark S- or M-cones.

Figure 12I:
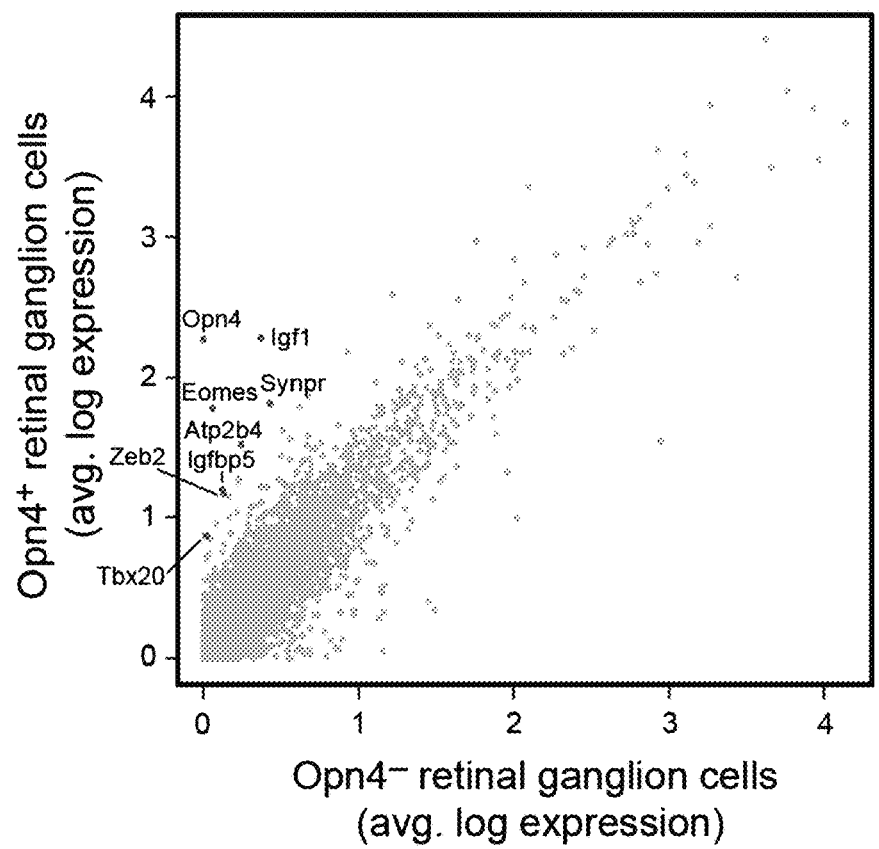

Applicants identified cluster 25 as cones by their expression of Opn1mw, Opn1sw, Arr3, and other cone-specific genes. Applicants compared genome-wide gene expression in 336 cells (in cluster 25) expressing only Opn1sw (the blue-light-sensitive opsin) to expression in 551 cells (in the same cluster) expressing only Opn1mw (the green-light-sensitive opsin) (FIG. 12II). Eight genes differed in expression by at least 2-fold (and at $p<10^{-9}$) between the two cell populations. One such gene, Thrb, encodes the receptor for thyroid hormone, a key developmental regulator of the dorsal-ventral patterning that shapes differential opsin expression (Roberts et al., 2006). Two other genes, Smug1 and Ccdc136, have been shown to be concentrated in dorsal and ventral cones respectively (Corbo et al., 2007), consistent with Applicants' assignment of them to M- and S-cones.

Retinal ganglion cells. Retinal ganglion cells (RGCs), the sole output neuron class from the retina, are believed to consist of about 20 types, of which several have known molecular markers (Masland and Sanes, 2015). RGCs altogether comprise less than 1% of the cells in the retina (Jeon et al., 1998). In Applicants' analysis of 44,808 cells, Applicants identified a single RGC cluster, consisting of less than 1% of all cells analyzed. Opn4, the gene encoding melanopsin, is a known marker of a distinct RGC type (Hattar et al., 2002); among the 432 RGCs, Applicants identified 26 cells expressing Opn4. These 26 cells expressed seven genes at least two-fold more strongly than the 406 Opn4-RGCs did (p<109, FIG. 12I); one of these seven genes was Eomes, recently shown to be required for development and maintenance of melanopsin-containing RGCs (Mao et al., 2014).

Human bone marrow cells. Human bone marrow cells contain multipotent haematopoietic stem cells which differentiate into two types of progenitors: lymphoid stem cells and myeloid stem cells. Lymphoid stem cells differentiate to prolymphocytes which develop into T, B and NK cells (i.e., peripheral blood mononuclear cells), while myeloid stem cells differentiate into three types of cell lines: granulocyte-monocyte progenitors, erythroid progenitors, and megakaryocytes. Peripheral blood mononuclear cells (PBMCs) consist of blood cells with a round nucleus which are involved in fighting diseases such as leukemias, cancers, and infectious diseases. Applicants' analysis of 471 single-cell transcription profiles prepared by Drop-Seq identified 8 clusters of gene markers which correlated to known cell types of haematopoietic stem cells.

Discussion

Here Applicants have described Drop-Seq, a new technology for simultaneously analyzing genome-wide expression in unconstrained numbers of individual cells. Applicants first validated Drop-Seq by profiling mixtures of intact human and mouse cells. Applicants then used Drop-Seq to ascertain cell states in a nominally homogeneous cell population and cell types in a complex tissue. To analyze cell states, Applicants profiled the cell cycle at near-continuous temporal resolution across 1,001 asynchronously growing cells from two species, uncovering novel cell cycle-regulated genes with evolutionarily conserved expression oscillations. To analyze cell types, Applicants profiled 44,808 individual cells from the mouse retina, an accessible portion of the central nervous system. Applicants identified 39 transcriptionally distinct cell populations in the retina, revealed novel relationships among those cells, and nominated new cell type-specific markers, two of which Applicants validated by immunohistochemistry.

In other embodiments of the technology, the application of the technology can be used to identify novel biomarkers of a disease, such as cancer or an autoimmune disease, by identifying cell populations, cell markers, or combinations of cell populations, that are specifically present in a disease state versus a healthy state.

In a further application, the Drop-Seq technology can be applied to disease modeling or prognosticating disease. The single-cell technique can be utilized to diagnose diseases with unclear etiologies or origins. For example, cancer of unknown primary tissue could be traced to a tissue-of-origin by identifying rare cells in the tissue that express markers of a cell-type of a particular tissue.

As discussed above, the Drop-Seq process generates STAMPs (single-cell transcriptomes attached to microparticles). Hence, the microparticle has a stable record of the mRNAs present in a cell and therefore can be probed for expression of different genes. For example, since the Drop-Seq technology can be utilized to rapidly sequence genes in parallel, it would be possible to probe those genes associated with a phenotype difference in microbiomes associated with human bodies. The technology can therefore be extended to analyze molecules, organelles, cellular fragments (e.g., synapses), whole cells, or collection of cells (i.e., organoids).

To become widely adopted, and to advance biology, a new technology should possess these characteristics:

1. It should fill an unmet scientific need. Biologists are quickly recognizing the scientific opportunities enabled by ascertaining transcriptional variation at the cellular level. Current methods, however, can profile only up to a few hundred cells per day, at a cost of $3-$50 per cell. By contrast, a single scientist employing Drop-Seq can completely prepare 10,000 single-cell libraries for sequencing, for about 6 cents per cell. Applicants hope that ease, speed, and low cost facilitate exuberant experimentation, careful replication, and many cycles of experiments, analyses, ideas, and more experiments.

2. It should be easy to adopt. The simpler a technology, the greater the likelihood that it can be adopted by the scientists who will know how to put it to good use. Drop-Seq utilizes equipment that is available to any biology lab—a small inverted microscope and syringe pumps such as those routinely used for microinjection. A Drop-Seq setup can be constructed quickly and inexpensively (FIG. 21 and Extended Experimental Procedures). Drop-Seq also uses two novel reagents: the microfluidic devices for droplet preparation, and the beads to individually barcode each cell's RNA. Applicants designed the microfluidics devices (through 30 design iterations) to be simple, passive devices that could be readily constructed in any academic or commercial microfluidics facility, and Applicants provide a CAD file to enable this. The barcoded beads described here will be available upon the publication of this paper (Extended Experimental Procedures). Applicants' supplemental materials include detailed protocols for interested readers.

3. It should be thoroughly tested to provide a clear understanding of the technology's advantages and limitations. Here Applicants used mixtures of mouse and human cells to carefully measure both single-cell purity and the frequency of cell doublets—the first work that Applicants are aware of to test any single-cell analysis strategy in this way. Applicants find that Applicants can tune two key quality parameters—cell-cell doublets and contaminating RNA—by adjusting the input cell concentration, and that at lower cell concentrations (still accommodating a throughput of 1,200 cells per hour) Drop-Seq compares favorably to existing technology for both doublets and purity. Applicants' results suggest that other methods of isolating single cells from a cell suspension, such as fluorescence activated cell sorting (FACS) or microfluidics, are also vulnerable to doublets and single-cell impurities. The analysis of Applicants' retina dataset suggests that even relatively impure libraries generated in "ultra-high-throughput" modes (100 cells per µl, allowing the processing of 10,000 cells per hour at ~10% doublet and impurity rates) can yield a rich, robust and biologically validated cell classification, but other tissues or applications may require using purer modes of Drop-Seq. Applicants would always suggest that pilot analyses begin with one of Drop-Seq's higher-purity modes.

The other major quality metric of a single-cell profiling technology is capture efficiency. Applicants estimated Drop-Seq's capture efficiency to be about 12%, based on analyses of synthetic RNA "spike-ins," which Applicants then corroborated by highly sensitive digital PCR measurements of ten genes. Studies of single-cell digital expression profiling methods in the past year have reported capture rates of 3%, 3.4%, and 48%, though these rates have not been estimated or corrected in uniform ways; Applicants chose a particularly conservative estimation method to arrive at the 12% estimate for Drop-Seq and suggest that a great need in single-cell genomics is for uniform comparison strategies and metrics. Applicants' analysis of the retina indicates that capturing only ~12% of each cell's transcriptome (and sequencing less than that) may allow even subtle cell type differences (e.g. among 21 amacrine cell populations) to be recognized; this extends an idea proposed in a recent study of 301 cortical cells (Pollen et al., 2014). The ability to analyze so many cells may help to elucidate biological patterns that would otherwise be elusive, as these patterns are then shared across large numbers of analyzed cells in ways that overwhelm the biological, technical and statistical-sampling noise that exists at the single-cell level.

Unsupervised computational analysis of Drop-Seq data identified 39 transcriptionally distinct retinal cell populations; all turned out to belong to known cell classes, and most appeared to correspond to known or hypothesized retinal cell types and subtypes, based on expression of previously validated markers (FIGS. 11 and 12). It is a particular strength of the retina that establishing correspondence between cluster and type was in many cases straightforward; classification has not proceeded sufficiently far in most other parts of the brain to permit such validation, which is why initial validation in a tissue like the retina was so important. Many of these cell populations especially those within the amacrine class-nominated new distinguishing markers for cells previously identified only by morphology and physiology.

Many interesting questions surround the definition of cell types from transcriptomics data. For example, are there always clear expression thresholds beyond which two groups of cells are distinct types, or are distinctions sometimes graded and continuous? More importantly, how do transcriptional differences among cell populations give rise to anatomical and physiological differences? The throughput afforded by Drop-Seq may enable such questions to be comprehensively addressed in whole tissues, by providing sufficient numbers of profiles to appreciate patterns of expression even in rare cell types.

Applicants see many other important applications of Drop-Seq in biology, beyond the identification of cell types and cell states. Genome-scale genetic studies are identifying large numbers of genes in which genetic variation contributes to disease risk; but biology has lacked similarly high-throughput ways of connecting genes to specific cell populations and their unique functional responses. Finding the cellular sites and biological activities of so many genes will be important for going from genetic leads to biological insights. High-throughput single-cell transcriptomics could localize the expression of risk genes to specific cell types, and in conjunction with genetic perturbations, could also help to systematically relate each gene to (i) the cell types most affected by loss or perturbation of those genes; and (ii) the alterations in cell state elicited by such perturbations. Such approaches could help cross the daunting gap from high-throughput gene discovery to (harder-to-acquire) real insights about the etiology of human diseases (McCarroll et al., 2014).

The coupling of Drop-Seq to additional perturbations—such as small molecules, mutations (natural or engineered), pathogens, or other stimuli—could be used to generate an information-rich, multi-dimensional readout of the influence of perturbations on many kinds of cells. When studying the effects of a mutation, for example, Drop-Seq could simultaneously reveal the ways in which the same mutation impacts many cell types in both cell-autonomous and cell-nonautonomous ways.

The functional implications of a gene's expression are a product not just of the gene or encoded protein's intrinsic properties, but also of the entire cell-level context in which the gene is expressed. Applicants hope Drop-Seq will enable the abundant and routine discovery of such relationships in many areas of biology.

Experimental Procedures

Device fabrication. Microfluidic devices were designed using AutoCAD software (Autodesk, Inc.), and the components tested using COMSOL Multiphysics (COMSOL Inc.). A CAD file is also available in the supplement.

Devices were fabricated using a bio-compatible, silicon-based polymer, polydimethylsiloxane (PDMS) via replica molding using the epoxy-based photo resist SU8 as the master, as previously described (Mazutis et al., 2013; McDonald et al., 2000). The PDMS devices were then rendered hydrophobic by flowing in Aquapel (Rider, Mass., USA) through the channels, drying out the excess fluid by flowing in pressurized air, and baking the device at 65° C. for 10 minutes.

Barcoded microparticle synthesis. Bead functionalization and reverse direction phosphoramidite synthesis were performed by Chemgenes Corp (Wilmington, Mass.). "Split-and-pool" cycles were accomplished by removing the dry resin from each column, hand mixing, and weighing out four equal portions before returning the resin for an additional cycle of synthesis. Full details (including availability of the beads) are described in Extended Experimental Procedures.

Drop-Seq procedure. A complete, in-depth description of the protocol, including the composition and catalogue numbers for all reagents, can be found in Extended Experimental Procedures. In brief, droplets ~1 nL in size were generated using the co-flow microfluidic device described above, in which barcoded microparticles, suspended in lysis buffer, were flowed at a rate equal to that of a single-cell suspension, so that the droplets were composed of an equal amount of each component. As soon as droplet generation was complete, droplets were broken with perfluorooctanol in 30 mL of 6×SSC. The addition of a large aqueous volume to the droplets reduces hybridization events after droplet breakage, because DNA base pairing follows second-order kinetics (Britten and Kohne, 1968; Wetmur and Davidson, 1968). The beads were then washed and resuspended in a reverse transcriptase mix. After incubation for 30 min at 25° C. and 90 min at 42° C., the beads were washed and resuspended in Exonuclease I mix and incubated for 45 min at 37° C. The beads were washed, counted, aliquoted into PCR tubes, and PCR amplified (see Extended Experimental Procedures for details). The PCR reactions were purified and pooled, and the amplified cDNA quantified on a BioAnalysis High Sensitivity Chip (Agilent). The 3'-ends were fragmented and amplified for sequencing using the Nextera XT DNA sample prep kit (Illumina) using custom primers that enabled the specific amplification of only the 3' ends (Table 9). The libraries were purified and quantitated on a High Sensitivity Chip, and sequenced on the Illumina NextSeq 500. All details regarding reaction conditions, primers used, and sequencing specifications can be found in the Extended Experimental Procedures.

Alignment and estimation of digital expression levels. Raw sequence data was filtered, adapter- and polyA-trimmed, and aligned to either the mouse (mm10) genome for retina experiments, or a combined mouse (mm10)-human (hg19) mega-reference, using STAR v2.4.0 (Dobin et al., 2013). All reads with the same cell barcode were grouped together, and reads from the same cell aligning to the same gene, with UMIs within ED=1, were merged. On each cell, for each gene, the unique UMIs were counted; this count was then placed into a digital expression matrix. The matrix was ordered by the sum of all UMIs per cell, and a cumulative sum plot was generated. Applicants determined the number of STAMPs by estimating the first inflection point (FIG. 14B), which Applicants empirically found to always be close to the estimated number of amplified STAMPs. Additional details can be found in Extended Experimental Procedures.

Cell cycle analysis of HEK and 3T3 cells. Gene sets reflecting five phases of the HeLa cell cycle (G1/S, S, G2/M, M and M/G1) were taken from Whitfield et al. (Whitfield et al., 2002), with some modification (Extended Experimental Procedures). A phase-specific score was generated for each cell, across all five phases, using averaged normalized expression levels ($\log_2(\text{TPM}+1)$) of the genes in each gene set. Cells were then ordered along the cell cycle by comparing the patterns of these five phase scores per cell. To identify cell cycle-regulated genes, Applicants used a sliding window approach, and identified windows of maximal and minimal average expression, both for ordered cells, and for shuffled cells, to evaluate the false-discovery rate. Full details may be found in Extended Experimental Procedures.

Generation of whole retina suspension. Suspensions were prepared from the retinas of 14-day-old (P14) C57BL/6 mice by adapting previously described methods (Barres et al., 1988). See Extended Experimental Procedures for additional details.

Principal components and clustering analysis of retina data. Principal components analysis (PCA) was first performed on a 13,155-cell "training set" of the 49,300-cell dataset, using single-cell libraries with >900 genes. Applicants found their approach was more effective in discovering structures corresponding to rare cell types than performing PCA on the full dataset, which was dominated by numerous, tiny rod photoreceptors (Extended Experimental Procedures). 384 genes that showed either significant variability or structure within this training set were used to learn the principal components (PCs). Thirty-two statistically significant PCs were identified using a permutation test and independently confirmed using a modified resampling procedure (Chung and Storey, 2014). To visualize the organization of cell-types in the retina, Applicants projected individual cells within the training set based on their scores along the significant PCs onto a single two-dimensional map using t-Distributed Stochastic Neighbor Embedding (t-SNE) (van der Maaten and Hinton, 2008). The remaining 36,145 single-cell libraries (<900 genes detected) were next projected on to this t-SNE map, based on their representation within the PC-subspace of the training set (Berman et al., 2014; Shekhar et al., 2014). This approach mitigates the impact of noisy variation in the lower complexity libraries due to gene dropouts, and was also reliable in the sense that when Applicants withheld from the tSNE all cells from a given cluster and then tried to project them, these withheld cells were not spuriously assigned to another cluster by the projection (Table 10). Furthermore, cells are not allowed to be projected based on similarity to less than 10 cells (see Extended Experimental Procedures). Point clouds on the t-SNE map represent cell-types, and density clustering (Ester et al., 1996) identified these regions, using two sets of parameters for defining both large and small clusters. Differential expression testing (McDavid et al., 2013) was then used to confirm that clusters were distinct from each other. Hierarchical clustering based on Euclidean distance and complete linkage was used to build a tree relating the clusters. Applicants noted expression of several rod-specific genes, such as Rho and Nrl, in every cell cluster, an observation that has been made in another retinal cell gene expression study (Siegert et al., 2012). This likely arises from solubilization of these high-abundance transcripts during cell suspension preparation. Additional information regarding retinal cell data analysis can be found in the Extended Experimental Procedures.

Example 3: Extended Experimental Procedures for Example 2

Bead Synthesis. Bead functionalization and reverse direction phosphoramidite synthesis (5' to 3') were performed by Chemgenes Corp. Toyopearl HW-65S resin (30 micron mean particle diameter) was purchased from Tosoh Biosciences, and surface alcohols were functionalized with a PEG derivative to generate an 18-carbon long, flexible-chain linker. The functionalized bead was then used as a solid support for reverse direction phosphoramidite synthesis (5'→3') on an Expedite 8909 DNA/RNA synthesizer using DNA Synthesis at 10 micromole cycle scale and a coupling time of 3 minutes. Amidites used were: $N^6$-Benzoyl-3'-O-DMT-2'-deoxy adenosine-5'-cyanoethyl-N,N-diisopropyl-phosphoramidite (dA-$N^6$-Bz-CEP); $N^4$-Acetyl-3'-O-DMT-2'-deoxy-cytidine-5'-cyanoethyl-N,N-diisopropyl-phosphoramidite (dC-$N^4$-Ac-CEP); $N^2$-DMF-3'-O-DMT-2'-deoxy guanosine-5'-cyanoethyl-N,N-diisopropyl-phosphoramidite (dG-$N^2$-DMF-CEP); and 3'-O-DMT-2'-deoxy thymidine-5'-cyanoethyl-N,N-diisopropyl-phosphoramidite (T-CEP). Acetic anhydride and N-methylimidazole were used in the capping step; ethylthiotetrazole was used in the activation step; iodine was used in the oxidation step, and dichloroacetic acid was used in the deblocking step. After each of the twelve split-and-pool phosphoramidite synthesis cycles, beads were removed from the synthesis column, pooled, hand-mixed, and apportioned into four equal portions by mass; these bead aliquots were then placed in a separate synthesis column and reacted with either dG, dC, dT, or dA phosphoramidite. This process was repeated 12 times for a total of 4^12=16,777,216 unique barcode sequences. For complete details regarding the barcoded bead sequences used.

Cell Culture. Human 293 T cells were purchased as well as the murine NIH/3T3 cells. 293T and 3T3 cells were grown in DMEM supplemented with 10% FBS and 1% penicillin-streptomycin.

Cells were grown to a confluence of 30-60% and treated with TrypLE for five min, quenched with equal volume of growth medium, and spun down at 300×g for 5 min. The supernatant was removed, and cells were resuspended in 1 mL of 1×PBS+0.2% BSA and re-spun at 300×g for 3 min. The supernatant was again removed, and the cells re-suspended in 1 mL of 1×PBS, passed through a 40-micron cell strainer and counted. For Drop-Seq, cells were diluted to the final concentration in 1×PBS+200 µg/mL BSA.

Generation of Whole Retina Suspensions. Single cell suspensions were prepared from P14 mouse retinas by adapting previously described methods for purifying retinal ganglion cells from rat retina (Barres et al., 1988). Briefly, mouse retinas were digested in a papain solution (40 U papain/10 mL DPBS) for 45 minutes. Papain was then neutralized in a trypsin inhibitor solution (0.15% ovomucoid in DPBS) and the tissue was triturated to generate a single cell suspension. Following trituration, the cells were pelleted and resuspended and the cell suspension was filtered through a 20 µm Nitex mesh filter to eliminate any clumped cells and this suspension was then used for Drop-Seq. The cells were then diluted in DPBS+0.2% BSA to either 200 cells/µl (replicates 1-6) or 30 cells/µl (replicate 7).

Retina suspensions were processed through Drop-Seq on four separate days. One library was prepared on day 1 (replicate 1); two libraries on day 2 (replicates 2 and 3); three libraries on day 3 (replicates 4-6); and one library on day 4 (replicate 7, high purity). To replicates 4-6, human HEK cells were spiked in at a concentration of 1 cell/µl (0.5%) but the wide range of cell sizes in the retina data made it impossible to calibrate single-cell purity or doublets using the cross-species comparison method. Each of the seven replicates was sequenced separately.

Drop-Seq

Preparation of beads. Beads (either Barcoded Bead SeqA or Barcoded Bead SeqB; Table 9 and see note at end of Extended Experimental Procedures) were washed twice with 30 mL of 100% EtOH and twice with 30 mL of TE/TW (10 mM Tris pH 8.0, 1 mM EDTA, 0.01% Tween). The bead pellet was resuspended in 10 mL TE/TW and passed through a 100 µm filter into a 50 mL Falcon tube for long-term storage at 4° C. The stock concentration of beads (in beads/µL) was assessed using a Fuchs-Rosenthal cell counter purchased from INCYTO. For Drop-Seq, an aliquot of beads was removed from the stock tube, washed in 500 µL of Drop-Seq Lysis Buffer (DLB, 200 mM Tris pH 7.5, 6% Ficoll PM-400, 0.2% Sarkosyl, 20 mM EDTA), then resuspended in the appropriate volume of DLB+50 mM DTT for a bead concentration of 100 beads/µL.

Droplet generation. The two aqueous suspensions—the single-cell suspension and the bead suspension—were loaded into 3 mL plastic syringes containing a 6.4 mm magnetic stir disc. Droplet generation oil was loaded into a 10 mL plastic syringe. The three syringes were connected to a 125 µm coflow device (FIG. 15A) by 0.38 mm inner-diameter polyethylene tubing, and injected using syringe pumps at flow rates of 4.1 mL/hr for each aqueous suspension, and 14 mL/hr for the oil, resulting in ~125 µm emulsion drops with a volume of ~1 nanoliter each. For movie generation, the flow was visualized under an optical microscope at 10× magnification and imaged at ~1000-2000 frames per second using a FASTCAM SA5 color camera. Droplets were collected in 50 mL falcon tubes; the collection tube was changed out for every 1 mL of combined aqueous flow volume to reduce the amount of soluble RNA in solution upon droplet breakage.

During droplet generation, the beads were kept in suspension by continuous, gentle magnetic stirring. The uniformity in droplet size and the occupancy of beads were evaluated by observing aliquots of droplets under an optical microscope with bright-field illumination; in each experiment, greater than 95% of the bead-occupied droplets contained only a single bead.

Droplet breakage. The oil from the bottom of each aliquot of droplets was removed with a P1000 pipette, after which 30 mL 6×SSC at room temperature was added. To break droplets, Applicants added 600 µL of Perfluoro-1-octanol, and shook the tube vigorously by hand for about 20 seconds. The tube was then centrifuged for 1 minute at 1000×g. To reduce the likelihood of annealed mRNAs dissociating from the beads, the sample was kept on ice for the remainder of the breakage protocol. The supernatant was removed to roughly 5 mL above the oil-aqueous interface, and the beads washed with an additional 30 mL of room temperature 6×SSC, the aqueous layer transferred to a new tube, and centrifuged again. The supernatant was removed, and the bead pellet transferred to non-stick 1.5 mL microcentrifuge tubes. The pellet was then washed twice with 1 mL of room temperature 6×SSC, and once with 300 µL of 5× Maxima H-RT buffer (EP0751).

Reverse transcription and Exonuclease I treatment. To a pellet of 90,000 beads, 200 µL of RT mix was added, where the RT mix contained 1× Maxima RT buffer, 4% Ficoll PM-400, 1 mM dNTPs, 1 U/µL Rnase Inhibitor, 2.5 µM Template_Switch_Oligo (Table 9), and 10 U/µL Maxima H-RT. Ficoll was included to reduce settling, and because of its ability to improve RT efficiency (Lareu et al., 2007). The beads were incubated at room temperature for 30 minutes, followed by 42° C. for 90 minutes. The beads were then washed once with 1 mL 1×TE+0.5% Sodium Dodecyl Sulfate, twice with 1 mL TE/TW, and once with 10 mM Tris pH 7.5. The bead pellet was then resuspended in 200 µL of exonuclease I mix containing 1× Exonuclease I Buffer and 1 U/µL Exonuclease I, and incubated at 37° C. for 45 minutes.

The beads were then washed once with 1 mL TE/SDS, twice with 1 mL TE/TW, once with 1 mL ddH$_2$O, and resuspended in ddH$_2$O. Bead concentration was determined using a Fuchs-Rosenthal cell counter. Aliquots of 1000 beads were amplified by PCR in a volume of 50 µL using 1× Hifi HotStart Readymix and 0.8 µM Template_Switch_PCR primer (Table 9).

The aliquots were thermocycled as follows: 95° C. 3 min; then four cycles of: 98° C. for 20 sec, 65° C. for 45 sec, 72° C. for 3 min; then X cycles of: 98° C. for 20 sec, 67° C. for 20 sec, 72° C. for 3 min; then a final extension step of 5 min. For the human-mouse experiment using cultured cells, X was 8 cycles; for the dissociated retina experiment, X was 9 cycles. Pairs of aliquots were pooled together after PCR and purified with 0.6× Agencourt AMPure XP beads according to the manufacturer's instructions, and eluted in 10 µL of H$_2$O. Aliquots were pooled according to the number of STAMPs to be sequenced, and the concentration of the pool quantified on a BioAnalyzer High Sensitivity Chip.

Preparation of Drop-Seq cDNA library for sequencing. To prepare 3'-end cDNA fragments for sequencing, four aliquots of 600 pg of cDNA of each sample was used as input in standard Nextera XT tagmentation reactions, performed according to the manufacturer's instructions except that 200 nM of the custom primers P5_TSO_Hybrid and Nextera_N701 (Table 9) were used in place of the kit's provided oligonucleotides. The samples were then amplified as follows: 95° C. for 30 sec; 11 cycles of 95° C. for 10 sec, 55° C. for 30 sec, 72° C. for 30 sec; then a final extension step of 72° C. for 5 min.

Pairs of the 4 aliquots were pooled together, and then purified using 0.6× Agencourt AMPure XP Beads according to the manufacturer's instructions, and eluted in 10 µL of water. The two 10 µL aliquots were combined together and the concentration determined using a BioAnalyzer High Sensitivity Chip. The average size of sequenced libraries was between 450 and 650 bp.

The libraries were sequenced on the Illumina NextSeq, using 4.67 pM in a volume of 3 mL HT1, and 3 mL of 0.3 µM Read1CustSeqA or Read1CustSeqB (Table 9 and see note at the end of Extended Experimental Procedures) for priming of read 1. Read 1 was 20 bp (bases 1-12 cell barcode, bases 13-20 UMI); read 2 (paired end) was 50 bp for the human-mouse experiment, and 60 bp for the retina experiment.

Species contamination experiment. To determine the origin of off-species contamination of STAMP libraries (FIG. 15E), Applicants: (1) performed Drop-Seq exactly as above (control experiment) with a HEK/3T3 cell suspension mixture of 100 cells/µL in concentration; (2) performed microfluidic co-flow step with HEK and 3T3 cells separately, each at a concentration of 100 cells/µL, and then mixed droplets prior to breakage; and (3) performed STAMP generation through exonuclease digestion, with the HEK and 3T3 cells separately, then mixed equal numbers of STAMPs prior to PCR amplification. A single 1000 microparticle aliquot was amplified for each of the three conditions, then purified and quantified on a BioAnalyzer High Sensitivity DNA chip. 600 pg of each library was used in a single Nextera Tagmentation reaction as described above, except that each of the three libraries was individually barcoded with the primers Nextera_N701 (condition 1), Nextera_N702 (condition 2), or Nextera_N703 (condition 3), and a total of 12 PCR cycles were used in the Nextera PCR instead of 11. The resulting library was quantified on a High Sensitivity DNA chip, and run at a concentration of 25 pM on the MiSeq using 0.5 µM Read1CustSeqA as a custom primer for read 1.

Soluble RNA experiments. To quantify the number of primer annealing sites, 20,000 beads were incubated with 10 µM of polyadenylated synthetic RNA (synRNA, Table 9) in 2×SSC for 5 min at room temperature, and washed three times with 200 µL of TE-TW, then resuspended in 10 µL of TE-TW. The beads were then incubated at 65° C. for 5 minutes, and 1 µL of supernatant was removed for spectrophotometric analysis on the Nanodrop 2000. The concentration was compared with beads that had been treated the same way, except no synRNA was added.

To determine whether the bead-bound primers were capable of reverse transcription, and to measure the homogeneity of the cell barcode sequence on the bead surface, beads were washed with TE-TW, and added at a concentration of 100/µL to the reverse transcriptase mix described above. This mix was then co-flowed into the standard Drop-Seq 120-micron co-flow device with 200 nM SynRNA in 1×PBS+0.02% BSA. Droplets were collected and incubated at 42° C. for 30 minutes. 150 µL of 50 mM EDTA was added to the emulsion, followed by 12 µL of perfluorooctanoic acid to break the emulsion. The beads were washed twice in 1 mL TE-TW, followed by one wash in H$_2$O, then resuspended in TE. Eleven beads were handpicked under a microscope into a 50 µL PCR mix containing 1× Kapa HiFi Hotstart PCR mastermix, 400 nM P7-TSO_Hybrid, and 400 nM TruSeq_F (Table 9). The PCR reaction was cycled as follows: 98° C. for 3 min; 12 cycles of: 98° C. for 20 s, 70° C. for 15 s, 72° C. for 1 min; then a final 72° C. incubation for 5 min. The resulting amplicon was purified on a Zymo DNA Clean and Concentrator 5 column, and run on a BioAnalyzer High Sensitivity Chip to estimate concentration. The amplicon was then diluted to 2 nM and sequenced on an Illumina MiSeq. Read 1, primed using the standard Illumina TruSeq primer, was a 20 bp molecular barcode on the SynRNA, while Read 2, primed with CustSynRNASeq, contained the 12 bp cell barcode and 8 bp UMI.

To estimate the efficiency of Drop-Seq, Applicants used a set of external RNAs. Applicants diluted the ERCC spike-ins to 0.32% of the stock in 1×PBS+1 U/µL RNase Inhibitor+200 µg/mL BSA (NEB), and used this in place of the cell flow in the Drop-Seq protocol, so that each bead was incubated with ~100,000 ERCC mRNA molecules per nanoliter droplet. Sequence reads were aligned to a dual ERCC-human (hg19) reference, using the human sequence as "bait," which dramatically reduced the number of low-quality alignments to ERCC transcripts reported by STAR compared with alignment to an ERCC-only reference.

Standard mRNA-seq. To compare Drop-Seq average expression data to standard mRNAseq data, Applicants used 1.815 ug of purified RNA from 3T3 cells, from which Applicants also prepared and sequenced 550 STAMPs. The RNA was used in the TruSeq Stranded mRNA Sample Preparation kit according to the manufacturer's instructions. For NextSeq 500 sequencing, 0.72 pM of Drop-Seq library was combined with 0.48 pM of the mRNAseq library.

In-solution template switch amplification. To compare Drop-Seq average expression data to mRNAseq libraries prepared by a standard, in-solution template switch amplification approach, 5 ng of purified RNA from 3T3 cells, from which Applicants also prepared and sequenced 550 STAMPs, was diluted in 2.75 µl of H$_2$O. To the RNA, 1 µl of 10 µM UMI_SMARTdT primer was added (Table 9) and heated to 72° C., followed by incubation at 4° C. for 1 min, after which Applicants added 2 µl 20% Ficoll PM-400, 2 µl 5× RT Buffer (Maxima H-kit), 1 µl 10 mM dNTPs, 0.5 µl 50 µM Template_Switch_Oligo (Table 9), and 0.5 µl Maxima H-RT. The RT was incubated at 42° C. for 90 minutes, followed by heat inactivation for 5 min at 85° C. An RNase cocktail (0.5 µl RNase I, Epicentre N6901K, and 0.5 µl RNase H) was added to remove the terminal riboGs from the template switch oligo, and the sample incubated for 30 min at 37° C. Then, 0.4 µl of M Template_Switch_PCR primer was added, along with 25 µl 2× Kapa Hifi supermix, and 13.6 µl H$_2$O. The sample was cycled as follows: 95° C. 3 min; 14 cycles of: 98° C. 20 s, 67° C. 20 s, and 72° C. 3 min; then 72° C. 5 min. The samples were purified with 0.6 AMPure XP beads according to the manufacturer's instructions, and eluted in 10 µl. 600 pg of amplified cDNA was used as input into a Nextera XT reaction. 0.6 pM of library was sequenced on a NextSeq 500, multiplexed with three other samples; Read1CustSeqB was used to prime read 1.

Droplet digital PCR (ddPCR) experiments. To quantify the efficiency of Drop-Seq, 50,000 HEK cells, prepared in an identical fashion as in Drop-Seq, were pelleted and RNA purified using the Qiagen RNeasy Plus Kit according to the manufacturer's protocol. The eluted RNA was diluted to a final concentration of 1 cell-equivalent per microliter in an RT-ddPCR reaction containing RT-ddPCR supermix, and a gene primer-probe set. Droplets were produced using Bio- Rad ddPCR droplet generation system, and thermocycled with the manufacturer's recommended protocol, and droplet fluorescence analyzed on the BioRad QX100 droplet reader. Concentrations of RNA and confidence intervals were computed by BioRad QuantaSoft software. Three replicates of 50,000 HEK cells were purified in parallel, and the concentration of each gene in each replicate was measured two independent times. The probes used were: ACTB (hs01060665_g1), B2M (hs00984230_m1), CCNB1 (mm03053893), EEF2 (hs00157330_m1), ENO1 (hs00361415_m1), GAPDH (hs02758991_g1), PSMB4 (hs01123843_g1), TOP2A (hs01032137_m1), YBX3 (hs01124964_m1), and YWHAH (hs00607046_m1).

To estimate the RNA hybridization efficiency of Drop-Seq, human brain total RNA was diluted to 40 ng/µl in a volume of 20 µl and combined with 20 µl of barcoded primer beads resuspended in Drop-Seq lysis buffer (DLB, composition shown below) at a concentration of 2,000 beads/µl. The solution was incubated at 15 minutes with rotation, then spun down and the supernatant transferred to a fresh tube. The beads were washed 3 times with 100 µl of 6×SSC, resuspended in 50 µl H2O, and heated to 72° C. for 5 min to elute RNA off the beads. The elution step was repeated once and the elutions pooled. All steps of the hybridization (RNA input, hybridization supernatant, three washes, and combined elution) were separately purified using the Qiagen RNeasy Plus Mini Kit according to the manufacturers' instructions. Various dilutions of the elutions were used in RT-ddPCR reactions with primers and probes for either ACTB or GAPDH.

Fluidigm C1 experiments. C1 experiments were performed as previously described (Shalek et al., 2014). Briefly, suspensions of 3T3 and HEK cells were stained with calcein violet and calcein orange (Life Technologies) according to the manufacturer's recommendations, diluted down to a concentration of 250,000 cells per mL, and mixed 1:1. This cell mixture was then loaded into two medium C1 cell capture chips from Fluidigm and, after loading, caught cells were visualized and identified using DAPI and TRITC fluorescence. Bright field images were used to identify ports with >1 cell (a total of 12 were identified from the two C1 chips used, out of 192 total). After C1-mediated whole transcriptome amplification, libraries were made using Nextera XT (Illumina), and loaded on a NextSeq 500 at 2.2 pM. Single-read sequencing (60 bp) was performed to mimic the read structure in DropSeq, and the reads aligned as per below.

Read alignment and generation of digital expression data. Raw sequence data was first filtered to remove all read pairs with a barcode base quality of less than 10. The second read (50 or 60 bp) was then trimmed at the 5' end to remove any TSO adapter sequence, and at the 3' end to remove polyA tails of length 6 or greater, then aligned to either the mouse (mm10) genome (retina experiments) or a combined mouse (mm10)-human (hg19) mega-reference, using STAR v2.4.0 a with default setting.

Uniquely mapped reads were grouped by cell barcode. To digitally count gene transcripts, a list of UMIs in each gene, within each cell, was assembled, and UMIs within ED=1 were merged together. The total number of unique UMI sequences was counted, and this number was reported as the number of transcripts of that gene for a given cell.

To distinguish cell barcodes arising from STAMPs, rather than those that corresponded to beads never exposed to cell lysate, Applicants ordered the digital expression matrix by the total number of transcripts per cell barcode, and plotted the cumulative fraction of all transcripts in the matrix for each successively smaller cell barcode. Empirically, Applicants' data always displays a "knee," at a cell barcode number close to the estimate number of STAMPs amplified (FIG. 14B). All cell barcodes larger than this cutoff were used in downstream analysis, while the remaining cell barcodes were discarded.

Cell cycle analysis of HEK and 3T3 cells. Gene sets reflecting five phases of the HeLa cell cycle (G1/S, S, G2/M, M and M/G1) were taken from Whitfield et al. (Whitfield et al., 2002) (Table 3), and refined by examining the correlation between the expression pattern of each gene and the average expression pattern of all genes in the respective gene-set, and excluding genes with a low correlation (R<0.3). This step removed genes that were identified as phase-specific in Hela cells but did not correlate with that phase in Applicants' single cell data. The remaining genes in each refined gene-set were highly correlated (not shown). Applicants then averaged the normalized expression levels ($\log_2(TPM+1)$) of the genes in each gene-set to define the phase-specific scores of each cell. These scores were then subjected to two normalization steps. First, for each phase, the scores were centered and divided by their standard deviation. Second, the normalized scores of each cell were centered and normalized.

To order cells according to their progression along the cell cycle, Applicants first compared the pattern of phase-specific scores, of each cell, to eight potential patterns along the cell cycle: only G1/S is on, both G1/S and S, only S, only G2/M, G2/M and M, only M, only M/G1, M/G1 and G1. Applicants also added a ninth pattern for equal scores of all phases (either all active or all inactive). Each pattern was defined simply as a vector of ones for active programs and zeros for inactive programs. Applicants then classified the cells to the defined patterns based on the maximal correlation of the phase-specific scores to these potential patterns. Importantly, none of the cells were classified to the ninth pattern of equal activity, while multiple cells were classified to each of the other patterns. To further order the cells within each class Applicants sorted the cells based on their relative correlation with the preceding and succeeding patterns, thereby smoothing the transitions between classes (FIG. 10A).

To identify cell cycle-regulated genes Applicants used the cell cycle ordering defined above and a sliding window approach with a window size of 100 cells. Applicants identified the windows with maximal average expression and minimal average expression for each gene and used a two-sample t-test to assign an initial p-value for the difference between maximal and minimal windows. A similar analysis was performed after shuffling the order of cells in order to generate control p-values that can be used to evaluate false-discovery rate (FDR). Specifically, Applicants examined for each potential p-value threshold, how many genes pass that threshold in the cell-cycle ordered and in the randomly-ordered analyses to assign FDR. Genes were defined as being previously known to be cell-cycle regulated if they were included in a cell cycle GO/KEGG/REACTOME gene set, or reported in a recent genome-wide study of gene expression in synchronized replicating cells (Bar-Joseph et al., 2008).

Unsupervised dimensionality reduction and clustering analysis of retina data. P14 mouse retina suspensions were processed through Drop-Seq in seven different replicates on four separate days, and each sequenced separately. Raw digital expression matrices were generated for the seven sequencing runs. The inflection points (number of cells) for each sample replicate were as follows: 6,600, 9,000, 6,120, 7,650, 7,650, 8280, and 4000. The full 49,300 cells were merged together in a single matrix, and first normalized by the number of UMIs by dividing by the total number of UMIs per cell, then multiplied by 10,000. All calculations and data were then performed in log space (i.e. ln(transcripts-per-10,000+1)).

Initial downsampling and identification of highly variable genes. Rod photoreceptors constitute 60-70% of the retinal cell population. Furthermore, they are significantly smaller than other retinal cell types (Carter-Dawson and LaVail, 1979), and as a result yielded significantly fewer genes (and higher levels of noise) in Applicants' single cell data. In Applicants' preliminary computational experiments, performing unsupervised dimensionality reduction on the full dataset resulted in representations that were dominated by noisy variation within the numerous rod subset; this compromised Applicants' ability to resolve the heterogeneity within other cell-types that were comparatively smaller in frequency (e.g. amacrines, microglia). Thus, to increase the power of unsupervised dimensionality reduction techniques for discovering these types Applicants first downsampled the 49,300-cell dataset to extract single-cell libraries where 900 or more genes were detected, resulting in a 13,155-cell "training set". Applicants reasoned that this "training set" would be enriched for rare cell types that are larger in size at the expense of "noisy" rod cells. The remaining 36,145 cells (henceforth "projection set") were then directly embedded onto to the low dimensional representation learned from the training set (see below). This enabled us to leverage the full statistical power of Applicants' data to define and annotate cell types.

Applicants first identified the set of genes that was most variable across the training set, after controlling for the relationship between mean expression and variability. Applicants calculated the mean and a dispersion measure (variance/mean) for each gene across all 13,155 single cells, and placed genes into 20 bins based on their average expression. Within each bin, Applicants then z-normalized the dispersion measure of all genes within the bin, in order to identify outlier genes whose expression values were highly variable even when compared to genes with similar average expression. Applicants used a z-score cutoff of 1.7 to identify 384 significantly variable genes, which as expected, consisted of markers for distinct retinal cell types.

Principal Components Analysis. Applicants ran Principal Components Analysis (PCA) on Applicants' training set as previously described (Shalek et al., 2013), using the prcomp function in R, after scaling and centering the data along each gene. Applicants used only the previously identified "highly variable" genes as input to the PCA in order to ensure robust identification of the primary structures in the data.

While the number of principal components returned is equal to the number of profiled cells, only a small fraction of these components explain a statistically significant proportion of the variance, as compared to a null model. Applicants used two approaches to identify statistically significant PCs for further analysis: (1) Applicants performed 10000 independent randomizations of the data such that within each realization, the values along every row (gene) of the scaled expression matrix are randomly permuted. This operation randomizes the pairwise correlations between genes while leaving the expression distribution of every gene unchanged. PCA was performed on each of these 10000 "randomized" datasets. Significant PCs in the unpermuted data were identified as those with larger eigenvalues compared to the highest eigenvalues across the 10000 randomized datasets (p<0.01, Bonferroni corrected). (2) Applicants modified a randomization approach ('jack straw') proposed by Chung and Storey (Chung and Storey, 2014) and which Applicants have previously applied to single-cell RNA-seq data (Shalek et al., 2014). Briefly, Applicants performed 1,000 PCAs on the input data, but in each analysis, Applicants randomly 'scrambled' 1% of the genes to empirically estimate a null distribution of scores for every gene. Applicants used the joint-null criterion (Leek and Storey, 2011) to identify PCs that had gene scores significantly different from the respective null distributions (p<0.01, Bonferroni corrected). Both (1) and (2) yielded 32 'significant' PCs. Visual inspection confirmed that none of these PCs was primarily driven by mitochondrial, housekeeping, or hemoglobin genes. As expected, markers for distinct retinal cell types were highly represented among the genes with the largest scores (+ve and −ve) along these PCs (Table 5).

t-SAE representation and post-hoc projection of remaining cells. Because canonical markers for different retinal cell types were strongly represented along the significant PCs (FIG. 17), Applicants reasoned that the loadings for individual cells in the training set along the principal eigenvectors (also "PC subspace representation") could be used to separate out distinct cell types in the data. Applicants note that these loadings leverage information from the 384 genes in the PCA, and therefore are more robust to technical noise than single-cell measurements of individual genes. Applicants used these PC loadings as input for t-Distributed Stochastic Neighbor Embedding (tSNE) (van der Maaten and Hinton, 2008), as implemented in the tsne package in R with the "perplexity" parameter set to 30. The t-SNE procedure returns a two-dimensional embedding of single cells. Cells with similar expression signatures of genes within Applicants' variable set, and therefore similar PC loadings, will likely localize near each other in the embedding, and hence distinct cell types should form two-dimensional point clouds across the tSNE map.

Prior to identifying and annotating the clusters, Applicants projected the remaining 36,145 cells (the projection set) onto the tSNE map of the training set by the following procedure:

(1) Applicants projected these cells onto the subspace defined by the significant PCs identified from the training set. Briefly, Applicants centered and scaled the 384×36,145 expression matrix corresponding to the projection set, considering only the highly variable genes, the scaling parameters of training set were used to center and scale each row. Applicants then multiplied the transpose of this scaled expression matrix with the 384×32 gene scores matrix learned from the training set PCA. This yields a PC "loadings" for the cells in the projection set along the 32 significant PCs learned on the training set.

(2) Based on its PC loadings, each cell in the projection set was independently embedded on to the tSNE map of the training set introduced earlier using a mathematical framework consistent with the original tSNE algorithm (Shekhar et al., 2014). Applicants note that while this approach does not discover novel clusters outside of the ones identified from the training set, it sharpens the distinctions between different clusters by leveraging the statistical power of the full dataset. Moreover, the cells are projected based on their PC signatures, not the raw gene expression values, which makes Applicants' approach more robust against technical noise in individual gene measurements.

See section "Embedding the projection set onto the tSNE map" below for full details.

One potential concern with this "post-hoc projection approach" was the possibility that a cell type that is completely absent from the training set might be spuriously projected into one of the defined clusters. Applicants tested the projection algorithm on a control dataset to explore this possibility, and placed stringent conditions to ensure that only cell types adequately represented within the training set are projected to avoid spurious assignments (see "'Out of sample" projection test'). Using this approach, 97% of the cells in the projection set were successfully embedded, resulting in a tSNE map consisting of 48296 out of 49300 sequenced cells (Table 10).

As an additional validation of Applicants' approach, it was noted that the relative frequencies of different cell types identified after clustering the full data (see below) closely matches estimates in the literature (Table 1). With the exception of the rods, all the other cell-types were enriched at a median value of 2.3× in the training set compared to their frequency of the full data. This strongly suggests that Applicants' downsampling approach indeed increases the representation of other cell types at the expense of the rod cells, enabling us to discover PCs that define these cells.

Density clustering to identify cell-t-pes. To automatically identify putative cell types on the tSNE map, Applicants used a density clustering approach implemented in the DBSCAN R package (Ester et al., 1996), setting the reachability distance parameter (eps) to 1.9, and removing clusters less than 50 cells. The majority of the removed cells included singleton cells that were located between the interfaces of bigger clusters. As a result of these steps, Applicants were able to assign 44808 cells (91% of the data) into 49 clusters.

Applicants next examined the 49 total clusters, to ensure that the identified clusters truly represented distinct cellular classifications, as opposed to over-partitioning. Applicants performed a post-hoc test where Applicants searched for differentially expressed genes (McDavid et al., 2013) between every pair of clusters (requiring at least 10 genes, each with an average expression difference greater than 1 natural log value between clusters with a Bonferroni corrected p<0.01). Applicants iteratively merged cluster pairs that did not satisfy this criterion, starting with the two most related pairs (lowest number of differentially expressed genes). This process resulted in 10 merged clusters, leaving 39 remaining.

Applicants then computed average gene expression for each of the 39 remaining clusters, and calculated Euclidean distances between all pairs, using this data as input for complete-linkage hierarchical clustering and dendrogram assembly. Applicants then compared each of the 39 clusters to the remaining cells using a likelihood-ratio test (McDavid et al., 2013) to identify marker genes that were differentially expressed in the cluster.

Embedding the projection set onto the tSNE map. Applicants used the computational approach in Shekhar et al (Shekhar et al., 2014) and Berman et al. (Berman et al., 2014) to project new cells onto an existing tSNE map. First, the expression vector of the cell is reduced to include only the set of highly variable genes, and subsequently centered and scaled along each gene using the mean and standard deviation of the gene expression in the training set. This scaled expression vector z (dimensions 1×384) is multiplied with the scores matrix of the genes S (dimensions 384×32), to obtain its "loadings" along the significant PCs u (dimensions 1×32). Thus, u'=z'·S.

u (dimensions 1×32) denotes the representation of the new cell in the PC subspace identified from the training set. Applicants note a point of consistency here in that performing the above dot product on a scaled expression vector of a cell z taken from the training set recovers its correct subspace representation u, as it ought to be the case.

Given the PC loadings of the cells in the training set $\{u^i\}$ (i=1, 2, . . . $N_{train}$) and their tSNE coordinates $\{y^i\}$ (i=1, 2, . . . $N_{train}$), the task now is to find the tSNE coordinates y' of the new cell based on its loadings vector u'. As in the original tSNE framework (van der Maaten and Hinton, 2008), Applicants "locate" the new cell in the subspace relative to the cells in the training set by computing a set of transition probabilities, $$p(u' \mid u^i) = \frac{\exp(-d(u', u^i)^2/2\sigma_{u'}^2)}{\sum_{\{u^i\}} \exp(-d(u', u^i)^2/2\sigma_{u'}^2)}.$$

Here, d(., .) represents Euclidean distances, and the bandwidth $\sigma_{u'}$ is chosen by a simple binary search in order to constrain the Shannon entropy associated with p(u'|u$^i$) to log$_2$(30), where 30 corresponds to the value of the perplexity parameter used in the tSNE embedding of the training set. Note that $\sigma_{u'}$ is chosen independently for each cell.

A corresponding set of transition probabilities in the low dimensional embedding are defined based on the Student's t-distribution as, $$q(y' \mid y^i) = \frac{(1 + d(y', y^i)^2)^{-1}}{\sum_{\{y^i\}} (1 + d(y', y^i)^2)^{-1}}$$

where y' are the coordinates of the new cell that are unknown. Applicants calculate these by minimizing the Kullback-Leibler divergence between p(u'|u$^i$) and q(y'|y$^i$), $$y' = \operatorname{argmin} \sum_i p(u' \mid u^i) \log \frac{p(u' \mid u^i)}{q(y' \mid y^i)}$$

This is a non-convex objective function with respect to its arguments, and is minimized using the Nelder-Mead simplex algorithm, as implemented in the Matlab function fminsearch. This procedure can be parallelized across all cells in the projection set.

A few notes on the implementation,
1. Since this is a post-hoc projection, and p(u'|u$^i$) is only a relative measure of pairwise similarity in that it is always constrained to sum to 1, Applicants wanted to avoid the possibility of new cells being embedded on the tSNE map by virtue of their high relative similarity to one or two training cells ("short circuiting"). In other words, Applicants chose to project only those cells that were drawn from regions of the PC subspace that were well represented in the training set by at least a few cells.

Thus, Applicants retained a cell u' for projection only if p(u'|u$^i$)>p$_{thres}$ as true for at least N$_{min}$ cells in the training set (p$_{thres}$=5×10$^{-3}$, N$_{min}$=10). Applicants calibrated the values for p$_{thres}$ and N$_{min}$ by testing the projection algorithm on cases where the projection set was known to be completely different from the training set to ensure that such cells were largely rejected by this constraint. (see Section "'Out of sample" projection test')
2. For cells that pass the constraint in pt. 1., the initial value of the tSNE coordinate y'₀ is set to, $$y'_0 = \sum_i p(u' \mid u^i) y^i$$

i.e. a weighted average of the tSNE coordinates of the training set with the weights set to the pairwise similarity in the PC subspace representation.
3. A cell satisfying the condition in 1. is said to be "successfully projected" to a location y'* when a minimum of the KL divergence could be found within the maximum number of iterations. However since the program is non-convex and is guaranteed to only find local minima, Applicants wanted to explore if a better minima could be found. Briefly, Applicants uniformly sampled points from a 25×25 grid centered on y'* to check for points where the value of the KL-divergence was within 5% of its value at y'* or lower. Whenever this condition was satisfied (<2%) of the time, Applicants re-ran the optimization by setting the new point as the initial value.

"Out of sample" projection test. In order to test the post-hoc projection method, Applicants conducted the following computational experiment wherein each of the 39 distinct clusters on the tSNE map was synthetically "removed" from the tSNE map, and then reprojected cell-by-cell on the tSNE map of the remaining clusters using the procedure outlined above. Only cells from the training set were used in these calculations.

Assuming Applicants' cluster distinctions are correct, in each of these 39 experiments, the cluster that is being reprojected represents an "out of sample" cell type. Thus successful assignments of these cells into one of the remaining 38 clusters would be spurious. For each of the 39 clusters that was removed and reprojected, Applicants classified the cells into three groups based on the result of the projection method (1) Cells that did not satisfy the condition 1. in the previous section (i.e. did not have a high relative similarity to at least $N_{min}$ training cells), and therefore "failed" to project.
(2) Cells that were successfully assigned a tSNE coordinate y', but that could not be assigned into any of the existing clusters according to the condition below.
(3) Cells that were successfully assigned a tSNE coordinate y', and which were "wrongly assigned" to one of the existing clusters. A cell was assigned to a cluster whose centroid was closest to y' if and only if the distance between y' and the centroid was smaller than the cluster radius (the distance of the farthest point from the centroid).

Encouragingly for all of the 39 "out of sample" projection experiments, only a small fraction of cells were spuriously assigned to one of the clusters, i.e. satisfied (3) above with the parameters $p_{thres}=5\times10^{-3}$ and $N_{min}=10$ (Table 10). This provided confidence that Applicants' post-hoc embedding of the projection set would not spuriously assign distinct cell types into one of the existing clusters.

Downsampling analyses of retina data. To generate the 500-cell and 2000-cell downsampled tSNE plots shown in FIG. 11F, cells were randomly sampled from the high-purity replicate (replicate 7), and used as input for PCA and tSNE. The 500-cell tSNE was clustered using a reachability distance parameter (eps) of 5.5, while the 2000-cell tSNE was clustered using an eps value of 3.0. Unclustered cells were removed. To generate the 9,431-cell downsampled tSNE plot, 10,000 cells were randomly sampled from the full dataset, and the cells expressing transcripts from more than 900 genes were used in principal components analysis and tSNE; the remaining (smaller) cells were projected onto the tSNE embedding, and clustered using an eps value of 2.0, resulting in a plot with 9,431 cells.

Immunohistochemistry. Wild-type C57 mice or Mito-P mice, which express CFP in nGnG amacrine and Type 1 bipolar cells (Kay et al., 2011), were euthanized by intraperitoneal injection of pentobarbital. Eyes were fixed in 4% PFA in PBS on ice for one hour, followed by dissection and post-fixation of retinas for an additional 30 mins, then rinsed with PBS. Retinas were frozen and sectioned at 20 μm in a cryostat. Sections were incubated with primary antibodies (chick anti-GFP [Abcam] or rabbit anti-PPP1R17 [Atlas]) overnight at 4° C., and with secondary antibodies (Invitrogen and Jackson ImmunoResearch) for 2 hrs at room temperature. Sections were then mounted using Fluoromount G (Southern Biotech) and viewed with an Olympus FVB confocal microscope.

Note on bead surface primers and custom sequencing primers. During the course of experiments for this paper, Applicants used two batches of beads that had two slightly different sequences (Barcoded Bead SeqA and Barcoded Bead SeqB, Table 9). Barcoded Bead SeqA was used in the human-mouse experiments, and in replicates 1-3 of the retina experiment. Replicates 4-7 were performed with Barcoded Bead SeqB. To prime read 1 for Drop-Seq libraries produced using Barcoded Bead SeqA beads, Read1CustSeqA was used; to prime read 2 for Drop-Seq libraries produced using Barcoded Bead SeqB beads, Read1CustSeqB was used. ChemGenes plans to manufacture large-scale numbers of beads harboring the Barcoded Bead SeqB sequence. These beads should be used with Read1CustSeqB.

Additional Notes Regarding Drop-Seq Implementation

Cell and bead concentrations. Applicants' experiments have shown that the cell concentration used in Drop-Seq has a strong, linear relationship to the purity and doublet rates of the resulting libraries (FIGS. 9A, 9B, and 14D). Cell concentration also linearly affects throughput: ~10,000 single-cell libraries can be processed per hour when cells are used at a final concentration of 100 cells/ul, and ~1,200 can be processed when cells are used at a final concentration of 12.5 cells/ul. The trade-off between throughput and purity is likely to affect users differently, depending on the specific scientific questions being asked. Currently, for the standard experiments, Applicants use a final concentration of 50 cells/ul, tolerating a small percentage of doubles and cell contaminants, to be able to easily and reliably process 10,000 cells over the course of a couple of hours. As recommended above, Applicants currently favor loading beads at a concentration of 120/ul (final concentration in droplets=60/ul), which empirically yields a <5% bead doublet rate.

Drop-Seq start-up costs. The main pieces of equipment required to implement Drop-Seq are three syringe pumps (KD Legato 100 pumps, list price ~$2,000 each) a standard inverted microscope (Motic AE31, list price ~$1,900), and a magnetic stirrer (V&P scientific, #710D2, list price ~$1,200). A fast camera (used to monitor droplet generation in real time) is not necessary for the great majority of users (droplet quality can easily be monitored by simply placing 3 ul of droplets in a Fuchs-Rosenthal hemocytometer with 17 ul of droplet generation oil to dilute the droplets into a single plane of focus).

Example 4: Tables for Examples 2 and 3

TABLE 1

Ascertainment of cell types and frequencies in the mouse retina by Drop-Seq. The sizes of the 39 annotated cell clusters produced from Drop-Seq were used to estimate their fractions of the total cell population. These data were compared with those obtained by microscopy techniques (Jeon et al., 1998).

| Cell class | Percentage of retina (Jeon et al., 1998) (%) | Percentage of cell population in Drop-Seq (%) |
|---|---|---|
| Rod photoreceptors | 79.9 | 65.6 |
| Cone photoreceptors | 2.1 | 4.2 |
| Muller glia | 2.8 | 3.6 |
| Retinal ganglion cells | 0.5 | 1.0 |
| Horizontal cells | 0.5 | 0.6 |
| Amacrine cells | 7.0 | 9.9 |
| Bipolar cells | 7.3 | 14 |

TABLE 1-continued

Ascertainment of cell types and frequencies in the mouse retina by Drop-Seq. The sizes of the 39 annotated cell clusters produced from Drop-Seq were used to estimate their fractions of the total cell population. These data were compared with those obtained by microscopy techniques (Jeon et al., 1998).

| Cell class | Percentage of retina (Jeon et al., 1998) (%) | Percentage of cell population in Drop-Seq (%) |
|---|---|---|
| Microglia | — | 0.2 |
| Retinal endothelial cells | — | 0.6 |
| Astrocytes | — | 0.1 |

TABLE 1

Edit distance relationships among UMIs. For the data in FIG. 3G, the sequences of the UMIs for each ERCC gene detected in each cell barcode were collapsed at an edit distance of 1, including only substitutions (left column) or with both substitutions and insertions/deletions (right column). A control UMI set was prepared for each gene, using an equal number of UMIs sampled randomly across all genes/cells. The percent of the original UMIs that were collapsed for each condition are reported in the table.

| UMI Sampling | % Reduction in UMI counts | |
|---|---|---|
| | Substitution-only collapse | Indel and substitution collapse |
| Within a gene | 68.2% | 76.1% |
| Across genes | 19.1% | 45.7% |

TABLE 2

Top 100 genes represented in each of the first 5 principal components calculated from the human (HEK) single-cell expression data.

| PC1 | PC2 | PC3 | PC4 | PC5 |
|---|---|---|---|---|
| OPTN | CENPE | MT-RNR2 | CCNB1 | PAPOLA |
| H1F0 | CENPF | DDX21 | PSRC1 | DTL |
| CREBRF | KIF14 | GPATCH4 | CDC20 | TAF7 |
| RHOU | TPX2 | WDR43 | AURKA | RTN4 |
| NEAT1 | TOP2A | LYAR | PLK1 | TOP1 |
| PRSS23 | AURKA | FAM211A | CKS2 | CDCA7 |
| RIT1 | DLGAP5 | MYBBP1A | KIF20A | E2F3 |
| CDKN1A | DEPDC1 | GNL3 | HMMR | HSP90AA1 |
| MAF | SGOL2 | NCL | PTTG1 | TUG1 |
| MALAT1 | PRC1 | RSL1D1 | CENPA | HSPH1 |
| CCNE2 | CCNB1 | RPF2 | CDCA3 | DYNLL1 |
| DDIT3 | ASPM | MYC | BUB1 | ZNF367 |
| MAP1A | ARL6IP1 | DKC1 | CCNB2 | MORF4L2 |
| MTRNR2L12 | HMMR | LARP1 | TUBA1C | AASDHPPT |
| PPP1R15A | PLK1 | NOP58 | PIF1 | HNRNPH3 |
| ATXN1 | MALAT1 | CD3EAP | DEPDC1 | HSP90AB1 |
| DGCR8 | MKI67 | SLC6A15 | SGOL2 | HIST1H2AC |
| MT-RNR2 | CDCA3 | PA2G4 | KIF2C | KTN1 |
| TES | TTK | NOP14 | AURKB | ZRANB2 |
| FNIP1 | CDC20 | SNHG3 | TIMM10 | HIST1H2BD |
| SAT1 | SMC4 | DNAJC2 | TPX2 | ZNF738 |
| ZNF608 | BUB1 | HEATR1 | TUBB4B | PSMD10 |
| WDR76 | CKS2 | NOP16 | CENPE | PSMD14 |
| NFIB | TACC3 | NOP56 | CDCA8 | SET |
| ERO1LB | CKAP2 | SET | UBE2C | SSB |
| MXD1 | GTSE1 | PUS7 | G2E3 | EIF4G2 |
| TSPYL4 | CKAP5 | WDR3 | GOT1 | PIGW |
| ARID4A | ANLN | RRP15 | RNF26 | HNRNPR |
| HOXA3 | G2E3 | MTRNR2L12 | FAM64A | FUBP1 |
| DDAH2 | NCAPG | NOLC1 | GAS2L3 | SNHG3 |
| CLU | KIF18A | QTRTD1 | NDC80 | ZC3H15 |
| FAM46A | NDC80 | LTV1 | TMEM115 | PAIP2 |
| ARID5B | HMGB2 | MRTO4 | XRCC4 | DHX29 |
| IFI27L2 | CDCA8 | SCD | FAM83D | HSP90B1 |

TABLE 2-continued

Top 100 genes represented in each of the first 5 principal components calculated from the human (HEK) single-cell expression data.

| PC1 | PC2 | PC3 | PC4 | PC5 |
|---|---|---|---|---|
| SCN9A | PIF1 | NOB1 | NAMPTL | ATP6V1G1 |
| KCTD7 | UBE2C | SLC16A1 | MPV17L2 | HNRNPH2 |
| TTLL7 | NUF2 | POLR3G | KPNA2 | GOLM1 |
| PCDH17 | KIF20A | KCTD12 | ARL6IP1 | CMTM6 |
| PLAT | KPNA2 | SLC1A3 | DHRS7B | HNRNPU |
| NAB1 | KIF11 | MTRNR2L8 | PRC1 | CAP1 |
| CAPRIN2 | KIF23 | PAK1IP1 | CDKN3 | STIP1 |
| LYPD1 | KIF4A | MT-ND5 | HSPA1B | JAK1 |
| TMSB4X | SFPQ | NOL8 | TACC3 | QKI |
| N4BP2 | PSRC1 | MT-ND2 | BUB1B | PFDN4 |
| TM7SF2 | BUB1B | DHX37 | INCENP | MIS18A |
| TMEM107 | KIF20B | UTP14A | DTWD2 | MSH6 |
| ZNF226 | KDM5B | DPH2 | SAPCD2 | PPP1CB |
| PHTF1 | BIRC5 | MTRNR2L1 | CCDC86 | C11orf58 |
| MTRNR2L8 | HP1BP3 | NPM1 | KRT10 | ZNF280B |
| MTRNR2L3 | CASC5 | NOC3L | TRMT61B | DNAJA1 |
| DLG3 | BRD8 | FASN | DYNLL1 | EID1 |
| TMSB15A | PRRC2C | SERBP1 | DEPDC1B | FAM200B |
| UHRF1 | CENPA | TSR1 | MGARP | RDX |
| GATA6 | NUSAP1 | RIOK1 | EIF1 | VBP1 |
| NOVA1 | DBF4 | MT-RNR1 | PPP1R11 | ANP32E |
| C22orf46 | CALM2 | RRS1 | CUTC | SKIL |
| RFX7 | INCENP | NAA15 | TTK | PTTG1 |
| ZNF280B | ECT2 | WDR4 | PEX3 | CSNK1A1L |
| GKAP1 | EIF4G3 | TAF1D | MRPL12 | RAB7A |
| CYP1B1 | KIF5B | UTP20 | CDC25B | CTNNB1 |
| ZNF107 | C6orf62 | TNPO2 | DNAJC17 | CHMP5 |
| LRRCC1 | NIPBL | CDK6 | PPM1B | PRPF40A |
| ZNF200 | CEP350 | ST6GALNAC2 | HN1 | MRFAP1 |
| DTL | PRR11 | NAA25 | CALM2 | INA |
| OTUD7B | CKAP2L | FAM216A | BRI3 | ARCN1 |
| ULK1 | CCDC18 | TCOF1 | SAP30 | NUP37 |
| HIST1H2BJ | CEP70 | C10orf2 | PSMF1 | ENAH |
| MED13L | RBBP6 | HRK | ECT2 | STK32C |
| WEE1 | ARID4B | RRP1B | SPAG5 | SNRPB2 |
| RAB9B | KIF2C | NOP2 | MED30 | DYNC1I2 |
| SIPA1L2 | SGOL1 | BCAT1 | TNIP2 | CFL2 |
| FADS2 | CCNB2 | AMD1 | DUSP14 | BTF3 |
| ZDBF2 | ACIN1 | MIR17HG | TMEM99 | TIPIN |
| KIF1A | CDC27 | POLR1A | RAB28 | ARV1 |
| ATF3 | U2SURP | MDN1 | BIRC5 | NACA |
| GADD45A | ARHGAP11A | RRP12 | DOHH | CHMP2B |
| NEXN | CCNA2 | PWP1 | MAD2L1 | ILF2 |
| PPP1R9A | CDKN1B | RCC1 | BOLA1 | RPL5 |
| BNIP3L | TRA2A | GRB14 | C14orf119 | SLTM |
| C4orf21 | RSF1 | C8orf33 | DCPS | NAP1L3 |
| NPHP3 | DR1 | MTHFD1L | PDIA5 | PIK3R3 |
| TRPS1 | TUBB4B | AKAP1 | SART1 | ADAR |
| COLEC12 | BOD1L1 | POU3F2 | MRPS2 | HNRNPK |
| ZFHX3 | NCAPD2 | TTLL12 | MIOS | CAPRIN1 |
| SNAPC5 | KIF4B | FAM208B | CSTB | METAP2 |
| REV3L | CDCA2 | EIF5B | RANGAP1 | CSNK1A1 |
| REST | USP9X | CEBPZ | TFCP2 | NCKAP1 |
| ANKRD12 | RANGAP1 | STARD7 | MAP7D1 | CBX1 |
| YPEL5 | SON | CDV3 | CETN3 | CDV3 |
| UBE2H | CCAR1 | PNO1 | GTPBP6 | KRR1 |
| SERPINB1 | TNRC6B | ABCE1 | RACGAP1 | KPNA4 |
| ZNF367 | GOLGA4 | JSRP1 | CKAP5 | HMMR |
| SMARCA1 | SRRM2 | PAWR | SPR | TMEM167A |
| BAZ2B | LBR | TIMM44 | SAMD8 | MMADHC |
| SESN3 | PTTG1 | TWISTNB | MRPL3 | ISCU |
| C1orf63 | NEK2 | TFRC | FBXO38 | NACA2 |
| HOXA-AS4 | AURKB | MT-ND4 | ZNRD1 | FXR1 |
| ZFP90 | RBMX | IPO7 | CENPF | HSPA14 |
| NFAT5 | HEXIM1 | MTPAP | C8orf76 | PSMD4 |
| ZNF711 | CCDC88A | HSPD1 | PES1 | MARCH5 |

TABLE 3

Genes used for each phase of the cell cycle for the analysis in FIG. 4.

| G1/S | S | G2/M | M | M/G1 |
|---|---|---|---|---|
| ACD | ABCC5 | ANLN | AHI1 | AGFG1 |
| ACYP1 | ABHD10 | AP3D1 | AKIRIN2 | AGPAT3 |
| ADAMTS1 | ANKRD18A | ARHGAP19 | ANKRD40 | AKAP13 |
| ANKRD10 | ASF1B | ARL4A | ANLN | AMD1 |
| APEX2 | ATAD2 | ARMC1 | ANP32B | ANP32E |
| ARGLU1 | BBS2 | ASXL1 | ANP32E | ANTXR1 |
| ATAD2 | BIVM | ATL2 | ARHGAP19 | BAG3 |
| BARD1 | BLM | AURKB | ARL6IP1 | BTBD3 |
| BRD7 | BMI1 | BCLAF1 | ASXL1 | CBX3 |
| C1orf63 | BRCA1 | BORA | ATF7IP | CDC42 |
| C7orf41 | BRIP1 | BRD8 | AURKA | CDK7 |
| C14orf142 | C5orf42 | BUB3 | BIRC2 | CDKN3 |
| CAPN7 | C11orf82 | C2orf69 | BIRC5 | CEP70 |
| CASP2 | CALD1 | C14orf80 | BUB1 | CNIH4 |
| CASP8AP2 | CALM2 | CASP3 | CADM1 | CTR9 |
| CCNE1 | CASP2 | CBX5 | CCDC88A | CWC15 |
| CCNE2 | CCDC14 | CCDC107 | CCDC90B | DCP1A |
| CDC6 | CCDC84 | CCNA2 | CCNA2 | DCTN6 |
| CDC25A | CCDC150 | CCNF | CCNB2 | DEXI |
| CDCA7 | CDC7 | CDC16 | CDC20 | DKC1 |
| CDCA7L | CDC45 | CDC25C | CDC25B | DNAJB6 |
| CEP57 | CDCA5 | CDCA2 | CDC27 | DSP |
| CHAF1A | CDKN2AIP | CDCA3 | CDC42EP1 | DYNLL1 |
| CHAF1B | CENPM | CDCA8 | CDCA3 | EIF4E |
| CLSPN | CENPQ | CDK1 | CENPA | ELP3 |
| CREBZF | CERS6 | CDKN1B | CENPE | FAM60A |
| CTSD | CHML | CDKN2C | CENPF | FAM189B |
| DIS3 | COQ9 | CDR2 | CEP55 | FOPNL |
| DNAJC3 | CPNE8 | CENPL | CFLAR | FOXK2 |
| DONSON | CREBZF | CEP350 | CIT | FXR1 |
| DSCC1 | CRLS1 | CFD | CKAP2 | G3BP1 |
| DTL | DCAF16 | CFLAR | CKAP5 | GATA2 |
| E2F1 | DEPDC7 | CHEK2 | CKS1B | GNB1 |
| EIF2A | DHFR | CKAP2 | CKS2 | GRPEL1 |
| ESD | DNA2 | CKAP5 | CNOT10 | GSPT1 |
| FAM105B | DNAJB4 | CYTH2 | CNTROB | GTF3C4 |
| FAM122A | DONSON | DCAF7 | CTCF | HIF1A |
| FLAD1 | DSCC1 | DHX8 | CTNNA1 | HMG20B |
| GINS2 | DYNC1LI2 | DNAJB1 | CTNND1 | HMGCR |
| GINS3 | E2F8 | ENTPD5 | DEPDC1 | HSD17B11 |
| GMNN | EIF4EBP2 | ESPL1 | DEPDC1B | HSPA8 |
| HELLS | ENOSF1 | FADD | DIAPH3 | ILF2 |
| HOXB4 | ESCO2 | FAM83D | DLGAP5 | JMJD1C |
| HRAS | EXO1 | FAN1 | DNAJA1 | KDM5B |
| HSF2 | EZH2 | FANCD2 | DNAJB1 | KIAA0586 |
| INSR | FAM178A | G2E3 | DR1 | KIF5B |
| INTS8 | FANCA | GABPB1 | DZIP3 | KPNB1 |
| IVNS1ABP | FANCI | GAS1 | E2F5 | KRAS |
| KIAA1147 | FEN1 | GAS2L3 | ECT2 | LARP1 |
| KIAA1586 | GCLM | H2AFX | FAM64A | LARP7 |
| LNPEP | GOLGA8A | HAUS8 | FOXM1 | LRIF1 |
| LUC7L3 | GOLGA8B | HINT3 | FYN | LYAR |
| MCM2 | H1F0 | HIPK2 | G2E3 | MORF4L2 |
| MCM4 | HELLS | HJURP | GADD45A | MRPL19 |
| MCM5 | HIST1H2AC | HMGB2 | GAS2L3 | MRPS2 |
| MCM6 | HIST1H4C | HN1 | GOT1 | MRPS18B |
| MDM1 | INTS7 | HP1BP3 | GRK6 | MSL1 |
| MED31 | KAT2A | HRSP12 | GTSE1 | MTPN |
| MRI1 | KAT2B | IFNAR1 | HCFC1 | NCOA3 |
| MSH2 | KDELC1 | IQGAP3 | HMG20B | NFIA |
| NASP | KIAA1598 | KATNA1 | HMGB3 | NFIC |
| NEAT1 | LMO4 | KCTD9 | HMMR | NUCKS1 |
| NKTR | LYRM7 | KDM4A | HN1 | NUFIP2 |
| NPAT | MAN1A2 | KIAA1524 | HP1BP3 | NUP37 |
| NUP43 | MAP3K2 | KIF5B | HPS4 | ODF2 |
| ORC1 | MASTL | KIF11 | HS2ST1 | OPN3 |
| OSBPL6 | MBD4 | KIF20B | HSPA8 | PAK1IP1 |
| PANK2 | MCM8 | KIF22 | HSPA13 | PBK |
| PCDH7 | MLF1IP | KIF23 | INADL | PCF11 |
| PCNA | MYCBP2 | KIFC1 | KIF2C | PLIN3 |
| PLCXD1 | NAB1 | KLF6 | KIF5B | PPP2CA |
| PMS1 | NEAT1 | KPNA2 | KIF14 | PPP2R2A |
| PNN | NFE2L2 | LBR | KIF20B | PPP6R3 |
| POLD3 | NRD1 | LIX1L | KLF9 | PRC1 |
| RAB23 | NSUN3 | LMNB1 | LBR | PSEN1 |
| RECQL4 | NT5DC1 | MAD2L1 | LMNA | PTMS |
| RMI2 | NUP160 | MALAT1 | MCM4 | PTTG1 |
| RNF113A | OGT | MELK | MDC1 | RAD21 |
| RNPC3 | ORC3 | MGAT2 | MIS18BP1 | RAN |
| SEC62 | OSGIN2 | MID1 | MKI67 | RHEB |
| SKP2 | PHIP | MIS18BP1 | MLLT4 | RPL13A |
| SLBP | PHTF1 | MND1 | MZT1 | SLC39A10 |
| SLC25A36 | PHTF2 | NCAPD3 | NCAPD2 | SNUPN |
| SNHG10 | PKMYT1 | NCAPH | NCOA5 | SRSF3 |
| SRSF7 | POLA1 | NCOA5 | NEK2 | STAG1 |
| SSR3 | PRIM1 | NDC80 | NUF2 | SYNCRIP |
| TAF15 | PTAR1 | NEIL3 | NUP35 | TAF9 |
| TIPIN | RAD18 | NFIC | NUP98 | TCERG1 |
| TOPBP1 | RAD51 | NIPBL | NUSAP1 | TLE3 |
| TRA2A | RAD51AP1 | NMB | ODF2 | TMEM138 |
| TTC14 | RBBP8 | NR3C1 | ORAOV1 | TOB2 |
| UBR7 | REEP1 | NUCKS1 | PBK | TOP1 |
| UHRF1 | RFC2 | NUMA1 | PCF11 | TROAP |
| UNG | RHOBTB3 | NUSAP1 | PLK1 | TSC22D1 |
| USP53 | RMI1 | PIF1 | POC1A | TULP4 |
| VPS72 | RPA2 | PKNOX1 | POM121 | UBE2D3 |
| WDR76 | RRM1 | POLQ | PPP1R10 | VANGL1 |
| ZMYND19 | RRM2 | PPP1R2 | PRPSAP1 | VCL |
| ZNF367 | RSRC2 | PSMD11 | PRR11 | WIPF2 |
| ZRANB2 | SAP30BP | PSRC1 | PSMG3 | WWC1 |
| | SLC38A2 | RANGAP1 | PTP4A1 | YY1 |
| | SP1 | RCCD1 | PTPN9 | ZBTB7A |
| | SRSF5 | RDH11 | PWP1 | ZCCHC10 |
| | SVIP | RNF141 | QRICH1 | ZNF24 |
| | TOP2A | SAP30 | RAD51C | ZNF281 |
| | TTC31 | SKA3 | RANGAP1 | ZNF593 |
| | TTLL7 | SMC4 | RBM8A | |
| | TYMS | STAT1 | RCAN1 | |
| | UBE2T | STIL | RERE | |
| | UBL3 | STK17B | RNF126 | |
| | USP1 | SUCLG2 | RNF141 | |
| | ZBED5 | TFAP2A | RNPS1 | |
| | ZWINT | TIMP1 | RRP1 | |
| | | TMEM99 | SEPHS1 | |
| | | TMPO | SETD8 | |
| | | TNPO2 | SFPQ | |
| | | TOP2A | SGOL2 | |
| | | TRAIP | SHCBP1 | |
| | | TRIM59 | SMARCB1 | |
| | | TRMT2A | SMARCD1 | |
| | | TTF2 | SPAG5 | |
| | | TUBA1A | SPTBN1 | |
| | | TUBB | SRF | |
| | | TUBB2A | SRSF3 | |
| | | TUBB4B | SS18 | |
| | | TUBD1 | SUV420H1 | |
| | | UACA | TACC3 | |
| | | UBE2C | THRAP3 | |
| | | VPS25 | TLE3 | |
| | | VTA1 | TMEM138 | |
| | | WSB1 | TNPO1 | |
| | | ZNF587 | | |
| | | | TOMM34 | |
| | | ZNHIT2 | TPX2 | |
| | | | TRIP13 | |
| | | | TSG101 | |
| | | | TSN | |

TABLE 3-continued

Genes used for each phase of the cell cycle for the analysis in FIG. 4.

| G1/S | S | G2/M | M | M/G1 |
|---|---|---|---|---|
|  |  |  | TTK |  |
|  |  |  | TUBB4B |  |
|  |  |  | TXNDC9 |  |
|  |  |  | TXNRD1 |  |
|  |  |  | UBE2D3 |  |
|  |  |  | USP13 |  |
|  |  |  | USP16 |  |
|  |  |  | VANGL1 |  |
|  |  |  | WIBG |  |
|  |  |  | WSB1 |  |
|  |  |  | YWHAH |  |
|  |  |  | ZC3HC1 |  |
|  |  |  | ZFX |  |
|  |  |  | ZMYM1 |  |
|  |  |  | ZNF207 |  |

TABLE 4

List of cell cycle regulated genes identified from the analysis of 589 HEK and 412 3T3 cells.

| human gene | cluster | mouse gene | Intersection All genes | Intersection novel genes | annotation |
|---|---|---|---|---|---|
| CCNE2 | 1 | Shmt1 |  |  |  |
| CDC6 | 1 | Zmym1 | ACTB | ACTB |  |
| CLSPN | 1 | Meaf6 | AKIRIN2 | ARHGAP11A |  |
| DTL | 1 | Usp37 | ANLN | ARL6IP6 |  |
| MCM3 | 1 | Msh6 | ANP32E | ARPC2 |  |
| MCM5 | 1 | Rbbp4 | ARHGAP11A | ATF4 | TF |
| MCM6 | 1 | Bri3bp | ARL6IP1 | CCAR1 |  |
| MSH6 | 1 | Rrp8 | ARL6IP6 | CCDC18 |  |
| PCNA | 1 | Mb21d1 | ARPC2 | CDCA4 | CC |
| UNG | 1 | Wdhd1 | ASF1B | DNAJC9 |  |
| ADAMTS1 | 1 | Mcm5 | ASPM | DNMT1 |  |
| ARL6IP6 | 1 | Smarca5 | ATAD2 | E2F7 | TF/CC |
| ATAD2 | 1 | Slc1a5 | ATF4 | FTH1 |  |
| BLM | 1 | Nap1l4 | AURKA | GOLGA2 |  |
| C4orf21 | 1 | Nolc1 | AURKB | GPSM2 |  |
| CASP8AP2 | 1 | D10Wsu102e | BIRC5 | H3F3B | CC |
| CCNE1 | 1 | Ckap4 | BLM | HIST1H1E | CC |
| CDCA7 | 1 | Timeless | BORA | MBNL1 |  |
| CHAF1A | 1 | Zfp367 | BRD8 | MCMBP | CC |
| CHAF1B | 1 | Zmynd19 | BRIP1 | MRPL17 |  |
| E2F1 | 1 | Cdc25a | BUB1 | NCAPG | CC |
| E2F8 | 1 | Atp2b1 | BUB1B | NDUFA1 |  |
| FEN1 | 1 | Smarcc1 | BUB3 | NXT1 |  |
| GINS2 | 1 | Ccnd2 | CALM2 | OSBPL8 |  |
| HIST1H2BK | 1 | Lbh | CASC5 | OTUB1 |  |
| MCM2 | 1 | Maff | CASP8AP2 | PARPBP | CC |
| MCM7 | 1 | Casp3 | CBX5 | PRRC2C |  |
| MCM10 | 1 | Tnfaip8 | CCAR1 | RPL26 |  |
| MCMBP | 1 | Amotl1 | CCDC18 | SNHG3 |  |
| MMS22L | 1 | Rfc1 | CCNA2 | SRP9 |  |
| PKMYT1 | 1 | Cdc42ep3 | CCNB1 | TCF19 | TF |
| PRIM1 | 1 | Gpr180 | CCNB2 | TK1 |  |
| RAD51 | 1 | Oaf | CCNE1 | TUBA1C |  |
| RFC4 | 1 | Gins3 | CCNE2 | UBC |  |
| SLBP | 1 | Cdc7 | CCNF | WDHD1 |  |
| SNHG3 | 1 | Cactin | CDC6 | ZFHX4 | TF |
| TIPIN | 1 | Eps8 | CDC20 |  |  |
| TK1 | 1 | Slk | CDC27 |  |  |
| TMEM97 | 1 | Smc3 | CDC45 |  |  |
| UHRF1 | 1 | Alad | CDCA2 |  |  |
| WDR76 | 1 | Nasp | CDCA3 |  |  |
| XRCC2 | 1 | Smc5 | CDCA4 |  |  |
| ZMYND19 | 1 | Fen1 | CDCA7 |  |  |
| ZNF367 | 1 | Ctnnal1 | CDCA8 |  |  |
| CDC45 | 1 | Enkd1 | CDK1 |  |  |
| DNAJC9 | 1 | Tjp2 | CDK5RAP2 |  |  |
| DSCC1 | 1 | Nup43 | CDKN1B |  |  |
| DUT | 1 | Dek | CDKN2C |  |  |
| EXO1 | 1 | Slbp | CENPA |  |  |
| FBXO5 | 1 | Ung | CENPE |  |  |
| H1F0 | 1 | Paics | CENPF |  |  |
| HELLS | 1 | Gins2 | CEP55 |  |  |
| HIST1H4C | 1 | Umps | CHAF1A |  |  |
| HSPB11 | 1 | Pdlim1 | CHAF1B |  |  |
| IRS4 | 1 | Gart | CKAP2 |  |  |

TABLE 4-continued

List of cell cycle regulated genes identified from the analysis of 589 HEK and 412 3T3 cells.

| human gene | cluster | mouse gene | Intersection All genes | novel genes | annotation |
|---|---|---|---|---|---|
| KIAA0101 | 1 | Whsc1 | CKAP2L | | |
| MCM4 | 1 | Baz1b | CKAP5 | | |
| MLF1IP | 1 | Efnb2 | CKS1B | | |
| MSH2 | 1 | Pola2 | CLSPN | | |
| POLD3 | 1 | Ivns1abp | CTCF | | |
| PSMC3IP | 1 | Dnaaf2 | DBF4 | | |
| RAD51AP1 | 1 | Trmt2a | DLGAP5 | | |
| RRM2 | 1 | E2f1 | DNAJC9 | | |
| TCF19 | 1 | Chaf1b | DNMT1 | | |
| TYMS | 1 | Syngr2 | DSCC1 | | |
| UBE2T | 1 | Mcmbp | DTL | | |
| ACAA1 | 1 | Cdt1 | E2F1 | | |
| ACYP1 | 1 | Pold3 | E2F7 | | |
| ALDOA | 1 | Ubr7 | E2F8 | | |
| ARID3A | 1 | Grsf1 | ECT2 | | |
| ARPC2 | 1 | Dck | ERCC6L | | |
| ARPC5 | 1 | Atad5 | ESPL1 | | |
| ASF1B | 1 | Casp8ap2 | EXO1 | | |
| ASRGL1 | 1 | Orc2 | FAM64A | | |
| ATP5E | 1 | Siya1 | FAM83D | | |
| ATP6V1D | 1 | Cdca7 | FBXO5 | | |
| ATP6V1F | 1 | Rif1 | FEN1 | | |
| ATP6V0E2 | 1 | Ptrh2 | FOXM1 | | |
| B2M | 1 | Arl6ip6 | FTH1 | | |
| BRIP1 | 1 | Rnf168 | G2E3 | | |
| C1orf21 | 1 | Tfrc | GAS2L3 | | |
| C3orf14 | 1 | Fancl | GINS2 | | |
| C4orf48 | 2 | Clspn | GMNN | | |
| C5orf22 | 2 | Lig1 | GOLGA2 | | |
| C19orf53 | 2 | Gmnn | GPSM2 | | |
| C21orf58 | 2 | Dtl | GTSE1 | | |
| CALM1 | 2 | Uhrf1 | H1F0 | | |
| CAMTA1 | 2 | Ccne1 | H3F3B | | |
| CARHSP1 | 2 | Fam111a | HAT1 | | |
| CCDC51 | 2 | Tcf19 | HELLS | | |
| CDCA4 | 2 | Dnmt1 | HEXIM1 | | |
| CLTB | 2 | Msh2 | HIST1H1E | | |
| COX6B1 | 2 | Orc6 | HJURP | | |
| COX7C | 2 | Mcm6 | HMGB2 | | |
| COX8A | 2 | Pcna-ps2 | HMMR | | |
| COX17 | 2 | Mcm2 | HN1 | | |
| DDX46 | 2 | Hells | HP1BP3 | | |
| DGCR8 | 2 | Haus6 | INCENP | | |
| DMC1 | 2 | Ccne2 | KDM5B | | |
| DNMT1 | 2 | Ppat | KIF2C | | |
| DONSON | 2 | Dscc1 | KIF11 | | |
| DTYMK | 2 | Cdc6 | KIF14 | | |
| E2F7 | 2 | Rpa2 | KIF15 | | |
| ERCC6L | 2 | Atad2 | KIF18A | | |
| FADS1 | 2 | Mcm3 | KIF20A | | |
| FAM178A | 2 | Pcna | KIF20B | | |
| FANCA | 2 | Mcm7 | KIF23 | | |
| FAU | 2 | Chaf1a | KIFC1 | | |
| FTH1 | 2 | Hat1 | LIG1 | | |
| FTL | 2 | Rrm2 | LUC7L3 | | |
| GAPDH | 2 | Slfn9 | MALAT1 | | |
| GGCT | 2 | Rfc3 | MBNL1 | | |
| GMNN | 2 | Mcm4 | MCM2 | | |
| H2AFZ | 3 | Ldlr | MCM3 | | |
| HAUS1 | 3 | Amotl2 | MCM4 | | |
| HAUS5 | 3 | Topbp1 | MCM5 | | |
| HOMEZ | 3 | Ncapd3 | MCM6 | | |
| LAGE3 | 3 | Haus8 | MCM7 | | |
| LIG1 | 3 | Rbl1 | MCM10 | | |
| MED31 | 3 | Rrm1 | MCMBP | | |
| MGST3 | 3 | Elovl5 | MED31 | | |
| MRPL17 | 3 | Dhfr | MELK | | |
| MSANTD3 | 3 | Usp1 | MIS18BP1 | | |
| MYBL2 | 3 | Ncapg2 | MKI67 | | |
| MYL6 | 3 | Asf1b | MLF1IP | | |
| NASP | 3 | Dcaf15 | MRPL17 | | |
| NDUFA1 | 3 | Tssc4 | MSH2 | | |

TABLE 4-continued

List of cell cycle regulated genes identified from the analysis of 589 HEK and 412 3T3 cells.

| | | | Intersection | | |
|---|---|---|---|---|---|
| human gene | cluster | mouse gene | All genes | novel genes | annotation |
| NDUFB1 | 3 | Hjurp | MSH6 | | |
| NDUFB2 | 3 | Hist1h2ak | NASP | | |
| NDUFS5 | 3 | Nup155 | NCAPD2 | | |
| NPAT | 3 | Skp2 | NCAPG | | |
| NPC2 | 3 | Tdp2 | NCAPH | | |
| NXT1 | 3 | Cbx5 | NDC80 | | |
| OPTN | 3 | Hspa14 | NDUFA1 | | |
| ORC6 | 3 | Mcm10 | NEK2 | | |
| PGK1 | 3 | Prim1 | NUF2 | | |
| PHTF1 | 3 | Exo1 | NUSAP1 | | |
| PIGX | 3 | Apbb1ip | NXT1 | | |
| PLSCR1 | 3 | Eri1 | ODF2 | | |
| POLA1 | 3 | Smchd1 | ORC6 | | |
| POLR2H | 3 | Dnajc9 | OSBPL8 | | |
| POU4F1 | 3 | Akap11 | OTUB1 | | |
| PPDPF | 3 | Mlf1ip | PARPBP | | |
| RABIF | 3 | Tyms | PCNA | | |
| RFC2 | 3 | Nfx1 | PCNT | | |
| RNASEH2A | 3 | E2f7 | PKNOX1 | | |
| RNASEH2C | 3 | Ubap2 | PLK1 | | |
| RPA3 | 3 | Chtf18 | POLA1 | | |
| RPS5 | 3 | Stub1 | POLD3 | | |
| RRM1 | 3 | Esco2 | PPP2R5C | | |
| S100A10 | 3 | Ezh2 | PRC1 | | |
| SEMA3C | 3 | Pold1 | PRIM1 | | |
| SERF2 | 3 | Apbb2 | PRR11 | | |
| SHFM1 | 3 | E2f8 | PRRC2C | | |
| SLC25A4 | 3 | Cyp51 | PSRC1 | | |
| SLC25A5 | 3 | Rad54l | PTTG1 | | |
| SNHG1 | 3 | Nxt1 | RACGAP1 | | |
| SNHG9 | 3 | Pola1 | RAD51 | | |
| SNRPD2 | 3 | Rpa3 | RAD51AP1 | | |
| SNX10 | 3 | Fbxo5 | RANGAP1 | | |
| SRP9 | 3 | Il1rl1 | RBBP6 | | |
| SS18L2 | 3 | Fhl2 | RFC2 | | |
| SSR4 | 3 | Mis18a | RFC4 | | |
| STMN1 | 3 | Tex30 | RPA3 | | |
| SVIP | 3 | Idh2 | RPL26 | | |
| TCEB1 | 3 | Mybl1 | RRM1 | | |
| TIMP1 | 3 | Prkca | RRM2 | | |
| TM7SF2 | 3 | Red | SGOL1 | | |
| TMSB10 | 3 | Blm | SGOL2 | | |
| TOPBP1 | 3 | Rpa1 | SKA2 | | |
| TPM4 | 3 | Pole | SLBP | | |
| TTLL7 | 3 | Rfc2 | SMC4 | | |
| TUBA1A | 3 | Mtbp | SNHG3 | | |
| UBA52 | 3 | Nup107 | SPAG5 | | |
| UBR7 | 3 | Sqle | SPC25 | | |
| USMG5 | 3 | Cenph | SRP9 | | |
| USP1 | 3 | Plk4 | TACC3 | | |
| WDHD1 | 3 | Apitd1 | TCF19 | | |
| YBEY | 3 | Lrr1 | TIPIN | | |
| ZNF260 | 3 | Haus3 | TK1 | | |
| ZNF428 | 3 | Slc25a1 | TMPO | | |
| ZNF711 | 3 | Acat2 | TOP2A | | |
| ZNF720 | 3 | Sc4mol | TOPBP1 | | |
| ACTB | 3 | Smc6 | TPX2 | | |
| AIG1 | 3 | Cdca5 | TRIM59 | | |
| ANKRD36C | 3 | Tk1 | TTK | | |
| ANXA5 | 3 | Thbs1 | TUBA1C | | |
| ARL136 | 3 | Cdc45 | TUBB4B | | |
| BAD | 3 | Cyr61 | TYMS | | |
| BUB3 | 3 | Brca1 | UACA | | |
| C2orf68 | 3 | Lphn2 | UBC | | |
| C19orf43 | 3 | Rad51 | UBE2C | | |
| CBX5 | 3 | Rad51ap1 | UBE2T | | |
| CCDC14 | 3 | Rbmx2 | UBR7 | | |
| CCNL2 | 3 | Nup85 | UHRF1 | | |
| CDADC1 | 3 | Pradc1 | UNG | | |
| CDK1 | 3 | Tipin | USP1 | | |
| CDKN2C | 3 | Rad18 | WDHD1 | | |
| CIRBP | 3 | Ankrd1 | ZFHX4 | | |

TABLE 4-continued

List of cell cycle regulated genes identified from the analysis of 589 HEK and 412 3T3 cells.

| human gene | cluster | mouse gene | Intersection All genes | novel genes | annotation |
|---|---|---|---|---|---|
| CREB5 | 3 | Fignl1 | ZMYM1 | | |
| DBF4B | 3 | Tanc2 | ZMYND19 | | |
| DDX17 | 3 | Rfc4 | | | |
| DPP9 | 3 | Brip1 | | | |
| DUSP3 | 3 | Etaa1 | | | |
| ELF1 | 3 | Slc7a1 | | | |
| FAM76A | 3 | Ank3 | | | |
| FAM126A | 4 | Cdca8 | | | |
| FAM192A | 4 | Ncapg | | | |
| FANCD2 | 4 | Nuf2 | | | |
| FKBP2 | 4 | Gas2l3 | | | |
| FOXC1 | 4 | Ndc80 | | | |
| FOXM1 | 4 | Pbk | | | |
| GATAD2B | 4 | Cdkn1b | | | |
| GNPTAB | 4 | Cdkn2c | | | |
| GOLGA8B | 4 | G2e3 | | | |
| GPX4 | 4 | Smc2 | | | |
| GTPBP3 | 4 | Tuba1c | | | |
| HIST1H1C | 4 | Racgap1 | | | |
| HIST1H1E | 4 | Kif11 | | | |
| HIST2H2AC | 4 | Incenp | | | |
| HJURP | 4 | Cep55 | | | |
| HOXA3 | 4 | Dbf4 | | | |
| HOXA10 | 4 | Kif2c | | | |
| HOX67 | 4 | Fam83d | | | |
| IGF2BP2 | 4 | Ccna2 | | | |
| ING3 | 4 | Prc1 | | | |
| IQGAP3 | 4 | Hmgb2 | | | |
| JUN | 4 | Aurkb | | | |
| KIAA1524 | 4 | Top2a | | | |
| KIFC1 | 4 | Kif22 | | | |
| LARP7 | 4 | Shcbp1 | | | |
| LRRC49 | 4 | Ect2 | | | |
| MAF | 4 | Mis18bp1 | | | |
| MED21 | 4 | Spc25 | | | |
| MELK | 4 | Kif4 | | | |
| N4BP2L2 | 4 | Ccnf | | | |
| NMT2 | 4 | Cenpl | | | |
| NT5C | 4 | Sgol1 | | | |
| OSBPL3 | 4 | Sgol2 | | | |
| OTUB1 | 4 | Casc5 | | | |
| PERP | 4 | Mki67 | | | |
| RAB5B | 4 | Fam64a | | | |
| RBM23 | 4 | Kif20b | | | |
| RBMS1 | 4 | H1f0 | | | |
| ROCK1 | 4 | Smc4 | | | |
| SCP2 | 4 | Kif15 | | | |
| SKA2 | 4 | Prr11 | | | |
| SP3 | 4 | Cdk1 | | | |
| SRSF5 | 5 | Flii | | | |
| TFAP2A | 5 | Adprhl2 | | | |
| THG1L | 5 | Col6a1 | | | |
| TIMM176 | 5 | Ubc | | | |
| TMPO | 5 | Mcph1 | | | |
| TROAP | 5 | Col16a1 | | | |
| TSC22D3 | 5 | Cenpn | | | |
| TSIX | 5 | Trip13 | | | |
| TUBB | 5 | Mrpl17 | | | |
| TUBGCP3 | 5 | Parva | | | |
| UBA5 | 5 | Myadm | | | |
| UBC | 5 | Ercc6l | | | |
| XIST | 5 | Arhgef40 | | | |
| XXYLT1 | 5 | Pdgfrb | | | |
| YWHAB | 5 | Cd81 | | | |
| ZNF503 | 5 | Ska1 | | | |
| ZNF503-AS2 | 5 | Hist1h1e | | | |
| ZNF703 | 5 | Ccdc53 | | | |
| ZWINT | 5 | Espl1 | | | |
| AASDH | 5 | Aaas | | | |
| AKIRIN2 | 5 | Sp1 | | | |
| ANKRD11 | 5 | Mad2l1 | | | |

TABLE 4-continued

List of cell cycle regulated genes identified from the analysis of 589 HEK and 412 3T3 cells.

| human gene | cluster | mouse gene | Intersection All genes | novel genes | annotation |
|---|---|---|---|---|---|
| APC | 5 | Rsu1 | | | |
| ARHGAP11A | 5 | Cryab | | | |
| ARID2 | 5 | Egln2 | | | |
| ASH1L | 5 | Tmpo | | | |
| ATF4 | 5 | Mastl | | | |
| ATL2 | 5 | Ephx1 | | | |
| BEX1 | 5 | Tpgs2 | | | |
| BOD1L1 | 5 | Lclat1 | | | |
| BORA | 5 | Rhno1 | | | |
| BTAF1 | 5 | Foxm1 | | | |
| C6orf62 | 5 | Atf4 | | | |
| C10orf118 | 5 | BC003965 | | | |
| CARD8 | 5 | Osbpl8 | | | |
| CASC5 | 5 | Lmnb1 | | | |
| CCDC18 | 5 | Fez2 | | | |
| CCDC88A | 5 | Ndufv1 | | | |
| CCNA2 | 5 | Osbpl9 | | | |
| CCNB2 | 5 | Otub1 | | | |
| CCNF | 5 | Atxn10 | | | |
| CDC27 | 5 | Gtse1 | | | |
| CDCA2 | 5 | Fam173a | | | |
| CDKN1B | 5 | Gemin6 | | | |
| CENPA | 5 | Bgn | | | |
| CENPI | 5 | Rfc5 | | | |
| CEP44 | 5 | Malat1 | | | |
| CEP350 | 5 | Fer | | | |
| CKAP2 | 5 | Ncaph2 | | | |
| CKAP2L | 5 | Meg3 | | | |
| CKS1B | 5 | Cdca2 | | | |
| CLCN3 | 5 | Stil | | | |
| COASY | 5 | Pcnt | | | |
| CSNK1G3 | 5 | Tubb5 | | | |
| CTCF | 5 | Mdc1 | | | |
| DCP1A | 5 | Cuta | | | |
| DEPDC1B | 5 | Tuba1b | | | |
| DIAPH2 | 5 | Cst3 | | | |
| DR1 | 5 | Slc35f5 | | | |
| DSC3 | 5 | Ttk | | | |
| DST | 5 | Tsen2 | | | |
| EIF1B | 5 | Raf1 | | | |
| EIF4G3 | 5 | Urod | | | |
| ESPL1 | 5 | Ttf2 | | | |
| FAM64A | 5 | Srgap2 | | | |
| FAM83D | 5 | Ndufa1 | | | |
| GAS2L3 | 5 | Ubb | | | |
| GOLGA4 | 5 | Cntln | | | |
| GPSM2 | 5 | Ctcf | | | |
| GTPBP6 | 5 | Fra10ac1 | | | |
| HMGB2 | 5 | Pmp22 | | | |
| HN1 | 5 | Thsd7a | | | |
| HP1BP3 | 5 | Angptl2 | | | |
| ICT1 | 5 | Ube2t | | | |
| INO80D | 5 | Pknox1 | | | |
| ITSN2 | 5 | Cxcl12 | | | |
| KDM5B | 5 | Vamp5 | | | |
| KIAA0586 | 5 | Ercc5 | | | |
| KIF2C | 5 | Kif18a | | | |
| KIF4B | 5 | Ebag9 | | | |
| KIF5B | 5 | Sap30 | | | |
| KIF15 | 5 | Ska3 | | | |
| MALAT1 | 5 | Ccdc34 | | | |
| MAP9 | 5 | Atp6v1g1 | | | |
| MSX2 | 5 | Fbln2 | | | |
| MT-ND5 | 5 | Cenpq | | | |
| MT-RNR1 | 5 | Adat2 | | | |
| MT-RNR2 | 5 | Dlk1 | | | |
| NCAPD2 | 5 | Lsm3 | | | |
| NCOA2 | 5 | Xiap | | | |
| NEK2 | 5 | Hirip3 | | | |
| NUSAP1 | 5 | Stag2 | | | |
| OSBPL8 | 5 | Skiv2l | | | |
| PBRM1 | 5 | Cenpc1 | | | |

TABLE 4-continued

List of cell cycle regulated genes identified from the analysis of 589 HEK and 412 3T3 cells.

| human gene | cluster | mouse gene | Intersection All genes | novel genes | annotation |
|---|---|---|---|---|---|
| PCLO | 5 | Hcfc1r1 | | | |
| PDZD8 | 5 | Cdk5rap2 | | | |
| PHACTR4 | 5 | Stx4a | | | |
| PHF20L1 | 5 | Gen1 | | | |
| PPP1R12A | 5 | Fam3c | | | |
| PRR11 | 5 | Uaca | | | |
| PTBP3 | 5 | Chrac1 | | | |
| PTPN1 | 5 | Pcif1 | | | |
| RACGAP1 | 5 | Ing1 | | | |
| RANGAP1 | 5 | Add1 | | | |
| RC3H1 | 5 | Gabarap | | | |
| RICTOR | 5 | Rnf24 | | | |
| RUFY1 | 5 | Zrsr2 | | | |
| SAFB | 5 | Tbk1 | | | |
| SERTAD2 | 5 | Lsm2 | | | |
| SGOL1 | 5 | Dbnl | | | |
| SMC4 | 5 | Smoc2 | | | |
| SPAG5 | 5 | Puf60 | | | |
| SPG11 | 5 | Ppp1r35 | | | |
| SRRM2 | 5 | Bub3 | | | |
| TAF3 | 5 | Melk | | | |
| THUMPD1 | 5 | Kifc1 | | | |
| TJP1 | 5 | Dock1 | | | |
| TLE3 | 5 | Gabpb1 | | | |
| TRIO | 5 | Zwilch | | | |
| TUBA1C | 5 | Mbnl1 | | | |
| TUBB4B | 5 | Gmn | | | |
| UACA | 5 | Med31 | | | |
| UBE2D1 | 5 | Ncaph | | | |
| UBLCP1 | 5 | Ifit2 | | | |
| USP9X | 5 | Id2 | | | |
| VPS13A | 5 | Cdca4 | | | |
| WAC | 5 | Ddx49 | | | |
| WDR36 | 5 | Cope | | | |
| WDR53 | 5 | Gsg2 | | | |
| YTHDC1 | 5 | Sass6 | | | |
| ZC3H4 | 5 | Arf2 | | | |
| ZCCHC11 | 5 | Nfu1 | | | |
| ZFR | 5 | Id3 | | | |
| ZIC5 | 5 | Apip | | | |
| ZMAT2 | 5 | H3f3b | | | |
| ZMYM1 | 5 | Cat | | | |
| ZMYND8 | 5 | Trim59 | | | |
| ZNF280D | 5 | Lpp | | | |
| ZNF281 | 5 | Dcaf7 | | | |
| ZNF638 | 5 | Rasl11a | | | |
| ZNF652 | 5 | Rtkn2 | | | |
| ZYG116 | 5 | Ska2 | | | |
| ANLN | 5 | Bicc1 | | | |
| ARL6IP1 | 5 | Golga2 | | | |
| ASPM | 5 | Col1a1 | | | |
| AURKA | 6 | Anln | | | |
| AURKB | 6 | Kif20a | | | |
| BIRC5 | 6 | Cenpf | | | |
| BRD8 | 6 | Ckap2 | | | |
| BUB1 | 6 | Cenpa | | | |
| BUB1B | 6 | Bub1 | | | |
| CCNB1 | 6 | Hmmr | | | |
| CDC20 | 6 | Ckap2l | | | |
| CDCA3 | 6 | Aurka | | | |
| CDCA8 | 6 | Pttg1 | | | |
| CENPE | 6 | Plk1 | | | |
| CENPF | 6 | Cenpe | | | |
| CKAP5 | 6 | Tacc3 | | | |
| CKS2 | 6 | Tpx2 | | | |
| DBF4 | 6 | Tubb4b | | | |
| DEPDC1 | 6 | Cdc20 | | | |
| DLGAP5 | 6 | Aspm | | | |
| ECT2 | 6 | Ccnb1 | | | |
| G2E3 | 6 | Ckap5 | | | |
| GTSE1 | 6 | Ube2c | | | |
| HMMR | 6 | Arhgap11a | | | |

TABLE 4-continued

List of cell cycle regulated genes identified from the
analysis of 589 HEK and 412 3T3 cells.

| human gene | cluster | mouse gene | Intersection All genes | novel genes | annotation |
|---|---|---|---|---|---|
| INCENP | 6 | Birc5 | | | |
| KIF11 | 6 | Kif23 | | | |
| KIF14 | 6 | Nusap1 | | | |
| KIF18A | 7 | Serpinb8 | | | |
| KIF20A | 7 | Gm10184 | | | |
| KIF20B | 7 | Gas5 | | | |
| KIF23 | 7 | Dnm3os | | | |
| KPNA2 | 7 | Chchd7 | | | |
| MKI67 | 7 | Cstb | | | |
| NCAPG | 7 | Smtn | | | |
| NDC80 | 7 | Fam172a | | | |
| NUF2 | 7 | Cdkn3 | | | |
| PIF1 | 7 | Dlgap5 | | | |
| PLK1 | 7 | Mgea5 | | | |
| PRC1 | 7 | Opa3 | | | |
| PSRC1 | 7 | Tax1bp1 | | | |
| SGOL2 | 7 | Parpbp | | | |
| TACC3 | 7 | Nup37 | | | |
| TOP2A | 7 | Gas1 | | | |
| TPX2 | 7 | Grem2 | | | |
| TTK | 7 | Uhrf1bp1l | | | |
| UBE2C | 7 | Ccnb2 | | | |
| ABCC5 | 7 | Brd8 | | | |
| ABI1 | 7 | Cdc25c | | | |
| ACIN1 | 7 | Nek2 | | | |
| ANP32E | 7 | Cmas | | | |
| ARFGEF2 | 7 | Mrps16 | | | |
| ARHGAP5 | 7 | Hyls1 | | | |
| ARHGAP12 | 7 | Stk11 | | | |
| ARHGAP19 | 7 | Diap3 | | | |
| ARIH1 | 7 | Bora | | | |
| ATF7IP | 7 | Cit | | | |
| BPGM | 7 | Rangap1 | | | |
| C10orf32 | 7 | Tm7sf3 | | | |
| C11orf54 | 7 | Arl2bp | | | |
| CALM2 | 7 | Elp3 | | | |
| CAMLG | 7 | Map2k2 | | | |
| CCAR1 | 7 | Specc1l | | | |
| CCNJ | 7 | H2afx | | | |
| CDK5RAP2 | 7 | Smarcb1 | | | |
| CEP70 | 7 | Rad23a | | | |
| COMMD2 | 7 | Fzr1 | | | |
| CREBRF | 7 | Rfk | | | |
| CTNND1 | 7 | Bax | | | |
| CUL5 | 7 | Cdkn2d | | | |
| DCP2 | 7 | Rhoq | | | |
| DDX21 | 7 | Ccdc77 | | | |
| DESI2 | 7 | Tgif1 | | | |
| DHX36 | 7 | Calm2 | | | |
| DHX37 | 7 | Rpl13a-ps1 | | | |
| EP300 | 7 | Reep4 | | | |
| EVI5 | 7 | Ccdc18 | | | |
| EXPH5 | 7 | Itfg1 | | | |
| FASTKD1 | 7 | Lhfpl2 | | | |
| GAPVD1 | 7 | Zfhx4 | | | |
| GOT1 | 7 | Arl6ip1 | | | |
| H3F3B | 7 | Zbed3 | | | |
| HEXIM1 | 7 | Rab7 | | | |
| HMGB3 | 7 | Nucks1 | | | |
| HMGCR | 7 | Fam198b | | | |
| HSPA1B | 7 | Nfe2l1 | | | |
| HSPA5 | 7 | Mat2b | | | |
| HSPH1 | 7 | Tmem138 | | | |
| KIF4A | 7 | Ccng2 | | | |
| LARP4B | 7 | Ccng1 | | | |
| LBR | 7 | Chd2 | | | |
| LIX1L | 7 | Armcx1 | | | |
| LRIF1 | 7 | Cep128 | | | |
| LUC7L3 | 7 | Dnajc10 | | | |
| MARK2 | 7 | E2f5 | | | |
| MBNL1 | 7 | Chchd6 | | | |
| MIS18BP1 | 7 | Fgfr1op | | | |

TABLE 4-continued

List of cell cycle regulated genes identified from the analysis of 589 HEK and 412 3T3 cells.

| | | | Intersection | | |
|---|---|---|---|---|---|
| human gene | cluster | mouse gene | All genes | novel genes | annotation |
| MT-ND1 | 7 | Ppa2 | | | |
| MT-ND2 | 7 | Rbbp6 | | | |
| MT-ND4 | 7 | Acot9 | | | |
| MT-ND4L | 7 | Rhou | | | |
| MTRNR2L8 | 7 | Rad21 | | | |
| MTRNR2L12 | 7 | Kif14 | | | |
| NFKB1 | 7 | Asxl1 | | | |
| NIPBL | 7 | Cep110 | | | |
| ODF2 | 7 | Ppp2r5c | | | |
| PARPBP | 7 | Mesdc2 | | | |
| PCM1 | 7 | Pdha1 | | | |
| PCNT | 7 | Mapre1 | | | |
| PDE6D | 7 | Gja1 | | | |
| PICALM | 7 | Zfand6 | | | |
| POLR2B | 7 | Cdca3 | | | |
| PRRC2C | 7 | Terf1 | | | |
| PTPN13 | 7 | Rbms3 | | | |
| PTTG1 | 7 | Slc7a5 | | | |
| PUM1 | 7 | Cpne3 | | | |
| RAB7L1 | 7 | Ptms | | | |
| RAB14 | 7 | Cdc25b | | | |
| RB1CC1 | 7 | Pcf11 | | | |
| RBBP6 | 7 | Ddit4 | | | |
| RBMX | 7 | Carkd | | | |
| RNF26 | 7 | Ndufc1 | | | |
| RRP15 | 7 | Ncapd2 | | | |
| RSF1 | 7 | Mrpl51 | | | |
| SAPCD2 | 7 | Bola3 | | | |
| SATB2 | 7 | Uhrf2 | | | |
| SEC62 | 7 | Bub1b | | | |
| SENP6 | 7 | Golga5 | | | |
| SESN2 | 7 | Spag5 | | | |
| SETD2 | 7 | Trappc2l | | | |
| SF1 | 7 | Psrc1 | | | |
| SFPQ | 7 | Dynll1 | | | |
| SLC7A11 | 7 | Vbp1 | | | |
| SLC39A10 | 7 | Gpsm2 | | | |
| SMEK2 | 7 | Ubxn6 | | | |
| SNAPC3 | 7 | Dnajb4 | | | |
| SON | 7 | Glrx3 | | | |
| SRSF3 | 7 | Sar1a | | | |
| STX18 | 7 | Cenpw | | | |
| TAF7 | 7 | Hn1 | | | |
| TFCP2 | 7 | Odf2 | | | |
| TGS1 | 7 | Atg3 | | | |
| TMEM19 | 7 | Echs1 | | | |
| TOX4 | 7 | Fzd2 | | | |
| UBXN4 | 7 | Arl8b | | | |
| UNKL | 7 | Hexim1 | | | |
| USP7 | 7 | Pnrc2 | | | |
| VEZF1 | 7 | Atp6ap2 | | | |
| WBP11 | 7 | Cks1b | | | |
| WDR43 | 7 | Unc50 | | | |
| WSB1 | 7 | Akirin2 | | | |
| ZC3H11A | 7 | Cebpb | | | |
| ZC3H14 | 7 | C330027C09Rik | | | |
| ZNF148 | 7 | Cdc27 | | | |
| ZNF318 | 7 | Cd164 | | | |
| | 7 | F3 | | | |
| | 7 | Pcnp | | | |
| | 7 | Hp1bp3 | | | |
| | 7 | Nde1 | | | |
| | 7 | Ccdc104 | | | |
| | 8 | Arpc2 | | | |
| | 8 | Snhg3 | | | |
| | 8 | Marcksl1 | | | |
| | 8 | Dhx29 | | | |
| | 8 | Sbno1 | | | |
| | 8 | Dnajc19 | | | |
| | 8 | Socs4 | | | |
| | 8 | Hnrnpc | | | |
| | 8 | Rps14 | | | |

TABLE 4-continued

List of cell cycle regulated genes identified from the analysis of 589 HEK and 412 3T3 cells.

| human gene | cluster | mouse gene | Intersection All genes | novel genes | annotation |
|---|---|---|---|---|---|
| | 8 | Gltscr2 | | | |
| | 8 | Ncl | | | |
| | 8 | Csnk1a1 | | | |
| | 8 | Ercc1 | | | |
| | 8 | Oraov1 | | | |
| | 8 | Ccnd1 | | | |
| | 8 | Myeov2 | | | |
| | 8 | Rala | | | |
| | 8 | Itga5 | | | |
| | 8 | Serbp1 | | | |
| | 8 | Naca | | | |
| | 8 | Vim | | | |
| | 8 | Impact | | | |
| | 8 | Hnrnpu | | | |
| | 8 | Snrpa | | | |
| | 8 | Sox4 | | | |
| | 8 | Pycr2 | | | |
| | 8 | Celf4 | | | |
| | 8 | Srp9 | | | |
| | 8 | Sltm | | | |
| | 8 | Hspa9 | | | |
| | 8 | Rpl15 | | | |
| | 8 | Pus3 | | | |
| | 8 | Tsc22d1 | | | |
| | 8 | Mrpl21 | | | |
| | 8 | St13 | | | |
| | 8 | Cwc15 | | | |
| | 8 | Gpx7 | | | |
| | 8 | Dhx38 | | | |
| | 8 | Hspb8 | | | |
| | 8 | Timm13 | | | |
| | 8 | Rnf11 | | | |
| | 8 | Snrpd3 | | | |
| | 8 | Arl3 | | | |
| | 8 | Zfp36l2 | | | |
| | 8 | Strap | | | |
| | 8 | Ddx6 | | | |
| | 8 | Eif2s1 | | | |
| | 8 | Nrbp1 | | | |
| | 8 | Hsp90ab1 | | | |
| | 8 | Zfp36l1 | | | |
| | 8 | Pdcd4 | | | |
| | 8 | Hmgn3 | | | |
| | 8 | Atp5j | | | |
| | 8 | Ikbkap | | | |
| | 8 | Tbca | | | |
| | 8 | Npm1 | | | |
| | 8 | Fth1 | | | |
| | 8 | Banf1 | | | |
| | 8 | Psmc5 | | | |
| | 8 | Hspa4 | | | |
| | 8 | Slc41a1 | | | |
| | 8 | Rpl32 | | | |
| | 8 | Cct8 | | | |
| | 8 | S100a6 | | | |
| | 8 | Gm6563 | | | |
| | 8 | Top1 | | | |
| | 8 | Syncrip | | | |
| | 8 | Zfc3h1 | | | |
| | 8 | Kdm5b | | | |
| | 8 | Mrpl38 | | | |
| | 8 | Rps24 | | | |
| | 8 | Gm4204 | | | |
| | 8 | Tes | | | |
| | 8 | Rpl26 | | | |
| | 8 | Nol8 | | | |
| | 8 | Arf4 | | | |
| | 8 | Tardbp | | | |
| | 8 | Gnb2l1 | | | |
| | 8 | Nrf1 | | | |
| | 8 | Hsp90aa1 | | | |
| | 8 | Hdgf | | | |

TABLE 4-continued

List of cell cycle regulated genes identified from the analysis of 589 HEK and 412 3T3 cells.

| human gene | cluster | mouse gene | Intersection All genes | novel genes | annotation |
|---|---|---|---|---|---|
| | 8 | Stat3 | | | |
| | 8 | Zbtb38 | | | |
| | 8 | Hmga2 | | | |
| | 8 | Nufip2 | | | |
| | 8 | Sh3glb1 | | | |
| | 8 | Irf2bp2 | | | |
| | 8 | Scistm1 | | | |
| | 8 | Canx | | | |
| | 8 | Rps21 | | | |
| | 8 | Exo5 | | | |
| | 8 | Ubtd1 | | | |
| | 8 | Hspd1 | | | |
| | 8 | Anp32e | | | |
| | 8 | Lmna | | | |
| | 8 | Ogfr | | | |
| | 8 | Rps3 | | | |
| | 8 | Mex3a | | | |
| | 8 | MPP1 | | | |
| | 8 | Pfn1 | | | |
| | 8 | Prrc2c | | | |
| | 8 | Crlf3 | | | |
| | 8 | Ubtf | | | |
| | 8 | Bzw1 | | | |
| | 8 | Rpl4 | | | |
| | 8 | Lgals1 | | | |
| | 8 | Actb | | | |
| | 8 | Ccar1 | | | |
| | 8 | Adar | | | |
| | 8 | Ddx3x | | | |
| | 8 | Tlk2 | | | |
| | 8 | Dcun1d5 | | | |
| | 8 | Luzp1 | | | |
| | 8 | Tomm70a | | | |
| | 8 | Ccdc6 | | | |
| | 8 | Luc7l3 | | | |
| | 8 | Gm9843 | | | |
| | 8 | Rsl1d1 | | | |
| | 8 | Rtn4 | | | |

TABLE 5

List of highest gene loadings in each of the top 40 principal components from the 44,808 retina STAMPs.

| Top and bottom genes | PC1 | PC2 | PC3 | PC4 | PC5 | PC6 | PC7 | PC8 | PC9 | PC10 |
|---|---|---|---|---|---|---|---|---|---|---|
| 1 | CP | ATP1B1 | ISL1 | PDE6H | PRKCA | EBF3 | SNCG | THY1 | CBLN2 | SLIT2 |
| 2 | CAR14 | SNHG11 | TRPM1 | ARR3 | CCDC136 | SLC6A9 | NRN1 | SLC17A6 | C1QL1 | TACR3 |
| 3 | SLC1A3 | PAX6 | GNG13 | GUCA1A | KCNE2 | LGR5 | SLC17A6 | NRN1 | IGFBP2 | NXPH1 |
| 4 | APOE | ELAVL3 | VSX2 | PDE6C | ABLIM1 | EBF1 | NEFM | NELL2 | C1QL2 | PDE1A |
| 5 | CD9 | SLC6A1 | SCG2 | GNAT2 | CAR8 | PRDM13 | NEFL | LPL | OLFM3 | GLRA1 |
| 6 | COL9A1 | GAD1 | GPR179 | OPN1MW | SEBOX | ZFP8Q4A | FXYD7 | TFAP2C | TBX3 | NETO1 |
| 7 | RLBP1 | VSNL1 | PCP2 | GNGT2 | VSTM2B | NFIX | RGS4 | BHLHE22 | GNG2 | NTNG1 |
| 8 | AQP4 | STMN2 | GRM6 | OPN1SW | STRIP2 | PTPRF | NELL2 | NPNT | CARTPT | CDH8 |
| 9 | ID3 | SPOCK3 | QPCT | RP1 | PDE6H | PTPRT | STMN2 | CPLX2 | GAP43 | ZFHX4 |
| 10 | SPC25 | GAD2 | TRNP1 | GNB1 | ARR3 | NEFL | CHRNA6 | FXYD7 | NFIA | A330008L17RIK |
| 11 | PDPN | SPARCL1 | NDNF | KCNE2 | PDE6C | NHLH2 | THY1 | AI593442 | MEIS2 | TMEFF2 |
| 12 | CRYM | CPLX2 | CAR8 | THRB | OPN1MW | LAMP5 | RPRM | MAF | NR4A2 | ESAM |
| 13 | ABCA8A | CDK14 | B3GALT2 | CNGB3 | PCP2 | CALB2 | ELAVL2 | RG54 | COL11A1 | PRDM8 |
| 14 | TIMP3 | TFAP2B | TGFB2 | CST3 | LRRTM4 | PPP1R17 | UCHL1 | ALCAM | SYT7 | SLITRK6 |
| 15 | HES1 | DLGAP1 | PRKCA | FAM19A3 | CEP112 | CRABP1 | GAP43 | CXCL14 | 2610017I09RIK | CACNA2D3 |
| 16 | CYR61 | C1QL1 | DKK3 | CD59A | TPBG | SNCG | NEFH | NECAB1 | TFAP2B | BHLHE22 |
| 17 | ZFP36L1 | GNG2 | FRMD3 | MFGE8 | ZBTB20 | NCKAP5 | FSTL1 | GAD2 | OPTC | A730046J19RIK |
| 18 | GPR37 | TKT | SIX3OS1 | HOPX | ADAMTS5 | IER5 | KCNIP4 | PTN | VIP | SEBOX |
| 19 | SPARC | DNER | CACNA2D3 | BTG2 | OPN1SW | NEFM | CALB2 | CRABP1 | COL23A1 | QPCT |
| 20 | ESPN | RBFOX1 | PAX6 | HSPA1A | GUCA1A | HS6ST2 | CDK14 | ELAVL2 | SLC4A3 | GRIK1 |
| -1 | SNHG11 | GNG13 | CLDN5 | ABLIM1 | SCGN | GAD1 | NHLH2 | 1500016L03RIK | SLC5A7 | CDH9 |
| -2 | SCG2 | TRPM1 | ELTD1 | ISL1 | A730046J19RIK | SLC6A1 | SLC6A9 | CALB1 | GNG7 | HS3ST4 |
| -3 | ATP1B1 | PCP2 | CD93 | PCP2 | CDH8 | NPNT | NECAB1 | TMEFF2 | RIMS1 | RELN |
| -4 | UCHL1 | GPR179 | PTPRB | TRPM1 | VSX1 | C1QL2 | CRABP1 | BAI1 | CALB2 | NFIA |
| -5 | ELAVL3 | GRM6 | CTLA2A | CAR8 | PTPRZ1 | LPL | TFAP2C | SLC4A3 | NPY | PTPRZ1 |
| -6 | SPOCK3 | ISL1 | PLTP | GPR179 | GSG1 | MEIS2 | LGR5 | SEPT4 | CXCL14 | BC046251 |
| -7 | GABRA1 | VSX2 | LY6C1 | TGFB2 | SLIT2 | C1QL1 | LAMP5 | TFAP2B | RBFOX1 | SLC5A7 |
| -8 | VSNL1 | TRNP1 | RAMP2 | PRKCA | ZFHX4 | SLIT2 | PRDM13 | SOWAHA | IGFBP7 | EPHA7 |
| -9 | STMN2 | CAR8 | FAM101B | GNG13 | GRIK1 | PCP4L1 | NFIX | SGK1 | NHLH2 | SOX6 |
| -10 | GAD1 | QPCT | MGP | QPCT | PDE1A | GAD2 | IER5 | TPM3 | PCP4L1 | RIMS1 |
| -11 | ISL1 | FRMD3 | RGS5 | SPARCL1 | NETO1 | ZFHX4 | ZFP804A | VIM | SOX2 | NEUROD2 |
| -12 | GNG13 | SEBOX | EGFL7 | VSTM2B | GABRA1 | DLGAP1 | PTPRF | NPY | SCG2 | CHODL |
| -13 | TRNP1 | NDNF | GNG11 | TRNP1 | TACR3 | CXCL14 | NCKAP5 | TPM3-RS7 | ARL4C | GNG2 |
| -14 | RBFOX1 | CACNA2D3 | IGFBP7 | VSX2 | SLITRK6 | CBLN2 | GRIK2 | NEBL | PCDH10 | GABRR2 |
| -15 | TFAP2B | B3GALT2 | SEPP1 | GRM6 | A330008L17RIK | ALDOC | FILIP1L | SLC5A7 | POMC | ISL1 |
| -16 | B3GALT2 | STRIP2 | VWA1 | COL4A1 | NXPH1 | RND3 | PTPRT | NEFH | SPOCK3 | COL1A2 |
| -17 | CPLX2 | TGFB2 | ITM2A | CACNA2D3 | OTOR | SPOCK3 | EBF3 | GNG7 | SPARCL1 | GRM6 |
| -18 | FRMD3 | GABRR2 | COL4A1 | COL4A2 | CAMK4 | FILIP1L | GAD2 | C1QL1 | ESPN | NDNF |
| -19 | GNG2 | PRKCA | SLC7A5 | NDNF | ESAM | SCGN | BHLHE22 | ZFP804A | LPL | IGFN1 |
| -20 | PCP4L1 | RNF152 | FN1 | B3GALT2 | FEZF2 | SCGN | NR2F2 | FBXW7 | CALB1 | |

TABLE 5-continued

List of highest gene loadings in each of the top 40 principal components from the 44,808 retina STAMPs.

Top and bottom genes

| PC11 | PC12 | PC13 | PC14 | PC15 | PC16 | PC17 | PC18 | PC19 | PC20 | PC21 |
|------|------|------|------|------|------|------|------|------|------|------|
| FOSB | CARTPT | OPTC | VSX1 | GNB1 | CCK | OLFM3 | CBLN2 | CARTPT | OPTC | IGF1 |
| ZFP36 | 2610017I09RIK | GNB1 | RELN | RP1 | OTOR | CAR2 | NETO1 | NR4A2 | ALDH1A1 | IGFN1 |
| JUNB | TFAP2B | CST3 | CCK | CST3 | LECT1 | LAMP5 | SYT6 | LRRTM1 | ITM2A | TFAP2C |
| EGR1 | NR4A2 | RP1 | LECT1 | SLC16A1 | UNC13C | GJD2 | CDH9 | NFIA | SNED1 | LAMP5 |
| FOS | GABRA2 | ATP1A2 | PCP4L1 | HS3ST4 | CABP2 | DYNC1I1 | TACR3 | VIP | SNCA | CARTPT |
| ATF3 | CBLN2 | SNED1 | CDH8 | S1PR1 | GSG1 | SLC6A9 | NPY | RPRM | TAC2 | CABP2 |
| NR4A1 | FBXW7 | IGFBP2 | TNNT1 | KCNJ10 | COL11A1 | GRIA3 | HS3ST4 | SCG2 | PVRL3 | PCDH17 |
| DUSP1 | VIP | MEST | IGF1 | CDH9 | C1QL1 | TBX3 | NFIX | 2610017I09RIK | LY6E | PTPRF |
| IER2 | SYT6 | FSTL1 | IGFN1 | ABCA8A | SCGN | AI593442 | NXPH1 | LHX4 | PTGDS | NR2F2 |
| KLF4 | HPGD | IGF2 | ZFHX4 | BC046251 | NHLH2 | PTPRF | RIMS1 | EPHA7 | CLDN5 | NR4A2 |
| PPP1R15A | SLC5A7 | CDKN1C | SCG2 | NEUROD2 | RELN | IGFBP2 | COL11A1 | NFIX | MEST | FN1 |
| KLF6 | NNAT | HTRA1 | A33000BL17RIK | WIPI1 | TFAP2C | THY1 | PDE1A | GPR22 | CTLA2A | HS3ST4 |
| BTG2 | GAD1 | PTGDS | SIX3OS1 | LY6C1 | CST3 | NEFH | C1QL1 | TNNT1 | IGFBP2 | HTRA1 |
| CYR61 | GRIA3 | NXPH1 | GJD1 | ABCA8B | GNB1 | DLGAP1 | NHLH2 | PTPRZ1 | RAMP2 | SLC6A9 |
| NFKBIZ | SCG2 | WLS | RPRM | CLDN5 | RP1 | ABLIM1 | GAP43 | HS6ST2 | VWA1 | HS6ST2 |
| RP1 | GRIK2 | PVRL3 | UNC13C | SPC25 | CRABP1 | BC046251 | GNG7 | BHLHE22 | LY6C1 | SLC17A8 |
| GNB1 | RIMS1 | HSPA1A | GJC1 | KDR | NFIB | CNTN4 | TBX3 | TFAP2C | CTSH | COL11A1 |
| JUN | CALB2 | SGK1 | GNGT2 | HSPA1B | EBF3 | FILIP1L | NR2F2 | ISL1 | SLC7A5 | OPTC |
| GM26669 | KCND3 | HSPA1B | LAMP5 | NETO1 | TBX3 | CDKN1C | NR4A2 | NECAB1 | PPP1R17 | NECAB1 |
| ADAMTS1 | CAR2 | ALDH1A1 | GNG13 | CAV1 | A730046J19RIK | RBFOX1 | CHODL | SOX6 | TAC1 | 2610017I0RIK |
| OPTC | 1500016L03RIK | GNGT2 | GSG1 | OPTC | NEUROD2 | 2610017I09RIK | HPGD | IGFN1 | MGP | PPP1R17 |
| CD59A | LPL | GNAT2 | OTOR | ATP1A2 | NXPH1 | KCND3 | FBXW7 | PCDH17 | RGS5 | IGFBP5 |
| GNAT2 | BHLHE22 | FAM19A3 | FSTL1 | FAM19A3 | BC046251 | IGFBP5 | 2610017I09RIK | IGFBP5 | GJC1 | SNCA |
| GNGT2 | MAF | GSG1 | GRIK1 | IGFBP2 | LAMP5 | IGFN1 | LECT1 | IGFBP2 | SERPINE2 | LECT1 |
| PDE6C | CXCL14 | LHX4 | FEZF2 | ALDH1A1 | NFIA | NR4A2 | UNC13C | FN1 | CALD1 | CCK |
| OPN1MW | TFAP2C | PDE6C | NNAT | ZFP36 | NETO1 | GRIK2 | DNER | PPP1R17 | RGS4 | RGS5 |
| ARR3 | NPNT | ARR3 | LHX4 | SNED1 | TACR3 | GABRA2 | LAMP5 | OLFM3 | COL1A2 | EBF1 |
| ATP1A2 | CPLX2 | OPN1MW | SLJTRK6 | PTGDS | PDE1A | RND3 | SHISA9 | CABP2 | COL4A2 | MGP |
| PDE6H | SGK1 | NNAT | KCNIP4 | COL11A1 | SLIT2 | PPP1R17 | CCK | GABRA1 | NR2F2 | NEUROD2 |
| NFIB | TMEFF2 | PDE6H | NFIB | IGFBP7 | EPHA7 | ALCAM | GJD2 | HS3ST4 | COL4A1 | MEIS2 |
| PTGDS | TPM3 | CNGB3 | CNTN4 | FAM19A3 | CDH9 | CACNG4 | DYNC1I1 | RELN | IGFN1 | IGF2 |
| KCNE2 | SOWAHA | KCNE2 | SOX6 | GSG1 | SOX6 | CRABP1 | SLC6A9 | KCND3 | SEPT4 | CHODL |
| PTN | ARL4C | CACNG4 | RP1 | JUNB | HPGD | CAMK4 | MAF | WLS | COX412 | CDHB |
| CLU | AI593442 | OTOR | GLRA1 | NR4A1 | RND3 | B230312C02RIK | CACNG4 | PRDM8 | S1PR3 | CALD1 |
| FAM19A3 | SLC4A3 | PTPRZ1 | GNB1 | FOSB | WLS | 1500016L03RIK | SLC17A8 | GLRA1 | MAF | TAC1 |
| OPN1SW | TPM3-RS7 | KDR | VSX2 | OTOR | SLC17A8 | PCDH17 | TFAP2B | SNCA | TFAP2C | PRDM13 |
| ENPP2 | MEIS2 | DNER | PCDH10 | NBL1 | COL1A2 | CARTPT | ALCAM | FEZF2 | ID4 | GJC1 |
| NUDT4 | PTN | CLDN5 | NFIA | ATF3 | DYNC1I1 | VIP | OPTC | AI593442 | 2610017I09RIK | LGR5 |
| SPARC | VIM | OPN1SW | MEST | NNAT | PCDH10 | HS3ST4 | RGS2 | PCDH10 | ANXA1 | GRIK2 |
| VIM | CALB1 | VEGFA | CST3 | NFIB | HS3ST4 | | NEUROD2 | CDH9 | ATP1A2 | TNNT1 |

| PC22 | PC23 | PC24 | PC25 | PC26 | PC27 | PC28 | PC29 | PC30 | PC31 | PC32 |
|------|------|------|------|------|------|------|------|------|------|------|
| 2610017I09RIK | IGF2 | CARTPT | HBB-BS | HPGD | PPP1R17 | CHN2 | PTGDS | GJD2 | PDLIM3 | PCDH17 |
| NEFH | HBA-A1 | MAF | HBA-A1 | IGF2 | HBA-A1 | RELN | GPR22 | DYNC1I1 | ALDH1A1 | PMEPA1 |
| C1QL2 | HBB-BS | PPP1R17 | 2610017I09RIK | IGFBP5 | HBB-BS | DNER | CHN2 | NPY | RBP1 | GSG1 |

TABLE 5-continued

List of highest gene loadings in each of the top 40 principal components from the 44,808 retina STAMPs.

| Top and bottom genes | | | | | | | |
|---|---|---|---|---|---|---|---|
| PC33 | PC34 | PC35 | PC36 | PC37 | PC38 | PC39 | PC40 |
| IGFBP2 | VIP | GPR22 | VIP | TAC2 | MT2 | IGFN1 | GRIK1 | TTR | CCND1 | HOPX | PPP1R17 |
| THY1 | ID4 | GNG2 | ID4 | TAC1 | CXCL12 | EBF1 | PCP4L1 | GABRA1 | FEZF2 | ITM2A | IGFBP5 |
| TBX3 | CXCL12 | NR4A2 | CXCL12 | C1QL2 | 2610017I09RIK | NETO1 | GPR22 | CARTPT | SLITRK6 | GSTA4 | HOPX |
| GAD1 | IGFBP5 | IGFBP5 | IGFBP5 | GRIK1 | TAC2 | ALDH1A1 | NNAT | SYT7 | VSNL1 | CHN2 | BAI1 |
| OLFM3 | ALDOC | GRIK1 | ALDOC | CXCL14 | LAMP5 | VIP | DDR1 | SCG2 | B2M | SLC17A8 | RBP1 |
| KCND3 | NR4A2 | SLC4A4 | NR4A2 | NXPH1 | MT1 | PCP4L1 | SLITRK6 | DNER | ARL4C | CCND1 | UCHL1 |
| NFIX | CBLN2 | CAMK4 | CBLN2 | B230312C02RIK | NETO1 | NPNT | PMEPA1 | SPOCK3 | BHLHE22 | DBI | LHX4 |
| DKK3 | HS6ST2 | KCND3 | IGFBP2 | LHX2 | PTGDS | GRIK1 | PCDH17 | TAC1 | 2610017I09RIK | DAPL1 | NFIB |
| PMEPA1 | IGFBP2 | C1QL1 | CRIM1 | GPR22 | IGF1 | VSX1 | SLC6A1 | PRDM13 | MT1 | RDH10 | GAS1 |
| NCKAP5 | CRIM1 | ID4 | LRRTM1 | IGF2 | CST3 | SLITRK6 | SHISA9 | PTPRT | ELAVL2 | PRDX6 | DDR1 |
| ID4 | LRRTM1 | LY6C1 | SYT7 | ELAVL2 | LHX4 | COL11A1 | TAC1 | RPRM | MT2 | GPR22 | CALD1 |
| SYT7 | LECT1 | ELAVL2 | SOX6 | OPTC | PDE1A | CBLN2 | SYT7 | SHISA9 | PTPRF | SBSPON | VEGFA |
| SOX6 | CHN2 | LGR5 | HPGD | NFIB | B2M | SEPT4 | ZBTB20 | MAF | NPNT | NNAT | NR2F2 |
| HPGD | GABRA2 | PCP4L1 | CHODL | NETO1 | ELAVL2 | LPL | VSTM2B | PCDH17 | NCKAP5 | S1PR3 | BHLHE22 |
| CHODL | SLC4A4 | DNER | SLC17A6 | TBX3 | CHRNA6 | COL1A2 | PTPRT | EBF1 | PCDH10 | MT2 | TBX3 |
| SLC17A6 | SNED1 | NFIA | SIX3OS1 | NFIX | NNAT | A330008L17RIK | TNNT1 | SERPINE2 | ATF3 | ANXA1 | NR4A1 |
| SIX3OS1 | MLC1 | IGFN1 | TAC2 | NFIX | GSG1 | NNAT | CCK | ID4 | DNER | RPRM | ALDH1A1 |
| TAC2 | TAC1 | HBA-A1 | VIP | HBB-BS | WLS | WLS | CAR2 | SLC17A8 | SLC17A8 | GM129 | HEXB |
| VIP | TAC1 | HBB-BS | SYT6 | HBA-A1 | IGF2 | CAR2 | PCDH10 | PMEPA1 | AI593442 | ABCA8B | SOX6 |
| SYT6 | 2610017I09RIK | PCDH17 | TAC1 | WLS | PCDH10 | PCDH10 | PPP1R17 | LECT1 | NXPH1 | PTGDS | CCK |
| TAC1 | CXCL14 | CHN2 | SNCA | RND3 | PCDH17 | PCDH17 | C1QL2 | HPGD | MAF | KLF4 | HPGD |
| SNCA | C1QL2 | SLC6A1 | FXYD6 | PPP1R17 | VIP | LECT1 | RND3 | NEUROD2 | LHX2 | SHISA9 | KCNIP4 |
| FXYD6 | CDKN1C | ELAVL2 | ELAVL2 | CCK | CAMK4 | CXCL12 | NXPH1 | NR2F2 | SLC4A4 | DIO2 | COL11A1 |
| ELAVL2 | SNCA | PCDH10 | SERPINE2 | RBP1 | PRDM8 | CAMK4 | EBF3 | CBLN2 | GRIA3 | SNED1 | SERPINE2 |
| SERPINE2 | ALDH1A1 | CBLN2 | LAMP5 | GNB1 | NR4A2 | ZFHX4 | CACNG4 | NNAT | NNAT | CRIM1 | GABRR2 |
| LAMP5 | SERPINE2 | TKT | IGFBP5 | CHN2 | PPP1R17 | TBX3 | COL11A1 | CXCL14 | CXCL14 | SLITRK2 | WLS |
| IGFBP5 | PMEPA1 | TAC2 | GRIA3 | UNC13C | CCK | NFIX | B3GALT2 | FOS | FOS | HEXB | SLC17A8 |
| GRIA3 | MGP | HPGD | NNAT | NR4A2 | RNF152 | GPR22 | OLFM3 | GABRA2 | GABRA2 | GAS1 | ATF3 |
| NNAT | WLS | MGP | STMN2 | HS6ST2 | CARTPT | PRDM8 | HPGD | RBFOX1 | LAMP5 | TIMP3 | SEPP1 |
| STMN2 | MEIS2 | GABRA1 | NR4A2 | RP1 | GJD2 | TAC1 | TTR | SLITRK6 | ALDOC | ENPP2 | B2M |
| NR4A2 | CALD1 | SHISA9 | NECAB1 | HSPA1B | CAR2 | TACR3 | PTPRZ1 | NFIX | CABP2 | TTR | GRIK1 |
| NECAB1 | ELAVL2 | CALD1 | B2M | SHISA9 | A730046J19RIK | GLRA1 | CABP2 | CRIM1 | PRDM8 | HSPA1B | A730046J19RIK |
| B2M | HPGD | UNC13C | IGFN1 | VWA1 | ALDH1A1 | EPHA7 | B2M | VIP | NR4A2 | NRP1 | LECT1 |
| IGFN1 | CCND1 | RBP1 | CNGB3 | PCDH10 | ALDH1A1 | B230312C02RIK | CAMK4 | VEGFA | NEUROD2 | PPAP2B | SLITRK6 |
| CNGB3 | S1PR3 | ALDOC | SLC6A9 | ALDOC | PCDH17 | SLC4A4 | C1QL1 | IGF2 | EGR1 | GM26669 | CACNA2D3 |
| SLC6A9 | AI593442 | RBP1 | CALD1 | SEPT4 | NPNT | NPNT | 2610017I09RIK | DDR1 | SCG2 | S1PR1 | MAF |
| CALD1 | RELN | QPCT | | TTR | NELL2 | B2M | 2610017I09RIK | CCK | GM13889 | PPP1R17 | VIP |
| | | PTGDS | | | | | | | | | |

| PC33 | PC34 | PC35 | PC36 | PC37 | PC38 | PC39 | PC40 |
|---|---|---|---|---|---|---|---|
| PTPRT | ARL4C | TTR | TPM3-RS7 | HEXB | TPM3-RS7 | CDKN1C | SLC17A8 |
| PCDH10 | RPRM | GM129 | CDKN1C | ATF3 | TPM3 | HSPA1B | GM26669 |
| TPBG | SLC17A8 | GM26669 | TRX3 | TTR | TAC2 | HSPA1A | ATF3 |
| IGFBP5 | NPNT | PTGDS | RND3 | PMEPA1 | SHISA9 | CXCL12 | TTR |
| RPRM | BHLHE22 | KCND3 | TPM3 | GM26924 | RGS2 | KLF4 | CDKN1C |
| NR2F2 | TPM3-RS7 | VIP | ANGEL2 | RBP1 | NFKBIA | TAC2 | CALD1 |
| LECT1 | CAMK4 | IGF2 | SYT6 | B2M | NR2F2 | NR4A2 | MT2 |
| CDK14 | TBX3 | TPM3-RS7 | PCDH17 | MAF | ELAVL2 | GM26924 | TAC2 |

TABLE 5-continued

List of highest gene loadings in each of the top 40 principal components from the 44,808 retina STAMPs.

| Top and bottom genes | | | | | | |
|---|---|---|---|---|---|---|
| DIO2 | PTGDS | TPM3 | TPBG | PTGDS | IGF1 | SHISA9 | ADAMTS1 |
| TBX3 | SLITRK6 | CRIM1 | IGFN1 | MT2 | MAF | HS6ST2 | VSTM2B |
| SLITRK6 | TPM3 | RBP1 | NCKAP5 | NFKBIZ | PPP1R17 | NNAT | UTP14B |
| CDKN1C | FIUP1L | ANGEL2 | GRIK2 | KCND3 | ID4 | RELN | CXCL12 |
| SHISA9 | GM26924 | ILDR2 | NFIX | SYT6 | HS6ST2 | PRDM8 | NFKBIZ |
| PTPRF | EBF1 | SHISA9 | NFIB | PRDM8 | HEXB | LRRTM1 | CHN2 |
| NNAT | CHN2 | KCNIP4 | ALCAM | MT1 | ILDR2 | ID1 | DNER |
| CALB2 | ELAVL2 | TRPM3 | CAR2 | SEPP1 | MT1 | WLS | ID4 |
| SOX6 | PRDM13 | TAC2 | CHN2 | HOPX | GM26924 | LY6C1 | NR2E1 |
| GABRA2 | RBFOX1 | WLS | CHRNA6 | DDR1 | NEFH | ALCAM | GLRA1 |
| UNC13C | GM13889 | GRIK2 | NEURDD2 | SLC4A4 | NNAT | CAR2 | NXPH1 |
| TAC1 | LPL | FZD5 | GSG1 | KLF6 | SYT7 | RGS4 | SOWAHA |
| TAC2 | AI593442 | HEXB | PTPRT | GM129 | GLRA1 | ANGEL2 | TPM3-RS7 |
| ELAVL2 | SLC4A4 | ATF3 | TAC2 | HSPA1A | TAC1 | SLC17A8 | TPM3 |
| GRIK2 | VIP | HSPA1A | RBP1 | PVRL3 | MT2 | LAMB1 | HSPA1B |
| NCKAP5 | MAF | HSPA1B | TTR | CXCL12 | PTGDS | SERPINE2 | HSPA1A |
| VIP | TAC1 | CTSH | COL11A1 | FOS | HSPA1A | NPY | EGR1 |
| NFIX | COL11A1 | IER5 | PMEPA1 | NPY | GRIA3 | TAC1 | OLFM3 |
| SCG2 | RND3 | NFKBIA | PTPRF | SOX6 | HSPA1B | VIP | JUND |
| KCND3 | LRRTM1 | RGS2 | WLS | OPTC | VIP | NFIB | PTGDS |
| PRDM8 | IGF1 | PCDH17 | EPHA7 | COL11A1 | GM13889 | PCDH17 | FOS |
| CHN2 | GAD2 | SEPP1 | SERPINE2 | HTRA1 | MT1 | IGFBP5 | SLIT2 |
| ATP1B3 | SYT6 | PPP1R17 | CAMK4 | PPP1R15A | A330069E16RIK | A330069E16RIK | FEZF2 |
| NPY | CXCL14 | SGK1 | PDLIM3 | PPP1R17 | CXCL12 | CXCL12 | DDR1 |
| MAF | TPBG | GPR22 | HOPX | NBL1 | KLF4 | CARTPT | SIX3OS1 |
| TFAP2B | CHRNA6 | LHX2 | BAI1 | DUSP6 | PCDH10 | HEXB | HOPX |
| NEUROD2 | SERPINE2 | SERPINE2 | LRRTM1 | A330069E16RIK | CDKN1C | GPR22 | TAC1 |
| CRABP1 | CBLN2 | DDR1 | CARTPT | CROT | TKT | CNGB3 | CBLN2 |
| ALDOC | PDLIM3 | SLC17A8 | IGFBP2 | HSPA1B | TPRG | VWA1 | PDLIM3 |
| NPNT | SCG2 | SAT1 | NPY | PTN | KCND3 | GM129 | RPRM |
| FXYD6 | HS6ST2 | PON2 | A730046I19RIK | PTPRT | CHRNA6 | CABP2 | SLC6A9 |
| DKK3 | PTPRF | B2M | HSPA1B | GPX8 | NHLH2 | FZD5 | PDE1A |
| | | | | | BHLHE22 | GRIA3 | |

TABLE 6

Genes differentially expressed in each of the 39 retinal cell clusters.

| | myAUC | myDiff | power | cluster # |
|---|---|---|---|---|
| cluster no. 1 DE = 190 | | | | |
| CALB1 | 0.966 | 3.615047 | 0.466 | 1 |
| SLC4A3 | 0.963 | 3.448571 | 0.463 | 1 |
| TPM3 | 0.965 | 3.151521 | 0.465 | 1 |
| SEPT4 | 0.964 | 2.939258 | 0.464 | 1 |
| VIM | 0.944 | 2.937992 | 0.444 | 1 |
| SEPT7 | 0.968 | 2.808893 | 0.468 | 1 |
| 1500016L03RIK | 0.896 | 2.777389 | 0.396 | 1 |
| LHX1 | 0.862 | 2.524691 | 0.362 | 1 |
| ATP1B1 | 0.913 | 2.520540 | 0.413 | 1 |
| BAI1 | 0.855 | 2.451809 | 0.355 | 1 |
| CD47 | 0.904 | 2.425913 | 0.404 | 1 |
| TPM3-RS7 | 0.850 | 2.340003 | 0.350 | 1 |
| SNHG11 | 0.906 | 2.329016 | 0.406 | 1 |
| PCSK1N | 0.910 | 2.295309 | 0.410 | 1 |
| C1QL1 | 0.863 | 2.257023 | 0.363 | 1 |
| PPP1R1A | 0.872 | 2.200677 | 0.372 | 1 |
| NEBL | 0.840 | 2.187973 | 0.340 | 1 |
| MAGED1 | 0.901 | 2.143543 | 0.401 | 1 |
| GNAS | 0.936 | 2.121058 | 0.436 | 1 |
| PCBD1 | 0.837 | 2.100263 | 0.337 | 1 |
| TMEFF2 | 0.837 | 2.087888 | 0.337 | 1 |
| SMARCA4 | 0.907 | 2.073006 | 0.407 | 1 |
| LRRC4 | 0.833 | 2.057230 | 0.333 | 1 |
| UTRN | 0.803 | 1.995075 | 0.303 | 1 |
| ADRA2A | 0.813 | 1.993091 | 0.313 | 1 |
| TFAP2B | 0.899 | 1.986766 | 0.399 | 1 |
| MYO6 | 0.860 | 1.972649 | 0.360 | 1 |
| NDRG4 | 0.882 | 1.970533 | 0.382 | 1 |
| GNG2 | 0.825 | 1.959108 | 0.325 | 1 |
| TMEM132A | 0.816 | 1.954705 | 0.316 | 1 |
| GM16551 | 0.799 | 1.945718 | 0.299 | 1 |
| ONECUT2 | 0.807 | 1.931103 | 0.307 | 1 |
| NDRG1 | 0.906 | 1.920706 | 0.406 | 1 |
| A330050F15RIK | 0.804 | 1.915932 | 0.304 | 1 |
| TKT | 0.855 | 1.910653 | 0.355 | 1 |
| COL27A1 | 0.726 | 1.883251 | 0.226 | 1 |
| SGK1 | 0.821 | 1.876982 | 0.321 | 1 |
| FAM126A | 0.802 | 1.858034 | 0.302 | 1 |
| WNK4 | 0.784 | 1.841538 | 0.284 | 1 |
| TAGLN3 | 0.815 | 1.782407 | 0.315 | 1 |
| SLC12A2 | 0.803 | 1.768314 | 0.303 | 1 |
| SLC4A5 | 0.781 | 1.760906 | 0.281 | 1 |
| LSAMP | 0.829 | 1.738595 | 0.329 | 1 |
| SYT2 | 0.779 | 1.713377 | 0.279 | 1 |
| LY6E | 0.747 | 1.701416 | 0.247 | 1 |
| STMN2 | 0.827 | 1.697169 | 0.327 | 1 |
| LMO1 | 0.769 | 1.657498 | 0.269 | 1 |
| SEPT8 | 0.784 | 1.654456 | 0.284 | 1 |
| PROX1 | 0.846 | 1.646287 | 0.346 | 1 |
| CHGB | 0.841 | 1.628412 | 0.341 | 1 |
| NPY | 0.737 | 1.627193 | 0.237 | 1 |
| GALNT18 | 0.765 | 1.620340 | 0.265 | 1 |
| ZEB2 | 0.793 | 1.616501 | 0.293 | 1 |
| SOWAHA | 0.752 | 1.605413 | 0.252 | 1 |
| LIMA1 | 0.773 | 1.599290 | 0.273 | 1 |
| THRSP | 0.758 | 1.592738 | 0.258 | 1 |
| MEGF11 | 0.765 | 1.587717 | 0.265 | 1 |
| UCHL1 | 0.809 | 1.585799 | 0.309 | 1 |
| F2R | 0.742 | 1.585087 | 0.242 | 1 |
| RCN2 | 0.798 | 1.581440 | 0.298 | 1 |
| VWC2 | 0.763 | 1.571960 | 0.263 | 1 |
| PCSK6 | 0.735 | 1.571878 | 0.235 | 1 |
| ITGB5 | 0.745 | 1.557512 | 0.245 | 1 |
| APP | 0.822 | 1.550700 | 0.322 | 1 |
| TUBB2A | 0.817 | 1.540466 | 0.317 | 1 |
| BC030476 | 0.750 | 1.535140 | 0.250 | 1 |
| CDC42EP4 | 0.754 | 1.512842 | 0.254 | 1 |
| PTPRO | 0.748 | 1.502980 | 0.248 | 1 |
| RGS3 | 0.746 | 1.501006 | 0.246 | 1 |
| 2410066E13RIK | 0.768 | 1.487613 | 0.268 | 1 |
| WFDC10 | 0.718 | 1.485101 | 0.218 | 1 |
| ANK2 | 0.855 | 1.477172 | 0.355 | 1 |
| CTTNBP2 | 0.741 | 1.474312 | 0.241 | 1 |
| FAM124A | 0.721 | 1.474108 | 0.221 | 1 |
| TNR | 0.729 | 1.463381 | 0.229 | 1 |
| RBFOX2 | 0.768 | 1.456189 | 0.268 | 1 |
| SPARCL1 | 0.767 | 1.446874 | 0.267 | 1 |
| THSD7A | 0.783 | 1.441073 | 0.283 | 1 |
| PACSIN1 | 0.799 | 1.440395 | 0.299 | 1 |
| VAT1L | 0.751 | 1.429302 | 0.251 | 1 |
| SYT11 | 0.786 | 1.425350 | 0.286 | 1 |
| AKAP12 | 0.739 | 1.424278 | 0.239 | 1 |
| ABHD10 | 0.763 | 1.411246 | 0.263 | 1 |
| PTPRT | 0.729 | 1.406432 | 0.229 | 1 |
| RCAN2 | 0.754 | 1.405642 | 0.254 | 1 |
| KIF3A | 0.793 | 1.398151 | 0.293 | 1 |
| LRP11 | 0.758 | 1.397326 | 0.258 | 1 |
| RTN1 | 0.801 | 1.393281 | 0.301 | 1 |
| FKBP3 | 0.807 | 1.383785 | 0.307 | 1 |
| NEFL | 0.814 | 1.374162 | 0.314 | 1 |
| CD59A | 0.753 | 1.372191 | 0.253 | 1 |
| CDH4 | 0.748 | 1.371678 | 0.248 | 1 |
| TMOD1 | 0.746 | 1.367990 | 0.246 | 1 |
| FAIM2 | 0.751 | 1.367737 | 0.251 | 1 |
| CTNNA2 | 0.739 | 1.362929 | 0.239 | 1 |
| SEPT6 | 0.737 | 1.357596 | 0.237 | 1 |
| MAB21L2 | 0.751 | 1.352143 | 0.251 | 1 |
| MSI2 | 0.844 | 1.351412 | 0.344 | 1 |
| ONECUT1 | 0.723 | 1.348846 | 0.223 | 1 |
| ANGPT2 | 0.716 | 1.342637 | 0.216 | 1 |
| THSD7B | 0.709 | 1.318613 | 0.209 | 1 |
| SNAP25 | 0.905 | 1.316286 | 0.405 | 1 |
| NEFM | 0.766 | 1.311134 | 0.266 | 1 |
| SCD2 | 0.753 | 1.296970 | 0.253 | 1 |
| FAM84B | 0.734 | 1.296355 | 0.234 | 1 |
| MGARP | 0.888 | 1.277813 | 0.388 | 1 |
| APPL2 | 0.758 | 1.261116 | 0.258 | 1 |
| DNER | 0.752 | 1.256005 | 0.252 | 1 |
| PFKFB3 | 0.706 | 1.250256 | 0.206 | 1 |
| MT1 | 0.729 | 1.246724 | 0.229 | 1 |
| LMO4 | 0.742 | 1.245222 | 0.242 | 1 |
| ZFP804A | 0.746 | 1.241753 | 0.246 | 1 |
| RABEP1 | 0.771 | 1.228045 | 0.271 | 1 |
| OSBPL1A | 0.729 | 1.227105 | 0.229 | 1 |
| YWHAG | 0.763 | 1.225112 | 0.263 | 1 |
| PDE3A | 0.702 | 1.219989 | 0.202 | 1 |
| CACNG3 | 0.717 | 1.219146 | 0.217 | 1 |
| REEP5 | 0.751 | 1.204753 | 0.251 | 1 |
| KLF13 | 0.706 | 1.196781 | 0.206 | 1 |
| TMX4 | 0.753 | 1.186779 | 0.253 | 1 |
| SNCG | 0.712 | 1.184574 | 0.212 | 1 |
| SNRPN | 0.732 | 1.180677 | 0.232 | 1 |
| SLC24A2 | 0.705 | 1.172493 | 0.205 | 1 |
| GNAI1 | 0.726 | 1.153326 | 0.226 | 1 |
| MLLT11 | 0.733 | 1.153193 | 0.233 | 1 |
| DST | 0.742 | 1.150327 | 0.242 | 1 |
| ADARB1 | 0.742 | 1.147777 | 0.242 | 1 |
| ANKRD29 | 0.706 | 1.145796 | 0.206 | 1 |
| ST8SIA3 | 0.703 | 1.129373 | 0.203 | 1 |
| PLCB4 | 0.765 | 1.116768 | 0.265 | 1 |
| BEX2 | 0.762 | 1.114780 | 0.262 | 1 |
| FAM115A | 0.746 | 1.114026 | 0.246 | 1 |
| PLEKHA1 | 0.751 | 1.113187 | 0.251 | 1 |
| MPC1 | 0.706 | 1.109670 | 0.206 | 1 |
| MOCS2 | 0.739 | 1.107821 | 0.239 | 1 |
| COX5A | 0.776 | 1.104444 | 0.276 | 1 |
| TUBA1A | 0.774 | 1.100378 | 0.274 | 1 |
| PLCH1 | 0.705 | 1.097744 | 0.205 | 1 |
| PIK3R3 | 0.711 | 1.092873 | 0.211 | 1 |
| TSPAN3 | 0.771 | 1.087383 | 0.271 | 1 |
| EMC9 | 0.703 | 1.086119 | 0.203 | 1 |
| UHRF1BP1L | 0.710 | 1.081116 | 0.210 | 1 |
| NAV1 | 0.713 | 1.074276 | 0.213 | 1 |
| INA | 0.724 | 1.066690 | 0.224 | 1 |
| HAUS8 | 0.708 | 1.065310 | 0.208 | 1 |
| HSP90AB1 | 0.800 | 1.059681 | 0.300 | 1 |
| NDN | 0.733 | 1.058386 | 0.233 | 1 |
| NEFH | 0.707 | 1.052242 | 0.207 | 1 |
| GATSL2 | 0.702 | 1.046289 | 0.202 | 1 |
| TPM1 | 0.728 | 1.044557 | 0.228 | 1 |
| STMN3 | 0.743 | 1.042409 | 0.243 | 1 |
| ZWINT | 0.717 | 1.028737 | 0.217 | 1 |

TABLE 6-continued

Genes differentially expressed in each of the 39 retinal cell clusters.

| | | | |
|---|---|---|---|
| SPOCK3 | 0.704 | 1.026265 | 0.204 | 1 |
| ELAVL3 | 0.730 | 1.019721 | 0.230 | 1 |
| ATP6V1A | 0.761 | 1.013906 | 0.261 | 1 |
| LDHA | 0.298 | −1.429546 | 0.202 | 1 |
| H3F3B | 0.226 | −1.724698 | 0.274 | 1 |
| EPB4.1 | 0.297 | −1.890330 | 0.203 | 1 |
| A930011O12RIK | 0.289 | −1.908058 | 0.211 | 1 |
| TMA7 | 0.292 | −1.922734 | 0.208 | 1 |
| CRX | 0.295 | −1.940202 | 0.205 | 1 |
| HMGN1 | 0.173 | −2.030775 | 0.327 | 1 |
| MPP4 | 0.297 | −2.122800 | 0.203 | 1 |
| CNGB1 | 0.289 | −2.144480 | 0.211 | 1 |
| FAM57B | 0.269 | −2.148614 | 0.231 | 1 |
| GUCA1B | 0.298 | −2.192529 | 0.202 | 1 |
| AIPL1 | 0.269 | −2.202228 | 0.231 | 1 |
| PDE6A | 0.284 | −2.233229 | 0.216 | 1 |
| RDH12 | 0.291 | −2.272536 | 0.209 | 1 |
| GNB1 | 0.187 | −2.284490 | 0.313 | 1 |
| NEUROD1 | 0.238 | −2.422956 | 0.262 | 1 |
| NRL | 0.224 | −2.424409 | 0.276 | 1 |
| UNC119 | 0.193 | −2.478130 | 0.307 | 1 |
| NR2E3 | 0.217 | −2.484357 | 0.283 | 1 |
| RS1 | 0.222 | −2.534411 | 0.278 | 1 |
| SLC24A1 | 0.230 | −2.558786 | 0.270 | 1 |
| PRPH2 | 0.154 | −2.572327 | 0.346 | 1 |
| ROM1 | 0.184 | −2.594330 | 0.316 | 1 |
| RP1 | 0.190 | −2.660436 | 0.310 | 1 |
| PDE6B | 0.190 | −2.707960 | 0.310 | 1 |
| TULP1 | 0.163 | −2.748272 | 0.337 | 1 |
| CNGA1 | 0.215 | −2.752815 | 0.285 | 1 |
| RCVRN | 0.175 | −2.769719 | 0.325 | 1 |
| PDE6G | 0.160 | −2.791625 | 0.340 | 1 |
| PDC | 0.133 | −2.805456 | 0.367 | 1 |
| GNGT1 | 0.123 | −2.821179 | 0.377 | 1 |
| RPGRIP1 | 0.195 | −2.867157 | 0.305 | 1 |
| GNAT1 | 0.158 | −2.923872 | 0.342 | 1 |
| RHO | 0.121 | −2.940345 | 0.379 | 1 |
| SAG | 0.118 | −2.967888 | 0.382 | 1 |
| cluster no. 2 DE = 174 | | | | |
| NEFL | 0.984 | 3.829399 | 0.484 | 2 |
| NEFM | 0.953 | 3.464532 | 0.453 | 2 |
| SNCG | 0.938 | 3.269859 | 0.438 | 2 |
| CALB2 | 0.884 | 3.081448 | 0.384 | 2 |
| STMN2 | 0.944 | 2.861225 | 0.444 | 2 |
| THY1 | 0.900 | 2.782679 | 0.400 | 2 |
| ATP1B1 | 0.916 | 2.633335 | 0.416 | 2 |
| SLC17A6 | 0.879 | 2.610603 | 0.379 | 2 |
| NRN1 | 0.868 | 2.509114 | 0.368 | 2 |
| UCHL1 | 0.909 | 2.411926 | 0.409 | 2 |
| GAP43 | 0.867 | 2.314068 | 0.367 | 2 |
| STMN3 | 0.906 | 2.200448 | 0.406 | 2 |
| CDK14 | 0.855 | 2.189091 | 0.355 | 2 |
| YWHAH | 0.854 | 2.103748 | 0.354 | 2 |
| RGS4 | 0.775 | 2.052411 | 0.275 | 2 |
| NELL2 | 0.801 | 2.005519 | 0.301 | 2 |
| SNHG11 | 0.847 | 1.998298 | 0.347 | 2 |
| RTN1 | 0.872 | 1.992219 | 0.372 | 2 |
| FXYD7 | 0.815 | 1.921975 | 0.315 | 2 |
| INA | 0.857 | 1.864647 | 0.357 | 2 |
| TPPP3 | 0.789 | 1.858532 | 0.289 | 2 |
| TUBB2A | 0.851 | 1.844621 | 0.351 | 2 |
| RBPMS | 0.796 | 1.835589 | 0.296 | 2 |
| MEG3 | 0.835 | 1.831667 | 0.335 | 2 |
| SCN2A1 | 0.798 | 1.825259 | 0.298 | 2 |
| TUBB3 | 0.814 | 1.819493 | 0.314 | 2 |
| VSNL1 | 0.793 | 1.812314 | 0.293 | 2 |
| APP | 0.848 | 1.800057 | 0.348 | 2 |
| MFSD6 | 0.791 | 1.774345 | 0.291 | 2 |
| OLFM1 | 0.832 | 1.767142 | 0.332 | 2 |
| CEND1 | 0.806 | 1.753636 | 0.306 | 2 |
| KIF5A | 0.806 | 1.715671 | 0.306 | 2 |
| ZWINT | 0.822 | 1.713431 | 0.322 | 2 |
| BASP1 | 0.839 | 1.707778 | 0.339 | 2 |
| CHRNA6 | 0.751 | 1.703049 | 0.251 | 2 |
| NAP1L5 | 0.826 | 1.688741 | 0.326 | 2 |
| SCN1A | 0.761 | 1.675414 | 0.261 | 2 |
| SPARCL1 | 0.806 | 1.650738 | 0.306 | 2 |
| RAB6B | 0.826 | 1.648695 | 0.326 | 2 |
| SNCA | 0.746 | 1.628302 | 0.246 | 2 |
| DNER | 0.806 | 1.625146 | 0.306 | 2 |
| MYT1L | 0.782 | 1.602185 | 0.282 | 2 |
| TAGLN3 | 0.789 | 1.596353 | 0.289 | 2 |
| NSG2 | 0.791 | 1.591428 | 0.291 | 2 |
| NDRG4 | 0.818 | 1.579659 | 0.318 | 2 |
| KCNIP4 | 0.724 | 1.575295 | 0.224 | 2 |
| MAP1A | 0.761 | 1.564301 | 0.261 | 2 |
| FGF12 | 0.759 | 1.554984 | 0.259 | 2 |
| CPLX2 | 0.757 | 1.547165 | 0.257 | 2 |
| LSAMP | 0.764 | 1.532664 | 0.264 | 2 |
| NSG1 | 0.773 | 1.531646 | 0.273 | 2 |
| GNG3 | 0.798 | 1.526804 | 0.298 | 2 |
| TTC3 | 0.863 | 1.526759 | 0.363 | 2 |
| SNRPN | 0.786 | 1.524628 | 0.286 | 2 |
| MGST3 | 0.763 | 1.521974 | 0.263 | 2 |
| POU4F1 | 0.708 | 1.493041 | 0.208 | 2 |
| RBFOX1 | 0.756 | 1.490707 | 0.256 | 2 |
| 2900011O08RIK | 0.797 | 1.489750 | 0.297 | 2 |
| S100A10 | 0.739 | 1.487422 | 0.239 | 2 |
| CALM2 | 0.848 | 1.470176 | 0.348 | 2 |
| CPLX1 | 0.711 | 1.458879 | 0.211 | 2 |
| CAMK2N1 | 0.791 | 1.455445 | 0.291 | 2 |
| GABBR2 | 0.734 | 1.435871 | 0.234 | 2 |
| RBPMS2 | 0.735 | 1.422357 | 0.235 | 2 |
| ELAVL2 | 0.716 | 1.416182 | 0.216 | 2 |
| REEP5 | 0.767 | 1.411279 | 0.267 | 2 |
| ACOT7 | 0.763 | 1.408963 | 0.263 | 2 |
| LYNX1 | 0.732 | 1.398066 | 0.232 | 2 |
| CHRNB3 | 0.724 | 1.396429 | 0.224 | 2 |
| RAB6A | 0.802 | 1.365048 | 0.302 | 2 |
| SYT11 | 0.789 | 1.361853 | 0.289 | 2 |
| RPH3A | 0.769 | 1.361064 | 0.269 | 2 |
| MGLL | 0.731 | 1.351262 | 0.231 | 2 |
| CAPNS1 | 0.766 | 1.336082 | 0.266 | 2 |
| ELAVL4 | 0.739 | 1.327648 | 0.239 | 2 |
| MLLT11 | 0.754 | 1.324574 | 0.254 | 2 |
| APBB2 | 0.733 | 1.324301 | 0.233 | 2 |
| HPCA | 0.735 | 1.312442 | 0.235 | 2 |
| PPP2R2C | 0.729 | 1.312231 | 0.229 | 2 |
| MYO1B | 0.703 | 1.310809 | 0.203 | 2 |
| PCDHA2 | 0.752 | 1.310031 | 0.252 | 2 |
| SULT4A1 | 0.720 | 1.305228 | 0.220 | 2 |
| ROBO2 | 0.735 | 1.276553 | 0.235 | 2 |
| ATL1 | 0.728 | 1.276524 | 0.228 | 2 |
| YWHAB | 0.828 | 1.272542 | 0.328 | 2 |
| BEND6 | 0.719 | 1.270603 | 0.219 | 2 |
| AHNAK2 | 0.713 | 1.266931 | 0.213 | 2 |
| TUBA1A | 0.825 | 1.258349 | 0.325 | 2 |
| RESP18 | 0.702 | 1.244231 | 0.202 | 2 |
| NRXN1 | 0.719 | 1.242874 | 0.219 | 2 |
| ATP2B2 | 0.719 | 1.240608 | 0.219 | 2 |
| EPHA5 | 0.723 | 1.231067 | 0.223 | 2 |
| SPOCK2 | 0.735 | 1.228244 | 0.235 | 2 |
| TMEM130 | 0.726 | 1.225743 | 0.226 | 2 |
| YWHAG | 0.751 | 1.224966 | 0.251 | 2 |
| SRGAP1 | 0.707 | 1.220082 | 0.207 | 2 |
| STMN4 | 0.722 | 1.214691 | 0.222 | 2 |
| GNAS | 0.823 | 1.206586 | 0.323 | 2 |
| EBF1 | 0.717 | 1.202313 | 0.217 | 2 |
| KIF5C | 0.748 | 1.199040 | 0.248 | 2 |
| TPM1 | 0.735 | 1.195887 | 0.235 | 2 |
| TTLL7 | 0.707 | 1.194259 | 0.207 | 2 |
| HSP90AB1 | 0.844 | 1.192653 | 0.344 | 2 |
| ENO2 | 0.784 | 1.190777 | 0.284 | 2 |
| INPP5F | 0.710 | 1.175178 | 0.210 | 2 |
| L1CAM | 0.714 | 1.174820 | 0.214 | 2 |
| SERINC1 | 0.776 | 1.172132 | 0.276 | 2 |
| KIFAP3 | 0.781 | 1.169721 | 0.281 | 2 |
| TMSB10 | 0.748 | 1.167262 | 0.248 | 2 |
| ATPIF1 | 0.773 | 1.160103 | 0.273 | 2 |
| MAPT | 0.751 | 1.153592 | 0.251 | 2 |
| EMB | 0.704 | 1.153408 | 0.204 | 2 |
| SYN2 | 0.713 | 1.152558 | 0.213 | 2 |
| CALM3 | 0.757 | 1.147375 | 0.257 | 2 |
| SCG2 | 0.767 | 1.144454 | 0.267 | 2 |
| RAB3C | 0.735 | 1.143869 | 0.235 | 2 |

TABLE 6-continued

Genes differentially expressed in each of the 39 retinal cell clusters.

| Gene | | | | |
|---|---|---|---|---|
| TMOD2 | 0.733 | 1.143826 | 0.233 | 2 |
| PCP4 | 0.743 | 1.137348 | 0.243 | 2 |
| LDHB | 0.729 | 1.136283 | 0.229 | 2 |
| OGFRL1 | 0.728 | 1.132671 | 0.228 | 2 |
| PLS3 | 0.701 | 1.129242 | 0.201 | 2 |
| OSBPL1A | 0.713 | 1.127818 | 0.213 | 2 |
| SYT4 | 0.736 | 1.109372 | 0.236 | 2 |
| CD47 | 0.749 | 1.108135 | 0.249 | 2 |
| CNTN1 | 0.716 | 1.100946 | 0.216 | 2 |
| SPOCK3 | 0.713 | 1.096385 | 0.213 | 2 |
| KLC1 | 0.761 | 1.081218 | 0.261 | 2 |
| DPYSL2 | 0.722 | 1.070807 | 0.222 | 2 |
| CBX6 | 0.706 | 1.069450 | 0.206 | 2 |
| GNAO1 | 0.801 | 1.066166 | 0.301 | 2 |
| RBFOX3 | 0.706 | 1.062023 | 0.206 | 2 |
| SEPT3 | 0.710 | 1.061409 | 0.210 | 2 |
| RTN3 | 0.764 | 1.054404 | 0.264 | 2 |
| TXN1 | 0.741 | 1.045930 | 0.241 | 2 |
| CYGB | 0.712 | 1.041602 | 0.212 | 2 |
| DSTN | 0.736 | 1.028947 | 0.236 | 2 |
| NEFH | 0.701 | 1.028807 | 0.201 | 2 |
| EPB4.1L3 | 0.735 | 1.024561 | 0.235 | 2 |
| NDN | 0.729 | 1.022810 | 0.229 | 2 |
| YWHAQ | 0.735 | 1.021231 | 0.235 | 2 |
| ATP6V1G2 | 0.713 | 1.019868 | 0.213 | 2 |
| CYB5R3 | 0.702 | 1.016407 | 0.202 | 2 |
| GPRASP1 | 0.742 | 1.013893 | 0.242 | 2 |
| RIT2 | 0.711 | 1.012204 | 0.211 | 2 |
| PDCD4 | 0.741 | 1.004699 | 0.241 | 2 |
| H3F3B | 0.271 | −1.176930 | 0.229 | 2 |
| DDX5 | 0.276 | −1.193109 | 0.224 | 2 |
| GNB1 | 0.239 | −1.628273 | 0.261 | 2 |
| TMA7 | 0.290 | −1.756221 | 0.210 | 2 |
| PDE6A | 0.298 | −1.916518 | 0.202 | 2 |
| RDH12 | 0.299 | −1.978256 | 0.201 | 2 |
| NEUROD1 | 0.265 | −1.982771 | 0.235 | 2 |
| AIPL1 | 0.277 | −2.036910 | 0.223 | 2 |
| NRL | 0.241 | −2.048768 | 0.259 | 2 |
| CRX | 0.293 | −2.064793 | 0.207 | 2 |
| CNGA1 | 0.239 | −2.128658 | 0.261 | 2 |
| RS1 | 0.239 | −2.132605 | 0.261 | 2 |
| UNC119 | 0.212 | −2.193079 | 0.288 | 2 |
| HMGN1 | 0.156 | −2.204076 | 0.344 | 2 |
| ROM1 | 0.206 | −2.223073 | 0.294 | 2 |
| SLC24A1 | 0.243 | −2.273294 | 0.257 | 2 |
| NR2E3 | 0.229 | −2.289315 | 0.271 | 2 |
| TULP1 | 0.174 | −2.369311 | 0.326 | 2 |
| PDE6B | 0.202 | −2.391414 | 0.298 | 2 |
| PDE6G | 0.180 | −2.394168 | 0.320 | 2 |
| RP1 | 0.203 | −2.416303 | 0.297 | 2 |
| PRPH2 | 0.164 | −2.440696 | 0.336 | 2 |
| RCVRN | 0.183 | −2.450023 | 0.317 | 2 |
| GNAT1 | 0.175 | −2.524310 | 0.325 | 2 |
| RHO | 0.130 | −2.595284 | 0.370 | 2 |
| SAG | 0.129 | −2.599480 | 0.371 | 2 |
| GNGT1 | 0.129 | −2.621825 | 0.371 | 2 |
| RPGRIP1 | 0.204 | −2.684191 | 0.296 | 2 |
| PDC | 0.139 | −2.696102 | 0.361 | 2 |
| cluster no. 3 DE = 162 | | | | |
| RIMS1 | 0.992 | 4.082215 | 0.492 | 3 |
| CALB2 | 0.959 | 3.407422 | 0.459 | 3 |
| SCG2 | 0.951 | 2.785881 | 0.451 | 3 |
| NPY | 0.904 | 2.685796 | 0.404 | 3 |
| SPOCK3 | 0.945 | 2.678047 | 0.445 | 3 |
| SNHG11 | 0.942 | 2.664892 | 0.442 | 3 |
| SLC5A7 | 0.889 | 2.523739 | 0.389 | 3 |
| GAD1 | 0.893 | 2.305332 | 0.393 | 3 |
| PCP4 | 0.927 | 2.304931 | 0.427 | 3 |
| ATP1B1 | 0.915 | 2.244273 | 0.415 | 3 |
| GNG7 | 0.872 | 2.199902 | 0.372 | 3 |
| SPARCL1 | 0.877 | 2.152659 | 0.377 | 3 |
| CHAT | 0.839 | 2.117764 | 0.339 | 3 |
| IGFBP7 | 0.874 | 2.106632 | 0.374 | 3 |
| KCNC1 | 0.862 | 2.034054 | 0.362 | 3 |
| CXCL14 | 0.836 | 2.027676 | 0.336 | 3 |
| RBFOX1 | 0.842 | 2.010200 | 0.342 | 3 |
| NHLH2 | 0.857 | 1.965244 | 0.357 | 3 |
| PCP4L1 | 0.858 | 1.946188 | 0.358 | 3 |
| HECW1 | 0.840 | 1.932796 | 0.340 | 3 |
| RGS7BP | 0.817 | 1.924553 | 0.317 | 3 |
| MEGF11 | 0.822 | 1.915714 | 0.322 | 3 |
| LSAMP | 0.846 | 1.876113 | 0.346 | 3 |
| GABRD | 0.818 | 1.867550 | 0.318 | 3 |
| CACNA2D1 | 0.817 | 1.822163 | 0.317 | 3 |
| ID4 | 0.811 | 1.814870 | 0.311 | 3 |
| CMTM8 | 0.807 | 1.803043 | 0.307 | 3 |
| KCNAB1 | 0.797 | 1.796360 | 0.297 | 3 |
| PPFIBP1 | 0.812 | 1.772586 | 0.312 | 3 |
| ZMAT4 | 0.809 | 1.764427 | 0.309 | 3 |
| TGFB3 | 0.799 | 1.762589 | 0.299 | 3 |
| RPH3A | 0.864 | 1.751654 | 0.364 | 3 |
| NNAT | 0.826 | 1.742048 | 0.326 | 3 |
| CALB1 | 0.822 | 1.723125 | 0.322 | 3 |
| CACNG2 | 0.801 | 1.702459 | 0.301 | 3 |
| CALM1 | 0.934 | 1.694273 | 0.434 | 3 |
| PCDH10 | 0.781 | 1.688172 | 0.281 | 3 |
| PAPPA2 | 0.743 | 1.682248 | 0.243 | 3 |
| SOX2OT | 0.798 | 1.681475 | 0.298 | 3 |
| SCG3 | 0.850 | 1.653641 | 0.350 | 3 |
| DLGAP1 | 0.805 | 1.626709 | 0.305 | 3 |
| CHN1 | 0.835 | 1.617582 | 0.335 | 3 |
| GPR123 | 0.778 | 1.617023 | 0.278 | 3 |
| FAM184B | 0.787 | 1.601364 | 0.287 | 3 |
| SLC32A1 | 0.796 | 1.599822 | 0.296 | 3 |
| COL25A1 | 0.764 | 1.584211 | 0.264 | 3 |
| PPM1L | 0.775 | 1.568651 | 0.275 | 3 |
| CHGB | 0.881 | 1.563185 | 0.381 | 3 |
| MEG3 | 0.866 | 1.563114 | 0.366 | 3 |
| GABRA2 | 0.758 | 1.561233 | 0.258 | 3 |
| CNTNAP2 | 0.811 | 1.558861 | 0.311 | 3 |
| LIN7A | 0.837 | 1.506146 | 0.337 | 3 |
| CAMK2N1 | 0.830 | 1.503683 | 0.330 | 3 |
| A830010M20RIK | 0.761 | 1.495505 | 0.261 | 3 |
| APBA1 | 0.756 | 1.494915 | 0.256 | 3 |
| CPLX2 | 0.795 | 1.493169 | 0.295 | 3 |
| MAGI3 | 0.762 | 1.479676 | 0.262 | 3 |
| CTTNBP2 | 0.780 | 1.474337 | 0.280 | 3 |
| SLC6A1 | 0.797 | 1.471722 | 0.297 | 3 |
| TFAP2B | 0.838 | 1.458329 | 0.338 | 3 |
| GABRA4 | 0.731 | 1.443690 | 0.231 | 3 |
| ISL1 | 0.866 | 1.442516 | 0.366 | 3 |
| FAM49B | 0.785 | 1.430077 | 0.285 | 3 |
| CAMK2A | 0.736 | 1.425387 | 0.236 | 3 |
| CDK14 | 0.773 | 1.414271 | 0.273 | 3 |
| GSTO1 | 0.715 | 1.408011 | 0.215 | 3 |
| GRIA3 | 0.746 | 1.402325 | 0.246 | 3 |
| TENM2 | 0.740 | 1.390000 | 0.240 | 3 |
| CAPZA2 | 0.805 | 1.363952 | 0.305 | 3 |
| TAGLN3 | 0.781 | 1.361440 | 0.281 | 3 |
| SYT11 | 0.787 | 1.343219 | 0.287 | 3 |
| GALNT15 | 0.718 | 1.338314 | 0.218 | 3 |
| MAPK10 | 0.747 | 1.333658 | 0.247 | 3 |
| SOX2 | 0.748 | 1.328242 | 0.248 | 3 |
| GRIA2 | 0.810 | 1.314674 | 0.310 | 3 |
| SNRPN | 0.765 | 1.302095 | 0.265 | 3 |
| STXBP6 | 0.715 | 1.300343 | 0.215 | 3 |
| PSD3 | 0.724 | 1.295147 | 0.224 | 3 |
| BASP1 | 0.786 | 1.289016 | 0.286 | 3 |
| ARL4C | 0.730 | 1.279132 | 0.230 | 3 |
| SYNPR | 0.776 | 1.278017 | 0.276 | 3 |
| HLF | 0.782 | 1.276773 | 0.282 | 3 |
| NAP1L5 | 0.796 | 1.275991 | 0.296 | 3 |
| APP | 0.736 | 1.275816 | 0.236 | 3 |
| NREP | 0.818 | 1.271487 | 0.318 | 3 |
| PTPRD | 0.801 | 1.264783 | 0.301 | 3 |
| NRCAM | 0.742 | 1.263960 | 0.242 | 3 |
| CD47 | 0.788 | 1.255114 | 0.288 | 3 |
| PODXL2 | 0.767 | 1.235972 | 0.267 | 3 |
| STMN3 | 0.779 | 1.235054 | 0.279 | 3 |
| NEFH | 0.713 | 1.230658 | 0.213 | 3 |
| DAPK1 | 0.726 | 1.224896 | 0.226 | 3 |
| ELAVL3 | 0.770 | 1.220472 | 0.270 | 3 |
| VSTM2A | 0.709 | 1.220317 | 0.209 | 3 |
| REEP5 | 0.747 | 1.212653 | 0.247 | 3 |
| CYFIP2 | 0.737 | 1.198555 | 0.237 | 3 |

TABLE 6-continued

Genes differentially expressed in each of the 39 retinal cell clusters.

| Gene | | | | |
|---|---|---|---|---|
| AMIGO2 | 0.719 | 1.193345 | 0.219 | 3 |
| GNG3 | 0.783 | 1.192467 | 0.283 | 3 |
| CHD3 | 0.758 | 1.190095 | 0.258 | 3 |
| DTNB | 0.717 | 1.187726 | 0.217 | 3 |
| NPTN | 0.778 | 1.186421 | 0.278 | 3 |
| DIRAS2 | 0.721 | 1.182766 | 0.221 | 3 |
| PGM2L1 | 0.750 | 1.178870 | 0.250 | 3 |
| KIF5C | 0.760 | 1.178481 | 0.260 | 3 |
| SYT1 | 0.855 | 1.177984 | 0.355 | 3 |
| LDHB | 0.778 | 1.172023 | 0.278 | 3 |
| ELMOD1 | 0.748 | 1.164081 | 0.248 | 3 |
| PLCH1 | 0.704 | 1.162078 | 0.204 | 3 |
| EDIL3 | 0.725 | 1.160835 | 0.225 | 3 |
| NRXN2 | 0.766 | 1.157403 | 0.266 | 3 |
| FAM115A | 0.738 | 1.155208 | 0.238 | 3 |
| MED12L | 0.710 | 1.151691 | 0.210 | 3 |
| MXRA7 | 0.776 | 1.145751 | 0.276 | 3 |
| DNM3 | 0.796 | 1.143089 | 0.296 | 3 |
| VSTM2L | 0.703 | 1.141293 | 0.203 | 3 |
| 1700025G04RIK | 0.723 | 1.129913 | 0.223 | 3 |
| ATP2B2 | 0.721 | 1.129631 | 0.221 | 3 |
| SNCB | 0.786 | 1.128583 | 0.286 | 3 |
| TTC3 | 0.820 | 1.121625 | 0.320 | 3 |
| SV2A | 0.778 | 1.119631 | 0.278 | 3 |
| MGLL | 0.731 | 1.117164 | 0.231 | 3 |
| ESPN | 0.725 | 1.107524 | 0.225 | 3 |
| FEZ1 | 0.713 | 1.105736 | 0.213 | 3 |
| CELF4 | 0.802 | 1.102736 | 0.302 | 3 |
| TMEM191C | 0.709 | 1.102454 | 0.209 | 3 |
| PRAF2 | 0.719 | 1.093227 | 0.219 | 3 |
| CYGB | 0.729 | 1.086962 | 0.229 | 3 |
| PCDHA2 | 0.724 | 1.084084 | 0.224 | 3 |
| GPM6A | 0.774 | 1.076995 | 0.274 | 3 |
| SEPT11 | 0.701 | 1.075883 | 0.201 | 3 |
| ZCCHC18 | 0.727 | 1.075250 | 0.227 | 3 |
| 6430548M08RIK | 0.736 | 1.071386 | 0.236 | 3 |
| ITM2C | 0.754 | 1.051279 | 0.254 | 3 |
| ATP6V1E1 | 0.784 | 1.048681 | 0.284 | 3 |
| SLC4A10 | 0.714 | 1.048067 | 0.214 | 3 |
| GABRB3 | 0.707 | 1.045363 | 0.207 | 3 |
| HPCAL1 | 0.723 | 1.028678 | 0.223 | 3 |
| CACNA2D2 | 0.710 | 1.018877 | 0.210 | 3 |
| YWHAH | 0.728 | 1.009599 | 0.228 | 3 |
| CST3 | 0.282 | −1.475405 | 0.218 | 3 |
| GNB1 | 0.240 | −1.654043 | 0.260 | 3 |
| HMGN1 | 0.189 | −1.827649 | 0.311 | 3 |
| AIPL1 | 0.290 | −1.857153 | 0.210 | 3 |
| RCVRN | 0.207 | −2.042189 | 0.293 | 3 |
| UNC119 | 0.221 | −2.055898 | 0.279 | 3 |
| NRL | 0.242 | −2.067154 | 0.258 | 3 |
| CNGA1 | 0.240 | −2.096207 | 0.260 | 3 |
| ROM1 | 0.209 | −2.116826 | 0.291 | 3 |
| NR2E3 | 0.240 | −2.136288 | 0.260 | 3 |
| PDC | 0.166 | −2.152007 | 0.334 | 3 |
| PDE6G | 0.192 | −2.152778 | 0.308 | 3 |
| PDE6B | 0.213 | −2.158794 | 0.287 | 3 |
| SLC24A1 | 0.253 | −2.169851 | 0.247 | 3 |
| RP1 | 0.215 | −2.179412 | 0.285 | 3 |
| TULP1 | 0.186 | −2.181446 | 0.314 | 3 |
| RPGRIP1 | 0.226 | −2.203667 | 0.274 | 3 |
| RS1 | 0.237 | −2.206460 | 0.263 | 3 |
| PRPH2 | 0.177 | −2.226499 | 0.323 | 3 |
| GNGT1 | 0.154 | −2.289551 | 0.346 | 3 |
| GNAT1 | 0.187 | −2.336430 | 0.313 | 3 |
| SAG | 0.143 | −2.366434 | 0.357 | 3 |
| RHO | 0.148 | −2.382665 | 0.352 | 3 |
| cluster no. 4 DE = 84 | | | | |
| TAC1 | 0.957 | 3.797157 | 0.457 | 4 |
| CALB2 | 0.901 | 2.593063 | 0.401 | 4 |
| SNHG11 | 0.924 | 2.325381 | 0.424 | 4 |
| IGFBP7 | 0.837 | 2.280199 | 0.337 | 4 |
| PAX6 | 0.913 | 2.258708 | 0.413 | 4 |
| NHLH2 | 0.869 | 2.201437 | 0.369 | 4 |
| GRIA2 | 0.915 | 2.170104 | 0.415 | 4 |
| AI593442 | 0.810 | 2.066669 | 0.310 | 4 |
| PCP4 | 0.892 | 2.063350 | 0.392 | 4 |
| SPOCK3 | 0.845 | 2.017115 | 0.345 | 4 |
| COL25A1 | 0.778 | 1.916207 | 0.278 | 4 |
| KCTD12 | 0.742 | 1.898538 | 0.242 | 4 |
| CXCL14 | 0.765 | 1.846094 | 0.265 | 4 |
| OGFRL1 | 0.824 | 1.840851 | 0.324 | 4 |
| GBX2 | 0.726 | 1.819879 | 0.226 | 4 |
| LHX9 | 0.757 | 1.816715 | 0.257 | 4 |
| KCNIP4 | 0.751 | 1.748102 | 0.251 | 4 |
| TKT | 0.815 | 1.737069 | 0.315 | 4 |
| PCDH8 | 0.704 | 1.720415 | 0.204 | 4 |
| CELF4 | 0.896 | 1.718605 | 0.396 | 4 |
| STMN2 | 0.794 | 1.687253 | 0.294 | 4 |
| MEG3 | 0.889 | 1.662832 | 0.389 | 4 |
| DNER | 0.808 | 1.653824 | 0.308 | 4 |
| ZFHX3 | 0.765 | 1.644741 | 0.265 | 4 |
| A830036E02RIK | 0.710 | 1.606762 | 0.210 | 4 |
| SIX6 | 0.755 | 1.580762 | 0.255 | 4 |
| NDRG4 | 0.824 | 1.563205 | 0.324 | 4 |
| HLF | 0.782 | 1.551737 | 0.282 | 4 |
| GRIN2B | 0.702 | 1.522238 | 0.202 | 4 |
| SNCA | 0.734 | 1.483602 | 0.234 | 4 |
| SERPINI1 | 0.734 | 1.415131 | 0.234 | 4 |
| LY6H | 0.701 | 1.377466 | 0.201 | 4 |
| GRIA4 | 0.724 | 1.373989 | 0.224 | 4 |
| SPARCL1 | 0.724 | 1.358443 | 0.224 | 4 |
| NSG2 | 0.727 | 1.353166 | 0.227 | 4 |
| CDK14 | 0.720 | 1.340365 | 0.220 | 4 |
| SCN3A | 0.708 | 1.309240 | 0.208 | 4 |
| NRXN2 | 0.734 | 1.297254 | 0.234 | 4 |
| NAV1 | 0.714 | 1.289989 | 0.214 | 4 |
| ATP1B1 | 0.800 | 1.284113 | 0.300 | 4 |
| STXBP1 | 0.719 | 1.259255 | 0.219 | 4 |
| ELAVL3 | 0.761 | 1.253246 | 0.261 | 4 |
| NUDT4 | 0.751 | 1.236266 | 0.251 | 4 |
| CALM1 | 0.881 | 1.220586 | 0.381 | 4 |
| PNMAL2 | 0.728 | 1.206131 | 0.228 | 4 |
| APP | 0.774 | 1.200908 | 0.274 | 4 |
| TTC3 | 0.829 | 1.190737 | 0.329 | 4 |
| BASP1 | 0.744 | 1.183024 | 0.244 | 4 |
| RPH3A | 0.717 | 1.156227 | 0.217 | 4 |
| CYGB | 0.704 | 1.143763 | 0.204 | 4 |
| GPM6A | 0.730 | 1.143690 | 0.230 | 4 |
| AGAP1 | 0.713 | 1.142972 | 0.213 | 4 |
| AUTS2 | 0.704 | 1.127089 | 0.204 | 4 |
| RTN1 | 0.767 | 1.123584 | 0.267 | 4 |
| SLC6A1 | 0.704 | 1.115752 | 0.204 | 4 |
| SLC22A17 | 0.712 | 1.112067 | 0.212 | 4 |
| SOX4 | 0.725 | 1.096108 | 0.225 | 4 |
| ANK3 | 0.747 | 1.082388 | 0.247 | 4 |
| NAP1L5 | 0.711 | 1.054049 | 0.211 | 4 |
| CALM2 | 0.785 | 1.011094 | 0.285 | 4 |
| MARCKSL1 | 0.711 | 1.007890 | 0.211 | 4 |
| LDHA | 0.288 | −1.329895 | 0.212 | 4 |
| HMGN1 | 0.234 | −1.362895 | 0.266 | 4 |
| UNC119 | 0.256 | −1.364415 | 0.244 | 4 |
| NEUROD1 | 0.269 | −1.652305 | 0.231 | 4 |
| GNB1 | 0.221 | −1.671553 | 0.279 | 4 |
| SLC24A1 | 0.275 | −1.699003 | 0.225 | 4 |
| RS1 | 0.266 | −1.730768 | 0.234 | 4 |
| RPGRIP1 | 0.250 | −1.738476 | 0.250 | 4 |
| TULP1 | 0.212 | −1.762716 | 0.288 | 4 |
| NR2E3 | 0.250 | −1.799965 | 0.250 | 4 |
| GNAT1 | 0.216 | −1.817149 | 0.284 | 4 |
| CNGA1 | 0.253 | −1.822516 | 0.247 | 4 |
| NRL | 0.252 | −1.843815 | 0.248 | 4 |
| RCVRN | 0.213 | −1.877735 | 0.287 | 4 |
| PRPH2 | 0.190 | −1.894117 | 0.310 | 4 |
| RHO | 0.169 | −1.917425 | 0.331 | 4 |
| ROM1 | 0.213 | −1.930023 | 0.287 | 4 |
| RP1 | 0.231 | −1.971244 | 0.269 | 4 |
| PDE6G | 0.206 | −2.001563 | 0.294 | 4 |
| SAG | 0.159 | −2.004070 | 0.341 | 4 |
| PDE6B | 0.223 | −2.036922 | 0.277 | 4 |
| GNGT1 | 0.164 | −2.084646 | 0.336 | 4 |
| PDC | 0.163 | −2.170946 | 0.337 | 4 |
| cluster no. 5 DE = 159 | | | | |
| CALB2 | 0.823 | 3.123037 | 0.323 | 5 |
| TAC1 | 0.833 | 2.626378 | 0.333 | 5 |

TABLE 6-continued

Genes differentially expressed in each of the 39 retinal cell clusters.

| Gene | | | | |
|---|---|---|---|---|
| TPBG | 0.876 | 2.533358 | 0.376 | 5 |
| C1QL1 | 0.924 | 2.527843 | 0.424 | 5 |
| CXCL14 | 0.901 | 2.230271 | 0.401 | 5 |
| SYNPR | 0.925 | 2.131719 | 0.425 | 5 |
| STMN2 | 0.886 | 2.086199 | 0.386 | 5 |
| PCDH10 | 0.797 | 2.043265 | 0.297 | 5 |
| SNHG11 | 0.922 | 2.035822 | 0.422 | 5 |
| NRXN3 | 0.923 | 2.007402 | 0.423 | 5 |
| CHGB | 0.916 | 2.006283 | 0.416 | 5 |
| DLGAP1 | 0.862 | 1.951491 | 0.362 | 5 |
| GAD1 | 0.895 | 1.927132 | 0.395 | 5 |
| SLC6A1 | 0.882 | 1.917232 | 0.382 | 5 |
| ATP1B1 | 0.889 | 1.878433 | 0.389 | 5 |
| GRIA3 | 0.852 | 1.861206 | 0.352 | 5 |
| AI593442 | 0.831 | 1.830170 | 0.331 | 5 |
| PAX6 | 0.867 | 1.815993 | 0.367 | 5 |
| MEIS2 | 0.888 | 1.783257 | 0.388 | 5 |
| DTNBP1 | 0.850 | 1.781289 | 0.350 | 5 |
| MEG3 | 0.905 | 1.740870 | 0.405 | 5 |
| SLC32A1 | 0.859 | 1.720626 | 0.359 | 5 |
| CD47 | 0.872 | 1.714293 | 0.372 | 5 |
| LSAMP | 0.847 | 1.699605 | 0.347 | 5 |
| 2900011O08RIK | 0.840 | 1.682621 | 0.340 | 5 |
| RPH3A | 0.865 | 1.676398 | 0.365 | 5 |
| NRXN2 | 0.862 | 1.671095 | 0.362 | 5 |
| ZFHX3 | 0.794 | 1.649873 | 0.294 | 5 |
| CDK5R1 | 0.856 | 1.647661 | 0.356 | 5 |
| GAD2 | 0.798 | 1.638829 | 0.298 | 5 |
| FILIP1L | 0.769 | 1.637232 | 0.269 | 5 |
| B2M | 0.800 | 1.608359 | 0.300 | 5 |
| P2RY1 | 0.777 | 1.585637 | 0.277 | 5 |
| NSG2 | 0.825 | 1.585339 | 0.325 | 5 |
| OGFRL1 | 0.850 | 1.573178 | 0.350 | 5 |
| STMN1 | 0.823 | 1.572466 | 0.323 | 5 |
| C1QL2 | 0.769 | 1.565457 | 0.269 | 5 |
| ZEB2 | 0.831 | 1.544523 | 0.331 | 5 |
| NHLH2 | 0.808 | 1.538909 | 0.308 | 5 |
| SYT7 | 0.808 | 1.527501 | 0.308 | 5 |
| RGS8 | 0.796 | 1.505359 | 0.296 | 5 |
| ELAVL3 | 0.838 | 1.485639 | 0.338 | 5 |
| UACA | 0.774 | 1.475738 | 0.274 | 5 |
| SYT6 | 0.747 | 1.459682 | 0.247 | 5 |
| CPLX2 | 0.827 | 1.458139 | 0.327 | 5 |
| FRMD5 | 0.787 | 1.433194 | 0.287 | 5 |
| FAM19A5 | 0.762 | 1.430612 | 0.262 | 5 |
| BHLHE22 | 0.764 | 1.426500 | 0.264 | 5 |
| TUBB2A | 0.822 | 1.419453 | 0.322 | 5 |
| VSNL1 | 0.804 | 1.414648 | 0.304 | 5 |
| STXBP6 | 0.747 | 1.412450 | 0.247 | 5 |
| PCDH8 | 0.731 | 1.408067 | 0.231 | 5 |
| TKT | 0.843 | 1.399775 | 0.343 | 5 |
| BASP1 | 0.828 | 1.397467 | 0.328 | 5 |
| EPB4.1L4A | 0.763 | 1.393019 | 0.263 | 5 |
| A030009H04RIK | 0.803 | 1.387965 | 0.303 | 5 |
| GPM6A | 0.841 | 1.376807 | 0.341 | 5 |
| NAP1L5 | 0.808 | 1.375097 | 0.308 | 5 |
| PCDH17 | 0.799 | 1.369359 | 0.299 | 5 |
| GABBR2 | 0.754 | 1.368149 | 0.254 | 5 |
| SYT11 | 0.845 | 1.347546 | 0.345 | 5 |
| LRRN3 | 0.721 | 1.338672 | 0.221 | 5 |
| CALB1 | 0.776 | 1.334921 | 0.276 | 5 |
| SV2A | 0.850 | 1.332636 | 0.350 | 5 |
| SCN3A | 0.760 | 1.325687 | 0.260 | 5 |
| RYR2 | 0.782 | 1.321029 | 0.282 | 5 |
| HUNK | 0.729 | 1.315880 | 0.229 | 5 |
| BAI3 | 0.725 | 1.314119 | 0.225 | 5 |
| PCSK2 | 0.737 | 1.311312 | 0.237 | 5 |
| ADCY2 | 0.739 | 1.311003 | 0.239 | 5 |
| GNG3 | 0.799 | 1.308365 | 0.299 | 5 |
| TFAP2A | 0.759 | 1.308229 | 0.259 | 5 |
| ZMAT4 | 0.754 | 1.305568 | 0.254 | 5 |
| FLRT3 | 0.763 | 1.304117 | 0.263 | 5 |
| GABRA3 | 0.746 | 1.300341 | 0.246 | 5 |
| DPP6 | 0.780 | 1.298661 | 0.280 | 5 |
| RASGRF1 | 0.745 | 1.298565 | 0.245 | 5 |
| SPOCK3 | 0.705 | 1.294629 | 0.205 | 5 |
| CELF4 | 0.842 | 1.286985 | 0.342 | 5 |
| SPARCL1 | 0.778 | 1.281146 | 0.278 | 5 |
| ELAVL4 | 0.751 | 1.274854 | 0.251 | 5 |
| GRIA4 | 0.784 | 1.270207 | 0.284 | 5 |
| PKIA | 0.775 | 1.269100 | 0.275 | 5 |
| ATRNL1 | 0.720 | 1.259867 | 0.220 | 5 |
| UCHL1 | 0.773 | 1.241952 | 0.273 | 5 |
| CRHR2 | 0.708 | 1.227419 | 0.208 | 5 |
| GRIA2 | 0.817 | 1.223394 | 0.317 | 5 |
| CACNG3 | 0.750 | 1.222476 | 0.250 | 5 |
| CDH4 | 0.729 | 1.217037 | 0.229 | 5 |
| NDRG4 | 0.774 | 1.214021 | 0.274 | 5 |
| 8430419L09RIK | 0.718 | 1.208866 | 0.218 | 5 |
| STMN3 | 0.783 | 1.205826 | 0.283 | 5 |
| NRXN1 | 0.744 | 1.199941 | 0.244 | 5 |
| DIO2 | 0.722 | 1.194141 | 0.222 | 5 |
| ANK3 | 0.796 | 1.193807 | 0.296 | 5 |
| DPYSL4 | 0.777 | 1.187574 | 0.277 | 5 |
| STMN4 | 0.747 | 1.182336 | 0.247 | 5 |
| ROBO2 | 0.705 | 1.181819 | 0.205 | 5 |
| CLMP | 0.760 | 1.181079 | 0.260 | 5 |
| UTRN | 0.733 | 1.177432 | 0.233 | 5 |
| MLLT11 | 0.756 | 1.174966 | 0.256 | 5 |
| RELN | 0.707 | 1.172184 | 0.207 | 5 |
| STK32B | 0.712 | 1.171383 | 0.212 | 5 |
| ATP1A1 | 0.773 | 1.171164 | 0.273 | 5 |
| TMX4 | 0.773 | 1.170468 | 0.273 | 5 |
| GAP43 | 0.739 | 1.169587 | 0.239 | 5 |
| PLCB1 | 0.709 | 1.165435 | 0.209 | 5 |
| SCN2A1 | 0.727 | 1.161847 | 0.227 | 5 |
| CDK14 | 0.755 | 1.157752 | 0.255 | 5 |
| UBASH3B | 0.731 | 1.143693 | 0.231 | 5 |
| MYT1L | 0.730 | 1.141047 | 0.230 | 5 |
| 6330403K07RIK | 0.723 | 1.140026 | 0.223 | 5 |
| TTC3 | 0.833 | 1.133517 | 0.333 | 5 |
| FGF14 | 0.708 | 1.123639 | 0.208 | 5 |
| NRCAM | 0.715 | 1.121937 | 0.215 | 5 |
| LPHN3 | 0.733 | 1.121325 | 0.233 | 5 |
| NRSN1 | 0.758 | 1.116765 | 0.258 | 5 |
| BRINP1 | 0.731 | 1.116028 | 0.231 | 5 |
| DCLK1 | 0.745 | 1.111968 | 0.245 | 5 |
| SUSD4 | 0.709 | 1.111055 | 0.209 | 5 |
| 4833424O15RIK | 0.722 | 1.108714 | 0.222 | 5 |
| CHGA | 0.776 | 1.098459 | 0.276 | 5 |
| PBX1 | 0.777 | 1.097487 | 0.277 | 5 |
| KIF5C | 0.747 | 1.090766 | 0.247 | 5 |
| PCP4 | 0.829 | 1.082855 | 0.329 | 5 |
| SNCA | 0.718 | 1.080615 | 0.218 | 5 |
| NCDN | 0.740 | 1.079821 | 0.240 | 5 |
| GNAS | 0.820 | 1.079212 | 0.320 | 5 |
| CYFIP2 | 0.764 | 1.073980 | 0.264 | 5 |
| PTPRK | 0.702 | 1.064478 | 0.202 | 5 |
| GM1673 | 0.729 | 1.060925 | 0.229 | 5 |
| HMGCS1 | 0.753 | 1.060691 | 0.253 | 5 |
| RTN1 | 0.800 | 1.055933 | 0.300 | 5 |
| IGSF8 | 0.740 | 1.055664 | 0.240 | 5 |
| SNRPN | 0.754 | 1.038591 | 0.254 | 5 |
| THRA | 0.772 | 1.020305 | 0.272 | 5 |
| CHD3 | 0.753 | 1.009107 | 0.253 | 5 |
| GNB1 | 0.248 | −1.603950 | 0.252 | 5 |
| HMGN1 | 0.209 | −1.639410 | 0.291 | 5 |
| UNC119 | 0.251 | −1.776276 | 0.249 | 5 |
| GNAT1 | 0.224 | −1.788295 | 0.276 | 5 |
| NEUROD1 | 0.273 | −1.859046 | 0.227 | 5 |
| RP1 | 0.233 | −1.902106 | 0.267 | 5 |
| PDE6B | 0.237 | −1.916995 | 0.263 | 5 |
| NRL | 0.260 | −1.922926 | 0.240 | 5 |
| RCVRN | 0.219 | −1.936805 | 0.281 | 5 |
| ROM1 | 0.219 | −2.012157 | 0.281 | 5 |
| CNGA1 | 0.253 | −2.027682 | 0.247 | 5 |
| PDC | 0.180 | −2.058464 | 0.320 | 5 |
| PRPH2 | 0.189 | −2.124104 | 0.311 | 5 |
| RHO | 0.175 | −2.140480 | 0.325 | 5 |
| RS1 | 0.247 | −2.154422 | 0.253 | 5 |
| SAG | 0.166 | −2.161915 | 0.334 | 5 |
| NR2E3 | 0.249 | −2.164806 | 0.251 | 5 |
| GNGT1 | 0.160 | −2.165857 | 0.340 | 5 |

TABLE 6-continued

Genes differentially expressed in each of the 39 retinal cell clusters.

| | | | | |
|---|---|---|---|---|
| RPGRIP1 | 0.244 | −2.166108 | 0.256 | 5 |
| SLC24A1 | 0.259 | −2.174069 | 0.241 | 5 |
| TULP1 | 0.195 | −2.237394 | 0.305 | 5 |
| PDE6G | 0.190 | −2.267903 | 0.310 | 5 |
| cluster no. 6 DE = 156 | | | | |
| NPNT | 0.945 | 2.486780 | 0.445 | 6 |
| ARL4C | 0.938 | 2.467107 | 0.438 | 6 |
| BHLHE22 | 0.917 | 2.421611 | 0.417 | 6 |
| CPLX2 | 0.942 | 2.362730 | 0.442 | 6 |
| LPL | 0.920 | 2.288892 | 0.420 | 6 |
| FILIP1L | 0.897 | 2.194008 | 0.397 | 6 |
| TKT | 0.925 | 2.156892 | 0.425 | 6 |
| NRXN2 | 0.932 | 2.155552 | 0.432 | 6 |
| SIX3 | 0.923 | 2.092244 | 0.423 | 6 |
| SLIT2 | 0.911 | 2.087468 | 0.411 | 6 |
| SNHG11 | 0.935 | 2.050363 | 0.435 | 6 |
| SLC6A1 | 0.885 | 1.911315 | 0.385 | 6 |
| PAX6 | 0.894 | 1.818176 | 0.394 | 6 |
| PTN | 0.892 | 1.811793 | 0.392 | 6 |
| RBFOX1 | 0.853 | 1.801588 | 0.353 | 6 |
| DLGAP1 | 0.867 | 1.797541 | 0.367 | 6 |
| GRIA2 | 0.898 | 1.738590 | 0.398 | 6 |
| HBEGF | 0.812 | 1.719168 | 0.312 | 6 |
| 2900011O08RIK | 0.863 | 1.692404 | 0.363 | 6 |
| MEIS2 | 0.887 | 1.620756 | 0.387 | 6 |
| DTNBP1 | 0.839 | 1.601648 | 0.339 | 6 |
| GAD1 | 0.851 | 1.596819 | 0.351 | 6 |
| ATP1B1 | 0.888 | 1.593981 | 0.388 | 6 |
| ASAP1 | 0.841 | 1.587659 | 0.341 | 6 |
| FEZ1 | 0.823 | 1.583525 | 0.323 | 6 |
| SPOCK3 | 0.826 | 1.577292 | 0.326 | 6 |
| PCDH10 | 0.841 | 1.552813 | 0.341 | 6 |
| VSNL1 | 0.819 | 1.543639 | 0.319 | 6 |
| NECAB1 | 0.807 | 1.542009 | 0.307 | 6 |
| GAD2 | 0.800 | 1.511610 | 0.300 | 6 |
| NRCAM | 0.809 | 1.495982 | 0.309 | 6 |
| GUCY1A3 | 0.855 | 1.487265 | 0.355 | 6 |
| ID4 | 0.791 | 1.477149 | 0.291 | 6 |
| BASP1 | 0.849 | 1.466807 | 0.349 | 6 |
| PDE4B | 0.803 | 1.466115 | 0.303 | 6 |
| KCNIP1 | 0.807 | 1.464399 | 0.307 | 6 |
| CXCL14 | 0.771 | 1.455123 | 0.271 | 6 |
| KCNC1 | 0.798 | 1.426647 | 0.298 | 6 |
| RPH3A | 0.835 | 1.420630 | 0.335 | 6 |
| FAM155A | 0.804 | 1.420487 | 0.304 | 6 |
| UCHL1 | 0.826 | 1.419570 | 0.326 | 6 |
| DAPK1 | 0.786 | 1.411956 | 0.286 | 6 |
| TTC3 | 0.887 | 1.400846 | 0.387 | 6 |
| DPYSL4 | 0.796 | 1.396161 | 0.296 | 6 |
| GABBR2 | 0.746 | 1.395801 | 0.246 | 6 |
| CCDC88B | 0.779 | 1.375544 | 0.279 | 6 |
| SLC32A1 | 0.807 | 1.368830 | 0.307 | 6 |
| C1QL1 | 0.772 | 1.360801 | 0.272 | 6 |
| STMN2 | 0.812 | 1.357504 | 0.312 | 6 |
| ELAVL3 | 0.820 | 1.350815 | 0.320 | 6 |
| RND3 | 0.779 | 1.347967 | 0.279 | 6 |
| GPM6A | 0.835 | 1.344385 | 0.335 | 6 |
| MEG3 | 0.875 | 1.342623 | 0.375 | 6 |
| A030009H04RIK | 0.792 | 1.333141 | 0.292 | 6 |
| ZFHX3 | 0.768 | 1.332239 | 0.268 | 6 |
| RGS7BP | 0.769 | 1.324127 | 0.269 | 6 |
| NDRG4 | 0.822 | 1.318106 | 0.322 | 6 |
| RPS6KA4 | 0.748 | 1.311023 | 0.248 | 6 |
| ADARB1 | 0.798 | 1.302663 | 0.298 | 6 |
| FRMD5 | 0.798 | 1.291730 | 0.298 | 6 |
| TUBB2A | 0.825 | 1.288930 | 0.325 | 6 |
| CTNND2 | 0.771 | 1.287176 | 0.271 | 6 |
| CDK5R1 | 0.788 | 1.279842 | 0.288 | 6 |
| SV2A | 0.826 | 1.279755 | 0.326 | 6 |
| PRKCB | 0.782 | 1.272974 | 0.282 | 6 |
| CACNG4 | 0.807 | 1.269842 | 0.307 | 6 |
| UNC5D | 0.741 | 1.260066 | 0.241 | 6 |
| PRMT8 | 0.753 | 1.258728 | 0.253 | 6 |
| CACNA2D1 | 0.769 | 1.257272 | 0.269 | 6 |
| GNG3 | 0.817 | 1.251172 | 0.317 | 6 |
| AUTS2 | 0.781 | 1.247146 | 0.281 | 6 |
| STMN3 | 0.820 | 1.245952 | 0.320 | 6 |
| FAIM2 | 0.772 | 1.244633 | 0.272 | 6 |
| PNMAL2 | 0.804 | 1.239124 | 0.304 | 6 |
| UBASH3B | 0.720 | 1.237485 | 0.220 | 6 |
| RUNX1T1 | 0.768 | 1.222632 | 0.268 | 6 |
| LRP8 | 0.761 | 1.212309 | 0.261 | 6 |
| STMN1 | 0.775 | 1.209730 | 0.275 | 6 |
| 6430548M08RIK | 0.803 | 1.207834 | 0.303 | 6 |
| MPP6 | 0.761 | 1.206435 | 0.261 | 6 |
| GPR123 | 0.736 | 1.204882 | 0.236 | 6 |
| LHFPL2 | 0.719 | 1.202920 | 0.219 | 6 |
| COL6A1 | 0.747 | 1.199489 | 0.247 | 6 |
| DHCR24 | 0.745 | 1.195008 | 0.245 | 6 |
| DUSP26 | 0.791 | 1.193817 | 0.291 | 6 |
| ALCAM | 0.712 | 1.183433 | 0.212 | 6 |
| INPP4B | 0.736 | 1.177319 | 0.236 | 6 |
| CLMN | 0.701 | 1.175226 | 0.201 | 6 |
| TSC22D1 | 0.819 | 1.174524 | 0.319 | 6 |
| SNRPN | 0.792 | 1.174384 | 0.292 | 6 |
| CELF4 | 0.835 | 1.173654 | 0.335 | 6 |
| HUNK | 0.737 | 1.169421 | 0.237 | 6 |
| TNC | 0.723 | 1.167862 | 0.223 | 6 |
| TFAP2A | 0.734 | 1.161882 | 0.234 | 6 |
| RASAL2 | 0.740 | 1.156727 | 0.240 | 6 |
| FGD6 | 0.741 | 1.156173 | 0.241 | 6 |
| ELAVL4 | 0.762 | 1.149500 | 0.262 | 6 |
| GNG2 | 0.760 | 1.147975 | 0.260 | 6 |
| LPHN3 | 0.713 | 1.131097 | 0.213 | 6 |
| PLCH1 | 0.734 | 1.129860 | 0.234 | 6 |
| PCDH17 | 0.730 | 1.127561 | 0.230 | 6 |
| AI848285 | 0.704 | 1.120084 | 0.204 | 6 |
| MYH10 | 0.779 | 1.111490 | 0.279 | 6 |
| TMEM191C | 0.740 | 1.110693 | 0.240 | 6 |
| GRIA4 | 0.752 | 1.109848 | 0.252 | 6 |
| THRA | 0.801 | 1.109794 | 0.301 | 6 |
| RASGRF1 | 0.710 | 1.104095 | 0.210 | 6 |
| CHN1 | 0.759 | 1.098900 | 0.259 | 6 |
| CDC42EP4 | 0.706 | 1.091060 | 0.206 | 6 |
| KIF5C | 0.779 | 1.081707 | 0.279 | 6 |
| GAS7 | 0.763 | 1.080142 | 0.263 | 6 |
| FSCN1 | 0.753 | 1.069197 | 0.253 | 6 |
| 6330403K07RIK | 0.713 | 1.065402 | 0.213 | 6 |
| TAGLN3 | 0.766 | 1.056235 | 0.266 | 6 |
| BC048943 | 0.768 | 1.055497 | 0.268 | 6 |
| ATP6V1G2 | 0.749 | 1.049524 | 0.249 | 6 |
| GABRA3 | 0.738 | 1.046500 | 0.238 | 6 |
| HPCA | 0.749 | 1.045573 | 0.249 | 6 |
| FUT9 | 0.706 | 1.043984 | 0.206 | 6 |
| CERS5 | 0.745 | 1.040396 | 0.245 | 6 |
| FAM115A | 0.777 | 1.038889 | 0.277 | 6 |
| SFXN1 | 0.726 | 1.037528 | 0.226 | 6 |
| MLLT11 | 0.773 | 1.035476 | 0.273 | 6 |
| SYNPR | 0.758 | 1.032318 | 0.258 | 6 |
| CX3CL1 | 0.708 | 1.025068 | 0.208 | 6 |
| MAPT | 0.773 | 1.017509 | 0.273 | 6 |
| DAAM1 | 0.744 | 1.012920 | 0.244 | 6 |
| CMIP | 0.752 | 1.011512 | 0.252 | 6 |
| DKK3 | 0.836 | 1.011427 | 0.336 | 6 |
| IGSF8 | 0.733 | 1.003250 | 0.233 | 6 |
| TENM4 | 0.703 | 1.002356 | 0.203 | 6 |
| NSG2 | 0.752 | 1.001377 | 0.252 | 6 |
| NRSN1 | 0.747 | 1.000763 | 0.247 | 6 |
| CST3 | 0.293 | −1.465866 | 0.207 | 6 |
| UNC119 | 0.276 | −1.522563 | 0.224 | 6 |
| HMGN1 | 0.218 | −1.541634 | 0.282 | 6 |
| ROM1 | 0.257 | −1.544670 | 0.243 | 6 |
| GNB1 | 0.254 | −1.581356 | 0.246 | 6 |
| RPGRIP1 | 0.279 | −1.586358 | 0.221 | 6 |
| NEUROD1 | 0.296 | −1.619679 | 0.204 | 6 |
| NRL | 0.281 | −1.643732 | 0.219 | 6 |
| CNGA1 | 0.281 | −1.691412 | 0.219 | 6 |
| PRPH2 | 0.220 | −1.692216 | 0.280 | 6 |
| TULP1 | 0.227 | −1.729834 | 0.273 | 6 |
| NR2E3 | 0.278 | −1.736613 | 0.222 | 6 |
| RP1 | 0.256 | −1.749063 | 0.244 | 6 |
| RS1 | 0.278 | −1.760521 | 0.222 | 6 |
| PDE6B | 0.253 | −1.770264 | 0.247 | 6 |
| PDE6G | 0.227 | −1.826063 | 0.273 | 6 |
| SLC24A1 | 0.290 | −1.831021 | 0.210 | 6 |

TABLE 6-continued

Genes differentially expressed in each of the 39 retinal cell clusters.

| Gene | | | | |
|---|---|---|---|---|
| SAG | 0.180 | −1.853215 | 0.320 | 6 |
| RCVRN | 0.234 | −1.864629 | 0.266 | 6 |
| GNAT1 | 0.222 | −1.882724 | 0.278 | 6 |
| GNGT1 | 0.190 | −1.891447 | 0.310 | 6 |
| RHO | 0.184 | −1.906823 | 0.316 | 6 |
| PDC | 0.188 | −1.952769 | 0.312 | 6 |
| cluster no. 7 DE = 164 | | | | |
| CXCL14 | 0.953 | 2.823229 | 0.453 | 7 |
| CPLX2 | 0.965 | 2.782527 | 0.465 | 7 |
| MAF | 0.874 | 2.663386 | 0.374 | 7 |
| AI593442 | 0.929 | 2.533839 | 0.429 | 7 |
| ID4 | 0.900 | 2.369125 | 0.400 | 7 |
| LPL | 0.929 | 2.294283 | 0.429 | 7 |
| GAD2 | 0.909 | 2.222806 | 0.409 | 7 |
| NPNT | 0.872 | 2.100390 | 0.372 | 7 |
| SNHG11 | 0.933 | 2.095661 | 0.433 | 7 |
| SPOCK3 | 0.907 | 2.024941 | 0.407 | 7 |
| PAX6 | 0.906 | 1.900148 | 0.406 | 7 |
| NRXN2 | 0.889 | 1.824692 | 0.389 | 7 |
| GRIA2 | 0.907 | 1.794039 | 0.407 | 7 |
| NDRG4 | 0.889 | 1.706384 | 0.389 | 7 |
| 2900011O08RIK | 0.866 | 1.702616 | 0.366 | 7 |
| DTNBP1 | 0.860 | 1.674204 | 0.360 | 7 |
| C1QL1 | 0.836 | 1.656812 | 0.336 | 7 |
| ASAP1 | 0.848 | 1.646246 | 0.348 | 7 |
| ATP1B1 | 0.904 | 1.636111 | 0.404 | 7 |
| SIX3 | 0.866 | 1.635263 | 0.366 | 7 |
| SLC6A1 | 0.852 | 1.618210 | 0.352 | 7 |
| FILIP1L | 0.801 | 1.610463 | 0.301 | 7 |
| HBEGF | 0.809 | 1.597965 | 0.309 | 7 |
| PDE4B | 0.838 | 1.597787 | 0.338 | 7 |
| GUCY1A3 | 0.864 | 1.582330 | 0.364 | 7 |
| GAD1 | 0.851 | 1.579238 | 0.351 | 7 |
| TNC | 0.793 | 1.575202 | 0.293 | 7 |
| CRYBB3 | 0.732 | 1.574911 | 0.232 | 7 |
| ADARB1 | 0.842 | 1.560392 | 0.342 | 7 |
| MMP9 | 0.744 | 1.559409 | 0.244 | 7 |
| DNER | 0.836 | 1.558484 | 0.336 | 7 |
| SPARCL1 | 0.843 | 1.550294 | 0.343 | 7 |
| DDAH1 | 0.829 | 1.541302 | 0.329 | 7 |
| DLGAP1 | 0.827 | 1.529146 | 0.327 | 7 |
| UACA | 0.780 | 1.515731 | 0.280 | 7 |
| MEIS2 | 0.864 | 1.513207 | 0.364 | 7 |
| RBFOX1 | 0.805 | 1.507393 | 0.305 | 7 |
| TKT | 0.856 | 1.505182 | 0.356 | 7 |
| PCDH7 | 0.764 | 1.500815 | 0.264 | 7 |
| BHLHE22 | 0.799 | 1.499124 | 0.299 | 7 |
| CLMN | 0.781 | 1.470727 | 0.281 | 7 |
| SLC32A1 | 0.819 | 1.466542 | 0.319 | 7 |
| BASP1 | 0.846 | 1.464820 | 0.346 | 7 |
| ELMO1 | 0.787 | 1.457100 | 0.287 | 7 |
| CACNG4 | 0.843 | 1.450213 | 0.343 | 7 |
| TUBB2A | 0.849 | 1.445571 | 0.349 | 7 |
| GNG2 | 0.827 | 1.438293 | 0.327 | 7 |
| GNG3 | 0.863 | 1.436732 | 0.363 | 7 |
| DKK3 | 0.893 | 1.435250 | 0.393 | 7 |
| KCNA6 | 0.749 | 1.425320 | 0.249 | 7 |
| NECAB1 | 0.792 | 1.419522 | 0.292 | 7 |
| KCNAB1 | 0.799 | 1.416904 | 0.299 | 7 |
| ALDOC | 0.847 | 1.409296 | 0.347 | 7 |
| LMO4 | 0.743 | 1.409237 | 0.243 | 7 |
| 6430548M08RIK | 0.830 | 1.391242 | 0.330 | 7 |
| FAM155A | 0.818 | 1.381329 | 0.318 | 7 |
| PNMAL2 | 0.836 | 1.374099 | 0.336 | 7 |
| KCNC1 | 0.817 | 1.373826 | 0.317 | 7 |
| ARL4C | 0.783 | 1.370410 | 0.283 | 7 |
| SCN3A | 0.775 | 1.364878 | 0.275 | 7 |
| SYT7 | 0.778 | 1.363974 | 0.278 | 7 |
| KIF5C | 0.828 | 1.361801 | 0.328 | 7 |
| TFAP2C | 0.770 | 1.353114 | 0.270 | 7 |
| FEZ1 | 0.792 | 1.342916 | 0.292 | 7 |
| PTN | 0.817 | 1.337424 | 0.317 | 7 |
| CELF4 | 0.871 | 1.326774 | 0.371 | 7 |
| TTC3 | 0.867 | 1.304565 | 0.367 | 7 |
| CPNE6 | 0.779 | 1.303567 | 0.279 | 7 |
| SV2A | 0.842 | 1.297245 | 0.342 | 7 |
| CTSL | 0.838 | 1.288834 | 0.338 | 7 |
| MYH10 | 0.809 | 1.279803 | 0.309 | 7 |
| GABBR2 | 0.754 | 1.279715 | 0.254 | 7 |
| FRMD5 | 0.810 | 1.278237 | 0.310 | 7 |
| PAK3 | 0.798 | 1.275646 | 0.298 | 7 |
| PRKCB | 0.771 | 1.274230 | 0.271 | 7 |
| ELAVL3 | 0.811 | 1.271094 | 0.311 | 7 |
| ADARB2 | 0.740 | 1.270445 | 0.240 | 7 |
| ARHGEF9 | 0.788 | 1.265682 | 0.288 | 7 |
| HUNK | 0.784 | 1.259809 | 0.284 | 7 |
| OGFRL1 | 0.809 | 1.255789 | 0.309 | 7 |
| CPNE5 | 0.746 | 1.249717 | 0.246 | 7 |
| THRA | 0.835 | 1.245177 | 0.335 | 7 |
| KCNA1 | 0.753 | 1.239065 | 0.253 | 7 |
| KCNIP1 | 0.761 | 1.237502 | 0.261 | 7 |
| SLIT2 | 0.767 | 1.237248 | 0.267 | 7 |
| DPYSL4 | 0.786 | 1.232672 | 0.286 | 7 |
| C1QL2 | 0.751 | 1.228475 | 0.251 | 7 |
| THY1 | 0.774 | 1.227368 | 0.274 | 7 |
| PRUNE2 | 0.760 | 1.221889 | 0.260 | 7 |
| ALCAM | 0.713 | 1.207316 | 0.213 | 7 |
| DHCR24 | 0.776 | 1.189385 | 0.276 | 7 |
| STMN3 | 0.826 | 1.187067 | 0.326 | 7 |
| CD302 | 0.706 | 1.182568 | 0.206 | 7 |
| PRRT4 | 0.736 | 1.180616 | 0.236 | 7 |
| PCSK2 | 0.749 | 1.162396 | 0.249 | 7 |
| DAPK1 | 0.751 | 1.145777 | 0.251 | 7 |
| SEZ6L | 0.717 | 1.139465 | 0.217 | 7 |
| SFXN1 | 0.757 | 1.133703 | 0.257 | 7 |
| SYNPR | 0.800 | 1.123498 | 0.300 | 7 |
| VPS41 | 0.772 | 1.123170 | 0.272 | 7 |
| NSG2 | 0.798 | 1.120197 | 0.298 | 7 |
| CCDC88B | 0.730 | 1.113578 | 0.230 | 7 |
| STMN2 | 0.785 | 1.107607 | 0.285 | 7 |
| MLLT11 | 0.797 | 1.107556 | 0.297 | 7 |
| A030009H04RIK | 0.780 | 1.107031 | 0.280 | 7 |
| VSNL1 | 0.752 | 1.103676 | 0.252 | 7 |
| TAGLN3 | 0.802 | 1.102230 | 0.302 | 7 |
| ELAVL4 | 0.743 | 1.101000 | 0.243 | 7 |
| LHFPL2 | 0.715 | 1.100922 | 0.215 | 7 |
| FRRS1L | 0.713 | 1.100870 | 0.213 | 7 |
| CERS5 | 0.750 | 1.098213 | 0.250 | 7 |
| RND3 | 0.726 | 1.095740 | 0.226 | 7 |
| SNRPN | 0.789 | 1.095115 | 0.289 | 7 |
| GABRA3 | 0.732 | 1.090441 | 0.232 | 7 |
| PPFIBP1 | 0.706 | 1.080047 | 0.206 | 7 |
| GAS7 | 0.770 | 1.079250 | 0.270 | 7 |
| INPP4B | 0.710 | 1.078757 | 0.210 | 7 |
| ATP6V1D | 0.816 | 1.078276 | 0.316 | 7 |
| FGD6 | 0.721 | 1.073414 | 0.221 | 7 |
| SPAG5 | 0.701 | 1.072308 | 0.201 | 7 |
| ATP6V1G2 | 0.767 | 1.068453 | 0.267 | 7 |
| HPCA | 0.758 | 1.064513 | 0.258 | 7 |
| ARHGAP24 | 0.776 | 1.063113 | 0.276 | 7 |
| UBASH3B | 0.720 | 1.061516 | 0.220 | 7 |
| NAP1L5 | 0.804 | 1.060330 | 0.304 | 7 |
| CACNG3 | 0.726 | 1.057606 | 0.226 | 7 |
| MXRA7 | 0.781 | 1.057379 | 0.281 | 7 |
| ADCY2 | 0.733 | 1.055474 | 0.233 | 7 |
| SYT11 | 0.792 | 1.054558 | 0.292 | 7 |
| NPTX2 | 0.712 | 1.054379 | 0.212 | 7 |
| RPS6KA4 | 0.712 | 1.051053 | 0.212 | 7 |
| UTRN | 0.714 | 1.049219 | 0.214 | 7 |
| BC048943 | 0.793 | 1.047734 | 0.293 | 7 |
| LPHN3 | 0.745 | 1.043811 | 0.245 | 7 |
| MAPT | 0.764 | 1.036973 | 0.264 | 7 |
| CTNND2 | 0.734 | 1.032653 | 0.234 | 7 |
| AUTS2 | 0.749 | 1.032249 | 0.249 | 7 |
| SEPT11 | 0.742 | 1.032183 | 0.242 | 7 |
| DAAM1 | 0.774 | 1.031598 | 0.274 | 7 |
| PCP4L1 | 0.801 | 1.029783 | 0.301 | 7 |
| CACNB4 | 0.709 | 1.012396 | 0.209 | 7 |
| MPP6 | 0.713 | 1.012265 | 0.213 | 7 |
| MARCKS | 0.788 | 1.005504 | 0.288 | 7 |
| GNB1 | 0.279 | −1.346821 | 0.221 | 7 |
| CST3 | 0.298 | −1.460907 | 0.202 | 7 |
| HMGN1 | 0.231 | −1.484621 | 0.269 | 7 |
| ROM1 | 0.265 | −1.549354 | 0.235 | 7 |
| NEUROD1 | 0.297 | −1.576758 | 0.203 | 7 |

TABLE 6-continued

Genes differentially expressed in each of the 39 retinal cell clusters.

| | | | | |
|---|---|---|---|---|
| CNGA1 | 0.290 | −1.593189 | 0.210 | 7 |
| RPGRIP1 | 0.294 | −1.594350 | 0.206 | 7 |
| RP1 | 0.270 | −1.600478 | 0.230 | 7 |
| TULP1 | 0.236 | −1.643426 | 0.264 | 7 |
| NRL | 0.284 | −1.667221 | 0.216 | 7 |
| PDE6G | 0.239 | −1.675754 | 0.261 | 7 |
| RCVRN | 0.248 | −1.702941 | 0.252 | 7 |
| PDE6B | 0.252 | −1.720612 | 0.248 | 7 |
| SLC24A1 | 0.296 | −1.738209 | 0.204 | 7 |
| GNGT1 | 0.202 | −1.745068 | 0.298 | 7 |
| PRPH2 | 0.215 | −1.759684 | 0.285 | 7 |
| RS1 | 0.283 | −1.786494 | 0.217 | 7 |
| GNAT1 | 0.231 | −1.791925 | 0.269 | 7 |
| PDC | 0.196 | −1.850697 | 0.304 | 7 |
| SAG | 0.181 | −1.888991 | 0.319 | 7 |
| RHO | 0.184 | −1.898958 | 0.316 | 7 |
| cluster no. 8 DE = 145 | | | | |
| TAC2 | 0.842 | 3.118377 | 0.342 | 8 |
| TAC1 | 0.795 | 2.770889 | 0.295 | 8 |
| STMN2 | 0.906 | 2.529338 | 0.406 | 8 |
| GAP43 | 0.840 | 2.159206 | 0.340 | 8 |
| NAP1L5 | 0.913 | 2.129231 | 0.413 | 8 |
| ATP1B1 | 0.916 | 2.091522 | 0.416 | 8 |
| C1QL1 | 0.847 | 2.085033 | 0.347 | 8 |
| CXCL14 | 0.750 | 2.075283 | 0.250 | 8 |
| MEG3 | 0.891 | 2.041950 | 0.391 | 8 |
| SNHG11 | 0.891 | 2.017042 | 0.391 | 8 |
| 6330403K07RIK | 0.824 | 1.993265 | 0.324 | 8 |
| 2900011O08RIK | 0.866 | 1.975900 | 0.366 | 8 |
| UCHL1 | 0.861 | 1.947723 | 0.361 | 8 |
| ELAVL2 | 0.762 | 1.912945 | 0.262 | 8 |
| STMN3 | 0.861 | 1.816792 | 0.361 | 8 |
| CBLN2 | 0.711 | 1.800970 | 0.211 | 8 |
| SPOCK3 | 0.809 | 1.777251 | 0.309 | 8 |
| NCAM2 | 0.788 | 1.760593 | 0.288 | 8 |
| TUBB2A | 0.861 | 1.711072 | 0.361 | 8 |
| TFAP2B | 0.808 | 1.701796 | 0.308 | 8 |
| SNCA | 0.784 | 1.697970 | 0.284 | 8 |
| SLC32A1 | 0.809 | 1.663189 | 0.309 | 8 |
| SCG2 | 0.824 | 1.651755 | 0.324 | 8 |
| STMN4 | 0.809 | 1.645436 | 0.309 | 8 |
| CPNE5 | 0.789 | 1.634672 | 0.289 | 8 |
| RTN1 | 0.852 | 1.593975 | 0.352 | 8 |
| VSNL1 | 0.806 | 1.570547 | 0.306 | 8 |
| IMPACT | 0.827 | 1.556732 | 0.327 | 8 |
| SORCS1 | 0.773 | 1.555793 | 0.273 | 8 |
| GAD2 | 0.778 | 1.543560 | 0.278 | 8 |
| BASP1 | 0.832 | 1.538785 | 0.332 | 8 |
| CPLX2 | 0.799 | 1.530079 | 0.299 | 8 |
| MEIS2 | 0.819 | 1.506350 | 0.319 | 8 |
| GNG2 | 0.785 | 1.503115 | 0.285 | 8 |
| OXR1 | 0.753 | 1.492338 | 0.253 | 8 |
| GNG3 | 0.817 | 1.478047 | 0.317 | 8 |
| CELF4 | 0.859 | 1.464056 | 0.359 | 8 |
| DNER | 0.783 | 1.449112 | 0.283 | 8 |
| TTC3 | 0.889 | 1.424931 | 0.389 | 8 |
| LSAMP | 0.793 | 1.418734 | 0.293 | 8 |
| NRXN2 | 0.815 | 1.414066 | 0.315 | 8 |
| YWHAH | 0.794 | 1.410703 | 0.294 | 8 |
| NECAB1 | 0.765 | 1.405108 | 0.265 | 8 |
| SERPINE2 | 0.701 | 1.401238 | 0.201 | 8 |
| A030009H04RIK | 0.788 | 1.397833 | 0.288 | 8 |
| ZWINT | 0.808 | 1.388499 | 0.308 | 8 |
| SLC6A1 | 0.797 | 1.385051 | 0.297 | 8 |
| SYT11 | 0.816 | 1.379877 | 0.316 | 8 |
| GPRASP1 | 0.799 | 1.359056 | 0.299 | 8 |
| 4833424O15RIK | 0.751 | 1.355348 | 0.251 | 8 |
| AI593442 | 0.713 | 1.339073 | 0.213 | 8 |
| C1QL2 | 0.722 | 1.335015 | 0.222 | 8 |
| MLLT11 | 0.782 | 1.331374 | 0.282 | 8 |
| GRIA2 | 0.831 | 1.326882 | 0.331 | 8 |
| MARCKS | 0.827 | 1.322535 | 0.327 | 8 |
| SYT6 | 0.714 | 1.321108 | 0.214 | 8 |
| NRSN1 | 0.757 | 1.319183 | 0.257 | 8 |
| TFAP2A | 0.713 | 1.313087 | 0.213 | 8 |
| KIF5C | 0.784 | 1.312896 | 0.284 | 8 |
| SYN2 | 0.711 | 1.309829 | 0.211 | 8 |
| TENM1 | 0.730 | 1.298569 | 0.230 | 8 |
| EPB4.1L4A | 0.713 | 1.296585 | 0.213 | 8 |
| PAX6 | 0.784 | 1.290939 | 0.284 | 8 |
| NDN | 0.805 | 1.284206 | 0.305 | 8 |
| GPM6A | 0.815 | 1.282328 | 0.315 | 8 |
| FXYD6 | 0.740 | 1.268025 | 0.240 | 8 |
| GNAS | 0.849 | 1.267517 | 0.349 | 8 |
| SYT7 | 0.738 | 1.267166 | 0.238 | 8 |
| SNRPN | 0.765 | 1.264829 | 0.265 | 8 |
| SPOCK2 | 0.771 | 1.263568 | 0.271 | 8 |
| PNMAL2 | 0.771 | 1.259210 | 0.271 | 8 |
| MAPT | 0.770 | 1.244983 | 0.270 | 8 |
| MYT1L | 0.752 | 1.241489 | 0.252 | 8 |
| HSP90AB1 | 0.873 | 1.236035 | 0.373 | 8 |
| BEX2 | 0.803 | 1.234094 | 0.303 | 8 |
| NDRG4 | 0.787 | 1.229175 | 0.287 | 8 |
| TKT | 0.747 | 1.227076 | 0.247 | 8 |
| GAD1 | 0.734 | 1.218844 | 0.234 | 8 |
| TCEAL5 | 0.748 | 1.204026 | 0.248 | 8 |
| TENM4 | 0.719 | 1.203590 | 0.219 | 8 |
| NSG2 | 0.743 | 1.203252 | 0.243 | 8 |
| SYNGR3 | 0.735 | 1.190339 | 0.235 | 8 |
| YWHAG | 0.770 | 1.184824 | 0.270 | 8 |
| GRIA3 | 0.714 | 1.181042 | 0.214 | 8 |
| FSTL5 | 0.737 | 1.177141 | 0.237 | 8 |
| NSG1 | 0.744 | 1.176358 | 0.244 | 8 |
| SPARCL1 | 0.762 | 1.174529 | 0.262 | 8 |
| TMX4 | 0.753 | 1.169642 | 0.253 | 8 |
| REEP5 | 0.734 | 1.166393 | 0.234 | 8 |
| SYNPR | 0.769 | 1.155357 | 0.269 | 8 |
| TUBA1A | 0.793 | 1.148357 | 0.293 | 8 |
| NGFRAP1 | 0.765 | 1.133358 | 0.265 | 8 |
| TMSB10 | 0.770 | 1.132117 | 0.270 | 8 |
| CACNA2D2 | 0.723 | 1.117231 | 0.223 | 8 |
| CALM2 | 0.801 | 1.114501 | 0.301 | 8 |
| RBFOX1 | 0.712 | 1.114299 | 0.212 | 8 |
| PRKAR1B | 0.731 | 1.103338 | 0.231 | 8 |
| GM1673 | 0.720 | 1.098747 | 0.220 | 8 |
| SERINC1 | 0.791 | 1.098697 | 0.291 | 8 |
| SV2A | 0.782 | 1.095818 | 0.282 | 8 |
| APP | 0.748 | 1.089714 | 0.248 | 8 |
| ZCCHC18 | 0.740 | 1.081228 | 0.240 | 8 |
| CALM3 | 0.773 | 1.071503 | 0.273 | 8 |
| GPRASP2 | 0.738 | 1.069399 | 0.238 | 8 |
| RAB6B | 0.736 | 1.066369 | 0.236 | 8 |
| GRIA4 | 0.729 | 1.065619 | 0.229 | 8 |
| LRRC4C | 0.701 | 1.059002 | 0.201 | 8 |
| KIF5A | 0.709 | 1.050514 | 0.209 | 8 |
| DTNBP1 | 0.720 | 1.042708 | 0.220 | 8 |
| RAB6A | 0.752 | 1.040196 | 0.252 | 8 |
| CD200 | 0.709 | 1.038274 | 0.209 | 8 |
| CHGA | 0.752 | 1.036109 | 0.252 | 8 |
| KIF3A | 0.743 | 1.036025 | 0.243 | 8 |
| CDK5R1 | 0.735 | 1.035358 | 0.235 | 8 |
| ACOT7 | 0.715 | 1.035198 | 0.215 | 8 |
| CACNG4 | 0.739 | 1.032652 | 0.239 | 8 |
| TPM1 | 0.732 | 1.026026 | 0.232 | 8 |
| OLFM1 | 0.705 | 1.021312 | 0.205 | 8 |
| ELAVL3 | 0.744 | 1.019574 | 0.244 | 8 |
| KIFAP3 | 0.762 | 1.019268 | 0.262 | 8 |
| D3BWG0562E | 0.717 | 1.014043 | 0.217 | 8 |
| EPB4.1 | 0.292 | −1.765515 | 0.208 | 8 |
| GNB1 | 0.237 | −1.768119 | 0.263 | 8 |
| NEUROD1 | 0.267 | −1.803015 | 0.233 | 8 |
| HMGN1 | 0.185 | −1.892020 | 0.315 | 8 |
| AIPL1 | 0.297 | −1.980059 | 0.203 | 8 |
| UNC119 | 0.225 | −2.011676 | 0.275 | 8 |
| RP1 | 0.218 | −2.092140 | 0.282 | 8 |
| NR2E3 | 0.243 | −2.160752 | 0.257 | 8 |
| NRL | 0.239 | −2.167337 | 0.261 | 8 |
| CNGA1 | 0.229 | −2.233635 | 0.271 | 8 |
| ROM1 | 0.197 | −2.307381 | 0.303 | 8 |
| PDE6B | 0.210 | −2.319014 | 0.290 | 8 |
| RPGRIP1 | 0.231 | −2.350954 | 0.269 | 8 |
| PRPH2 | 0.170 | −2.376545 | 0.330 | 8 |
| PDE6G | 0.187 | −2.377062 | 0.313 | 8 |
| RS1 | 0.230 | −2.386965 | 0.270 | 8 |
| SLC24A1 | 0.240 | −2.450802 | 0.260 | 8 |

TABLE 6-continued

Genes differentially expressed in each of the 39 retinal cell clusters.

| Gene | | | | |
|---|---|---|---|---|
| GNAT1 | 0.176 | −2.480741 | 0.324 | 8 |
| SAG | 0.140 | −2.481892 | 0.360 | 8 |
| RCVRN | 0.187 | −2.497213 | 0.313 | 8 |
| RHO | 0.146 | −2.536232 | 0.354 | 8 |
| GNGT1 | 0.133 | −2.654791 | 0.367 | 8 |
| TULP1 | 0.165 | −2.680406 | 0.335 | 8 |
| PDC | 0.144 | −2.702042 | 0.356 | 8 |
| cluster no. 9 DE = 145 | | | | |
| TFAP2B | 0.913 | 2.692482 | 0.413 | 9 |
| ATP1B1 | 0.940 | 2.501021 | 0.440 | 9 |
| C1QL1 | 0.921 | 2.473758 | 0.421 | 9 |
| CBLN2 | 0.903 | 2.412823 | 0.403 | 9 |
| MARCKS | 0.932 | 2.121128 | 0.432 | 9 |
| SNHG11 | 0.938 | 2.107667 | 0.438 | 9 |
| OLFM3 | 0.817 | 2.099649 | 0.317 | 9 |
| FILIP1L | 0.824 | 2.028323 | 0.324 | 9 |
| SLC6A1 | 0.888 | 1.981368 | 0.388 | 9 |
| NRXN2 | 0.882 | 1.930215 | 0.382 | 9 |
| GAD1 | 0.888 | 1.921463 | 0.388 | 9 |
| CACNA2D2 | 0.851 | 1.807684 | 0.351 | 9 |
| CHGA | 0.879 | 1.793344 | 0.379 | 9 |
| C1QL2 | 0.838 | 1.774575 | 0.338 | 9 |
| BASP1 | 0.866 | 1.743280 | 0.366 | 9 |
| GAP43 | 0.818 | 1.741537 | 0.318 | 9 |
| IGFBP2 | 0.769 | 1.726564 | 0.269 | 9 |
| TBX3 | 0.788 | 1.699690 | 0.288 | 9 |
| TFAP2A | 0.806 | 1.692081 | 0.306 | 9 |
| SYT7 | 0.773 | 1.670252 | 0.273 | 9 |
| LRRN3 | 0.806 | 1.657383 | 0.306 | 9 |
| ADARB1 | 0.839 | 1.646173 | 0.339 | 9 |
| UCHL1 | 0.864 | 1.644685 | 0.364 | 9 |
| PAX6 | 0.862 | 1.638791 | 0.362 | 9 |
| MEG3 | 0.907 | 1.603859 | 0.407 | 9 |
| DTNBP1 | 0.818 | 1.591595 | 0.318 | 9 |
| 6430548M08RIK | 0.838 | 1.587475 | 0.338 | 9 |
| ELAVL3 | 0.838 | 1.578197 | 0.338 | 9 |
| KCNAB1 | 0.817 | 1.568133 | 0.317 | 9 |
| GNG2 | 0.797 | 1.564002 | 0.297 | 9 |
| NPTX2 | 0.756 | 1.555687 | 0.256 | 9 |
| AI593442 | 0.796 | 1.544986 | 0.296 | 9 |
| CELF4 | 0.886 | 1.538491 | 0.386 | 9 |
| FRMD5 | 0.828 | 1.522471 | 0.328 | 9 |
| EEF1E1 | 0.810 | 1.514397 | 0.310 | 9 |
| WBSCR17 | 0.788 | 1.491530 | 0.288 | 9 |
| PDE3A | 0.761 | 1.485254 | 0.261 | 9 |
| RGS8 | 0.793 | 1.484142 | 0.293 | 9 |
| ELOVL6 | 0.784 | 1.477738 | 0.284 | 9 |
| MEIS2 | 0.840 | 1.475665 | 0.340 | 9 |
| GNG3 | 0.848 | 1.474628 | 0.348 | 9 |
| SLC32A1 | 0.815 | 1.466099 | 0.315 | 9 |
| ID4 | 0.756 | 1.412435 | 0.256 | 9 |
| SYNPR | 0.826 | 1.410647 | 0.326 | 9 |
| PRKAR2B | 0.775 | 1.395009 | 0.275 | 9 |
| LIN7A | 0.849 | 1.394313 | 0.349 | 9 |
| MAPT | 0.808 | 1.376944 | 0.308 | 9 |
| GABRA3 | 0.779 | 1.365007 | 0.279 | 9 |
| RYR2 | 0.766 | 1.360686 | 0.266 | 9 |
| NDRG4 | 0.822 | 1.358598 | 0.322 | 9 |
| PRKCE | 0.808 | 1.355495 | 0.308 | 9 |
| LOXL2 | 0.729 | 1.349178 | 0.229 | 9 |
| ATP2B4 | 0.739 | 1.348942 | 0.239 | 9 |
| NETO2 | 0.745 | 1.311499 | 0.245 | 9 |
| ALDOC | 0.789 | 1.306160 | 0.289 | 9 |
| WDR1 | 0.781 | 1.305461 | 0.281 | 9 |
| GRIA3 | 0.760 | 1.295841 | 0.260 | 9 |
| PHACTR3 | 0.773 | 1.289285 | 0.273 | 9 |
| FABP3 | 0.744 | 1.276022 | 0.244 | 9 |
| TUBB2A | 0.815 | 1.274976 | 0.315 | 9 |
| LSAMP | 0.793 | 1.272650 | 0.293 | 9 |
| SLC6A11 | 0.755 | 1.267563 | 0.255 | 9 |
| DLGAP1 | 0.769 | 1.263219 | 0.269 | 9 |
| NAV1 | 0.788 | 1.259667 | 0.288 | 9 |
| CPNE6 | 0.754 | 1.258456 | 0.254 | 9 |
| TMEM191C | 0.749 | 1.258008 | 0.249 | 9 |
| SOX5 | 0.723 | 1.251003 | 0.223 | 9 |
| CPLX3 | 0.800 | 1.243626 | 0.300 | 9 |
| BC048943 | 0.813 | 1.230504 | 0.313 | 9 |
| SEMA6A | 0.748 | 1.229853 | 0.248 | 9 |
| CCDC88B | 0.726 | 1.229532 | 0.226 | 9 |
| STMN3 | 0.814 | 1.228264 | 0.314 | 9 |
| CLMP | 0.711 | 1.227889 | 0.211 | 9 |
| HABP4 | 0.785 | 1.219840 | 0.285 | 9 |
| KIF5C | 0.805 | 1.219184 | 0.305 | 9 |
| MARCKSL1 | 0.788 | 1.217008 | 0.288 | 9 |
| VSNL1 | 0.757 | 1.216340 | 0.257 | 9 |
| LHX9 | 0.721 | 1.197847 | 0.221 | 9 |
| GABRG2 | 0.752 | 1.191982 | 0.252 | 9 |
| ARHGAP20 | 0.723 | 1.191230 | 0.223 | 9 |
| KCNA1 | 0.724 | 1.188659 | 0.224 | 9 |
| ATP2B1 | 0.807 | 1.184449 | 0.307 | 9 |
| TPM1 | 0.770 | 1.181575 | 0.270 | 9 |
| SV2A | 0.806 | 1.181132 | 0.306 | 9 |
| NSG1 | 0.782 | 1.178500 | 0.282 | 9 |
| TTC3 | 0.842 | 1.174244 | 0.342 | 9 |
| NAP1L5 | 0.796 | 1.164618 | 0.296 | 9 |
| A030009H04RIK | 0.780 | 1.164223 | 0.280 | 9 |
| DPYSL2 | 0.770 | 1.157861 | 0.270 | 9 |
| THY1 | 0.740 | 1.146696 | 0.240 | 9 |
| GPRASP1 | 0.810 | 1.145215 | 0.310 | 9 |
| SPOCK3 | 0.767 | 1.142882 | 0.267 | 9 |
| MLLT11 | 0.780 | 1.141012 | 0.280 | 9 |
| RTN1 | 0.809 | 1.140966 | 0.309 | 9 |
| CHD3 | 0.776 | 1.135535 | 0.276 | 9 |
| HSD17B12 | 0.790 | 1.135531 | 0.290 | 9 |
| RUNX1T1 | 0.759 | 1.130153 | 0.259 | 9 |
| ITM2C | 0.799 | 1.124268 | 0.299 | 9 |
| HSP90AB1 | 0.842 | 1.112076 | 0.342 | 9 |
| SRGAP3 | 0.742 | 1.110121 | 0.242 | 9 |
| GNAS | 0.841 | 1.102581 | 0.341 | 9 |
| CHGB | 0.803 | 1.091361 | 0.303 | 9 |
| NSG2 | 0.757 | 1.091212 | 0.257 | 9 |
| OXR1 | 0.757 | 1.084787 | 0.257 | 9 |
| SYT11 | 0.778 | 1.081871 | 0.278 | 9 |
| CYFIP2 | 0.748 | 1.077168 | 0.248 | 9 |
| ZEB2 | 0.742 | 1.075057 | 0.242 | 9 |
| DPP6 | 0.743 | 1.072735 | 0.243 | 9 |
| CD47 | 0.784 | 1.071126 | 0.284 | 9 |
| IMPACT | 0.764 | 1.070542 | 0.264 | 9 |
| HSPA12A | 0.755 | 1.068676 | 0.255 | 9 |
| SH3BP5 | 0.716 | 1.067537 | 0.216 | 9 |
| RBFOX2 | 0.741 | 1.063177 | 0.241 | 9 |
| TPPP | 0.713 | 1.062940 | 0.213 | 9 |
| SNCB | 0.789 | 1.062761 | 0.289 | 9 |
| COL23A1 | 0.760 | 1.056620 | 0.260 | 9 |
| CALM3 | 0.777 | 1.053213 | 0.277 | 9 |
| TKT | 0.775 | 1.051475 | 0.275 | 9 |
| EPB4.1L4A | 0.701 | 1.043584 | 0.201 | 9 |
| FBXO32 | 0.705 | 1.032729 | 0.205 | 9 |
| GM1673 | 0.732 | 1.019184 | 0.232 | 9 |
| FAM115A | 0.749 | 1.016772 | 0.249 | 9 |
| ECE1 | 0.704 | 1.007563 | 0.204 | 9 |
| YWHAG | 0.760 | 1.007454 | 0.260 | 9 |
| GNB1 | 0.254 | −1.559334 | 0.246 | 9 |
| HMGN1 | 0.215 | −1.594457 | 0.285 | 9 |
| RP1 | 0.248 | −1.629751 | 0.252 | 9 |
| UNC119 | 0.267 | −1.642090 | 0.233 | 9 |
| NR2E3 | 0.271 | −1.829500 | 0.229 | 9 |
| CNGA1 | 0.268 | −1.870963 | 0.232 | 9 |
| TULP1 | 0.211 | −1.901678 | 0.289 | 9 |
| ROM1 | 0.231 | −1.909354 | 0.269 | 9 |
| RPGRIP1 | 0.259 | −1.928781 | 0.241 | 9 |
| NRL | 0.257 | −1.975762 | 0.243 | 9 |
| PRPH2 | 0.194 | −1.981809 | 0.306 | 9 |
| SLC24A1 | 0.266 | −1.993990 | 0.234 | 9 |
| PDE6G | 0.205 | −2.045103 | 0.295 | 9 |
| RS1 | 0.259 | −2.057027 | 0.241 | 9 |
| PDE6B | 0.227 | −2.071134 | 0.273 | 9 |
| RCVRN | 0.215 | −2.076463 | 0.285 | 9 |
| GNAT1 | 0.204 | −2.091716 | 0.296 | 9 |
| SAG | 0.157 | −2.182196 | 0.343 | 9 |

TABLE 6-continued

Genes differentially expressed in each of the 39 retinal cell clusters.

| | | | | |
|---|---|---|---|---|
| PDC | 0.170 | −2.185807 | 0.330 | 9 |
| RHO | 0.163 | −2.201967 | 0.337 | 9 |
| GNGT1 | 0.163 | −2.222527 | 0.337 | 9 |
| cluster no. 10 DE = 120 | | | | |
| VIP | 0.767 | 3.830134 | 0.267 | 10 |
| CARTPT | 0.830 | 2.551837 | 0.330 | 10 |
| CBLN2 | 0.897 | 2.371861 | 0.397 | 10 |
| SLC6A1 | 0.912 | 2.250550 | 0.412 | 10 |
| GABRA2 | 0.841 | 2.143980 | 0.341 | 10 |
| SNHG11 | 0.945 | 2.134197 | 0.445 | 10 |
| NR4A2 | 0.835 | 2.098562 | 0.335 | 10 |
| NNAT | 0.800 | 2.051593 | 0.300 | 10 |
| CBLN4 | 0.727 | 2.045730 | 0.227 | 10 |
| TFAP2B | 0.876 | 2.024379 | 0.376 | 10 |
| GAD1 | 0.855 | 1.986823 | 0.355 | 10 |
| 6430548M08RIK | 0.876 | 1.940600 | 0.376 | 10 |
| NAP1L5 | 0.892 | 1.812106 | 0.392 | 10 |
| NRSN1 | 0.822 | 1.779217 | 0.322 | 10 |
| GRIA3 | 0.750 | 1.767426 | 0.250 | 10 |
| MEG3 | 0.912 | 1.766291 | 0.412 | 10 |
| SYT6 | 0.739 | 1.722186 | 0.239 | 10 |
| GAD2 | 0.795 | 1.711410 | 0.295 | 10 |
| CELF4 | 0.909 | 1.695323 | 0.409 | 10 |
| 2900011O08RIK | 0.847 | 1.663963 | 0.347 | 10 |
| STMN4 | 0.794 | 1.657861 | 0.294 | 10 |
| ATP1B1 | 0.885 | 1.613084 | 0.385 | 10 |
| RAB3C | 0.824 | 1.612804 | 0.324 | 10 |
| CACNA2D2 | 0.800 | 1.543215 | 0.300 | 10 |
| TKT | 0.827 | 1.542467 | 0.327 | 10 |
| MARCKS | 0.861 | 1.534529 | 0.361 | 10 |
| RNF220 | 0.820 | 1.519204 | 0.320 | 10 |
| PAX6 | 0.826 | 1.494666 | 0.326 | 10 |
| GAP43 | 0.736 | 1.494533 | 0.236 | 10 |
| ELAVL3 | 0.829 | 1.476012 | 0.329 | 10 |
| LRRTM1 | 0.745 | 1.466343 | 0.245 | 10 |
| 4833424O15RIK | 0.735 | 1.455809 | 0.235 | 10 |
| NDRG4 | 0.835 | 1.451943 | 0.335 | 10 |
| SLC32A1 | 0.824 | 1.449471 | 0.324 | 10 |
| HS6ST2 | 0.717 | 1.430399 | 0.217 | 10 |
| SYT1 | 0.914 | 1.419385 | 0.414 | 10 |
| GNG2 | 0.765 | 1.399822 | 0.265 | 10 |
| ZCCHC12 | 0.711 | 1.393990 | 0.211 | 10 |
| UCHL1 | 0.797 | 1.376379 | 0.297 | 10 |
| HLF | 0.815 | 1.374388 | 0.315 | 10 |
| VSNL1 | 0.745 | 1.358259 | 0.245 | 10 |
| GNG3 | 0.826 | 1.316743 | 0.326 | 10 |
| A030009H04RIK | 0.787 | 1.309649 | 0.287 | 10 |
| TTC3 | 0.866 | 1.305950 | 0.366 | 10 |
| BASP1 | 0.796 | 1.302431 | 0.296 | 10 |
| GPM6A | 0.847 | 1.301211 | 0.347 | 10 |
| SYNPR | 0.808 | 1.298962 | 0.308 | 10 |
| TAGLN3 | 0.796 | 1.289770 | 0.296 | 10 |
| DLGAP1 | 0.744 | 1.260355 | 0.244 | 10 |
| GPRASP1 | 0.802 | 1.252102 | 0.302 | 10 |
| SLC6A11 | 0.734 | 1.251426 | 0.234 | 10 |
| KIF5C | 0.790 | 1.248227 | 0.290 | 10 |
| NDN | 0.799 | 1.209617 | 0.299 | 10 |
| ELAVL4 | 0.715 | 1.195958 | 0.215 | 10 |
| GABRG2 | 0.766 | 1.191704 | 0.266 | 10 |
| NSG2 | 0.748 | 1.180941 | 0.248 | 10 |
| RUNX1T1 | 0.711 | 1.177126 | 0.211 | 10 |
| PNMAL2 | 0.766 | 1.175260 | 0.266 | 10 |
| NSG1 | 0.771 | 1.173586 | 0.271 | 10 |
| CHD5 | 0.711 | 1.168834 | 0.211 | 10 |
| SV2A | 0.812 | 1.167811 | 0.312 | 10 |
| GABRA3 | 0.702 | 1.163683 | 0.202 | 10 |
| BEX1 | 0.754 | 1.160868 | 0.254 | 10 |
| GRM1 | 0.704 | 1.158057 | 0.204 | 10 |
| NGFRAP1 | 0.793 | 1.157896 | 0.293 | 10 |
| SPOCK3 | 0.730 | 1.139949 | 0.230 | 10 |
| 6330403K07RIK | 0.723 | 1.136823 | 0.223 | 10 |
| IMPACT | 0.756 | 1.136763 | 0.256 | 10 |
| GRIA4 | 0.705 | 1.134038 | 0.205 | 10 |
| STMN2 | 0.719 | 1.126131 | 0.219 | 10 |
| MAPT | 0.773 | 1.125378 | 0.273 | 10 |
| MARCKSL1 | 0.764 | 1.124830 | 0.264 | 10 |
| PAK3 | 0.730 | 1.118891 | 0.230 | 10 |
| ZCCHC18 | 0.765 | 1.116777 | 0.265 | 10 |
| CACNG3 | 0.702 | 1.116442 | 0.202 | 10 |
| GRIA2 | 0.788 | 1.114119 | 0.288 | 10 |
| YWHAH | 0.753 | 1.111748 | 0.253 | 10 |
| SYT4 | 0.745 | 1.111249 | 0.245 | 10 |
| TCEAL5 | 0.733 | 1.104752 | 0.233 | 10 |
| SYT11 | 0.783 | 1.101958 | 0.283 | 10 |
| STMN3 | 0.750 | 1.099315 | 0.250 | 10 |
| NRXN2 | 0.768 | 1.098278 | 0.268 | 10 |
| SLC22A17 | 0.754 | 1.090749 | 0.254 | 10 |
| LY6H | 0.721 | 1.080063 | 0.221 | 10 |
| FXYD6 | 0.727 | 1.064334 | 0.227 | 10 |
| FAM115A | 0.734 | 1.055395 | 0.234 | 10 |
| GM1673 | 0.723 | 1.055283 | 0.223 | 10 |
| GNAS | 0.822 | 1.047020 | 0.322 | 10 |
| APP | 0.755 | 1.039216 | 0.255 | 10 |
| CACNG4 | 0.730 | 1.037850 | 0.230 | 10 |
| ZWINT | 0.752 | 1.036807 | 0.252 | 10 |
| TMEM130 | 0.701 | 1.032886 | 0.201 | 10 |
| D3BWG0562E | 0.716 | 1.025310 | 0.216 | 10 |
| LIN7A | 0.775 | 1.021321 | 0.275 | 10 |
| MLLT11 | 0.750 | 1.017950 | 0.250 | 10 |
| RTN1 | 0.801 | 1.016598 | 0.301 | 10 |
| BEX2 | 0.797 | 1.008599 | 0.297 | 10 |
| SNRPN | 0.753 | 1.000211 | 0.253 | 10 |
| GNB1 | 0.252 | −1.543483 | 0.248 | 10 |
| HMGN1 | 0.216 | −1.579673 | 0.284 | 10 |
| CNGA1 | 0.274 | −1.673428 | 0.226 | 10 |
| UNC119 | 0.245 | −1.746828 | 0.255 | 10 |
| NRL | 0.262 | −1.796001 | 0.238 | 10 |
| NEUROD1 | 0.277 | −1.806110 | 0.223 | 10 |
| NR2E3 | 0.256 | −1.883207 | 0.244 | 10 |
| PDE6B | 0.229 | −1.927154 | 0.271 | 10 |
| ROM1 | 0.218 | −1.942172 | 0.282 | 10 |
| RP1 | 0.231 | −1.972704 | 0.269 | 10 |
| TULP1 | 0.205 | −1.993368 | 0.295 | 10 |
| PRPH2 | 0.192 | −2.009075 | 0.308 | 10 |
| RCVRN | 0.217 | −2.034673 | 0.283 | 10 |
| PDE6G | 0.197 | −2.035379 | 0.303 | 10 |
| GNAT1 | 0.205 | −2.035699 | 0.295 | 10 |
| SLC24A1 | 0.258 | −2.054582 | 0.242 | 10 |
| GNGT1 | 0.164 | −2.075342 | 0.336 | 10 |
| RS1 | 0.255 | −2.087538 | 0.245 | 10 |
| RPGRIP1 | 0.240 | −2.097159 | 0.260 | 10 |
| SAG | 0.155 | −2.153542 | 0.345 | 10 |
| PDC | 0.169 | −2.178552 | 0.331 | 10 |
| RHO | 0.160 | −2.190204 | 0.340 | 10 |
| cluster no. 11 DE = 111 | | | | |
| SLC6A1 | 0.931 | 2.333915 | 0.431 | 11 |
| PCDH17 | 0.863 | 2.136196 | 0.363 | 11 |
| DNER | 0.885 | 2.116049 | 0.385 | 11 |
| ID4 | 0.806 | 2.095898 | 0.306 | 11 |
| TFAP2B | 0.830 | 2.083132 | 0.330 | 11 |
| SNHG11 | 0.930 | 2.057025 | 0.430 | 11 |
| SYT7 | 0.813 | 2.030645 | 0.313 | 11 |
| ATP1B1 | 0.914 | 1.999429 | 0.414 | 11 |
| GAD1 | 0.851 | 1.909032 | 0.351 | 11 |
| MEIS2 | 0.877 | 1.853622 | 0.377 | 11 |
| SYNPR | 0.879 | 1.830302 | 0.379 | 11 |
| SPARCL1 | 0.787 | 1.809269 | 0.287 | 11 |
| FRMD5 | 0.838 | 1.786740 | 0.338 | 11 |
| TKT | 0.863 | 1.751565 | 0.363 | 11 |
| GRIA2 | 0.861 | 1.721134 | 0.361 | 11 |
| AI848285 | 0.734 | 1.720216 | 0.234 | 11 |
| GFRA1 | 0.753 | 1.715834 | 0.253 | 11 |
| MEG3 | 0.905 | 1.705098 | 0.405 | 11 |
| NDRG4 | 0.850 | 1.687578 | 0.350 | 11 |
| NAP1L5 | 0.848 | 1.685433 | 0.348 | 11 |
| PAX6 | 0.822 | 1.680286 | 0.322 | 11 |
| ESRRG | 0.754 | 1.614605 | 0.254 | 11 |
| PTPRT | 0.714 | 1.601504 | 0.214 | 11 |
| NRXN2 | 0.825 | 1.588975 | 0.325 | 11 |
| 6430548M08RIK | 0.813 | 1.574957 | 0.313 | 11 |
| ADARB1 | 0.801 | 1.564237 | 0.301 | 11 |
| ELAVL3 | 0.828 | 1.553803 | 0.328 | 11 |
| BASP1 | 0.839 | 1.545173 | 0.339 | 11 |
| GAD2 | 0.764 | 1.519852 | 0.264 | 11 |

TABLE 6-continued

Genes differentially expressed in each of the 39 retinal cell clusters.

| | | | | |
|---|---|---|---|---|
| ZFHX3 | 0.783 | 1.488418 | 0.283 | 11 |
| GABRG2 | 0.811 | 1.485814 | 0.311 | 11 |
| CACNA2D2 | 0.763 | 1.479819 | 0.263 | 11 |
| VSNL1 | 0.757 | 1.475157 | 0.257 | 11 |
| SV2A | 0.838 | 1.462079 | 0.338 | 11 |
| CELF4 | 0.867 | 1.458085 | 0.367 | 11 |
| DPP6 | 0.778 | 1.451701 | 0.278 | 11 |
| DUSP26 | 0.785 | 1.449344 | 0.285 | 11 |
| CHN2 | 0.719 | 1.444832 | 0.219 | 11 |
| TSHZ1 | 0.701 | 1.403224 | 0.201 | 11 |
| DYNC1I1 | 0.719 | 1.398013 | 0.219 | 11 |
| DLGAP1 | 0.763 | 1.388125 | 0.263 | 11 |
| SLC32A1 | 0.776 | 1.339618 | 0.276 | 11 |
| APP | 0.827 | 1.335361 | 0.327 | 11 |
| VSTM2B | 0.708 | 1.333834 | 0.208 | 11 |
| 2900011O08RIK | 0.788 | 1.318652 | 0.288 | 11 |
| LDHB | 0.766 | 1.315407 | 0.266 | 11 |
| SPOCK3 | 0.772 | 1.315060 | 0.272 | 11 |
| TTC3 | 0.855 | 1.308993 | 0.355 | 11 |
| ELAVL4 | 0.723 | 1.307010 | 0.223 | 11 |
| CYGB | 0.743 | 1.300364 | 0.243 | 11 |
| NRSN1 | 0.756 | 1.299498 | 0.256 | 11 |
| GNG3 | 0.804 | 1.280594 | 0.304 | 11 |
| NRXN1 | 0.725 | 1.273732 | 0.225 | 11 |
| KIF5C | 0.766 | 1.262018 | 0.266 | 11 |
| TMEM191C | 0.728 | 1.250965 | 0.228 | 11 |
| RIT2 | 0.737 | 1.246639 | 0.237 | 11 |
| PCP4 | 0.706 | 1.237709 | 0.206 | 11 |
| RGS8 | 0.709 | 1.234002 | 0.209 | 11 |
| PNMAL2 | 0.770 | 1.228431 | 0.270 | 11 |
| STMN3 | 0.807 | 1.225751 | 0.307 | 11 |
| FABP3 | 0.704 | 1.222551 | 0.204 | 11 |
| CALY | 0.729 | 1.220655 | 0.229 | 11 |
| CHN1 | 0.749 | 1.219803 | 0.249 | 11 |
| A030009H04RIK | 0.740 | 1.205040 | 0.240 | 11 |
| SIX6 | 0.711 | 1.201685 | 0.211 | 11 |
| DKK3 | 0.804 | 1.196969 | 0.304 | 11 |
| GPRASP1 | 0.788 | 1.175368 | 0.288 | 11 |
| TMX4 | 0.746 | 1.167458 | 0.246 | 11 |
| DHCR24 | 0.702 | 1.159663 | 0.202 | 11 |
| SYT11 | 0.750 | 1.142552 | 0.250 | 11 |
| NSG2 | 0.709 | 1.124489 | 0.209 | 11 |
| RPH3A | 0.713 | 1.118261 | 0.213 | 11 |
| AUTS2 | 0.710 | 1.102486 | 0.210 | 11 |
| GPM6A | 0.778 | 1.101162 | 0.278 | 11 |
| CYFIP2 | 0.731 | 1.094488 | 0.231 | 11 |
| CD47 | 0.738 | 1.094214 | 0.238 | 11 |
| GRIA4 | 0.709 | 1.066388 | 0.209 | 11 |
| PBX1 | 0.760 | 1.064081 | 0.260 | 11 |
| PRKACB | 0.721 | 1.048412 | 0.221 | 11 |
| SYT4 | 0.708 | 1.043194 | 0.208 | 11 |
| MAPT | 0.729 | 1.037623 | 0.229 | 11 |
| SERINC1 | 0.789 | 1.037343 | 0.289 | 11 |
| GABRA1 | 0.728 | 1.031688 | 0.228 | 11 |
| TAGLN3 | 0.715 | 1.030901 | 0.215 | 11 |
| ZWINT | 0.730 | 1.019322 | 0.230 | 11 |
| KCNC1 | 0.722 | 1.018621 | 0.222 | 11 |
| CHD3 | 0.705 | 1.017770 | 0.205 | 11 |
| ATP6V1G2 | 0.717 | 1.016268 | 0.217 | 11 |
| SNCB | 0.769 | 1.015930 | 0.269 | 11 |
| HMGN1 | 0.215 | −1.563282 | 0.285 | 11 |
| GNB1 | 0.242 | −1.670947 | 0.258 | 11 |
| NEUROD1 | 0.282 | −1.681634 | 0.218 | 11 |
| UNC119 | 0.251 | −1.717318 | 0.249 | 11 |
| NR2E3 | 0.268 | −1.718845 | 0.232 | 11 |
| CNGA1 | 0.260 | −1.814289 | 0.240 | 11 |
| ROM1 | 0.231 | −1.833284 | 0.269 | 11 |
| SLC24A1 | 0.277 | −1.869445 | 0.223 | 11 |
| RPGRIP1 | 0.248 | −1.918559 | 0.252 | 11 |
| TULP1 | 0.204 | −1.929248 | 0.296 | 11 |
| RS1 | 0.257 | −1.929959 | 0.243 | 11 |
| RP1 | 0.229 | −1.939595 | 0.271 | 11 |
| NRL | 0.255 | −1.968506 | 0.245 | 11 |
| PRPH2 | 0.194 | −1.989465 | 0.306 | 11 |
| PDE6B | 0.225 | −2.074086 | 0.275 | 11 |
| RCVRN | 0.214 | −2.090257 | 0.286 | 11 |
| GNAT1 | 0.200 | −2.097595 | 0.300 | 11 |
| RHO | 0.164 | −2.136073 | 0.336 | 11 |
| PDE6G | 0.195 | −2.169314 | 0.305 | 11 |
| PDC | 0.164 | −2.204122 | 0.336 | 11 |
| SAG | 0.152 | −2.236181 | 0.348 | 11 |
| GNGT1 | 0.154 | −2.283434 | 0.346 | 11 |
| cluster no. 12 DE = 68 | | | | |
| SLC6A1 | 0.874 | 2.180099 | 0.374 | 12 |
| CBLN2 | 0.754 | 1.928113 | 0.254 | 12 |
| PAX6 | 0.828 | 1.886874 | 0.328 | 12 |
| TKT | 0.826 | 1.848995 | 0.326 | 12 |
| SNHG11 | 0.868 | 1.828275 | 0.368 | 12 |
| TFAP2B | 0.804 | 1.768165 | 0.304 | 12 |
| NAP1L5 | 0.824 | 1.752147 | 0.324 | 12 |
| GAD1 | 0.768 | 1.707274 | 0.268 | 12 |
| PCDH10 | 0.714 | 1.651388 | 0.214 | 12 |
| SIX3 | 0.714 | 1.622442 | 0.214 | 12 |
| MEG3 | 0.863 | 1.616915 | 0.363 | 12 |
| CELF4 | 0.845 | 1.583306 | 0.345 | 12 |
| ATP1B1 | 0.822 | 1.555753 | 0.322 | 12 |
| SYNPR | 0.745 | 1.536495 | 0.245 | 12 |
| 2900011O08RIK | 0.770 | 1.510272 | 0.270 | 12 |
| CACNG4 | 0.753 | 1.474837 | 0.253 | 12 |
| FRMD5 | 0.749 | 1.458548 | 0.249 | 12 |
| MEIS2 | 0.722 | 1.457447 | 0.222 | 12 |
| ZFHX3 | 0.712 | 1.448061 | 0.212 | 12 |
| BASP1 | 0.781 | 1.447063 | 0.281 | 12 |
| RPH3A | 0.721 | 1.422091 | 0.221 | 12 |
| GRIA2 | 0.795 | 1.402898 | 0.295 | 12 |
| GUCY1A3 | 0.713 | 1.393783 | 0.213 | 12 |
| DPYSL4 | 0.718 | 1.360517 | 0.218 | 12 |
| PNMAL2 | 0.744 | 1.343839 | 0.244 | 12 |
| RUNX1T1 | 0.713 | 1.335288 | 0.213 | 12 |
| ELAVL3 | 0.748 | 1.329163 | 0.248 | 12 |
| RAB3C | 0.710 | 1.324800 | 0.210 | 12 |
| NRSN1 | 0.721 | 1.306849 | 0.221 | 12 |
| UCHL1 | 0.736 | 1.300785 | 0.236 | 12 |
| TTC3 | 0.832 | 1.295748 | 0.332 | 12 |
| ADARB1 | 0.723 | 1.277937 | 0.223 | 12 |
| GNG3 | 0.765 | 1.263270 | 0.265 | 12 |
| NDRG4 | 0.744 | 1.253376 | 0.244 | 12 |
| A030009H04RIK | 0.706 | 1.252601 | 0.206 | 12 |
| SV2A | 0.785 | 1.240701 | 0.285 | 12 |
| DUSP26 | 0.715 | 1.211692 | 0.215 | 12 |
| APC | 0.753 | 1.150275 | 0.253 | 12 |
| GPRASP1 | 0.737 | 1.147836 | 0.237 | 12 |
| GPM6A | 0.752 | 1.141256 | 0.252 | 12 |
| TMX4 | 0.707 | 1.122604 | 0.207 | 12 |
| RTN1 | 0.749 | 1.119089 | 0.249 | 12 |
| NRXN2 | 0.709 | 1.113600 | 0.209 | 12 |
| LDHB | 0.705 | 1.097431 | 0.205 | 12 |
| NGFRAP1 | 0.709 | 1.075985 | 0.209 | 12 |
| NDN | 0.708 | 1.061856 | 0.208 | 12 |
| BEX2 | 0.754 | 1.041420 | 0.254 | 12 |
| MARCKS | 0.731 | 1.019699 | 0.231 | 12 |
| HMGN1 | 0.250 | −1.195481 | 0.250 | 12 |
| GNB1 | 0.268 | −1.266009 | 0.232 | 12 |
| RP1 | 0.280 | −1.277829 | 0.220 | 12 |
| NR2E3 | 0.296 | −1.336009 | 0.204 | 12 |
| RPGRIP1 | 0.290 | −1.341698 | 0.210 | 12 |
| RCVRN | 0.261 | −1.376084 | 0.239 | 12 |
| NRL | 0.292 | −1.393005 | 0.208 | 12 |
| UNC119 | 0.266 | −1.397189 | 0.234 | 12 |
| PRPH2 | 0.232 | −1.433849 | 0.268 | 12 |
| TULP1 | 0.238 | −1.438510 | 0.262 | 12 |
| ROM1 | 0.258 | −1.441911 | 0.242 | 12 |
| RS1 | 0.292 | −1.451877 | 0.208 | 12 |
| PDE6B | 0.265 | −1.484310 | 0.235 | 12 |
| GNAT1 | 0.238 | −1.516590 | 0.262 | 12 |
| CNGA1 | 0.285 | −1.525788 | 0.215 | 12 |
| RHO | 0.205 | −1.537955 | 0.295 | 12 |
| SAG | 0.196 | −1.550193 | 0.304 | 12 |
| PDC | 0.212 | −1.561538 | 0.288 | 12 |
| GNGT1 | 0.204 | −1.581874 | 0.296 | 12 |
| PDE6G | 0.228 | −1.637557 | 0.272 | 12 |
| cluster no. 13 DE = 163 | | | | |
| SCG2 | 0.963 | 2.746757 | 0.463 | 13 |
| LAMP5 | 0.949 | 2.686845 | 0.449 | 13 |

TABLE 6-continued

Genes differentially expressed in each of the 39 retinal cell clusters.

| Gene | | | | |
|---|---|---|---|---|
| TFAP2B | 0.960 | 2.600604 | 0.460 | 13 |
| SLC6A1 | 0.939 | 2.455520 | 0.439 | 13 |
| GAD1 | 0.910 | 2.214303 | 0.410 | 13 |
| RASGRP1 | 0.917 | 2.098422 | 0.417 | 13 |
| CBLN2 | 0.897 | 2.019754 | 0.397 | 13 |
| GAP43 | 0.868 | 2.007008 | 0.368 | 13 |
| GRIA3 | 0.912 | 1.939880 | 0.412 | 13 |
| SNHG11 | 0.940 | 1.931816 | 0.440 | 13 |
| PCDH17 | 0.888 | 1.870311 | 0.388 | 13 |
| CBLN1 | 0.848 | 1.804900 | 0.348 | 13 |
| TAGLN3 | 0.895 | 1.804474 | 0.395 | 13 |
| GM2694 | 0.836 | 1.763564 | 0.336 | 13 |
| TFAP2A | 0.867 | 1.742085 | 0.367 | 13 |
| SPARCL1 | 0.896 | 1.727535 | 0.396 | 13 |
| PDGFRA | 0.838 | 1.722897 | 0.338 | 13 |
| RAB3C | 0.902 | 1.716234 | 0.402 | 13 |
| NAP1L5 | 0.901 | 1.703198 | 0.401 | 13 |
| GUCY1A3 | 0.893 | 1.681253 | 0.393 | 13 |
| CELF4 | 0.919 | 1.676011 | 0.419 | 13 |
| SPOCK3 | 0.903 | 1.642174 | 0.403 | 13 |
| LNX1 | 0.863 | 1.623297 | 0.363 | 13 |
| SEMA3A | 0.816 | 1.615345 | 0.316 | 13 |
| LRRTM1 | 0.867 | 1.602351 | 0.367 | 13 |
| NSG1 | 0.838 | 1.594951 | 0.338 | 13 |
| TMEM179 | 0.841 | 1.593475 | 0.341 | 13 |
| FRMD5 | 0.886 | 1.585843 | 0.386 | 13 |
| ATP1B1 | 0.912 | 1.585191 | 0.412 | 13 |
| AI593442 | 0.845 | 1.575313 | 0.345 | 13 |
| GJC1 | 0.793 | 1.560209 | 0.293 | 13 |
| CYGB | 0.879 | 1.519598 | 0.379 | 13 |
| PHLDA1 | 0.818 | 1.515132 | 0.318 | 13 |
| MEG3 | 0.909 | 1.503058 | 0.409 | 13 |
| DPP6 | 0.886 | 1.502219 | 0.386 | 13 |
| DKK3 | 0.892 | 1.481844 | 0.392 | 13 |
| KCNIP1 | 0.855 | 1.481648 | 0.355 | 13 |
| NDRG4 | 0.878 | 1.480199 | 0.378 | 13 |
| SYN2 | 0.844 | 1.477726 | 0.344 | 13 |
| SLC32A1 | 0.856 | 1.462162 | 0.356 | 13 |
| ELAVL4 | 0.818 | 1.457094 | 0.318 | 13 |
| ISOC1 | 0.759 | 1.449689 | 0.259 | 13 |
| ALDOC | 0.874 | 1.444666 | 0.374 | 13 |
| FNBP1L | 0.829 | 1.440875 | 0.329 | 13 |
| ELAVL3 | 0.862 | 1.418171 | 0.362 | 13 |
| SV2A | 0.891 | 1.416160 | 0.391 | 13 |
| GRIA4 | 0.865 | 1.408494 | 0.365 | 13 |
| RGS17 | 0.785 | 1.404754 | 0.285 | 13 |
| UCHL1 | 0.837 | 1.390501 | 0.337 | 13 |
| NRSN1 | 0.875 | 1.376384 | 0.375 | 13 |
| PTPRM | 0.803 | 1.366832 | 0.303 | 13 |
| NSG2 | 0.858 | 1.361192 | 0.358 | 13 |
| DNM3 | 0.890 | 1.359611 | 0.390 | 13 |
| CLMP | 0.784 | 1.357481 | 0.284 | 13 |
| GNG3 | 0.838 | 1.348245 | 0.338 | 13 |
| 2900011O08RIK | 0.845 | 1.338735 | 0.345 | 13 |
| LHX9 | 0.815 | 1.337030 | 0.315 | 13 |
| VAMP4 | 0.854 | 1.335530 | 0.354 | 13 |
| CAMKV | 0.815 | 1.331781 | 0.315 | 13 |
| DTNBP1 | 0.846 | 1.329320 | 0.346 | 13 |
| GAD2 | 0.805 | 1.326719 | 0.305 | 13 |
| ANK3 | 0.838 | 1.323306 | 0.338 | 13 |
| BASP1 | 0.865 | 1.316675 | 0.365 | 13 |
| FGF10 | 0.748 | 1.308488 | 0.248 | 13 |
| STMN3 | 0.861 | 1.296175 | 0.361 | 13 |
| FUT9 | 0.783 | 1.296115 | 0.283 | 13 |
| IMPACT | 0.842 | 1.295463 | 0.342 | 13 |
| SYT4 | 0.862 | 1.289100 | 0.362 | 13 |
| PAX6 | 0.864 | 1.287430 | 0.364 | 13 |
| TENM1 | 0.790 | 1.285335 | 0.290 | 13 |
| MAPT | 0.830 | 1.283527 | 0.330 | 13 |
| RGS8 | 0.823 | 1.279287 | 0.323 | 13 |
| NECAB1 | 0.789 | 1.268538 | 0.289 | 13 |
| GRM1 | 0.751 | 1.253073 | 0.251 | 13 |
| CALN1 | 0.773 | 1.247262 | 0.273 | 13 |
| CACNA2D2 | 0.838 | 1.237957 | 0.338 | 13 |
| ZWINT | 0.860 | 1.220447 | 0.360 | 13 |
| RBFOX2 | 0.793 | 1.217025 | 0.293 | 13 |
| OPCML | 0.772 | 1.212407 | 0.272 | 13 |
| E130218I03RIK | 0.871 | 1.204019 | 0.371 | 13 |
| LMO4 | 0.803 | 1.203676 | 0.303 | 13 |
| ATP6V1G2 | 0.820 | 1.202503 | 0.320 | 13 |
| GABRA2 | 0.761 | 1.202476 | 0.261 | 13 |
| MARCKS | 0.867 | 1.199734 | 0.367 | 13 |
| TCEAL5 | 0.795 | 1.195481 | 0.295 | 13 |
| SYNPR | 0.800 | 1.181298 | 0.300 | 13 |
| GABRA3 | 0.767 | 1.176700 | 0.267 | 13 |
| MLLT11 | 0.810 | 1.174360 | 0.310 | 13 |
| VSTM2L | 0.775 | 1.171942 | 0.275 | 13 |
| A030009H04RIK | 0.799 | 1.167220 | 0.299 | 13 |
| ASPH | 0.848 | 1.166139 | 0.348 | 13 |
| SNRPN | 0.819 | 1.165623 | 0.319 | 13 |
| DNER | 0.814 | 1.158918 | 0.314 | 13 |
| TMEM191C | 0.811 | 1.156170 | 0.311 | 13 |
| PRKAR1A | 0.858 | 1.150894 | 0.358 | 13 |
| TTC3 | 0.867 | 1.150786 | 0.367 | 13 |
| HPGD | 0.742 | 1.145794 | 0.242 | 13 |
| SH3BGRL | 0.818 | 1.143089 | 0.318 | 13 |
| TUBB2A | 0.858 | 1.142518 | 0.358 | 13 |
| ITM2C | 0.855 | 1.132688 | 0.355 | 13 |
| DLG2 | 0.755 | 1.127546 | 0.255 | 13 |
| EPB4.1L4A | 0.758 | 1.123112 | 0.258 | 13 |
| SLC6A5 | 0.757 | 1.122854 | 0.257 | 13 |
| LSAMP | 0.790 | 1.119316 | 0.290 | 13 |
| SLC24A2 | 0.751 | 1.117128 | 0.251 | 13 |
| RUNX1T1 | 0.796 | 1.116379 | 0.296 | 13 |
| SNCB | 0.829 | 1.114629 | 0.329 | 13 |
| CRABP1 | 0.723 | 1.112187 | 0.223 | 13 |
| MARCKSL1 | 0.786 | 1.109417 | 0.286 | 13 |
| NGFRAP1 | 0.841 | 1.105288 | 0.341 | 13 |
| GRIA2 | 0.843 | 1.099977 | 0.343 | 13 |
| LDHB | 0.836 | 1.091893 | 0.336 | 13 |
| 6330403K07RIK | 0.716 | 1.089339 | 0.216 | 13 |
| RTN1 | 0.835 | 1.088449 | 0.335 | 13 |
| CPLX3 | 0.837 | 1.084019 | 0.337 | 13 |
| PAK3 | 0.780 | 1.083627 | 0.280 | 13 |
| GNAS | 0.836 | 1.081193 | 0.336 | 13 |
| NRXN2 | 0.809 | 1.081039 | 0.309 | 13 |
| PJA2 | 0.823 | 1.077566 | 0.323 | 13 |
| VSNL1 | 0.759 | 1.077335 | 0.259 | 13 |
| PRKCE | 0.808 | 1.072516 | 0.308 | 13 |
| TMX4 | 0.787 | 1.065684 | 0.287 | 13 |
| SYT11 | 0.821 | 1.064647 | 0.321 | 13 |
| CFL1 | 0.829 | 1.063733 | 0.329 | 13 |
| STEAP2 | 0.779 | 1.060304 | 0.279 | 13 |
| ABAT | 0.753 | 1.048614 | 0.253 | 13 |
| GM1673 | 0.772 | 1.046935 | 0.272 | 13 |
| 6430548M08RIK | 0.807 | 1.045290 | 0.307 | 13 |
| CALM1 | 0.890 | 1.044110 | 0.390 | 13 |
| VSTM2A | 0.755 | 1.039415 | 0.255 | 13 |
| SERP2 | 0.757 | 1.039018 | 0.257 | 13 |
| DLGAP1 | 0.758 | 1.032184 | 0.258 | 13 |
| WDR1 | 0.775 | 1.031819 | 0.275 | 13 |
| BEX2 | 0.825 | 1.030974 | 0.325 | 13 |
| GRIK2 | 0.727 | 1.028371 | 0.227 | 13 |
| LINGO1 | 0.726 | 1.021154 | 0.226 | 13 |
| HSP90AB1 | 0.835 | 1.017052 | 0.335 | 13 |
| NCALD | 0.744 | 1.014432 | 0.244 | 13 |
| NDN | 0.803 | 1.013667 | 0.303 | 13 |
| YWHAH | 0.767 | 1.006233 | 0.267 | 13 |
| PIP4K2A | 0.728 | 1.006224 | 0.228 | 13 |
| GNB1 | 0.250 | −1.654835 | 0.250 | 13 |
| HMGN1 | 0.219 | −1.661459 | 0.281 | 13 |
| UNC119 | 0.271 | −1.736377 | 0.229 | 13 |
| NR2E3 | 0.259 | −1.757150 | 0.241 | 13 |
| ROM1 | 0.226 | −2.024256 | 0.274 | 13 |
| RS1 | 0.250 | −2.076870 | 0.250 | 13 |
| RP1 | 0.229 | −2.081436 | 0.271 | 13 |
| NRL | 0.264 | −2.089632 | 0.236 | 13 |
| NEUROD1 | 0.268 | −2.094220 | 0.232 | 13 |
| PDC | 0.174 | −2.144862 | 0.326 | 13 |
| PDE6B | 0.225 | −2.217360 | 0.275 | 13 |
| SLC24A1 | 0.253 | −2.275124 | 0.247 | 13 |
| CNGA1 | 0.251 | −2.284090 | 0.249 | 13 |
| GNAT1 | 0.190 | −2.284263 | 0.310 | 13 |
| PRPH2 | 0.185 | −2.326461 | 0.315 | 13 |
| RCVRN | 0.207 | −2.339004 | 0.293 | 13 |
| PDE6G | 0.200 | −2.346579 | 0.300 | 13 |

TABLE 6-continued

Genes differentially expressed in each of the 39 retinal cell clusters.

| Gene | | | | |
|---|---|---|---|---|
| TULP1 | 0.192 | −2.351777 | 0.308 | 13 |
| GNGT1 | 0.156 | −2.405413 | 0.344 | 13 |
| SAG | 0.153 | −2.429798 | 0.347 | 13 |
| RHO | 0.157 | −2.459338 | 0.343 | 13 |
| RPGRIP1 | 0.224 | −2.497198 | 0.276 | 13 |
| cluster no. 14 DE = 127 | | | | |
| CARTPT | 0.995 | 5.703726 | 0.495 | 14 |
| TFAP2B | 0.971 | 3.040128 | 0.471 | 14 |
| GNG2 | 0.921 | 2.521110 | 0.421 | 14 |
| GAD1 | 0.935 | 2.313316 | 0.435 | 14 |
| RAB3C | 0.906 | 2.257741 | 0.406 | 14 |
| 6430548M08RIK | 0.917 | 2.251898 | 0.417 | 14 |
| MARCKS | 0.949 | 2.228788 | 0.449 | 14 |
| C1QL1 | 0.891 | 2.174893 | 0.391 | 14 |
| GPR22 | 0.860 | 2.130602 | 0.360 | 14 |
| PCP4 | 0.929 | 2.085684 | 0.429 | 14 |
| 2610017I09RIK | 0.880 | 2.047078 | 0.380 | 14 |
| 4833424O15RIK | 0.884 | 2.046187 | 0.384 | 14 |
| ATP1B1 | 0.930 | 2.002380 | 0.430 | 14 |
| C1QL2 | 0.851 | 1.948192 | 0.351 | 14 |
| RPH3A | 0.886 | 1.922752 | 0.386 | 14 |
| SYT10 | 0.826 | 1.921924 | 0.326 | 14 |
| CAMK4 | 0.844 | 1.906300 | 0.344 | 14 |
| ISOC1 | 0.833 | 1.836812 | 0.333 | 14 |
| SLC35D3 | 0.829 | 1.831320 | 0.329 | 14 |
| NR4A2 | 0.816 | 1.806155 | 0.316 | 14 |
| GRIA3 | 0.827 | 1.723420 | 0.327 | 14 |
| NRXN2 | 0.841 | 1.694523 | 0.341 | 14 |
| KIT | 0.791 | 1.692597 | 0.291 | 14 |
| RPRM | 0.787 | 1.685930 | 0.287 | 14 |
| CELF4 | 0.901 | 1.684178 | 0.401 | 14 |
| PBX1 | 0.896 | 1.668218 | 0.396 | 14 |
| SYT7 | 0.822 | 1.654737 | 0.322 | 14 |
| SYT4 | 0.833 | 1.635617 | 0.333 | 14 |
| KCNIP1 | 0.830 | 1.617504 | 0.330 | 14 |
| FBXW7 | 0.841 | 1.574306 | 0.341 | 14 |
| ITM2C | 0.876 | 1.542051 | 0.376 | 14 |
| TENM1 | 0.766 | 1.538949 | 0.266 | 14 |
| NAP1L5 | 0.860 | 1.532501 | 0.360 | 14 |
| CACNA2D2 | 0.808 | 1.530876 | 0.308 | 14 |
| GNG3 | 0.851 | 1.511727 | 0.351 | 14 |
| ELAVL4 | 0.791 | 1.506871 | 0.291 | 14 |
| POU3F3 | 0.772 | 1.496067 | 0.272 | 14 |
| TFAP2A | 0.793 | 1.479966 | 0.293 | 14 |
| HOMER2 | 0.725 | 1.453440 | 0.225 | 14 |
| TBX3 | 0.763 | 1.424956 | 0.263 | 14 |
| CAR8 | 0.751 | 1.411188 | 0.251 | 14 |
| TSHZ1 | 0.787 | 1.379317 | 0.287 | 14 |
| BC048943 | 0.816 | 1.375829 | 0.316 | 14 |
| SLC32A1 | 0.799 | 1.373823 | 0.299 | 14 |
| CAMKV | 0.782 | 1.366152 | 0.282 | 14 |
| PDE3A | 0.744 | 1.357171 | 0.244 | 14 |
| CNKSR2 | 0.725 | 1.353715 | 0.225 | 14 |
| SNHG11 | 0.855 | 1.350103 | 0.355 | 14 |
| GABRA2 | 0.753 | 1.348395 | 0.253 | 14 |
| UCHL1 | 0.839 | 1.339151 | 0.339 | 14 |
| STMN2 | 0.816 | 1.321500 | 0.316 | 14 |
| AMIGO2 | 0.761 | 1.315679 | 0.261 | 14 |
| YWHAH | 0.814 | 1.293229 | 0.314 | 14 |
| MARCKSL1 | 0.784 | 1.286051 | 0.284 | 14 |
| ANKS1B | 0.759 | 1.281614 | 0.259 | 14 |
| NDRG4 | 0.813 | 1.274413 | 0.313 | 14 |
| GAP43 | 0.749 | 1.266684 | 0.249 | 14 |
| AUTS2 | 0.783 | 1.256839 | 0.283 | 14 |
| SYNPR | 0.820 | 1.249817 | 0.320 | 14 |
| ATP2B1 | 0.869 | 1.238571 | 0.369 | 14 |
| GRM1 | 0.726 | 1.231165 | 0.226 | 14 |
| CPLX3 | 0.835 | 1.226050 | 0.335 | 14 |
| EPB4.1L4A | 0.746 | 1.225236 | 0.246 | 14 |
| SOBP | 0.717 | 1.225089 | 0.217 | 14 |
| LRRN3 | 0.732 | 1.221377 | 0.232 | 14 |
| CYGB | 0.762 | 1.207406 | 0.262 | 14 |
| E530001K10RIK | 0.717 | 1.204510 | 0.217 | 14 |
| COL23A1 | 0.771 | 1.203158 | 0.271 | 14 |
| VSNL1 | 0.742 | 1.194754 | 0.242 | 14 |
| GM27031 | 0.701 | 1.194087 | 0.201 | 14 |
| YWHAG | 0.788 | 1.175123 | 0.288 | 14 |
| A030009H04RIK | 0.773 | 1.169740 | 0.273 | 14 |
| PHACTR3 | 0.756 | 1.169124 | 0.256 | 14 |
| RYR2 | 0.743 | 1.167697 | 0.243 | 14 |
| ZCCHC18 | 0.790 | 1.167592 | 0.290 | 14 |
| NFIA | 0.720 | 1.165989 | 0.220 | 14 |
| EFR3A | 0.790 | 1.165206 | 0.290 | 14 |
| ELAVL3 | 0.757 | 1.164312 | 0.257 | 14 |
| SH3BGRL | 0.726 | 1.143244 | 0.226 | 14 |
| PAX6 | 0.795 | 1.121544 | 0.295 | 14 |
| CTNNA2 | 0.743 | 1.115757 | 0.243 | 14 |
| VAMP4 | 0.726 | 1.103188 | 0.226 | 14 |
| SCG2 | 0.843 | 1.100054 | 0.343 | 14 |
| LIN7A | 0.801 | 1.099208 | 0.301 | 14 |
| IMPACT | 0.745 | 1.093091 | 0.245 | 14 |
| NGFRAP1 | 0.787 | 1.076352 | 0.287 | 14 |
| ARHGAP20 | 0.706 | 1.071535 | 0.206 | 14 |
| PODXL2 | 0.773 | 1.071004 | 0.273 | 14 |
| ID4 | 0.704 | 1.060790 | 0.204 | 14 |
| SPOCK3 | 0.761 | 1.053007 | 0.261 | 14 |
| BASP1 | 0.790 | 1.045714 | 0.290 | 14 |
| GRM5 | 0.713 | 1.040980 | 0.213 | 14 |
| DPP6 | 0.740 | 1.039731 | 0.240 | 14 |
| FAM49A | 0.706 | 1.037227 | 0.206 | 14 |
| MLLT11 | 0.749 | 1.033558 | 0.249 | 14 |
| ACOT7 | 0.736 | 1.033349 | 0.236 | 14 |
| RIT2 | 0.729 | 1.029466 | 0.229 | 14 |
| 6330403K07RIK | 0.710 | 1.028243 | 0.210 | 14 |
| SERPINE2 | 0.706 | 1.024427 | 0.206 | 14 |
| TMSB10 | 0.795 | 1.017801 | 0.295 | 14 |
| WDR1 | 0.746 | 1.015410 | 0.246 | 14 |
| SNCB | 0.802 | 1.013614 | 0.302 | 14 |
| STMN3 | 0.751 | 1.009106 | 0.251 | 14 |
| ZEB2 | 0.734 | 1.007237 | 0.234 | 14 |
| TTC3 | 0.821 | 1.005346 | 0.321 | 14 |
| TRANK1 | 0.710 | 1.001051 | 0.210 | 14 |
| HMGN1 | 0.252 | −1.261384 | 0.248 | 14 |
| GNB1 | 0.278 | −1.308646 | 0.222 | 14 |
| RP1 | 0.272 | −1.542408 | 0.228 | 14 |
| UNC119 | 0.251 | −1.556548 | 0.249 | 14 |
| RCVRN | 0.262 | −1.576865 | 0.238 | 14 |
| PDE6G | 0.243 | −1.595753 | 0.257 | 14 |
| ROM1 | 0.252 | −1.638720 | 0.248 | 14 |
| TULP1 | 0.238 | −1.644062 | 0.262 | 14 |
| CNGA1 | 0.290 | −1.645086 | 0.210 | 14 |
| PDC | 0.207 | −1.653719 | 0.293 | 14 |
| GNAT1 | 0.231 | −1.672780 | 0.269 | 14 |
| PDE6B | 0.255 | −1.698852 | 0.245 | 14 |
| PRPH2 | 0.219 | −1.700665 | 0.281 | 14 |
| NRL | 0.285 | −1.702971 | 0.215 | 14 |
| GNGT1 | 0.191 | −1.727437 | 0.309 | 14 |
| NR2E3 | 0.274 | −1.735667 | 0.226 | 14 |
| SLC24A1 | 0.284 | −1.736471 | 0.216 | 14 |
| SAG | 0.186 | −1.773021 | 0.314 | 14 |
| RPGRIP1 | 0.260 | −1.792548 | 0.240 | 14 |
| RHO | 0.186 | −1.793033 | 0.314 | 14 |
| RS1 | 0.268 | −1.840885 | 0.232 | 14 |
| cluster no. 15 DE = 69 | | | | |
| SLC17A8 | 1.000 | 3.971625 | 0.500 | 15 |
| LAMP5 | 0.940 | 2.673730 | 0.440 | 15 |
| A930001A20RIK | 0.889 | 2.597410 | 0.389 | 15 |
| CAR3 | 0.835 | 2.514193 | 0.335 | 15 |
| TFAP2B | 0.905 | 2.503643 | 0.405 | 15 |
| GRIA3 | 0.826 | 2.061066 | 0.326 | 15 |
| GABRA2 | 0.842 | 2.031614 | 0.342 | 15 |
| PCP4 | 0.909 | 1.973695 | 0.409 | 15 |
| CDC7 | 0.832 | 1.955872 | 0.332 | 15 |
| SNHG11 | 0.887 | 1.937983 | 0.387 | 15 |
| VSTM2L | 0.832 | 1.918272 | 0.332 | 15 |
| STMN2 | 0.849 | 1.904450 | 0.349 | 15 |
| CAMK2N1 | 0.861 | 1.838364 | 0.361 | 15 |
| THSD7A | 0.787 | 1.831897 | 0.287 | 15 |
| ITM2B | 0.910 | 1.821993 | 0.410 | 15 |
| SPHKAP | 0.831 | 1.715234 | 0.331 | 15 |
| RBFOX1 | 0.735 | 1.705497 | 0.235 | 15 |
| OLFM1 | 0.839 | 1.659507 | 0.339 | 15 |
| CACNG4 | 0.815 | 1.640851 | 0.315 | 15 |
| PDE1C | 0.762 | 1.600665 | 0.262 | 15 |

TABLE 6-continued

Genes differentially expressed in each of the 39 retinal cell clusters.

| Gene | | | | |
|---|---|---|---|---|
| NXPH1 | 0.756 | 1.565593 | 0.256 | 15 |
| TFAP2A | 0.747 | 1.543928 | 0.247 | 15 |
| CELF4 | 0.841 | 1.542615 | 0.341 | 15 |
| CADM3 | 0.799 | 1.512073 | 0.299 | 15 |
| SLC24A3 | 0.743 | 1.506017 | 0.243 | 15 |
| HPGD | 0.706 | 1.448453 | 0.206 | 15 |
| GPHN | 0.809 | 1.446959 | 0.309 | 15 |
| GNG3 | 0.818 | 1.418323 | 0.318 | 15 |
| NEUROD2 | 0.737 | 1.357057 | 0.237 | 15 |
| 2900011O08RIK | 0.772 | 1.324460 | 0.272 | 15 |
| NXPH3 | 0.734 | 1.317785 | 0.234 | 15 |
| MARCKS | 0.815 | 1.293783 | 0.315 | 15 |
| RAB3C | 0.739 | 1.288257 | 0.239 | 15 |
| CDK14 | 0.739 | 1.286933 | 0.239 | 15 |
| SORCS1 | 0.717 | 1.234444 | 0.217 | 15 |
| CALM1 | 0.893 | 1.233054 | 0.393 | 15 |
| A830010M20RIK | 0.747 | 1.230927 | 0.247 | 15 |
| SIX6 | 0.750 | 1.213235 | 0.250 | 15 |
| NSG2 | 0.731 | 1.208784 | 0.231 | 15 |
| SNCB | 0.795 | 1.174871 | 0.295 | 15 |
| NREP | 0.813 | 1.167885 | 0.313 | 15 |
| TAGLN3 | 0.765 | 1.156591 | 0.265 | 15 |
| NSG1 | 0.707 | 1.149341 | 0.207 | 15 |
| CHGA | 0.768 | 1.148225 | 0.268 | 15 |
| MEG3 | 0.820 | 1.127476 | 0.320 | 15 |
| GRIA2 | 0.786 | 1.124935 | 0.286 | 15 |
| ELAVL3 | 0.721 | 1.121228 | 0.221 | 15 |
| NNAT | 0.713 | 1.097324 | 0.213 | 15 |
| CALM2 | 0.818 | 1.097061 | 0.318 | 15 |
| NRXN2 | 0.746 | 1.092058 | 0.246 | 15 |
| TCEAL5 | 0.701 | 1.076692 | 0.201 | 15 |
| PGM2L1 | 0.749 | 1.071344 | 0.249 | 15 |
| RUNX1T1 | 0.726 | 1.057725 | 0.226 | 15 |
| RTN1 | 0.787 | 1.038594 | 0.287 | 15 |
| NRXN3 | 0.757 | 1.036936 | 0.257 | 15 |
| HLF | 0.729 | 1.032907 | 0.229 | 15 |
| TTC3 | 0.783 | 1.000773 | 0.283 | 15 |
| A030009H04RIK | 0.710 | 1.000074 | 0.210 | 15 |
| GNAT1 | 0.299 | −1.040079 | 0.201 | 15 |
| GNB1 | 0.299 | −1.128978 | 0.201 | 15 |
| PDE6G | 0.299 | −1.189289 | 0.201 | 15 |
| PRPH2 | 0.281 | −1.204277 | 0.219 | 15 |
| TULP1 | 0.275 | −1.241916 | 0.225 | 15 |
| SAG | 0.232 | −1.259884 | 0.268 | 15 |
| ROM1 | 0.278 | −1.321566 | 0.222 | 15 |
| RCVRN | 0.291 | −1.325043 | 0.209 | 15 |
| PDC | 0.246 | −1.329612 | 0.254 | 15 |
| GNGT1 | 0.240 | −1.347078 | 0.260 | 15 |
| RHO | 0.227 | −1.442002 | 0.273 | 15 |
| cluster no. 16 DE = 97 | | | | |
| LAMP5 | 0.946 | 2.657760 | 0.446 | 16 |
| GJD2 | 0.928 | 2.371019 | 0.428 | 16 |
| DNER | 0.912 | 2.349418 | 0.412 | 16 |
| TFAP2B | 0.937 | 2.307419 | 0.437 | 16 |
| SLC6A9 | 0.877 | 2.261401 | 0.377 | 16 |
| DYNC1I1 | 0.871 | 2.238846 | 0.371 | 16 |
| CAR2 | 0.951 | 2.212296 | 0.451 | 16 |
| TMEM132A | 0.830 | 2.024931 | 0.330 | 16 |
| HSPA12A | 0.882 | 2.015750 | 0.382 | 16 |
| EIF1B | 0.886 | 2.008369 | 0.386 | 16 |
| NCALD | 0.858 | 1.949536 | 0.358 | 16 |
| RNF152 | 0.834 | 1.859704 | 0.334 | 16 |
| CALM1 | 0.949 | 1.848818 | 0.449 | 16 |
| CPLX3 | 0.910 | 1.811801 | 0.410 | 16 |
| GRIA3 | 0.813 | 1.803783 | 0.313 | 16 |
| CALB1 | 0.817 | 1.799962 | 0.317 | 16 |
| ATP1B1 | 0.887 | 1.769979 | 0.387 | 16 |
| NDRG4 | 0.841 | 1.747721 | 0.341 | 16 |
| CAMKV | 0.808 | 1.717383 | 0.308 | 16 |
| CCSAP | 0.761 | 1.662431 | 0.261 | 16 |
| PTPRF | 0.775 | 1.659107 | 0.275 | 16 |
| RCAN2 | 0.772 | 1.642853 | 0.272 | 16 |
| STAC2 | 0.756 | 1.591278 | 0.256 | 16 |
| DLGAP1 | 0.780 | 1.588752 | 0.280 | 16 |
| DAB1 | 0.780 | 1.587313 | 0.280 | 16 |
| SCN1A | 0.754 | 1.580647 | 0.254 | 16 |
| SLC24A2 | 0.728 | 1.578024 | 0.228 | 16 |
| ZYX | 0.743 | 1.492083 | 0.243 | 16 |
| NFIA | 0.764 | 1.487009 | 0.264 | 16 |
| PROX1 | 0.827 | 1.483800 | 0.327 | 16 |
| PLCH1 | 0.751 | 1.482505 | 0.251 | 16 |
| FGF1 | 0.739 | 1.462304 | 0.239 | 16 |
| ELAVL3 | 0.781 | 1.425611 | 0.281 | 16 |
| ZFP804A | 0.727 | 1.413891 | 0.227 | 16 |
| FSTL5 | 0.765 | 1.396307 | 0.265 | 16 |
| PHLDA1 | 0.707 | 1.389106 | 0.207 | 16 |
| PPP1R1A | 0.773 | 1.373425 | 0.273 | 16 |
| 6430548M08RIK | 0.808 | 1.371200 | 0.308 | 16 |
| LSAMP | 0.751 | 1.359807 | 0.251 | 16 |
| SPOCK3 | 0.746 | 1.352438 | 0.246 | 16 |
| KCNMA1 | 0.784 | 1.346329 | 0.284 | 16 |
| PAK7 | 0.751 | 1.343190 | 0.251 | 16 |
| ATP6V1G2 | 0.757 | 1.336798 | 0.257 | 16 |
| KIF5C | 0.756 | 1.296446 | 0.256 | 16 |
| TSPAN7 | 0.854 | 1.277924 | 0.354 | 16 |
| FBXW7 | 0.753 | 1.273232 | 0.253 | 16 |
| SYNPR | 0.759 | 1.263414 | 0.259 | 16 |
| CACNG3 | 0.704 | 1.254853 | 0.204 | 16 |
| DARC | 0.722 | 1.251447 | 0.222 | 16 |
| OSBPL1A | 0.724 | 1.244547 | 0.224 | 16 |
| MEG3 | 0.832 | 1.232034 | 0.332 | 16 |
| SV2A | 0.810 | 1.225364 | 0.310 | 16 |
| A030009H04RIK | 0.718 | 1.223471 | 0.218 | 16 |
| TAGLN3 | 0.764 | 1.222365 | 0.264 | 16 |
| ANKS1B | 0.716 | 1.213048 | 0.216 | 16 |
| GRIA4 | 0.728 | 1.165564 | 0.228 | 16 |
| SLC32A1 | 0.719 | 1.163084 | 0.219 | 16 |
| QDPR | 0.713 | 1.151071 | 0.213 | 16 |
| TCEAL5 | 0.724 | 1.146794 | 0.224 | 16 |
| RIT2 | 0.742 | 1.138978 | 0.242 | 16 |
| TPI1 | 0.790 | 1.128863 | 0.290 | 16 |
| DPP6 | 0.712 | 1.125116 | 0.212 | 16 |
| BNIP3 | 0.705 | 1.116162 | 0.205 | 16 |
| PODXL2 | 0.750 | 1.108498 | 0.250 | 16 |
| ZEB2 | 0.706 | 1.105841 | 0.206 | 16 |
| RAB3C | 0.706 | 1.104219 | 0.206 | 16 |
| TUBB2A | 0.758 | 1.097099 | 0.258 | 16 |
| PHYHIPL | 0.721 | 1.053411 | 0.221 | 16 |
| NSG2 | 0.707 | 1.039994 | 0.207 | 16 |
| CADM3 | 0.724 | 1.033579 | 0.224 | 16 |
| PNMAL2 | 0.726 | 1.032390 | 0.226 | 16 |
| ITM2C | 0.757 | 1.031738 | 0.257 | 16 |
| GRIA2 | 0.742 | 1.020469 | 0.242 | 16 |
| NRXN3 | 0.740 | 1.019019 | 0.240 | 16 |
| SPHKAP | 0.713 | 1.014996 | 0.213 | 16 |
| ANK3 | 0.715 | 1.004342 | 0.215 | 16 |
| HMGN1 | 0.215 | −1.521153 | 0.285 | 16 |
| GNB1 | 0.229 | −1.683458 | 0.271 | 16 |
| CNGA1 | 0.271 | −1.708074 | 0.229 | 16 |
| UNC119 | 0.244 | −1.715525 | 0.256 | 16 |
| RPGRIP1 | 0.264 | −1.737171 | 0.236 | 16 |
| ROM1 | 0.234 | −1.740653 | 0.266 | 16 |
| NRL | 0.265 | −1.762281 | 0.235 | 16 |
| RS1 | 0.265 | −1.774883 | 0.235 | 16 |
| PDE6B | 0.237 | −1.791541 | 0.263 | 16 |
| RP1 | 0.240 | −1.818556 | 0.260 | 16 |
| PRPH2 | 0.201 | −1.822970 | 0.299 | 16 |
| RCVRN | 0.225 | −1.829448 | 0.275 | 16 |
| PDE6G | 0.212 | −1.836061 | 0.288 | 16 |
| GNGT1 | 0.177 | −1.911169 | 0.323 | 16 |
| NR2E3 | 0.252 | −1.935120 | 0.248 | 16 |
| SLC24A1 | 0.268 | −1.939047 | 0.232 | 16 |
| TULP1 | 0.202 | −1.958300 | 0.298 | 16 |
| PDC | 0.178 | −1.988325 | 0.322 | 16 |
| GNAT1 | 0.203 | −2.005405 | 0.297 | 16 |
| RHO | 0.170 | −2.014559 | 0.330 | 16 |
| SAG | 0.157 | −2.131605 | 0.343 | 16 |
| cluster no. 17 DE = 99 | | | | |
| NHLH2 | 0.955 | 2.801308 | 0.455 | 17 |
| PTPRF | 0.938 | 2.711222 | 0.438 | 17 |
| IGF1 | 0.893 | 2.396873 | 0.393 | 17 |
| SLC6A9 | 0.922 | 2.391729 | 0.422 | 17 |
| LAMP5 | 0.894 | 2.317776 | 0.394 | 17 |
| NECAB1 | 0.845 | 2.034798 | 0.345 | 17 |

TABLE 6-continued

Genes differentially expressed in each of the 39 retinal cell clusters.

| Gene | myAUC | myDiff | power | cluster |
|---|---|---|---|---|
| NFIX | 0.842 | 2.031417 | 0.342 | 17 |
| QDPR | 0.864 | 2.017375 | 0.364 | 17 |
| RPH3A | 0.861 | 1.948967 | 0.361 | 17 |
| TFAP2C | 0.804 | 1.906681 | 0.304 | 17 |
| EBF3 | 0.816 | 1.897681 | 0.316 | 17 |
| ZFP804A | 0.806 | 1.817066 | 0.306 | 17 |
| CPLX3 | 0.918 | 1.803041 | 0.418 | 17 |
| CRABP1 | 0.796 | 1.772659 | 0.296 | 17 |
| NR2F2 | 0.779 | 1.746596 | 0.279 | 17 |
| HPCA | 0.804 | 1.734854 | 0.304 | 17 |
| ELAVL3 | 0.846 | 1.731296 | 0.346 | 17 |
| NRSN1 | 0.810 | 1.674821 | 0.310 | 17 |
| IER5 | 0.778 | 1.651591 | 0.278 | 17 |
| PTPRT | 0.756 | 1.624019 | 0.256 | 17 |
| DAB1 | 0.802 | 1.623759 | 0.302 | 17 |
| TUBB2A | 0.848 | 1.623271 | 0.348 | 17 |
| LGR5 | 0.757 | 1.617618 | 0.257 | 17 |
| NCALD | 0.795 | 1.603750 | 0.295 | 17 |
| VSTM2A | 0.740 | 1.554722 | 0.240 | 17 |
| CELF4 | 0.872 | 1.530692 | 0.372 | 17 |
| SULF2 | 0.760 | 1.520666 | 0.260 | 17 |
| MGLL | 0.754 | 1.520539 | 0.254 | 17 |
| PAX6 | 0.816 | 1.498468 | 0.316 | 17 |
| SLC24A3 | 0.781 | 1.478973 | 0.281 | 17 |
| PAM | 0.742 | 1.475693 | 0.242 | 17 |
| CABP1 | 0.775 | 1.471362 | 0.275 | 17 |
| CACNG3 | 0.735 | 1.458559 | 0.235 | 17 |
| SLC32A1 | 0.764 | 1.449804 | 0.264 | 17 |
| HS6ST2 | 0.707 | 1.397958 | 0.207 | 17 |
| THRA | 0.819 | 1.389414 | 0.319 | 17 |
| NAV1 | 0.774 | 1.379521 | 0.274 | 17 |
| SPARCL1 | 0.752 | 1.366591 | 0.252 | 17 |
| DPP6 | 0.726 | 1.359750 | 0.226 | 17 |
| TCF4 | 0.820 | 1.358693 | 0.320 | 17 |
| NECAB2 | 0.717 | 1.353128 | 0.217 | 17 |
| APP | 0.828 | 1.351232 | 0.328 | 17 |
| LY6H | 0.730 | 1.336108 | 0.230 | 17 |
| TTC3 | 0.870 | 1.328177 | 0.370 | 17 |
| SYT4 | 0.748 | 1.315258 | 0.248 | 17 |
| EBF1 | 0.701 | 1.310439 | 0.201 | 17 |
| CALB2 | 0.802 | 1.299700 | 0.302 | 17 |
| TKT | 0.761 | 1.294344 | 0.261 | 17 |
| CAMKV | 0.709 | 1.291859 | 0.209 | 17 |
| SPHKAP | 0.771 | 1.288256 | 0.271 | 17 |
| FSTL5 | 0.725 | 1.283969 | 0.225 | 17 |
| THY1 | 0.723 | 1.277498 | 0.223 | 17 |
| SUSD4 | 0.709 | 1.255558 | 0.209 | 17 |
| GRIA4 | 0.735 | 1.236041 | 0.235 | 17 |
| 4930447C04RIK | 0.756 | 1.222306 | 0.256 | 17 |
| SEZ6 | 0.713 | 1.213564 | 0.213 | 17 |
| FILIP1L | 0.701 | 1.211433 | 0.201 | 17 |
| MARCKSL1 | 0.744 | 1.207456 | 0.244 | 17 |
| ANK3 | 0.761 | 1.200975 | 0.261 | 17 |
| NRXN3 | 0.807 | 1.168788 | 0.307 | 17 |
| NDUFC2 | 0.787 | 1.159975 | 0.287 | 17 |
| GPM6A | 0.780 | 1.143074 | 0.280 | 17 |
| ITM2C | 0.768 | 1.128670 | 0.268 | 17 |
| SV2A | 0.779 | 1.093330 | 0.279 | 17 |
| SNHG11 | 0.825 | 1.085316 | 0.325 | 17 |
| LSAMP | 0.709 | 1.058888 | 0.209 | 17 |
| GAS6 | 0.767 | 1.058520 | 0.267 | 17 |
| CAMK2N1 | 0.762 | 1.055403 | 0.262 | 17 |
| SCG3 | 0.751 | 1.049366 | 0.251 | 17 |
| NSG2 | 0.706 | 1.049170 | 0.206 | 17 |
| CRMP1 | 0.709 | 1.036034 | 0.209 | 17 |
| MEG3 | 0.839 | 1.025407 | 0.339 | 17 |
| NREP | 0.775 | 1.017209 | 0.275 | 17 |
| PGRMC1 | 0.723 | 1.013992 | 0.223 | 17 |
| PPP1R1A | 0.707 | 1.008115 | 0.207 | 17 |
| INA | 0.720 | 1.004427 | 0.220 | 17 |
| HMGN1 | 0.257 | −1.196552 | 0.243 | 17 |
| CST3 | 0.297 | −1.331354 | 0.203 | 17 |
| GNB1 | 0.257 | −1.407515 | 0.243 | 17 |
| CNGA1 | 0.284 | −1.538745 | 0.216 | 17 |
| UNC119 | 0.258 | −1.566938 | 0.242 | 17 |
| NEUROD1 | 0.288 | −1.572623 | 0.212 | 17 |
| ROM1 | 0.243 | −1.577979 | 0.257 | 17 |
| NRL | 0.281 | −1.587397 | 0.219 | 17 |
| PRPH2 | 0.211 | −1.721597 | 0.289 | 17 |
| SLC24A1 | 0.279 | −1.725891 | 0.221 | 17 |
| TULP1 | 0.219 | −1.731480 | 0.281 | 17 |
| RP1 | 0.244 | −1.732042 | 0.256 | 17 |
| NR2E3 | 0.264 | −1.737427 | 0.236 | 17 |
| RS1 | 0.266 | −1.747543 | 0.234 | 17 |
| RCVRN | 0.233 | −1.757940 | 0.267 | 17 |
| RPGRIP1 | 0.258 | −1.766938 | 0.242 | 17 |
| PDE6G | 0.220 | −1.771881 | 0.280 | 17 |
| PDE6B | 0.236 | −1.776243 | 0.264 | 17 |
| GNAT1 | 0.216 | −1.796601 | 0.284 | 17 |
| PDC | 0.191 | −1.801008 | 0.309 | 17 |
| RHO | 0.181 | −1.842355 | 0.319 | 17 |
| SAG | 0.174 | −1.848204 | 0.326 | 17 |
| GNGT1 | 0.181 | −1.878152 | 0.319 | 17 | cluster no. 18 DE = 76

| Gene | myAUC | myDiff | power | cluster |
|---|---|---|---|---|
| NHLH2 | 0.940 | 2.577919 | 0.440 | 18 |
| PCDH17 | 0.926 | 2.518747 | 0.426 | 18 |
| NFIX | 0.896 | 2.289617 | 0.396 | 18 |
| HPCA | 0.894 | 2.165617 | 0.394 | 18 |
| NFIB | 0.850 | 2.151836 | 0.350 | 18 |
| CHN2 | 0.865 | 1.981338 | 0.365 | 18 |
| NECAB1 | 0.834 | 1.930261 | 0.334 | 18 |
| CELF4 | 0.944 | 1.891838 | 0.444 | 18 |
| COL12A1 | 0.769 | 1.884139 | 0.269 | 18 |
| PRDM13 | 0.795 | 1.854160 | 0.295 | 18 |
| D3BWG0562E | 0.830 | 1.829089 | 0.330 | 18 |
| TCF4 | 0.892 | 1.827289 | 0.392 | 18 |
| NRXN1 | 0.767 | 1.826387 | 0.267 | 18 |
| SOCS2 | 0.795 | 1.761385 | 0.295 | 18 |
| ANK3 | 0.844 | 1.673902 | 0.344 | 18 |
| TFAP2C | 0.759 | 1.629828 | 0.259 | 18 |
| STMN2 | 0.749 | 1.556131 | 0.249 | 18 |
| ZFP804A | 0.719 | 1.551147 | 0.219 | 18 |
| APP | 0.875 | 1.546885 | 0.375 | 18 |
| ELAVL3 | 0.783 | 1.506019 | 0.283 | 18 |
| ARHGAP20 | 0.719 | 1.505211 | 0.219 | 18 |
| MEG3 | 0.880 | 1.462490 | 0.380 | 18 |
| SLC32A1 | 0.765 | 1.444429 | 0.265 | 18 |
| NAV1 | 0.762 | 1.417519 | 0.262 | 18 |
| SEMA4G | 0.729 | 1.383182 | 0.229 | 18 |
| MARCKSL1 | 0.776 | 1.359972 | 0.276 | 18 |
| PIK3R3 | 0.745 | 1.354144 | 0.245 | 18 |
| THRA | 0.820 | 1.353685 | 0.320 | 18 |
| NCALD | 0.736 | 1.337872 | 0.236 | 18 |

TABLE 6-continued

Genes differentially expressed in each of the 39 retinal cell clusters.

| Gene | myAUC | myDiff | power | cluster # |
|---|---|---|---|---|
| NSG1 | 0.742 | 1.320977 | 0.242 | 18 |
| PTPRS | 0.743 | 1.286383 | 0.243 | 18 |
| NREP | 0.840 | 1.285992 | 0.340 | 18 |
| CABP1 | 0.725 | 1.262818 | 0.225 | 18 |
| SIX3 | 0.787 | 1.251619 | 0.287 | 18 |
| SLC6A9 | 0.710 | 1.245464 | 0.210 | 18 |
| RPH3A | 0.752 | 1.238243 | 0.252 | 18 |
| TTC3 | 0.842 | 1.233544 | 0.342 | 18 |
| GRIA2 | 0.777 | 1.228039 | 0.277 | 18 |
| CD47 | 0.753 | 1.210868 | 0.253 | 18 |
| ATP1B1 | 0.801 | 1.167177 | 0.301 | 18 |
| ZCCHC18 | 0.720 | 1.164194 | 0.220 | 18 |
| PLEKHA1 | 0.752 | 1.163094 | 0.252 | 18 |
| GPM6A | 0.788 | 1.153552 | 0.288 | 18 |
| PNMAL2 | 0.748 | 1.130451 | 0.248 | 18 |
| GRIA4 | 0.725 | 1.120343 | 0.225 | 18 |
| RTN1 | 0.773 | 1.099410 | 0.273 | 18 |
| TUBB2A | 0.769 | 1.094495 | 0.269 | 18 |
| CAMK2N1 | 0.742 | 1.088043 | 0.242 | 18 |
| CALM2 | 0.798 | 1.074762 | 0.298 | 18 |
| TAGLN3 | 0.719 | 1.054396 | 0.219 | 18 |
| NRXN3 | 0.754 | 1.040204 | 0.254 | 18 |
| PAX6 | 0.734 | 1.034451 | 0.234 | 18 |
| NGFRAP1 | 0.739 | 1.019194 | 0.239 | 18 |
| HMGN1 | 0.251 | -1.229929 | 0.249 | 18 |
| CST3 | 0.291 | -1.416269 | 0.209 | 18 |
| GNB1 | 0.247 | -1.445738 | 0.253 | 18 |
| RPGRIP1 | 0.283 | -1.546356 | 0.217 | 18 |
| NRL | 0.289 | -1.564782 | 0.211 | 18 |
| NEUROD1 | 0.283 | -1.620185 | 0.217 | 18 |
| NR2E3 | 0.275 | -1.669162 | 0.225 | 18 |
| PDE6B | 0.254 | -1.672037 | 0.246 | 18 |
| UNC119 | 0.244 | -1.678390 | 0.256 | 18 |
| RP1 | 0.248 | -1.709894 | 0.252 | 18 |
| SLC24A1 | 0.287 | -1.717416 | 0.213 | 18 |
| PDC | 0.198 | -1.748702 | 0.302 | 18 |
| ROM1 | 0.230 | -1.751335 | 0.270 | 18 |
| TULP1 | 0.218 | -1.761842 | 0.282 | 18 |
| PDE6G | 0.226 | -1.763229 | 0.274 | 18 |
| RCVRN | 0.231 | -1.769978 | 0.269 | 18 |
| SAG | 0.184 | -1.774554 | 0.316 | 18 |
| CNGA1 | 0.265 | -1.786474 | 0.235 | 18 |
| GNGT1 | 0.189 | -1.797833 | 0.311 | 18 |
| RS1 | 0.268 | -1.853854 | 0.232 | 18 |
| GNAT1 | 0.214 | -1.946696 | 0.286 | 18 |
| PRPH2 | 0.202 | -1.956290 | 0.298 | 18 |
| RHO | 0.180 | -2.007748 | 0.320 | 18 | cluster no. 19 DE = 115

| Gene | myAUC | myDiff | power | cluster # |
|---|---|---|---|---|
| LAMP5 | 0.966 | 2.812286 | 0.466 | 19 |
| GABRA1 | 0.897 | 2.484680 | 0.397 | 19 |
| SLC24A3 | 0.927 | 2.393144 | 0.427 | 19 |
| NHLH2 | 0.945 | 2.383320 | 0.445 | 19 |
| LY6H | 0.876 | 2.116752 | 0.376 | 19 |
| EBF1 | 0.874 | 2.024209 | 0.374 | 19 |
| SNHG11 | 0.922 | 1.988360 | 0.422 | 19 |
| NDRG4 | 0.876 | 1.960583 | 0.376 | 19 |
| CDH22 | 0.815 | 1.785911 | 0.315 | 19 |
| SPHKAP | 0.886 | 1.743169 | 0.386 | 19 |
| PNMAL2 | 0.867 | 1.735673 | 0.367 | 19 |
| SIX3 | 0.851 | 1.695121 | 0.351 | 19 |
| PTPRT | 0.803 | 1.687676 | 0.303 | 19 |
| PTGDS | 0.783 | 1.682383 | 0.283 | 19 |
| SLC6A9 | 0.811 | 1.678064 | 0.311 | 19 |
| CAMKV | 0.818 | 1.675469 | 0.318 | 19 |
| NRXN2 | 0.848 | 1.674929 | 0.348 | 19 |
| ELAVL3 | 0.862 | 1.653420 | 0.362 | 19 |
| PTPRD | 0.849 | 1.648261 | 0.349 | 19 |
| SYT13 | 0.813 | 1.625862 | 0.313 | 19 |
| CHN2 | 0.797 | 1.618956 | 0.297 | 19 |
| AQP6 | 0.736 | 1.613186 | 0.236 | 19 |
| CABP1 | 0.840 | 1.607853 | 0.340 | 19 |
| TCF4 | 0.879 | 1.577171 | 0.379 | 19 |
| LDHB | 0.829 | 1.565948 | 0.329 | 19 |
| RAB3C | 0.777 | 1.545867 | 0.277 | 19 |
| PRDM13 | 0.768 | 1.521082 | 0.268 | 19 |
| INA | 0.852 | 1.511391 | 0.352 | 19 |
| SIX6 | 0.783 | 1.490271 | 0.283 | 19 |
| KCTD8 | 0.766 | 1.472089 | 0.266 | 19 |
| MEG3 | 0.905 | 1.468522 | 0.405 | 19 |
| PAX6 | 0.823 | 1.451718 | 0.323 | 19 |
| APP | 0.852 | 1.450537 | 0.352 | 19 |
| OGFRL1 | 0.821 | 1.437451 | 0.321 | 19 |
| ATP1B1 | 0.855 | 1.426796 | 0.355 | 19 |
| 6430548M08RIK | 0.803 | 1.419158 | 0.303 | 19 |
| NECAB1 | 0.749 | 1.374682 | 0.249 | 19 |
| VAT1L | 0.743 | 1.371743 | 0.243 | 19 |
| NNAT | 0.722 | 1.357449 | 0.222 | 19 |
| NRSN1 | 0.790 | 1.356337 | 0.290 | 19 |
| DPP6 | 0.765 | 1.355499 | 0.265 | 19 |
| NSG1 | 0.771 | 1.344649 | 0.271 | 19 |
| TKT | 0.806 | 1.341063 | 0.306 | 19 |
| CDK14 | 0.761 | 1.337859 | 0.261 | 19 |
| FRRS1L | 0.709 | 1.335420 | 0.209 | 19 |
| OSBPL1A | 0.752 | 1.329635 | 0.252 | 19 |
| MGLL | 0.763 | 1.294623 | 0.263 | 19 |
| GABRG2 | 0.757 | 1.291374 | 0.257 | 19 |
| GNG3 | 0.828 | 1.268832 | 0.328 | 19 |
| GRIA2 | 0.830 | 1.263501 | 0.330 | 19 |
| BASP1 | 0.810 | 1.253882 | 0.310 | 19 |
| STMN3 | 0.809 | 1.238855 | 0.309 | 19 |
| GAS7 | 0.711 | 1.233308 | 0.211 | 19 |
| CELF4 | 0.831 | 1.232486 | 0.331 | 19 |
| SPOCK3 | 0.771 | 1.231314 | 0.271 | 19 |
| DLG2 | 0.718 | 1.209247 | 0.218 | 19 |
| STMN4 | 0.732 | 1.207910 | 0.232 | 19 |

TABLE 6-continued

Genes differentially expressed in each of the 39 retinal cell clusters.

| Gene | myAUC | avg_diff | pct | cluster # |
|---|---|---|---|---|
| ZFP804A | 0.711 | 1.206180 | 0.211 | 19 |
| SPARCL1 | 0.760 | 1.196819 | 0.260 | 19 |
| THRA | 0.783 | 1.194146 | 0.283 | 19 |
| MLLT11 | 0.751 | 1.190315 | 0.251 | 19 |
| GRIA3 | 0.722 | 1.173347 | 0.222 | 19 |
| TCEAL5 | 0.740 | 1.171672 | 0.240 | 19 |
| GABRB2 | 0.707 | 1.167103 | 0.207 | 19 |
| LHFP | 0.721 | 1.165278 | 0.221 | 19 |
| HMGCS1 | 0.731 | 1.155608 | 0.231 | 19 |
| UBASH3B | 0.710 | 1.154651 | 0.210 | 19 |
| TMEM215 | 0.764 | 1.134491 | 0.264 | 19 |
| TAGLN3 | 0.797 | 1.134360 | 0.297 | 19 |
| HSD17B12 | 0.778 | 1.130471 | 0.278 | 19 |
| SLC32A1 | 0.733 | 1.119009 | 0.233 | 19 |
| ABAT | 0.708 | 1.118345 | 0.208 | 19 |
| CALM2 | 0.829 | 1.105143 | 0.329 | 19 |
| ATPIF1 | 0.795 | 1.102584 | 0.295 | 19 |
| GNAS | 0.833 | 1.076868 | 0.333 | 19 |
| SYT4 | 0.779 | 1.071587 | 0.279 | 19 |
| TTC3 | 0.832 | 1.066694 | 0.332 | 19 |
| CAMK2N1 | 0.768 | 1.054984 | 0.268 | 19 |
| TUBB2A | 0.780 | 1.041674 | 0.280 | 19 |
| RIT2 | 0.712 | 1.039586 | 0.212 | 19 |
| PIK3R3 | 0.717 | 1.034720 | 0.217 | 19 |
| SV2A | 0.772 | 1.033485 | 0.272 | 19 |
| CAMK2A | 0.701 | 1.028493 | 0.201 | 19 |
| NGFRAP1 | 0.770 | 1.026982 | 0.270 | 19 |
| A030009H04RIK | 0.719 | 1.026299 | 0.219 | 19 |
| GPM6A | 0.792 | 1.021982 | 0.292 | 19 |
| NAP1L5 | 0.759 | 1.016867 | 0.259 | 19 |
| MAPT | 0.724 | 1.007727 | 0.224 | 19 |
| NDN | 0.717 | 1.007103 | 0.217 | 19 |
| ATP6V1G2 | 0.711 | 1.000069 | 0.211 | 19 |
| CST3 | 0.295 | −1.464654 | 0.205 | 19 |
| GNB1 | 0.232 | −1.731344 | 0.268 | 19 |
| HMGN1 | 0.193 | −1.764691 | 0.307 | 19 |
| FAM57B | 0.287 | −1.846219 | 0.213 | 19 |
| UNC119 | 0.235 | −1.869744 | 0.265 | 19 |
| AIPL1 | 0.299 | −1.912009 | 0.201 | 19 |
| NEUROD1 | 0.267 | −1.949197 | 0.233 | 19 |
| CNGA1 | 0.258 | −2.018138 | 0.242 | 19 |
| ROM1 | 0.220 | −2.018487 | 0.280 | 19 |
| RP1 | 0.224 | −2.025188 | 0.276 | 19 |
| NR2E3 | 0.250 | −2.051380 | 0.250 | 19 |
| PDE6B | 0.216 | −2.080446 | 0.284 | 19 |
| RS1 | 0.250 | −2.098084 | 0.250 | 19 |
| PRPH2 | 0.185 | −2.112352 | 0.315 | 19 |
| RCVRN | 0.209 | −2.119590 | 0.291 | 19 |
| SLC24A1 | 0.260 | −2.160451 | 0.240 | 19 |
| NRL | 0.243 | −2.171600 | 0.257 | 19 |
| PDE6G | 0.194 | −2.189464 | 0.306 | 19 |
| TULP1 | 0.190 | −2.209461 | 0.310 | 19 |
| GNAT1 | 0.190 | −2.263062 | 0.310 | 19 |
| SAG | 0.144 | −2.317843 | 0.356 | 19 |
| GNGT1 | 0.153 | −2.323731 | 0.347 | 19 |
| RHO | 0.162 | −2.332956 | 0.338 | 19 |
| RPGRIP1 | 0.228 | −2.401760 | 0.272 | 19 |
| PDC | 0.156 | −2.470951 | 0.344 | 19 |

| Gene | myAUC | Diff power | pct | cluster # | ge |
|---|---|---|---|---|---|
| cluster no. 20 DE = 43 | | | | | |
| PPP1R17 | 0.909 | 3.02 | 8071 0.409 | 20 | PPP1R |
| EBF3 | 0.791 | 2.15 | 8191 0.291 | 20 | EB |
| LGR5 | 0.772 | 2.11 | 3992 0.272 | 20 | LG |
| EBF1 | 0.743 | 1.97 | 8420 0.243 | 20 | EB |
| IGFBP5 | 0.726 | 1.93 | 2417 0.226 | 20 | IGFB |
| TCF4 | 0.834 | 1.74 | 0057 0.334 | 20 | TC |
| PNMAL2 | 0.785 | 1.72 | 2746 0.285 | 20 | PNMA |
| ZFP804A | 0.714 | 1.71 | 2913 0.214 | 20 | ZFP80 |
| ELAVL3 | 0.751 | 1.65 | 7175 0.251 | 20 | ELAV |
| SNCA | 0.723 | 1.63 | 1290 0.223 | 20 | SN |
| LY6H | 0.712 | 1.60 | 0690 0.212 | 20 | LY |
| INA | 0.743 | 1.58 | 6423 0.243 | 20 | I |
| CACNG4 | 0.702 | 1.42 | 8349 0.202 | 20 | CACN |
| MARCKS | 0.777 | 1.38 | 4398 0.277 | 20 | MARC |
| GRIA2 | 0.746 | 1.29 | 4026 0.246 | 20 | GRI |
| SPHKAP | 0.722 | 1.28 | 5598 0.222 | 20 | SPHK |
| CALB2 | 0.719 | 1.27 | 4202 0.219 | 20 | CAL |
| MEG3 | 0.813 | 1.26 | 2649 0.313 | 20 | ME |
| BASP1 | 0.724 | 1.23 | 1810 0.224 | 20 | BAS |
| RTN1 | 0.750 | 1.22 | 6570 0.250 | 20 | RT |
| CELF4 | 0.769 | 1.22 | 0263 0.269 | 20 | CEL |
| NEUROD4 | 0.719 | 1.14 | 3353 0.219 | 20 | NEURO |
| GNG3 | 0.711 | 1.10 | 4068 0.211 | 20 | GN |
| SYT1 | 0.807 | 1.04 | 4134 0.307 | 20 | SY |
| TTC3 | 0.768 | 1.02 | 9450 0.268 | 20 | TT |
| HMGN1 | 0.273 | −1.01 | 4397 0.227 | 20 | HMG |
| GNB1 | 0.284 | −1.07 | 5547 0.216 | 20 | GN |
| ROM1 | 0.274 | −1.14 | 4841 0.226 | 20 | RO |
| UNC119 | 0.276 | −1.17 | 8787 0.224 | 20 | UNC1 |
| GNAT1 | 0.261 | −1.19 | 3799 0.239 | 20 | GNA |
| GNGT1 | 0.225 | −1.28 | 0242 0.275 | 20 | GNG |
| PDE6G | 0.253 | −1.28 | 9229 0.247 | 20 | PDE |
| PRPH2 | 0.237 | −1.30 | 6099 0.263 | 20 | PRP |
| RP1 | 0.270 | −1.31 | 2369 0.230 | 20 | R |
| RHO | 0.219 | −1.31 | 4846 0.281 | 20 | R |
| RCVRN | 0.254 | −1.31 | 7434 0.246 | 20 | RCV |
| RS1 | 0.290 | −1.31 | 7916 0.210 | 20 | R |
| PDC | 0.224 | −1.32 | 7322 0.276 | 20 | P |
| TULP1 | 0.243 | −1.33 | 8314 0.257 | 20 | TUL |
| PDE6B | 0.266 | −1.34 | 2076 0.234 | 20 | PDE |
| CNGA1 | 0.283 | −1.37 | 9756 0.217 | 20 | CNG |
| RPGRIP1 | 0.282 | −1.42 | 3791 0.218 | 20 | RPGRI |
| SAG | 0.196 | −1.47 | 6851 0.304 | 20 | S |
| cluster no. 21 DE = 45 | | | | | |
| NHLH2 | 0.943 | 3.05 | 4281 0.443 | 21 | NHL |
| NFIX | 0.847 | 2.29 | 9079 0.347 | 21 | NF |

TABLE 6-continued

Genes differentially expressed in each of the 39 retinal cell clusters.

| | | | | |
|---|---|---|---|---|
| CRABP1 0.842 | 2.27 | 6418 0.342 | 21 | CRAB |
| CCK 0.742 | 2.07 | 4822 0.242 | 21 | C |
| GRIK2 0.782 | 2.07 | 0961 0.282 | 21 | GRI |
| HPCA 0.803 | 2.00 | 5328 0.303 | 21 | HP |
| ELAVL3 0.824 | 1.88 | 8644 0.324 | 21 | ELAV |
| PRKCB 0.802 | 1.86 | 1453 0.302 | 21 | PRK |
| CNTN6 0.738 | 1.83 | 6086 0.238 | 21 | CNT |
| NCKAP5 0.741 | 1.83 | 1134 0.241 | 21 | NCKA |
| LGR5 0.714 | 1.74 | 8355 0.214 | 21 | LG |
| EBF1 0.734 | 1.71 | 4978 0.234 | 21 | EB |
| NRXN1 0.724 | 1.69 | 3385 0.224 | 21 | NRX |
| CELF4 0.853 | 1.68 | 7320 0.353 | 21 | CEL |
| TCF4 0.839 | 1.67 | 9788 0.339 | 21 | TC |
| PRDM13 0.709 | 1.67 | 9478 0.209 | 21 | PRDM |
| CHN2 0.721 | 1.62 | 1249 0.221 | 21 | CH |
| GNAL 0.708 | 1.58 | 7639 0.208 | 21 | GN |
| KCND3 0.701 | 1.57 | 6876 0.201 | 21 | KCN |
| ZFP804A 0.710 | 1.56 | 4564 0.210 | 21 | ZFP80 |
| SLC24A3 0.751 | 1.54 | 4541 0.251 | 21 | SLC24 |
| APC 0.810 | 1.49 | 8604 0.310 | 21 | A |
| ANK3 0.775 | 1.40 | 2792 0.275 | 21 | AN |
| CAMK2N1 0.768 | 1.37 | 7643 0.268 | 21 | CAMK2 |
| PNMAL2 0.740 | 1.36 | 3728 0.240 | 21 | PNMA |
| GRIA2 0.765 | 1.32 | 0910 0.265 | 21 | GRI |
| SPHKAP 0.749 | 1.30 | 6807 0.249 | 21 | SPHK |
| CALM2 0.811 | 1.26 | 1951 0.311 | 21 | CAL |
| MEG3 0.844 | 1.24 | 7565 0.344 | 21 | ME |
| APP 0.745 | 1.13 | 2361 0.245 | 21 | A |
| TTC3 0.794 | 1.11 | 6633 0.294 | 21 | TT |
| GPM6A 0.706 | 1.10 | 4331 0.206 | 21 | GPM |
| UNC119 0.296 | −1.16 | 3773 0.204 | 21 | UNC1 |
| RP1 0.295 | −1.18 | 0835 0.205 | 21 | R |
| ROM1 0.285 | −1.18 | 8372 0.215 | 21 | RO |
| PDE6G 0.275 | −1.19 | 3017 0.225 | 21 | PDE |
| PDE6B 0.286 | −1.24 | 4644 0.214 | 21 | PDE |
| TULP1 0.264 | −1.25 | 7146 0.236 | 21 | TUL |
| RHO 0.234 | −1.26 | 0099 0.266 | 21 | R |
| RCVRN 0.272 | −1.27 | 2038 0.228 | 21 | RCV |
| SAG 0.226 | −1.28 | 7003 0.274 | 21 | S |
| PRPH2 0.250 | −1.29 | 1410 0.250 | 21 | PRP |
| PDC 0.235 | −1.29 | 4464 0.265 | 21 | P |
| GNGT1 0.234 | −1.29 | 5401 0.266 | 21 | GNG |
| GNAT1 0.262 | −1.29 | 9206 0.238 | 21 | GNA |

| | myAUC | myDiff | power | cluster # |
|---|---|---|---|---|
| cluster no. 22 DE = 51 | | | | |
| LAMP5 | 0.944 | 2.824713 | 0.444 | 22 |
| TFAP2B | 0.872 | 2.223340 | 0.372 | 22 |
| CACNG4 | 0.834 | 1.969710 | 0.334 | 22 |
| ZFP804A | 0.751 | 1.834667 | 0.251 | 22 |
| DPP6 | 0.764 | 1.729152 | 0.264 | 22 |
| GRIA1 | 0.718 | 1.703136 | 0.218 | 22 |
| NEUROD2 | 0.712 | 1.641371 | 0.212 | 22 |
| CELF4 | 0.860 | 1.622471 | 0.360 | 22 |
| PAX6 | 0.803 | 1.597197 | 0.303 | 22 |
| SLC6A9 | 0.760 | 1.571800 | 0.260 | 22 |
| MEG3 | 0.866 | 1.469502 | 0.366 | 22 |
| 2900011O08RIK | 0.729 | 1.446080 | 0.229 | 22 |
| ELAVL3 | 0.749 | 1.390450 | 0.249 | 22 |
| RAB3C | 0.713 | 1.382919 | 0.213 | 22 |
| NRSN1 | 0.702 | 1.336043 | 0.202 | 22 |
| PNMAL2 | 0.747 | 1.334122 | 0.247 | 22 |
| TCF4 | 0.788 | 1.329726 | 0.288 | 22 |
| GRIA2 | 0.780 | 1.313318 | 0.280 | 22 |
| MARCKSL1 | 0.716 | 1.298641 | 0.216 | 22 |
| SLC32A1 | 0.704 | 1.296328 | 0.204 | 22 |
| SNHG11 | 0.784 | 1.279440 | 0.284 | 22 |
| MAPT | 0.702 | 1.244966 | 0.202 | 22 |
| NRXN2 | 0.701 | 1.211145 | 0.201 | 22 |
| GNG3 | 0.760 | 1.195139 | 0.260 | 22 |
| NAP1L5 | 0.724 | 1.176074 | 0.224 | 22 |
| TTC3 | 0.805 | 1.171854 | 0.305 | 22 |
| TAGLN3 | 0.710 | 1.156623 | 0.210 | 22 |
| PTPRD | 0.717 | 1.099502 | 0.217 | 22 |
| BASP1 | 0.727 | 1.088889 | 0.227 | 22 |
| THRA | 0.713 | 1.076652 | 0.213 | 22 |
| SV2A | 0.747 | 1.060584 | 0.247 | 22 |
| SNCB | 0.757 | 1.048856 | 0.257 | 22 |
| PLEKHA1 | 0.702 | 1.025231 | 0.202 | 22 |
| GPM6A | 0.708 | 1.019030 | 0.208 | 22 |
| HMGN1 | 0.273 | −1.040507 | 0.227 | 22 |
| GNB1 | 0.285 | −1.170599 | 0.215 | 22 |
| PDE6B | 0.293 | −1.193748 | 0.207 | 22 |
| RP1 | 0.295 | −1.213102 | 0.205 | 22 |
| UNC119 | 0.278 | −1.263254 | 0.222 | 22 |
| PRPH2 | 0.245 | −1.315824 | 0.255 | 22 |
| PDE6G | 0.264 | −1.337712 | 0.236 | 22 |
| RPGRIP1 | 0.288 | −1.352712 | 0.212 | 22 |
| PDC | 0.226 | −1.365109 | 0.274 | 22 |
| TULP1 | 0.248 | −1.369050 | 0.252 | 22 |
| GNAT1 | 0.254 | −1.389822 | 0.246 | 22 |
| NR2E3 | 0.292 | −1.390392 | 0.208 | 22 |
| ROM1 | 0.261 | −1.428090 | 0.239 | 22 |
| GNGT1 | 0.219 | −1.443382 | 0.281 | 22 |
| RCVRN | 0.259 | −1.447967 | 0.241 | 22 |
| SAG | 0.208 | −1.466971 | 0.292 | 22 |
| RHO | 0.216 | −1.494424 | 0.284 | 22 |
| cluster no. 23 DE = 67 | | | | |
| TFAP2B | 0.928 | 2.494440 | 0.428 | 23 |
| GAD1 | 0.917 | 2.437951 | 0.417 | 23 |
| FBXW7 | 0.917 | 2.420581 | 0.417 | 23 |
| 2610017I09RIK | 0.846 | 2.309127 | 0.346 | 23 |
| PCP4 | 0.938 | 2.265534 | 0.438 | 23 |
| SLC6A1 | 0.885 | 2.235858 | 0.385 | 23 |
| DKK3 | 0.939 | 2.182791 | 0.439 | 23 |
| CELF4 | 0.935 | 2.157447 | 0.435 | 23 |
| GUCY1A3 | 0.889 | 2.108061 | 0.389 | 23 |
| SIX3 | 0.889 | 2.095564 | 0.389 | 23 |
| C1QL2 | 0.822 | 2.067956 | 0.322 | 23 |
| GUCY1B3 | 0.865 | 2.029309 | 0.365 | 23 |

TABLE 6-continued

Genes differentially expressed in each of the 39 retinal cell clusters.

| | | | | |
|---|---|---|---|---|
| CBFA2T3 | 0.786 | 2.026242 | 0.286 | 23 |
| POU3F3 | 0.772 | 1.859852 | 0.272 | 23 |
| NAP1L5 | 0.860 | 1.807160 | 0.360 | 23 |
| TKT | 0.836 | 1.783663 | 0.336 | 23 |
| HPGD | 0.751 | 1.778162 | 0.251 | 23 |
| SNHG11 | 0.895 | 1.776925 | 0.395 | 23 |
| ADARB1 | 0.803 | 1.745295 | 0.303 | 23 |
| GAD2 | 0.747 | 1.658875 | 0.247 | 23 |
| LRRN3 | 0.768 | 1.658143 | 0.268 | 23 |
| CACNG4 | 0.822 | 1.640376 | 0.322 | 23 |
| OLFM1 | 0.774 | 1.633329 | 0.274 | 23 |
| MEG3 | 0.894 | 1.607437 | 0.394 | 23 |
| ELAVL4 | 0.717 | 1.469508 | 0.217 | 23 |
| KCNIP1 | 0.731 | 1.459041 | 0.231 | 23 |
| KCND3 | 0.724 | 1.426750 | 0.224 | 23 |
| ELAVL3 | 0.756 | 1.383776 | 0.256 | 23 |
| SLC32A1 | 0.738 | 1.352046 | 0.238 | 23 |
| GNG3 | 0.797 | 1.337489 | 0.297 | 23 |
| NDRG4 | 0.760 | 1.318015 | 0.260 | 23 |
| HAP1 | 0.735 | 1.314020 | 0.235 | 23 |
| FRMD5 | 0.721 | 1.311942 | 0.221 | 23 |
| APC | 0.800 | 1.285337 | 0.300 | 23 |
| TMX4 | 0.759 | 1.279036 | 0.259 | 23 |
| SCG2 | 0.808 | 1.243538 | 0.308 | 23 |
| GRIA2 | 0.774 | 1.215973 | 0.274 | 23 |
| LDHB | 0.727 | 1.201661 | 0.227 | 23 |
| TTC3 | 0.838 | 1.197850 | 0.338 | 23 |
| BASP1 | 0.772 | 1.194948 | 0.272 | 23 |
| MARCKSL1 | 0.704 | 1.159591 | 0.204 | 23 |
| GPRASP1 | 0.738 | 1.153237 | 0.238 | 23 |
| PAX6 | 0.748 | 1.152232 | 0.248 | 23 |
| HSD17B12 | 0.736 | 1.142303 | 0.236 | 23 |
| SIX3OS1 | 0.721 | 1.135949 | 0.221 | 23 |
| IMPACT | 0.704 | 1.129338 | 0.204 | 23 |
| 6430548M08RIK | 0.708 | 1.125889 | 0.208 | 23 |
| TRIM9 | 0.711 | 1.124665 | 0.211 | 23 |
| TAGLN3 | 0.728 | 1.095091 | 0.228 | 23 |
| SNCB | 0.779 | 1.067869 | 0.279 | 23 |
| HMGN1 | 0.286 | −1.009380 | 0.214 | 23 |
| GNB1 | 0.270 | −1.275684 | 0.230 | 23 |
| UNC119 | 0.280 | −1.310248 | 0.220 | 23 |
| ROM1 | 0.271 | −1.317239 | 0.229 | 23 |
| RPGRIP1 | 0.295 | −1.333701 | 0.205 | 23 |
| TULP1 | 0.243 | −1.374221 | 0.257 | 23 |
| PDE6G | 0.255 | −1.375311 | 0.245 | 23 |
| RCVRN | 0.266 | −1.381017 | 0.234 | 23 |
| PRPH2 | 0.236 | −1.387400 | 0.264 | 23 |
| PDE6B | 0.278 | −1.393976 | 0.222 | 23 |
| RP1 | 0.274 | −1.402082 | 0.226 | 23 |
| RS1 | 0.293 | −1.450358 | 0.207 | 23 |
| GNGT1 | 0.219 | −1.451672 | 0.281 | 23 |
| RHO | 0.212 | −1.459768 | 0.288 | 23 |
| SAG | 0.209 | −1.461985 | 0.291 | 23 |
| PDC | 0.215 | −1.492115 | 0.285 | 23 |
| GNAT1 | 0.243 | −1.525967 | 0.257 | 23 | cluster no. 24 DE = 49

| myAUC | m | yDiff power | r clus | t |
|---|---|---|---|---|
| RHO 0.945 | 1.8 | 57266 0.44 | 5 2 | 4 |
| GNAT1 0.889 | 1.7 | 80155 0.38 | 9 2 | 4 G |
| SLC24A1 0.802 | 1.7 | 43717 0.30 | 2 2 | 4 SLC |
| PDE6B 0.855 | 1.7 | 43134 0.35 | 5 2 | 4 P |
| PDC 0.919 | 1.7 | 00660 0.41 | 9 2 | 4 |
| CNGA1 0.812 | 1.6 | 80377 0.31 | 2 2 | 4 C |
| RP1 0.840 | 1.6 | 73527 0.34 | 0 2 | 4 |
| SAG 0.930 | 1.6 | 50156 0.43 | 0 2 | 4 |
| NR2E3 0.810 | 1.6 | 44369 0.31 | 0 2 | 4 N |
| NRL 0.808 | 1.6 | 44321 0.30 | 8 2 | 4 |
| GNB1 0.867 | 1.6 | 19807 0.36 | 7 2 | 4 |
| GNGT1 0.902 | 1.6 | 08430 0.40 | 2 2 | 4 G |
| PRPH2 0.880 | 1.5 | 97904 0.38 | 0 2 | 4 P |
| PDE6A 0.737 | 1.5 | 88021 0.23 | 7 2 | 4 P |
| PDE6G 0.856 | 1.5 | 58813 0.35 | 6 2 | 4 P |
| RCVRN 0.842 | 1.5 | 36418 0.34 | 2 2 | 4 R |
| RPGRIP1 0.794 | 1.5 | 33882 0.29 | 4 2 | 4 RPG |
| RS1 0.790 | 1.5 | 19606 0.29 | 0 2 | 4 |
| GUCA1B 0.707 | 1.5 | 06131 0.20 | 7 2 | 4 GU |
| CNGB1 0.715 | 1.4 | 95706 0.21 | 5 2 | 4 C |
| ROM1 0.820 | 1.4 | 77666 0.32 | 0 2 | 4 |
| RDH12 0.704 | 1.4 | 27972 0.20 | 4 2 | 4 R |
| FAM57B 0.731 | 1.3 | 66885 0.23 | 1 2 | 4 FA |
| TULP1 0.835 | 1.3 | 49889 0.33 | 5 2 | 4 T |
| AIPL1 0.706 | 1.1 | 64169 0.20 | 6 2 | 4 A |
| HMGN1 0.797 | 1.1 | 36452 0.29 | 7 2 | 4 H |
| UNC119 0.732 | 1.0 | 69530 0.23 | 2 2 | 4 UN |
| SERINC1 0.281 | −1.0 | 08401 0.21 | 9 2 | 4 SER |
| BEX2 0.291 | −1.0 | 15902 0.20 | 9 2 | 4 |
| ITM2B 0.266 | −1.0 | 43926 0.23 | 4 2 | 4 I |
| YWHAB 0.253 | −1.0 | 51200 0.24 | 7 2 | 4 Y |
| MAP4 0.290 | −1.0 | 88812 0.21 | 0 2 | 4 |
| HSP90AB1 0.209 | −1.1 | 88043 0.29 | 1 2 | 4 HSP9 |
| GNAS 0.229 | −1.2 | 07829 0.27 | 1 2 | 4 |
| TMSB10 0.290 | −1.3 | 40497 0.21 | 0 2 | 4 TM |
| HMGN3 0.283 | −1.3 | 53477 0.21 | 7 2 | 4 H |
| SCG3 0.286 | −1.3 | 66486 0.21 | 4 2 | 4 |
| CPLX3 0.261 | −1.4 | 40524 0.23 | 9 2 | 4 C |
| TTC3 0.215 | −1.4 | 59532 0.28 | 5 2 | 4 |
| CELF4 0.277 | −1.4 | 77617 0.22 | 3 2 | 4 C |
| ITM2C 0.274 | −1.5 | 36542 0.22 | 6 2 | 4 I |
| GPM6A 0.282 | −1.6 | 04191 0.21 | 8 2 | 4 G |
| PTPRD 0.290 | −1.6 | 22257 0.21 | 0 2 | 4 P |
| APP 0.289 | −1.6 | 28911 0.21 | 1 2 | 4 |
| NRXN3 0.262 | −1.6 | 82084 0.23 | 8 2 | 4 N |
| NME1 0.253 | −1.6 | 87771 0.24 | 7 2 | 4 |
| GNAO1 0.225 | −1.9 | 02619 0.27 | 5 2 | 4 G |

TABLE 6-continued

Genes differentially expressed in each of the 39 retinal cell clusters.

| | CALM1 0.173 | −1.9 | 04185 0.32 | 7 2 | 4 C |
|---|---|---|---|---|---|
| | MEG3 0.178 | −2.1 | 49534 0.32 | 2 2 | 4 |

| | myAUC | myDiff | power | cluster # |
|---|---|---|---|---|
| cluster no. 25 DE = 14 | | | | |
| PDE6H | 0.981 | 3.791576 | 0.481 | 25 |
| OPN1SW | 0.832 | 3.587490 | 0.332 | 25 |
| GNGT2 | 0.964 | 3.261674 | 0.464 | 25 |
| OPN1MW | 0.891 | 3.211129 | 0.391 | 25 |
| ARR3 | 0.918 | 3.071492 | 0.418 | 25 |
| GNAT2 | 0.941 | 3.020245 | 0.441 | 25 |
| PDE6C | 0.879 | 2.613656 | 0.379 | 25 |
| KCNE2 | 0.853 | 2.337871 | 0.353 | 25 |
| GUCA1A | 0.881 | 1.790297 | 0.381 | 25 |
| CD59A | 0.725 | 1.742573 | 0.225 | 25 |
| CCDC136 | 0.730 | 1.673432 | 0.230 | 25 |
| GNB3 | 0.831 | 1.569696 | 0.331 | 25 |
| SCG3 | 0.756 | 1.297292 | 0.256 | 25 |
| 4930447C04RIK | 0.703 | 1.275268 | 0.203 | 25 |
| cluster no. 26 DE = 87 | | | | |
| PCP2 | 0.988 | 3.533209 | 0.488 | 26 |
| TRPM1 | 0.990 | 3.445746 | 0.490 | 26 |
| GNG13 | 0.968 | 2.839805 | 0.468 | 26 |
| ISL1 | 0.948 | 2.719519 | 0.448 | 26 |
| CAR8 | 0.913 | 2.699407 | 0.413 | 26 |
| PRKCA | 0.937 | 2.609664 | 0.437 | 26 |
| GPR179 | 0.900 | 2.431366 | 0.400 | 26 |
| CALM1 | 0.988 | 2.421322 | 0.488 | 26 |
| QPCT | 0.875 | 2.374165 | 0.375 | 26 |
| VSX2 | 0.895 | 2.348176 | 0.395 | 26 |
| PCP4 | 0.945 | 2.313286 | 0.445 | 26 |
| GRM6 | 0.873 | 2.232811 | 0.373 | 26 |
| GNAO1 | 0.948 | 2.215946 | 0.448 | 26 |
| LRTM1 | 0.886 | 2.179512 | 0.386 | 26 |
| TRNP1 | 0.855 | 2.159361 | 0.355 | 26 |
| CACNA2D3 | 0.803 | 2.101927 | 0.303 | 26 |
| NME1 | 0.917 | 2.066828 | 0.417 | 26 |
| GM4792 | 0.870 | 2.059987 | 0.370 | 26 |
| LIN7A | 0.875 | 2.018521 | 0.375 | 26 |
| PROX1 | 0.850 | 2.002116 | 0.350 | 26 |
| ABLIM1 | 0.874 | 1.975136 | 0.374 | 26 |
| CABP5 | 0.840 | 1.934630 | 0.340 | 26 |
| VSTM2B | 0.782 | 1.934535 | 0.282 | 26 |
| STRIP2 | 0.761 | 1.913167 | 0.261 | 26 |
| SEBOX | 0.763 | 1.858373 | 0.263 | 26 |
| RPA1 | 0.790 | 1.856293 | 0.290 | 26 |
| CCDC136 | 0.803 | 1.850276 | 0.303 | 26 |
| CHGB | 0.903 | 1.837030 | 0.403 | 26 |
| B3GALT2 | 0.775 | 1.744162 | 0.275 | 26 |
| MAP4 | 0.873 | 1.732032 | 0.373 | 26 |
| RNF152 | 0.743 | 1.723092 | 0.243 | 26 |
| ZBTB20 | 0.807 | 1.707863 | 0.307 | 26 |
| CNTN4 | 0.737 | 1.705791 | 0.237 | 26 |
| IFT20 | 0.804 | 1.668409 | 0.304 | 26 |
| CASP7 | 0.725 | 1.663103 | 0.225 | 26 |
| TMSB10 | 0.844 | 1.659561 | 0.344 | 26 |
| ITM2C | 0.829 | 1.654655 | 0.329 | 26 |
| NDNF | 0.746 | 1.643132 | 0.246 | 26 |
| TGFB2 | 0.782 | 1.633774 | 0.282 | 26 |
| GNB3 | 0.844 | 1.600635 | 0.344 | 26 |
| PTPRD | 0.810 | 1.574528 | 0.310 | 26 |
| CLTB | 0.779 | 1.568857 | 0.279 | 26 |
| PRDM8 | 0.706 | 1.551374 | 0.206 | 26 |
| CAR10 | 0.758 | 1.546273 | 0.258 | 26 |
| NEUROD4 | 0.787 | 1.443959 | 0.287 | 26 |
| KCNMA1 | 0.746 | 1.443881 | 0.246 | 26 |
| GABRR1 | 0.702 | 1.424760 | 0.202 | 26 |
| MAP6 | 0.704 | 1.389962 | 0.204 | 26 |
| CPLX3 | 0.833 | 1.368767 | 0.333 | 26 |
| CNTNAP2 | 0.705 | 1.357327 | 0.205 | 26 |
| REV3L | 0.745 | 1.315953 | 0.245 | 26 |
| HMGN3 | 0.760 | 1.309377 | 0.260 | 26 |
| HSPA12A | 0.710 | 1.264275 | 0.210 | 26 |
| CAMSAP2 | 0.701 | 1.226712 | 0.201 | 26 |
| PPP3CA | 0.768 | 1.224280 | 0.268 | 26 |
| ANK3 | 0.715 | 1.182166 | 0.215 | 26 |
| DNAJA1 | 0.713 | 1.141870 | 0.213 | 26 |
| ZFP365 | 0.701 | 1.138197 | 0.201 | 26 |
| APLP2 | 0.840 | 1.116573 | 0.340 | 26 |
| ATP2B1 | 0.827 | 1.109752 | 0.327 | 26 |
| 2010107E04RIK | 0.807 | 1.078386 | 0.307 | 26 |
| GLS | 0.729 | 1.030787 | 0.229 | 26 |
| MACF1 | 0.729 | 1.028031 | 0.229 | 26 |
| NRXN3 | 0.726 | 1.013354 | 0.226 | 26 |
| ROM1 | 0.247 | −1.535062 | 0.253 | 26 |
| CST3 | 0.258 | −1.542458 | 0.242 | 26 |
| PRPH2 | 0.199 | −1.778911 | 0.301 | 26 |
| FAM57B | 0.266 | −1.812713 | 0.234 | 26 |
| AIPL1 | 0.282 | −1.854518 | 0.218 | 26 |
| PDE6A | 0.288 | −1.862827 | 0.212 | 26 |
| NRL | 0.236 | −1.917565 | 0.264 | 26 |
| SLC24A1 | 0.247 | −1.968291 | 0.253 | 26 |
| CNGA1 | 0.234 | −1.993041 | 0.266 | 26 |
| NR2E3 | 0.232 | −2.003551 | 0.268 | 26 |
| RS1 | 0.232 | −2.056603 | 0.268 | 26 |
| TULP1 | 0.179 | −2.057501 | 0.321 | 26 |
| RP1 | 0.204 | −2.067114 | 0.296 | 26 |
| GNAT1 | 0.181 | −2.080109 | 0.319 | 26 |
| PDE6B | 0.199 | −2.104653 | 0.301 | 26 |
| RPGRIP1 | 0.217 | −2.108733 | 0.283 | 26 |
| PDE6G | 0.180 | −2.114659 | 0.320 | 26 |
| GNB1 | 0.165 | −2.145253 | 0.335 | 26 |
| RCVRN | 0.188 | −2.149677 | 0.312 | 26 |
| GNGT1 | 0.146 | −2.187446 | 0.354 | 26 |
| RHO | 0.143 | −2.216846 | 0.357 | 26 |
| SAG | 0.133 | −2.285265 | 0.367 | 26 |
| PDC | 0.141 | −2.289428 | 0.359 | 26 |

| | | | yDiff | | |
|---|---|---|---|---|---|
| | myAUC | m | powe | r clus | t |
| cluster no. 27 DE = 27 | | | | | |
| GRIK1 0.916 | | 3.0 | 10898 0.41 | 6 2 | 7 G |
| GSG1 0.872 | | 2.6 | 94718 0.37 | 2 2 | 7 |
| OTOR 0.811 | | 2.5 | 74650 0.31 | 1 2 | 7 |
| NNAT 0.810 | | 2.5 | 09846 0.31 | 0 2 | 7 |
| FAM19A3 0.808 | | 2.1 | 90301 0.30 | 8 2 | 7 FAM |
| SLITRK6 0.722 | | 1.9 | 42192 0.22 | 2 2 | 7 SLI |
| LHX4 0.775 | | 1.9 | 30099 0.27 | 5 2 | 7 |
| PCP4 0.841 | | 1.6 | 79884 0.34 | 1 2 | 7 |
| PHYHIPL 0.742 | | 1.6 | 59067 0.24 | 2 2 | 7 PHY |
| SPHKAP 0.770 | | 1.6 | 43517 0.27 | 0 2 | 7 SP |
| CACNA2D1 0.707 | | 1.6 | 00775 0.20 | 7 2 | 7 CACN |
| CABP5 0.756 | | 1.5 | 47771 0.25 | 6 2 | 7 C |
| SCGN 0.711 | | 1.5 | 42676 0.21 | 1 2 | 7 |
| BC030499 0.704 | | 1.4 | 55994 0.20 | 4 2 | 7 BC03 |
| LRTM1 0.754 | | 1.4 | 08952 0.25 | 4 2 | 7 L |
| NME1 0.777 | | 1.3 | 17789 0.27 | 7 2 | 7 |
| CADPS 0.715 | | 1.2 | 34166 0.21 | 5 2 | 7 C |
| NEUROD4 0.732 | | 1.2 | 22587 0.23 | 2 2 | 7 NEU |
| VSX2 0.709 | | 1.1 | 50766 0.20 | 9 2 | 7 |

TABLE 6-continued

Genes differentially expressed in each of the 39 retinal cell clusters.

| | | | | | |
|---|---|---|---|---|---|
| NRXN3 0.718 | 1.1 | 38040 0.21 | 8 2 | 7 N | |
| APP 0.733 | 1.1 | 24188 0.23 | 3 2 | 7 | |
| PRPH2 0.281 | −1.0 | 16461 0.21 | 9 2 | 7 P | |
| SAG 0.255 | −1.0 | 43850 0.24 | 5 2 | 7 | |
| GNAT1 0.289 | −1.0 | 51331 0.21 | 1 2 | 7 G | |
| RCVRN 0.299 | −1.0 | 59446 0.20 | 1 2 | 7 R | |
| PDC 0.261 | −1.0 | 75620 0.23 | 9 2 | 7 | |
| RHO 0.261 | −1.0 | 94430 0.23 | 9 2 | 7 | |

| | myAUC | myDiff | power | cluster # |
|---|---|---|---|---|
| | | cluster no. 28 DE = 48 | | |
| SLIT2 | 0.911 | 2.494784 | 0.411 | 28 |
| SCGN | 0.910 | 2.432819 | 0.410 | 28 |
| CDH8 | 0.874 | 2.307964 | 0.374 | 28 |
| SCG2 | 0.930 | 2.181234 | 0.430 | 28 |
| ZFHX4 | 0.851 | 2.178856 | 0.351 | 28 |
| VSX1 | 0.779 | 1.895571 | 0.279 | 28 |
| NETO1 | 0.751 | 1.891687 | 0.251 | 28 |
| GABRA1 | 0.861 | 1.787593 | 0.361 | 28 |
| PDE1A | 0.752 | 1.652362 | 0.252 | 28 |
| NEUROD4 | 0.854 | 1.610346 | 0.354 | 28 |
| GRIA2 | 0.837 | 1.599678 | 0.337 | 28 |
| CADPS | 0.828 | 1.587531 | 0.328 | 28 |
| CHRNA6 | 0.747 | 1.566433 | 0.247 | 28 |
| NTNG1 | 0.770 | 1.535756 | 0.270 | 28 |
| IGF1 | 0.745 | 1.475532 | 0.245 | 28 |
| TACR3 | 0.706 | 1.466025 | 0.206 | 28 |
| LRTM1 | 0.810 | 1.446170 | 0.310 | 28 |
| LHX4 | 0.769 | 1.437311 | 0.269 | 28 |
| GRIK1 | 0.740 | 1.435103 | 0.240 | 28 |
| TNNT1 | 0.717 | 1.388436 | 0.217 | 28 |
| PTPRD | 0.808 | 1.388278 | 0.308 | 28 |
| THSD7A | 0.765 | 1.381783 | 0.265 | 28 |
| ESAM | 0.708 | 1.372116 | 0.208 | 28 |
| A730046J19RIK | 0.711 | 1.372055 | 0.211 | 28 |
| NRXN3 | 0.819 | 1.340482 | 0.319 | 28 |
| SPHKAP | 0.761 | 1.298899 | 0.261 | 28 |
| GLRA1 | 0.711 | 1.292095 | 0.211 | 28 |
| CAR10 | 0.758 | 1.238441 | 0.258 | 28 |
| BC030499 | 0.717 | 1.204192 | 0.217 | 28 |
| PGM2L1 | 0.735 | 1.189284 | 0.235 | 28 |
| TMEM215 | 0.713 | 1.158325 | 0.213 | 28 |
| PCP4L1 | 0.717 | 1.150546 | 0.217 | 28 |
| GUCY1B3 | 0.726 | 1.146479 | 0.226 | 28 |
| CNTN1 | 0.713 | 1.136843 | 0.213 | 28 |
| FRMD3 | 0.704 | 1.067778 | 0.204 | 28 |
| SAMSN1 | 0.719 | 1.063324 | 0.219 | 28 |
| HMGN3 | 0.745 | 1.013834 | 0.245 | 28 |
| APP | 0.761 | 1.009757 | 0.261 | 28 |
| GNB1 | 0.281 | −1.213742 | 0.219 | 28 |
| PRPH2 | 0.262 | −1.246574 | 0.238 | 28 |
| TULP1 | 0.270 | −1.255972 | 0.230 | 28 |
| RCVRN | 0.288 | −1.299880 | 0.212 | 28 |
| GNGT1 | 0.251 | −1.319077 | 0.249 | 28 |
| GNAT1 | 0.263 | −1.357660 | 0.237 | 28 |
| SAG | 0.220 | −1.392674 | 0.280 | 28 |
| PDE6G | 0.262 | −1.411349 | 0.238 | 28 |
| PDC | 0.228 | −1.424123 | 0.272 | 28 |
| RHO | 0.225 | −1.457060 | 0.275 | 28 |
| | | cluster no. 29 DE = 39 | | |
| SLIT2 | 0.817 | 2.116591 | 0.317 | 29 |
| GABRA1 | 0.832 | 2.006228 | 0.332 | 29 |
| PCDH17 | 0.702 | 1.882124 | 0.202 | 29 |
| WLS | 0.708 | 1.845341 | 0.208 | 29 |
| PCDH10 | 0.727 | 1.819161 | 0.227 | 29 |
| ZFHX4 | 0.726 | 1.772755 | 0.226 | 29 |
| GLRA1 | 0.744 | 1.767981 | 0.244 | 29 |
| A730046J19RIK | 0.706 | 1.664659 | 0.206 | 29 |
| SLC24A3 | 0.739 | 1.605346 | 0.239 | 29 |
| NRXN3 | 0.824 | 1.586941 | 0.324 | 29 |
| KCNMA1 | 0.754 | 1.572355 | 0.254 | 29 |
| FAM19A3 | 0.708 | 1.512326 | 0.208 | 29 |
| CABP5 | 0.747 | 1.504850 | 0.247 | 29 |
| TMEM215 | 0.728 | 1.483366 | 0.228 | 29 |
| PHYHIPL | 0.738 | 1.470131 | 0.238 | 29 |
| PTPRD | 0.786 | 1.461384 | 0.286 | 29 |
| SPHKAP | 0.755 | 1.453958 | 0.255 | 29 |
| CADPS | 0.761 | 1.431341 | 0.261 | 29 |
| MEG3 | 0.863 | 1.430565 | 0.363 | 29 |
| LRTM1 | 0.754 | 1.359036 | 0.254 | 29 |
| THSD7A | 0.703 | 1.356030 | 0.203 | 29 |
| NEUROD4 | 0.762 | 1.294731 | 0.262 | 29 |
| NME1 | 0.772 | 1.192665 | 0.272 | 29 |
| VSX2 | 0.726 | 1.181568 | 0.226 | 29 |
| SCG3 | 0.707 | 1.048887 | 0.207 | 29 |
| APP | 0.718 | 1.021875 | 0.218 | 29 |
| ROM1 | 0.288 | −1.125274 | 0.212 | 29 |
| PDE6B | 0.285 | −1.189444 | 0.215 | 29 |
| RP1 | 0.293 | −1.195551 | 0.207 | 29 |
| TULP1 | 0.261 | −1.220904 | 0.239 | 29 |
| GNB1 | 0.262 | −1.221726 | 0.238 | 29 |
| PRPH2 | 0.250 | −1.249883 | 0.250 | 29 |
| SAG | 0.222 | −1.257367 | 0.278 | 29 |
| GNAT1 | 0.257 | −1.311936 | 0.243 | 29 |
| RCVRN | 0.261 | −1.362927 | 0.239 | 29 |
| PDC | 0.222 | −1.366220 | 0.278 | 29 |
| RHO | 0.220 | −1.378427 | 0.280 | 29 |
| PDE6G | 0.248 | −1.428805 | 0.252 | 29 |
| GNGT1 | 0.220 | −1.431648 | 0.280 | 29 |

| myAUC | my Diff | power | cluster # | ge |
|---|---|---|---|---|
| | | cluster no. 30 DE = 60 | | |
| NFIA 0.850 | 2.23 | 6944 0.350 | 30 | NF |
| NEUROD4 0.909 | 2.12 | 5019 0.409 | 30 | NEURO |
| LHX4 0.870 | 2.05 | 9044 0.370 | 30 | LH |
| EPHA7 0.805 | 1.93 | 1362 0.305 | 30 | EPH |
| CABP5 0.825 | 1.86 | 8986 0.325 | 30 | CAB |
| HLF 0.786 | 1.81 | 5451 0.286 | 30 | H |
| PTPRZ1 0.786 | 1.75 | 6697 0.286 | 30 | PTPR |
| ATP2B1 0.923 | 1.72 | 8502 0.423 | 30 | ATP2 |
| TMEM215 0.810 | 1.69 | 9286 0.310 | 30 | TMEM2 |
| CDH9 0.714 | 1.66 | 4116 0.214 | 30 | CD |
| LMO4 0.794 | 1.64 | 8088 0.294 | 30 | LM |
| SULF2 0.759 | 1.64 | 4281 0.259 | 30 | SUL |
| GUCY1A3 0.809 | 1.60 | 6336 0.309 | 30 | GUCY1 |
| SYT4 0.797 | 1.59 | 7987 0.297 | 30 | SY |
| GM4792 0.762 | 1.58 | 3695 0.262 | 30 | GM47 |
| GRM6 0.776 | 1.56 | 8053 0.276 | 30 | GR |
| CAR10 0.794 | 1.53 | 4313 0.294 | 30 | CAR |
| GABRR2 0.714 | 1.51 | 5185 0.214 | 30 | GABR |
| NDNF 0.753 | 1.50 | 7846 0.253 | 30 | ND |
| NRXN3 0.829 | 1.50 | 5059 0.329 | 30 | NRX |

TABLE 6-continued

Genes differentially expressed in each of the 39 retinal cell clusters.

| Gene | Val1 | Val2 | Val3 | Cluster | Label |
|---|---|---|---|---|---|
| KCNG4 0.701 | 1.48 | 2390 0.201 | 30 | KCN |
| GNAO1 0.862 | 1.44 | 6431 0.362 | 30 | GNA |
| VIPR2 0.733 | 1.42 | 0776 0.233 | 30 | VIP |
| FRMD3 0.751 | 1.40 | 6949 0.251 | 30 | FRM |
| SAMSN1 0.748 | 1.40 | 4241 0.248 | 30 | SAMS |
| THSD7A 0.753 | 1.40 | 1838 0.253 | 30 | THSD |
| SOX4 0.722 | 1.35 | 3433 0.222 | 30 | SO |
| APP 0.808 | 1.30 | 8034 0.308 | 30 | A |
| GPR179 0.789 | 1.30 | 2301 0.289 | 30 | GPR1 |
| TUBB2A 0.781 | 1.28 | 1518 0.281 | 30 | TUBB |
| LPHN2 0.705 | 1.26 | 1045 0.205 | 30 | LPH |
| PFKP 0.768 | 1.25 | 3969 0.268 | 30 | PF |
| ISL1 0.814 | 1.23 | 4990 0.314 | 30 | IS |
| PROX1 0.776 | 1.21 | 4681 0.276 | 30 | PRO |
| RRBP1 0.705 | 1.16 | 9975 0.205 | 30 | RRB |
| GABRB3 0.703 | 1.16 | 0288 0.203 | 30 | GABR |
| MEIS2 0.709 | 1.13 | 1658 0.209 | 30 | MEI |
| GNG13 0.728 | 1.09 | 5088 0.228 | 30 | GNG |
| LIN7A 0.754 | 1.08 | 9638 0.254 | 30 | LIN |
| GRIA2 0.755 | 1.02 | 6466 0.255 | 30 | GRI |
| HMGN1 0.256 | −1.17 | 6538 0.244 | 30 | HMG |
| ROM1 0.290 | −1.26 | 0595 0.210 | 30 | RO |
| RPGRIP1 0.273 | −1.55 | 6331 0.227 | 30 | RPGRI |
| RS1 0.279 | −1.57 | 7275 0.221 | 30 | R |
| GNGT1 0.219 | −1.58 | 9959 0.281 | 30 | GNG |
| RP1 0.255 | −1.60 | 4790 0.245 | 30 | R |
| GNB1 0.225 | −1.61 | 1631 0.275 | 30 | GN |
| NRL 0.272 | −1.62 | 8679 0.228 | 30 | N |
| NR2E3 0.271 | −1.64 | 1338 0.229 | 30 | NR2 |
| CNGA1 0.272 | −1.66 | 4166 0.228 | 30 | CNG |
| PDE6B 0.248 | −1.67 | 9470 0.252 | 30 | PDE |
| TULP1 0.222 | −1.68 | 8332 0.278 | 30 | TUL |
| PRPH2 0.212 | −1.69 | 0732 0.288 | 30 | PRP |
| SLC24A1 0.280 | −1.69 | 0999 0.220 | 30 | SLC24 |
| PDE6G 0.227 | −1.72 | 7951 0.273 | 30 | PDE |
| SAG 0.180 | −1.74 | 5533 0.320 | 30 | S |
| GNAT1 0.217 | −1.75 | 8815 0.283 | 30 | GNA |
| RCVRN 0.223 | −1.82 | 2401 0.277 | 30 | RCV |
| PDC 0.186 | −1.83 | 3586 0.314 | 30 | P |
| RHO 0.180 | −1.85 | 2674 0.320 | 30 | R | cluster no. 31 DE = 58

| Gene | Val1 | Val2 | Val3 | Cluster | Label |
|---|---|---|---|---|---|
| LHX4 0.834 | 1.94 | 0702 0.334 | 31 | LH |
| SCGN 0.830 | 1.88 | 5197 0.330 | 31 | SC |
| GSG1 0.798 | 1.78 | 8603 0.298 | 31 | GS |
| NEUROD4 0.859 | 1.76 | 0730 0.359 | 31 | NEURO |
| FRMD3 0.823 | 1.75 | 3604 0.323 | 31 | FRM |
| PCP2 0.899 | 1.74 | 5442 0.399 | 31 | PC |
| SCG2 0.863 | 1.69 | 1052 0.363 | 31 | SC |
| SPHKAP 0.803 | 1.68 | 8447 0.303 | 31 | SPHK |
| LPHN2 0.778 | 1.68 | 5417 0.278 | 31 | LPH |
| CABP5 0.752 | 1.63 | 6734 0.252 | 31 | CAB |
| B3GALT2 0.786 | 1.61 | 2381 0.286 | 31 | B3GAL |
| GUCY1A3 0.797 | 1.57 | 4051 0.297 | 31 | GUCY1 |
| GNG13 0.855 | 1.57 | 2693 0.355 | 31 | GNG |
| LMO4 0.763 | 1.54 | 9801 0.263 | 31 | LM |
| PTPRZ1 0.720 | 1.47 | 1441 0.220 | 31 | PTPR |
| CDH11 0.701 | 1.46 | 3621 0.201 | 31 | CDH |
| ST18 0.709 | 1.46 | 0354 0.209 | 31 | ST |
| CAR10 0.772 | 1.45 | 5466 0.272 | 31 | CAR |
| CADPS 0.770 | 1.41 | 8726 0.270 | 31 | CAD |
| GNB3 0.830 | 1.41 | 6090 0.330 | 31 | GN |
| BHLHE23 0.705 | 1.38 | 4752 0.205 | 31 | BHLHE |
| SLC24A3 0.721 | 1.29 | 4047 0.221 | 31 | SLC24 |
| GRM6 0.754 | 1.28 | 4539 0.254 | 31 | GR |
| NRXN3 0.791 | 1.26 | 7068 0.291 | 31 | NRX |
| LIN7A 0.768 | 1.25 | 5294 0.268 | 31 | LIN |
| RAB3C 0.710 | 1.25 | 1581 0.210 | 31 | RAB |
| PTPRD 0.740 | 1.23 | 6538 0.240 | 31 | PTP |
| ISL1 0.803 | 1.22 | 8409 0.303 | 31 | IS |
| PROX1 0.749 | 1.21 | 1165 0.249 | 31 | PRO |
| FAM184A 0.722 | 1.20 | 6153 0.222 | 31 | FAM18 |
| SAMSN1 0.713 | 1.20 | 3743 0.213 | 31 | SAMS |
| VSX2 0.749 | 1.19 | 7906 0.249 | 31 | VS |
| GM4792 0.721 | 1.14 | 0953 0.221 | 31 | GM47 |
| GPR179 0.746 | 1.10 | 2994 0.246 | 31 | GPR1 |
| GUCY1B3 0.703 | 1.07 | 1395 0.203 | 31 | GUCY1 |

TABLE 6-continued

Genes differentially expressed in each of the 39 retinal cell clusters.

| | | | | |
|---|---|---|---|---|
| KCNMA1 0.708 | 1.06 | 2611 0.208 | 31 | KCNM |
| CLTB 0.720 | 1.05 | 8852 0.220 | 31 | CL |
| NREP 0.768 | 1.04 | 1988 0.268 | 31 | NR |
| NME1 0.766 | 1.02 | 1691 0.266 | 31 | NM |
| TCF4 0.724 | 1.01 | 5121 0.224 | 31 | TC |
| ROM1 0.282 | −1.31 | 8723 0.218 | 31 | RO |
| RPGRIP1 0.290 | −1.38 | 7286 0.210 | 31 | RPGRI |
| RP1 0.260 | −1.45 | 1372 0.240 | 31 | R |
| TULP1 0.242 | −1.47 | 2154 0.258 | 31 | TUL |
| PRPH2 0.236 | −1.47 | 3241 0.264 | 31 | PRP |
| NR2E3 0.283 | −1.49 | 2186 0.217 | 31 | NR2 |
| CNGA1 0.280 | −1.52 | 3041 0.220 | 31 | CNG |
| SLC24A1 0.291 | −1.57 | 2972 0.209 | 31 | SLC24 |
| PDE6B 0.250 | −1.62 | 5189 0.250 | 31 | PDE |
| NRL 0.274 | −1.63 | 0936 0.226 | 31 | N |
| GNB1 0.217 | −1.66 | 5855 0.283 | 31 | GN |
| RCVRN 0.233 | −1.66 | 8240 0.267 | 31 | RCV |
| RS1 0.266 | −1.70 | 2551 0.234 | 31 | R |
| PDE6G 0.228 | −1.70 | 7456 0.272 | 31 | PDE |
| GNAT1 0.222 | −1.71 | 8310 0.278 | 31 | GNA |
| SAG 0.184 | −1.74 | 9072 0.316 | 31 | S |
| RHO 0.185 | −1.76 | 0460 0.315 | 31 | R |
| PDC 0.188 | −1.79 | 5587 0.312 | 31 | P | cluster no. 32 DE = 81

| | myAUC | myDiff | power | cluster # |
|---|---|---|---|---|
| IGFN1 | 0.906 | 2.609491 | 0.406 | 32 |
| VSX1 | 0.915 | 2.599423 | 0.415 | 32 |
| GM4792 | 0.916 | 2.180753 | 0.416 | 32 |
| RELN | 0.823 | 2.118713 | 0.323 | 32 |
| KCNMA1 | 0.866 | 1.893963 | 0.366 | 32 |
| GABRR2 | 0.825 | 1.851548 | 0.325 | 32 |
| GNB3 | 0.904 | 1.829577 | 0.404 | 32 |
| NDNF | 0.827 | 1.827548 | 0.327 | 32 |
| FN1 | 0.770 | 1.821386 | 0.270 | 32 |
| TMSB10 | 0.882 | 1.803877 | 0.382 | 32 |
| GNG13 | 0.903 | 1.777596 | 0.403 | 32 |
| HS3ST4 | 0.749 | 1.761498 | 0.249 | 32 |
| CDH9 | 0.746 | 1.710895 | 0.246 | 32 |
| TRNP1 | 0.838 | 1.698429 | 0.338 | 32 |
| B3GALT2 | 0.814 | 1.691321 | 0.314 | 32 |
| CADPS | 0.842 | 1.679079 | 0.342 | 32 |
| GRM6 | 0.863 | 1.668717 | 0.363 | 32 |
| PTPRD | 0.849 | 1.654509 | 0.349 | 32 |
| LRTM1 | 0.843 | 1.632109 | 0.343 | 32 |
| CABP2 | 0.752 | 1.631417 | 0.252 | 32 |
| NME1 | 0.885 | 1.576501 | 0.385 | 32 |
| GABRA1 | 0.816 | 1.567486 | 0.316 | 32 |
| GPR179 | 0.821 | 1.563361 | 0.321 | 32 |
| IGF1 | 0.781 | 1.547194 | 0.281 | 32 |
| ADCY2 | 0.719 | 1.544332 | 0.219 | 32 |
| NRXN3 | 0.849 | 1.526952 | 0.349 | 32 |
| THSD7A | 0.786 | 1.515832 | 0.286 | 32 |

TABLE 6-continued

Genes differentially expressed in each of the 39 retinal cell clusters.

| | | | | |
|---|---|---|---|---|
| GRIA2 | 0.827 | 1.451331 | 0.327 | 32 |
| TTYH1 | 0.863 | 1.434237 | 0.363 | 32 |
| PROX1 | 0.810 | 1.418727 | 0.310 | 32 |
| GUCY1A3 | 0.781 | 1.414072 | 0.281 | 32 |
| SULF2 | 0.722 | 1.410361 | 0.222 | 32 |
| BC030499 | 0.734 | 1.321296 | 0.234 | 32 |
| SNCB | 0.837 | 1.317248 | 0.337 | 32 |
| SH3BGRL | 0.722 | 1.302330 | 0.222 | 32 |
| CAR10 | 0.764 | 1.297869 | 0.264 | 32 |
| FSCN1 | 0.709 | 1.288708 | 0.209 | 32 |
| 4930447C04RIK | 0.737 | 1.286988 | 0.237 | 32 |
| ASIC3 | 0.715 | 1.284343 | 0.215 | 32 |
| TMEM215 | 0.725 | 1.282754 | 0.225 | 32 |
| TUBB2A | 0.789 | 1.250102 | 0.289 | 32 |
| GNAO1 | 0.855 | 1.247950 | 0.355 | 32 |
| SLC4A10 | 0.704 | 1.241247 | 0.204 | 32 |
| LPHN2 | 0.718 | 1.218956 | 0.218 | 32 |
| FRMD3 | 0.728 | 1.173764 | 0.228 | 32 |
| ATP2B1 | 0.855 | 1.171837 | 0.355 | 32 |
| PLK5 | 0.756 | 1.171749 | 0.256 | 32 |
| RIT2 | 0.715 | 1.170071 | 0.215 | 32 |
| SAMSN1 | 0.721 | 1.164145 | 0.221 | 32 |
| NAP1L5 | 0.762 | 1.144805 | 0.262 | 32 |
| PCP4L1 | 0.730 | 1.119889 | 0.230 | 32 |
| MYO5A | 0.707 | 1.115274 | 0.207 | 32 |
| GLS | 0.764 | 1.097304 | 0.264 | 32 |
| GUCY1B3 | 0.711 | 1.095756 | 0.211 | 32 |
| TPI1 | 0.772 | 1.082205 | 0.272 | 32 |
| MEG3 | 0.831 | 1.080701 | 0.331 | 32 |
| CAMK2B | 0.706 | 1.058614 | 0.206 | 32 |
| MIF | 0.772 | 1.047922 | 0.272 | 32 |
| TGFB2 | 0.737 | 1.045723 | 0.237 | 32 |
| PLCB4 | 0.724 | 1.021512 | 0.224 | 32 |
| GABRG2 | 0.706 | 1.011047 | 0.206 | 32 |
| HMGN1 | 0.260 | −1.184526 | 0.240 | 32 |
| CST3 | 0.289 | −1.381971 | 0.211 | 32 |
| TULP1 | 0.239 | −1.536871 | 0.261 | 32 |
| NRL | 0.277 | −1.561603 | 0.223 | 32 |
| RPGRIP1 | 0.275 | −1.597091 | 0.225 | 32 |
| SLC24A1 | 0.276 | −1.639280 | 0.224 | 32 |
| RP1 | 0.250 | −1.663774 | 0.250 | 32 |
| GNB1 | 0.206 | −1.720470 | 0.294 | 32 |
| NR2E3 | 0.269 | −1.722247 | 0.231 | 32 |
| GNAT1 | 0.225 | −1.727259 | 0.275 | 32 |
| CNGA1 | 0.260 | −1.776749 | 0.240 | 32 |
| PRPH2 | 0.200 | −1.839337 | 0.300 | 32 |
| SAG | 0.175 | −1.845768 | 0.325 | 32 |
| PDE6G | 0.212 | −1.904791 | 0.288 | 32 |
| PDE6B | 0.229 | −1.905210 | 0.271 | 32 |
| RS1 | 0.254 | −1.915177 | 0.246 | 32 |
| RCVRN | 0.220 | −1.923512 | 0.280 | 32 |
| GNGT1 | 0.174 | −1.926394 | 0.326 | 32 |
| RHO | 0.175 | −1.927010 | 0.325 | 32 |
| PDC | 0.173 | −1.986239 | 0.327 | 32 | cluster no. 33 DE = 47

| myAUC | m | yDiff powe | r clus | t |
|---|---|---|---|---|
| SCGN 0.832 | 2.3 | 88592 0.33 | 2 3 | 3 |
| VSX1 0.785 | 2.2 | 63301 0.28 | 5 3 | 3 |
| SCG2 0.843 | 2.1 | 13311 0.34 | 3 3 | 3 |
| ISL1 0.857 | 2.0 | 29040 0.35 | 7 3 | 3 |
| CCK 0.706 | 1.9 | 93466 0.20 | 6 3 | 3 |
| GRM6 0.817 | 1.8 | 09452 0.31 | 7 3 | 3 |
| GABRA1 0.805 | 1.7 | 68523 0.30 | 5 3 | 3 GA |
| RELN 0.729 | 1.7 | 64877 0.22 | 9 3 | 3 |
| UNC13C 0.726 | 1.6 | 81823 0.22 | 6 3 | 3 UN |

TABLE 6-continued

Genes differentially expressed in each of the 39 retinal cell clusters.

| Gene | myAUC | myDiff | val1 | val2 | cluster # | label |
|---|---|---|---|---|---|---|
| GNG13 | 0.837 | 1.6 | 70562 0.33 | 7 3 | 3 | G |
| FRMD3 | 0.749 | 1.6 | 58409 0.24 | 9 3 | 3 | F |
| PTPRZ1 | 0.724 | 1.6 | 36544 0.22 | 4 3 | 3 | PT |
| CADPS | 0.757 | 1.5 | 04070 0.25 | 7 3 | 3 | C |
| TRPM1 | 0.848 | 1.4 | 72669 0.34 | 8 3 | 3 | T |
| BC030499 | 0.710 | 1.4 | 54178 0.21 | 0 3 | 3 | BC03 |
| SAMSN1 | 0.710 | 1.3 | 71458 0.21 | 0 3 | 3 | SA |
| NEUROD4 | 0.750 | 1.3 | 61455 0.25 | 0 3 | 3 | NEU |
| PCP4L1 | 0.711 | 1.3 | 31851 0.21 | 1 3 | 3 | PC |
| LRTM1 | 0.737 | 1.3 | 30798 0.23 | 7 3 | 3 | L |
| APLP2 | 0.830 | 1.2 | 66608 0.33 | 0 3 | 3 | A |
| LIN7A | 0.740 | 1.2 | 23872 0.24 | 0 3 | 3 | L |
| GNB3 | 0.765 | 1.2 | 19286 0.26 | 5 3 | 3 | |
| PROX1 | 0.716 | 1.2 | 04813 0.21 | 6 3 | 3 | P |
| GPR179 | 0.717 | 1.1 | 92149 0.21 | 7 3 | 3 | GP |
| HMGN3 | 0.728 | 1.1 | 83215 0.22 | 8 3 | 3 | H |
| SCG3 | 0.729 | 1.1 | 68200 0.22 | 9 3 | 3 | |
| MAP4 | 0.750 | 1.1 | 05830 0.25 | 0 3 | 3 | |
| FAM171B | 0.711 | 1.0 | 92140 0.21 | 1 3 | 3 | FAM |
| PTPRD | 0.705 | 1.0 | 69875 0.20 | 5 3 | 3 | P |
| GNAO1 | 0.771 | 1.0 | 68373 0.27 | 1 3 | 3 | G |
| NME1 | 0.740 | 1.0 | 58745 0.24 | 0 3 | 3 | |
| SLC12A5 | 0.703 | 1.0 | 03819 0.20 | 3 3 | 3 | SLC |
| NRXN3 | 0.702 | 1.0 | 00143 0.20 | 2 3 | 3 | N |
| TULP1 | 0.293 | −1.0 | 56098 0.20 | 7 3 | 3 | T |
| PRPH2 | 0.250 | −1.2 | 74321 0.25 | 0 3 | 3 | P |
| PDE6B | 0.276 | −1.2 | 80609 0.22 | 4 3 | 3 | P |
| RCVRN | 0.266 | −1.2 | 86723 0.23 | 4 3 | 3 | R |
| NRL | 0.298 | −1.2 | 87522 0.20 | 2 3 | 3 | |
| RP1 | 0.280 | −1.2 | 88988 0.22 | 0 3 | 3 | |
| NR2E3 | 0.299 | −1.2 | 92005 0.20 | 1 3 | 3 | N |
| PDC | 0.223 | −1.3 | 61036 0.27 | 7 3 | 3 | |
| GNGT1 | 0.226 | −1.3 | 64027 0.27 | 4 3 | 3 | G |
| SAG | 0.210 | −1.3 | 86078 0.29 | 0 3 | 3 | |
| GNAT1 | 0.246 | −1.3 | 91683 0.25 | 4 3 | 3 | G |
| GNB1 | 0.240 | −1.3 | 95529 0.26 | 0 3 | 3 | |
| PDE6G | 0.251 | −1.4 | 09619 0.24 | 9 3 | 3 | P |
| RHO | 0.213 | −1.4 | 52949 0.28 | 7 3 | 3 | |

| | myAUC | myDiff | power | cluster # |
|---|---|---|---|---|
| | cluster no. 34 DE = 147 | | | |
| GLUL | 0.983 | 3.674486 | 0.483 | 34 |
| APOE | 0.984 | 3.656912 | 0.484 | 34 |
| RLBP1 | 0.972 | 3.488780 | 0.472 | 34 |
| CLU | 0.954 | 3.300240 | 0.454 | 34 |
| SLC1A3 | 0.949 | 3.248626 | 0.449 | 34 |
| ACSL3 | 0.974 | 3.168933 | 0.474 | 34 |
| CYR61 | 0.778 | 3.161355 | 0.278 | 34 |
| CAR14 | 0.906 | 3.093884 | 0.406 | 34 |
| SPC25 | 0.907 | 3.027510 | 0.407 | 34 |
| COL9A1 | 0.909 | 2.992981 | 0.409 | 34 |
| JUN | 0.836 | 2.955412 | 0.336 | 34 |
| DKK3 | 0.954 | 2.932319 | 0.454 | 34 |
| CP | 0.899 | 2.916545 | 0.399 | 34 |
| ID3 | 0.858 | 2.906750 | 0.358 | 34 |
| DBI | 0.935 | 2.847955 | 0.435 | 34 |
| CRYM | 0.889 | 2.732641 | 0.389 | 34 |
| HES1 | 0.812 | 2.692426 | 0.312 | 34 |
| CD9 | 0.869 | 2.679822 | 0.369 | 34 |
| SPARC | 0.943 | 2.675237 | 0.443 | 34 |
| FOS | 0.791 | 2.665697 | 0.291 | 34 |
| AQP4 | 0.855 | 2.656964 | 0.355 | 34 |
| GPR37 | 0.875 | 2.652731 | 0.375 | 34 |
| DAPL1 | 0.852 | 2.601035 | 0.352 | 34 |
| KDR | 0.861 | 2.589813 | 0.361 | 34 |
| PTN | 0.872 | 2.531457 | 0.372 | 34 |
| ZFP36L1 | 0.773 | 2.523635 | 0.273 | 34 |
| TIMP3 | 0.839 | 2.505126 | 0.339 | 34 |
| ABCA8A | 0.830 | 2.472855 | 0.330 | 34 |
| MFGE8 | 0.890 | 2.441779 | 0.390 | 34 |
| PRDX6 | 0.846 | 2.426776 | 0.346 | 34 |
| PDPN | 0.813 | 2.317330 | 0.313 | 34 |
| ID2 | 0.756 | 2.307350 | 0.256 | 34 |
| SIX3OS1 | 0.835 | 2.306322 | 0.335 | 34 |
| DUSP1 | 0.707 | 2.262662 | 0.207 | 34 |
| SPON1 | 0.817 | 2.237870 | 0.317 | 34 |
| MT1 | 0.747 | 2.202169 | 0.247 | 34 |
| PPAP2B | 0.792 | 2.196871 | 0.292 | 34 |
| ESPN | 0.807 | 2.190774 | 0.307 | 34 |
| IER2 | 0.727 | 2.190246 | 0.227 | 34 |
| SAT1 | 0.786 | 2.185923 | 0.286 | 34 |
| CROT | 0.798 | 2.153557 | 0.298 | 34 |
| NUDT4 | 0.848 | 2.150174 | 0.348 | 34 |
| CRYAB | 0.771 | 2.112165 | 0.271 | 34 |
| VIM | 0.814 | 2.088221 | 0.314 | 34 |
| EGR1 | 0.748 | 2.088219 | 0.248 | 34 |
| SOX9 | 0.740 | 2.082991 | 0.240 | 34 |
| RDH10 | 0.780 | 2.082476 | 0.280 | 34 |
| CAR2 | 0.913 | 2.045093 | 0.413 | 34 |
| ID1 | 0.733 | 2.038664 | 0.233 | 34 |
| GNAI2 | 0.802 | 2.032953 | 0.302 | 34 |
| VEGFA | 0.776 | 2.021208 | 0.276 | 34 |
| NDRG2 | 0.791 | 2.017386 | 0.291 | 34 |
| CDH2 | 0.817 | 2.011985 | 0.317 | 34 |
| ENPP2 | 0.740 | 2.002079 | 0.240 | 34 |
| FLT1 | 0.768 | 1.988472 | 0.268 | 34 |
| COL23A1 | 0.777 | 1.987731 | 0.277 | 34 |
| MLC1 | 0.752 | 1.962605 | 0.252 | 34 |
| FXYD1 | 0.746 | 1.938091 | 0.246 | 34 |
| TRPM3 | 0.768 | 1.927747 | 0.268 | 34 |
| COX4I2 | 0.754 | 1.915573 | 0.254 | 34 |
| FXYD6 | 0.724 | 1.911993 | 0.224 | 34 |
| SOX2 | 0.737 | 1.898436 | 0.237 | 34 |
| TSC22D4 | 0.763 | 1.895771 | 0.263 | 34 |
| E130114P18RIK | 0.743 | 1.893771 | 0.243 | 34 |
| PBXIP1 | 0.739 | 1.893285 | 0.239 | 34 |
| GPM6A | 0.846 | 1.881375 | 0.346 | 34 |
| DDR1 | 0.734 | 1.861470 | 0.234 | 34 |

TABLE 6-continued

Genes differentially expressed in each of the 39 retinal cell clusters.

| Gene | | | | |
|---|---|---|---|---|
| ATP1B3 | 0.750 | 1.841852 | 0.250 | 34 |
| TGFB2 | 0.795 | 1.836747 | 0.295 | 34 |
| CAV1 | 0.718 | 1.808574 | 0.218 | 34 |
| CACNG4 | 0.784 | 1.804662 | 0.284 | 34 |
| UTP14B | 0.709 | 1.801134 | 0.209 | 34 |
| IL33 | 0.706 | 1.782774 | 0.206 | 34 |
| SBSPON | 0.710 | 1.779906 | 0.210 | 34 |
| KCNJ10 | 0.708 | 1.778244 | 0.208 | 34 |
| VCAM1 | 0.701 | 1.776161 | 0.201 | 34 |
| GAS1 | 0.706 | 1.770890 | 0.206 | 34 |
| WIPI1 | 0.754 | 1.729124 | 0.254 | 34 |
| PON2 | 0.714 | 1.720217 | 0.214 | 34 |
| GPM6B | 0.823 | 1.671461 | 0.323 | 34 |
| CNN3 | 0.739 | 1.664857 | 0.239 | 34 |
| RTN4 | 0.883 | 1.661778 | 0.383 | 34 |
| ALDOC | 0.803 | 1.656881 | 0.303 | 34 |
| JUND | 0.742 | 1.643157 | 0.242 | 34 |
| CD63 | 0.726 | 1.593887 | 0.226 | 34 |
| BSG | 0.854 | 1.587853 | 0.354 | 34 |
| SLMAP | 0.741 | 1.575019 | 0.241 | 34 |
| TIMP2 | 0.703 | 1.573740 | 0.203 | 34 |
| TTYH1 | 0.861 | 1.556066 | 0.361 | 34 |
| ITM2B | 0.852 | 1.552977 | 0.352 | 34 |
| SCD2 | 0.757 | 1.552154 | 0.257 | 34 |
| SYNPR | 0.751 | 1.549654 | 0.251 | 34 |
| PAK3 | 0.718 | 1.514124 | 0.218 | 34 |
| OGFRL1 | 0.738 | 1.499757 | 0.238 | 34 |
| CTSL | 0.787 | 1.492531 | 0.287 | 34 |
| RCN2 | 0.701 | 1.447565 | 0.201 | 34 |
| CD81 | 0.765 | 1.434966 | 0.265 | 34 |
| ATP1A1 | 0.711 | 1.429682 | 0.211 | 34 |
| MARCKS | 0.793 | 1.390002 | 0.293 | 34 |
| HTRA1 | 0.721 | 1.369298 | 0.221 | 34 |
| LAPTM4A | 0.737 | 1.348239 | 0.237 | 34 |
| ENO1 | 0.785 | 1.330226 | 0.285 | 34 |
| PFN2 | 0.730 | 1.324261 | 0.230 | 34 |
| SLC16A1 | 0.727 | 1.315201 | 0.227 | 34 |
| PAX6 | 0.721 | 1.279765 | 0.221 | 34 |
| PRDX1 | 0.702 | 1.197453 | 0.202 | 34 |
| TCF4 | 0.738 | 1.190289 | 0.238 | 34 |
| CDKN1B | 0.722 | 1.184339 | 0.222 | 34 |
| RTN3 | 0.743 | 1.050844 | 0.243 | 34 |
| MGARP | 0.836 | 1.038173 | 0.336 | 34 |
| TSPAN3 | 0.718 | 1.021941 | 0.218 | 34 |
| HSP90AA1 | 0.234 | −1.192803 | 0.266 | 34 |
| HMGN1 | 0.196 | −1.565337 | 0.304 | 34 |
| SLC6A6 | 0.299 | −1.608774 | 0.201 | 34 |
| MAP1B | 0.292 | −1.609128 | 0.208 | 34 |
| TMA7 | 0.272 | −1.689161 | 0.228 | 34 |
| STX3 | 0.298 | −1.711322 | 0.202 | 34 |
| SYT1 | 0.269 | −1.758105 | 0.231 | 34 |
| UNC119 | 0.221 | −1.758329 | 0.279 | 34 |
| CRX | 0.297 | −1.766956 | 0.203 | 34 |
| CNGB1 | 0.293 | −1.776328 | 0.207 | 34 |
| SNAP25 | 0.257 | −1.829279 | 0.243 | 34 |
| PDE6A | 0.287 | −1.834439 | 0.213 | 34 |
| FAM57B | 0.261 | −1.845724 | 0.239 | 34 |
| MPP4 | 0.298 | −1.849733 | 0.202 | 34 |
| AIPL1 | 0.277 | −1.875251 | 0.223 | 34 |
| GNB1 | 0.184 | −1.966538 | 0.316 | 34 |
| NRL | 0.233 | −1.974974 | 0.267 | 34 |
| RS1 | 0.234 | −1.987316 | 0.266 | 34 |
| SLC24A1 | 0.241 | −1.988035 | 0.259 | 34 |
| NEUROD1 | 0.241 | −2.000359 | 0.259 | 34 |
| RP1 | 0.205 | −2.033017 | 0.295 | 34 |
| CNGA1 | 0.229 | −2.048482 | 0.271 | 34 |
| RCVRN | 0.190 | −2.103059 | 0.310 | 34 |
| PDE6B | 0.202 | −2.104712 | 0.298 | 34 |
| ROM1 | 0.189 | −2.109556 | 0.311 | 34 |
| NR2E3 | 0.226 | −2.125234 | 0.274 | 34 |
| PDE6G | 0.178 | −2.131050 | 0.322 | 34 |
| A930011O12RIK | 0.237 | −2.131781 | 0.263 | 34 |
| TULP1 | 0.171 | −2.188185 | 0.329 | 34 |
| GNAT1 | 0.173 | −2.189741 | 0.327 | 34 |
| PDC | 0.148 | −2.206493 | 0.352 | 34 |
| PRPH2 | 0.159 | −2.230242 | 0.341 | 34 |
| GNGT1 | 0.140 | −2.230657 | 0.360 | 34 |
| RHO | 0.141 | −2.253663 | 0.359 | 34 |
| RPGRIP1 | 0.210 | −2.271849 | 0.290 | 34 |
| SAG | 0.131 | −2.316081 | 0.369 | 34 |
| cluster no. 35 DE = 164 | | | | |
| IGFBP5 | 0.980 | 3.971539 | 0.480 | 35 |
| IGF2 | 0.969 | 3.900102 | 0.469 | 35 |
| PTN | 0.967 | 3.682716 | 0.467 | 35 |
| S100B | 0.935 | 3.590062 | 0.435 | 35 |
| PDGFRA | 0.935 | 3.318071 | 0.435 | 35 |
| CST3 | 0.999 | 3.249334 | 0.499 | 35 |
| APOE | 0.969 | 2.946241 | 0.469 | 35 |
| ALDOC | 0.949 | 2.788765 | 0.449 | 35 |
| CTGF | 0.840 | 2.723195 | 0.340 | 35 |
| ID3 | 0.891 | 2.635791 | 0.391 | 35 |
| SPARC | 0.977 | 2.633834 | 0.477 | 35 |
| MLC1 | 0.882 | 2.632886 | 0.382 | 35 |
| NTRK2 | 0.878 | 2.607959 | 0.378 | 35 |
| RGS5 | 0.854 | 2.582399 | 0.354 | 35 |
| DBI | 0.929 | 2.569035 | 0.429 | 35 |
| CNTNAP2 | 0.890 | 2.499012 | 0.390 | 35 |
| 1500015O10RIK | 0.759 | 2.470979 | 0.259 | 35 |
| GFAP | 0.796 | 2.454143 | 0.296 | 35 |
| ATP1A2 | 0.882 | 2.442214 | 0.382 | 35 |
| LECT1 | 0.820 | 2.435971 | 0.320 | 35 |
| CP | 0.888 | 2.423026 | 0.388 | 35 |
| PPAP2B | 0.858 | 2.381629 | 0.358 | 35 |
| SLC1A3 | 0.873 | 2.359476 | 0.373 | 35 |
| CD9 | 0.882 | 2.341085 | 0.382 | 35 |
| FXYD6 | 0.856 | 2.288842 | 0.356 | 35 |
| SCD2 | 0.878 | 2.195817 | 0.378 | 35 |
| CLU | 0.938 | 2.194379 | 0.438 | 35 |
| CXCL12 | 0.822 | 2.156066 | 0.322 | 35 |
| SLC4A4 | 0.809 | 2.154664 | 0.309 | 35 |
| ITM2B | 0.960 | 2.154164 | 0.460 | 35 |
| SLC30A10 | 0.812 | 2.149123 | 0.312 | 35 |
| CLEC18A | 0.731 | 2.137565 | 0.231 | 35 |
| TIMP3 | 0.815 | 2.122132 | 0.315 | 35 |
| CRIM1 | 0.804 | 2.079012 | 0.304 | 35 |
| SLC6A11 | 0.799 | 2.061326 | 0.299 | 35 |
| PRDX6 | 0.828 | 2.056543 | 0.328 | 35 |
| GLUL | 0.902 | 2.039792 | 0.402 | 35 |
| IGFBP2 | 0.762 | 2.038345 | 0.262 | 35 |
| CLDN10 | 0.759 | 2.007019 | 0.259 | 35 |
| TSC22D4 | 0.805 | 1.983938 | 0.305 | 35 |
| CRIP1 | 0.784 | 1.981687 | 0.284 | 35 |
| GPM6B | 0.894 | 1.956617 | 0.394 | 35 |
| CD36 | 0.713 | 1.930346 | 0.213 | 35 |
| MGST1 | 0.793 | 1.926971 | 0.293 | 35 |
| MGLL | 0.813 | 1.906835 | 0.313 | 35 |
| SPON1 | 0.794 | 1.903975 | 0.294 | 35 |
| MT1 | 0.762 | 1.901464 | 0.262 | 35 |
| FN1 | 0.742 | 1.898765 | 0.242 | 35 |
| CGNL1 | 0.727 | 1.886294 | 0.227 | 35 |
| EPAS1 | 0.769 | 1.878394 | 0.269 | 35 |
| DDAH1 | 0.831 | 1.877818 | 0.331 | 35 |
| PAM | 0.815 | 1.876076 | 0.315 | 35 |
| VIM | 0.816 | 1.805763 | 0.316 | 35 |
| TGFB2 | 0.824 | 1.793167 | 0.324 | 35 |
| PDLIM3 | 0.744 | 1.782440 | 0.244 | 35 |
| NPC2 | 0.807 | 1.762614 | 0.307 | 35 |
| PDPN | 0.798 | 1.757502 | 0.298 | 35 |
| CTSL | 0.856 | 1.746857 | 0.356 | 35 |
| ID2 | 0.770 | 1.744332 | 0.270 | 35 |
| LAPTM4A | 0.810 | 1.727350 | 0.310 | 35 |
| B2M | 0.749 | 1.719217 | 0.249 | 35 |
| FXYD1 | 0.774 | 1.684176 | 0.274 | 35 |
| MT3 | 0.756 | 1.655593 | 0.256 | 35 |
| GJA1 | 0.748 | 1.648157 | 0.248 | 35 |
| 1810037I17RIK | 0.781 | 1.644679 | 0.281 | 35 |
| LCAT | 0.731 | 1.627679 | 0.231 | 35 |
| ID4 | 0.760 | 1.626869 | 0.260 | 35 |
| CMTM5 | 0.748 | 1.625331 | 0.248 | 35 |
| MMD2 | 0.807 | 1.619960 | 0.307 | 35 |
| GPX8 | 0.733 | 1.614363 | 0.233 | 35 |
| AGT | 0.754 | 1.613099 | 0.254 | 35 |
| AP1S2 | 0.734 | 1.593596 | 0.234 | 35 |
| CTSD | 0.755 | 1.587762 | 0.255 | 35 |
| PMP22 | 0.715 | 1.581249 | 0.215 | 35 |

TABLE 6-continued

Genes differentially expressed in each of the 39 retinal cell clusters.

| | | | | |
|---|---|---|---|---|
| CNN3 | 0.768 | 1.550185 | 0.268 | 35 |
| TRPM3 | 0.720 | 1.527377 | 0.220 | 35 |
| CD81 | 0.805 | 1.514989 | 0.305 | 35 |
| TMEM47 | 0.743 | 1.510235 | 0.243 | 35 |
| SNED1 | 0.725 | 1.495801 | 0.225 | 35 |
| NDRG2 | 0.766 | 1.486505 | 0.266 | 35 |
| CDH13 | 0.708 | 1.469163 | 0.208 | 35 |
| JUN | 0.742 | 1.464296 | 0.242 | 35 |
| HES1 | 0.739 | 1.463197 | 0.239 | 35 |
| SERPINH1 | 0.739 | 1.457804 | 0.239 | 35 |
| QK | 0.771 | 1.444155 | 0.271 | 35 |
| BCAN | 0.731 | 1.443889 | 0.231 | 35 |
| ANXA5 | 0.723 | 1.441585 | 0.223 | 35 |
| ABHD4 | 0.735 | 1.440876 | 0.235 | 35 |
| PAX8 | 0.704 | 1.424204 | 0.204 | 35 |
| PLA2G16 | 0.703 | 1.398253 | 0.203 | 35 |
| 6330403K07RIK | 0.718 | 1.387964 | 0.218 | 35 |
| RCN1 | 0.711 | 1.387198 | 0.211 | 35 |
| FBXO2 | 0.723 | 1.385921 | 0.223 | 35 |
| CRYAB | 0.713 | 1.384143 | 0.213 | 35 |
| ITGB1 | 0.743 | 1.382103 | 0.243 | 35 |
| MAP4K4 | 0.740 | 1.374146 | 0.240 | 35 |
| METRN | 0.721 | 1.367026 | 0.221 | 35 |
| CTNNBIP1 | 0.730 | 1.364700 | 0.230 | 35 |
| ATP1A1 | 0.763 | 1.364599 | 0.263 | 35 |
| CNTN1 | 0.742 | 1.359653 | 0.242 | 35 |
| APPL2 | 0.720 | 1.347765 | 0.220 | 35 |
| TCEAL3 | 0.756 | 1.330603 | 0.256 | 35 |
| NFIA | 0.705 | 1.316319 | 0.205 | 35 |
| MYO6 | 0.743 | 1.310000 | 0.243 | 35 |
| SOX2 | 0.709 | 1.306380 | 0.209 | 35 |
| LSAMP | 0.731 | 1.294332 | 0.231 | 35 |
| BTBD3 | 0.701 | 1.285695 | 0.201 | 35 |
| NFIB | 0.726 | 1.284242 | 0.226 | 35 |
| SPARCL1 | 0.774 | 1.275405 | 0.274 | 35 |
| CD63 | 0.712 | 1.268344 | 0.212 | 35 |
| TSPAN3 | 0.826 | 1.263679 | 0.326 | 35 |
| SOX9 | 0.725 | 1.263136 | 0.225 | 35 |
| SYT11 | 0.710 | 1.252546 | 0.210 | 35 |
| DKK3 | 0.819 | 1.250533 | 0.319 | 35 |
| ADD3 | 0.761 | 1.231412 | 0.261 | 35 |
| OGFRL1 | 0.710 | 1.229288 | 0.210 | 35 |
| TES | 0.701 | 1.187409 | 0.201 | 35 |
| DAD1 | 0.715 | 1.143170 | 0.215 | 35 |
| CDH2 | 0.744 | 1.142469 | 0.244 | 35 |
| APP | 0.767 | 1.135626 | 0.267 | 35 |
| GNAS | 0.806 | 1.122998 | 0.306 | 35 |
| BSG | 0.772 | 1.113302 | 0.272 | 35 |
| PSAP | 0.756 | 1.094708 | 0.256 | 35 |
| LMAN1 | 0.753 | 1.089473 | 0.253 | 35 |
| CRIP2 | 0.718 | 1.082840 | 0.218 | 35 |
| LAMP1 | 0.751 | 1.065592 | 0.251 | 35 |
| LAMP2 | 0.715 | 1.045180 | 0.215 | 35 |
| SORBS2 | 0.703 | 1.035769 | 0.203 | 35 |
| SIX3 | 0.733 | 1.025975 | 0.233 | 35 |
| SEPT2 | 0.722 | 1.024609 | 0.222 | 35 |
| PAK3 | 0.703 | 1.016054 | 0.203 | 35 |
| LRPAP1 | 0.709 | 1.015462 | 0.209 | 35 |
| D4WSU53E | 0.293 | −1.205302 | 0.207 | 35 |
| HSP90AA1 | 0.233 | −1.301165 | 0.267 | 35 |
| HMGN1 | 0.214 | −1.515951 | 0.286 | 35 |
| UNC119 | 0.265 | −1.543727 | 0.235 | 35 |
| TMA7 | 0.282 | −1.609110 | 0.218 | 35 |
| RS1 | 0.258 | −1.739989 | 0.242 | 35 |
| EPB4.1 | 0.294 | −1.784873 | 0.206 | 35 |
| ROM1 | 0.228 | −1.795256 | 0.272 | 35 |
| SNAP25 | 0.269 | −1.797526 | 0.231 | 35 |
| A930011O12RIK | 0.269 | −1.804349 | 0.231 | 35 |
| RP1 | 0.237 | −1.805896 | 0.263 | 35 |
| NRL | 0.269 | −1.838217 | 0.231 | 35 |
| NR2E3 | 0.251 | −1.864726 | 0.249 | 35 |
| GNB1 | 0.199 | −1.937908 | 0.301 | 35 |
| PRPH2 | 0.189 | −1.965544 | 0.311 | 35 |
| CNGA1 | 0.249 | −1.979693 | 0.251 | 35 |
| NEUROD1 | 0.257 | −1.983968 | 0.243 | 35 |
| CNGB1 | 0.290 | −1.997218 | 0.210 | 35 |
| RCVRN | 0.209 | −2.010392 | 0.291 | 35 |
| RPGRIP1 | 0.236 | −2.027461 | 0.264 | 35 |
| SYT1 | 0.262 | −2.027895 | 0.238 | 35 |
| GNAT1 | 0.203 | −2.043737 | 0.297 | 35 |
| PDE6A | 0.291 | −2.060641 | 0.209 | 35 |
| TULP1 | 0.203 | −2.069090 | 0.297 | 35 |
| FAM57B | 0.254 | −2.158818 | 0.246 | 35 |
| PDE6B | 0.206 | −2.203795 | 0.294 | 35 |
| PDE6G | 0.188 | −2.230095 | 0.312 | 35 |
| SLC24A1 | 0.245 | −2.235394 | 0.255 | 35 |
| PDC | 0.159 | −2.252119 | 0.341 | 35 |
| GNGT1 | 0.151 | −2.277344 | 0.349 | 35 |
| RHO | 0.143 | −2.360853 | 0.357 | 35 |
| SAG | 0.138 | −2.476095 | 0.362 | 35 |
| cluster no. 36 DE = 153 | | | | |
| OPTC | 0.947 | 4.425130 | 0.447 | 36 |
| CRHBP | 0.964 | 3.776445 | 0.464 | 36 |
| ATP1A2 | 0.951 | 3.648260 | 0.451 | 36 |
| COL9A1 | 0.976 | 3.554007 | 0.476 | 36 |
| PTGDS | 0.915 | 3.501014 | 0.415 | 36 |
| COL18A1 | 0.946 | 3.487830 | 0.446 | 36 |
| GJA1 | 0.923 | 3.420054 | 0.423 | 36 |
| FBLN1 | 0.906 | 3.182397 | 0.406 | 36 |
| IGFBP2 | 0.885 | 3.142612 | 0.385 | 36 |
| PTN | 0.915 | 3.008914 | 0.415 | 36 |
| PENK | 0.787 | 2.989587 | 0.287 | 36 |
| CP | 0.950 | 2.984993 | 0.450 | 36 |
| FBN2 | 0.911 | 2.956232 | 0.411 | 36 |
| DAPL1 | 0.863 | 2.902905 | 0.363 | 36 |
| SNED1 | 0.879 | 2.890684 | 0.379 | 36 |
| FSTL1 | 0.908 | 2.867043 | 0.408 | 36 |
| APOE | 0.978 | 2.824762 | 0.478 | 36 |
| PVRL3 | 0.899 | 2.796596 | 0.399 | 36 |
| SPARC | 0.956 | 2.740817 | 0.456 | 36 |
| FBN1 | 0.858 | 2.736953 | 0.358 | 36 |
| TIMP3 | 0.894 | 2.725876 | 0.394 | 36 |
| ATP1B3 | 0.887 | 2.707483 | 0.387 | 36 |
| COL23A1 | 0.899 | 2.618279 | 0.399 | 36 |
| DKK3 | 0.960 | 2.573613 | 0.460 | 36 |
| RELN | 0.859 | 2.549885 | 0.359 | 36 |
| TSC22D1 | 0.901 | 2.516971 | 0.401 | 36 |
| APP | 0.951 | 2.481702 | 0.451 | 36 |
| MFAP4 | 0.829 | 2.416559 | 0.329 | 36 |
| NTRK2 | 0.858 | 2.412425 | 0.358 | 36 |
| MEST | 0.869 | 2.407366 | 0.369 | 36 |
| LTBP1 | 0.846 | 2.364761 | 0.346 | 36 |
| VCAN | 0.805 | 2.364323 | 0.305 | 36 |
| OGN | 0.794 | 2.342607 | 0.294 | 36 |
| FAM129A | 0.805 | 2.301763 | 0.305 | 36 |
| ALDH1A1 | 0.771 | 2.278916 | 0.271 | 36 |
| COL9A2 | 0.808 | 2.241696 | 0.308 | 36 |
| IQGAP2 | 0.797 | 2.216483 | 0.297 | 36 |
| NBL1 | 0.810 | 2.211997 | 0.310 | 36 |
| MFAP2 | 0.807 | 2.209952 | 0.307 | 36 |
| IGFBP7 | 0.829 | 2.206748 | 0.329 | 36 |
| MDK | 0.795 | 2.178341 | 0.295 | 36 |
| COL2A1 | 0.792 | 2.165488 | 0.292 | 36 |
| ZIC1 | 0.775 | 2.152048 | 0.275 | 36 |
| TMPRSS11E | 0.747 | 2.138906 | 0.247 | 36 |
| RHOJ | 0.813 | 2.116804 | 0.313 | 36 |
| TRPM3 | 0.813 | 2.116794 | 0.313 | 36 |
| COL9A3 | 0.788 | 2.116159 | 0.288 | 36 |
| NUDT4 | 0.864 | 2.107740 | 0.364 | 36 |
| FMOD | 0.776 | 2.038997 | 0.276 | 36 |
| BMP4 | 0.764 | 2.005755 | 0.264 | 36 |
| SFRP1 | 0.775 | 2.003735 | 0.275 | 36 |
| SLC6A13 | 0.740 | 1.996986 | 0.240 | 36 |
| SLC13A4 | 0.759 | 1.992519 | 0.259 | 36 |
| WFDC1 | 0.745 | 1.992328 | 0.245 | 36 |
| CTSL | 0.889 | 1.973272 | 0.389 | 36 |
| SERPINH1 | 0.797 | 1.970538 | 0.297 | 36 |
| LTBP3 | 0.776 | 1.954298 | 0.276 | 36 |
| PKP4 | 0.778 | 1.935166 | 0.278 | 36 |
| CCND2 | 0.733 | 1.887738 | 0.233 | 36 |
| HTRA1 | 0.778 | 1.884120 | 0.278 | 36 |
| MGST1 | 0.756 | 1.883879 | 0.256 | 36 |
| FOLR1 | 0.750 | 1.882648 | 0.250 | 36 |
| COL4A5 | 0.756 | 1.862932 | 0.256 | 36 |
| CPQ | 0.756 | 1.838248 | 0.256 | 36 |

TABLE 6-continued

Genes differentially expressed in each of the 39 retinal cell clusters.

| Gene | | | | |
|---|---|---|---|---|
| GAS1 | 0.744 | 1.835410 | 0.244 | 36 |
| CTSD | 0.841 | 1.824145 | 0.341 | 36 |
| OCIAD2 | 0.741 | 1.818916 | 0.241 | 36 |
| LIPA | 0.746 | 1.818661 | 0.246 | 36 |
| ZIC4 | 0.711 | 1.807990 | 0.211 | 36 |
| LAPTM4A | 0.849 | 1.799329 | 0.349 | 36 |
| SGK1 | 0.742 | 1.797747 | 0.242 | 36 |
| B3GALTL | 0.760 | 1.785010 | 0.260 | 36 |
| OLFML2A | 0.723 | 1.760141 | 0.223 | 36 |
| CD63 | 0.761 | 1.734796 | 0.261 | 36 |
| TGFB2 | 0.798 | 1.720278 | 0.298 | 36 |
| CGN | 0.735 | 1.702379 | 0.235 | 36 |
| BMP2 | 0.729 | 1.701840 | 0.229 | 36 |
| LRP1 | 0.733 | 1.697547 | 0.233 | 36 |
| SDC2 | 0.757 | 1.685581 | 0.257 | 36 |
| TKT | 0.792 | 1.652767 | 0.292 | 36 |
| GLDC | 0.725 | 1.644414 | 0.225 | 36 |
| CLDN19 | 0.741 | 1.636605 | 0.241 | 36 |
| TNFRSF21 | 0.714 | 1.626433 | 0.214 | 36 |
| COL11A1 | 0.723 | 1.621136 | 0.223 | 36 |
| TENM4 | 0.743 | 1.620626 | 0.243 | 36 |
| NFIB | 0.761 | 1.612994 | 0.261 | 36 |
| VIM | 0.779 | 1.590580 | 0.279 | 36 |
| GNG11 | 0.717 | 1.589828 | 0.217 | 36 |
| CTSH | 0.716 | 1.586077 | 0.216 | 36 |
| CNTN1 | 0.733 | 1.583022 | 0.233 | 36 |
| HES1 | 0.757 | 1.576002 | 0.257 | 36 |
| SHISA2 | 0.736 | 1.573728 | 0.236 | 36 |
| MAB21L2 | 0.752 | 1.549083 | 0.252 | 36 |
| DEFB9 | 0.706 | 1.541091 | 0.206 | 36 |
| ILDR2 | 0.709 | 1.510602 | 0.209 | 36 |
| GPX8 | 0.716 | 1.484254 | 0.216 | 36 |
| PAM | 0.736 | 1.479638 | 0.236 | 36 |
| ABI3BP | 0.711 | 1.477928 | 0.211 | 36 |
| CD59A | 0.728 | 1.450541 | 0.228 | 36 |
| PODXL2 | 0.765 | 1.434651 | 0.265 | 36 |
| SLC41A1 | 0.710 | 1.434087 | 0.210 | 36 |
| CD81 | 0.780 | 1.424905 | 0.280 | 36 |
| CLU | 0.795 | 1.422895 | 0.295 | 36 |
| SLC6A6 | 0.827 | 1.411126 | 0.327 | 36 |
| PAX6 | 0.752 | 1.379180 | 0.252 | 36 |
| MT-ND6 | 0.709 | 1.365749 | 0.209 | 36 |
| MT-ND5 | 0.839 | 1.364084 | 0.339 | 36 |
| PLXNB2 | 0.701 | 1.363449 | 0.201 | 36 |
| FLRT1 | 0.703 | 1.311944 | 0.203 | 36 |
| TMEM176B | 0.705 | 1.288783 | 0.205 | 36 |
| SDC4 | 0.741 | 1.282822 | 0.241 | 36 |
| BSG | 0.792 | 1.276199 | 0.292 | 36 |
| GM26924 | 0.759 | 1.260216 | 0.259 | 36 |
| MT-ND2 | 0.832 | 1.231683 | 0.332 | 36 |
| RRBP1 | 0.721 | 1.223343 | 0.221 | 36 |
| SLC2A1 | 0.725 | 1.220867 | 0.225 | 36 |
| CAR14 | 0.716 | 1.170677 | 0.216 | 36 |
| CD47 | 0.717 | 1.167718 | 0.217 | 36 |
| PDIA3 | 0.727 | 1.157075 | 0.227 | 36 |
| GLUL | 0.810 | 1.149020 | 0.310 | 36 |
| RCN2 | 0.716 | 1.108386 | 0.216 | 36 |
| MT-ND4 | 0.810 | 1.009844 | 0.310 | 36 |
| SYT1 | 0.291 | −1.338995 | 0.209 | 36 |
| HSP90AA1 | 0.202 | −1.484852 | 0.298 | 36 |
| RS1 | 0.240 | −1.616647 | 0.260 | 36 |
| CNGA1 | 0.263 | −1.629758 | 0.237 | 36 |
| SNAP25 | 0.279 | −1.656418 | 0.221 | 36 |
| HMGN1 | 0.195 | −1.672425 | 0.305 | 36 |
| PDE6A | 0.293 | −1.773595 | 0.207 | 36 |
| GNB1 | 0.208 | −1.790238 | 0.292 | 36 |
| SLC24A1 | 0.246 | −1.800033 | 0.254 | 36 |
| AIPL1 | 0.285 | −1.800568 | 0.215 | 36 |
| UNC119 | 0.225 | −1.801700 | 0.275 | 36 |
| A930011O12RIK | 0.250 | −1.828064 | 0.250 | 36 |
| ROM1 | 0.211 | −1.886096 | 0.289 | 36 |
| NEUROD1 | 0.245 | −1.893158 | 0.255 | 36 |
| FAM57B | 0.258 | −1.960973 | 0.242 | 36 |
| NR2E3 | 0.238 | −1.986178 | 0.262 | 36 |
| PDE6B | 0.210 | −2.023997 | 0.290 | 36 |
| MGARP | 0.241 | −2.025761 | 0.259 | 36 |
| RPGRIP1 | 0.225 | −2.056657 | 0.275 | 36 |
| CNGB1 | 0.284 | −2.060958 | 0.216 | 36 |
| NRL | 0.235 | −2.076837 | 0.265 | 36 |
| TULP1 | 0.187 | −2.098105 | 0.313 | 36 |
| RP1 | 0.204 | −2.140954 | 0.296 | 36 |
| GNGT1 | 0.151 | −2.144535 | 0.349 | 36 |
| RCVRN | 0.203 | −2.146519 | 0.297 | 36 |
| PDC | 0.153 | −2.195983 | 0.347 | 36 |
| RHO | 0.143 | −2.197936 | 0.357 | 36 |
| PDE6G | 0.185 | −2.223749 | 0.315 | 36 |
| GNAT1 | 0.181 | −2.279163 | 0.319 | 36 |
| SAG | 0.133 | −2.287358 | 0.367 | 36 |
| PRPH2 | 0.165 | −2.298866 | 0.335 | 36 |
| cluster no. 37 DE = 236 | | | | |
| IGFBP7 | 0.980 | 3.838996 | 0.480 | 37 |
| CLDN5 | 0.944 | 3.452232 | 0.444 | 37 |
| RGS5 | 0.778 | 3.413786 | 0.278 | 37 |
| PTPRB | 0.938 | 3.322368 | 0.438 | 37 |
| SPARCL1 | 0.977 | 3.260195 | 0.477 | 37 |
| SPARC | 0.985 | 3.222677 | 0.485 | 37 |
| ITM2A | 0.928 | 3.082648 | 0.428 | 37 |
| COL4A1 | 0.923 | 3.047394 | 0.423 | 37 |
| ELTD1 | 0.934 | 3.005777 | 0.434 | 37 |
| LY6C1 | 0.843 | 2.932233 | 0.343 | 37 |
| CTLA2A | 0.883 | 2.913169 | 0.383 | 37 |
| PLTP | 0.880 | 2.911192 | 0.380 | 37 |
| FLT1 | 0.945 | 2.907156 | 0.445 | 37 |
| FN1 | 0.895 | 2.874017 | 0.395 | 37 |
| CD93 | 0.896 | 2.763199 | 0.396 | 37 |
| RAMP2 | 0.900 | 2.687166 | 0.400 | 37 |
| BSG | 0.959 | 2.670912 | 0.459 | 37 |
| SEPP1 | 0.867 | 2.663650 | 0.367 | 37 |
| GPR116 | 0.888 | 2.662459 | 0.388 | 37 |
| FAM101B | 0.869 | 2.611442 | 0.369 | 37 |
| MGP | 0.747 | 2.598253 | 0.247 | 37 |
| COL4A2 | 0.884 | 2.569211 | 0.384 | 37 |
| EGFL7 | 0.861 | 2.554202 | 0.361 | 37 |
| SLCO1A4 | 0.819 | 2.547434 | 0.319 | 37 |
| TMSB4X | 0.958 | 2.538077 | 0.458 | 37 |
| LY6E | 0.880 | 2.518953 | 0.380 | 37 |
| SPOCK2 | 0.887 | 2.484721 | 0.387 | 37 |
| GNG11 | 0.852 | 2.460344 | 0.352 | 37 |
| SLC7A5 | 0.832 | 2.450158 | 0.332 | 37 |
| CD34 | 0.849 | 2.334600 | 0.349 | 37 |
| VWA1 | 0.836 | 2.320906 | 0.336 | 37 |
| ITGB1 | 0.848 | 2.317870 | 0.348 | 37 |
| ABCB1A | 0.837 | 2.296619 | 0.337 | 37 |
| TM4SF1 | 0.819 | 2.273045 | 0.319 | 37 |
| PECAM1 | 0.833 | 2.249158 | 0.333 | 37 |
| LAMA4 | 0.840 | 2.246115 | 0.340 | 37 |
| CDH5 | 0.843 | 2.239309 | 0.343 | 37 |
| ETS1 | 0.824 | 2.194360 | 0.324 | 37 |
| SLCO1C1 | 0.775 | 2.175053 | 0.275 | 37 |
| SERPINH1 | 0.825 | 2.169857 | 0.325 | 37 |
| ESAM | 0.825 | 2.149808 | 0.325 | 37 |
| SLC16A1 | 0.835 | 2.128338 | 0.335 | 37 |
| AU021092 | 0.815 | 2.116002 | 0.315 | 37 |
| SLC2A1 | 0.871 | 2.108619 | 0.371 | 37 |
| KLF2 | 0.782 | 2.108125 | 0.282 | 37 |
| NRP1 | 0.794 | 2.092760 | 0.294 | 37 |
| IFITM3 | 0.800 | 2.075435 | 0.300 | 37 |
| MFSD2A | 0.771 | 2.062993 | 0.271 | 37 |
| ENG | 0.803 | 2.050977 | 0.303 | 37 |
| LAMB1 | 0.794 | 2.044396 | 0.294 | 37 |
| GNAI2 | 0.858 | 2.034857 | 0.358 | 37 |
| CALD1 | 0.771 | 2.033018 | 0.271 | 37 |
| APOD | 0.731 | 2.014340 | 0.231 | 37 |
| B2M | 0.807 | 2.012573 | 0.307 | 37 |
| TPM4 | 0.812 | 2.011884 | 0.312 | 37 |
| TSC22D1 | 0.865 | 1.988874 | 0.365 | 37 |
| NID1 | 0.786 | 1.988835 | 0.286 | 37 |
| AHNAK | 0.770 | 1.972169 | 0.270 | 37 |
| MYL12A | 0.799 | 1.968519 | 0.299 | 37 |
| HTRA3 | 0.785 | 1.966620 | 0.285 | 37 |
| KDR | 0.851 | 1.957857 | 0.351 | 37 |
| VIM | 0.825 | 1.918437 | 0.325 | 37 |
| MYH9 | 0.792 | 1.914794 | 0.292 | 37 |
| ECE1 | 0.810 | 1.899870 | 0.310 | 37 |
| EPAS1 | 0.790 | 1.873475 | 0.290 | 37 |

TABLE 6-continued

Genes differentially expressed in each of the 39 retinal cell clusters.

| | | | | |
|---|---|---|---|---|
| LY6A | 0.714 | 1.841976 | 0.214 | 37 |
| FOXQ1 | 0.774 | 1.840602 | 0.274 | 37 |
| TEK | 0.756 | 1.838929 | 0.256 | 37 |
| NES | 0.766 | 1.837284 | 0.266 | 37 |
| ECSCR | 0.750 | 1.827206 | 0.250 | 37 |
| PALMD | 0.770 | 1.814667 | 0.270 | 37 |
| SLC7A1 | 0.757 | 1.765044 | 0.257 | 37 |
| ACTB | 0.956 | 1.764859 | 0.456 | 37 |
| RGCC | 0.731 | 1.760596 | 0.231 | 37 |
| MSN | 0.775 | 1.756457 | 0.275 | 37 |
| PTRF | 0.750 | 1.756409 | 0.250 | 37 |
| ANXA3 | 0.767 | 1.756155 | 0.267 | 37 |
| BC028528 | 0.764 | 1.746908 | 0.264 | 37 |
| VWF | 0.738 | 1.729667 | 0.238 | 37 |
| SLC9A3R2 | 0.747 | 1.721684 | 0.247 | 37 |
| FZD6 | 0.758 | 1.719270 | 0.258 | 37 |
| ANXA2 | 0.762 | 1.715881 | 0.262 | 37 |
| SLC39A10 | 0.752 | 1.715856 | 0.252 | 37 |
| TIE1 | 0.748 | 1.715698 | 0.248 | 37 |
| PPIC | 0.754 | 1.692879 | 0.254 | 37 |
| KITL | 0.723 | 1.688131 | 0.223 | 37 |
| APLNR | 0.730 | 1.686510 | 0.230 | 37 |
| PLXND1 | 0.731 | 1.679477 | 0.231 | 37 |
| SRGN | 0.750 | 1.678497 | 0.250 | 37 |
| CRIP2 | 0.780 | 1.677601 | 0.280 | 37 |
| SPTBN1 | 0.865 | 1.671355 | 0.365 | 37 |
| RRBP1 | 0.798 | 1.669390 | 0.298 | 37 |
| SLC39A8 | 0.726 | 1.665669 | 0.226 | 37 |
| LTBP4 | 0.715 | 1.659100 | 0.215 | 37 |
| ARPC1B | 0.754 | 1.646160 | 0.254 | 37 |
| CSRP2 | 0.769 | 1.644461 | 0.269 | 37 |
| FLI1 | 0.748 | 1.643560 | 0.248 | 37 |
| AGRN | 0.769 | 1.641418 | 0.269 | 37 |
| ARL4A | 0.765 | 1.635757 | 0.265 | 37 |
| TCF4 | 0.826 | 1.630606 | 0.326 | 37 |
| CLEC14A | 0.724 | 1.627629 | 0.224 | 37 |
| RASIP1 | 0.742 | 1.626477 | 0.242 | 37 |
| APP | 0.858 | 1.625496 | 0.358 | 37 |
| CTNNB1 | 0.815 | 1.624392 | 0.315 | 37 |
| ARHGAP29 | 0.757 | 1.621671 | 0.257 | 37 |
| RHOB | 0.765 | 1.620359 | 0.265 | 37 |
| MYO1B | 0.744 | 1.616759 | 0.244 | 37 |
| KANK3 | 0.738 | 1.614200 | 0.238 | 37 |
| ITGA1 | 0.739 | 1.600712 | 0.239 | 37 |
| UACA | 0.745 | 1.596853 | 0.245 | 37 |
| CDKN1A | 0.737 | 1.596169 | 0.237 | 37 |
| NFKBIA | 0.767 | 1.588506 | 0.267 | 37 |
| LMO2 | 0.739 | 1.587364 | 0.239 | 37 |
| ABLIM1 | 0.817 | 1.586307 | 0.317 | 37 |
| TPM3-RS7 | 0.753 | 1.572490 | 0.253 | 37 |
| CTSH | 0.736 | 1.560486 | 0.236 | 37 |
| ID3 | 0.798 | 1.551172 | 0.298 | 37 |
| SLC3A2 | 0.803 | 1.550705 | 0.303 | 37 |
| ITGA6 | 0.721 | 1.549646 | 0.221 | 37 |
| ABCG2 | 0.719 | 1.534372 | 0.219 | 37 |
| EMCN | 0.734 | 1.531817 | 0.234 | 37 |
| TMEM252 | 0.712 | 1.530900 | 0.212 | 37 |
| PTPRG | 0.737 | 1.520704 | 0.237 | 37 |
| TAGLN2 | 0.736 | 1.519652 | 0.236 | 37 |
| S1PR1 | 0.730 | 1.512398 | 0.230 | 37 |
| SDPR | 0.706 | 1.511013 | 0.206 | 37 |
| UTRN | 0.727 | 1.510283 | 0.227 | 37 |
| SLC40A1 | 0.725 | 1.509780 | 0.225 | 37 |
| ID1 | 0.737 | 1.507196 | 0.237 | 37 |
| CD200 | 0.755 | 1.505153 | 0.255 | 37 |
| EOGT | 0.710 | 1.504481 | 0.210 | 37 |
| PLS3 | 0.716 | 1.490015 | 0.216 | 37 |
| ATOX1 | 0.781 | 1.479614 | 0.281 | 37 |
| HSPG2 | 0.709 | 1.475721 | 0.209 | 37 |
| CGNL1 | 0.724 | 1.470055 | 0.224 | 37 |
| RHOC | 0.718 | 1.454245 | 0.218 | 37 |
| ADAM10 | 0.752 | 1.454056 | 0.252 | 37 |
| CYB5R3 | 0.744 | 1.446513 | 0.244 | 37 |
| GIMAP6 | 0.708 | 1.440910 | 0.208 | 37 |
| LAPTM4A | 0.788 | 1.437107 | 0.288 | 37 |
| ZFP36L1 | 0.757 | 1.431819 | 0.257 | 37 |
| FOXP1 | 0.728 | 1.428272 | 0.228 | 37 |
| GNB4 | 0.709 | 1.426711 | 0.209 | 37 |
| LRRC58 | 0.804 | 1.426417 | 0.304 | 37 |
| WWTR1 | 0.733 | 1.425046 | 0.233 | 37 |
| LSR | 0.717 | 1.424805 | 0.217 | 37 |
| REEP3 | 0.734 | 1.421046 | 0.234 | 37 |
| CNN2 | 0.719 | 1.419514 | 0.219 | 37 |
| ANXA5 | 0.720 | 1.413657 | 0.220 | 37 |
| RHOJ | 0.724 | 1.411383 | 0.224 | 37 |
| H2-D1 | 0.720 | 1.410003 | 0.220 | 37 |
| CLIC4 | 0.725 | 1.395593 | 0.225 | 37 |
| PFN1 | 0.761 | 1.389536 | 0.261 | 37 |
| ACTN4 | 0.759 | 1.381403 | 0.259 | 37 |
| MYO10 | 0.759 | 1.373926 | 0.259 | 37 |
| ROBO4 | 0.704 | 1.372148 | 0.204 | 37 |
| TMSB10 | 0.793 | 1.367258 | 0.293 | 37 |
| CLIC1 | 0.710 | 1.356832 | 0.210 | 37 |
| ABHD2 | 0.706 | 1.345547 | 0.206 | 37 |
| PTBP3 | 0.704 | 1.338826 | 0.204 | 37 |
| LEF1 | 0.706 | 1.336777 | 0.206 | 37 |
| LAMC1 | 0.704 | 1.334944 | 0.204 | 37 |
| S100A13 | 0.702 | 1.331773 | 0.202 | 37 |
| RBMS1 | 0.704 | 1.324417 | 0.204 | 37 |
| GPCPD1 | 0.736 | 1.311359 | 0.236 | 37 |
| RALB | 0.706 | 1.301303 | 0.206 | 37 |
| TPM3 | 0.740 | 1.300676 | 0.240 | 37 |
| LIMCH1 | 0.727 | 1.300556 | 0.227 | 37 |
| QK | 0.738 | 1.296033 | 0.238 | 37 |
| MAOA | 0.703 | 1.294644 | 0.203 | 37 |
| LRP8 | 0.711 | 1.293956 | 0.211 | 37 |
| NFIB | 0.713 | 1.286120 | 0.213 | 37 |
| FERMT2 | 0.723 | 1.282462 | 0.223 | 37 |
| SERINC3 | 0.766 | 1.277661 | 0.266 | 37 |
| TPM1 | 0.733 | 1.268704 | 0.233 | 37 |
| OSTF1 | 0.712 | 1.264445 | 0.212 | 37 |
| PODXL | 0.738 | 1.258107 | 0.238 | 37 |
| DOCK9 | 0.706 | 1.254311 | 0.206 | 37 |
| PPFIBP1 | 0.702 | 1.247757 | 0.202 | 37 |
| SELM | 0.718 | 1.243887 | 0.218 | 37 |
| IQGAP1 | 0.718 | 1.237155 | 0.218 | 37 |
| NOTCH1 | 0.701 | 1.224235 | 0.201 | 37 |
| WASF2 | 0.701 | 1.195270 | 0.201 | 37 |
| KLF6 | 0.703 | 1.182019 | 0.203 | 37 |
| RAC1 | 0.723 | 1.178323 | 0.223 | 37 |
| HES1 | 0.708 | 1.178252 | 0.208 | 37 |
| SYNM | 0.715 | 1.159417 | 0.215 | 37 |
| HIP1 | 0.712 | 1.133942 | 0.212 | 37 |
| ARPC3 | 0.705 | 1.129207 | 0.205 | 37 |
| GPX1 | 0.718 | 1.126453 | 0.218 | 37 |
| TNFAIP1 | 0.702 | 1.126067 | 0.202 | 37 |
| ACTN1 | 0.703 | 1.105354 | 0.203 | 37 |
| MYH10 | 0.715 | 1.105079 | 0.215 | 37 |
| CAPNS1 | 0.712 | 1.100011 | 0.212 | 37 |
| HSP90AB1 | 0.823 | 1.063223 | 0.323 | 37 |
| ITM2B | 0.775 | 1.046377 | 0.275 | 37 |
| CTNNA1 | 0.735 | 1.045557 | 0.235 | 37 |
| ARPC5 | 0.714 | 1.035917 | 0.214 | 37 |
| ARPC2 | 0.741 | 1.002383 | 0.241 | 37 |
| GNB2 | 0.709 | 1.000695 | 0.209 | 37 |
| CD2AP | 0.705 | 1.000147 | 0.205 | 37 |
| GNB1 | 0.250 | −1.474782 | 0.250 | 37 |
| TMA7 | 0.293 | −1.657448 | 0.207 | 37 |
| HSP90AA1 | 0.188 | −1.688760 | 0.312 | 37 |
| ANP32E | 0.287 | −1.782614 | 0.213 | 37 |
| HMGN1 | 0.187 | −1.810023 | 0.313 | 37 |
| EPB4.1 | 0.297 | −1.825915 | 0.203 | 37 |
| CNGA1 | 0.245 | −1.839320 | 0.255 | 37 |
| CRX | 0.298 | −1.856625 | 0.202 | 37 |
| CKB | 0.258 | −1.875027 | 0.242 | 37 |
| SNAP25 | 0.270 | −1.886785 | 0.230 | 37 |
| PDE6A | 0.291 | −1.892818 | 0.209 | 37 |
| NEUROD1 | 0.252 | −1.945246 | 0.248 | 37 |
| SYT1 | 0.264 | −1.950146 | 0.236 | 37 |
| AIPL1 | 0.279 | −1.961332 | 0.221 | 37 |
| UNC119 | 0.213 | −1.984213 | 0.287 | 37 |
| FAM57B | 0.260 | −1.996296 | 0.240 | 37 |
| RS1 | 0.242 | −1.998138 | 0.258 | 37 |
| MGARP | 0.241 | −2.018440 | 0.259 | 37 |
| ROM1 | 0.207 | −2.054687 | 0.293 | 37 |
| RCVRN | 0.204 | −2.079733 | 0.296 | 37 |

TABLE 6-continued

Genes differentially expressed in each of the 39 retinal cell clusters.

| Gene | | | | Cluster |
|---|---|---|---|---|
| GNAT1 | 0.187 | −2.113967 | 0.313 | 37 |
| NRL | 0.235 | −2.122317 | 0.265 | 37 |
| SLC24A1 | 0.248 | −2.125249 | 0.252 | 37 |
| RP1 | 0.211 | −2.136068 | 0.289 | 37 |
| PRPH2 | 0.177 | −2.140244 | 0.323 | 37 |
| PDE6B | 0.206 | −2.170048 | 0.294 | 37 |
| NR2E3 | 0.229 | −2.230401 | 0.271 | 37 |
| PDE6G | 0.181 | −2.259370 | 0.319 | 37 |
| TULP1 | 0.177 | −2.260649 | 0.323 | 37 |
| PDC | 0.154 | −2.296981 | 0.346 | 37 |
| RHO | 0.144 | −2.311761 | 0.356 | 37 |
| A930011O12RIK | 0.240 | −2.318021 | 0.260 | 37 |
| GNGT1 | 0.142 | −2.329702 | 0.358 | 37 |
| SAG | 0.136 | −2.357981 | 0.364 | 37 |
| RPGRIP1 | 0.210 | −2.484476 | 0.290 | 37 |
| cluster no. 38 DE = 147 | | | | |
| RGS5 | 0.992 | 5.501167 | 0.492 | 38 |
| MGP | 0.992 | 4.465241 | 0.492 | 38 |
| IGFBP7 | 0.966 | 4.035969 | 0.466 | 38 |
| COL4A1 | 0.974 | 3.632199 | 0.474 | 38 |
| CALD1 | 0.989 | 3.427224 | 0.489 | 38 |
| COL4A2 | 0.925 | 3.164541 | 0.425 | 38 |
| ATP1A2 | 0.916 | 3.153645 | 0.416 | 38 |
| SERPINE2 | 0.867 | 3.078251 | 0.367 | 38 |
| ASPN | 0.904 | 3.066492 | 0.404 | 38 |
| KCNJ8 | 0.801 | 2.949732 | 0.301 | 38 |
| ABCC9 | 0.825 | 2.914127 | 0.325 | 38 |
| ITGA1 | 0.880 | 2.901163 | 0.380 | 38 |
| NID1 | 0.887 | 2.865895 | 0.387 | 38 |
| MYL9 | 0.848 | 2.784330 | 0.348 | 38 |
| SPARCL1 | 0.921 | 2.771803 | 0.421 | 38 |
| HIGD1B | 0.841 | 2.751780 | 0.341 | 38 |
| FSTL1 | 0.836 | 2.746793 | 0.336 | 38 |
| ITGB1 | 0.843 | 2.690748 | 0.343 | 38 |
| ITIH5 | 0.713 | 2.661303 | 0.213 | 38 |
| GNG11 | 0.837 | 2.649734 | 0.337 | 38 |
| COL1A2 | 0.814 | 2.596983 | 0.314 | 38 |
| COL3A1 | 0.785 | 2.565582 | 0.285 | 38 |
| PDGFRB | 0.856 | 2.494842 | 0.356 | 38 |
| GJC1 | 0.829 | 2.453495 | 0.329 | 38 |
| TM4SF1 | 0.768 | 2.425629 | 0.268 | 38 |
| CRIP1 | 0.720 | 2.420014 | 0.220 | 38 |
| IFITM3 | 0.799 | 2.413464 | 0.299 | 38 |
| CSPG4 | 0.761 | 2.403481 | 0.261 | 38 |
| SPARC | 0.940 | 2.383060 | 0.440 | 38 |
| MYO1B | 0.795 | 2.250938 | 0.295 | 38 |
| MYL12A | 0.804 | 2.246027 | 0.304 | 38 |
| SERPINH1 | 0.794 | 2.240935 | 0.294 | 38 |
| MCAM | 0.768 | 2.235239 | 0.268 | 38 |
| ART3 | 0.769 | 2.225034 | 0.269 | 38 |
| CASQ2 | 0.730 | 2.198628 | 0.230 | 38 |
| LAMA4 | 0.752 | 2.197344 | 0.252 | 38 |
| LAMB1 | 0.765 | 2.179149 | 0.265 | 38 |
| TPM4 | 0.786 | 2.173681 | 0.286 | 38 |
| CD248 | 0.769 | 2.172865 | 0.269 | 38 |
| TPM1 | 0.728 | 2.168649 | 0.228 | 38 |
| LAMC1 | 0.806 | 2.152352 | 0.306 | 38 |
| ETS1 | 0.744 | 2.113024 | 0.244 | 38 |
| GJA4 | 0.714 | 2.090454 | 0.214 | 38 |
| TIMP3 | 0.753 | 2.075556 | 0.253 | 38 |
| CFH | 0.713 | 2.068239 | 0.213 | 38 |
| EDNRA | 0.777 | 2.041461 | 0.277 | 38 |
| NDUFA4L2 | 0.790 | 2.032572 | 0.290 | 38 |
| SEPT7 | 0.903 | 2.026055 | 0.403 | 38 |
| EBF1 | 0.805 | 2.024674 | 0.305 | 38 |
| PTRF | 0.720 | 2.024501 | 0.220 | 38 |
| NOTCH3 | 0.722 | 2.014656 | 0.222 | 38 |
| SEPT11 | 0.798 | 2.003902 | 0.298 | 38 |
| PLAT | 0.750 | 2.002567 | 0.250 | 38 |
| S1PR3 | 0.755 | 1.999823 | 0.255 | 38 |
| UACA | 0.729 | 1.995204 | 0.229 | 38 |
| MYH9 | 0.760 | 1.981694 | 0.260 | 38 |
| RGS4 | 0.741 | 1.980531 | 0.241 | 38 |
| FLNA | 0.708 | 1.979751 | 0.208 | 38 |
| NAALAD2 | 0.753 | 1.962642 | 0.253 | 38 |
| S100A11 | 0.743 | 1.951513 | 0.243 | 38 |
| NRP1 | 0.785 | 1.946284 | 0.285 | 38 |
| SEPT4 | 0.805 | 1.932384 | 0.305 | 38 |
| BGN | 0.745 | 1.895552 | 0.245 | 38 |
| PPIC | 0.751 | 1.881210 | 0.251 | 38 |
| PCDH18 | 0.743 | 1.866156 | 0.243 | 38 |
| MAGED2 | 0.752 | 1.849301 | 0.252 | 38 |
| CNN2 | 0.721 | 1.848057 | 0.221 | 38 |
| NBL1 | 0.737 | 1.837023 | 0.237 | 38 |
| MARCKS | 0.837 | 1.808142 | 0.337 | 38 |
| VIM | 0.745 | 1.769597 | 0.245 | 38 |
| ARHGDIB | 0.705 | 1.769381 | 0.205 | 38 |
| B2M | 0.735 | 1.764019 | 0.235 | 38 |
| ADAP2 | 0.706 | 1.740003 | 0.206 | 38 |
| EPAS1 | 0.760 | 1.738220 | 0.260 | 38 |
| NR2F2 | 0.741 | 1.729772 | 0.241 | 38 |
| UTRN | 0.712 | 1.709004 | 0.212 | 38 |
| ID3 | 0.737 | 1.706232 | 0.237 | 38 |
| GUCY1A3 | 0.798 | 1.705109 | 0.298 | 38 |
| ACTB | 0.929 | 1.685265 | 0.429 | 38 |
| LAPTM4A | 0.815 | 1.676642 | 0.315 | 38 |
| RHOB | 0.727 | 1.667873 | 0.227 | 38 |
| RBMS1 | 0.708 | 1.644134 | 0.208 | 38 |
| LRRC58 | 0.827 | 1.640398 | 0.327 | 38 |
| MEF2C | 0.712 | 1.640375 | 0.212 | 38 |
| CCDC80 | 0.713 | 1.628830 | 0.213 | 38 |
| ANXA5 | 0.715 | 1.584120 | 0.215 | 38 |
| ITM2B | 0.851 | 1.582958 | 0.351 | 38 |
| FERMT2 | 0.705 | 1.565111 | 0.205 | 38 |
| CD63 | 0.718 | 1.561257 | 0.218 | 38 |
| MFGE8 | 0.772 | 1.548767 | 0.272 | 38 |
| WLS | 0.702 | 1.535632 | 0.202 | 38 |
| MPRIP | 0.725 | 1.530097 | 0.225 | 38 |
| SERINC3 | 0.738 | 1.514550 | 0.238 | 38 |
| SLC12A2 | 0.722 | 1.511126 | 0.222 | 38 |
| LHFP | 0.701 | 1.509888 | 0.201 | 38 |
| GINM1 | 0.703 | 1.495549 | 0.203 | 38 |
| CD81 | 0.819 | 1.485171 | 0.319 | 38 |
| VTN | 0.735 | 1.473185 | 0.235 | 38 |
| APP | 0.793 | 1.469747 | 0.293 | 38 |
| RAC1 | 0.714 | 1.426087 | 0.214 | 38 |
| TNFAIP1 | 0.705 | 1.405605 | 0.205 | 38 |
| OAZ2 | 0.706 | 1.349629 | 0.206 | 38 |
| NREP | 0.759 | 1.298044 | 0.259 | 38 |
| PTEN | 0.719 | 1.252699 | 0.219 | 38 |
| TMSB4X | 0.772 | 1.138718 | 0.272 | 38 |
| SPTBN1 | 0.716 | 1.048742 | 0.216 | 38 |
| LAMP1 | 0.737 | 1.039290 | 0.237 | 38 |
| D4WSU53E | 0.298 | −1.146991 | 0.202 | 38 |
| SNAP25 | 0.296 | −1.457235 | 0.204 | 38 |
| HSP90AA1 | 0.203 | −1.509721 | 0.297 | 38 |
| MGARP | 0.250 | −1.523003 | 0.250 | 38 |
| NEUROD1 | 0.277 | −1.532473 | 0.223 | 38 |
| HMGN1 | 0.188 | −1.744434 | 0.312 | 38 |
| SLC24A1 | 0.267 | −1.817590 | 0.233 | 38 |
| TMA7 | 0.271 | −1.832750 | 0.229 | 38 |
| FAM57B | 0.267 | −1.841072 | 0.233 | 38 |
| SYT1 | 0.265 | −1.845972 | 0.235 | 38 |
| CRX | 0.292 | −1.876962 | 0.208 | 38 |
| ELOVL4 | 0.297 | −1.878393 | 0.203 | 38 |
| CKB | 0.250 | −1.883214 | 0.250 | 38 |
| UNC119 | 0.220 | −1.904351 | 0.280 | 38 |
| NDUFA4 | 0.220 | −1.957810 | 0.280 | 38 |
| MPP4 | 0.295 | −1.968298 | 0.205 | 38 |
| AIPL1 | 0.278 | −1.972794 | 0.222 | 38 |
| EPB4.1 | 0.279 | −2.013098 | 0.221 | 38 |
| GNB1 | 0.192 | −2.027415 | 0.308 | 38 |
| NR2E3 | 0.232 | −2.098991 | 0.268 | 38 |
| 1810009A15RIK | 0.291 | −2.121394 | 0.209 | 38 |
| PDE6G | 0.188 | −2.141490 | 0.312 | 38 |
| PDE6A | 0.274 | −2.163994 | 0.226 | 38 |
| NRL | 0.233 | −2.193383 | 0.267 | 38 |
| CNGB1 | 0.282 | −2.220351 | 0.218 | 38 |
| RS1 | 0.227 | −2.230808 | 0.273 | 38 |
| TULP1 | 0.179 | −2.310206 | 0.321 | 38 |
| CNGA1 | 0.225 | −2.318757 | 0.275 | 38 |
| RCVRN | 0.188 | −2.319052 | 0.312 | 38 |
| RP1 | 0.201 | −2.341225 | 0.299 | 38 |
| RHO | 0.153 | −2.379167 | 0.347 | 38 |
| RPGRIP1 | 0.215 | −2.390692 | 0.285 | 38 |

TABLE 6-continued

Genes differentially expressed in each of the 39 retinal cell clusters.

| Gene | | | | |
|---|---|---|---|---|
| PDC | 0.147 | −2.404465 | 0.353 | 38 |
| A930011O12RIK | 0.231 | −2.444744 | 0.269 | 38 |
| GNAT1 | 0.174 | −2.450650 | 0.326 | 38 |
| SAG | 0.140 | −2.497791 | 0.360 | 38 |
| PDE6B | 0.194 | −2.533895 | 0.306 | 38 |
| PRPH2 | 0.151 | −2.581111 | 0.349 | 38 |
| ROM1 | 0.175 | −2.590215 | 0.325 | 38 |
| GNGT1 | 0.133 | −2.660261 | 0.367 | 38 |
| cluster no. 39 DE = 153 | | | | |
| CTSS | 0.978 | 4.653922 | 0.478 | 39 |
| HEXB | 0.976 | 4.292110 | 0.476 | 39 |
| C1QB | 0.970 | 3.878037 | 0.470 | 39 |
| C1QC | 0.948 | 3.834225 | 0.448 | 39 |
| APOE | 0.962 | 3.754892 | 0.462 | 39 |
| C1QA | 0.948 | 3.723967 | 0.448 | 39 |
| CCL4 | 0.754 | 3.720710 | 0.254 | 39 |
| B2M | 0.938 | 3.647541 | 0.438 | 39 |
| CX3CR1 | 0.903 | 3.520550 | 0.403 | 39 |
| LY86 | 0.903 | 3.481497 | 0.403 | 39 |
| P2RY12 | 0.880 | 3.398210 | 0.380 | 39 |
| CCL3 | 0.791 | 3.365822 | 0.291 | 39 |
| SEPP1 | 0.916 | 3.341246 | 0.416 | 39 |
| CSF1R | 0.895 | 3.191319 | 0.395 | 39 |
| LAPTM5 | 0.903 | 3.170011 | 0.403 | 39 |
| ZFP36 | 0.875 | 3.154473 | 0.375 | 39 |
| TYROBP | 0.873 | 3.084486 | 0.373 | 39 |
| JUNB | 0.862 | 3.023664 | 0.362 | 39 |
| NFKBIA | 0.805 | 3.015364 | 0.305 | 39 |
| KLF2 | 0.729 | 2.944302 | 0.229 | 39 |
| SIGLECH | 0.880 | 2.904145 | 0.380 | 39 |
| ATF3 | 0.751 | 2.874536 | 0.251 | 39 |
| TREM2 | 0.851 | 2.847238 | 0.351 | 39 |
| JUN | 0.901 | 2.800797 | 0.401 | 39 |
| CTSD | 0.895 | 2.785069 | 0.395 | 39 |
| RHOB | 0.863 | 2.668613 | 0.363 | 39 |
| SGK1 | 0.791 | 2.595234 | 0.291 | 39 |
| FCER1G | 0.820 | 2.594593 | 0.320 | 39 |
| SELPLG | 0.791 | 2.583273 | 0.291 | 39 |
| MPEG1 | 0.806 | 2.561161 | 0.306 | 39 |
| TMSB4X | 0.978 | 2.518332 | 0.478 | 39 |
| GPR34 | 0.776 | 2.484680 | 0.276 | 39 |
| SERPINE2 | 0.851 | 2.447607 | 0.351 | 39 |
| SPARC | 0.906 | 2.436520 | 0.406 | 39 |
| GRN | 0.813 | 2.425319 | 0.313 | 39 |
| IER5 | 0.773 | 2.410207 | 0.273 | 39 |
| NPC2 | 0.832 | 2.385903 | 0.332 | 39 |
| LGMN | 0.952 | 2.385703 | 0.452 | 39 |
| KLF6 | 0.744 | 2.379144 | 0.244 | 39 |
| LYZ2 | 0.746 | 2.374372 | 0.246 | 39 |
| EGR1 | 0.834 | 2.333774 | 0.334 | 39 |
| FCGR3 | 0.776 | 2.313824 | 0.276 | 39 |
| RGS2 | 0.803 | 2.307229 | 0.303 | 39 |
| 4632428N05RIK | 0.768 | 2.250471 | 0.268 | 39 |
| CTSZ | 0.821 | 2.233623 | 0.321 | 39 |
| CST3 | 0.964 | 2.231930 | 0.464 | 39 |
| ITGAM | 0.752 | 2.200036 | 0.252 | 39 |
| ACTB | 0.956 | 2.193357 | 0.456 | 39 |
| FYB | 0.773 | 2.190362 | 0.273 | 39 |
| TGFBR1 | 0.766 | 2.176746 | 0.266 | 39 |
| KCTD12 | 0.757 | 2.169558 | 0.257 | 39 |
| UNC93B1 | 0.746 | 2.159913 | 0.246 | 39 |
| AIF1 | 0.754 | 2.148845 | 0.254 | 39 |
| CYBA | 0.759 | 2.143158 | 0.259 | 39 |
| MAFB | 0.725 | 2.130408 | 0.225 | 39 |
| CTSB | 0.900 | 2.106910 | 0.400 | 39 |
| H2-D1 | 0.755 | 2.100278 | 0.255 | 39 |
| DUSP1 | 0.721 | 2.084336 | 0.221 | 39 |
| RNASE4 | 0.716 | 2.084032 | 0.216 | 39 |
| SERINC3 | 0.830 | 2.075356 | 0.330 | 39 |
| PTGS1 | 0.739 | 2.071713 | 0.239 | 39 |
| FCRLS | 0.746 | 2.055869 | 0.246 | 39 |
| UBC | 0.834 | 2.024625 | 0.334 | 39 |
| LAIR1 | 0.737 | 2.014039 | 0.237 | 39 |
| H2-K1 | 0.719 | 2.013817 | 0.219 | 39 |
| CTSL | 0.887 | 2.003522 | 0.387 | 39 |
| LY6E | 0.764 | 2.000438 | 0.264 | 39 |
| ITGB5 | 0.740 | 1.998945 | 0.240 | 39 |
| PSAP | 0.854 | 1.998267 | 0.354 | 39 |
| SAT1 | 0.739 | 1.997578 | 0.239 | 39 |
| LTC4S | 0.731 | 1.992351 | 0.231 | 39 |
| ARPC1B | 0.736 | 1.989627 | 0.236 | 39 |
| MARCKS | 0.877 | 1.984915 | 0.377 | 39 |
| CD53 | 0.716 | 1.979296 | 0.216 | 39 |
| LRRC58 | 0.877 | 1.965416 | 0.377 | 39 |
| APBB1IP | 0.709 | 1.956031 | 0.209 | 39 |
| BTG2 | 0.755 | 1.955286 | 0.255 | 39 |
| PLEK | 0.711 | 1.946862 | 0.211 | 39 |
| RGS10 | 0.737 | 1.924107 | 0.237 | 39 |
| IER2 | 0.721 | 1.912803 | 0.221 | 39 |
| PLXDC2 | 0.738 | 1.910001 | 0.238 | 39 |
| F11R | 0.714 | 1.890608 | 0.214 | 39 |
| IRF8 | 0.701 | 1.868279 | 0.201 | 39 |
| PLD4 | 0.731 | 1.865511 | 0.231 | 39 |
| CTSA | 0.754 | 1.835910 | 0.254 | 39 |
| FOS | 0.723 | 1.826721 | 0.223 | 39 |
| MAF | 0.714 | 1.823466 | 0.214 | 39 |
| ITM2B | 0.917 | 1.811843 | 0.417 | 39 |
| CD9 | 0.765 | 1.806437 | 0.265 | 39 |
| IFNGR1 | 0.742 | 1.805089 | 0.242 | 39 |
| JUND | 0.756 | 1.804582 | 0.256 | 39 |
| LPCAT2 | 0.767 | 1.791338 | 0.267 | 39 |
| CTSH | 0.725 | 1.784451 | 0.225 | 39 |
| MERTK | 0.706 | 1.779292 | 0.206 | 39 |
| TRF | 0.720 | 1.778704 | 0.220 | 39 |
| CD81 | 0.808 | 1.768962 | 0.308 | 39 |
| CLIC1 | 0.711 | 1.731795 | 0.211 | 39 |
| RRBP1 | 0.751 | 1.708872 | 0.251 | 39 |
| GPX1 | 0.731 | 1.694199 | 0.231 | 39 |
| MSN | 0.704 | 1.650198 | 0.204 | 39 |
| CREG1 | 0.725 | 1.641235 | 0.225 | 39 |
| TPM3-RS7 | 0.702 | 1.631400 | 0.202 | 39 |
| LAMP2 | 0.704 | 1.522471 | 0.204 | 39 |
| TIMP2 | 0.705 | 1.496183 | 0.205 | 39 |
| QK | 0.707 | 1.462699 | 0.207 | 39 |
| FTH1 | 0.853 | 1.383409 | 0.353 | 39 |
| TPM3 | 0.707 | 1.355049 | 0.207 | 39 |
| LAMP1 | 0.743 | 1.274744 | 0.243 | 39 |
| RPS9 | 0.740 | 1.227865 | 0.240 | 39 |
| GM9843 | 0.764 | 1.151216 | 0.264 | 39 |
| RPL32 | 0.759 | 1.139049 | 0.259 | 39 |
| RPS26 | 0.720 | 1.130727 | 0.220 | 39 |
| RPLP1 | 0.801 | 1.070725 | 0.301 | 39 |
| ANP32A | 0.299 | −1.167042 | 0.201 | 39 |
| HSP90AA1 | 0.239 | −1.203183 | 0.261 | 39 |
| LDHA | 0.291 | −1.203661 | 0.209 | 39 |
| PKM | 0.295 | −1.277540 | 0.205 | 39 |
| NDUFA4 | 0.273 | −1.304189 | 0.227 | 39 |
| MAP1B | 0.294 | −1.335660 | 0.206 | 39 |
| SYT1 | 0.285 | −1.366615 | 0.215 | 39 |
| FAM57B | 0.292 | −1.413749 | 0.208 | 39 |
| NRL | 0.279 | −1.427076 | 0.221 | 39 |
| ROM1 | 0.235 | −1.486101 | 0.265 | 39 |
| ANP32E | 0.287 | −1.504556 | 0.213 | 39 |
| TULP1 | 0.220 | −1.539643 | 0.280 | 39 |
| SLC25A4 | 0.273 | −1.541158 | 0.227 | 39 |
| MGARP | 0.256 | −1.541918 | 0.244 | 39 |
| CPE | 0.268 | −1.556102 | 0.232 | 39 |
| TMA7 | 0.277 | −1.583630 | 0.223 | 39 |
| SNAP25 | 0.275 | −1.599132 | 0.225 | 39 |
| PDE6G | 0.205 | −1.660203 | 0.295 | 39 |
| RS1 | 0.254 | −1.663552 | 0.246 | 39 |
| PRPH2 | 0.191 | −1.751501 | 0.309 | 39 |
| RCVRN | 0.213 | −1.764180 | 0.287 | 39 |
| GNAT1 | 0.205 | −1.772742 | 0.295 | 39 |
| SLC24A1 | 0.261 | −1.776117 | 0.239 | 39 |
| EPB4.1 | 0.280 | −1.821400 | 0.220 | 39 |
| PDE6A | 0.290 | −1.837114 | 0.210 | 39 |
| GNGT1 | 0.172 | −1.846910 | 0.328 | 39 |
| NEUROD1 | 0.248 | −1.869328 | 0.252 | 39 |
| UNC119 | 0.209 | −1.871789 | 0.291 | 39 |
| A930011O12RIK | 0.254 | −1.877904 | 0.246 | 39 |
| STX3 | 0.288 | −1.894001 | 0.212 | 39 |
| CNGA1 | 0.243 | −1.905085 | 0.257 | 39 |
| HMGN1 | 0.165 | −1.905216 | 0.335 | 39 |
| NR2E3 | 0.237 | −1.943295 | 0.263 | 39 |

TABLE 6-continued

Genes differentially expressed in each of the 39 retinal cell clusters.

| | | | | |
|---|---|---|---|---|
| RHO | 0.166 | −1.984178 | 0.334 | 39 |
| GNB1 | 0.182 | −2.006714 | 0.318 | 39 |
| PDC | 0.163 | −2.033191 | 0.337 | 39 |
| PDE6B | 0.205 | −2.102541 | 0.295 | 39 |
| RPGRIP1 | 0.221 | −2.105338 | 0.279 | 39 |
| SAG | 0.154 | −2.197799 | 0.346 | 39 |
| RP1 | 0.197 | −2.359118 | 0.303 | 39 |

Table 7. Differential gene expression between each pairwise combination of the 39 retinal cell clusters.

TABLE 8

Cost analysis of Drop-Seq.

| Reagents | Supplier | Catalog # | Cost for 10,000 cells ($) |
|---|---|---|---|
| Microfluidics costs (tubing, syringes, droplet generation oil, device fabrication) | N/A | N/A | 35.00 |
| DropSeq lysis buffer (Ficoll, Tris, Sarkosyl, EDTA, DTT) | N/A | N/A | 9.35 |
| Barcoded microparticles | Chemgenes | N/A | 137.20 |
| Maxima H-Reverse Transcriptase | Thermo | EP0753 | 53.10 |
| dNTP mix | Clontech | 639125 | 7.00 |
| RNase inhibitor | Lucigen | 30281-2 | 3.44 |
| Template switch oligo | IDT | N/A | 6.90 |
| Perfluorooctanol | Sigma | 370533 | 10.70 |
| Exonuclease I | NEB | M0293L | 3.46 |
| KAPA Hifi HotStart ReadyMix | KAPA BioSystems | KK2602 | 210.00 |
| Nextera XT DNA sample preparation kit | Illumina | FC-131-1096 | 120.80 |
| Ampure XP beads | Beckman Coulter | A63882 | 37.35 |
| BioAnalyzer High Sensitivity Chips | Agilent | 5067-4626 | 9.64 |
| Total cost: | | | $633.94 |
| Cost per cell: | | | $ 0.06 |

TABLE 9

Oligonucleotide sequences used in the preparation of Drop-Seq libraries.

| | |
|---|---|
| synRNA | rCrCrUrArCrArCrGrArCrGrCrUrCrUrUrCrCrGrArUrCrUrNrNrNrNrNrNrNrNrNrNrNrNrNrNrNrNrNrBrArArArArArArArArArArArArArArArArArArArArArA |
| Barcode Bead SeqA | 5'-Bead-Linker-TTTTTTTAAGCAGTGGTATCAACGCAGAGTACGTJJJJJJJJJJJJNNNNNNNNTTTTTTTTTTTTTTTTTTTTTTTTTTTTTT-3' |
| Barcode Bead SeqB | 5'-Bead-Linker-TTTTTTTAAGCAGTGGTATCAACGCAGAGTACJJJJJJJJJJJNNNNNNNNTTTTTTTTTTTTTTTTTTTTTTTTTTTTTT-3' |
| Template_Switch_Oligo | AAGCAGTGGTATCAACGCAGAGTGAATrGrGrG |
| TSO_PCR | AAGCAGTGGTATCAACGCAGAGT |
| P5-TSO_Hybrid | AATGATACGGCGACCACCGAGATCTACACGCCTGTCCGCGGAAGCAGTGGTATCAACGCAGAGT*A*C |
| Nextera_N701 | CAAGCAGAAGACGGCATACGAGATTCGCCTTAGTCTCGTGGGCTCGG |
| Nextera_N702 | CAAGCAGAAGACGGCATACGAGATCTAGTACGGTCTCGTGGGCTCGG |
| Nextera_N703 | CAAGCAGAAGACGGCATACGAGATTTCTGCCTGTCTCGTGGGCTCGG |
| Read1CustomSeqA | GCCTGTCCGCGGAAGCAGTGGTATCAACGCAGAGTACGT |
| Read1CustomSeqB | GCCTGTCCGCGGAAGCAGTGGTATCAACGCAGAGTAC |
| P7-TSO_Hybrid | CAAGCAGAAGACGGCATACGAGATCGTGATCGGTCTCGGCGGAAGCAGTGGTATCAACGCAGAGT*A*C |
| TruSeq_F | AATGATACGGCGACCACCGAGATCTACACTCTTTCCCTACACGACGCTCTTCCGATC*T |
| CustSynRNASeq | CGGTCTCGGCGGAAGCAGTGGTATCAACGCAGAGTAC |
| UMI_SMARTdT | AAGCAGTGGTATCAACGCAGAGTACNNNNNNNNNTTTTTTTTTTTTTTTTTTTTTTTTT |

"B" designates any base but "A",

"J" designates a split-and-pool synthesis round;

"N" designates a degenerate base.

"*" designates a phosphorothioate linkage.

All soluble primers were purchased from Integrated DNA Technologies, and purified by standard desalting except for the Template_Switch_Oligo, which was purified by ion-exchange-HPLC.

TABLE 10

"Out of sample" projection test. For each cluster, the "training" cells were removed from the tSNE plot, and then projected onto the tSNE. The number of cells that successfully project into the embedding, and the number of cells that become inappropriately incorporated into a different cluster were tabulated.

| Cluster # | # Cells in Cluster | # failed to project | # Projected | # Wrongly Assigned | % Wrongly Assigned |
|---|---|---|---|---|---|
| 1 | 153 | 153 | 0 | 0 | 0.00 |
| 2 | 271 | 271 | 0 | 0 | 0.00 |
| 3 | 201 | 201 | 0 | 0 | 0.00 |
| 4 | 46 | 46 | 0 | 0 | 0.00 |
| 5 | 63 | 62 | 1 | 0 | 0.00 |
| 6 | 173 | 156 | 17 | 9 | 5.20 |
| 7 | 277 | 272 | 5 | 5 | 1.81 |
| 8 | 115 | 115 | 0 | 0 | 0.00 |
| 9 | 275 | 275 | 0 | 0 | 0.00 |
| 10 | 155 | 153 | 2 | 2 | 1.29 |
| 11 | 165 | 162 | 3 | 3 | 1.82 |
| 12 | 175 | 175 | 0 | 0 | 0.00 |
| 13 | 46 | 40 | 6 | 5 | 10.87 |
| 14 | 89 | 89 | 0 | 0 | 0.00 |
| 15 | 52 | 44 | 8 | 6 | 11.54 |
| 16 | 179 | 179 | 0 | 0 | 0.00 |
| 17 | 284 | 284 | 0 | 0 | 0.00 |
| 18 | 64 | 63 | 1 | 1 | 1.56 |
| 19 | 108 | 107 | 1 | 0 | 0.00 |
| 20 | 206 | 206 | 0 | 0 | 0.00 |
| 21 | 154 | 154 | 0 | 0 | 0.00 |
| 22 | 180 | 180 | 0 | 0 | 0.00 |
| 23 | 183 | 182 | 1 | 1 | 0.55 |
| 24 | 3712 | 3417 | 295 | 180 | 4.85 |
| 25 | 1095 | 1071 | 24 | 18 | 1.64 |
| 26 | 1213 | 1212 | 1 | 0 | 0.00 |
| 27 | 323 | 318 | 5 | 4 | 1.24 |
| 28 | 339 | 330 | 9 | 7 | 2.06 |
| 29 | 332 | 324 | 8 | 6 | 1.81 |
| 30 | 447 | 426 | 21 | 18 | 4.03 |
| 31 | 346 | 340 | 6 | 3 | 0.87 |
| 32 | 235 | 233 | 2 | 2 | 0.85 |
| 33 | 453 | 450 | 3 | 3 | 0.66 |
| 34 | 784 | 784 | 0 | 0 | 0.00 |
| 35 | 27 | 27 | 0 | 0 | 0.00 |
| 36 | 43 | 43 | 0 | 0 | 0.00 |
| 37 | 145 | 139 | 6 | 5 | 3.45 |
| 38 | 30 | 30 | 0 | 0 | 0.00 |
| 39 | 17 | 17 | 0 | 0 | 0.00 |

REFERENCES

Andersen, B. B., Korbo, L., and Pakkenberg, B. (1992). A quantitative study of the human cerebellum with unbiased stereological techniques. The Journal of comparative neurology 326, 549-560.

Bar-Joseph, Z., Siegfried, Z., Brandeis, M., Brors, B., Lu, Y., Eils, R., Dynlacht, B. D., and Simon, I. (2008). Genome-wide transcriptional analysis of the human cell cycle identifies genes differentially regulated in normal and cancer cells. Proceedings of the National Academy of Sciences of the United States of America 105, 955-960.

Barres, B. A., Silverstein, B. E., Corey, D. P., and Chun, L. L. (1988). Immunological, morphological, and electrophysiological variation among retinal ganglion cells purified by panning. Neuron 1, 791-803.

Beer, N. R., Wheeler, E. K., Lee-Houghton, L., Watkins, N., Nasarabadi, S., Hebert, N., Leung, P., Arnold, D. W., Bailey, C. G., and Colston, B. W. (2008). On-chip single-copy real-time reverse-transcription PCR in isolated picoliter droplets. Analytical chemistry 80, 1854-1858.

Berman, G. J., Choi, D. M., Bialek, W., and Shaevitz, J. W. (2014). Mapping the stereotyped behaviour of freely moving fruit flies. Journal of the Royal Society, Interface/the Royal Society 11.

Brennecke, P., Anders, S., Kim, J. K., Kolodziejczyk, A. A., Zhang, X., Proserpio, V., Baying, B., Benes, V., Teichmann, S. A., Marioni, J. C., et al. (2013). Accounting for technical noise in single-cell RNA-seq experiments. Nature methods 10, 1093-1095.

Bringer, M. R., Gerdts, C. J., Song, H., Tice, J. D., and Ismagilov, R. F. (2004). Microfluidic systems for chemical kinetics that rely on chaotic mixing in droplets. Philosophical transactions Series A, Mathematical, physical, and engineering sciences 362, 1087-1104.

Britten, R. J., and Kohne, D. E. (1968). Repeated sequences in DNA. Hundreds of thousands of copies of DNA sequences have been incorporated into the genomes of higher organisms. Science 161, 529-540.

Brouzes, E., Medkova, M., Savenelli, N., Marran, D., Twardowski, M., Hutchison, J. B., Rothberg, J. M., Link, D. R., Perrimon, N., and Samuels, M. L. (2009). Droplet microfluidic technology for single-cell high-throughput screening. Proceedings of the National Academy of Sciences of the United States of America 106, 14195-14200.

Buettner, F., Natarajan, K. N., Casale, F. P., Proserpio, V., Scialdone, A., Theis, F. J., Teichmann, S. A., Marioni, J. C., and Stegle, O. (2015). Computational analysis of cell-to-cell heterogeneity in single-cell RNA-sequencing data reveals hidden subpopulations of cells. Nature biotechnology 33, 155-160.

Carter-Dawson, L. D., and LaVail, M. M. (1979). Rods and cones in the mouse retina. I. Structural analysis using light and electron microscopy. The Journal of comparative neurology 188, 245-262.

Cheong, H. K., Hwang, E., and Cheong, C. (2012). Rapid preparation of RNA samples using DNA-affinity chromatography and DNAzyme methods. Methods in molecular biology 941, 113-121.

Chung, N. C., and Storey, J. D. (2014). Statistical Significance of Variables Driving Systematic Variation in High-Dimensional Data. Bioinformatics.

Corbo, J. C., Myers, C. A., Lawrence, K. A., Jadhav, A. P., and Cepko, C. L. (2007). A typology of photoreceptor gene expression patterns in the mouse. Proceedings of the National Academy of Sciences of the United States of America 104, 12069-12074.

Descamps, F. J., Martens, E., Proost, P., Starckx, S., Van den Steen, P. E., Van Damme, J., and Opdenakker, G. (2005). Gelatinase B/matrix metalloproteinase-9 provokes cataract by cleaving lens betaBI crystallin. FASEB journal: official publication of the Federation of American Societies for Experimental Biology 19, 29-35.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Ester, M., Kriegel, H. P., Sander, J., and Xu, X. (1996). A density-based algorithm for discovering clusters in large spatial databases with noise. (Menlo Park, Calif.: AAAI Press).

Famiglietti, E. V., and Sundquist, S. J. (2010). Development of excitatory and inhibitory neurotransmitters in transitory cholinergic neurons, starburst amacrine cells, and GABAergic amacrine cells of rabbit retina, with implications for previsual and visual development of retinal ganglion cells. Visual neuroscience 27, 19-42.

Feigenspan, A., Teubner, B., Willecke, K., and Weiler, R. (2001). Expression of neuronal connexin36 in AII amacrine cells of the mammalian retina. The Journal of neuroscience the official journal of the Society for Neuroscience 21, 230-239.

Grun, D., Kester, L., and van Oudenaarden, A. (2014). Validation of noise models for single-cell transcriptomics. Nature methods 11, 637-640.

Guo, M. T., Rotem, A., Heyman, J. A., and Weitz, D. A. (2012). Droplet microfluidics for high-throughput biological assays. Lab on a chip 12, 2146-2155.

Hashimshony, T., Wagner, F., Sher, N., and Yanai, I. (2012). CEL-Seq: single-cell RNA-Seq by multiplexed linear amplification. Cell reports 2, 666-673.

Hattar, S., Liao, H. W., Takao, M., Berson, D. M., and Yau, K. W. (2002). Melanopsin-containing retinal ganglion cells: architecture, projections, and intrinsic photosensitivity. Science 295, 1065-1070.

Haverkamp, S., and Wassle, H. (2004). Characterization of an amacrine cell type of the mammalian retina immunoreactive for vesicular glutamate transporter 3. The Journal of comparative neurology 468, 251-263.

Hindson, B. J., Ness, K. D., Masquelier, D. A., Belgrader, P., Heredia, N. J., Makarewicz, A. J., Bright, I. J., Lucero, M. Y., Hiddessen, A. L., Legler, T. C., et al. (2011). High-throughput droplet digital PCR system for absolute quantitation of DNA copy number. Analytical chemistry 83, 8604-8610.

Hoon, M., Okawa, H., Della Santina, L., and Wong, R. O. (2014). Functional architecture of the retina: development and disease. Progress in retinal and eye research 42, 44-84.

Islam, S., Kjallquist, U., Moliner, A., Zajac, P., Fan, J. B., Lonnerberg, P., and Linnarsson, S. (2012). Highly multiplexed and strand-specific single-cell RNA 5' end sequencing. Nature protocols 7, 813-828.

Islam, S., Zeisel, A., Joost, S., La Manno, G., Zajac, P., Kasper, M., Lonnerberg, P., and Linnarsson, S. (2014). Quantitative single-cell RNA-seq with unique molecular identifiers. Nature methods 11, 163-166.

Jaitin, D. A., Kenigsberg, E., Keren-Shaul, H., Elefant, N., Paul, F., Zaretsky, I., Mildner, A., Cohen, N., Jung, S., Tanay, A., et al. (2014). Massively parallel single-cell RNA-seq for marker-free decomposition of tissues into cell types. Science 343, 776-779.

Jarosz, D. F., Brown, J. C., Walker, G. A., Datta, M. S., Ung, W. L., Lancaster, A. K., Rotem, A., Chang, A., Newby, G. A., Weitz, D. A., et al. (2014). Cross-kingdom chemical communication drives a heritable, mutually beneficial prion-based transformation of metabolism. Cell 158, 1083-1093.

Jeon, C. J., Strettoi, E., and Masland, R. H. (1998). The major cell populations of the mouse retina. The Journal of neuroscience: the official journal of the Society for Neuroscience 18, 8936-8946.

Kadonaga, J. T. (1991). Purification of sequence-specific binding proteins by DNA affinity chromatography. Methods in enzymology 208, 10-23.

Kay, J. N., Voinescu, P. E., Chu, M. W., and Sanes, J. R. (2011). Neurod6 expression defines new retinal amacrine cell subtypes and regulates their fate. Nature neuroscience 14, 965-972.

Kharchenko, P. V., Silberstein, L., and Scadden, D. T. (2014). Bayesian approach to single-cell differential expression analysis. Nature methods 11, 740-742.

Kivioja, T., Vaharautio, A., Karlsson, K., Bonke, M., Enge, M., Linnarsson, S., and Taipale, J. (2012). Counting absolute numbers of molecules using unique molecular identifiers. Nature methods 9, 72-74.

Kurimoto, K., Yabuta, Y., Ohinata, Y., Ono, Y., Uno, K. D., Yamada, R. G., Ueda, H. R., and Saitou, M. (2006). An improved single-cell cDNA amplification method for efficient high-density oligonucleotide microarray analysis. Nucleic acids research 34, e42.

Lareu, R. R., Harve, K. S., and Raghunath, M. (2007). Emulating a crowded intracellular environment in vitro dramatically improves RT-PCR performance. Biochemical and biophysical research communications 363, 171-177.

Leek, J. T., and Storey, J. D. (2011). The joint null criterion for multiple hypothesis tests. Applications in Genetics and Molecular Biology 10, 1-22.

Luo, L., Callaway, E. M., and Svoboda, K. (2008). Genetic dissection of neural circuits. Neuron 57, 634-660.

Mao, C. A., Li, H., Zhang, Z., Kiyama, T., Panda, S., Hattar, S., Ribelayga, C. P., Mills, S. L., and Wang, S. W. (2014). T-box transcription regulator Tbr2 is essential for the formation and maintenance of Opn4/melanopsin-expressing intrinsically photosensitive retinal ganglion cells. The Journal of neuroscience: the official journal of the Society for Neuroscience 34, 13083-13095.

Masland, R. H. (2012). The neuronal organization of the retina. Neuron 76, 266-280.

Masland, R. H., and Sanes, J. R. (2015). Retinal ganglion cell types: Current states and lessons for the brain. Ann Rev Neurosci in press.

Mazutis, L., Gilbert, J., Ung, W. L., Weitz, D. A., Griffiths, A. D., and Heyman, J. A. (2013). Single-cell analysis and sorting using droplet-based microfluidics. Nature protocols 8, 870-891.

McCarroll, S. A., Feng, G., and Hyman, S. E. (2014). Genome-scale neurogenetics: methodology and meaning. Nature neuroscience 17, 756-763.

McDavid, A., Finak, G., Chattopadyay, P. K., Dominguez, M., Lamoreaux, L., Ma, S. S., Roederer, M., and Gottardo, R. (2013). Data exploration, quality control and testing in single-cell qPCR-based gene expression experiments. Bioinformatics 29, 461-467.

McDonald, J. C., Duffy, D. C., Anderson, J. R., Chiu, D. T., Wu, H., Schueller, O. J., and Whitesides, G. M. (2000). Fabrication of microfluidic systems in poly(dimethylsiloxane). Electrophoresis 21, 27-40.

Mills, S. L., O'Brien, J. J., Li, W., O'Brien, J., and Massey, S. C. (2001). Rod pathways in the mammalian retina use connexin 36. The Journal of comparative neurology 436, 336-350.

Peres-Neto, P. R., Jackson, D. A., and Somers, K. M. (2005). How many principal components? stopping rules for determining the number of non-trivial axes revisited. Computational Statistics and Data Analysis 49, 974-997.

Petilla Interneuron Nomenclature, G., Ascoli, G. A., Alonso-Nanclares, L., Anderson, S. A., Barrionuevo, G., Benavides-Piccione, R., Burkhalter, A., Buzsaki, G., Cauli, B., Defelipe, J., et al. (2008). Petilla terminology: nomenclature of features of GABAergic interneurons of the cerebral cortex. Nature reviews Neuroscience 9, 557-568.

Picelli, S., Bjorklund, A. K., Faridani, O. R., Sagasser, S., Winberg, G., and Sandberg, R. (2013). Smart-seq2 for sensitive full-length transcriptome profiling in single cells. Nature methods 10, 1096-1098.

Pollen, A. A., Nowakowski, T. J., Shuga, J., Wang, X., Leyrat, A. A., Lui, J. H., Li, N., Szpankowski, L., Fowler, B., Chen, P., et al. (2014). Low-coverage single-cell mRNA sequencing reveals cellular heterogeneity and activated signaling pathways in developing cerebral cortex. Nature biotechnology.

Provis, J. M., Diaz, C. M., and Penfold, P. L. (1996). Microglia in human retina: a heterogeneous population with distinct ontogenies. Perspectives on developmental neurobiology 3, 213-222.

Roberts, M. R., Srinivas, M., Forrest, D., Morreale de Escobar, G., and Reh, T. A. (2006). Making the gradient: thyroid hormone regulates cone opsin expression in the developing mouse retina. Proceedings of the National Academy of Sciences of the United States of America 103, 6218-6223.

Sanes, J. R., and Zipursky, S. L. (2010). Design principles of insect and vertebrate visual systems. Neuron 66, 15-36.

Shalek, A. K., Satija, R., Adiconis, X., Gertner, R. S., Gaublomme, J. T., Raychowdhury, R., Schwartz, S., Yosef, N., Malboeuf, C., Lu, D., et al. (2013). Single-cell transcriptomics reveals bimodality in expression and splicing in immune cells. Nature 498, 236-240.

Shalek, A. K., Satija, R., Shuga, J., Trombetta, J. J., Gennert, D., Lu, D., Chen, P., Gertner, R. S., Gaublomme, J. T., Yosef, N., et al. (2014). Single-cell RNA-seq reveals dynamic paracrine control of cellular variation. Nature 510, 363-369.

Shekhar, K., Brodin, P., Davis, M. M., and Chakraborty, A. K. (2014). Automatic Classification of Cellular Expression by Nonlinear Stochastic Embedding (ACCENSE). Proceedings of the National Academy of Sciences of the United States of America 111, 202-207.

Siegert, S., Cabuy, E., Scherf, B. G., Kohler, H., Panda, S., Le, Y. Z., Fehling, H. J., Gaidatzis, D., Stadler, M. B., and Roska, B. (2012). Transcriptional code and disease map for adult retinal cell types. Nature neuroscience 15, 487-495, S481-482.

Srivastava, S. C., Pandey, D., Srivastava, N. P., and Bajpai, S. P. (2008). RNA Synthesis: phosphoramidites for RNA synthesis in the reverse direction. Highly efficient synthesis and application to convenient introduction of ligands, chromophores and modifications of synthetic RNA at the 3'-end. Nucleic acids symposium series, 103-104.

Starckx, S., Van den Steen, P. E., Verbeek, R., van Noort, J. M., and Opdenakker, G. (2003). A novel rationale for inhibition of gelatinase B in multiple sclerosis: MMP-9 destroys alpha B-crystallin and generates a promiscuous T cell epitope. Journal of neuroimmunology 141, 47-57.

Szel, A., Lukats, A., Fekete, T., Szepessy, Z., and Rohlich, P. (2000). Photoreceptor distribution in the retinas of subprimate mammals. Journal of the Optical Society of America A, Optics, image science, and vision 17, 568-579.

Tang, F., Barbacioru, C., Wang, Y., Nordman, E., Lee, C., Xu, N., Wang, X., Bodeau, J., Tuch, B. B., Siddiqui, A., et al. (2009). mRNA-Seq whole-transcriptome analysis of a single cell. Nature methods 6, 377-382.

Thorsen, T., Roberts, R. W., Arnold, F. H., and Quake, S. R. (2001). Dynamic pattern formation in a vesicle-generating microfluidic device. Physical review letters 86, 4163-4166.

Umbanhowar, P. B. P., V.; Weitz, D. A. (2000). Monodisperse Emulsion Generation via Drop Break Off in a Coflowing Stream. Langmuir 16, 347-351.

Utada, A. S., Fernandez-Nieves, A., Stone, H. A., and Weitz, D. A. (2007). Dripping to jetting transitions in coflowing liquid streams. Physical review letters 99, 094502.

van der Maaten, L., and Hinton, G. (2008). Visualizing Data using t-SNE. Journal of Machine Learning Research 9, 2579-2605.

Vogelstein, B., and Kinzler, K. W. (1999). Digital PCR. Proceedings of the National Academy of Sciences of the United States of America 96, 9236-9241.

Wetmur, J. G., and Davidson, N. (1968). Kinetics of renaturation of DNA. Journal of molecular biology 31, 349-370.

White, A. K., VanInsberghe, M., Petriv, O. I., Hamidi, M., Sikorski, D., Marra, M. A., Piret, J., Aparicio, S., and Hansen, C. L. (2011). High-throughput microfluidic single-cell RT-qPCR. Proceedings of the National Academy of Sciences of the United States of America 108, 13999-14004.

Whitfield, M. L., Sherlock, G., Saldanha, A. J., Murray, J. I., Ball, C. A., Alexander, K. E., Matese, J. C., Perou, C. M., Hurt, M. M., Brown, P. O., et al. (2002). Identification of genes periodically expressed in the human cell cycle and their expression in tumors. Molecular biology of the cell 13, 1977-2000.

Yang, Y., and Cvekl, A. (2005). Tissue-specific regulation of the mouse alphaA-crystallin gene in lens via recruitment of Pax6 and c-Maf to its promoter. Journal of molecular biology 351, 453-469.

Zhu, Y. Y., Machleder, E. M., Chenchik, A., Li, R., and Siebert, P. D. (2001). Reverse transcriptase template switching: a SMART approach for full-length cDNA library construction. BioTechniques 30, 892-897.

The invention is further described by the following numbered paragraphs:

1. A nucleotide- or oligonucleotide-adorned bead wherein said bead comprises:
   (a) a linker;
   (b) an identical sequence for use as a sequencing priming site;
   (c) a uniform or near-uniform nucleotide or oligonucleotide sequence;
   (d) a Unique Molecular Identifier which differs for each priming site;
   (e) optionally an oligonucleotide redundant sequence for capturing polyadenylated mRNAs and priming reverse transcription; and
   (f) optionally at least one other oligonucleotide barcode which provides an additional substrate for identification.

2. The nucleotide- or oligonucleotide-adorned bead of paragraph 1 wherein the nucleotide or oligonucleotide sequence on the surface of the bead is a molecular barcode.

3. The nucleotide- or oligonucleotide-adorned bead of paragraph 2 wherein the barcode ranges from 4 to 1000 nucleotides in length.

4. The nucleotide- or oligonucleotide-adorned bead according to paragraph 1 wherein the oligonucleotide sequence for capturing polyadenylated mRNAs and priming reverse transcription is an oligo dT sequence.

5. The nucleotide- or oligonucleotide-adorned bead according to paragraph 1 wherein the linker is a non-cleavable, straight-chain polymer.

6. The nucleotide- or oligonucleotide-adorned bead according to paragraph 1 wherein the linker is a chemically-cleavable, straight-chain polymer.

7. The nucleotide- or oligonucleotide-adorned bead according to paragraph 1 wherein the linker is a non-cleavable optionally substituted hydrocarbon polymer.

8. The nucleotide- or oligonucleotide-adorned bead according to paragraph 1 wherein the linker is a photolabile optionally substituted hydrocarbon polymer.

9. The nucleotide- or oligonucleotide-adorned bead according to paragraph 1 wherein the linker is a polyethylene glycol.

10. The nucleotide- or oligonucleotide-adorned bead according to paragraph 1 wherein the linker is a PEG-$C_3$ to PEG-$_{24}$.

11. A mixture comprising a plurality of nucleotide- or oligonucleotide-adorned beads, wherein said beads comprises:
   (a) a linker;
   (b) an identical sequence for use as a sequencing priming site;
   (c) a uniform or near-uniform nucleotide or oligonucleotide sequence;
   (d) a Unique Molecular Identifier which differs for each priming site;
   (e) an oligonucleotide redundant sequence for capturing polyadenylated mRNAs and priming reverse transcription; and
   (f) optionally at least one additional oligonucleotide sequences, which provide substrates for downstream molecular-biological reactions;
   wherein the uniform or near-uniform nucleotide or oligonucleotide sequence is the same across all the priming sites on any one bead, but varies among the oligonucleotides on an individual bead.

12. The mixture of paragraph 11 wherein the nucleotide or oligonucleotide sequence on the surface of the bead is a molecular barcode.

13. The mixture of paragraph 12 wherein the barcode ranges from 4 to 1000 nucleotides in length.

14. The mixture of paragraph 11 wherein the oligonucleotide sequence for capturing polyadenylated mRNAs and priming reverse transcription is an oligo dT sequence.

15. The mixture of paragraph 11 which comprises at least one oligonucleotide sequences, which provide for substrates for downstream molecular-biological reactions.

16. The mixture of paragraph 11 wherein the downstream molecular biological reactions are for reverse transcription of mature mRNAs; capturing specific portions of the transcriptome, priming for DNA polymerases and/or similar enzymes; or priming throughout the transcriptome or genome.

17. The mixture of paragraph 11 wherein the additional oligonucleotide sequence comprises a oligo-dT sequence.

18. The mixture of paragraph 11 wherein the additional oligonucleotide sequence comprises a primer sequence.

19. The mixture of paragraph 11 wherein the additional oligonucleotide sequence comprises a oligo-dT sequence and a primer sequence.

20. An error-correcting barcode bead wherein said bead comprises:
   (a) a linker;
   (b) an identical sequence for use as a sequencing priming site;
   (c) a uniform or near-uniform nucleotide or oligonucleotide sequence which comprises at least a nucleotide base duplicate;
   (d) a Unique Molecular Identifier which differs for each priming site; and
   (e) an oligonucleotide redundant for capturing polyadenylated mRNAs and priming reverse transcription;

21. A method wherein the barcode beads of paragraph 20 fail to hybridize to the mRNA thereby failing to undergo reverse transcription.

22. A kit which comprises a mixture of oligonucleotide bound beads of paragraph 1 and self-correcting barcode beads of paragraph 20.

23. A method for creating a composite single-cell sequencing library comprising:
   (a) merging one uniquely barcoded RNA capture microbead with a single-cell in an emulsion droplet having a diameter from 50 µm to 210 µm;
   (b) lysing the cell thereby capturing the RNA on the RNA capture microbead;
   (c) performing a reverse transcription reaction to convert the cells' RNA to first strand cDNA that is covalently linked to the RNA capture microbead; or conversely reverse transcribing within droplets and thereafter breaking droplets and collecting cDNA-attached beads;
   (d) preparing and sequencing a single composite RNA-Seq library, containing cell barcodes that record the cell-of-origin of each RNA, and molecular barcodes that distinguish among RNAs from the same cell.

24. A method for creating a composite single-cell sequencing library comprising:
   (a) merging one uniquely barcoded RNA capture microbead with a single-cell in an emulsion droplet having a diameter from 50 µm to 210 µm;
   (b) lysing the cell thereby capturing the RNA on the RNA capture microbead;
   (c) breaking droplets and pooling beads in solution;
   (d) performing a reverse transcription reaction to convert the cells' RNA to first strand cDNA that is covalently linked to the RNA capture microbead; or conversely reverse transcribing within droplets and thereafter breaking droplets and collecting cDNA-attached beads;
   (e) preparing and sequencing a single composite RNA-Seq library, containing cell barcodes that record the cell-of-origin of each RNA, and molecular barcodes that distinguish among RNAs from the same cell.

25. The method of paragraph 23 or paragraph 24, wherein the method of amplifying the cDNA-attached beads is template switch amplification.

26. The method of paragraph 23 or 24, wherein the method of amplifying the cDNA-attached beads is T7 linear application.

27. The method of paragraph 23 or paragraph 24, wherein the method of amplifying the cDNA-attached beads is exponential isothermal amplification.

28. The method of paragraph 23 or paragraph 24, wherein the emulsion droplet is formed via co-encapsulation comprising RNA capture microbead and composite single-cell.

29. The method of paragraph 25 wherein the emulsion droplet is at least 1.25 to times more than the volume of the RNA capture microbead.

30. The method of paragraph 29 wherein the emulsion droplet is at least 1.5 times the volume of the RNA capture microbead.

31. The method of paragraph 23 or paragraph 24, wherein the RNA is mRNA.

32. The method of paragraph 23 or paragraph 24 wherein the diameter of the emulsion droplet is 125 µm.

33. The method of paragraph 23 or paragraph 24 wherein the diameter of the RNA capture microbeads is from 10 µm to 95 µm.

34. A method for preparing a plurality of beads with unique nucleic acid sequence comprising:
   (a) performing polynucleotide synthesis on the surface of the plurality of beads in a pool-and-split process, such that in each cycle of synthesis the beads are split into a plurality of subsets wherein each subset is subjected to different chemical reactions;
   (b) repeating the pool-and-split process from anywhere from 2 cycles to 200 cycles.

35. The method of paragraph 34 wherein the polynucleotide synthesis is phosphoramidite synthesis.
36. The method of paragraph 34 wherein the polynucleotide synthesis is reverse direction phosphoramidite chemistry.
37. The method of paragraph 34 wherein each subset is subjected to a different nucleotide.
38. The method of paragraph 34 wherein each subset is subjected to a different canonical nucleotide.
39. The method of paragraph 34 is repeated three times.
40. The method of paragraph 34 is repeated four times.
41. The method of paragraph 34 is repeated twelve times.
42. The method of paragraph 34, wherein the linker covalently connecting the microbead to the oligonucleotide is polyethylene glycol.
43. The method of any one of paragraphs 34 through 42, wherein the diameter of the RNA capture microbeads is from 10 μm to 95 μm.
44. The method of any one of paragraphs 34 through 42 wherein multiple steps is twelve steps.
45. A method for simultaneously preparing a plurality of nucleotide- or oligonucleotide-adorned beads wherein a uniform, near-uniform, or patterned nucleotide or oligonucleotide sequence is synthesized upon any individual bead while vast numbers of different nucleotide or oligonucleotide sequences are simultaneously synthesized on different beads, comprising:
  (a) forming a mixture comprising a plurality of beads;
  (b) separating the beads into subsets;
  (c) extending the nucleotide or oligonucleotide sequence on the surface of the beads by adding an individual nucleotide via chemical synthesis;
  (d) pooling the subsets of beads in (c) into a single common pool;
  (e) repeating steps (b), (c) and (d) multiple times to produce a combinatorially a thousand or more nucleotide or oligonucleotide sequences; and
  (f) collecting the nucleotide- or oligonucleotide-adorned beads.
46. The method of paragraph 45 wherein the nucleotide or oligonucleotide sequence on the surface of the bead is a molecular barcode.
47. The method of paragraph 45 wherein the pool-and-split synthesis steps occur every 2-10 cycles, rather than every cycle.
48. The method of paragraph 45 wherein the barcode contains built-in error correction.
49. The method of paragraph 45 wherein the barcode ranges from 4 to 1000 nucleotides in length.
50. The method of paragraph 45 wherein the polynucleotide synthesis is phosphoramidite synthesis.
51. The method of paragraph 45 wherein the polynucleotide synthesis is reverse direction phosphoramidite chemistry.
52. The method of paragraph 45 wherein each subset is subjected to a different nucleotide.
53. The method of paragraph 45 further comprising wherein one or more subsets receive a cocktail of two nucleotides.
54. The method of paragraph 45 wherein each subset is subjected to a different canonical nucleotide.
55. The method of paragraph 45 wherein the bead is a microbead.
56. The method of paragraph 45 wherein the bead is a nanoparticle.
57. The method of paragraph 45 wherein the bead is a macrobead.
58. The method of paragraph 45 where the oligonucleotide sequence is a dinucleotide.
59. The method of paragraph 45 where the oligonucleotide sequence is a trinucleotide.
60. A method for simultaneously preparing a thousand or more nucleotide- or oligonucleotide-adorned beads wherein a uniform or near-uniform nucleotide or oligonucleotide sequence is synthesized upon any individual bead while a plurality of different nucleotide or oligonucleotide sequences are simultaneously synthesized on different beads, comprising:
  (a) forming a mixture comprising a plurality of beads;
  (b) separating the beads into subsets;
  (c) extending the nucleotide or oligonucleotide sequence on the surface of the beads by adding an individual nucleotide via chemical synthesis;
  (d) pooling the subsets of beads in (c) into a single common pool;
  (e) repeating steps (b), (c) and (d) multiple times to produce a combinatorially large number of nucleotide or oligonucleotide sequences; and
  (f) collecting the nucleotide- or oligonucleotide-adorned beads;
  (g) performing polynucleotide synthesis on the surface of the plurality of beads in a pool-and-split synthesis, such that in each cycle of synthesis the beads are split into a plurality of subsets wherein each subset is subjected to different chemical reactions;
  (h) repeating the pool-and-split synthesis multiple times.
61. The method of paragraph 60 wherein the nucleotide or oligonucleotide sequence on the surface of the bead is a molecular barcode.
62. The method of paragraph 60 wherein the pool-and-split synthesis steps occur every 2-10 cycles, rather than every cycle.
63. The method of paragraph 60 wherein the generated barcode contains built-in error correction.
64. The method of paragraph 60 wherein the barcode ranges from 4 to 1000 nucleotides in length.
65. The method of paragraph 60 wherein the polynucleotide synthesis is phosphoramidite synthesis.
66. The method of paragraph 60 wherein the polynucleotide synthesis is reverse direction phosphoramidite chemistry.
67. The method of paragraph 60 wherein each subset is subjected to a different nucleotide.
68. The method of paragraph 60 further comprising wherein one or more subsets receive a cocktail of two nucleotides.
69. The method of paragraph 60 wherein each subset is subjected to a different canonical nucleotide.
70. The method of paragraph 60 wherein the bead is a microbead.
71. The method of paragraph 60 wherein the bead is a nanoparticle.
72. The method of paragraph 60 wherein the bead is a macrobead.
73. The method of paragraph 60 where the oligonucleotide barcoded bead is a dinucleotide.
74. The method of paragraph 60 where the oligonucleotide barcoded bead is a trinucleotide.
75. The method of paragraph 45 or paragraph 60 wherein the pool-and-split synthesis is repeated twelve times.
76. The method of paragraph 45 or paragraph 60 wherein the diameter of the complexed bead is from 10 μm to 95 μm.
77. An apparatus for creating a composite single-cell sequencing library via a microfluidic system, comprising:
  a oil-surfactant inlet comprising a filter and a carrier fluid channel, wherein said carrier fluid channel further comprises a resistor;

an inlet for an analyte comprising a filter and a carrier fluid channel, wherein said carrier fluid channel further comprises a resistor;

an inlet for mRNA capture microbeads and lysis reagent comprising a filter and a carrier fluid channel, wherein said carrier fluid channel further comprises a resistor;

said carrier fluid channels have a carrier fluid flowing therein at an adjustable or predetermined flow rate;

wherein each said carrier fluid channels merge at a junction; and said junction being connected to a mixer, which contains an outlet for drops.

78. The apparatus of paragraph 77, wherein the analyte comprises a chemical reagent, a protein, a drug, an antibody, an enzyme, a nucleic acid, an organelle, a cell or any combination thereof.

79. The apparatus of paragraph 77 wherein said junction is connected to said mixer by a fluid carrier channel with a constriction for droplet pinch-off.

80. The apparatus of paragraph 77, wherein the analyte is a cell.

81. The apparatus of paragraph 77, wherein the analyte is a mammalian cell.

82. The apparatus of paragraph 77, wherein the analyte is complex tissue.

83. The apparatus of paragraph 81, wherein the cell is a brain cell.

84. The apparatus of paragraph 81, wherein the cell is a retina cell.

85. The apparatus of paragraph 81, wherein the cell is a human bone marrow cell.

86. The apparatus of paragraph 81, wherein the cell is a host-pathogen cell.

87. The apparatus of paragraph 77, wherein the lysis reagent comprises an anionic surfactant, such as sodium lauroyl sarcosine, or a chaotropic salt, such as guanidinium thiocyanate.

88. The apparatus of paragraph 77, wherein the filter comprises square PDMS.

89. The apparatus of paragraph 77, wherein the resistor is serpentine having a length from 7000-9000, width of 50-75 μm and depth of 100-150 mm.

90. The resistor of paragraph 89, which has a diameter of 50 μm.

91. The apparatus of paragraph 77, wherein the channels having a length of length of 8000-12,000 μm and width of 125-250 mm, and depth of 100-150 mm.

92. The channel of paragraph 89, wherein the diameter is 125 μm.

93. The apparatus of paragraph 77, wherein the mixer has a length of 7000-9000 μm and a width of 110-140 μm.

94. The mixer of paragraph 93, wherein the width is 125 μm.

95. The apparatus of paragraph 77, wherein the oil-surfactant is a PEG block polymer.

96. The apparatus of paragraph 95, wherein the PEG block polymer is BIORAD™ QX200 Droplet Generation Oil.

97. The apparatus of paragraph 77, wherein the carrier fluid is water-glycerol mixture.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A plurality of at least a thousand RNA capture microbeads wherein each RNA capture microbead comprises a plurality of capture oligonucleotides attached to the microbead surface, each capture oligonucleotide comprising:
   i. a linker;
   ii. a sequence for use as a sequencing priming site, wherein the sequence is identical on all beads;
   iii. a cell-of-origin barcode sequence that is the same for all capture oligonucleotides on the same bead but differs from the barcode sequence of capture oligonucleotides on other beads, wherein the maximum complexity of cell-of-origin barcodes for the plurality of RNA capture microbeads is $4^n$ where n is the length of the cell-of-origin barcode sequence and n is at least 6;
   iv. a unique molecular identifier (UMI) sequence that is different for each capture oligonucleotide on the same bead;
   v. a capture sequence that binds to cellular RNA and primes reverse transcription; and
   vi. optionally at least one additional oligonucleotide sequence which provides substrates for downstream molecular-biological reactions,
   and wherein the cell-of-origin barcode sequence is contiguous with the UMI sequence.

2. The plurality of RNA capture microbeads of claim 1, wherein the cell-of-origin barcode ranges from 6 to 1000 nucleotides in length.

3. The plurality of RNA capture microbeads according to claim 1, wherein the capture sequence that binds to cellular RNA and primes reverse transcription is an oligo dT sequence.

4. The plurality of RNA capture microbeads according to claim 1, wherein the linker is a non-cleavable, straight-chain polymer.

5. The plurality of RNA capture microbeads according to claim 1, wherein the linker is a chemically-cleavable, straight-chain polymer.

6. The plurality of RNA capture microbeads according to claim 1, wherein the linker is a non-cleavable optionally substituted hydrocarbon polymer.

7. The plurality of RNA capture microbeads according to claim 1, wherein the linker is a photolabile optionally substituted hydrocarbon polymer.

8. The plurality of RNA capture microbeads according to claim 1, wherein the linker is a polyethylene glycol.

9. The plurality of RNA capture microbeads to claim 1, wherein the linker is a $PEG_{-3}$ to $PEG_{-24}$.

10. The plurality of RNA capture microbeads of claim 1, which comprises the at least one additional oligonucleotide sequence which provides substrates for downstream molecular-biological reactions.

11. The plurality of RNA capture microbeads of claim 10, wherein the downstream molecular-biological reactions are for reverse transcription of mature mRNAs; capturing specific portions of the transcriptome, priming for DNA polymerases and/or similar enzymes; or priming throughout the transcriptome or genome.

12. The plurality of RNA capture microbeads of claim 10, wherein the additional oligonucleotide sequence comprises an oligo-dT sequence.

13. The plurality of RNA capture microbeads of claim 10, wherein the additional oligonucleotide sequence comprises a primer sequence which comprises the same sequence across all beads in the plurality of beads.

14. The plurality of RNA capture microbeads of claim 10, wherein the additional oligonucleotide sequence comprises an oligo-dT sequence and a primer sequence.

15. The plurality of RNA capture microbeads of claim 1, wherein the capture oligonucleotide comprises at least one chemically modified nucleotide.

16. The plurality of RNA capture microbeads of claim 1, wherein the bead material is porous.

17. The plurality of RNA capture microbeads of claim 16, wherein the bead material is methacrylate resin.

18. The plurality of RNA capture microbeads of claim 1, wherein the plurality of RNA capture microbeads comprise 100,000 to 10 million uniquely barcoded RNA capture microbeads.

19. The plurality of RNA capture microbeads of claim 1, wherein the cell-of-origin barcode is 6 to 12 nucleotides in length.

* * * * *

UNITED STATES PATENT AND TRADEMARK OFFICE
CERTIFICATE OF CORRECTION

| | | |
|---|---|---|
| PATENT NO. | : 11,566,279 B2 | Page 1 of 1 |
| APPLICATION NO. | : 16/244058 | |
| DATED | : January 31, 2023 | |
| INVENTOR(S) | : Aviv Regev et al. | |

It is certified that error appears in the above-identified patent and that said Letters Patent is hereby corrected as shown below:

On the Title Page

On the page 5, in item (56), in Column 2, under "Other Publications", Line 48, delete "Reporton" and insert -- Report on --.

On the page 6, in item (56), in Column 1, under "Other Publications", Line 22, delete "RevC," and insert -- Rev C, --.

On the page 6, in item (56), in Column 1, under "Other Publications", Line 37, delete "RevE," and insert -- Rev E, --.

In the Specification

In Column 49, Line 15, delete "1211)." and insert -- 12H). --.

In Column 62, Line 19, delete "t-SAE" and insert -- t-SNE --.

In Column 62, Line 48, delete "genes," and insert -- genes; --.

In Column 63, Line 25, delete "cell-t-pes." and insert -- cell-types. --.

In Columns 77-78, Line 66 (Table 4-continued), delete "ARL136" and insert -- ARL13B --.

Signed and Sealed this
Twenty-fifth Day of July, 2023

Katherine Kelly Vidal
*Director of the United States Patent and Trademark Office*

SEQUENCE LISTING

```
<160> NUMBER OF SEQ ID NOS: 63

<210> SEQ ID NO 1
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
tttttttttt tttttttttt tttttttttt                                      30

<210> SEQ ID NO 2
<211> LENGTH: 67
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (24)..(42)
<223> OTHER INFORMATION: a, c, u, g, unknown or other

<400> SEQUENCE: 2
ccuacacgac gcucuuccga ucunnnnnnn nnnnnnnnnn nnbaaaaaaa aaaaaaaaaa      60
aaaaaaa                                                               67

<210> SEQ ID NO 3
```

-continued

```
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (35)..(54)
<223> OTHER INFORMATION: a, c, t, g, unknown or other

<400> SEQUENCE: 3 ttttttttaag cagtggtatc aacgcagagt acgtnnnnnn nnnnnnnnnn nnnntttttt    60
tttttttttt tttttttttt tttt                                           84

<210> SEQ ID NO 4
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (33)..(52)
<223> OTHER INFORMATION: a, c, t, g, unknown or other

<400> SEQUENCE: 4 ttttttttaag cagtggtatc aacgcagagt acnnnnnnnn nnnnnnnnnn nntttttttt    60
tttttttttt tttttttttt tt                                             82

<210> SEQ ID NO 5
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 5
aagcagtggt atcaacgcag agtgaatggg                                     30

<210> SEQ ID NO 6
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
aagcagtggt atcaacgcag agt                                            23

<210> SEQ ID NO 7
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 7
aatgatacgg cgaccaccga gatctacacg cctgtccgcg gaagcagtgg tatcaacgca    60
gagtac    66

<210> SEQ ID NO 8
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
caagcagaag acggcatacg agattcgcct tagtctcgtg ggctcgg    47

<210> SEQ ID NO 9
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
caagcagaag acggcatacg agatctagta cggtctcgtg ggctcgg    47

<210> SEQ ID NO 10
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
caagcagaag acggcatacg agatttctgc ctgtctcgtg ggctcgg    47

<210> SEQ ID NO 11
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gcctgtccgc ggaagcagtg gtatcaacgc agagtacgt    39

<210> SEQ ID NO 12
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gcctgtccgc ggaagcagtg gtatcaacgc agagtac    37

<210> SEQ ID NO 13

```
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
caagcagaag acggcatacg agatcgtgat cggtctcggc ggaagcagtg gtatcaacgc      60
agagtac                                                               67

<210> SEQ ID NO 14
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
aatgatacgg cgaccaccga gatctacact ctttccctac acgacgctct tccgatct       58

<210> SEQ ID NO 15
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
cggtctcggc ggaagcagtg gtatcaacgc agagtac                              37

<210> SEQ ID NO 16
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (26)..(34)
<223> OTHER INFORMATION: a, c, t, g, unknown or other

<400> SEQUENCE: 16
aagcagtggt atcaacgcag agtacnnnnn nnnntttttt tttttttttt tttttttt       58

<210> SEQ ID NO 17
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
aaaaaaaaaa aa                                                         12

<210> SEQ ID NO 18
<211> LENGTH: 12
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 18
aatgctgtta cg                                                          12

<210> SEQ ID NO 19
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gcatctttcc cg                                                          12

<210> SEQ ID NO 20
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
gagcctgaga tg                                                          12

<210> SEQ ID NO 21
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
tagaacaaca ag                                                          12

<210> SEQ ID NO 22
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
tcatacaggc gg                                                          12

<210> SEQ ID NO 23
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
gatcacctgc ac                                                          12
```

<210> SEQ ID NO 24
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
gactggaccg tc                                                         12

<210> SEQ ID NO 25
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
ctcgaggcaa ga                                                         12

<210> SEQ ID NO 26
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
cttagttctt ag                                                         12

<210> SEQ ID NO 27
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ctgaggtcac gg                                                         12

<210> SEQ ID NO 28
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ctcttaaata tc                                                         12

<210> SEQ ID NO 29
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 29
tttttttttt tt                                              12

<210> SEQ ID NO 30
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
atcttaatca ac                                              12

<210> SEQ ID NO 31
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ccttcttttc ct                                              12

<210> SEQ ID NO 32
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
tcctctttcc ct                                              12

<210> SEQ ID NO 33
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
tcaccgacga ca                                              12

<210> SEQ ID NO 34
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gcacttcccg tt                                              12

<210> SEQ ID NO 35
<211> LENGTH: 12
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
cagaggaata aa                                                              12

<210> SEQ ID NO 36
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
cgctttctgc ac                                                              12

<210> SEQ ID NO 37
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
tcagaccctc gg                                                              12

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
aaattatgac gatgtgcttg                                                      20

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
cgttagatgg cagggccggg                                                      20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
aaattatgac gaagtttgta                                                      20
```

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
gttaaacgta ccctagctgt                                         20

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ttgccgtggt gtgtgggggt                                         20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
ttgccgtggt gttatggagg                                         20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
gttaaacgta ccgcaggttt                                         20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
aaattatgac gaagtttgta                                         20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 46
cgttagatgg catctaggct                                          20

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
gttaaacgta ccaaggcttg                                          20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ttgccgtgga gtcgtgaggg                                          20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
cgttagatgg cacctgtgta                                          20

<210> SEQ ID NO 50
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gttaaacgta ccatccggtg                                          20

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ttgccgtggt gtgtgggggt                                          20

<210> SEQ ID NO 52
<211> LENGTH: 20

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ttgccgtggt gttatggagg                                              20

<210> SEQ ID NO 53
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ttgccgtggt gtcgtgaggg                                              20

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
cgttagatgg cagggccggg                                              20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
cgttagatgg cacctgtgta                                              20

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
cgttagatgg catctaggct                                              20

<210> SEQ ID NO 57
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
```

```
aaattatgac gaagtttgta                                              20

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
aaattatgac gaagtttgta                                              20

<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
aaattatgac gatgtgcttg                                              20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
gttaaacgta ccctagctgt                                              20

<210> SEQ ID NO 61
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
gttaaacgta ccgcaggttt                                              20

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
gttaaacgta ccaaggcttg                                              20

<210> SEQ ID NO 63
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 63
gttaaacgta ccatccggtg                                              20
```